United States Patent
Ganesan et al.

(10) Patent No.: US 12,103,977 B2
(45) Date of Patent: Oct. 1, 2024

(54) TRISPECIFIC ANTIBODY TARGETING CD79b, CD20, AND CD3

(71) Applicant: Janssen Biotech, Inc., Horsham, PA (US)

(72) Inventors: Rajkumar Ganesan, Blue Bell, PA (US); Anna Kuchnio, Edegem (BE); Cassandra L. Lowenstein, Ambler, PA (US); Ulrike Philippar, Antwerp (BE); Sanjaya Singh, Blue Bell, PA (US); Nele Vloemans, Oostmalle (BE); Danlin Yang, Philadelphia, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 17/702,282

(22) Filed: Mar. 23, 2022

(65) Prior Publication Data

US 2022/0315663 A1    Oct. 6, 2022

Related U.S. Application Data

(60) Provisional application No. 63/286,309, filed on Dec. 6, 2021, provisional application No. 63/165,501, filed on Mar. 24, 2021.

(51) Int. Cl.
   *C07K 16/28*   (2006.01)
   *A61K 39/00*   (2006.01)
   *A61P 35/00*   (2006.01)

(52) U.S. Cl.
   CPC .......... *C07K 16/2896* (2013.01); *A61P 35/00* (2018.01); *C07K 16/2878* (2013.01);
   (Continued)

(58) Field of Classification Search
   CPC ............ C07K 16/2896; C07K 16/2878; C07K 16/2887; C07K 2317/24; C07K 2317/31;
   (Continued)

(56) References Cited

U.S. PATENT DOCUMENTS

| 6,737,056 B1 | 5/2004 | Presta |
| 8,236,308 B2 | 8/2012 | Kischel et al. |

(Continued)

FOREIGN PATENT DOCUMENTS

| WO | 0041474 A2 | 7/2000 |
| WO | 2006/028936 A2 | 3/2006 |

(Continued)

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-94. (Year: 1995).*

(Continued)

*Primary Examiner* — Aurora M Fontainhas
*Assistant Examiner* — Selam Berhane
(74) *Attorney, Agent, or Firm* — McCarter & English, LLP

(57) ABSTRACT

Provided herein are multispecific antibodies, including trispecific antibodies that bind to CD79b, CD20 and CD3, and bispecific antibodies that bind to CD79b and CD3, and multispecific antigen-binding fragments thereof. Also described are related polynucleotides capable of encoding the provided multispecific antibodies or multispecific antigen-binding fragments, cells expressing the provided multispecific antibodies or multispecific antigen-binding fragments, as well as associated vectors and detectably labeled multispecific antibodies or multispecific antigen-binding fragments. In addition, methods of producing and using the (Continued)

provided multispecific antibodies and multispecific antigen-binding fragments are described. Further provided herein are isolated antibodies that bind to CD79b and antigen-binding fragments thereof. Also described are related polynucleotides capable of encoding the provided CD79b-specific antibodies or antigen-binding fragments, cells expressing the provided CD79b-specific antibodies or antigen-binding fragments, as well as associated vectors and detectably labeled CD79b-specific antibodies or antigen-binding fragments. In addition, methods of producing and using the provided CD79b-specific antibodies and antigen-binding fragments are described.

35 Claims, 48 Drawing Sheets

Specification includes a Sequence Listing.

(52) U.S. Cl.
CPC .... *C07K 16/2887* (2013.01); *A61K 2039/505* (2013.01); *C07K 2317/24* (2013.01); *C07K 2317/31* (2013.01); *C07K 2317/55* (2013.01); *C07K 2317/565* (2013.01); *C07K 2317/622* (2013.01); *C07K 2317/73* (2013.01); *C07K 2317/76* (2013.01); *C07K 2317/92* (2013.01)

(58) Field of Classification Search
CPC .......... C07K 2317/55; C07K 2317/565; C07K 2317/622; C07K 2317/73; C07K 2317/76; C07K 2317/92; A61P 35/00; A61K 2039/505

See application file for complete search history.

(56) References Cited

U.S. PATENT DOCUMENTS

| 10,590,197 | B2* | 3/2020 | Finney ................. A61P 29/00 |
| 2009/0182127 | A1 | 7/2009 | Kjaergaard et al. |
| 2010/0015133 | A1 | 1/2010 | Igawa et al. |
| 2011/0123532 | A1 | 5/2011 | Gurney et al. |
| 2013/0167256 | A1 | 6/2013 | Green et al. |
| 2017/0355756 | A1* | 12/2017 | Julien ................. A61P 25/00 |

FOREIGN PATENT DOCUMENTS

| WO | 2007/059782 | A1 | 5/2007 | |
| WO | 2010/037836 | A2 | 4/2008 | |
| WO | WO-2008068048 | A2 * | 6/2008 | ............. A61P 31/10 |
| WO | 2008/119565 | A2 | 10/2008 | |
| WO | 2008/119566 | A2 | 10/2008 | |
| WO | 2008/119567 | A2 | 10/2008 | |
| WO | 2010/037837 | A2 | 4/2010 | |
| WO | 2010037838 | A2 | 4/2010 | |
| WO | 2010/051274 | A2 | 5/2010 | |
| WO | 2010/093627 | A2 | 8/2010 | |
| WO | 2016071004 | A1 | 5/2016 | |
| WO | 2016090210 | A1 | 6/2016 | |
| WO | 2019060695 | A1 | 3/2019 | |
| WO | 2021019389 | A1 | 2/2021 | |

OTHER PUBLICATIONS

Edwards et al., The remarkable flexibility of the human antibody repertoire; isolation of over one thousand different antibodies to a single protein, BLyS. J Mol Biol. Nov. 14, 2003;334(1):103-18. (Year: 2003).*

Kussie, Paul H., "A Single Engineered Amino Acid Substitution Changes Antibody Fine Specificity", 1994, Journal of Immunology 152(1): pp. 146-152. (Year: 1994).*

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*

A General Method Applicable to the Search for Similarities in the Amino Acid Sequence of Two Proteins, J. Mol. Biol. 48, pp. 444-453, 1970.

Aguilar-Hernandez MM, Blunt MD, Dobson R, et al., IL-4 enhances expression and function of surface IgM in CLL cells, Blood, vol. 127 No. 24, pp. 3015-3025, 2016, doi:10.1182/blood-2015-11-682906.

Andres Salmeron, Francisco Anchez-Madrid Maria Angeles Ursa, Manuel Fresno, and Balbino Alarcon, A conformational epitope expressed upon association of CD3-epsilon with either CD3-delta or CD3-gamma is the main target for recognition by anti-CD3 monoclonal antibodies, The Journal of Immunology, vol. 147, pp. 3047-3052, 1991.

Andrew G. Polson et al., Antibody-drug conjugates targeted to CD79 for the treatment of non-Hodgkin lymphoma, Blood vol. 110, pp. 616-623, 2007.

Arcari A, Chiappella A, Spina M, et al., Safety and efficacy of rituximab plus bendamustine in relapsed or refractory diffuse large B-cell lymphoma patients: an Italian retrospective multicenter study, Leuk Lymphoma, 57 (8), pp. 1823-1830, doi:10.3109/10428194.2015.1106536.

Astsaturov, I.A et al., Differential expression of B29 (CD79b) and mb-1 (CD79a) proteins in acute lymphoblastic leukaemia, Leukemia 10, pp. 769-773, 1996.

Ayad M. Al-Katib and Anwar N. Mohamed, Non-Hodgkin's lymphoma and chronic lymphocytic leukemia. Burlington, MA, Decision Resources Group, pp. 794-803, Nov. 2019.

Bargou R, Leo E, Zugmaier G, et al., Tumor regression in cancer patients by very low doses of a T cell-engaging antibody, Science, 321, 5891, pp. 974-977, 2008, doi:10.1126/science.1158545.

Bibikova E, Law B, Clevenger T, et al., High surface expression of CD49d (VLA-4) and CD79b correlates with acalabrutinib resistance in patients with chronic lymphocytic leukemia (CLL), Blood, 134 (Supplement_1):2571, 2019, doi: 10.1182/blood-2019-128872.

Bluemel et al., Epitope distance to the target cell membrane and antigen size determine the potency of T cell-mediated lysis by BiTE antibodies specific for a large melanoma surface antigen, Cancer Immunol Immunother, 59, pp. 1197-1209, 2010.

Brouwer-Visser J, Fiaschi N, Deering RP, et al., Baseline biomarkers of T-cell function correlate with clinical responses to odronextamab (REGN1979), and loss of CD20 target antigen expression identified as a mechanism of treatment resistance. 62nd ASH AnnualMeeting and Exposition, Dec. 5-8, 2020; Abstract 2108, Available from: https://ash.confex.com/ash/2020/webprogram/Paper137499.html. Accessed: Jun. 3, 2021.

Bubien JK, Zhou LJ, Bell PD, Frizzell RA, Tedder TF., Transfection of the CD20 cell surface molecule into ectopic cell types generates a Ca2+ conductance found constitutively in B lymphocytes, J Cell Biol. 121(5), pp. 1121-1132, 1993, doi:10.1083/jcb.121.5.1121.

Burger JA, Wiestner A., Targeting B cell receptor signalling in cancer: preclinical and clinical advances, Nat Rev Cancer, 18(3), pp. 148-167, 2018, doi:10.1038/nrc.2017.121.

Burt R, Warcel D, Fielding AK, Blinatumomab, a bispecific B-cell and T-cell engaging antibody, in the treatment of B-cell malignancies, Hum Vaccin Immunother, 5(3), pp. 594-602, doi:10.1080/21645515.2018.1540828.

Chames et al., Bispecific antibodies for cancer therapy The light at the end of the tunnel? MABS, Landes Bioscience, US, vol. 1, No. 6, pp. 539-547, Nov. 1, 2009.

Chothia et al. Canonical Structures for the Hypervariable Regions, of Immunoglobulins, J. Mol. Biol. 196: pp. 901-917, 1987.

Chothia et al. Conformations of Immunoglobulin Hypervariable Regions vol. I 342, pp. 877-883.

Chu PG, Arber DA, CD79: A review, Appl Immunohistochem Mol Morphol., 9(2), pp. 97-106, 2001, doi:10.1097/00129039-200106000-00001.

Cline, Perspectives For Gene Therapy: Inserting New Genetic Information Into Mammalian Cells By Physical Techniques and Viral Vectors, Pharmac. Ther. pp. 69-92, 1985.

(56) References Cited

OTHER PUBLICATIONS

Cragg MS, Chan HT, Fox MD, et al., The alternative transcript of CD79b is overexpressed in B-CLL and inhibits signaling for apoptosis, Blood, 100(9), pp. 3068-3076, 2002, doi:10.1182/blood.V100.9.3068.
Davis RE, Ngo VN, Lenz G, et al., Chronic active B-cell-receptor signalling in diffuse large B-cell lymphoma, Nature, 463 (7277), pp. 88-92, 2010, doi:10.1038/nature08638.
Dufner V, Sayehli CM, Chatterjee M, et al., Long-term outcome of patients with relapsed/refractory B-cell non-Hodgkin lymphoma treated with blinatumomab, Blood Adv. 3 (16), pp. 2491-2498, 2019, doi:10.1182/bloodadvances.2019000025.
Edelman G.M. et al. The Covalent Structure of an Entire γg Immunoglobulin Molecule, Proc. Natl. Acad. USA 63, pp. 78-85, 1969 PMID: 5257969.
Eon Kuek L, Leffler M, Mackay GA, Hulett MD., The MS4A family: counting past 1, 2 and 3, Immunol Cell Biol. 94 (1), pp. 11-23, 2016, doi:10.1038/icb.2015.48.
Evans AG, Rothberg PG, Burack WR, et al. Evolution to plasmablastic lymphoma evades CD19-directed chimeric antigen receptor T cells, Br J Haematol. 171 (2), pp. 205-209, 2015, doi:10.1111/bjh.13562.
Ferrara et al., The Carbohydrate at FcRIIIa Asn-162 An Element Required for High Affinity Binding to Non-Fucosylated IgG Glycoforms, The Journal of Biological Chemistry vol. 281, No. 8, pp. 5032-5036, Feb. 24, 2006.
Gadi et al. , In vivo sensitization of ovarian tumors to chemotherapy by expression of E. coli purine nucleoside phosphorylase in a small fraction of cells, Gene Ther. pp. 1738-1743, 2000.
Gamonet C, Bole-Richard E, Delherme A, et al. New CD20 alternative splice variants:molecular identification and differential expression within hematological B cell malignancies [published correction appears in Exp Hematol Oncol. 2015;5:10. Exp Hematol Oncol. 2016;5:7. Published Mar. 1, 2016. doi:10.1186/s40164-016-0036-3.
Gea-Banacloche JC. Rituximab-associated infections. Semin Hematol. 47(2), pp. 187-198, 2010, doi:10.1053/j.seminhematol.2010.01.002.
Guisado Vasco P, Villar Rodríguez JL, Ibañez Martínez J, González Cámpora R, Galera Davidson H. Immunohistochemical organization patterns of the follicular dendritic cells, myofibroblasts and macrophages in the human spleen—new considerations on thepathological diagnosis of splenectomy pieces. Int J Clin Exp Pathol. 3 (2), pp. 189-202, 2009, Published Dec. 10, 2009.
Guo B, Zhang L, Chiorazzi N, Rothstein TL. IL-4 rescues surface IgM expression in chronic lymphocytic leukemia. Blood, 128(4), pp. 553-562, 2016, doi:10.1182/blood-2015-11-682997.
He X, Kläsener K, Iype JM, et al. Continuous signaling of CD79b and CD19 is required for the fitness of Burkitt lymphoma B cells. EMBO J. 37 (11):e97980, 2018, doi:10.15252/embj.201797980.
Henry C, Deschamps M, Rohrlich PS, et al. Identification of an alternative CD20 transcript variant in B-cell malignancies coding for a novel protein associated to rituximab resistance, Blood, 115 (12), pp. 2420-2429, 2009, doi:10.1182/blood-2009-06-229112.
Hilde Revets, Patrick De Baetseller & Serge Muyldermans, Nanobodies as novel agents for cancer therapy, Expert Opinion on Biological Therapy, 5 (1), pp. 111-124, 2005.
Holt et al. Domain antibodies: proteins for therapy, Trends In Biotechnology vol. 21. No. 11, pp. 484-490, Nov. 2003.
Ito M, Zhao N, Zeng Z, Zhou X, Chang CC, Zu Y. Interleukin-2 functions in anaplastic large cell lymphoma cells through augmentation of extracellular signal-regulated kinases1/2 activation. Int J Biomed Sci. 3, pp. 181-190, 2011.
Jacoby E, Nguyen SM, Fountaine TJ, et al. CD19 CAR immune pressure induces Bprecursor acute lymphoblastic leukaemia lineage switch exposing inherent leukaemic plasticity. Nat Commun. 7, 12320, pp. 1-10, 2016. Published Jul. 27, 2016. doi:10.1038/ncomms12320.
Jahn L, Hombrink p. Hassan C, et al. Therapeutic targeting of the BCR-associated protein CD79b in a TCR-based approach is hampered by aberrant expression of CD79b, Blood, 125(6), pp. 949-958, 2015, doi:10.1182/blood-2014-07-587840.
Jain T, Litzow MR. Management of toxicities associated with novel immunotherapy agents in acute lymphoblastic leukemia. Ther Adv Hematol. 11, 2020, 2040620719899897, Published Jan. 20, 2020. doi:10.1177/2040620719899897.
Kamphorst AO, Wieland A, Nasti T, et al. Rescue of exhausted CD8 T cells by PD-1-targeted therapies is CD28-dependent. Science, 355 6332, pp. 423-1427, 2017, doi:10.1126/science.aaf0683.
Katsuhiro Mori, et al., Engineering Chinese Hamster Ovary Cells to Maximize Effector Function of Produced Antibodies Using FUT8 siRNA, Biotechnol Bioeng 88, pp. 901-908, 2004.
Kelesidis T, Daikos G, Boumpas D, Tsiodras S. Does rituximab increase the incidence of infectious complications? A Narrative Review. Int J Infect Dis. 15 (1):e2-e16., 2011, doi:10.1016/j.ijid.2010.03.025.
Klein C. Jamois C, Nielsen T. Anti-CD20 treatment for B-cell malignancies: current status and future directions, Expert Opin Biol Ther. 1 (2), pp. 161-181, 2021, dol:10.1080/14712598.2020.1822318.
Klein C, Lammens A, Schäfer W, et al. Epitope interactions of monoclonal antibodies targeting CD20 and their relationship to functional properties, MAbs, 5 (1), pp. 22-33, 2013, doi:10.4161/mabs.22771.
Klinger M, Brandl C, Zugmaier G, et al. Immunopharmacologic response of patients with B-lineage acute lymphoblastic leukemia to continuous infusion of T cell-engaging CD19/CD3-bispecific BiTE antibody blinatumomab, Blood, 119 (26), pp. 6226-6233, 2012, doi:10.1182/blood-2012-01-400515.
Kläsener K, Jellusova J, Andrieux G, et al. CD20 as a gatekeeper of the resting state of human B cells. Proc Natl Acad Sci U S A. 118 (7), pp. 1-10, 2021, e2021342118, doi:10.1073/pnas.2021342118.
Kobold S, Pantelyushin S, Rataj F, Vom Berg J. Rationale for combining bispecific T cell activating antibodies with checkpoint blockade for cancer therapy, Front Oncol. 8 (285), pp. 1-8, 2018, Published Jul. 25, 2018. doi:10.3389/fonc.2018.00285.
Kochenderfer, J.N. et al., Chemotherapy-refractory diffuse large B-cell lymphoma and indolent B-cell malignancies can be effectively treated with autologous T cells expressing an anti-CD19 chimeric antigen receptor, J Clin Oncol 33, pp. 540-549, 2015.
Kusumoto S, Arcaini L, Hong X, et al. Risk of HBV reactivation in patients with B-cell lymphomas receiving obinutuzumab or rituximab immunochemotherapy, Blood, 133 (2), pp. 137-146, 2019, doi:10.1182/blood-2018-04-848044.
Lee DSW, Rojas OL, Gommerman JL. B cell depletion therapies in autoimmune disease: advances and mechanistic insights, Nat Rev Drug Discov. 20 (3), pp. 179-199, 2021, doi:10.1038/s41573-020-00092-2.
Leong SR, Sukumaran S, Hristopoulos M, et al. An anti-CD3/anti-CLL-1 bispecific antibody for the treatment of acute myeloid leukemia, Blood, 129 (5), pp. 609-618, 2017, doi:10.1182/blood-2016-08-735365.
Li D, Lee D, Dere RC, et al. Evaluation and use of an anti-cynomolgus monkey CD79b surrogate antibody-drug conjugate to enable clinical development of polatuzumab vedotin, Br J Pharmacol. 176 (19), pp. 3805-3818, 2019, doi:10.1111/bph.14784.
Li J, Piskol R, Ybarra R, et al. CD3 bispecific antibody-induced cytokine release is dispensable for cytotoxic T cell activity. Sci Transl Med. 11 (508), 2019, eaax8861, doi:10.1126/scitransimed.aax8861.
Lu T, Gibiansky L, Lix, et al. Exposure-safety and exposure-efficacy analyses of polatuzumab vedotin in patients with relapsed or refractory diffuse large B-cell lymphoma, Leuk Lymphoma, 61 (12), pp. 2905-2914, 2020, doi:10.1080/10428194.2020.1795154.
MacCallum et al., "Antibody-Antigen Interactions: Contact Analysis and Binding Site Topography," J. Mol. Biol. 262:732, pp. 1-14, 1996.
Majzner RG, Mackall CL. Tumor antigen escape from CAR T-cell therapy, Cancer Discov. 8 (10), pp. 1219-1226, 2018, doi:10.1158/2159-8290.CD-18-0442.
Martin and Thornton, Structural Families in Loops of Homologous Proteins: Automatic Classification, Modelling and Application to Antibodies, J. Mol. Biol. 263, pp. 800-815, 1996.

(56) References Cited

OTHER PUBLICATIONS

Middleton O, Wheadon H, Michie A. Classical complement pathway. In: Ratcliffe MJH, ed. Encyclopedia of immunobiology, 1st ed. New York, NY: Elsevier; 2016: vol. 2, pp. 318-324, doi:10.1016/B978-0-12-374279-7.02014-2.
Myers and Miller, Computer Applications in the Biosciences, Biosci, 4, pp. 11-17, 1998.
Naeim F, Rao PN, Song SX, Phan RT. Chapter 2: principles of Immunophenotyping, In: Naeim F, Rao PN, Song SX, Phan RT, eds. Atlas of hematopathology: morphology, immunophenotype, cytogenetics, and molecular approaches, 2nd ed. Cambridge, MA:Academic Press; pp. 29-56, 2018, doi:10.1016/B978-0-12-809843-1.00002-4.
Nägele V, Kratzer A, Zugmaier G, et al. Changes in clinical laboratory parameters and pharmacodynamic markers in response to blinaturomab treatment of patients with relapsed/refractory ALL. Exp Hematol Oncol. 6 vol. 14, 2017, Published May 18, 2017. doi:10.1186/s40164-017-0074-5.
Olivier et al., EB66 cell line, a duck embryonic stem cell-derived substrate for the industrial production of therapeutic monoclonal antibodies with enhanced ADCC activity, mAbs 2:4, pp. 405-415, 2010.
O'Keefe TL, Williams GT, Davies SL, Neuberger MS. Mice carrying a CD20 gene disruption, Immunogenetics, 48 (2), pp. 125-132, 1998 doi:10.1007/s002510050412.
Palanca-Wessels, M.C.A. et al. Safety and activity of the anti-CD79B antibody-drug conjugate polatuzumab vedotin in relapsed or refractory B-cell non-Hodgkin lymphoma and chronic lymphocytic leukaemia: a phase 1 study. The Lancet Oncology 16, pp. 704-7152015.
Phelan JD, Young RM, Webster DE, et al. A multiprotein supercomplex controlling oncogenic signalling in lymphoma, Nature, 560 (7718) pp. 387-391, 2018, doi:10.1038/s41586-018-0290-0.
Phillip Holliger, Terence Prospero, and Greg Winter, Diabodies: Small bivalent and bispecific antibody fragments, Proc. Natl. Acad. Sci. USA, Proc. Natl. Acad. Sci. USA, Biophysics vol. 90, pp. 6444-6448, Jul. 1993.
Porter DL, Levine BL, Kalos M, Bagg A, June CH. Chimeric Antigen Receptor-Modified TCells in Chronic Lymphoid Leukemia, The New England Journal of Medicine, vol. 365, pp. 725-733, doi:10.1056/NEJMoa1103849.
Puri, K.D., Di Paolo, J.A. & Gold, M.R. B-cell receptor signaling inhibitors for treatment of autoimmune inflammatory diseases and B-cell malignancies. Int Rev Immunol 32, pp. 397-427, 2013.
Robert J. Scheuplein, Permeability of the Skin: a review of major concepts. Curr Probl Dermatol., vol. 7, pp. 172-186, 1978, doi:10.1159/000401285.
Robert L. Shields, et al., Lack of Fucose on Human IgG1 N-Linked Oligosaccharide Improves Binding to Human FcRIII and Antibody-dependent Cellular Toxicity, The Journal of Biological Chemistry, vol. 277, No. 30, Issue of Jul. 26, pp. 26733-26740, 2002.
Roda-Navarro Pedro et al., Understanding the Spatial Topology of Artificial Immunology Synapses Assembled in T Cell-Redirecting Strategies: A Major Issue in Cancer Immunotherapy, Frontiers In Cell and Developmental Biology, vol. 7, Jan. 10, 2020, pp. 1-5.
Sabatino JJ Jr, Wilson MR, Calabresi PA, Hauser SL, Schneck JP, Zamvil SS. Anti-CD20 therapy depletes activated myelin-specific CD8+ T cells in multiple sclerosis, Proc Natl Acad Sci U S A., 116 (51) pp. 25800-25807, 2019, doi:10.1073/pnas.1915309116.
Sacco KA, Abraham RS. Consequences of B-cell-depleting therapy:hypogammaglobulinemia and impaired B-cell reconstitution, Immunotherapy, 10 (8), pp. 713-728, 2018, doi:10.2217/imt-2017-0178.
Schröder C, Azimzadeh AM, Wu G, Price JO, Atkinson JB, Pierson RN. Anti-CD20 treatment depletes B-cells in blood and lymphatic tissue of cynomolgus monkeys. Transpl. Immunol, 12 (1), pp. 19-28, 2003, doi:10.1016/S0966-3274(03)00059-5.
Schuster, S.J. et al. Chimeric Antigen Receptor T Cells in Refractory B-Cell Lymphomas, The new England journal of Medicine 377, pp. 2545-2554 2017.
Shalabi H, Kraft IL, Wang HW, et al. Sequential loss of tumor surface antigens following chimeric antigen receptor T-cell therapies in diffuse large B-cell lymphoma, Haematologica, 103 (5), pp. e215-e218, doi:10.3324/haematol.2017.183459.
Singh A, Dees S, Grewal IS, Overcoming the challenges associated with CD3+ T-cell redirection in cancer, British Journal of Cancer, 124 (6) pp. 1037-1048, 2021, doi:10.1038/s41416-020-01225-5.
Sotillo, E. et al. Convergence of Acquired Mutations and Alternative Splicing of CD19 Enables Resistance to CART-19 Immunotherapy, Cancer Discov 5, pp. 1282-1295 2015.
Steffen Dickope et al., Format and geometries matter: Structure-based design defines the functionality of bispecific antibodies, Biotechnology Journal vol. 18, pp. 1221-1227, May 14, 2020.
Sun L. Laura et al., Pre-Clinical Characterization of T Cell-Dependent Bispecific Antibody Anti-CD79bICD3 As a Potential Therapy for B Cell Malignancies, Blood, vol. 124, No. 21, Nov. 14, 2014, Abstract.
Tedder TF, Schlossman SF. Phosphorylation of the B1 (CD20) molecule by normal and malignant human B lymphocytes. J Biol Chem. 263 (20), pp. 10009-10015, 1988.
Thomas A. Packard and John C. Cambier, B lymphocyte antigen receptor signaling: initiation, amplification, and regulation, F1000 Prime Reports, 5, 40, pp. 1-8, 2013.
Tomita A. Genetic and Epigenetic Modulation of CD20 Expression in B-Cell Malignancies: molecular mechanisms and significance to rituximab resistance, J Clin Exp Hematop, 56 (2), pp. 89-99, 2016, doi:10.3960/jsirt.56.89.
Toyohide Shinkawa et al., The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity, The Journal of Biological Chemistry, vol. 278, No. 5, Issue of Jan. 31, pp. 3466-3473, 2003.
Uchida J, Lee Y, Hasegawa M, et al. Mouse CD20 expression and function, Int Immunol. 16 (1), pp. 119-129, 2004, doi:10.1093/intimm/dxh009.
Verma V, Shrimall RK, Ahmad S, et al., PD-1 blockade in subprimed CD8 cells induces dysfunctional PD-1+CD38hi cells and anti-PD-1 resistance [published correction appears in Nat Immunol, Nat Immunol, 20 (9), pp. 1231-1243, doi:10.1038/s41590-019-0441-y.
Visco C, Tanasi I, Quaglia FM, Ferrarini l, Fraenza C, Krampera M. Oncogenic mutations of MYD88 and CD79b in diffuse large B-cell lymphoma and implications for clinical practice, Cancers (Basel), 12 (10) pgs., Published Oct. 10, 2020, 2020.
Waisman A, Ebering A. Unraveling the T-B tangle in anti-CD20 multiple sclerosis therapy. Proc Natl Acad Sci U S A., 116 (51), pp. 25376-25377, doi:10.1073/pnas.1919044116.
Ward et al., Binding activities of a repertoire of single immunoglobulin variable domains secreted from *Escherichia coli*, Letters to Nature, vol. 341, pp. 544-546, 1989.
Zhou et al. 2008, Development of A Simple and Rapid Method for Producing Non-Fucosylated Oligomannose Containing Antibodies With Increased Effector Function, Biotechnology and Bioengineering, vol. 99, No. 3, pp. 625-665, Feb. 15, 2008.
Zuccolo J, Deng L, Unruh TL, et al., Expression of MS4A and TMEM176 genes in human B lymphocytes, Frontiers in Immunology vol. 4, article 195, pp. 1-7, Published Jul. 15, 2013, doi:10.3389/fimmu.2013.00195.
International Search Report and Written Opinion in connection with International Patent Application No. PCT/EP2022/057654, dated Aug. 22, 2022, 25 pages.

\* cited by examiner

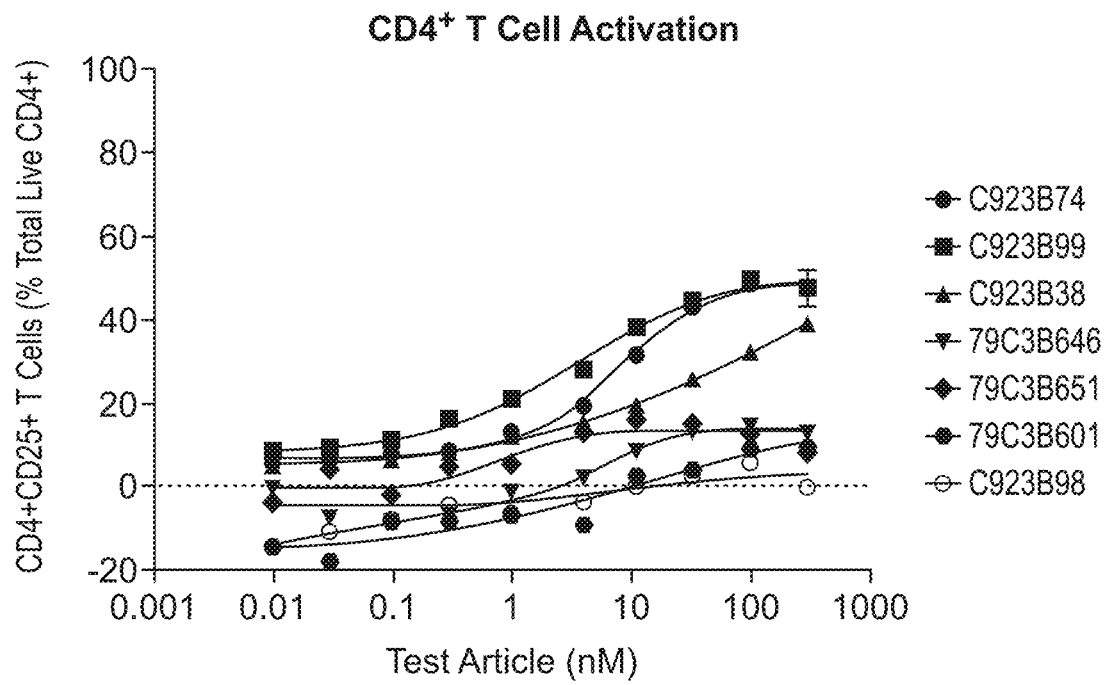
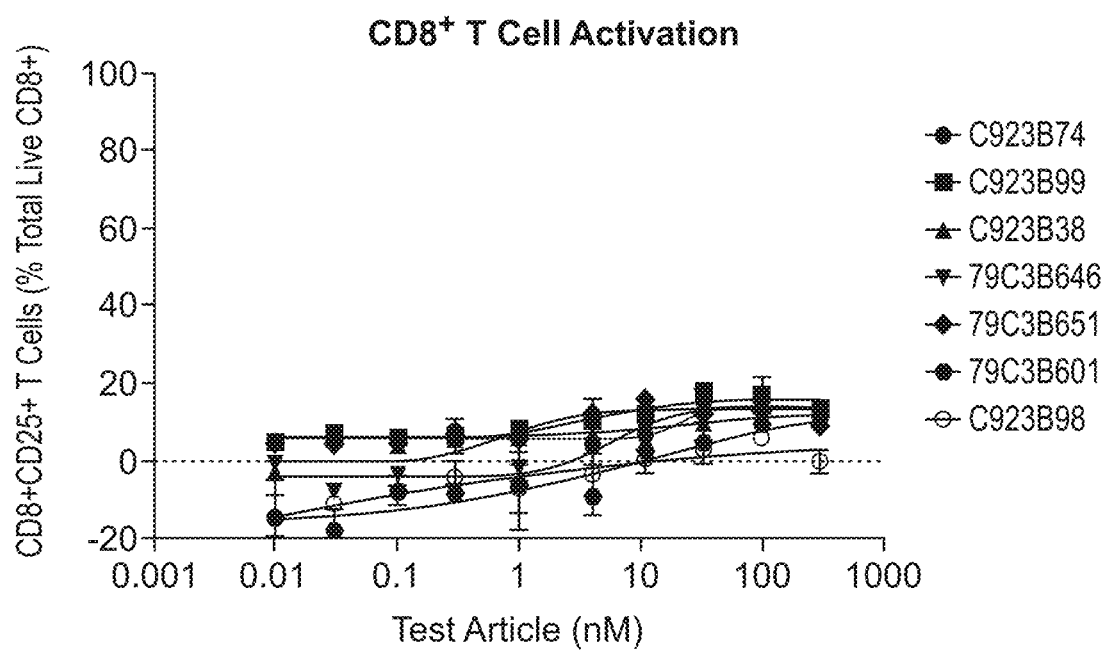

NHL at diagnosis

R/R to R-CHOP NHL

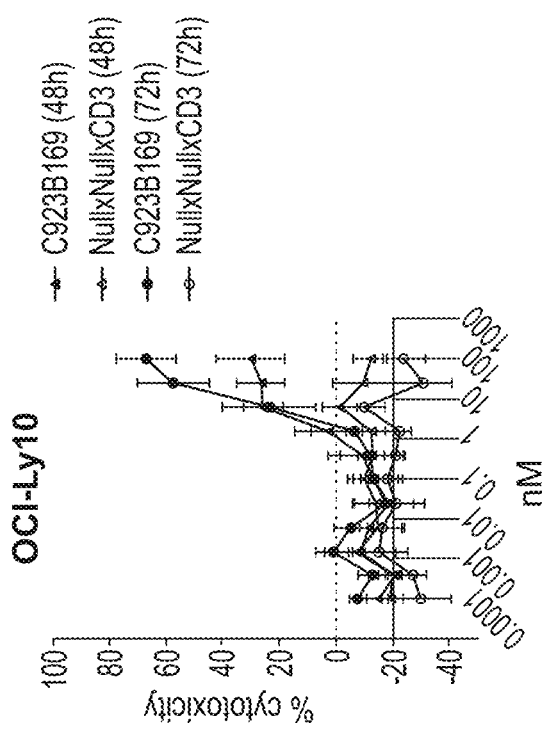
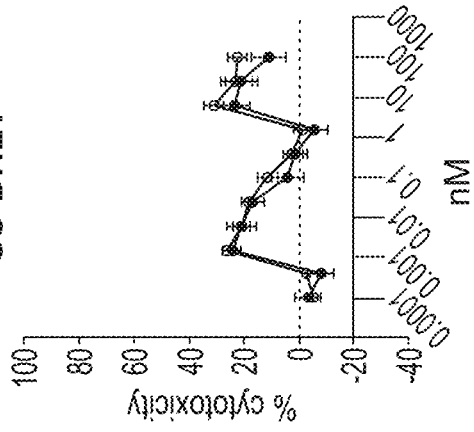
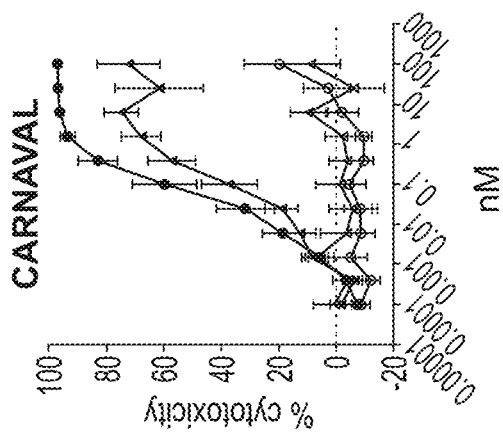
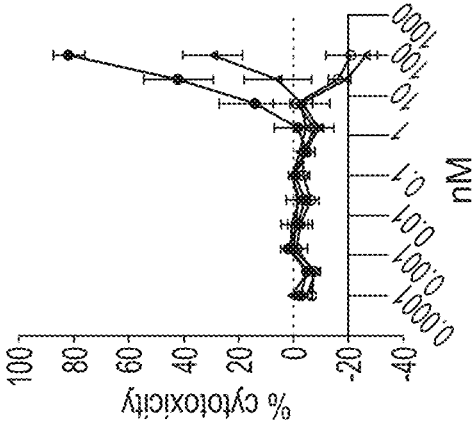
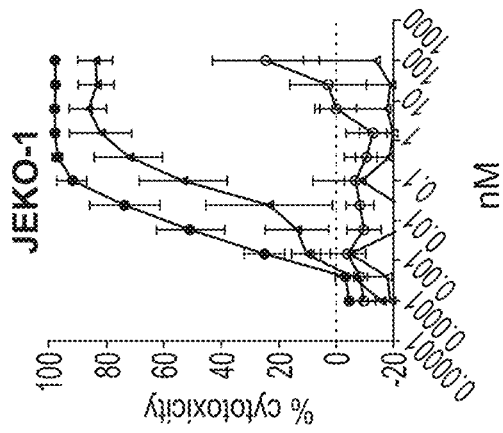
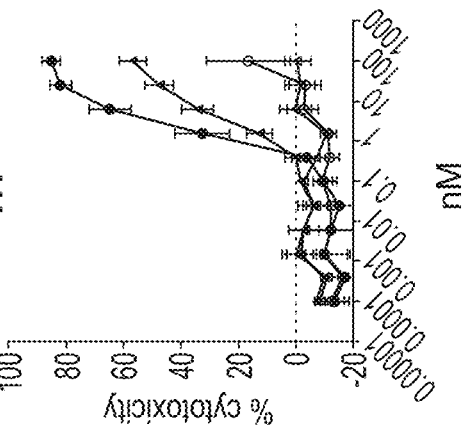
FIG. 16A JEKO-1
FIG. 16B CARNAVAL
FIG. 16C OCI-Ly10
FIG. 16D HT
FIG. 16E WILL-2
FIG. 16F SU-DHL1

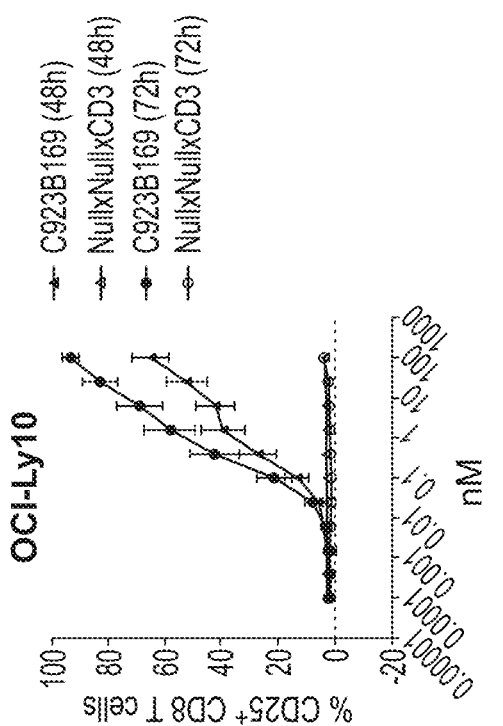
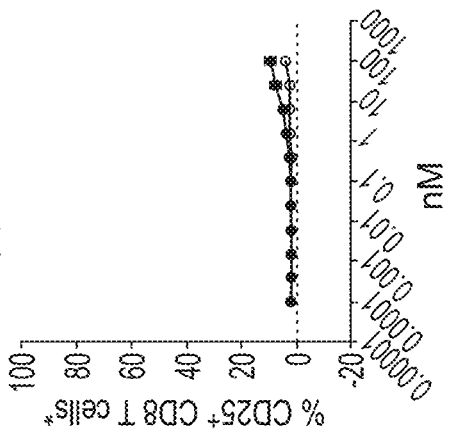
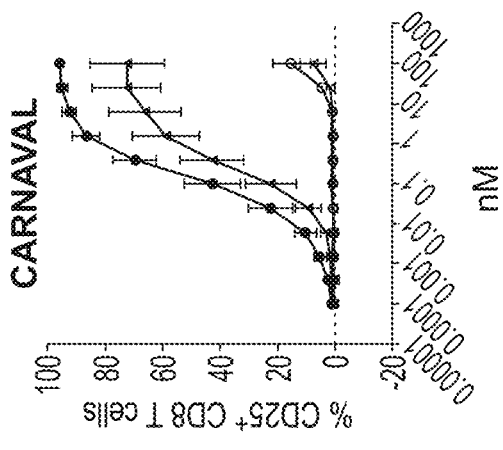
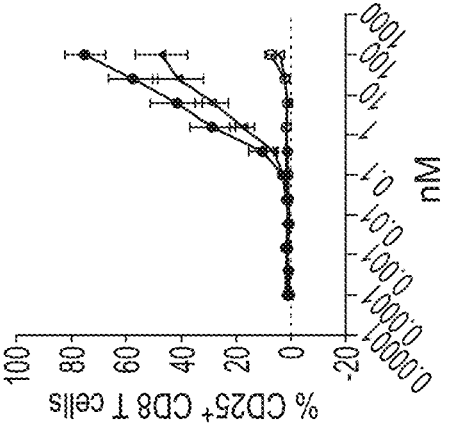
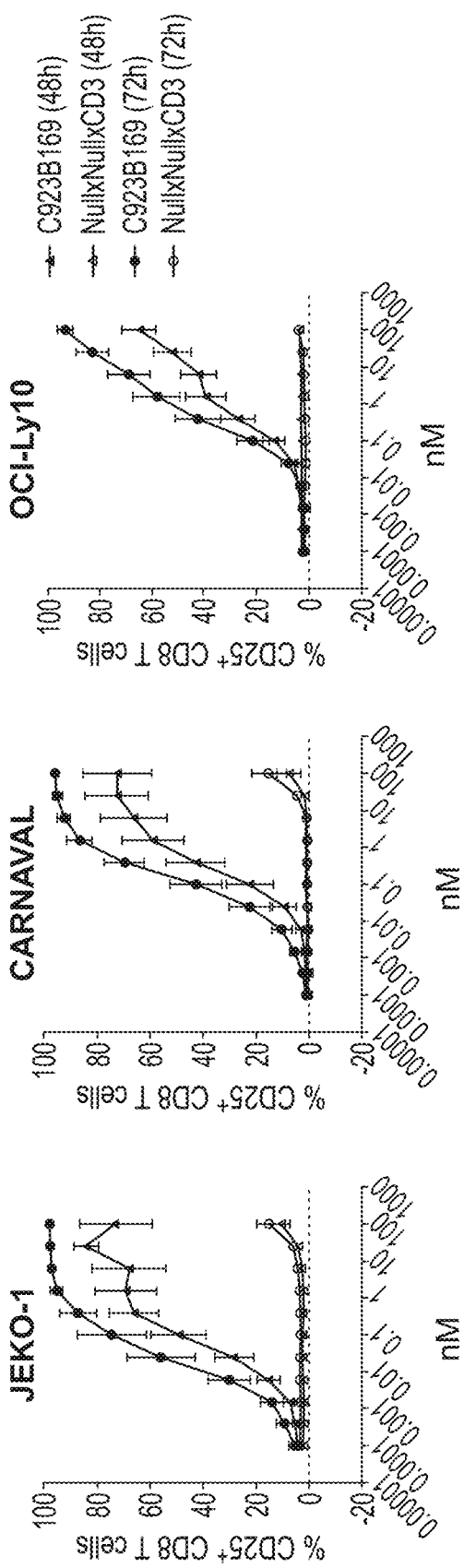
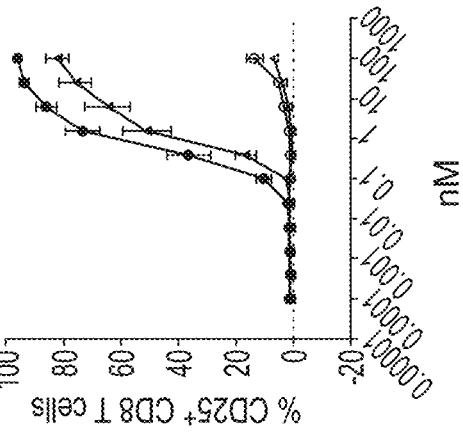

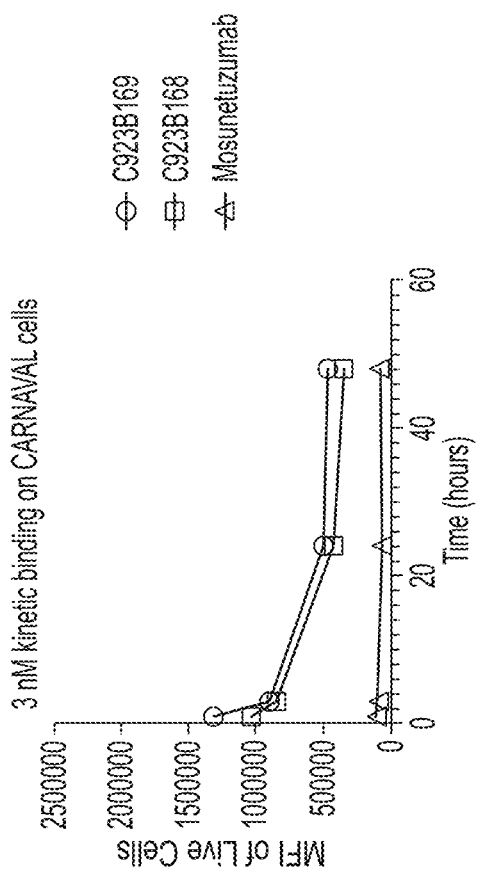
FIG. 27B
FIG. 27A
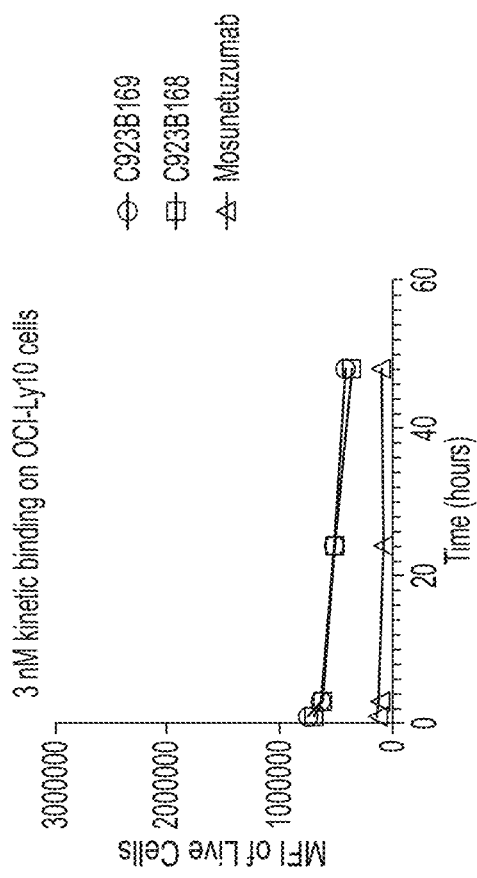
FIG. 27D
FIG. 27C
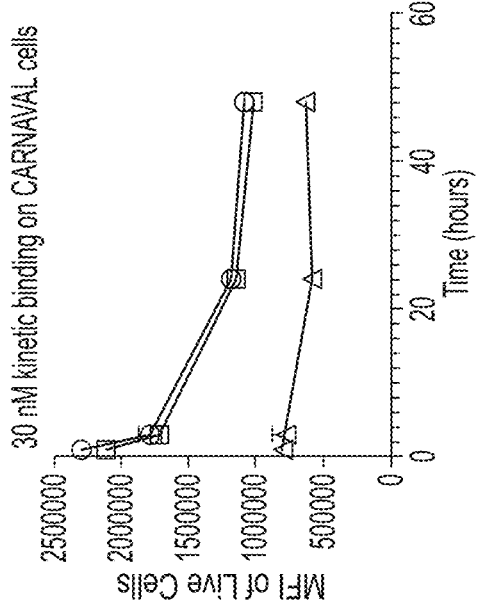
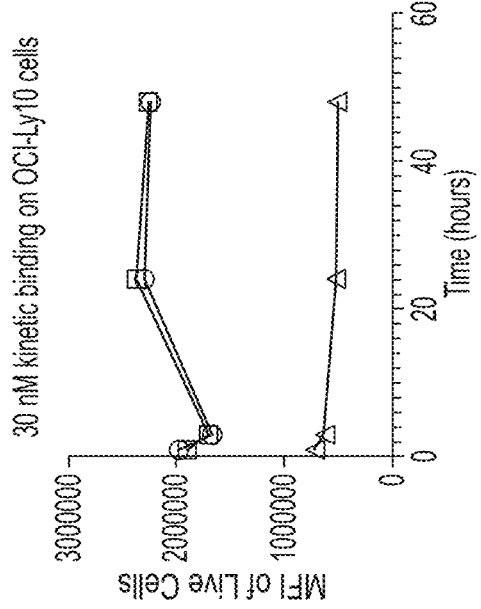

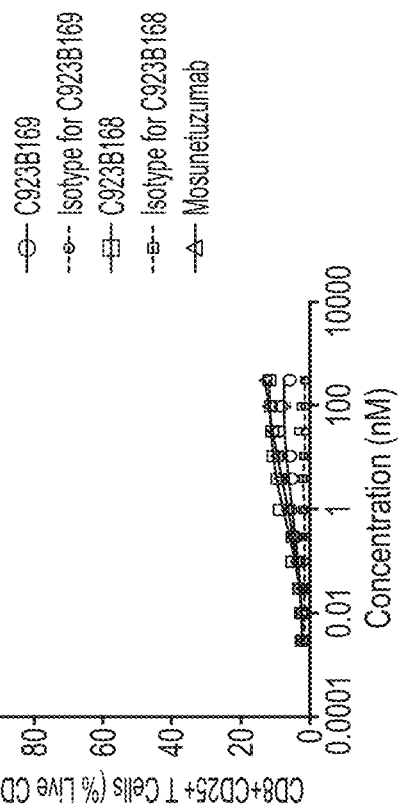
FIG. 30A Activated CD4+ T cells
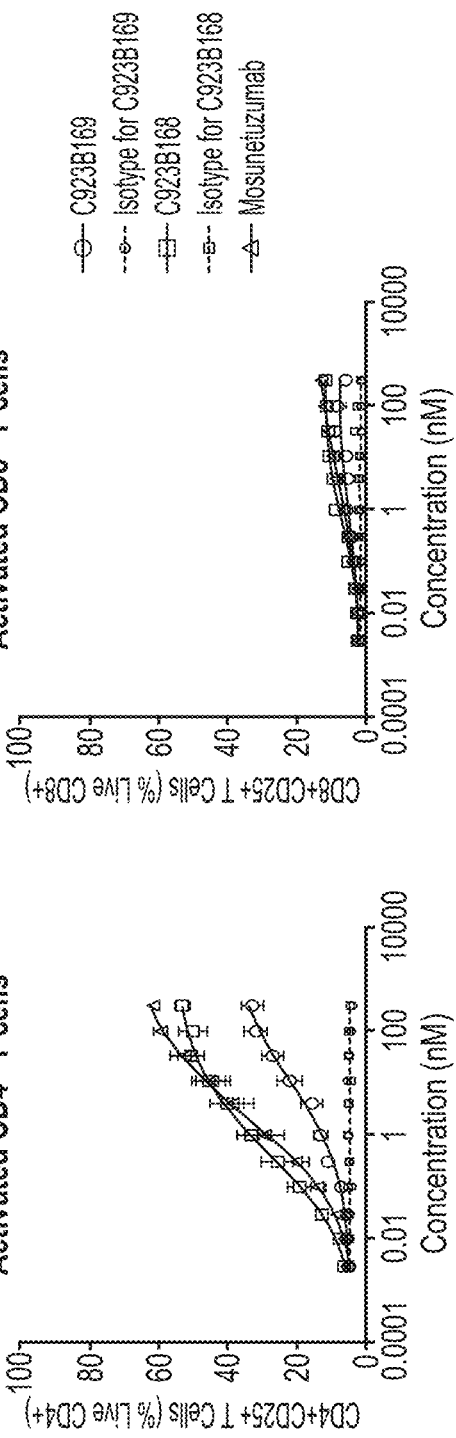
FIG. 30B Activated CD8+ T cells
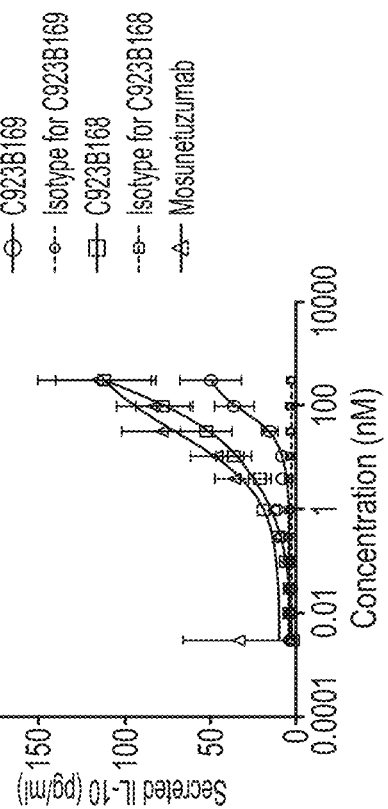
FIG. 30C Secreted IFN-γ levels
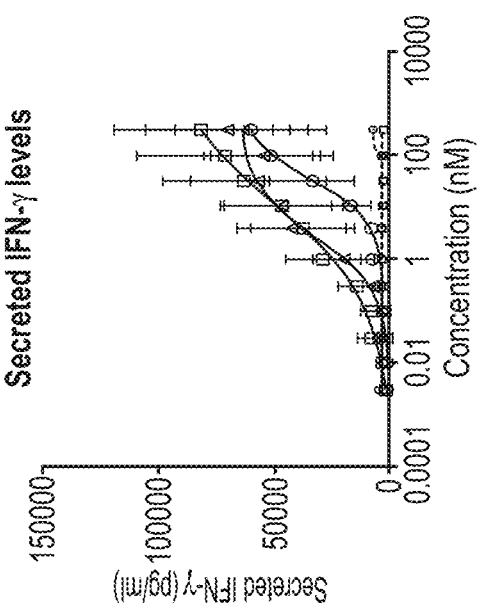
FIG. 30D Secreted IL-10 levels

TRISPECIFIC ANTIBODY TARGETING CD79b, CD20, AND CD3

CROSS-REFERENCE TO RELATED APPLICATIONS

This application claims the benefit of U.S. Provisional Application Ser. No. 63/165,501, filed 24 Mar. 2021 and U.S. Provisional Application Ser. No. 63/286,309, filed 6 Dec. 2021. The entire content of the aforementioned applications is incorporated herein by reference in its entirety.

SEQUENCE LISTING

The instant application contains a sequence listing which has been submitted electronically in ASCII format and is hereby incorporated by reference in its entirety. Said ASCII copy, created on Jan. 28, 2022, is named PRD4135USNP1_SL.txt and is 357,539 bytes in size.

TECHNICAL FIELD

The disclosure provided herein relates to multispecific antibodies that bind cluster of differentiation 79B protein (CD79b), cluster of differentiation 20 (CD20), and cluster of differentiation 3 (CD3), bispecific antibodies that bind CD79b and CD3, monoclonal antibodies that bind CD79b, as well as methods of producing and using the described antibodies.

BACKGROUND

Non-Hodgkin lymphoma (NHL) accounts for about 4% of all cancers. Despite improvements in available therapies, relapsed/refractory (R/R, sometimes referred to as r/r) NHLs are characterized by uniformly poor prognosis. Adoptive immunotherapy using T cells genetically engineered to express a chimeric antigen receptor (CAR) has shown promising results for the treatment of CD19-positive B cell malignancies. However, even with an initial overall response rate of approximately 60-80%, only 40% of patients achieve long-term, complete remission [1, 2]. There is emerging clinical data indicating disease relapse due to CD19 antigen loss in both acute lymphoblastic leukemia (ALL) and diffuse large B-cell lymphoma (DLBCL) patients [2, 4]. Accordingly, there is a need for targeting novel surface antigens.

T-cell redirection is a powerful and novel treatment that may address unmet medical needs of patients with B-cell malignancies whose disease no longer responds to standard chemo- or immunotherapies. CD20×CD3 and CD19×CD3 bispecific antibodies, show promising clinical response rates (10-12), and provide proof of concept (PoC) that this therapeutic approach can be highly effective in the clinical management of B-cell malignancies.

B cells, or B lymphocytes, are central components of adaptive immunity, responding to several different pathogens by producing antibodies, performing the role of antigen-presenting cells, secreting cytokines, and developing into memory B cells after activation [5]. B cells circulate in the blood and lymphatic systems. In the lymphoid organs, a B cell encounters its cognate antigen, and together with an additional signal from a T helper cell, the B cell can differentiate into effector plasma cells. These cells secrete specific antibodies that will circulate in the blood to target and eliminate antigens or pathogens [6].

To detect the antigen or pathogen, B cells have B cell receptors (BCRs) on the cell surface. The B-cell receptor is a multicomponent receptor composed of a transmembrane immunoglobulin molecule (mIg) and a disulfide linked heterodimer of CD79a (Igα) and CD79b (Igβ). CD79b is highly expressed in a wide range of B-cell lymphomas. Its expression plays a role in cancer cell viability of most DLBCL tumor models. Therefore, the development of resistance to CD79b targeted agents through antigen loss may be less likely, making it an attractive target for the development of novel immunotherapeutic approaches. In the clinic, Polatuzumab (POLIVY™), an antibody-drug conjugate (ADC) molecule targeting CD79b, has recently been approved for the treatment of r/r DLBCL [7]. Polatuzumab treatments results in an increase in complete response (CR) and duration of response (DOR) rates when combined with standard of care treatments (bendamustine and Rituximab), validating CD79b as a valuable clinical target [8].

The CD20 molecule (also called human B-lymphocyte-restricted differentiation antigen or Bp35) is a hydrophobic transmembrane protein that is over-expressed on most hematological malignancies in B cell linages. CD20 is found on the surface of greater than 90% of B cells from peripheral blood or lymphoid organs and is expressed during early pre-B cell development and remains until plasma cell differentiation. CD20 is present on both normal B cells as well as malignant B cells. In particular, CD20 is expressed on greater than 90% of B cell non-Hodgkin's lymphomas (NHL) (Anderson et al. (1984) Blood 63(6):1424-1433).

Targeting more than one lymphoma tumor antigen and engaging T-cells could lead to efficient killing of malignant plasma cells and minimal residual disease (MRD) negativity. Dual CD79b and CD20 targeting prevents tumor antigen escape, targets clonal populations (e.g., captures tumor cells that do not express enough CD79b or CD20 alone), improves tumor efficacy through avidity effects. The use of a low-affinity CD3-engaging arm may mitigate the potential risk of cytokine release syndrome (CRS). Accordingly, there is a need for therapeutic antibodies that target both CD79b and CD20 for the treatment of B-cell malignancies such as B-cell lymphomas and non-Hodgkin's lymphomas.

SUMMARY

In one aspect, provided herein are multispecific antibodies that bind, or specifically bind, to CD79b, CD20 and/or CD3 and multispecific antigen-binding fragments thereof. In some embodiments, provided herein are trispecific antibodies that bind, or specifically bind, to CD79b, CD20 and CD3 ("CD79b×CD20×CD3") and trispecific antigen-binding fragments thereof. In some embodiments, provided herein are bispecific antibodies that bind to CD79b and CD3 ("CD79b×CD3"), and bispecific antigen-binding fragments thereof. Also described are related polynucleotides capable of encoding the provided multispecific antibodies or multispecific antigen-binding fragments, cells expressing the provided multispecific antibodies or multispecific antigen-binding fragments, as well as associated vectors and detectably labeled multispecific antibodies or multispecific antigen-binding fragments. In addition, methods of using the provided multispecific antibodies are described. For example, the multispecific antibodies and multispecific antigen-binding fragments may be used to treat cancer (e.g., CD79b and/or CD20-expressing cancer); the multispecific antibodies may be used to diagnose or monitor CD79b and/or CD20-expressing cancer progression, regression, or stability; to determine whether or not a patient should be treated for cancer; or to determine whether or not a subject is afflicted with CD79b and/or CD20-expressing cancer and thus may be amenable to treatment with a CD79b and/or CD20-specific anti-cancer therapeutic, such as the CD79b×CD20×CD3 trispecific antibodies, or the CD79b×CD3 bispecific antibodies described herein.

The redirection of T-lymphocytes to tumor cells expressing CD79b and/or CD20 via the TCR/CD3 complex represents an attractive alternative approach. The TCR/CD3 complex of T-lymphocytes consists of either a TCR alpha (α)/beta (β) or TCR gamma (γ)/delta (δ) heterodimer coexpressed at the cell surface with the invariant subunits of CD3 labeled gamma (γ), delta (δ), epsilon (ε), zeta (ζ), and eta (η). In some embodiments, the multispecific antibodies or multispecific antigen-binding fragments described herein specifically bind to CD3ε.

CD79b×CD20×CD3-Trispecific Antibodies

In some embodiments, provided herein are isolated CD79b×CD20×CD3 trispecific antibody or antigen-binding fragment. In some embodiments, an isolated CD79b×CD20×CD3 trispecific antibody, or a trispecific binding fragment thereof, comprises: a) a first antigen-binding arm comprising a first heavy chain variable domain (VH1) and a first light chain variable domain (VL1); (b) a second antigen-binding arm comprising a second heavy chain variable domain (VH2) and a second light chain variable domain (VL2); and (c) a third antigen-binding arm comprising a third heavy chain variable domain (VH3) and a third light chain variable domain (VL3). In some embodiments, the first antigen binding arm binds to an epitope on CD79b; the second antigen binding arm binds to an epitope on CD3, and the third antigen binding arm binds to an epitope on CD20.

According to all aspects of the invention the CD79b×CD20×CD3 trispecific antibody or antigen-binding fragment may bind to a conformational epitope of CD79 made up of residues 30-42 (SEDRYRNPKGSAC; SEQ ID NO: 253), 50-52 (PRF), 81-86 (EMENP; SEQ ID NO: 254), and 144-148 (GFSTL; SEQ ID NO: 255). The residue numbers are those of human CD79B (P40259).

According to all aspects of the invention the CD79b×CD20×CD3 trispecific antibody or antigen-binding fragment may bind to a conformational epitope of CD3 encompassing residues 54-58 (GSEIL; SEQ ID NO: 257), 74-75 (NI), and 100-105 (PRGSKP; SEQ ID NO: 258). The residue numbers are those of human CD3E (P07766). In some embodiments, an isolated CD79b×CD20×CD3 trispecific antibody, or a trispecific binding fragment thereof, comprises: a) a first heavy chain portion (HC1); b) a light chain portion; c) a second heavy chain portion (HC2), wherein the HC1 and the LC form a first antigen-binding site that specifically binds a first antigen, the HC2 comprises a second antigen-binding site that specifically binds a second antigen, the HC1 or the HC2 further comprises a third antigen-binding site that specifically binds a third antigen, and the HC1 and HC2 each comprise a Fragment crystallizable (Fc) domain comprising a CH2-CH3 domain. In some embodiments, the first antigen-binding arm of the trispecific antibody, or a trispecific binding fragment thereof comprises a first heavy chain portion (HC1) comprising the VH1, and a light chain portion (LC) comprising the VL1. The VH1 and the VL1 form a first antigen-binding domain that binds a first antigen. The second antigen-binding arm of the trispecific antibody or trispecific binding fragment thereof comprises a second heavy chain portion (HC2) comprising the VH2 domain. The VH2 domain of the HC2 forms a second antigen-binding domain that binds a second antigen. The HC1 or the HC2 is further coupled to the third antigen-binding arm comprising the VH3 that forms a third antigen-binding domain that binds a third antigen. The HC1 and HC2 each optionally comprise a Fragment crystallizable (Fc) domain, where the Fc domain comprises a constant heavy chain region 2 (CH2) and CH3. In some embodiments, the first antigen is cluster of differentiation 79b (CD79b), and the second antigen is cluster of differentiation 3 (CD3), and the third antigen is cluster of differentiation 20 (CD20). In some embodiments, the first antigen is cluster of differentiation 79b (CD79b), and the second antigen is cluster of differentiation 20 (CD20), and the third antigen is cluster of differentiation 3 (CD3).

Some aspects of the CD79b×CD20×CD3 trispecific antibody, or a trispecific binding fragment thereof, are further described in the Detail Description and Examples sections below.

In some embodiments, the CD79b-binding arm (or "CD79b-specific arm") of the CD79b×CD20×CD3 trispecific antibody is derived from a CD79b antibody described herein (for example, from an antibody having the CDR sequences listed in Table 1a). In some embodiments, the CD79b-binding arm of the CD79b×CD20×CD3 trispecific antibody comprises any one variable heavy (VH) domain and any one variable light (VL) domain selected from Table 1b. In some embodiments, the CD79b-binding arm of the CD79b×CD20×CD3 trispecific antibody is derived from the CD79b antibody CD9B374 as described herein.

In some embodiments, the CD20-binding arm (or "CD20-specific arm") of the CD79b×CD20×CD3 trispecific antibody is derived from a CD20 antibody described herein (for example, from an antibody having the CDR sequences listed in Table 2a). In some embodiments, the CD20-binding arm of the CD79b×CD20×CD3 trispecific antibody comprises any one VH domain and any one VL domain selected from Table 2b. In some embodiments, the CD20-binding arm of the CD79b×CD20×CD3 trispecific antibody is derived from a CD20 antibody C20B648.

In some embodiments, the CD3-binding arm (or "CD3-specific arm") of the CD79b×CD20×CD3 trispecific antibody is derived from a CD3 antibody described herein (for example, from an antibody having the CDR sequences listed in Table 3). In some embodiments, the CD3-binding arm of the CD79b×CD20×CD3 trispecific antibody comprises any one VH domain and any one VL domain selected from Table 3. In some embodiments, the CD3-binding arm of the CD79b×CD20×CD3 trispecific antibody is derived from the monoclonal antibody CD3W245. In some embodiments, the CD3-binding arm of the CD79b×CD20×CD3 trispecific antibody is derived from the monoclonal antibody CD3B2030.

In some embodiments, the CD79b-, CD20- and/or CD3-specific arms of the CD79b×CD20×CD3-multispecific antibodies or antigen-binding fragments are IgG, or derivatives thereof. The IgG class is divided in four isotypes: IgG1, IgG2, IgG3 and IgG4 in humans. They share more than 95% homology in the amino acid sequences of the Fc regions but show major differences in the amino acid composition and structure of the hinge region. The Fc region mediates effector functions, such as antibody-dependent cellular cytotoxicity (ADCC) and complement-dependent cytotoxicity (CDC). In ADCC, the Fc region of an antibody binds to Fc receptors (FcTRs) on the surface of immune effector cells such as natural killers and macrophages, leading to the phagocytosis or lysis of the targeted cells. In CDC, the antibodies kill the targeted cells by triggering the complement cascade at the cell surface.

For many applications of therapeutic antibodies, Fc-mediated effector functions are not part of the mechanism of action. These Fc-mediated effector functions can be detrimental and potentially pose a safety risk by causing off-mechanism toxicity. Modifying effector functions can be achieved by engineering the Fc regions to reduce their binding to FcTRs or the complement factors. The binding of IgG to the activating (FcγRI, FcγRIIa, FcγRIIIa and FcγRIIIb) and inhibitory (FcγRIIb) FcTRs or the first component of complement (Clq) depends on residues located in the hinge region and the CH2 domain. Mutations have been introduced in IgG1, IgG2 and IgG4 to reduce or silence Fc functionalities.

In one embodiment, the antibody comprises an Fc region with one or more of the following properties: (a) reduced effector function when compared to the parent Fc; (b) reduced affinity to FcγRI, FcγRIIa, FcγRIIb, FcγRIIIb and/or FcγRIIIa, (c) reduced affinity to FcγRI (d) reduced affinity to FcγRIIa (e) reduced affinity to FcγRIIb, (f) reduced affinity to FcγRIIIb or (g) reduced affinity to FcγRIIIa.

In some embodiments, the CD3-specific antibody or antigen-binding fragment from which the CD3-specific arm of the trispecific antibody is derived is IgG, or a derivative thereof. In some embodiments, the CD3-specific antibody or antigen-binding fragment from which the CD3-specific arm of the trispecific antibody is derived is IgG1, or a derivative thereof. In some embodiments, for example, the Fc region of the CD3-specific IgG1 antibody from which the CD3-binding arm is derived comprises L234A, L235A, and D265S substitutions in its Fc region. In some embodiments, the CD3-specific antibody or antigen-binding fragment from which the CD3-specific arm of the trispecific antibody is derived is IgG4, or a derivative thereof. In some embodiments, for example, the Fc region of the CD3-specific IgG4 antibody from which the CD3-binding arm is derived comprises S228P, L234A, L235A, F405L, and R409K substitutions in its Fc region. In some embodiments, the CD3-specific antibody or antigen-binding fragment from which the CD3-specific arm of the trispecific antibody is derived binds CD3ε on primary human T cells and/or primary cynomolgus T cells. In some embodiments, the CD3-specific antibody or antigen-binding fragment from which the CD3-specific arm of the trispecific antibody is derived activates primary human CD4+ T cells and/or primary cynomolgus CD4+ T cells.

In addition to the described CD79b×CD20×CD3-multispecific antibodies, also provided are polynucleotide sequences capable of encoding the described CD79b×CD20×CD3-multispecific antibodies. In some embodiments, an isolated synthetic polynucleotide encoding the one or more CDRs of the heavy chain variable domain and/or one or more CDRs of the light chain variable domain of each antigen-binding arm of the CD79b×CD20×CD3 trispecific antibody or trispecific binding fragment is provided. In some embodiments, an isolated synthetic polynucleotide encoding one or more heavy chain variable domains (such as the HC1 and/or the HC2) and/or one or more light chain variable domains of the CD79b×CD20×CD3 trispecific antibody or trispecific binding fragment is provided. In some embodiments, an isolated synthetic polynucleotide encoding one or more polypeptide chains of the first, second, and/or third antigen-binding arms of the CD79b×CD20×CD3 trispecific antibody or trispecific binding fragment is provided. Vectors comprising the described polynucleotides are also provided, as are cells expressing the CD79b×CD20×CD3-multispecific antibodies provided herein. In another embodiment, an isolated cell expressing the trispecific antibody or trispecific binding fragment is provided. Also described are cells capable of expressing the disclosed vectors. These cells may be mammalian cells (such as 293 cells, 293F cells, CHO cells), insect cells (such as Sf7 cells), yeast cells, plant cells, or bacteria cells (such as *E. coli*). The described antibodies may also be produced by hybridoma cells. In some embodiments, methods for generating the CD79b×CD20×CD3 trispecific antibody or trispecific binding fragment by culturing cells is provided.

Further provided herein are pharmaceutical compositions comprising the CD79b×CD20×CD3 trispecific antibodies or antigen-binding fragments and a pharmaceutically acceptable carrier.

Methods of Using CD79B×CD20×CD3-Trispecific Antibodies

Methods of using the described CD79b×CD20×CD3-trispecific antibodies and trispecific antigen-binding fragments thereof are also disclosed. For example, the CD79b×CD20×CD3-multispecific antibodies and trispecific antigen-binding fragments thereof may be useful in the treatment of a CD79b and/or CD20-expressing cancer in a subject in need thereof. In some embodiments, the CD79b and/or CD20-expressing cancer is a lymphoma, such as diffuse large B-cell lymphoma (DLBCL), mantle cell lymphoma (MCL), marginal zone lymphoma (MZL), follicular lymphoma (FL), chronic lymphocytic leukemia (CLL), or Waldenström macroglobulinemia (WM). In some embodiments, the CD79b and/or CD20-expressing cancer is a relapsed or refractory form of lymphoma, such as a relapsed or refractory form of diffuse large B-cell lymphoma (DLBCL), mantle cell lymphoma (MCL), marginal zone lymphoma (MZL), follicular lymphoma (FL), chronic lymphocytic leukemia (CLL), or Waldenström macroglobulinemia (WM).

The described methods of treating CD79b and/or CD20-expressing cancer in a subject in need thereof include administering to the subject a therapeutically effective amount of a described CD79b×CD20×CD3-trispecific antibody or trispecific antigen-binding fragment thereof. In some embodiments, the subject is a mammal, preferably a human. In preferred embodiments are provided methods for treating a subject having cancer by administering a therapeutically effective amount of the CD79b×CD20×CD3 trispecific antibody or trispecific antigen-binding fragment to a patient in need thereof for a time sufficient to treat the cancer.

Further provided herein are methods for inhibiting growth or proliferation of cancer cells by administering a therapeutically effective amount of the CD79b×CD20×CD3 trispecific antibody or trispecific binding fragment to inhibit the growth or proliferation of cancer cells.

Also provided herein are methods of redirecting a T cell to a CD79b and/or CD20-expressing cancer cell by administering a therapeutically effective amount of the CD79b×CD20×CD3 trispecific antibody or trispecific binding fragment to redirect a T cell to a cancer.

The skilled person will understand that the methods of using the described CD79b×CD20×CD3-multispecific antibodies and multispecific antigen-binding fragments thereof may be specified in medical use format, for example in the form of CD79b×CD20×CD3-multispecific antibodies and multispecific antigen-binding fragments for use in the treatment of disease as defined herein, in particular cancer. This skilled person will also understand that the methods of using the described CD79b×CD20×CD3-multispecific antibodies and multispecific antigen-binding fragments thereof may be specified in so-called Swiss form, for example in the form of the use of CD79b×CD20×CD3-multispecific antibodies and multispecific antigen-binding fragments for the manufacture of a medicament for the treatment of disease as defined herein, in particular cancer. This applies throughout the disclosure.

CD79b×CD20×CD3-Specific Antibody Kits

Described herein are kits including the disclosed CD79b× CD20×CD3-multispecific antibodies. The described kits may be used to carry out the methods of using the CD79b× CD20×CD3-multispecific antibodies provided herein, or other methods known to those skilled in the art. In some embodiments the described kits may include the antibodies described herein and reagents for use in treating a CD20 and/or CD79b-expressing cancer. Accordingly, the described kits may include one or more of the trispecific antibodies, or a trispecific antigen-binding fragment(s) thereof, described herein and a vessel for containing the antibody or fragment when not in use, and/or instructions for use of the antibody or fragment, the antibody or fragment affixed to a solid support, and/or detectably labeled forms of the antibody or fragment, as described herein.

CD79b×CD3-Bispecific Antibodies

In some embodiments, provided herein are isolated CD79b×CD3 bispecific antibodies or antigen-binding fragments.

In some embodiments, an isolated CD79b×CD3 bispecific antibody, or a bispecific binding fragment thereof, comprises: a) a first antigen binding arm comprising a first heavy chain variable domain (VH1) and a first light chain variable domain (VL1); (b) a second antigen binding arm comprising a second heavy chain variable domain (VH2) and a second light chain variable domain (VL2), wherein the first antigen-binding arm binds to an epitope CD79b and the second antigen-binding arm binds to an epitope on CD3.

According to all aspects of the invention the CD79b×CD3 bispecific antibody, or a bispecific binding fragment thereof may bind to a conformational epitope of CD79 made up of residues 30-42 (SEDRYRNPKGSAC; SEQ ID NO: 253), 50-52 (PRF), 81-86 (EMENP; SEQ ID NO: 254), and 144-148 (GFSTL; SEQ ID NO: 255). The residue numbers are those of human CD79B (P40259).

According to all aspects of the invention the CD79b× CD20×CD3 bispecific antibody, or a bispecific binding fragment thereof may bind to a conformational epitope of CD3 encompassing residues 54-58 (GSEIL; SEQ ID NO: 257), 74-75 (NI), and 100-105 (PRGSKP; SEQ ID NO: 258). The residue numbers are those of human CD3E (P07766).

In some embodiments, an isolated CD79b×CD3 bispecific antibody, or a bispecific binding fragment thereof, comprises: a) a first heavy chain portion (HC1); b) a light chain portion; c) a second heavy chain portion (HC2), wherein the HC1 and the LC form a first antigen-binding site that specifically binds a first antigen, the HC2 comprises a second antigen-binding site that specifically binds a second antigen, and the HC1 and HC2 each comprise a Fragment crystallizable (Fc) domain comprising a CH2-CH3 domain. In some embodiments, the first antigen-binding arm of the CD79b×CD3 bispecific antibody, or a bispecific binding fragment thereof, comprises a first heavy chain portion (HC1) comprising the VH1, and a light chain portion (LC) comprising the VL1. The VH1 of the HC1 and the VL1 of the LC form a first antigen-binding domain that binds a first antigen. The second antigen-binding arm of the bispecific antibody or bispecific binding fragment thereof comprises a second heavy chain portion (HC2) comprising the VH2. The VH2 of the HC2 forms a second antigen-binding domain that binds a second antigen, and the HC1 and HC2 each optionally comprise a Fragment crystallizable (Fc) domain comprising a CH2-CH3 domain. In some embodiments, the first antigen is cluster of differentiation 79b (CD79b), and the second antigen is cluster of differentiation 3 (CD3). In some embodiments, the first antigen is cluster of differentiation 79b (CD79b), and the second antigen is cluster of differentiation 3 (CD3). Some aspects of the CD79b×CD3 bispecific antibody, or a bispecific binding fragment thereof, are further described in the Detail Description and Examples sections below.

In some embodiments, the CD79b-binding arm (or "CD79b-specific arm") of the CD79b×CD3 bispecific antibody is derived from a CD79b antibody described herein (for example, from an antibody having the CDR sequences listed in Table 1a). In some embodiments, the CD79b-binding arm of the CD79b×CD3 bispecific antibody comprises any one VH domain and any one VL domain selected from Table 1b.

In some embodiments, the CD3-binding arm (or "CD3-specific arm") of the CD79b×CD3 bispecific antibody is derived from a CD3 antibody described herein (for example, from an antibody having the CDR sequences listed in Table 3). In some embodiments, the CD3-binding arm of the CD79b×CD3 bispecific antibody comprises any one VH domain and any one VL domain selected from Table 3.

In some embodiments, the CD79b- or CD3-specific arm of the CD79b×CD3 bispecific antibodies or antigen-binding fragments are IgG, or derivatives thereof.

In one embodiment, the antibody comprises an Fc region with one or more of the following properties: (a) reduced effector function when compared to the parent Fc; (b) reduced affinity to FcγRI, FcγRIIa, FcγRIIb, FcγRIIIb and/or FcγRIIIa, (c) reduced affinity to FcγRI (d) reduced affinity to FcγRIIa (e) reduced affinity to FcγRIIb, (f) reduced affinity to FcγRIIIb or (g) reduced affinity to FcγRIIIa.

In some embodiments, the CD3-specific antibody or antigen-binding fragment from which the CD3-specific arm of the bispecific antibody is derived is IgG, or a derivative thereof. In some embodiments, the CD3-specific antibody or antigen-binding fragment from which the CD3-specific arm of the bispecific antibody is derived is IgG1, or a derivative thereof. In some embodiments, for example, the Fc region of the CD3-specific IgG1 antibody from which the CD3-binding arm is derived comprises L234A, L235A, and D265S substitutions in its Fc region. In some embodiments, the CD3-specific antibody or antigen-binding fragment from which the CD3-specific arm of the bispecific antibody is derived is IgG4, or a derivative thereof. In some embodiments, for example, the Fc region of the CD3-specific IgG4 antibody from which the CD3-binding arm is derived comprises S228P, L234A, L235A, F405L, and R409K substitutions in its Fc region. In some embodiments, the CD3-specific antibody or antigen-binding fragment from which the CD3-specific arm of the bispecific antibody is derived binds CD3ε on primary human T cells and/or primary cynomolgus T cells. In some embodiments, the CD3-specific antibody or antigen-binding fragment from which the CD3-specific arm of the bispecific antibody is derived activates primary human CD4+ T cells and/or primary cynomolgus CD4+ T cells.

In addition to the described CD79b×CD3 bispecific antibodies, also provided are polynucleotide sequences capable of encoding the described CD79b×CD3 bispecific antibodies. In some embodiments, an isolated synthetic polynucleotide encoding the one or more CDRs of the heavy chain variable domain and/or one or more CDRs of the light chain variable domain of each antigen-binding arm of the CD79b×CD3 bispecific antibody or bispecific binding fragment is provided. In some embodiments, an isolated synthetic polynucleotide encoding one or more heavy chain variable domains (such as the HC1 and/or the HC2) and/or one or more light chain variable domains of the CD79b×CD3 bispecific antibody or bispecific binding fragment is provided. In some embodiments, an isolated synthetic polynucleotide encoding one or more polypeptide chains of the first and/or second antigen-binding arms of the CD79b×CD3 bispecific antibody or bispecific binding fragment is provided. Vectors comprising the described polynucleotides are also provided, as are cells expressing the CD79b×CD3 bispecific antibodies provided herein. In another embodiment, an isolated cell expressing the bispecific antibody or bispecific binding fragment is provided. Also described are cells capable of expressing the disclosed vectors. These cells may be mammalian cells (such as 293 cells, 293F cells, CHO cells), insect cells (such as Sf7 cells), yeast cells, plant cells, or bacteria cells (such as *E. coli*). The described antibodies may also be produced by hybridoma cells. In some embodiments, methods for generating the CD79b×CD3 bispecific antibody or bispecific binding fragment by culturing cells is provided.

Further provided herein are pharmaceutical compositions comprising the CD79b×CD3 bispecific antibodies or antigen-binding fragments and a pharmaceutically acceptable carrier.

Methods of Using CD79b×CD3 Bispecific Antibodies

Methods of using the described CD79b×CD3 bispecific antibodies and bispecific antigen-binding fragments thereof are also disclosed. For example, the CD79b×CD3 bispecific antibodies and bispecific antigen-binding fragments thereof may be useful in the treatment of a CD79b-expressing cancer in a subject in need thereof. In some embodiments, the CD79b-expressing cancer is a lymphoma, such as diffuse large B-cell lymphoma (DLBCL), mantle cell lymphoma (MCL), marginal zone lymphoma (MZL), follicular lymphoma (FL), chronic lymphocytic leukemia (CLL), or Waldenström macroglobulinemia (WM). In some embodiments, the CD79b-expressing cancer is a relapsed or refractory form of the lymphoma.

The described methods of treating CD79b-expressing cancer in a subject in need thereof include administering to the subject a therapeutically effective amount of a described CD79b×CD3 bispecific antibody or bispecific antigen-binding fragment thereof. In some embodiments, the subject is a mammal, preferably a human. In preferred embodiments are provided methods for treating a subject having cancer by administering a therapeutically effective amount of the CD79b×CD3 bispecific antibody or bispecific antigen-binding fragment to a patient in need thereof for a time sufficient to treat the cancer.

Further provided herein are methods for inhibiting growth or proliferation of cancer cells by administering a therapeutically effective amount of the CD79b×CD3 bispecific antibody or bispecific binding fragment to inhibit the growth or proliferation of cancer cells.

Also provided herein are methods of redirecting a T cell to a CD79b-expressing cancer cell by administering a therapeutically effective amount of the CD79b×CD3 bispecific antibody or bispecific binding fragment to redirect a T cell to a cancer.

CD79b×CD3-Bispecific Antibody Kits

Described herein are kits including the disclosed CD79b×CD3 bispecific antibodies. The described kits may be used to carry out the methods of using the CD79b×CD3 bispecific antibodies provided herein, or other methods known to those skilled in the art. In some embodiments the described kits may include the antibodies described herein and reagents for use in treating a CD79b-expressing cancer. Accordingly, the described kits may include one or more of the bispecific antibodies, or a bispecific antigen-binding fragment(s) thereof, described herein and a vessel for containing the antibody or fragment when not in use, and/or instructions for use of the antibody or fragment, the antibody or fragment affixed to a solid support, and/or detectably labeled forms of the antibody or fragment, as described herein.

CD79b-Specific Antibodies

Also provided herein are antibodies that bind to CD79b and antigen-binding fragments thereof. Also described are related polynucleotides capable of encoding the provided CD79b-specific antibodies and antigen-binding fragments, cells expressing the provided antibodies and antigen-binding fragments, as well as associated vectors and detectably labeled antibodies and antigen-binding fragments. In addition, methods of using the provided antibodies and antigen-binding fragments are described. For example, the CD79b-specific antibodies and antigen-binding fragments may be used to treat cancer (e.g., CD79b-expressing cancer); the CD79b-specific antibodies and antigen-binding fragments may be used to diagnose or monitor CD79b-expressing cancer progression, regression, or stability; to determine whether or not a patient should be treated for cancer; or to determine whether or not a subject is afflicted with CD79b-expressing cancer and thus may be amenable to treatment with a CD79b-specific anti-cancer therapeutic, such as the multispecific antibodies against CD79b and CD3 described herein. Some aspects of the CD79b-specific antibody, or an antigen-binding fragment, are further described in the Detail Description and Examples sections below.

According to all aspects of the invention the CD79b specific antibody or antigen-binding fragment may bind to a conformational epitope of CD79 made up of residues 30-42 (SEDRYRNPKGSAC; SEQ ID NO: 253), 50-52 (PRF), 81-86 (EMENP; SEQ ID NO: 254), and 144-148 (GFSTL; SEQ ID NO: 255). The residue numbers are those of human CD79B (P40259).

Methods of Using CD79b-Specific Antibodies

Methods of using the described CD79b-specific antibodies or antigen-binding fragments are also disclosed. Particular antibodies for use in the methods discussed in this section include those with the set of CDRs described for antibodies in Table 1a. For example, these antibodies or antigen-binding fragments may be useful in treating cancer, by interfering with CD79b-receptor interactions or where the antibody is conjugated to a toxin, so targeting the toxin to the CD79b-expressing cancer. Further, these antibodies or antigen-binding fragments may be useful for detecting the presence of CD79b in a biological sample, such as blood or serum; for quantifying the amount of CD79b in a biological sample, such as blood or serum; for diagnosing CD79b-expressing cancer; determining a method of treating a subject afflicted with cancer; or monitoring the progression of CD79b-expressing cancer in a subject. In some embodiments, CD79b-expressing cancer may be a lymphoma, such as diffuse large B-cell lymphoma (DLBCL), mantle cell lymphoma (MCL), marginal zone lymphoma (MZL), follicular lymphoma (FL), chronic lymphocytic leukemia (CLL), or Waldenström macroglobulinemia (WM). In some embodiments, the CD79b-expressing cancer is a relapsed or refractory form of the lymphoma.

The described methods may be carried out before the subject receives treatment for CD79b-expressing cancer, such as treatment with a multispecific antibody against CD79b and CD3. Furthermore, the described methods may be carried out after the subject receives treatment for CD79b-expressing cancer, such as treatment with a multispecific antibody against CD79b and CD3 described herein.

The described methods of detecting CD79b in a biological sample include exposing the biological sample to one or more of the CD79b-specific antibodies or antigen-binding fragments described herein.

The described methods of diagnosing CD79b-expressing cancer in a subject also involve exposing the biological sample to one or more of the CD79b-specific antibodies or antigen-binding fragments described herein; however, the methods also include quantifying the amount of CD79b present in the sample; comparing the amount of CD79b present in the sample to a known standard or reference sample; and determining whether the subject's CD79b levels fall within the levels of CD79b associated with cancer.

Also described herein are methods of monitoring CD79b-expressing cancer in a subject. The described methods include exposing the biological sample to one or more of the CD79b-specific antibodies or antigen-binding fragments described herein; quantifying the amount of CD79b present in the sample that is bound by the antibody, or antigen-binding fragment thereof; comparing the amount of CD79b present in the sample to either a known standard or reference sample or the amount of CD79b in a similar sample previously obtained from the subject; and determining whether the subject's CD79b levels are indicative of cancer progression, regression or stable disease based on the difference in the amount of CD79b in the compared samples.

The samples obtained, or derived from, subjects are biological samples such as urine, blood, serum, plasma, saliva, ascites, circulating cells, circulating tumor cells, cells that are not tissue associated, tissues, surgically resected tumor tissue, biopsies, fine needle aspiration samples, or histological preparations.

The described CD79b-specific antibodies or antigen-binding fragments may be labeled for use with the described methods, or other methods known to those skilled in the art. For example, the antibodies described herein, or antigen-binding fragments thereof, may be labeled with a radiolabel, a fluorescent label, an epitope tag, biotin, a chromophore label, an ECL label, an enzyme, ruthenium, $^{111}$In-DOTA, $^{111}$In-diethylenetriaminepentaacetic acid (DTPA), horseradish peroxidase, alkaline phosphatase and beta-galactosidase, or poly-histidine or similar such labels known in the art.

CD79b-Specific Antibody Kits

Described herein are kits including the disclosed CD79b-specific antibodies or antigen-binding fragments thereof. The described kits may be used to carry out the methods of using the CD79b-specific antibodies or antigen-binding fragments provided herein, or other methods known to those skilled in the art. In some embodiments the described kits may include the antibodies or antigen-binding fragments described herein and reagents for use in detecting the presence of CD79b in a biological sample.

Accordingly, the described kits may include one or more of the antibodies, or an antigen-binding fragment(s) thereof, described herein and a vessel for containing the antibody or fragment when not in use, instructions for use of the antibody or fragment, the antibody or fragment affixed to a solid support, and/or detectably labeled forms of the antibody or fragment, as described herein.

BRIEF DESCRIPTION OF THE DRAWINGS

FIG. 1 discloses SEQ ID NO: 221.

FIGS. 8A-8C. CD79b×CD20×CD3 trispecific construct mediated B cell cytotoxicity and T cell activation. Cytotoxicity in B cells (FIG. 8A); CD4$^+$ T-cells (FIG. 8B) and CD8$^+$ T-cells are shown for the lead antibodies.

(FIG. 9A) B cell receptor (BCR) and CD79b structure (Burger et al 2018 (19)). (FIG. 9B) CD79b long and short isoform schematic representation. aa, amino acid. (FIG. 9C) CD20 structure (modified from Klein et al 2013 (20)). FIG. 9C discloses SEQ ID NOS 264 and 265, respectively, in order of appearance.

FIG. 11C shows CD20 and CD79b IHC expression in cell lines vs B-NHL samples. Scale 3, 2, 1, 0 represent high, medium, low, no detectable expression, respectively.

(FIG. 12A) CARNAVAL cell binding of C923B169. (FIG. 12B) OCI-Ly10 cell binding of C923B169. MFI, mean fluorescence intensity.

(FIG. 13A) CAR-NAVAL kinetic binding of C923B169. (FIG. 13B) OCI Ly10 kinetic binding of C923B169. MFI, mean fluorescence intensity.

(FIG. 14A) T cell binding: D327645. (FIG. 14B) T cell binding: D198013. (FIG. 14C) T cell binding: D221837.

FIGS. 16A-16H. C923B169-induced T cell-mediated cytotoxicity of different cancer cell lines. The percentage of cell line cytotoxicity was determined by FACS quantitation (Y-axis). CFSE-labeled cell lines were combined with CD3$^+$ pan T cells at a 5:1 effector-to-target ratio for either 48 or 72 hours with increasing concentrations (X-axis) of C923B169 or Null×Null×CD3. Values are averages of 5 to 6 individual T-cell donors. All cell lines are CD79b$^+$/CD20$^+$ except SU-DHL1 which is CD79b$^-$/CD20$^-$. Graphing of data was done in GraphPad Prism 9. Data from independent experiments were pooled and represented as mean±SEM. CFSE, carboxyfluorescein succinimidyl ester; FACS, fluorescence activated cell sorting; SEM, standard error of the mean. FIGS. 16G-16H demonstrate that C923B169 exhibits no cytotoxicity in CD79b$^-$/CD20$^-$ cells.

FIGS. 17A-17F. C923B169-induced T-cell activation in the presence of different cancer cell lines. The percentage of CD8 T-cell activation was determined by FACS quantitation (Y-axis) of CD25$^+$ cells. CFSE-labeled cell lines were combined with CD3$^+$ pan T cells at a 5:1 effector-to-target ratio for either 48 or 72 hours with increasing concentrations (X-axis) of C923B169 or Null×Null×CD3. Values are averages of 5 to 6 individual T-cell donors. All cell lines are CD79b$^+$/CD20$^+$ except SU-DHL1, which is CD79b$^-$/CD20$^-$. As SU-DHL1 secretes IL-2 and thus induces CD25 on T cells in the coculture system, for assessing % of CD25 on CD8 T cells, the gate was set relative to untreated wells with SU-DHL1 and T cells. Graphing of data was done in GraphPad Prism 9. Data from independent experiments were pooled and represented as mean±SEM. CFSE, carboxyfluorescein succinimidyl ester; FACS, fluorescence activated cell sorting; IL, interleukin; SEM, standard error of the mean.

(FIG. 20A) Activated CD4+ T cells by C923B169. (FIG. 20B) Activated CD8+ T cells by C923B169. (FIG. 20C) Secreted IFN γ levels by C923B169. (FIG. 20D) Secreted IL 10 levels by C923B169.

FIGS. 27A-27D. Binding kinetic profiles of C923B169, C923B168, and mosunetuzumab after 48-hour 37° C. incubation with CARNAVAL and OCI-Ly10 cell lines. MFI, mean fluorescence intensity.

FIGS. 30A-30D. Autologous B-cell depletion assay showing T-cell activation profiles of C923B169, C923B168, and mosunetuzumab.

DETAILED DESCRIPTION OF ILLUSTRATIVE EMBODIMENTS

Figure 1:
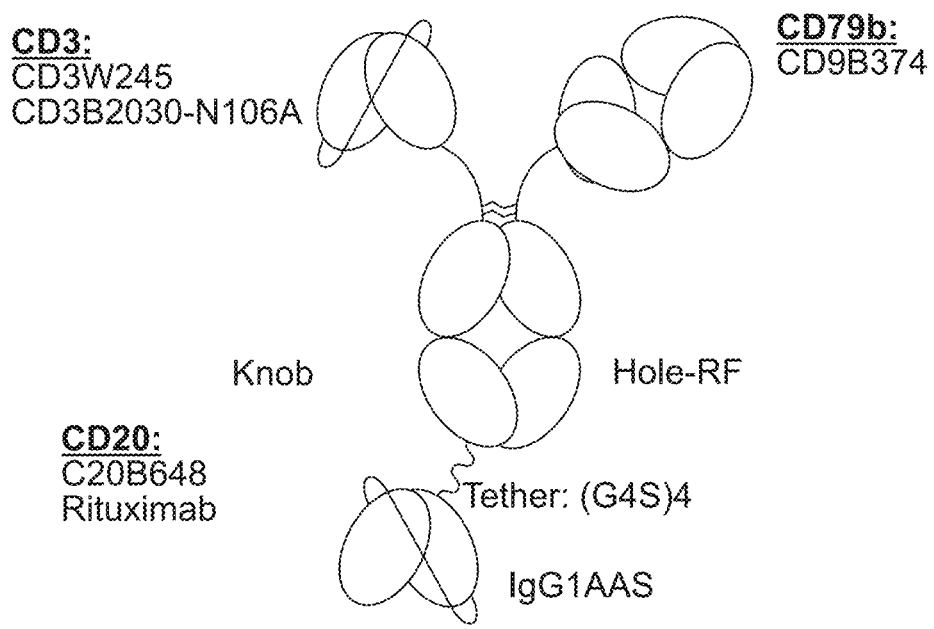
FIG. 1. Depiction of an exemplary CD79b×CD20×CD3 trispecific antibody.
Figure 2A:
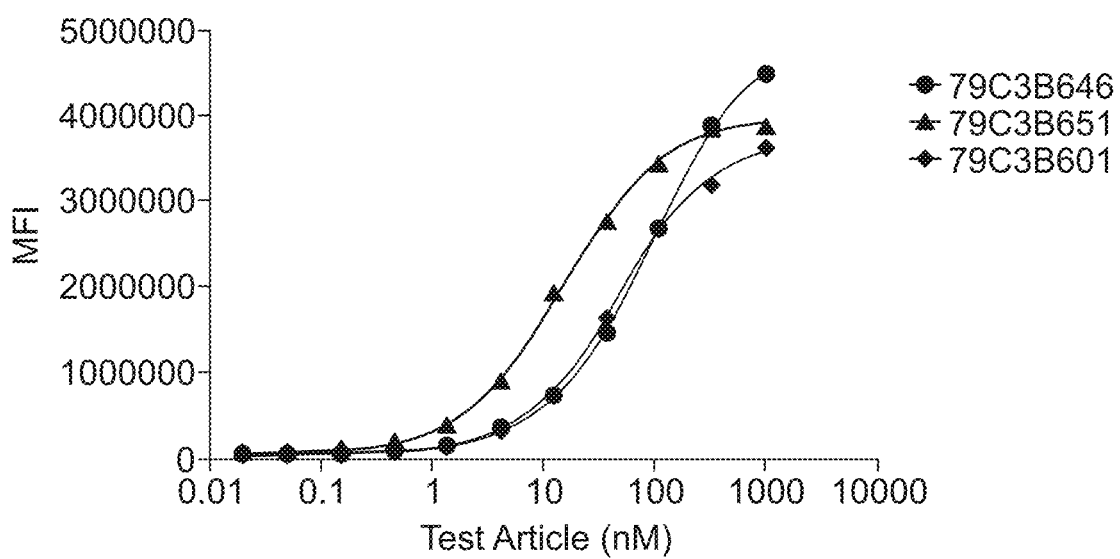
FIGS. 2A-2D. Binding affinities of selected CD79b×CD3 bsAbs in the HBL-1 cell line (FIG. 2A); the OCI-LY10 cell line (FIG. 2B); the Carnaval cell line (FIG. 2C); and the WILL-2 cell line (FIG. 2D). Circles correspond to the 79C3B646 bsAb; triangles correspond to the 79C3B651 bsAb; and diamonds correspond to the 79C3B601 bsAb.
Figure 2B:
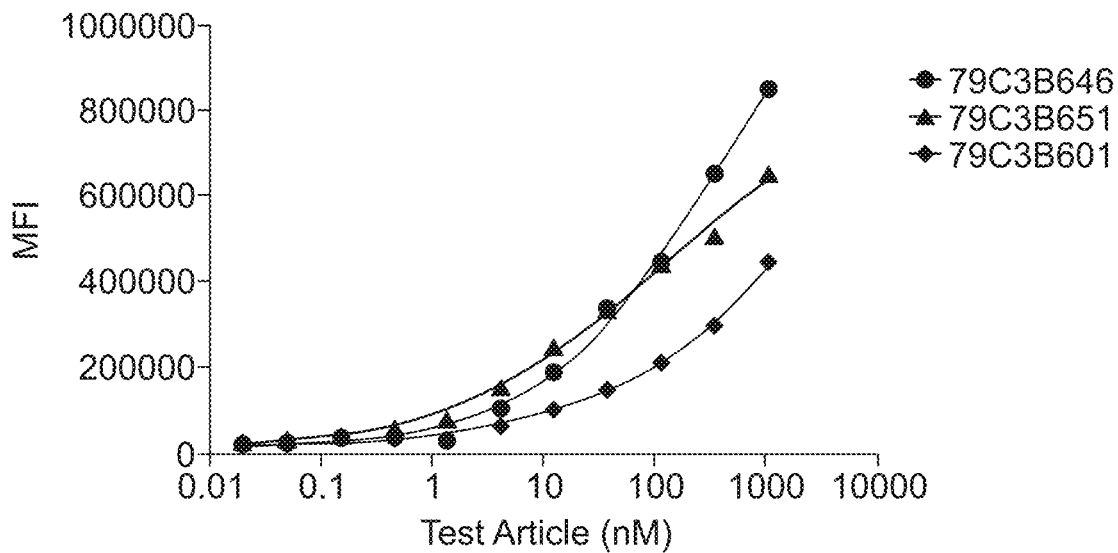
Figure 2C:
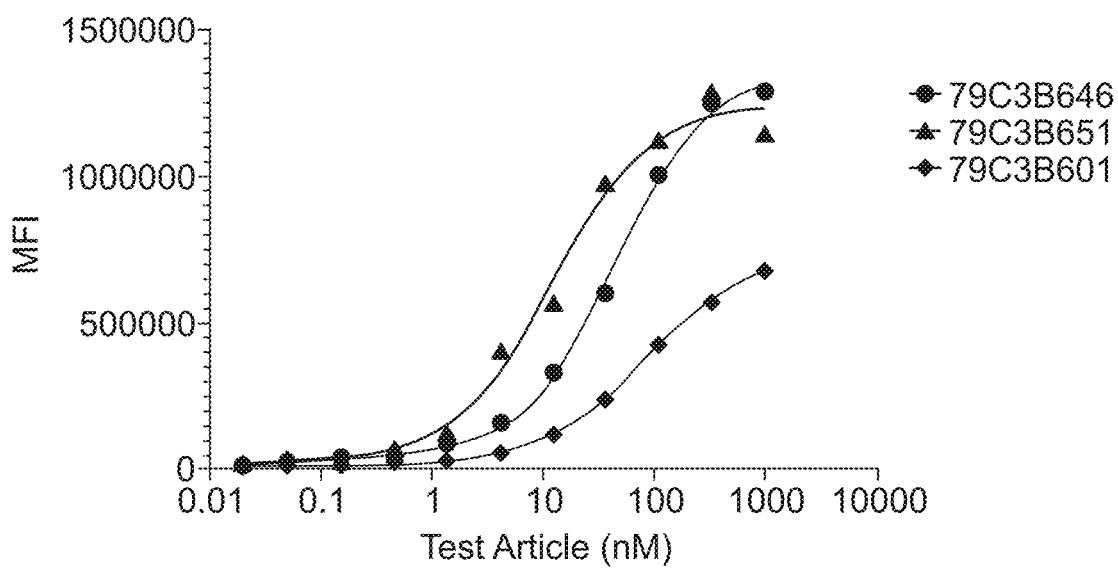
Figure 2D:
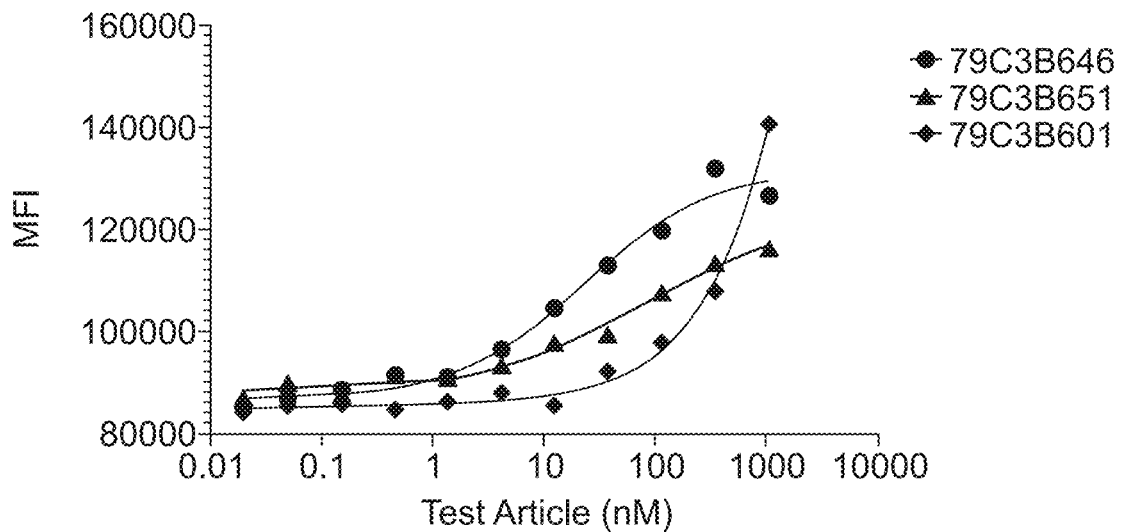
Figure 3A:
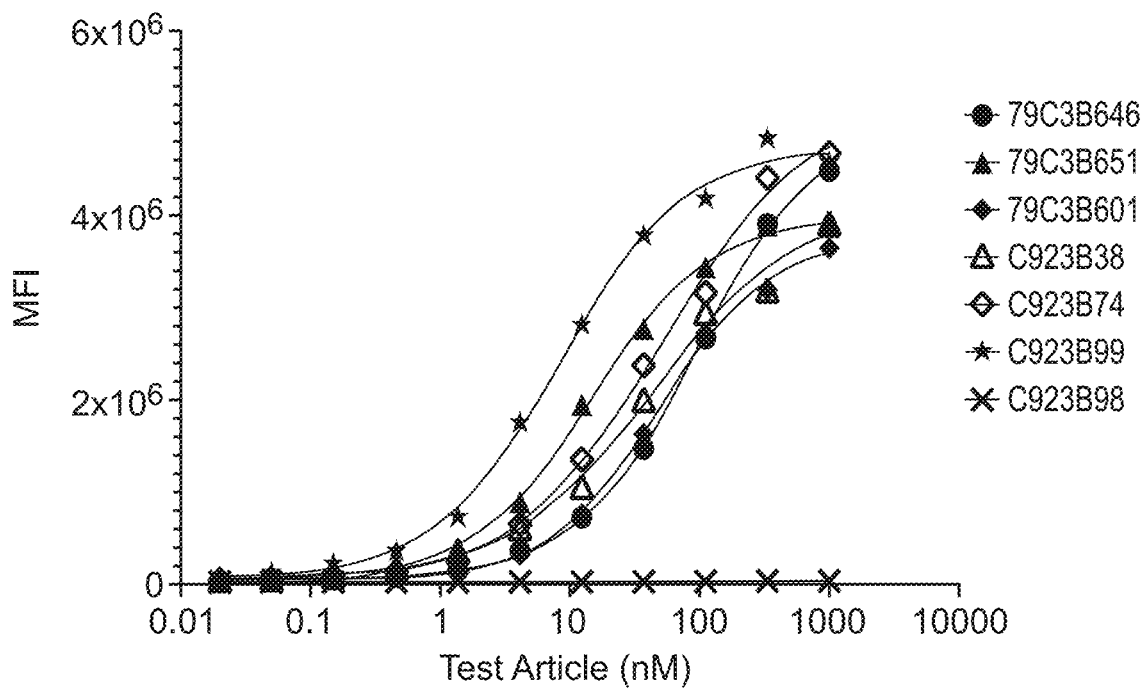
FIGS. 3A-3D. Binding affinities of selected CD79b× CD20×CD3 trispecific antibodies in the HBL-1 cell line (FIG. 3A); the OCI-LY10 cell line (FIG. 3B); the Carnaval cell line (FIG. 3C); and the WILL-2 cell line (FIG. 3D). Solid circles correspond to the 79C3B646 bsAb control; solid triangles correspond to the 79C3B651 bsAb control; and solid diamonds correspond to the 79C3B601 bsAb control. Open triangles correspond to trispecific antibody C923B38; open diamonds correspond to trispecific antibody C923B74; asterisks correspond to trispecific antibody C923B9; and X corresponds to control null trispecific antibody C923B98.
Figure 3B:
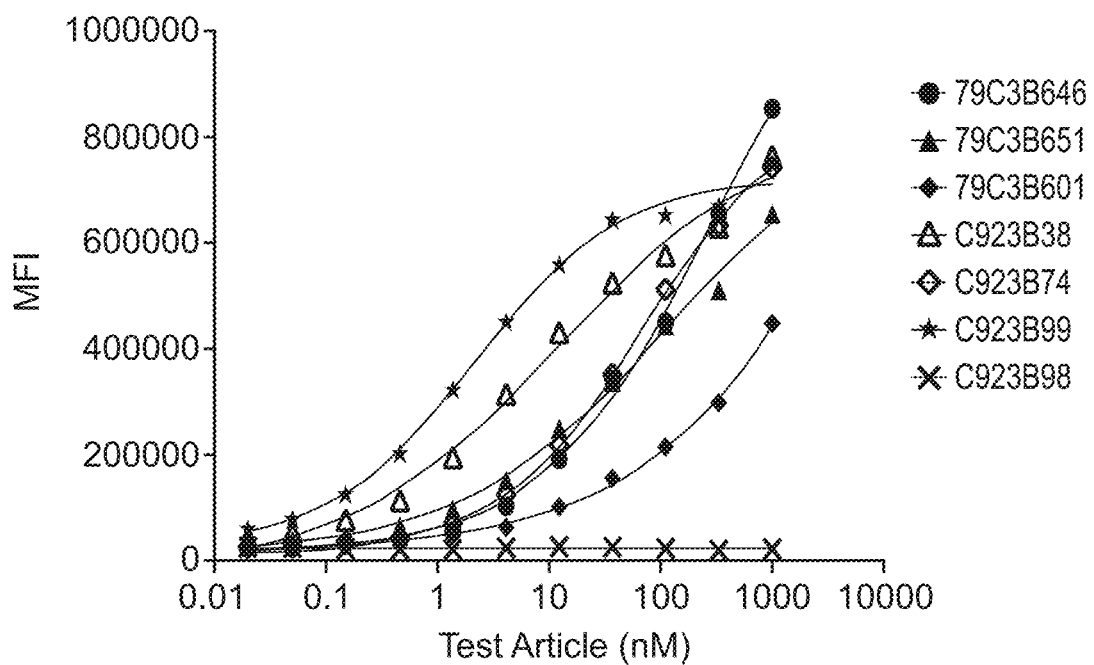
Figure 3C:
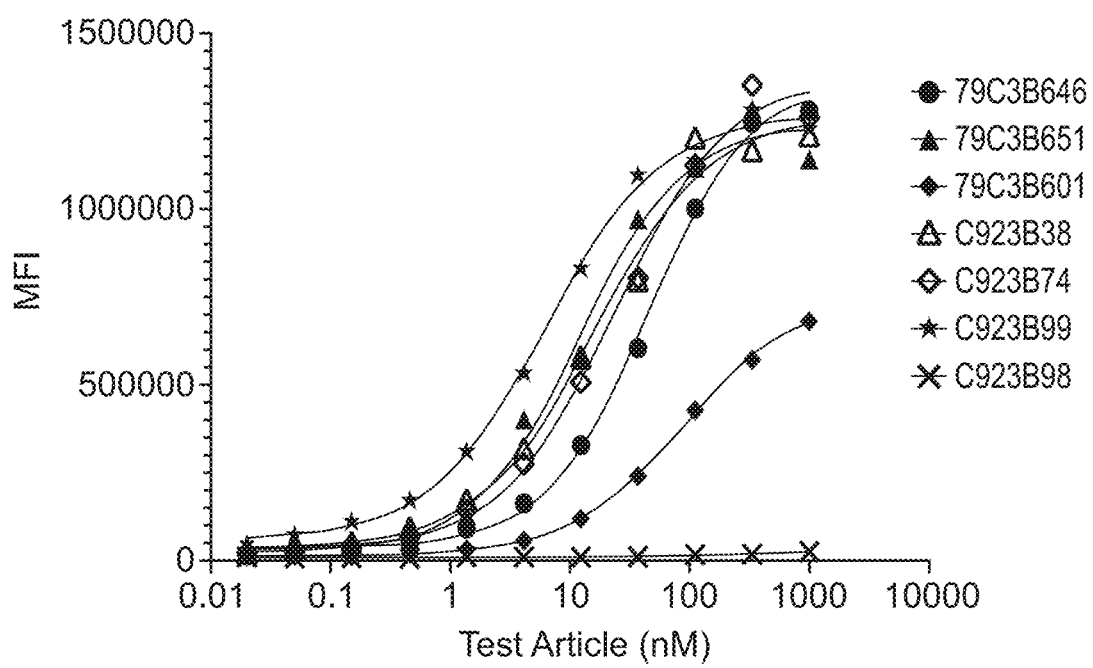
Figure 3D:
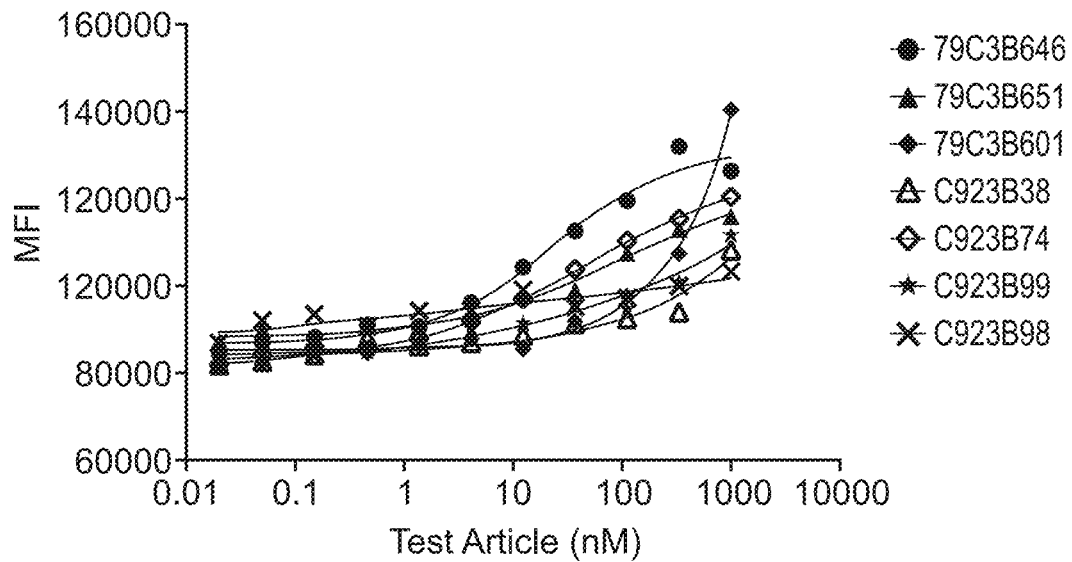
Figure 4A:
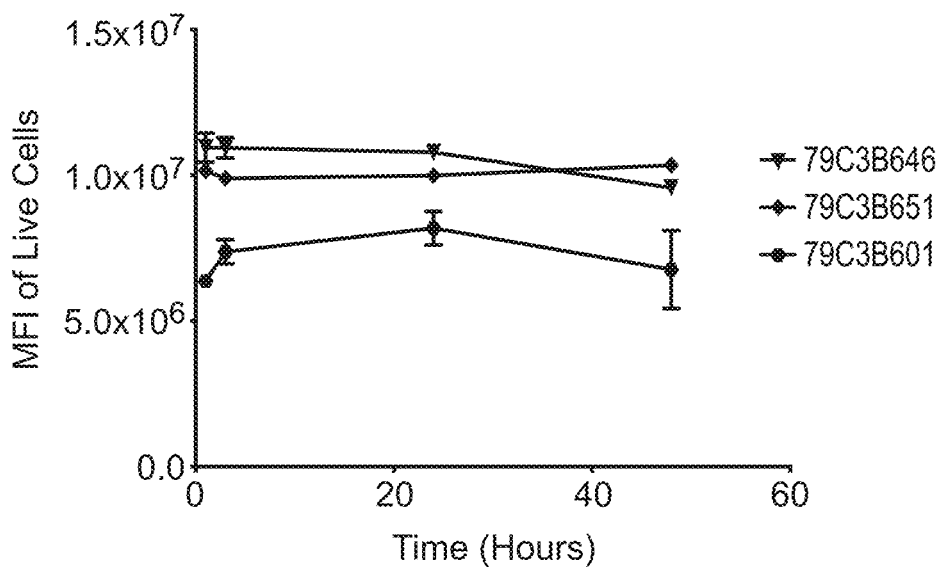
FIGS. 4A-4I. Binding kinetics of selected CD79b×CD3 bsAbs on DLBCL cell lines. Binding kinetics of the three selected bsAbs in HBL-1 cells at 300 nm (FIG. 4A). Binding kinetics of the three selected bsAbs in HBL-1 cells at 60 nm (FIG. 4B). Binding kinetics of the three selected bsAbs in HBL-1 cells at 12 nm (FIG. 4C). Binding kinetics of the three selected bsAbs in Carnaval cells at 300 nm (FIG. 4D). Binding kinetics of the three selected bsAbs in Carnaval cells at 60 nm (FIG. 4E). Binding kinetics of the three selected bsAbs in Carnaval cells at 12 nm (FIG. 4F). Binding kinetics of the three selected bsAbs in OCI-LY10 cells at 300 nm (FIG. 4G). Binding kinetics of the three selected bsAbs in OCI-LY10 cells at 60 nm (FIG. 4H). Binding kinetics of the three selected bsAbs in OCI-LY10 cells at 12 nm (FIG. 4I). Inverted triangles correspond to the 79C3B646 bsAb; diamonds correspond to the 79C3B651 bsAb; and squares correspond to the 79C3B601 bsAb.
Figure 4B:
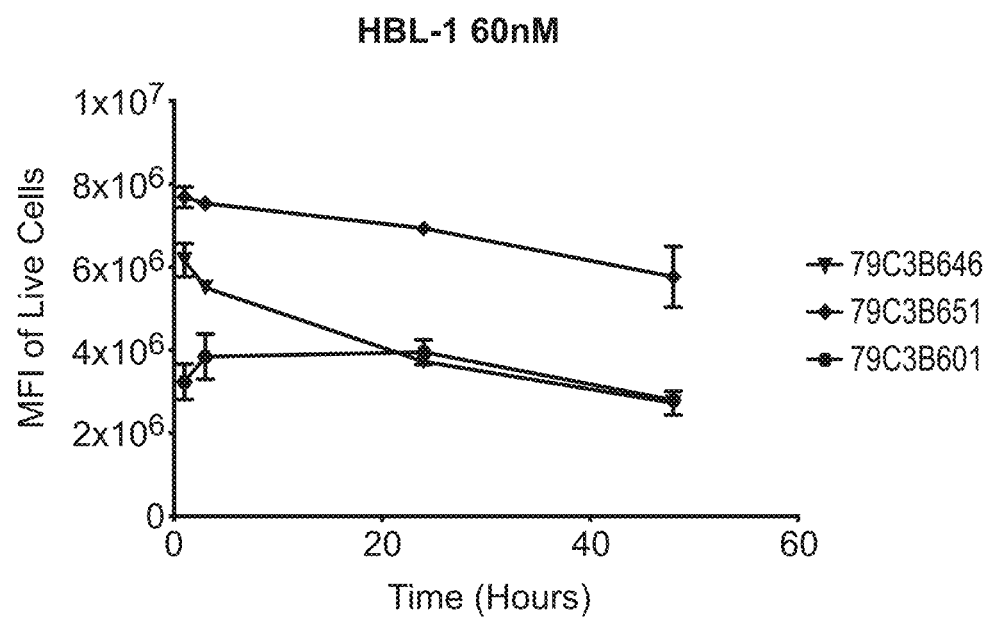
Figure 4C:
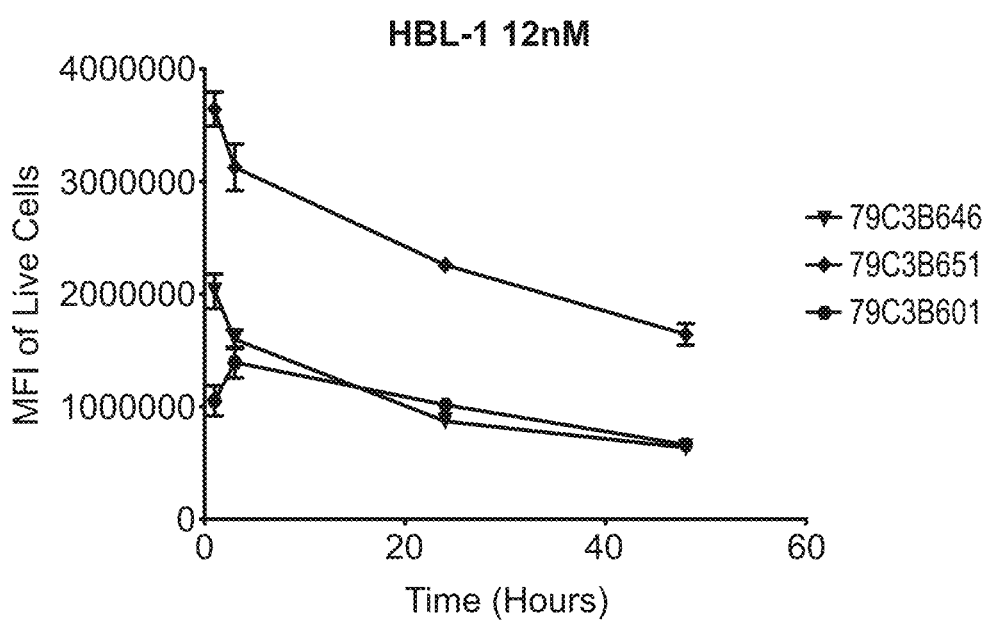
Figure 4D:
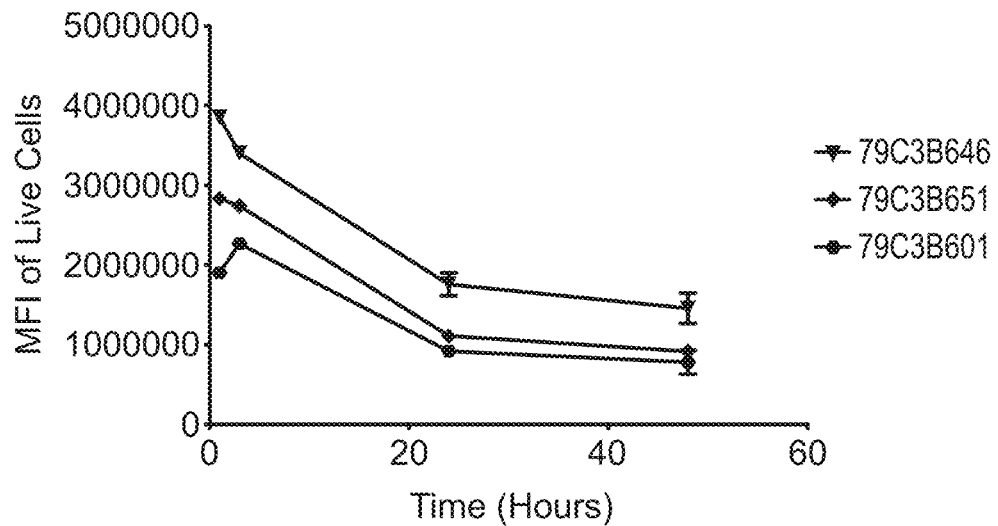
Figure 4E:
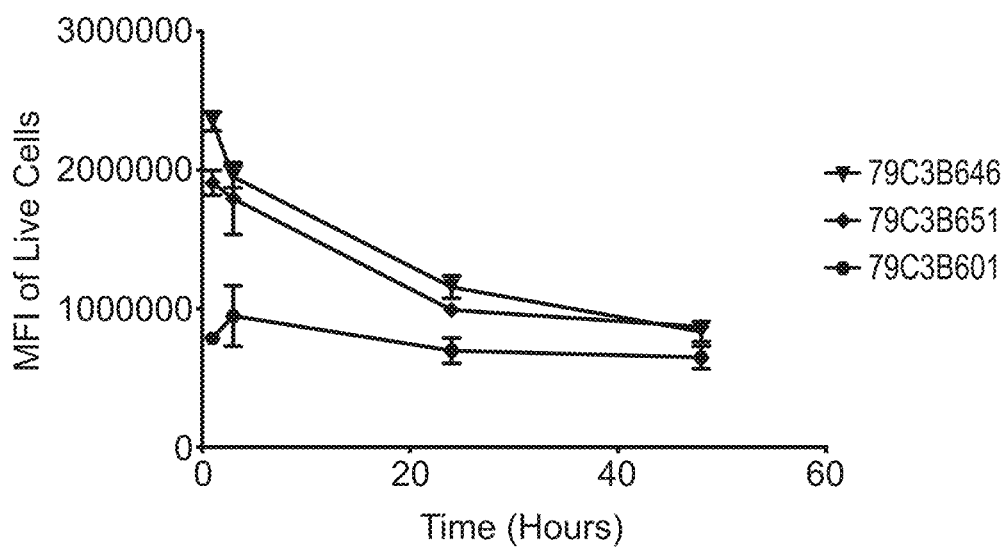
Figure 4F:
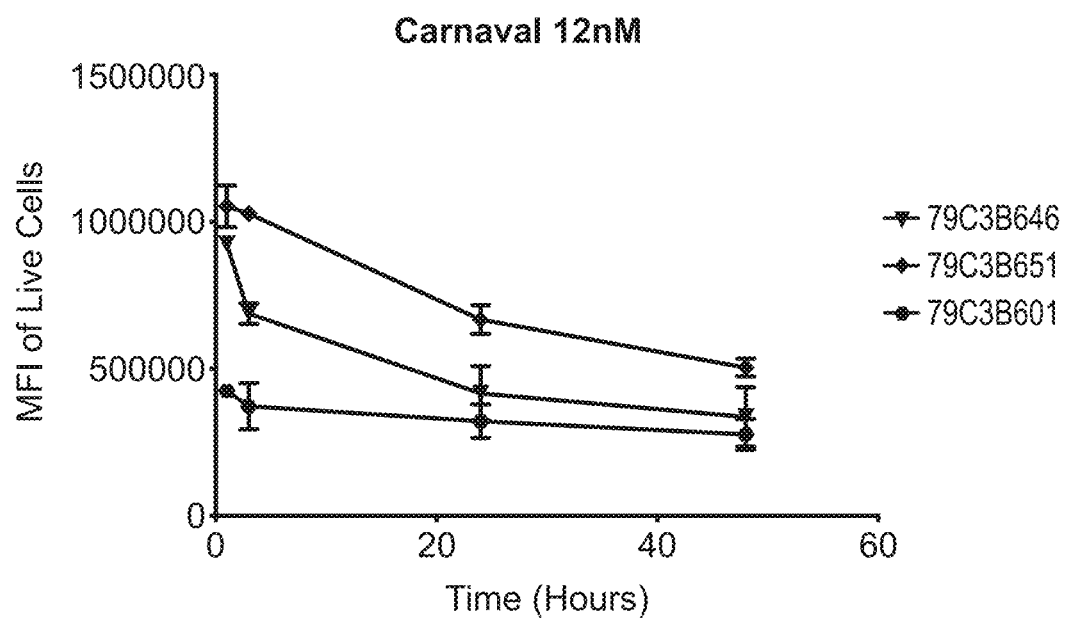
Figure 4G:
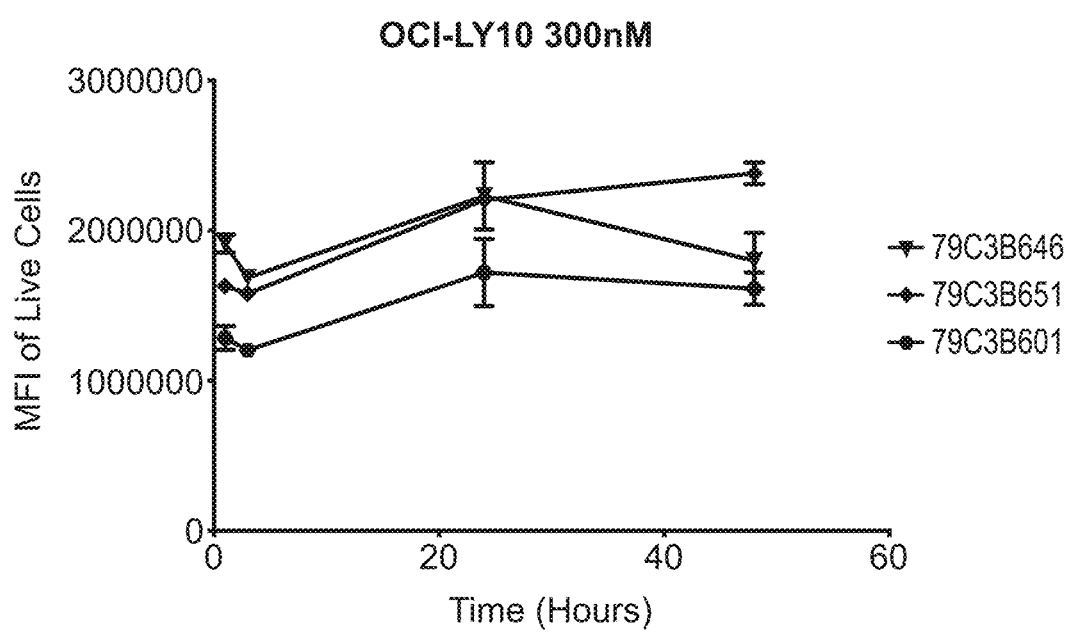
Figure 4H:
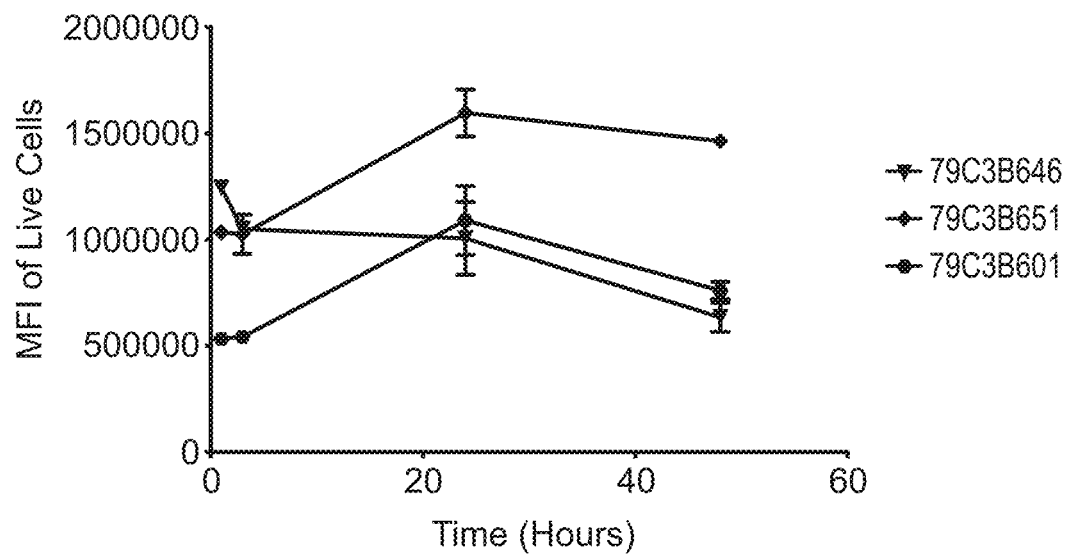
Figure 4I:
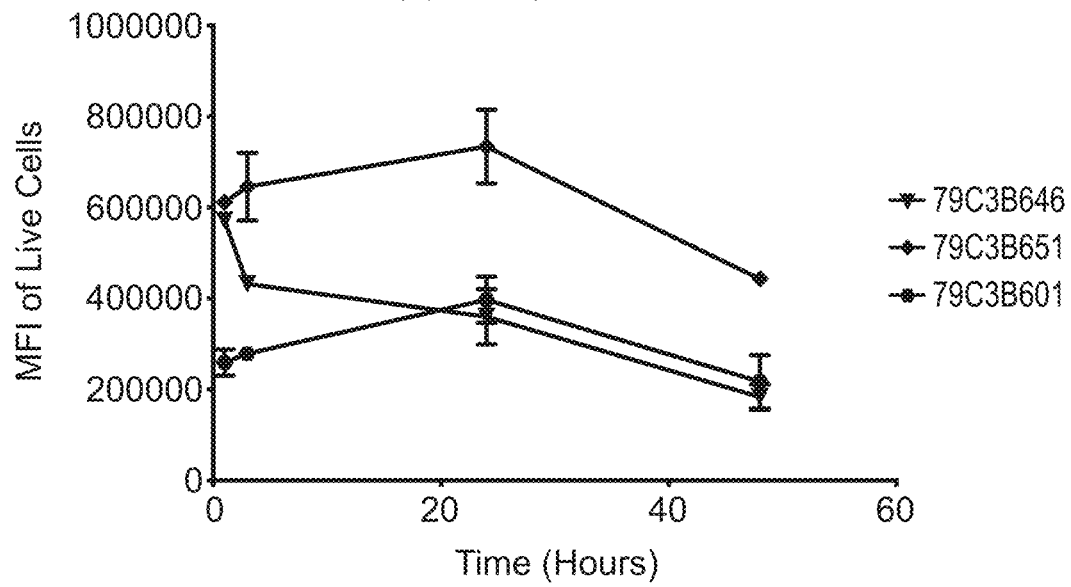
Figure 5A:
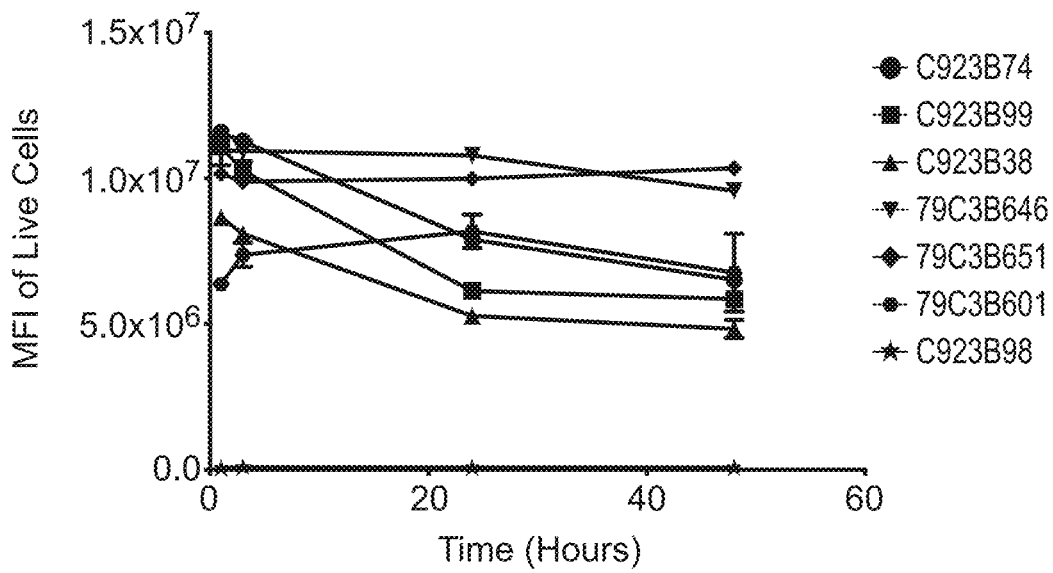
FIGS. 5A-5I. Binding kinetics of selected CD79b× CD20×CD3 trispecific antibodies on DLBCL cell lines. Binding kinetics of the selected antibodies in HBL-1 cells at 300 nm (FIG. 5A). Binding kinetics of the selected antibodies in HBL-1 cells at 60 nm (FIG. 5B). Binding kinetics of the selected antibodies in HBL-1 cells at 12 nm (FIG. 5C). Binding kinetics of the selected antibodies in Carnaval cells at 300 nm (FIG. 5D). Binding kinetics of the selected antibodies in Carnaval cells at 60 nm (FIG. 5E). Binding kinetics of the selected antibodies in Carnaval cells at 12 nm (FIG. 5F). Binding kinetics of the selected antibodies in OCI-LY10 cells at 300 nm (FIG. 5G). Binding kinetics of the selected antibodies in OCI-LY10 cells at 60 nm (FIG. 5H). Binding kinetics of the selected antibodies in OCI-LY10 cells at 12 nm (FIG. 5I). Inverted triangles correspond to the 79C3B646 bsAb control; diamonds correspond to the 79C3B651 bsAb control; and squares correspond to the 79C3B601 bsAb control. Triangles correspond to trispecific antibody C923B38; circles correspond to trispecific antibody C923B74; squares correspond to trispecific antibody C923B99; and asterisks correspond to control null trispecific antibody C923B98.
Figure 5B:
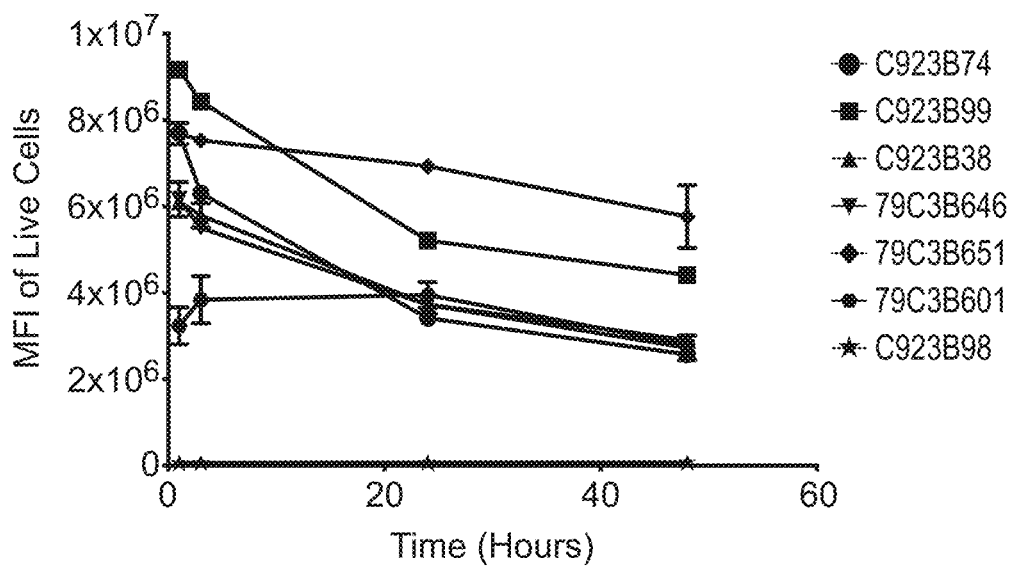
Figures 5C, 5D:
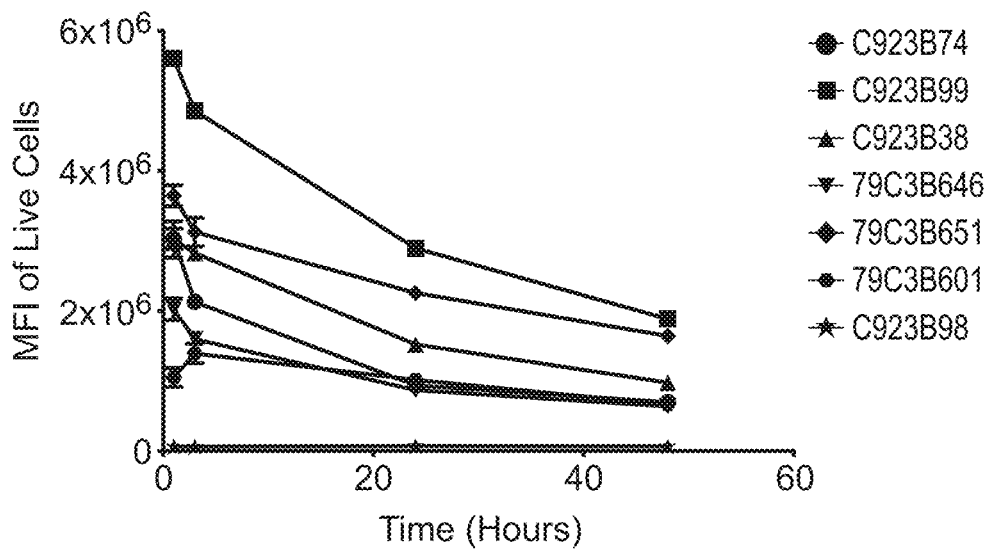
Figure 5E:
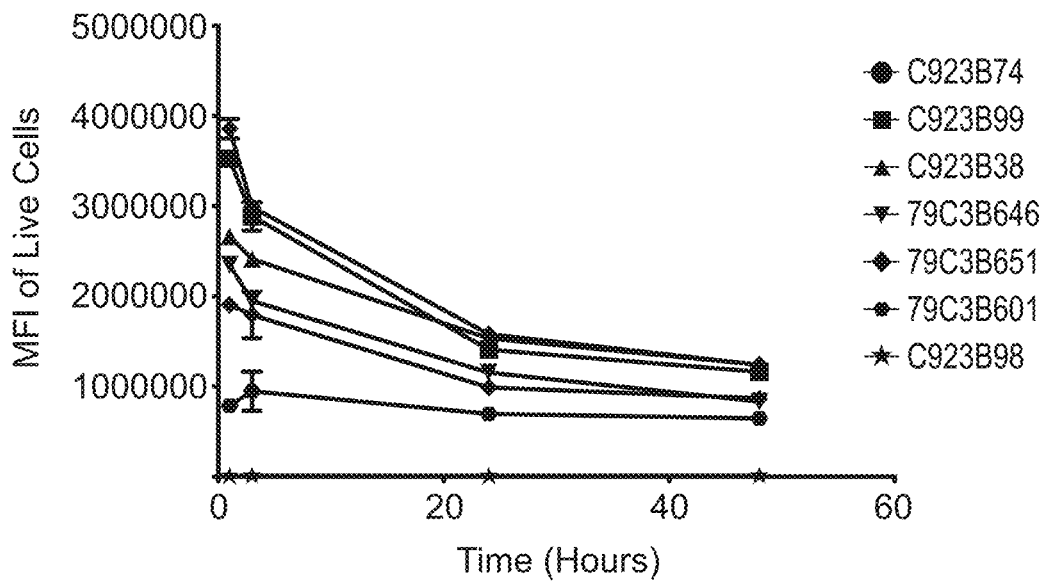
Figure 5F:
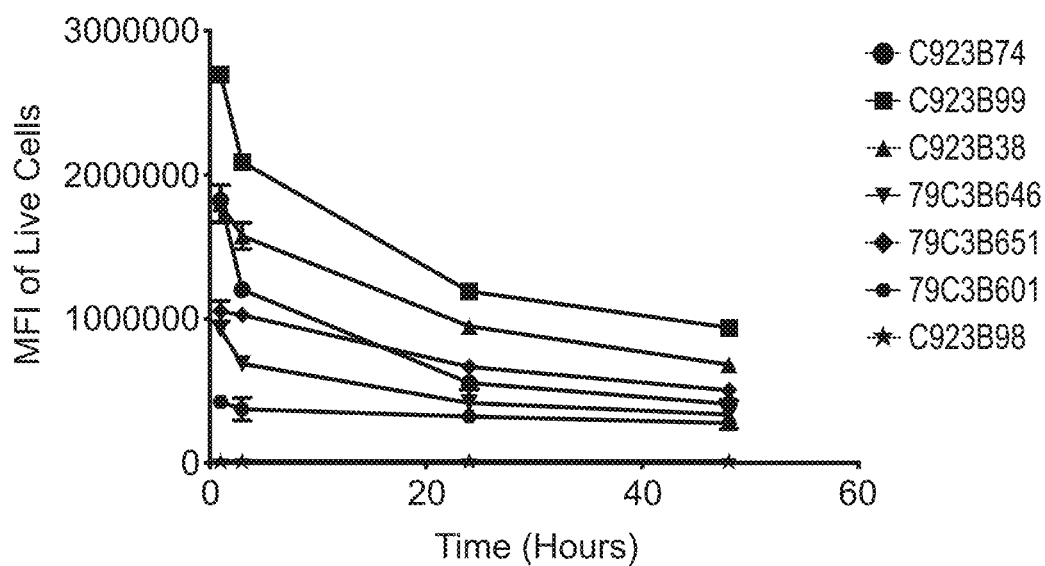
Figure 5G:
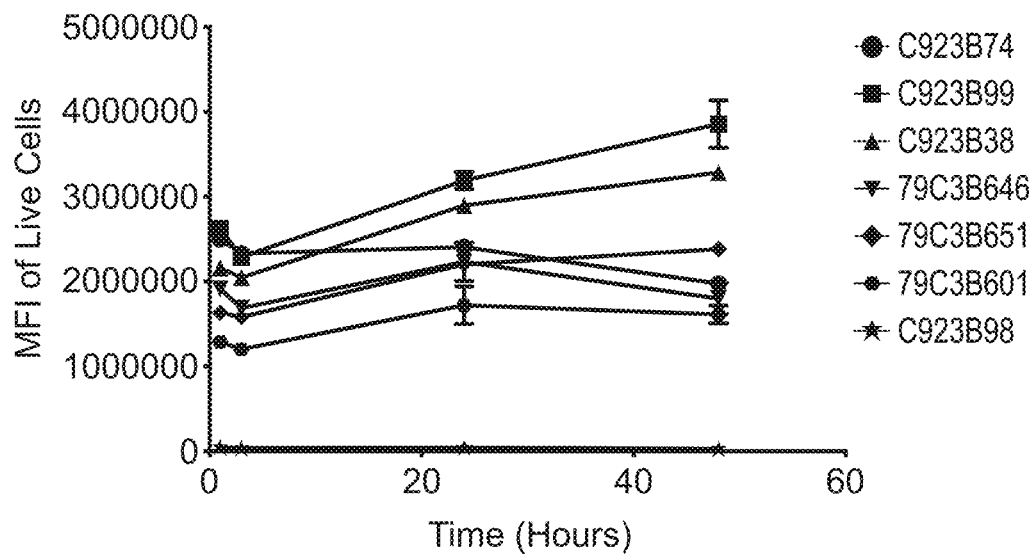
Figure 5H:
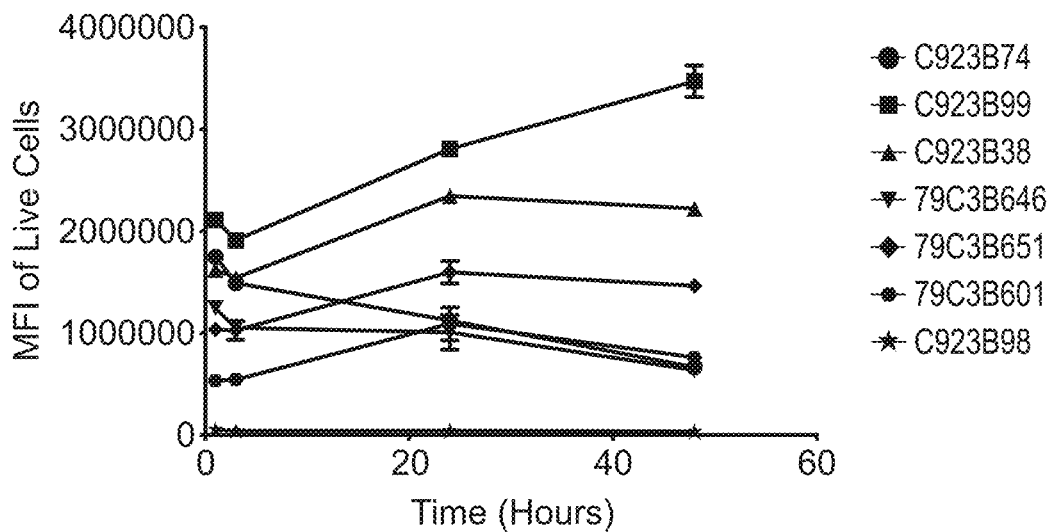
Figure 5I:
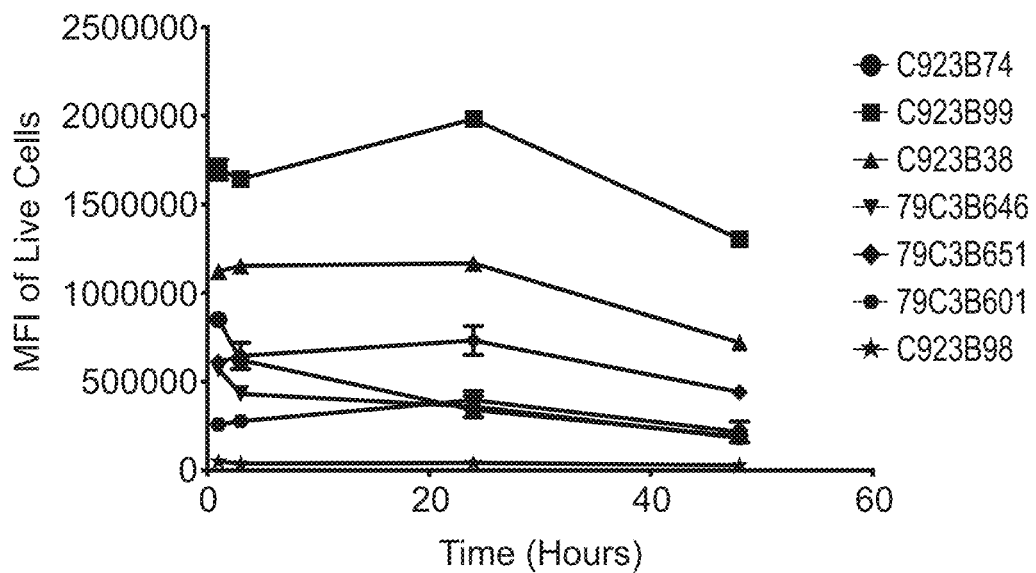
Figure 6A:
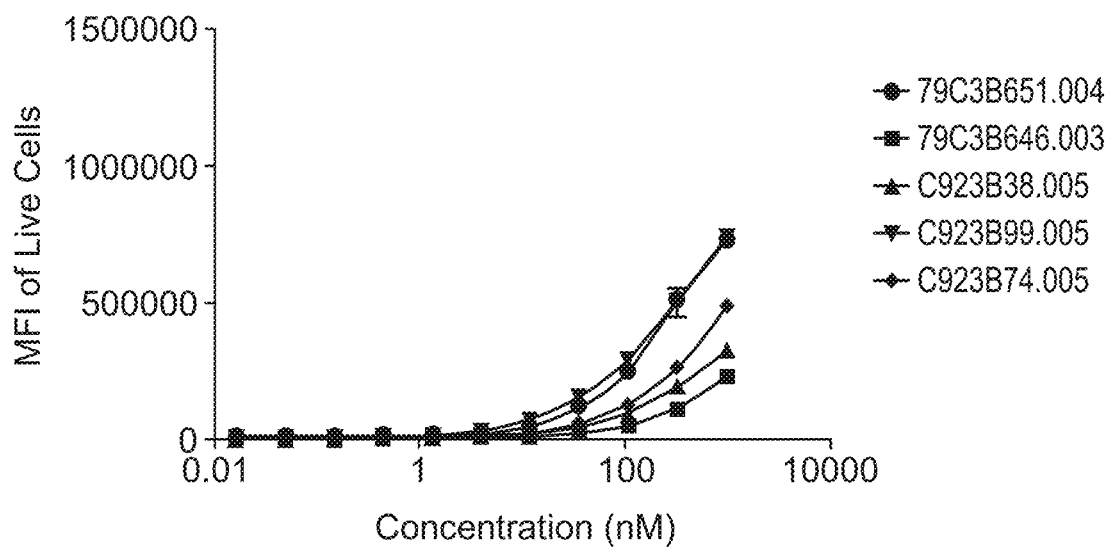
FIGS. 6A-6D. Primary pan T-cell binding of CD79b× CD20×CD3 trispecific antibodies and CD79b×CD3 bispecific antibodies. Binding kinetics of the selected antibodies in pan T-cell donor line D221837 (FIG. 6A). Binding kinetics of the selected antibodies in pan T-cell donor line D329312 (FIG. 6B). Binding kinetics of the selected antibodies in pan T-cell donor line D329335 (FIG. 6C). Binding kinetics of the selected antibodies in pan T-cell donor line D160115 (FIG. 6D). Circles correspond to the 79C3B651 bsAb; squares correspond to the 79C3B646 bsAb; triangles correspond to the trispecific antibody C923B38; inverted triangles correspond to the trispecific antibody C923B99; diamonds correspond to the trispecific antibody C923B74.
Figure 6B:
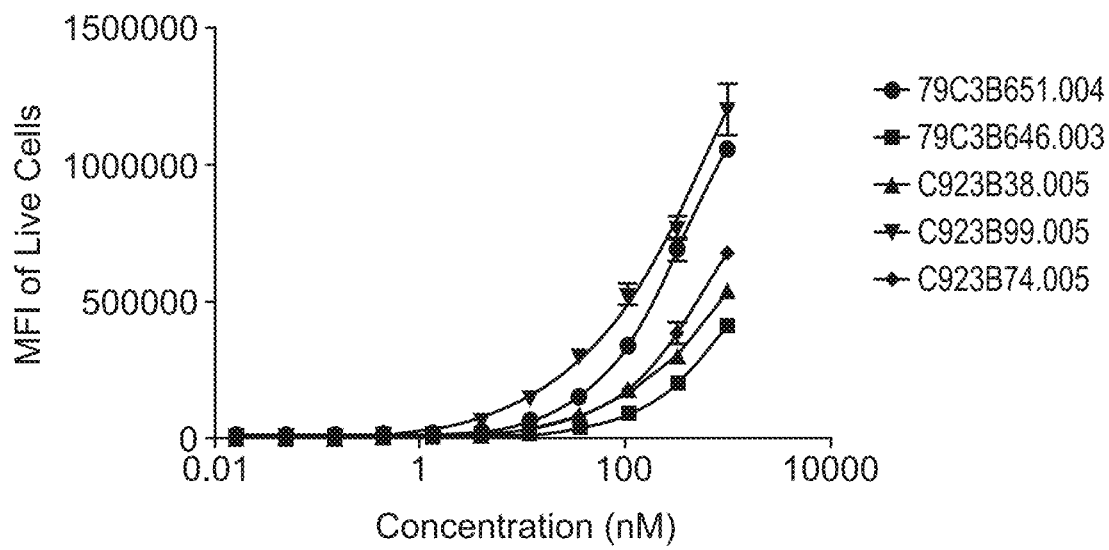
Figure 6C:
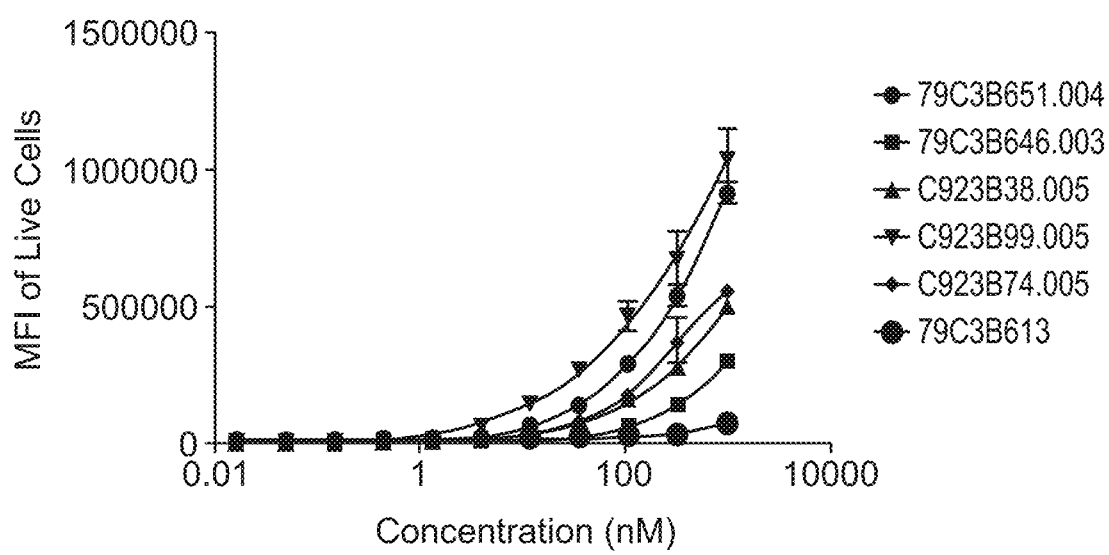
Figure 6D:
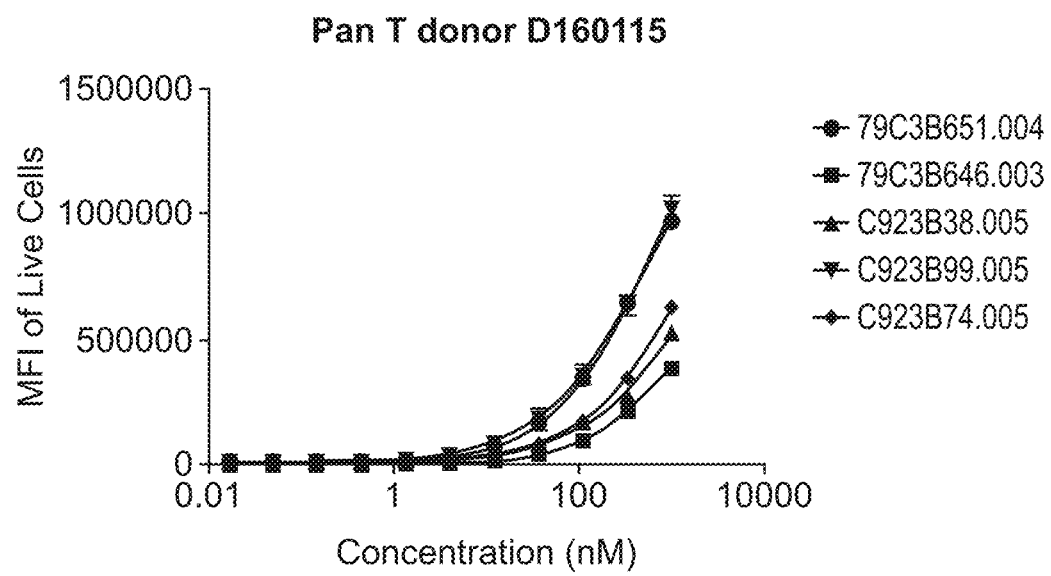

B-cell malignancies encompasses a variety of cancers including CLL, MCL, DLBCL, FL, and MZL and represent a significant unmet medical need. After the successes of small-molecule inhibitors targeting the BCR or apoptotic pathways, T-cell redirection approaches have been selected as one of the main areas of research and development. The off-the-shelf preparation of T-cell-engagers provides a new therapeutic option for a broad patient population, from frontline to heavily pretreated patients, including those who progressed after chimeric antigen receptor (CAR)-T cell therapy (28).

Non-Hodgkin lymphoma (NHL) is a heterogeneous group of malignancies, from B- or T-cell origin, accounting for about 4% of all malignancies in the US (29). Approximately 80% of NHLs are derived from the B-cell lineage and express B-cell differentiation antigens, including CD19, CD20, CD22, and CD79b. These surface antigens represent pivotal targets for current standard-of-care treatment. However, despite the improvements in the available therapies, B-NHLs carry a uniformly poor prognosis with 30% to 50% of DLBCL patients relapsing after rituximab-cyclophosphamide-hydroxydaunorubicin-oncovin-prednisone/prednisolone regimen (R-CHOP) therapy, and only 40% of patients with relapsed and refractory (R/R) disease achieving long-term complete remission upon CD19 CAR-T therapy (30). Emerging clinical trial data with CD20×CD3 bispecific antibodies appear to demonstrate that T-cell redirection may address the urgent unmet need of this growing population whose disease no longer responds to standard chemo- or immunotherapies.

Both CD79b and CD20 are well-validated therapeutic targets expressed in most B-cell malignancies; therefore, they serve as good surface antigens for use in therapeutic modalities. Dual antigen recognition on B cells with a trispecific T-cell redirecting antibody as described herein has the potential to enhance tumor binding through avidity effects, maximize tumor eradication in the presence of a heterogeneous cell population, and prevent tumor antigen escape from occurring, which has been observed with CD19- and CD20-targeting therapies (31-34).

DLBCL is the most prevalent subset of aggressive B-NHLs accounting for approximately 30% to 58% of all new cases of NHL diagnosed annually worldwide. Patient's shares in the R/R setting is dominated in the US and in Europe by the rituximab-ifosfamide-carboplatin-etoposide (R-ICE), rituximab-(dose-adjusted) etoposide-prednisolone-oncovin-cyclophosphamide-hydroxydaunorubicin (R-[DA]-EPOCH), and rituximab-dexamethasone-high-dose ara-C cytarabine-platinol (R-DHAP) regimens followed by rituximab-etoposide-solu-medrol-high-dose ara-C cytarabine-platinol (R-ESHAP) and bendamustine-rituximab (BR) regimens.

CAR-T therapies have been recently approved in this setting and are expected to represent an important uptake over the next decade. The entry of 3 anti-CD19 CAR-T therapies, ie, Yescarta, Kymriah, and Breyanzi into the R/R DLBCL space marks the entry of a new drug class for the treatment of NHL. All 3 therapies target chemorefractory patients, including those who experienced disease progression following allogeneic stem-cell transplantation (ASCT). The high costs associated with CAR-T therapies, the logistics involved in preparing the constructs, and the acute toxicity associated with treatment will impede their uptake and alternative treatment options are needed.

Monoclonal antibodies are dominating the R/R FL setting in terms of patient shares. The 2017 R/R patient share leader in the US was BR, followed by R-CHOP. Lenalidomide+rituximab, the so-called $R^2$ regimen, has been approved in 2019 and is recommended by National Comprehensive Cancer Network (NCCN) guidelines as treatment option for this patient population. Zydelig (idelalisib), a phosphoinositide 3-kinase (PI3K) inhibitor, is also approved for patients who have received 2 prior lines. Ukoniq (umbralisib) and Tazverik (tasemetostat) have been approved in 2020 for R/R patients after 2 or more lines of therapy. Unmet need is especially high for early R/R patients, who have limited effective treatment options.

The multispecific antibodies and multispecific antigen-binding fragments described herein address these and other related needs.

Definitions

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

"Isolated" means a biological component (such as a nucleic acid, peptide or protein) has been substantially separated, produced apart from, or purified away from other biological components of the organism in which the component naturally occurs, i.e., other chromosomal and extra-chromosomal DNA and RNA, and proteins. Nucleic acids, peptides and proteins that have been "isolated" thus include nucleic acids and proteins purified by standard purification methods. "Isolated" nucleic acids, peptides and proteins can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids. An "isolated" antibody or antigen-binding fragment, as used herein, is intended to refer to an antibody or antigen-binding fragment which is substantially free of other antibodies or antigen-binding fragments having different antigenic specificities (for instance, an isolated antibody that specifically binds to CD79b is substantially free of antibodies that specifically bind antigens other than CD79b). An isolated antibody that specifically binds to an epitope, isoform or variant of CD79b may, however, have cross-reactivity to other related antigens, for instance from other species (such as CD79b species homologs).

"Polynucleotide," synonymously referred to as "nucleic acid molecule," "nucleotides" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

"Synthetic nucleic acid sequenze," "synthetic polynucleotide," "synthetic oligonucleotide", "synthetic DNA." or "synthetic RNA" as used herein refers to a nucleic acid sequence, a polynucleotide, an oligonucleotide, DNA, or RNA that differs from one found in nature by having a different sequence than one found in nature or a chemical modification not found in nature. The definition of synthetic nucleic acid includes but is not limited to a DNA sequence created using biotechnology tools. Such tools include but are not limited to recombinant DNA technology, chemical synthesis. or directed use of nucleases (so called "genome editing" or "gene optimizing" technologies). The meaning of "substantially the same" can differ depending on the context in which the term is used. Because of the natural sequence variation likely to exist among heavy and light chains and the genes encoding them, one would expect to find some level of variation within the amino acid sequences or the genes encoding the antibodies or antigen-binding fragments described herein, with little or no impact on their unique binding properties (e.g., specificity and affinity). Such an expectation is due in part to the degeneracy of the genetic code, as well as to the evolutionary success of conservative amino acid sequence variations, which do not appreciably alter the nature of the encoded protein. Accordingly, in the context of nucleic acid sequences, "substantially the same" means at least 65% identity between two or more sequences. Preferably, the term refers to at least 70% identity between two or more sequences, more preferably at least 75% identity, more preferably at least 80% identity, more preferably at least 85% identity, more preferably at least 90% identity, more preferably at least 91% identity, more preferably at least 92% identity, more preferably at least 93% identity, more preferably at least 94% identity, more preferably at least 95% identity, more preferably at least 96% identity, more preferably at least 97% identity, more preferably at least 98% identity, and more preferably at least 99% or greater identity. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

The degree of variation that may occur within the amino acid sequence of a protein without having a substantial effect on protein function is much lower than that of a nucleic acid sequence, since the same degeneracy principles do not apply to amino acid sequences. Accordingly, in the context of an antibody or antigen-binding fragment, "substantially the same" means antibodies or antigen-binding fragments having 90%, 91%, 92%, 93%, 94%, 95%, 96%, 97%, 98%, or 99% identity to the antibodies or antigen-binding fragments described. Other embodiments include antibodies, or anti-gen-binding fragments, that have framework, scaffold, or other non-binding regions that do not share significant identity with the antibodies and antigen-binding fragments described herein, but do incorporate one or more CDRs or other sequences needed to confer binding that are 90%, 91%, 92%, 93%, 94%, 95%, 96%, 97%, 98%, or 99% identical to such sequences described herein.

A "clone" is a population of cells derived from a single cell or common ancestor by mitosis. A "cell line" is a clone of a primary cell that is capable of stable growth in vitro for many generations. In some examples provided herein, cells are transformed by transfecting the cells with DNA.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression or production of an antibody or antigen-binding fragment thereof may be within the cytoplasm of the cell, or into the extracellular milieu such as the growth medium of a cell culture.

The terms "treating" or "treatment" refer to any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, neurological examination, or psychiatric evaluations.

An "effective amount" or "therapeutically effective amount" refers to an amount effective, at dosages and for periods of time necessary, to achieve a desired therapeutic result. A therapeutically effective amount of an antibody described herein may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

"Antibody" refers to all isotypes of immunoglobulins (IgG, IgA, IgE, IgM, IgD, and IgY) including various monomeric, polymeric and chimeric forms, unless otherwise specified. Specifically encompassed by the term "antibody" are polyclonal antibodies, monoclonal antibodies (mAbs), and antibody-like polypeptides, such as chimeric antibodies and humanized antibodies.

The term "antigen-binding arm" refers to a portion of an antibody that includes an antigen-binding domain or an antigen-binding site that binds to an antigen (e.g., CD79b, CD20, or CD3), and optionally includes one or more other antibody regions (e.g., Fc domain). An antigen-binding arm is an example of an "antigen-binding region". "Antigen-binding fragments" are any proteinaceous structure that may exhibit binding affinity for a particular antigen. Similarly, "bispecific binding fragment" or "trispecific-binding fragment" are any proteinaceous structure that may exhibit binding affinity for two or three antigens, respectively. As used herein, the term "antigen-binding fragment", "bispecific binding fragment", or "trispecific-binding fragment" preferably refers to a fragment of the antigen-binding arm containing an antigen-binding domain. Binding fragments include those provided by any known technique, such as enzymatic cleavage, peptide synthesis, and recombinant techniques. Some binding fragments are composed of portions of intact antibodies that retain antigen-binding specificity of the parent antibody molecule. For example, binding fragments may comprise at least one variable region (either a heavy chain or light chain variable region) or one or more CDRs of an antibody known to bind a particular antigen. Examples of suitable binding fragments include, without limitation diabodies and single-chain molecules as well as Fab, F(ab')2, Fc, Fabc, and Fv molecules, single chain (Sc) antibodies, individual antibody light chains, individual antibody heavy chains, chimeric fusions between antibody chains or CDRs and other proteins, protein scaffolds, heavy chain monomers or dimers, light chain monomers or dimers, dimers consisting of one heavy and one light chain, a monovalent fragment consisting of the VL, VH, CL and CH1 domains, or a monovalent antibody as described in WO2007059782, bivalent fragments comprising two Fab fragments linked by a disulfide bridge at the hinge region, a Fd fragment consisting essentially of the VH and CH1 domains; a Fv fragment consisting essentially of the VL and VH domains of a single arm of an antibody, a dAb fragment (Ward et al., Nature 341, 544-546 (1989)), which consists essentially of a VH domain and also called domain antibodies (Holt et al; Trends Biotechnol. 2003 Nov. 21(11):484-90); camelid or nanobodies (Revets et al; Expert Opin Biol Ther. 2005 Jan. 5(1):111-24); an isolated complementarity determining region (CDR), and the like. All antibody isotypes may be used to produce binding fragments. Additionally, binding fragments may include non-antibody proteinaceous frameworks that may successfully incorporate polypeptide segments in an orientation that confers affinity for a given antigen of interest, such as protein scaffolds. Antigen-binding fragments, bispecific binding fragments, or trispecific-binding fragments may be recombinantly produced or produced by enzymatic or chemical cleavage of intact antibodies. The phrase "an antibody or antigen-binding fragment thereof", "a bispecific antibody or bispecific-binding fragment thereof", or "a trispecific antibody or trispecific binding fragment thereof" may be used to denote that a given antigen-binding fragment incorporates one or more amino acid segments of the antibody referred to in the phrase.

The term "antigen-binding domain" refers to the proteinaceous structure of an antigen-binding arm that exhibits binding affinity for a particular antigen. This proteinaceous structure is mediated by the complementarity determining regions (CDRs) of the antigen-binding domain.

The terms "CDR", and its plural "CDRs", refer to a complementarity determining region (CDR) of which three make up the binding character of a light chain variable region (CDRL1, CDRL2 and CDRL3) and three make up the binding character of a heavy chain variable domain (CDRH1, CDRH2 and CDRH3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions. The CDRs described herein are referred to by the AbM definition. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat et al., *Sequences of Proteins of Immunological Interest,* 5th ed. NIH Publication No. 91-3242 (1991); Chothia et al., "Canonical Structures For the Hypervariable Regions of Immunoglobulins," *J. Mol. Biol.* 196:901 (1987); and MacCallum et al., "Antibody-Antigen Interactions: Contact Analysis and Binding Site Topography," J. Mol. Biol. 262: 732 (1996)), each of which is hereby incorporated by reference in its entirety.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia et al., "Canonical Structures For the Hypervariable Regions of Immunoglobulins," *J. Mol. Biol.* 196: 901 (1987); Chothia et al., "Conformations of Immunoglobulin Hypervariable Regions," I 342:877 (1989); Martin and Thornton, "Structural Families in Loops of Homologous Proteins: Automatic Classification, Modelling and Application to Antibodies," *J. Mol. Biol.* 263:800 (1996), each of which is incorporated by reference in its entirety). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

As used herein the term "Fc" refers to the fragment crystallizable domain of an antibody, which comprises two constant heavy chain (CH) regions, CH2 and CH3. Herein, the amino acid residues of the Fc region are typically numbered according to the EU numbering scheme (Edelman, G. M. et al., Proc. Natl. Acad. USA, 63, 78-85 (1969). PMID: 5257969). These residues can be readily assigned according to alternative numbering schemes such as IMGT and Kabat (Kabat, E. A. et al., Sequences of proteins of immunological interest. 5th Edition—US Department of Health and Human Services, NIH publication no 91-3242, pp 662,680,689 (1991)) numbering as would be readily appreciated by one skilled in the art. For example, L234 according to EU numbering may also be represented as L247 according to Kabat.

The term "polypeptide" is used interchangeably with the term "protein" and in its broadest sense refers to a compound of two or more subunit amino acids, amino acid analogs or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein.

"Specifically binds" or "binds specifically" or derivatives thereof when used in the context of antibodies, or antibody fragments, represents binding via domains encoded by immunoglobulin genes or fragments of immunoglobulin genes to one or more epitopes of a protein of interest, without preferentially binding other molecules in a sample containing a mixed population of molecules. Typically, an antibody binds to a cognate antigen with a $K_d$ of less than about $1\times10^{-8}$ M, as measured by a surface plasmon resonance assay or a cell-binding assay. Phrases such as "[antigen]-specific" antibody (e.g., CD79b-specific antibody) are meant to convey that the recited antibody specifically binds the recited antigen. Wherever the term "binds" is used herein it is intended that this encompasses "specifically binds" and the terms may be interchanged as desired.

As used herein, the term "chimeric" refers to an antibody, or antigen-binding fragment thereof, having at least some portion of at least one variable domain derived from the antibody amino acid sequence of a non-human mammal, a rodent, or a reptile, while the remaining portions of the antibody, or antigen-binding fragment thereof, are derived from a human.

A "vector" is a replicon, such as plasmid, phage, cosmid, or virus in which another nucleic acid segment may be operably inserted so as to bring about the replication or expression of the segment.

As used herein, the term "host cell" can be any type of cell, e.g., a primary cell, a cell in culture, or a cell from a cell line. In some embodiments, the host cell is ex vivo or in vitro. In some embodiments, the host cell is not a human totipotent or human pluripotent stem cell. In specific embodiments, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome. The terms "expression" and "production" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications.

The term "subject" refers to human and non-human animals, including all vertebrates, e.g., mammals and non-mammals, such as non-human primates, mice, rabbits, sheep, dogs, cats, horses, cows, chickens, amphibians, and reptiles. In many embodiments of the described methods, the subject is a human.

The term "redirect" or "redirecting" as used herein refers to the ability of the described multispecific antibody (e.g., a CD79b×CD20×CD3 antibody, a CD79b×CD3 antibody) to traffic the activity of T cells effectively, from its inherent cognate specificity toward reactivity against CD79b and/or CD20-expressing cells. The term "sample" as used herein refers to a collection of similar fluids, cells, or tissues (e.g., surgically resected tumor tissue, biopsies, including fine needle aspiration), isolated from a subject, as well as fluids, cells, or tissues present within a subject. In some embodiments the sample is a biological fluid. Biological fluids are typically liquids at physiological temperatures and may include naturally occurring fluids present in, withdrawn from, expressed or otherwise extracted from a subject or biological source. Certain biological fluids derive from particular tissues, organs or localized regions and certain other biological fluids may be more globally or systemically situated in a subject or biological source. Examples of biological fluids include blood, serum and serosal fluids, plasma, lymph, urine, saliva, cystic fluid, tear drops, feces, sputum, mucosal secretions of the secretory tissues and organs, vaginal secretions, ascites fluids such as those associated with non-solid tumors, fluids of the pleural, pericardial, peritoneal, abdominal and other body cavities, fluids collected by bronchial lavage and the like. Biological fluids may also include liquid solutions contacted with a subject or biological source, for example, cell and organ culture medium including cell or organ conditioned medium, lavage fluids and the like. The term "sample," as used herein, encompasses materials removed from a subject or materials present in a subject. The relevant aspects of the invention may be performed ex vivo or in vitro based on isolated samples as required.

A "known standard" may be a solution having a known amount or concentration of CD79b and/or CD20, where the solution may be a naturally occurring solution, such as a sample from a patient known to have early, moderate, late, progressive, or static cancer, or the solution may be a synthetic solution such as buffered water having a known amount of CD79b and/or CD20 diluted therein. The known standards, described herein may include CD79b and/or CD20 isolated from a subject, recombinant or purified CD79b and/or CD20 protein, or a value of CD79b and/or CD20 concentration associated with a disease condition.

"Cluster of Differentiation CD79B protein" or "CD79b" refers to a B-cell antigen receptor (BCR) signaling component Igβ. The amino acid sequences of the various isoforms are retrievable from GenBank accession numbers AAH32651.1, EAW94232.1, AAH02975.2, NP_000617.1, and NP_001035022.1. The amino acid sequence of the full length CD79b sequence is shown below. The sequence includes the extracellular domain (residues 29-159) and the cytoplasmic domain (residues 181-229).

(SEQ ID NO: 252)
MARLALSPVPSHWMVALLLLLSAEPVPAARSEDRY

RNPKGSACSRIWQSPRFIARKRGFTVKMHCYMNSA

SGNVSWLWKQEMDENPQQLKLEKGRMEESQNESLA

TLTIQGIRFEDNGIYFCQQKCNNTSEVYQGCGTEL

RVMGFSTLAQLKQRNTLKDGIIMIQTLLIILFIIV

PIFLLLDKDDSKAGMEEDHTYEGLDIDQTATYEDI

VTLRTGEVKWSVGEHPGQE

"Cluster of Differentiation 20" or "CD20" refers to an antigenic determinant known to be detectable on B cells. Human CD20 is also called membrane-spanning 4-domains, subfamily A, member 1 (MS4A1). The human and murine amino acid and nucleic acid sequences can be found in a public database, such as GenBank, UniProt and Swiss-Prot. For example, the amino acid sequence of human CD20 can be found at Accession Nos. NP_690605.1 and NP_068769.2, and the nucleic acid sequence encoding transcript variants 1 and 3 of the human CD20 can be found at Accession No. NM_152866.2 and NM_021950.3, respectively.

The term "CD3" refers to the human CD3 protein multi-subunit complex. The CD3 protein multi-subunit complex is composed to 6 distinctive polypeptide chains. These include a CD37 chain (SwissProt P09693), a CD36 chain (SwissProt P04234), two CD3E chains (SwissProt P07766), and one CD3 ζ chain homodimer (SwissProt 20963), and which is associated with the T cell receptor α and β chain. The term "CD3" includes any CD3 variant, isoform and species homolog which is naturally expressed by cells (including T cells) or can be expressed on cells transfected with genes or cDNA encoding those polypeptides, unless noted.

A "CD79b×CD20×CD3 antibody" is a multispecific antibody, optionally a trispecific antibody, which comprises three different antigen-binding arms, one of which binds to the antigen CD79b, one of which binds to the antigen CD20, and one of which binds to CD3. A "CD79b×CD3 antibody" is a multispecific antibody, optionally a bispecific antibody, which comprises two different antigen-binding arms, one of which binds to the antigen CD79b and one of which binds to CD3. A "CD20×CD3 antibody" is a multispecific antibody, optionally a bispecific antibody, which comprises two different antigen-binding arms, one of which binds to the antigen CD20 and one of which binds to CD3. The term "multispecific antibody" is used herein in the broadest sense and specifically covers an antibody that has polyepitopic specificity. Multispecific antibodies include, but are not limited to, an antibody comprising a heavy chain variable domain (VH) and a light chain variable domain (VL), where the VHVL unit has polyepitopic specificity, antibodies having two or more $V_L$ and $V_H$ domains where each VHVL unit binds to a different epitope, antibodies having two or more single variable domains with each single variable domain binding to a different epitope, full length antibodies, and antibodies comprising one or more antibody fragments as well as antibodies comprising antibody fragments that have been linked covalently or non-covalently.

A multispecific antibody can be a bispecific antibody, a trispecific antibody, diabody, or similar molecule (see for instance *PNAS USA* 90(14), 6444-8 (1993) for a description of diabodies). The bispecific antibodies, trispecific antibodies, diabodies, and the like, provided herein may bind any suitable target in addition to a portion of CD79b or CD20. The term "bispecific antibody" is to be understood as an antibody having two different antigen-binding arms defined by different antibody sequences. The term "trispecific antibody" is to be understood as an antibody having three different antigen-binding arms defined by different antibody sequences. This can be understood as different target binding but includes as well binding to different epitopes in one target.

A "reference sample" is a sample that may be compared against another sample, such as a test sample, to allow for characterization of the compared sample. The reference sample will have some characterized property that serves as the basis for comparison with the test sample. For instance, a reference sample may be used as a benchmark for CD79b or CD20 levels that are indicative of a subject having cancer. The reference sample does not necessarily have to be analyzed in parallel with the test sample, thus in some instances the reference sample may be a numerical value or range previously determined to characterize a given condition, such as CD79b or CD20 levels that are indicative of cancer in a subject. The term also includes samples used for comparative purposes that are known to be associated with a physiologic state or disease condition, such as CD79b- or CD20-expressing cancer, but that have an unknown amount of CD79b or CD20.

"Relapsed" refers to the return of a disease or the signs and symptoms of a disease after a period of improvement after prior treatment with a therapeutic.

"Refractory" refers to a disease that does not respond to a treatment. A refractory disease can be resistant to a treatment before or at the beginning of the treatment, or a refractory disease can become resistant during a treatment.

The term "progression," as used in the context of progression of CD79b and/or CD20-expressing cancer, includes the change of a cancer from a less severe to a more severe state. This may include an increase in the number or severity of tumors, the degree of metastasis, the speed with which the cancer is growing or spreading, and the like. For example, "the progression of colon cancer" includes the progression of such a cancer from a less severe to a more severe state, such as the progression from stage I to stage II, from stage II to stage III, etc.

The term "regression," as used in the context of regression of CD79b and/or CD20-expressing cancer, includes the change of a cancer from a more severe to a less severe state. This could include a decrease in the number or severity of tumors, the degree of metastasis, the speed with which the cancer is growing or spreading, and the like. For example, "the regression of colon cancer" includes the regression of such a cancer from a more severe to a less severe state, such as the progression from stage III to stage II, from stage II to stage I, etc.

The term "stable" as used in the context of stable CD79b and/or CD20-expressing cancer, is intended to describe a disease condition that is not, or has not, changed significantly enough over a clinically relevant period of time to be considered a progressing cancer or a regressing cancer.

The embodiments described herein are not limited to particular methods, reagents, compounds, compositions or biological systems, which can, of course, vary.

Multispecific Antibodies

Multispecific antibodies that bind to CD79b, CD20, and/or CD3, and multispecific binding fragments thereof are provided herein. Such antibodies or antibody fragments may allow for more specific targeting to particular subsets of cells as compared to antibodies targeting only one or two of these targets.

Trispecific Antibodies

In some embodiments, provided herein are trispecific antibodies that bind to CD79b, CD20, and CD3, and trispecific binding fragments thereof. This can be achieved by, for example, making a molecule which comprises a first antigen-binding arm binding to CD79b, a second antigen-binding arm binding to CD3, and a third antigen-binding arm binding to the CD20. The antigen-binding arms can take any form that allows specific recognition of the target, for example the binding arm may be or may include a heavy chain variable domain, an Fv (combination of a heavy chain variable domain and a light chain variable domain), an single-chain Fv (scFv), an Fab, a binding domain based on a fibronectin type III domain (such as from fibronectin, or based on a consensus of the type III domains from fibronectin, or from tenascin or based on a consensus of the type III domains from tenascin, such as the Centyrin molecules from Janssen Biotech, Inc., see e.g. WO2010/051274 and WO2010/093627). In certain embodiments, the trispecific antibody comprises three antigen binding arms. In some embodiments, the trispecific antibody is comprised of an antibody (e.g. in IgG format) to which an additional antigen-binding arm, e.g. in the form of a single chain variable fragment, is fused, e.g. to the N or C-terminus of one of the heavy or one of the light chains of the antibody.

Accordingly, trispecific molecules comprising three different antigen-binding arms which bind CD79b, CD20, and CD3, respectively, are provided.

In some embodiments, the CD79b×CD20×CD3-multispecific antibody comprises: (a) a first antigen-binding arm comprising a first heavy chain variable domain (VH1) and a first light chain variable domain (VL1);

(b) a second antigen-binding arm comprising a second heavy chain variable domain (VH2) and a second light chain variable domain (VL2);

(c) a third antigen-binding arm comprising a third heavy chain variable domain (VH3) and a third light chain variable domain (VL3), wherein the first antigen-binding arm binds to an epitope on CD79b, the second antigen-binding arm binds to an epitope on CD3, and the third antigen-binding arm binds to an epitope on CD20.

In some embodiments, the VH1 comprises an amino acid sequence selected from SEQ ID NO: 35, SEQ ID NO: 39, SEQ ID NO: 43, SEQ ID NO: 45, SEQ ID NO: 49, SEQ ID NO: 55, SEQ ID NO: 59, SEQ ID NO: 63, SEQ ID NO: 67, and SEQ ID NO: 71.

In some embodiments, the VL1 comprises an amino acid sequence selected from SEQ ID NO: 37, SEQ ID NO: 41, SEQ ID NO: 47, SEQ ID NO: 51, SEQ ID NO: 53, SEQ ID NO: 57, SEQ ID NO: 61, SEQ ID NO: 65, SEQ ID NO: 69, and SEQ ID NO: 73.

In some embodiments, the VH2 comprises an amino acid sequence selected from SEQ ID NO: 97, SEQ ID NO: 101, SEQ ID NO: 103, SEQ ID NO: 105, SEQ ID NO: 107, SEQ ID NO: 196, and SEQ ID NO: 206.

In some embodiments, the VL2 comprises an amino acid sequence selected from SEQ ID NO: 99, SEQ ID NO: 109, SEQ ID NO: 201, and SEQ ID NO: 211.

In some embodiments, the VH3 comprises an amino acid sequence selected from SEQ ID NO: 126, SEQ ID NO: 130, SEQ ID NO: 134, and SEQ ID NO: 138.

In some embodiments, the VL3 comprises an amino acid sequence selected from SEQ ID NO: 128, SEQ ID NO: 132, SEQ ID NO: 136, and SEQ ID NO: 140.

In some embodiments, the VH1 and VL1 of the antigen-binding arm that binds to CD79b epitope are present in a diabody, a Fab, Fab', a F(ab')2, a Fv, a scFv, a Fd, a disulfide stabilized Fv fragment (dsFv), or a disulfide stabilized diabody (ds diabody).

In some embodiments, the VH2 and VL2 of the antigen-binding arm that binds to CD3 epitope are present in a diabody, a Fab, Fab', a F(ab')2, a Fv, a scFv, a Fd, a disulfide stabilized Fv fragment (dsFv), or a disulfide stabilized diabody (ds diabody).

In some embodiments, the VH3 and VL3 of the antigen-binding arm that binds to CD20 epitope are present in a diabody, a Fab, Fab', a F(ab')2, a Fv, a scFv, a Fd, a disulfide stabilized Fv fragment (dsFv), or a disulfide stabilized diabody (ds diabody).

In some embodiments, the first antigen-binding arm of the CD79b×CD20×CD3 multispecific antibody comprises a first heavy chain portion (HC1) comprising the VH1, and a light chain (LC) comprising the VL1, where the VH1 and VL1 pair to form a first antigen-binding domain that binds a first antigen. In some embodiments, the HC1 comprises, from N to C-terminus, the VH1, a first heavy chain constant domain (CH1), and a first Fc domain. In some embodiments, the VH1 and CH1 of the HC1 together with the LC form a fragment antigen binding (Fab) domain.

In some embodiments, the VH1 of the first antigen-binding arm is coupled to the VH3 of the third antigen-binding arm via the first Fc domain. In some embodiments, the first Fc domain of the first antigen-binding arm is coupled, via a first linker (L1), to the third antigen-binding arm, thereby forming a coupled first and third antigen-binding arm. The coupled first and third antigen-binding arms may comprise, from N to C-terminus, the VH1, the CH1 domain, and the Fc domain of the first antigen-binding arm, the first linker, and the third antigen-binding arm. In some embodiments, the third antigen-binding arm is a single-chain variable fragment (scFv) formed from the VH3 and VL3 of the third-antigen-binding arm.

In some embodiments, the second antigen-binding arm of the CD79b×CD20×CD3 multispecific antibody comprises a second heavy chain portion (HC2) comprising the second heavy chain variable domain (VH2) which forms a second antigen-binding domain that binds a second antigen. In some embodiments, the second binding arm comprises from N to C-terminus, a single-chain variable fragment (scFv) formed from the VH2 and VL2, and a second Fc domain.

In some embodiments, the VH2 of the second antigen-binding arm is coupled to the VH3 of the third antigen-binding arm via the second Fc domain. In some embodiments, the second Fc domain of the second antigen-binding arm is coupled, via a linker, to the third antigen-binding arm, thereby forming a coupled second and third antigen-binding arm. The coupled second and third antigen-binding arms may comprise, from N to C-terminus, the second antigen-binding domain, the second Fc domain, the first linker, and the third antigen-binding arm. In some embodiments, the third antigen-binding arm is a single-chain variable fragment (scFv) formed from the VH3 and VL3 of the third-antigen-binding arm.

In preferred embodiments, the CD79b×CD20×CD3-multispecific antibody is a trispecific antibody comprising a CD79b-specific binding arm comprising the first heavy chain portion (HC1) with the VH1 and the light chain portion (LC) with the VL1. The VH1 and VL1 pair to form a first antigen-binding domain that binds CD79b. The second antigen-binding arm of the trispecific antibody comprises the second heavy chain portion (HC2) with the VH2 that forms the second antigen-binding domain that binds the second antigen. The HC1 of the CD79b-specific binding arm or the HC2 of the second antigen-binding arm is coupled to the third antigen-binding arm comprising the VH3 domain, which forms the third antigen-binding domain that binds the third antigen. In some embodiments, the second antigen is CD20, and the third antigen is CD3. In some embodiments, the second antigen is CD3, and the third antigen is CD20.

In one embodiment, the CD79b×CD20×CD3-multispecific antibody is a trispecific antibody comprising a CD79b-specific binding arm comprising the HC1 with the VH1 and the LC with the VL1. The VH1 and VL1 pair to form the first CD79b-specific antigen-binding domain that binds CD79b. The second antigen-binding arm comprises the VH2 and VL2 that form the second antigen-binding domain that binds CD3. The third antigen-binding arm is coupled to the second antigen-binding arm and comprises the VH3 and VL3 that form the third antigen-binding domain that binds CD20.

In one embodiment, the CD79b×CD20×CD3-multispecific antibody is a trispecific antibody comprising a CD79b-specific binding arm comprising the HC1 with the VH1 and the LC with the VL1. The VH1 and VL1 pair to form the first CD79b-specific antigen-binding domain that binds CD79b. The second antigen-binding arm comprises the VH2 and VL2 that form the second antigen-binding domain that binds CD20. The third antigen-binding arm is coupled to the second antigen-binding arm and comprises the VH3 and VL3 that form the third antigen-binding domain that binds CD3.

In one embodiment, the CD79b×CD20×CD3-multispecific antibody is a trispecific antibody comprising a CD79b-specific binding arm comprising the HC1 with the VH1 and the LC with the VL1. The VH1 and VL1 pair to form the first CD79b-specific antigen-binding domain that binds CD79b. The second antigen-binding arm comprises the VH2 and VL2 that form the second antigen-binding domain that binds CD3. The third antigen-binding arm is coupled to the first CD79b-specific antigen-binding arm and comprises the VH3 and VL3 that form the third antigen-binding domain that binds CD20.

In one embodiment, the CD79b×CD20×CD3-multispecific antibody is a trispecific antibody comprising a CD79b-specific binding arm comprising the HC1 with the VH1 and the LC with the VL1. The VH1 and VL1 pair to form the first CD79b-specific antigen-binding domain that binds CD79b. The second antigen-binding arm comprises the VH2 and VL2 that form the second antigen-binding domain that binds CD20. The third antigen-binding arm is coupled to the first CD79b-specific antigen-binding arm and comprises the VH3 and VL3 that form the third antigen-binding domain that binds CD3.

In some embodiments, the HC1 with the VH1 and LC with VL1 of the first antigen-binding arm form an antigen-binding fragment (Fab) comprising the first antigen-binding domain. In some embodiments, the VH2 and VL2 of the second antigen-binding arm form a single-chain variable fragment (scFv) comprising the second antigen-binding domain. In some embodiments, the VH3 and VL3 of the third antigen-binding arm form a single-chain variable fragment (scFv) comprising the third antigen-binding domain.

In one embodiment, the CD79b-binding arm comprises an antigen-binding fragment (Fab), the CD3-binding arm comprises a single-chain variable fragment (scFv), and the CD20-binding arm comprises a single-chain variable fragment (scFv).

In some embodiments, the CD79b binding arm of the trispecific antibody comprises the HC1 and the LC. The HC1 may comprise constant heavy chain regions (CH1, CH2, and CH3) and the VH1. The LC may comprise the VL1. The VH1 and VL1 combine to form the CD79b antigen binding domain.

In some embodiments, CD3 binding arm of the trispecific antibody comprises the HC2. The HC2 may comprise constant heavy chain regions (CH2 and CH3), and a single-chain variable fragment (scFv) attached at the N-terminus of the CH2 region, wherein the scFv comprises the CD3 antigen binding domain.

In some embodiments, the trispecific antibody further comprises CD20 antigen-binding arm attached to the C-terminus of the CH3 region of the CD3 binding arm to form a CD3/CD20 binding arm. In some embodiments, the CD20 antigen-binding arm comprises a second single-chain variable fragment (scFv). In some embodiments, the CD3/CD20 arm may have the structure: scFV containing the CD3 binding domain, CH2 and CH3 regions, scFV containing the CD20 binding domain.

Bispecific Antibodies

In some embodiments, provided herein are bispecific antibodies that bind to CD79b and CD3, and bispecific binding fragments thereof. This can be achieved by, for example, making a molecule which comprises a first antigen-binding arm binding to CD79b, and a second antigen-binding arm binding to CD3. The antigen-binding arms can take any form that allows specific recognition of the target, for example the binding region may be or may include a heavy chain variable domain, an Fv (combination of a heavy chain variable domain and a light chain variable domain), an single-chain Fv (scFv), an Fab, a binding domain based on a fibronectin type III domain (such as from fibronectin, or based on a consensus of the type III domains from fibronectin, or from tenascin or based on a consensus of the type III domains from tenascin, such as the Centyrin molecules from Janssen Biotech, Inc., see e.g. WO2010/051274 and WO2010/093627). Accordingly, bispecific molecules comprising three different antigen-binding arms which bind CD79b and CD3, respectively, are provided.

In some embodiments, the CD79b×CD3 bispecific antibody comprises: (a) a first antigen binding arm comprising a first heavy chain variable domain (VH1) and a first light chain variable domain (VL1); and (b) a second antigen-binding arm comprising a first heavy chain variable domain (VH2) and a first light chain variable domain (VL2), wherein the first antigen-binding arm binds to an epitope on CD79b, and the second antigen-binding arm binds to an epitope on CD3.

In some embodiments, the VH1 and VL1 of the antigen binding arm that binds to CD79b epitope are present in a diabody, a Fab, Fab', a F(ab')2, a Fv, a scFv, a Fd, a disulfide stabilized Fv fragment (dsFv), or a disulfide stabilized diabody (ds diabody).

In some embodiments, the VH2 and VL2 of the antigen binding arm that binds to CD3 epitope are present in a diabody, a Fab, Fab', a F(ab')2, a Fv, a scFv, a Fd, a disulfide stabilized Fv fragment (dsFv), or a disulfide stabilized diabody (ds diabody).

In some embodiments, the first antigen-binding arm comprises a first heavy chain portion (HC1) comprising the VH1, and a light chain (LC) comprising the VL1. In some embodiments, the HC1 comprises, from N to C-terminus, the VH1, a first heavy chain constant domain (CH1), and a first Fc domain. In some embodiments, the VH1 and CH1 of the HC1 together with the LC form a fragment antigen binding (Fab) domain.

In some embodiments, the second antigen-binding arm comprises, from N to C-terminus, a single-chain variable fragment (scFv) formed from the VH2 and VL2, and a second Fc domain.

In some embodiments, the first binding arm of the CD79b×CD3-multispecific antibody comprises the HC1 comprising the VH1 and the LC comprising the VL1. The VH1 and VL1 pair to form a first antigen-binding domain that binds the first antigen of the bispecific antibody. The second antigen-binding arm of the bispecific antibody comprises a second heavy chain portion (HC2) comprising the VH2 that forms the second antigen-binding domain that specifically binds the second antigen. The HC1 and HC2 may each comprise a Fragment crystallizable (Fc) domain comprising a CH2-CH3 domain.

In some embodiments, the CD79b×CD3-bispecific antibody comprises a CD79b-specific binding arm comprising the HC1 with the VH1 and the LC with the VL1. The VH1 and VL1 pair to form the first antigen-binding domain that binds CD79b. The second antigen-binding arm of the bispecific antibody comprises the HC2 with the VH2 forming the second antigen-binding domain that binds CD3.

In some embodiments, the CD79b×CD3-bispecific antibody comprises a CD3-specific binding arm comprising the HC1 with the VH1 and the LC with the VL1. The VH1 and VL1 pair to form the first antigen-binding domain that binds CD3. The second antigen-binding are of the bispecific antibody comprises the HC2 with the VH2 forming a second antigen-binding domain that binds CD79b.

In some embodiments, the HC1 with the VH1 and LC with the VL1 form an antigen-binding fragment (Fab) comprising the first antigen-binding domain. In some embodiments, the HC2 with the VH2, together with VL2, forms a single-chain variable fragment (scFv) comprising the second antigen-binding domain.

In one embodiment, the CD79b-binding arm comprises an antigen-binding fragment (Fab), and the CD3-binding arm comprises a single-chain variable fragment (scFv).

In one embodiment, the CD3-binding arm comprises an antigen-binding fragment (Fab), and the CD79b-binding arm comprises a single-chain variable fragment (scFv).

In some embodiments, the multispecific antibodies (e.g., trispecific antibodies, bispecific antibodies) of the invention include antibodies having a full length antibody structure. "Full length antibody" as used herein refers to an antibody having two full length antibody heavy chains and two full length antibody light chains. A full length antibody heavy chain (HC) includes heavy chain variable and constant domains VH, CH1, CH2, and CH3. A full length antibody light chain (LC) includes light chain variable and constant domains VL and CL. The full length antibody may be lacking the C-terminal lysine (K) in either one or both heavy chains. The term "Fab-arm" or "half molecule" refers to one heavy chain-light chain pair that specifically binds an antigen. In some embodiments, one of the antigen-binding domains is a non-antibody based binding domain, e.g. a binding domain of based on a fibronectin type 3 domain, e.g. Centyrin.

CD79b-Binding Arm

The multispecific antibodies (e.g., trispecific or bispecific antibodies) described herein comprise an antigen-binding arm specific for CD79b. In some embodiments, the CD79b-binding arm binds human CD79b. In some embodiments, the CD79b-binding arm binds human CD79b and cynomolgus monkey CD79b. In some embodiments, the CD79b-binding arm binds human CD79b but not to cynomolgus monkey CD79b. In some embodiments, the CD79b-binding arm binds bind to an epitope including one or more residues from the CD79b extracellular domain (ECD). In some embodiments, the CD79b-binding arm binds to one or more residues of a polypeptide having the amino acid sequence of SEQ ID NO: 252. In some embodiments, the CD79b-binding arm binds to residues 30-42 (SEDRYRNPKGSAC; SEQ ID NO: 253), residues 50-52 (PRF), residues 81-86 (EMENP; SEQ ID NO: 254), and/or residues 144-148 (GFSTL; SEQ ID NO: 255) of human CD79b. Such CD79b-binding arms may bind to CD79b with an affinity of $5\times10^{-7}$M or less, such as $1\times10^{-7}$M or less, $5\times10^{-8}$M or less, $1\times10^{-8}$M or less, $5\times10^{-9}$M or less, $1\times10^{-9}$M or less, or $5\times10^{-10}$M or less. In one embodiment, the CD79b-binding arm binds to the CD79b with an affinity of about $1\times10^{-11}$M to $1\times10^{-9}$M. In one embodiment, the CD79b-binding arm binds to the CD79b with an affinity of about $1\times10^{-11}$M, about $2\times10^{-11}$M, about $3\times10^{-11}$M, about $4\times10^{-11}$M, about $5\times10^{-11}$M, about $6\times10^{-11}$M, about $7\times10^{-11}$M, about $8\times10^{-11}$M, about $9\times10^{-11}$M, $1\times10^{-10}$M, about $2\times10^{-10}$M, about $3\times10^{-10}$M, about $4\times10^{-10}$M, about $5\times10^{-10}$M, about $6\times10^{-10}$M, about $7\times10^{-10}$M, about $8\times10^{-10}$M, about $9\times10^{-10}$M or about $1\times10^{-9}$M.

Table 1a and Table 1b provide a summary of CDR (as defined by AbM) and VH and VL sequences of some exemplary CD79b-specific antibodies described herein:

TABLE 1a

CDR sequences of exemplary mAbs generated against human CD79b

| ID | HC-CDR1 | HC-CDR2 | HC-CDR3 | LC-CDR1 | LC-CDR2 | LC-CDR3 |
|---|---|---|---|---|---|---|
| CD9B374 | GASISSFYWS (SEQ ID NO: 1) | RISPSGKTN (SEQ ID NO: 2) | GEYSGTYSYSFDV (SEQ ID NO: 3) | RSSELLDSEDGNTYLD (SEQ ID NO: 4) | TLSYRAS (SEQ ID NO: 5) | MQRMEFPLT (SEQ ID NO: 6) |

TABLE 1a-continued

CDR sequences of exemplary mAbs generated against human CD79b

| ID | HC-CDR1 | HC-CDR2 | HC-CDR3 | LC-CDR1 | LC-CDR2 | LC-CDR3 |
|---|---|---|---|---|---|---|
| CD9B330 | GDSVSNNSATWN (SEQ ID NO: 13) | RTYYRSKWFDY (SEQ ID NO: 8) | VDIAYND (SEQ ID NO: 9) | SGSSSNIGNHGVN (SEQ ID NO: 10) | NDDLLPS (SEQ ID NO: 11) | AAWDDSLNGVV (SEQ ID NO: 12) |
| CD9B330-N31S | GDSVSSNSATWN (SEQ ID NO: 7) | RTYYRSKWEDY (SEQ ID NO: 8) | VDIAYND (SEQ ID NO: 9) | SGSSSNIGNHGVN (SEQ ID NO: 10) | NDDLLPS (SEQ ID NO: 11) | AAWDDSLNGVV (SEQ ID NO: 12) |
| CD9B643 | GVSISNYYWS (SEQ ID NO: 14) | RISPSGRTN (SEQ ID NO: 15) | GEYSGTYSYSEDI (SEQ ID NO: 16) | RSSQSLEDSDDGNTYLD (SEQ ID NO: 17) | TLSYRAS (SEQ ID NO: 5) | MQRMEFPLT (SEQ ID NO: 6) |
| CD9B321 | GDSVSSNSAAWN (SEQ ID NO: 18) | RTYYRSKWYND (SEQ ID NO: 8) | VNTTEDY (SEQ ID NO: 19) | SGSSSNIGKNAVS (SEQ ID NO: 20) | SDDLLSS (SEQ ID NO: 21) | AAWDDSLNGVV (SEQ ID NO: 12) |
| CD9B324 | GDSVSNNSATWN (SEQ ID NO: 13) | RTYYRSKWYND (SEQ ID NO: 8) | VDIAEDY (SEQ ID NO: 9) | SGSSSNIGNHGVN (SEQ ID NO: 10) | NDDLLPS (SEQ ID NO: 11) | AAWDDSLNGVV (SEQ ID NO: 12) |
| CD9B332 | GDSVSNNSATWN (SEQ ID NO: 13) | RTYYRSKWYND (SEQ ID NO: 8) | VDIAEDY (SEQ ID NO: 9) | SGSSSNIGNHGVN (SEQ ID NO: 10) | NDDLLPS (SEQ ID NO: 11) | AAWDDSLNGVV (SEQ ID NO: 12) |
| CD9B369 | GASISSYYWS (SEQ ID NO: 22) | RISNTGRTN (SEQ ID NO: 23) | GEYSGTFSYGFDI (SEQ ID NO: 24) | RSSLSLLDSDDGKIYLD (SEQ ID NO: 25) | TLSYRAS (SEQ ID NO: 5) | MQRMEFPLT (SEQ ID NO: 6) |
| CD9B381 | GASISSYYWS (SEQ ID NO: 22) | RIYSNGNIN (SEQ ID NO: 26) | GEYSGDESYSFDI (SEQ ID NO: 27) | RSSQSLLDSDDGNTYLD (SEQ ID NO: 28) | TLSYRAS (SEQ ID NO: 5) | MQRIEEPLT (SEQ ID NO: 29) |
| CD9B389 | GVSISNYYWS (SEQ ID NO: 14) | RISPSGRTN (SEQ ID NO: 15) | GEYSGTYSYSEDI (SEQ ID NO: 16) | RSSQSLFDSDDGNTYLD (SEQ ID NO: 17) | TLSYRAS (SEQ ID NO: 5) | MQRMEFPLT (SEQ ID NO: 6) |
| CD9B390 | GGSISNYYWS (SEQ ID NO: 30) | RIFYSGKTN (SEQ ID NO: 31) | GEYSGEYSYSEDI (SEQ ID NO: 32) | RSSQSLLDSDDGNTYVD (SEQ ID NO: 33) | TLSYRAS (SEQ ID NO: 5) | MQRMEFPLT (SEQ ID NO: 6) |

TABLE 1b

VH and VL sequences of exemplary mAbs generated against human CD79b

| ID | VH amino acid sequence SEQ ID NO | VH DNA SEQ ID NO | VL amino acid sequence SEQ ID NO | VL DNA sequence SEQ ID NO |
|---|---|---|---|---|
| CD9B374 | 35 | 36 | 37 | 38 or 213 |
| CD9B330 | 39 | 40 | 41 | 42 |
| CD9B330-N31S | 43 | 44 | 41 | 34 |
| CD9B643 | 45 | 46 | 47 | 48 or 214 |
| CD9B321 | 49 | 50 | 51 | 52 |
| CD9B324 | 39 | 40 | 53 | 54 |
| CD9B332 | 55 | 56 | 57 | 58 |
| CD9B369 | 59 | 60 | 61 | 62 |
| CD9B381 | 63 | 64 | 65 | 66 |
| CD9B389 | 67 | 68 | 69 | 70 |
| CD9B390 | 71 | 72 | 73 | 74 |

In some embodiments, the CD79b-binding arm comprises a heavy chain variable domain comprising a CDR1, a CDR2, and a CDR3 of any one of the antibodies described in Table 1a. In some embodiments, the CD79b-binding arm comprises a light chain variable region comprising a CDR1, a CDR2, and a CDR3 of any one of the antibodies described in Table 1a. In some embodiments, the CD79b-binding arm comprises a heavy chain variable domain comprising a CDR1, a CDR2, and a CDR3 of any one of the antibodies described in Table 1a and a light chain variable region comprising a CDR1, a CDR2, and a CDR3 of any one of the antibodies described in Table 1a. In some embodiments, the CD79b-binding arm competes for binding to CD79b with an antibody or antigen-binding comprising a heavy chain comprising a CDR1, a CDR2, and a CDR3 of any one of the antibodies described in Table 1a and a light chain comprising a CDR1, a CDR2, and a CDR3 of any one of the antibodies described in Table 1a.

In some embodiments, the CD79b-binding arm comprises a heavy chain variable domain of any one of the antibodies described in Table 1b. In some embodiments, the CD79b-binding arm comprises a light chain variable region of any one of the antibodies described in Table 1b. In some embodiments, the CD79b-binding arm comprises a heavy chain variable domain of any one of the antibodies described in Table 1b and a light chain variable region of any one of the antibodies described in Table 1b. In some embodiments, the CD79b-binding arm competes for binding to CD79b with an antibody or antigen-binding comprising a heavy chain variable domain of any one of the antibodies described in Table 1b and a light chain variable domain of any one of the antibodies described in Table 1b.

In some embodiments, the CD79b-binding arm comprises a heavy chain comprising a CDR1, a CDR2, and a CDR3 of any one of the antibodies described in Table 1a. In some embodiments, the CD79b-binding arm comprises a light chain comprising a CDR1, a CDR2, and a CDR3 of any one of the antibodies described in Table 1a. In some embodiments, the CD79b-binding arm comprises a heavy chain comprising a CDR1, a CDR2, and a CDR3 of any one of the antibodies described in Table 1a and a light chain comprising a CDR1, a CDR2, and a CDR3 of any one of the antibodies described in Table 1a.

In some embodiments, the CD79b-binding arm comprises a heavy chain comprising a heavy chain variable domain of any one of the antibodies described in Table 1b. In some embodiments, the CD79b-binding arm comprises a light chain comprising a light chain variable domain of any one of the antibodies described in Table 1b. In some embodiments, the CD79b-binding arm comprises a heavy chain comprising a heavy chain variable domain of any one of the antibodies described in Table 1b and a light chain comprising a light chain variable domain of any one of the antibodies described in Table 1b.

In some embodiments, the CD79b-binding arm comprises a heavy chain CDR1 comprising SEQ ID NO: 1, a heavy chain CDR2 comprising SEQ ID NO: 2, and a heavy chain CDR3 comprising SEQ ID NO: 3. In some embodiments, the CD79b-binding arm comprises a heavy chain CDR1 comprising SEQ ID NO: 1, a heavy chain CDR2 comprising SEQ ID NO: 2, a heavy chain CDR3 comprising SEQ ID NO: 3, a light chain CDR1 comprising SEQ ID NO: 4, a light chain CDR2 comprising SEQ ID NO: 5, and a light chain CDR3 comprising SEQ ID NO: 6. The CD79b-binding arm may comprise human framework sequences. In some embodiments, the CD79b-binding arm comprises a heavy chain variable domain substantially the same as, or identical to, SEQ ID NO: 35. In some embodiments, the CD79b-binding arm comprises a heavy chain variable domain substantially the same as, or identical to, SEQ ID NO: 35 and a light chain variable domain substantially the same as, or identical to, SEQ ID NO: 37. In some embodiments, the CD79b-binding arm comprises a heavy chain variable domain that is encoded by a nucleotide sequence substantially the same as, or identical to, SEQ ID NO: 36. In some embodiments, the CD79b-binding arm comprises a heavy chain variable domain that is encoded by a nucleotide sequence substantially the same as, or identical to, SEQ ID NO: 36 and a light chain variable domain that is encoded by a nucleotide sequence substantially the same as, or identical to, SEQ ID NO: 38 or 213.

In some embodiments, the CD79b-binding arm comprises a heavy chain CDR1 comprising SEQ ID NO: 13, a heavy chain CDR2 comprising SEQ ID NO: 8, and a heavy chain CDR3 comprising SEQ ID NO: 9. In some embodiments, the CD79b-binding arm comprises a heavy chain CDR1 comprising SEQ ID NO: 13, a heavy chain CDR2 comprising SEQ ID NO: 8, a heavy chain CDR3 comprising SEQ ID NO: 9, a light chain CDR1 comprising SEQ ID NO: 10, a light chain CDR2 comprising SEQ ID NO: 11, and a light chain CDR3 comprising SEQ ID NO: 12. The CD79b-binding arm may comprise human framework sequences. In some embodiments, the CD79b-binding arm comprises a heavy chain variable domain substantially the same as, or identical to, SEQ ID NO: 39. In some embodiments, the CD79b-binding arm comprises a heavy chain variable domain substantially the same as, or identical to, SEQ ID NO: 39 and a light chain variable domain substantially the same as, or identical to, SEQ ID NO: 41. In some embodiments, the CD79b-binding arm comprises a heavy chain variable domain that is encoded by a nucleotide sequence substantially the same as, or identical to, SEQ ID NO: 40. In some embodiments, the CD79b-binding arm comprises a heavy chain variable domain that is encoded by a nucleotide sequence substantially the same as, or identical to, SEQ ID NO: 40 and a light chain variable domain that is encoded by a nucleotide sequence substantially the same as, or identical to, SEQ ID NO: 42.

In some embodiments, the CD79b-binding arm comprises a heavy chain CDR1 comprising SEQ ID NO: 7, a heavy chain CDR2 comprising SEQ ID NO: 8, and a heavy chain CDR3 comprising SEQ ID NO: 9. In some embodiments, the CD79b-binding arm comprises a heavy chain CDR1 comprising SEQ ID NO: 7, a heavy chain CDR2 comprising SEQ ID NO: 8, a heavy chain CDR3 comprising SEQ ID NO: 9, a light chain CDR1 comprising SEQ ID NO: 10, a light chain CDR2 comprising SEQ ID NO: 11, and a light chain CDR3 comprising SEQ ID NO: 12. The CD79b-binding arm may comprise human framework sequences. In some embodiments, the CD79b-binding arm comprises a heavy chain variable domain substantially the same as, or identical to, SEQ ID NO: 43. In some embodiments, the CD79b-binding arm comprises a heavy chain variable domain substantially the same as, or identical to, SEQ ID NO: 43 and a light chain variable domain substantially the same as, or identical to, SEQ ID NO: 41. In some embodiments, the CD79b-binding arm comprises a heavy chain variable domain that is encoded by a nucleotide sequence substantially the same as, or identical to, SEQ ID NO: 44. In some embodiments, the CD79b-binding arm comprises a heavy chain variable domain that is encoded by a nucleotide sequence substantially the same as, or identical to, SEQ ID NO: 44 and a light chain variable domain that is encoded by a nucleotide sequence substantially the same as, or identical to, SEQ ID NO: 34.

In some embodiments, the CD79b-binding arm comprises a heavy chain CDR1 comprising SEQ ID NO: 14, a heavy chain CDR2 comprising SEQ ID NO: 15, and a heavy chain CDR3 comprising SEQ ID NO: 16. In some embodiments, the CD79b-binding arm comprises a heavy chain CDR1 comprising SEQ ID NO: 14, a heavy chain CDR2 comprising SEQ ID NO: 15, a heavy chain CDR3 comprising SEQ ID NO: 16, a light chain CDR1 comprising SEQ ID NO: 17, a light chain CDR2 comprising SEQ ID NO: 5, and a light chain CDR3 comprising SEQ ID NO: 6. The CD79b-binding arm may comprise human framework sequences. In some embodiments, the CD79b-binding arm comprises a heavy chain variable domain substantially the same as, or identical to, SEQ ID NO: 45. In some embodiments, the CD79b-binding arm comprises a heavy chain variable domain substantially the same as, or identical to, SEQ ID NO: 45 and a light chain variable domain substantially the same as, or identical to, SEQ ID NO: 47. In some embodiments, the CD79b-binding arm comprises a heavy chain variable domain that is encoded by a nucleotide sequence substantially the same as, or identical to, SEQ ID NO: 46. In some embodiments, the CD79b-binding arm comprises a heavy chain variable domain that is encoded by a nucleotide sequence substantially the same as, or identical to, SEQ ID NO: 46 and a light chain variable domain that is encoded by a nucleotide sequence substantially the same as, or identical to, SEQ ID NO: 48 or 214.

In some embodiments, the CD79b-binding arm comprises a heavy chain CDR1 comprising SEQ ID NO: 18, a heavy chain CDR2 comprising SEQ ID NO: 8, and a heavy chain CDR3 comprising SEQ ID NO: 19. In some embodiments, the CD79b-binding arm comprises a heavy chain CDR1 comprising SEQ ID NO: 18, a heavy chain CDR2 comprising SEQ ID NO: 8, a heavy chain CDR3 comprising SEQ ID NO: 19, a light chain CDR1 comprising SEQ ID NO: 20, a light chain CDR2 comprising SEQ ID NO: 21, and a light chain CDR3 comprising SEQ ID NO: 12. The CD79b-binding arm may comprise human framework sequences. In some embodiments, the CD79b-binding arm comprises a heavy chain variable domain substantially the same as, or identical to, SEQ ID NO: 49. In some embodiments, the CD79b-binding arm comprises a heavy chain variable domain substantially the same as, or identical to, SEQ ID NO: 49 and a light chain variable domain substantially the same as, or identical to, SEQ ID NO: 51. In some embodiments, the CD79b-binding arm comprises a heavy chain variable domain that is encoded by a nucleotide sequence substantially the same as, or identical to, SEQ ID NO: 50. In some embodiments, the CD79b-binding arm comprises a heavy chain variable domain that is encoded by a nucleotide sequence substantially the same as, or identical to, SEQ ID NO: 50 and a light chain variable domain that is encoded by a nucleotide sequence substantially the same as, or identical to, SEQ ID NO: 52.

In some embodiments, the CD79b-binding arm comprises a heavy chain CDR1 comprising SEQ ID NO: 13, a heavy chain CDR2 comprising SEQ ID NO: 8, and a heavy chain CDR3 comprising SEQ ID NO: 9. In some embodiments, the CD79b-binding arm comprises a heavy chain CDR1 comprising SEQ ID NO: 13, a heavy chain CDR2 comprising SEQ ID NO: 8, a heavy chain CDR3 comprising SEQ ID NO: 9, a light chain CDR1 comprising SEQ ID NO: 10, a light chain CDR2 comprising SEQ ID NO: 11, and a light chain CDR3 comprising SEQ ID NO: 12. The CD79b-binding arm may comprise human framework sequences. In some embodiments, the CD79b-binding arm comprises a heavy chain variable domain substantially the same as, or identical to, SEQ ID NO: 39. In some embodiments, the CD79b-binding arm comprises a heavy chain variable domain substantially the same as, or identical to, SEQ ID NO: 39 and a light chain variable domain substantially the same as, or identical to, SEQ ID NO: 53. In some embodiments, the CD79b-binding arm comprises a heavy chain variable domain that is encoded by a nucleotide sequence substantially the same as, or identical to, SEQ ID NO: 40. In some embodiments, the CD79b-binding arm comprises a heavy chain variable domain that is encoded by a nucleotide sequence substantially the same as, or identical to, SEQ ID NO: 40 and a light chain variable domain that is encoded by a nucleotide sequence substantially the same as, or identical to, SEQ ID NO: 54.

In some embodiments, the CD79b-binding arm comprises a heavy chain CDR1 comprising SEQ ID NO: 13, a heavy chain CDR2 comprising SEQ ID NO: 8, and a heavy chain CDR3 comprising SEQ ID NO: 9. In some embodiments, the CD79b-binding arm comprises a heavy chain CDR1 comprising SEQ ID NO: 13, a heavy chain CDR2 comprising SEQ ID NO: 8, a heavy chain CDR3 comprising SEQ ID NO: 9, a light chain CDR1 comprising SEQ ID NO: 10, a light chain CDR2 comprising SEQ ID NO: 11, and a light chain CDR3 comprising SEQ ID NO: 12. The CD79b-binding arm may comprise human framework sequences. In some embodiments, the CD79b-binding arm comprises a heavy chain variable domain substantially the same as, or identical to, SEQ ID NO: 55. In some embodiments, the CD79b-binding arm comprises a heavy chain variable domain substantially the same as, or identical to, SEQ ID NO: 55 and a light chain variable domain substantially the same as, or identical to, SEQ ID NO: 57. In some embodiments, the CD79b-binding arm comprises a heavy chain variable domain that is encoded by a nucleotide sequence substantially the same as, or identical to, SEQ ID NO: 56. In some embodiments, the CD79b-binding arm comprises a heavy chain variable domain that is encoded by a nucleotide sequence substantially the same as, or identical to, SEQ ID NO: 56 and a light chain variable domain that is encoded by a nucleotide sequence substantially the same as, or identical to, SEQ ID NO: 58.

In some embodiments, the CD79b-binding arm comprises a heavy chain CDR1 comprising SEQ ID NO: 22, a heavy chain CDR2 comprising SEQ ID NO: 23, and a heavy chain CDR3 comprising SEQ ID NO: 24. In some embodiments, the CD79b-binding arm comprises a heavy chain CDR1 comprising SEQ ID NO: 22, a heavy chain CDR2 comprising SEQ ID NO: 23, a heavy chain CDR3 comprising SEQ ID NO: 24, a light chain CDR1 comprising SEQ ID NO: 25, a light chain CDR2 comprising SEQ ID NO: 5, and a light chain CDR3 comprising SEQ ID NO: 6. The CD79b-binding arm may comprise human framework sequences. In some embodiments, the CD79b-binding arm comprises a heavy chain variable domain substantially the same as, or identical to, SEQ ID NO: 59. In some embodiments, the CD79b-binding arm comprises a heavy chain variable domain substantially the same as, or identical to, SEQ ID NO: 59 and a light chain variable domain substantially the same as, or identical to, SEQ ID NO: 61. In some embodiments, the CD79b-binding arm comprises a heavy chain variable domain that is encoded by a nucleotide sequence substantially the same as, or identical to, SEQ ID NO: 60. In some embodiments, the CD79b-binding arm comprises a heavy chain variable domain that is encoded by a nucleotide sequence substantially the same as, or identical to, SEQ ID NO: 60 and a light chain variable domain that is encoded by a nucleotide sequence substantially the same as, or identical to, SEQ ID NO: 62.

In some embodiments, the CD79b-binding arm comprises a heavy chain CDR1 comprising SEQ ID NO: 22, a heavy chain CDR2 comprising SEQ ID NO: 26, and a heavy chain CDR3 comprising SEQ ID NO: 27. In some embodiments, the CD79b-binding arm comprises a heavy chain CDR1 comprising SEQ ID NO: 22, a heavy chain CDR2 comprising SEQ ID NO: 26, a heavy chain CDR3 comprising SEQ ID NO: 27, a light chain CDR1 comprising SEQ ID NO: 28, a light chain CDR2 comprising SEQ ID NO: 5, and a light chain CDR3 comprising SEQ ID NO: 29. The CD79b-binding arm may comprise human framework sequences. In some embodiments, the CD79b-binding arm comprises a heavy chain variable domain substantially the same as, or identical to, SEQ ID NO: 63. In some embodiments, the CD79b-binding arm comprises a heavy chain variable domain substantially the same as, or identical to, SEQ ID NO: 63 and a light chain variable domain substantially the same as, or identical to, SEQ ID NO: 65. In some embodiments, the CD79b-binding arm comprises a heavy chain variable domain that is encoded by a nucleotide sequence substantially the same as, or identical to, SEQ ID NO: 64. In some embodiments, the CD79b-binding arm comprises a heavy chain variable domain that is encoded by a nucleotide sequence substantially the same as, or identical to, SEQ ID NO: 64 and a light chain variable domain that is encoded by a nucleotide sequence substantially the same as, or identical to, SEQ ID NO: 66.

In some embodiments, the CD79b-binding arm comprises a heavy chain CDR1 comprising SEQ ID NO: 14, a heavy chain CDR2 comprising SEQ ID NO: 15, and a heavy chain CDR3 comprising SEQ ID NO: 16. In some embodiments, the CD79b-binding arm comprises a heavy chain CDR1 comprising SEQ ID NO: 14, a heavy chain CDR2 comprising SEQ ID NO: 15, a heavy chain CDR3 comprising SEQ ID NO: 16, a light chain CDR1 comprising SEQ ID NO: 17, a light chain CDR2 comprising SEQ ID NO: 5, and a light chain CDR3 comprising SEQ ID NO: 6. The CD79b-binding arm may comprise human framework sequences. In some embodiments, the CD79b-binding arm comprises a heavy chain variable domain substantially the same as, or identical to, SEQ ID NO: 67. In some embodiments, the CD79b-binding arm comprises a heavy chain variable domain substantially the same as, or identical to, SEQ ID NO: 67 and a light chain variable domain substantially the same as, or identical to, SEQ ID NO: 69. In some embodiments, the CD79b-binding arm comprises a heavy chain variable domain that is encoded by a nucleotide sequence substantially the same as, or identical to, SEQ ID NO: 68. In some embodiments, the CD79b-binding arm comprises a heavy chain variable domain that is encoded by a nucleotide sequence substantially the same as, or identical to, SEQ ID NO: 68 and a light chain variable domain that is encoded by a nucleotide sequence substantially the same as, or identical to, SEQ ID NO: 70.

In some embodiments, the CD79b-binding arm comprises a heavy chain CDR1 comprising SEQ ID NO: 30, a heavy chain CDR2 comprising SEQ ID NO: 31, and a heavy chain CDR3 comprising SEQ ID NO: 32. In some embodiments, the CD79b-binding arm comprises a heavy chain CDR1 comprising SEQ ID NO: 30, a heavy chain CDR2 comprising SEQ ID NO: 31, a heavy chain CDR3 comprising SEQ ID NO: 32, a light chain CDR1 comprising SEQ ID NO: 33, a light chain CDR2 comprising SEQ ID NO: 5, and a light chain CDR3 comprising SEQ ID NO: 6. The CD79b-binding arm may comprise human framework sequences. In some embodiments, the CD79b-binding arm comprises a heavy chain variable domain substantially the same as, or identical to, SEQ ID NO: 71. In some embodiments, the CD79b-binding arm comprises a heavy chain variable domain substantially the same as, or identical to, SEQ ID NO: 71 and a light chain variable domain substantially the same as, or identical to, SEQ ID NO: 73. In some embodiments, the CD79b-binding arm comprises a heavy chain variable domain that is encoded by a nucleotide sequence substantially the same as, or identical to, SEQ ID NO: 72. In some embodiments, the CD79b-binding arm comprises a heavy chain variable domain that is encoded by a nucleotide sequence substantially the same as, or identical to, SEQ ID NO: 72 and a light chain variable domain that is encoded by a nucleotide sequence substantially the same as, or identical to, SEQ ID NO: 74.

The CD79b-binding arm may be derived from any species by recombinant means. For example, the CD79b antigen-binding arm may be derived from mouse, rat, goat, horse, swine, bovine, chicken, rabbit, camelid, donkey, human, or chimeric versions thereof. For use in administration to humans, non-human derived antigen-binding fragments may be genetically or structurally altered to be less antigenic upon administration to a human patient. In some embodiments, the CD79b-binding arm comprises antigen-binding fragments which is chimeric.

In some embodiments, the CD79b-binding arm comprises humanized antigen-binding fragments. Humanized antigen-binding fragments may be derived from chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies or antigen-binding fragments are human immunoglobulins (recipient antibody) or antigen-binding fragments in which residues from a complementary-determining region (CDR) of the recipient are replaced by residues from a CDR of a non-human species (donor antibody) such as mouse, rat or rabbit having the desired specificity, affinity, and capacity. In general, the humanized antibody antigen-binding fragments will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody antigen-binding fragments may include at least a portion of an immunoglobulin constant region (Fc), typically that of a human immunoglobulin.

CD20-Binding Arm

The multispecific antibodies (e.g., trispecific or bispecific antibodies) described herein may comprise an antigen-binding arm specific for CD20. In some embodiments, the CD20-binding arm binds human CD20. In some embodiments, CD20-binding arm binds human CD20 and cynomolgus monkey CD20, preferably the extracellular domain thereof. In some embodiments, CD20-binding arm binds human CD20 but not to cynomolgus monkey CD20. In some embodiments, the CD20-binding arm binds to the epitope on CD20 as rituximab. In some embodiments, the CD20-binding arm may bind to CD20 with an affinity of $5 \times 10^{-7}$M or less, such as $1 \times 10^{-7}$M or less, $5 \times 10^{-8}$M or less, $1 \times 10^{-8}$M or less, $5 \times 10^{-9}$M or less, or $1 \times 10^{-9}$M or less. In one embodiment, the CD20-binding arm binds to CD20 with an affinity of about $1 \times 10^{-9}$M, about $2 \times 10^{-9}$M, about $3 \times 10^{-9}$M, about $4 \times 10^{-9}$M, about $5 \times 10^{-9}$M, about $6 \times 10^{-9}$M, about $7 \times 10^{-9}$M, about $8 \times 10^{-9}$M, about $9 \times 10^{-9}$M, about $1 \times 10^{-8}$M, about $2 \times 10^{-8}$M, about $3 \times 10^{-8}$M, about $4 \times 10^{-8}$M, about $5 \times 10^{-8}$M, about $6 \times 10^{-8}$M, about $7 \times 10^{-8}$M, about $8 \times 10^{-8}$M, about $9 \times 10^{-8}$M, or about $1 \times 10^{-7}$M.

In some embodiments, the CD20-binding arm comprises a heavy chain CDR1, CDR2, and CDR3 derived from an antibody clone as described in Table 2a. In some embodiments, the CD20-binding arm comprises a light chain CDR1, CDR2, and CDR3 derived from an antibody clone as described in Table 2a. In some embodiments, the CD20-binding arm comprises heavy chain CDR1, CDR2, and CDR3 and light chain CDR1, CDR2, and CDR3 derived from an antibody clone as described in Table 2a. In some exemplary embodiments, the CD20-binding arm comprises heavy chain CDR1, CDR2, and CDR3 and light chain CDR1, CDR2, and CDR3 of clone C20B648.

In some exemplary embodiments, the CD20-binding arm comprises a heavy chain variable domain derived from an antibody clone as described in Table 2b. In some exemplary embodiments, the CD20-binding arm comprises heavy chain variable domain and light chain variable domain derived from an antibody clone as described in Table 2b.

Table 2a and Table 2b provide a summary of CDR and VH and VL sequences of some exemplary CD20-specific antibodies described herein:

TABLE 2a

CDR sequences of exemplary mAbs generated against human CD20

| ID | HC-CDR1 | HC-CDR2 | HC-CDR3 | LC-CDR1 | LC-CDR2 | LC-CDR3 |
|---|---|---|---|---|---|---|
| C20B22 | GYTFTSYNMH (SEQ ID NO: 115) | AIYPGNGDTS (SEQ ID NO: 116) | STYYGGDWYFNV (SEQ ID NO: 117) | RASSSVSYIH (SEQ ID NO: 118) | ATSNLAS (SEQ ID NO: 119) | QQWTSNPPT (SEQ ID NO: 120) |
| C20B648 | GYTFSSYNMH (SEQ ID NO: 121) | A1YPGAGDTS (SEQ ID NO: 122) | SNYYGSSGWYFDV (SEQ ID NO: 123) | RASLSVSSMH (SEQ ID NO: 124) | ATSNLAS (SEQ ID NO: 119) | QQWIFNPPT (SEQ ID NO: 125) |
| 5O10GL | GYTFTSYNMH (SEQ ID NO: 115) | AIYPGNGDTS (SEQ ID NO: 116) | VYYGSNYWYFDV (SEQ ID NO: 95) | RASSSVSYMH (SEQ ID NO: 96) | ATSNLAS (SEQ ID NO: 119) | QQWIFNPPT (SEQ ID NO: 125) |
| 4A16GL | GYTFSSYNMH (SEQ ID NO: 121) | AIYPGNGDTS (SEQ ID NO: 116) | SNYYGSSGWYFDV (SEQ ID NO: 123) | RASLSVSSMH (SEQ ID NO: 124) | ATSNLAS (SEQ ID NO: 119) | QQWIFNPPT (SEQ ID NO: 125) |

TABLE 2b

VH and VL sequences of exemplary mAbs generated against human CD20

| ID | VH amino acid sequence SEQ ID NO | VH DNA sequence SEQ ID NO | VL amino acid sequence SEQ ID NO | VL DNA sequence SEQ ID NO |
|---|---|---|---|---|
| C20B22 | 126 | 127 | 128 | 129 |
| C20B648 | 130 | 131 | 132 | 133 |
| 5O10GL | 134 | 135 | 136 | 137 |
| 4A16GL | 138 | 139 | 140 | 141 |

In some embodiments, the CD20-binding arm comprises a heavy chain variable domain comprising a CDR1, a CDR2, and a CDR3 of any one of the antibodies described in Table 2a. In some embodiments, the CD20-binding arm comprises a light chain variable domain comprising a CDR1, a CDR2, and a CDR3 of any one of the antibodies described in Table 2a. In some embodiments, the CD20-binding arm comprises a heavy chain variable domain comprising a CDR1, a CDR2, and a CDR3 of any one of the antibodies described in Table 2a and a light chain variable domain comprising a CDR1, a CDR2, and a CDR3 of any one of the antibodies described in Table 2a. In some embodiments, the CD20-binding arm competes for binding to CD20 with an antibody or antigen-binding comprising a heavy chain comprising a CDR1, a CDR2, and a CDR3 of any one of the antibodies described in Table 2a and a light chain comprising a CDR1, a CDR2, and a CDR3 of any one of the antibodies described in Table 2a.

In some embodiments, the CD20-binding arm comprises a heavy chain variable domain of any one of the antibodies described in Table 2b. In some embodiments, the CD20-binding arm comprises a light chain variable region of any one of the antibodies described in Table 2b. In some embodiments, the CD20-binding arm comprises a heavy chain variable domain of any one of the antibodies described in Table 2b and a light chain variable region of any one of the antibodies described in Table 2b. In some embodiments, the CD20-binding arm competes for binding to CD20 with an antibody or antigen-binding comprising a heavy chain variable domain of any one of the antibodies described in Table 2b and a light chain variable domain of any one of the antibodies described in Table 2b.

In some embodiments, the CD20-binding arm comprises a heavy chain comprising a CDR1, a CDR2, and a CDR3 of any one of the antibodies described in Table 2a. In some embodiments, the CD20-binding arm comprises a light chain comprising a CDR1, a CDR2, and a CDR3 of any one of the antibodies described in Table 2a. In some embodiments, the CD20-binding arm comprises a heavy chain comprising a CDR1, a CDR2, and a CDR3 of any one of the antibodies described in Table 2 and a light chain comprising a CDR1, a CDR2, and a CDR3 of any one of the antibodies described in Table 2a.

In some embodiments, the CD20-binding arm comprises a heavy chain comprising a heavy chain variable domain of any one of the antibodies described in Table 2b. In some embodiments, the CD20-binding arm comprises a light chain comprising a light chain variable domain of any one of the antibodies described in Table 2b. In some embodiments, the CD20-binding arm comprises a heavy chain comprising a heavy chain variable domain of any one of the antibodies described in Table 2b and a light chain comprising a light chain variable domain of any one of the antibodies described in Table 2b.

In some embodiments, the CD20-binding arm comprises a heavy chain CDR1 comprising SEQ ID NO: 115, a heavy chain CDR2 comprising SEQ ID NO: 116, and a heavy chain CDR3 comprising SEQ ID NO: 117. In some embodiments, the CD20-binding arm comprises a heavy chain CDR1 comprising SEQ ID NO: 115, a heavy chain CDR2 comprising SEQ ID NO: 116, a heavy chain CDR3 comprising SEQ ID NO: 117, a light chain CDR1 comprising SEQ ID NO: 118, a light chain CDR2 comprising SEQ ID NO: 119, and a light chain CDR3 comprising SEQ ID NO: 120. The CD20-binding arm may comprise human framework sequences. In some embodiments, the CD20-binding arm comprises a heavy chain variable domain substantially the same as, or identical to, SEQ ID NO: 126. In some embodiments, the CD20-binding arm comprises a heavy chain variable domain substantially the same as, or identical to, SEQ ID NO: 126 and a light chain variable domain substantially the same as, or identical to, SEQ ID NO: 128. In some embodiments, the CD20-binding arm comprises a heavy chain variable domain that is encoded by a nucleotide sequence substantially the same as, or identical to, SEQ ID NO: 127. In some embodiments, the CD20-binding arm comprises a heavy chain variable domain that is encoded by a nucleotide sequence substantially the same as, or identical to, SEQ ID NO: 127 and a light chain variable domain that is encoded by a nucleotide sequence substantially the same as, or identical to, SEQ ID NO: 129.

In some embodiments, the CD20-binding arm comprises a heavy chain CDR1 comprising SEQ ID NO: 121, a heavy chain CDR2 comprising SEQ ID NO: 122, and a heavy chain CDR3 comprising SEQ ID NO: 123. In some embodiments, the CD20-binding arm comprises a heavy chain CDR1 comprising SEQ ID NO: 121, a heavy chain CDR2 comprising SEQ ID NO: 122, a heavy chain CDR3 comprising SEQ ID NO: 123, a light chain CDR1 comprising SEQ ID NO: 124, a light chain CDR2 comprising SEQ ID NO: 119, and a light chain CDR3 comprising SEQ ID NO: 125. The CD20-binding arm may comprise human framework sequences. In some embodiments, the CD20-binding arm comprises a heavy chain variable domain substantially the same as, or identical to, SEQ ID NO: 130. In some embodiments, the CD20-binding arm comprises a heavy chain variable domain substantially the same as, or identical to, SEQ ID NO: 130 and a light chain variable domain substantially the same as, or identical to, SEQ ID NO: 132. In some embodiments, the CD20-binding arm comprises a heavy chain variable domain that is encoded by a nucleotide sequence substantially the same as, or identical to, SEQ ID NO: 131. In some embodiments, the CD20-binding arm comprises a heavy chain variable domain that is encoded by a nucleotide sequence substantially the same as, or identical to, SEQ ID NO: 131 and a light chain variable domain that is encoded by a nucleotide sequence substantially the same as, or identical to, SEQ ID NO: 133.

In some embodiments, the CD20-binding arm comprises a heavy chain CDR1 comprising SEQ ID NO: 115, a heavy chain CDR2 comprising SEQ ID NO: 116, and a heavy chain CDR3 comprising SEQ ID NO: 95. In some embodiments, the CD20-binding arm comprises a heavy chain CDR1 comprising SEQ ID NO: 115, a heavy chain CDR2 comprising SEQ ID NO: 116, a heavy chain CDR3 comprising SEQ ID NO: 95, a light chain CDR1 comprising SEQ ID NO: 96, a light chain CDR2 comprising SEQ ID NO: 119, and a light chain CDR3 comprising SEQ ID NO: 125. The CD20-binding arm may comprise human framework sequences. In some embodiments, the CD20-binding arm comprises a heavy chain variable domain substantially the same as, or identical to, SEQ ID NO: 134. In some embodiments, the CD20-binding arm comprises a heavy chain variable domain substantially the same as, or identical to, SEQ ID NO: 134 and a light chain variable domain substantially the same as, or identical to, SEQ ID NO: 136. In some embodiments, the CD20-binding arm comprises a heavy chain variable domain that is encoded by a nucleotide sequence substantially the same as, or identical to, SEQ ID NO: 135. In some embodiments, the CD20-binding arm comprises a heavy chain variable domain that is encoded by a nucleotide sequence substantially the same as, or identical to, SEQ ID NO: 135 and a light chain variable domain that is encoded by a nucleotide sequence substantially the same as, or identical to, SEQ ID NO: 137.

In some embodiments, the CD20-binding arm comprises a heavy chain CDR1 comprising SEQ ID NO: 121, a heavy chain CDR2 comprising SEQ ID NO: 116, and a heavy chain CDR3 comprising SEQ ID NO: 123. In some embodiments, the CD20-binding arm comprises a heavy chain CDR1 comprising SEQ ID NO: 121, a heavy chain CDR2 comprising SEQ ID NO: 116, a heavy chain CDR3 comprising SEQ ID NO: 123, a light chain CDR1 comprising SEQ ID NO: 124, a light chain CDR2 comprising SEQ ID NO: 119, and a light chain CDR3 comprising SEQ ID NO: 125. The CD20-binding arm may comprise human framework sequences. In some embodiments, the CD20-binding arm comprises a heavy chain variable domain substantially the same as, or identical to, SEQ ID NO: 138. In some embodiments, the CD20-binding arm comprises a heavy chain variable domain substantially the same as, or identical to, SEQ ID NO: 138 and a light chain variable domain substantially the same as, or identical to, SEQ ID NO: 140. In some embodiments, the CD20-binding arm comprises a heavy chain variable domain that is encoded by a nucleotide sequence substantially the same as, or identical to, SEQ ID NO: 139. In some embodiments, the CD20-binding arm comprises a heavy chain variable domain that is encoded by a nucleotide sequence substantially the same as, or identical to, SEQ ID NO: 139 and a light chain variable domain that is encoded by a nucleotide sequence substantially the same as, or identical to, SEQ ID NO: 141.

The CD20-binding arm may be derived from any species by recombinant means. For example, the CD20 antigen-binding arm may be derived from mouse, rat, goat, horse, swine, bovine, chicken, rabbit, camelid, donkey, human, or chimeric versions thereof. For use in administration to humans, non-human derived antigen-binding fragments may be genetically or structurally altered to be less antigenic upon administration to a human patient. In some embodiments, the CD20-binding arm comprises antigen-binding fragments which is chimeric In some embodiments, the CD20-binding arm comprises humanized antigen-binding fragments. Humanized antigen-binding fragments may be derived from chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies or antigen-binding fragments are human immunoglobulins (recipient antibody) or antigen-binding fragments in which residues from a complementary-determining region (CDR) of the recipient are replaced by residues from a CDR of a non-human species (donor antibody) such as mouse, rat or rabbit having the desired specificity, affinity, and capacity. In general, the humanized antibody antigen-binding fragments will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody antigen-binding fragments may include at least a portion of an immunoglobulin constant region (Fc), typically that of a human immunoglobulin.

CD3-Binding Arm

The multispecific antibodies (e.g., trispecific or bispecific antibodies) described herein comprise an antigen-binding arm that binds CD3. In some preferred embodiments, the CD3-specific arm of the multispecific antibodies described herein is derived from a CD3-specific antibody that binds and activates human primary T cells and/or cynomolgus monkey primary T cells. In some embodiments, the CD3-binding arm binds to an epitope at the N-terminus of CD3ε. In some embodiments, the CD3-binding arm binds to residues 54-58 (GSEIL; SEQ ID NO: 257), residues 74-75 (NI), and/or residues 100-105 (PRGSKP; SEQ ID NO: 258) of human CD3ε. In some embodiments, the CD3-binding arm binds to residues 22-35 (QDGNEEMGGITQTP (SEQ ID NO: 256)) of the CD3ε chain. Such CD3-binding arms may bind to CD3 with an affinity of $5 \times 10^{-7}$M or less, such as $1 \times 10^{-7}$M or less, $5 \times 10^{-8}$M or less, $1 \times 10^{-8}$M or less, $5 \times 10^{-9}$M or less, or $1 \times 10^{-9}$M or less. In one embodiment, the CD3-binding arm binds to the CD3 with an affinity of about $1 \times 10^{-8}$M, about $2 \times 10^{-8}$M, about $3 \times 10^{-8}$M, about $4×10^{-8}$M, about $5×10^{-8}$M, about $6×10^{-8}$M, about $7×10^{-8}$M, about $8×10^{-8}$M, about $9×10^{-8}$M, or about $1×10^{-8}$M.

In some embodiments, such CD3-binding arms may have weak binding (e.g., low micromolar or weaker) to CD3. Weak CD3 binding may result in better T cell fitness, lesser T-cell exhaustion, lower risk for cytokine release syndrome (CRS), better safety, and/or may enable co-stimulatory combinations to enhance T cell persistence.

Human CD3ε is described under UniProt P07766 (CD3E_HUMAN). An anti CD3ε antibody described in the state of the art is SP34 (Yang S J, The Journal of Immunology (1986) 137; 1097-1100). SP34 reacts with both primate and human CD3. SP34 is available from Pharmingen. A further anti CD3 antibody described in the state of the art is UCHT-1 (see WO2000041474). A further anti-CD3 antibody described in the state of the art is BC-3 (Fred Hutchinson Cancer Research Institute; used in Phase I/II trials of GvHD, Anasetti et al., Transplantation 54: 844 (1992)). SP34 differs from UCHT-1 and BC-3 in that SP-34 recognizes an epitope present on solely the F chain of CD3 (see Salmeron et al., (1991) J. Immunol. 147: 3047) whereas UCHT-1 and BC-3 recognize an epitope contributed by both the F and 7 chains. The sequence of an antibody with the same sequence as of antibody SP34 is mentioned in WO2008119565, WO2008119566, WO2008119567, WO2010037836, WO2010037837 and WO2010037838. A sequence which is 96% identical to VH of antibody SP34 is mentioned in U.S. Pat. No. 8,236,308 (WO2007042261).

In some embodiments, the CD3-binding arm contacts an epitope including the six N-terminal amino acids of CD3ε. In some embodiments, the CD3-specific binding arm of the multispecific antibody is derived from the mouse monoclonal antibody SP34, a mouse IgG3/lambda isotype. In some embodiments, the CD3-binding arm comprises the CDRs of antibody SP34. Such CD3-binding arms may bind to CD3 with an affinity of $5×10^{-7}$M or less, such as $1×10^{-7}$M or less, $5×10^{-8}$M or less, $1×10^{-8}$M or less, $5×10^{-9}$M or less, or $1×10^{-9}$M or less. The CD3-specific binding arm may be a humanized version of an arm of mouse monoclonal antibody SP34. Human framework adaptation (HFA) may be used to humanize the anti-CD3 antibody from which the CD3-specific arm is derived.

In some embodiments, the CD3-binding arm comprises a heavy chain CDR1, CDR2, and CDR3 of any one of the antibodies described in Table 3. In some embodiments, the CD3-binding arm comprises a light chain CDR1, CDR2, and CDR3 of any one of the antibodies described in Table 3. In some embodiments, the CD3-binding arm comprises a heavy chain comprising a CDR1, a CDR2, and a CDR3 of any one of the antibodies described in Table 3 and a light chain comprising a CDR1, a CDR2, and a CDR3 of any one of the antibodies described in Table 3. In some embodiments of the multispecific antibodies, the CD3-binding arm comprises a heavy chain and light chain pair selected from Table 3.

Table 3 provides a summary of examples of some CD3-specific antibodies described herein:

TABLE 3

Heavy chain and light chain CDR, VH, and VL sequences of exemplary CD3-specific antibodies and antigen-binding fragments

| ID | Heavy Chain | Light Chain |
|---|---|---|
| CD3B2030 | CDR1: GYTFTRSTMH (SEQ ID NO: 76)<br>CDR2: YINPSSAYTN (SEQ ID NO: 77)<br>CDR3: PQVHYDYNGFPY (SEQ ID NO: 78)<br>VH:<br>QVQLVQSGAEVKKPGSSVKVSCKASGYTFT<br>RSTMHWVKQAPGQGLEWIGYINPSSAYTNY<br>NQKFQGRVTLTADKSTSTAYMELSSLRSED<br>TAVYYCASPQVHYDYNGFPYWGQGTLVTV<br>SS (SEQ ID NO: 97)<br>VH DNA sequence (SEQ ID NO: 98) | CDR1: SASSSVSYMN (SEQ ID NO: 79)<br>CDR2: DSSKLAS (SEQ ID NO: 80)<br>CDR3: QQWSRNPPT (SEQ ID NO: 81)<br>VL:<br>EIVLTQSPATLSASPGERVTLSCSASSSVSYMNW<br>YQQKPGQAPRRWIYDSSKLASGVPARFSGSGSG<br>RDYTLTISSLEPEDFAVYYCQQWSRNPPTFGGGT<br>KVEIK (SEQ ID NO: 99)<br>VL DNA sequence (SEQ ID NO: 100) |
| CD3B2030-N106A | CDR1: GYTFTRSTMH (SEQ ID NO: 76)<br>CDR2: YINPSSAYTN (SEQ ID NO: 77)<br>CDR3: PQVHYDYAGFPY (SEQ ID NO: 75)<br>VH:<br>QVQLVQSGAEVKKPGSSVKVSCKASGYTFT<br>RSTMHWVKQAPGQGLEWIGYINPSSAYTNY<br>NQKFQGRVTLTADKSTSTAYMELSSLRSED<br>TAVYYCASPQVHYDYAGFPYWGQGTLVTV<br>SS (SEQ ID NO: 101)<br>VH DNA sequence (SEQ ID NO: 102) | CDR1: SASSSVSYMN (SEQ ID NO: 79)<br>CDR2: DSSKLAS (SEQ ID NO: 80)<br>CDR3: QQWSRNPPT (SEQ ID NO: 81)<br>VL:<br>EIVLTQSPATLSASPGERVTLSCSASSSVSYMNW<br>YQQKPGQAPRRWIYDSSKLASGVPARFSGSGSG<br>RDYTLTISSLEPEDFAVYYCQQWSRNPPTFGGGT<br>KVEIK (SEQ ID NO: 99)<br>VL DNA sequence (SEQ ID NO: 100) |
| CD3B2089 | CDR1: GYTFTRSTMH (SEQ ID NO: 76)<br>CDR2: YINPSSAYTN (SEQ ID NO: 77)<br>CDR3: PQVHYDYNGFPY (SEQ ID NO: 78)<br>VH:<br>QVQLVQSGAEVKKPGSSVKVSCKASGYTFT<br>RSTMHWVRQAPGQGLEWMGYINPSSAYTN<br>YAQKFQGRVTLTADKSTSTAYMELSSLRSE<br>DTAVYYCASPQVHYDYNGFPYWGQGTLVT<br>VSS (SEQ ID NO: 103)<br>VH DNA sequence (SEQ ID NO: 104) | CDR1: SASSSVSYMN (SEQ ID NO: 79)<br>CDR2: DSSKLAS (SEQ ID NO: 80)<br>CDR3: QQWSRNPPT (SEQ ID NO: 81)<br>VL:<br>EIVLTQSPATLSASPGERVTLSCSASSSVSYMNW<br>YQQKPGQAPRRWIYDSSKLASGVPARFSGSGSG<br>RDYTLTISSLEPEDFAVYYCQQWSRNPPTFGGGT<br>KVEIK<br>(SEQ ID NO: 99)<br>VL DNA sequence (SEQ ID NO: 100) |

TABLE 3-continued

Heavy chain and light chain CDR, VH, and VL sequences of exemplary CD3-specific antibodies and antigen-binding fragments

| ID | Heavy Chain | Light Chain |
|---|---|---|
| CD3B2089-N106G | CDR1: GYTFTRSTMH (SEQ ID NO: 76)<br>CDR2: YINPSSAYTN (SEQ ID NO: 77)<br>CDR3: PQVHYDYGGFPY (SEQ ID NO: 82)<br>VH:<br>QVQLVQSGAEVKKPGSSVKVSCKASGYTFT<br>RSTMHWVRQAPGQGLEWMGYINPSSAYTN<br>YAQKFQGRVTLTADKSTSTAYMELSSLRSE<br>DTAVYYCASPQVHYDYGGFPYWGQGTLVT<br>VSS (SEQ ID NO: 105)<br>VH DNA sequence (SEQ ID NO: 106) | CDR1: SASSSVSYMN (SEQ ID NO: 79)<br>CDR2: DSSKLAS (SEQ ID NO: 80)<br>CDR3: QQWSRNPPT (SEQ ID NO: 81)<br>VL:<br>EIVLTQSPATLSASPGERVTLSCSASSSVSYMNW<br>YQQKPGQAPRRWIYDSSKLASGVPARFSGSGSG<br>RDYTLTISSLEPEDFAVYYCQQWSRNPPTFGGGT<br>KVEIK (SEQ ID NO: 99)<br>VL DNA sequence (SEQ ID NO: 100) |
| CD3W245 | CDR 1: GFTFSRYNMN (SEQ ID NO: 83)<br>CDR 2: SISTSSNYIY (SEQ ID NO: 84)<br>CDR 3: GWGPFDY (SEQ ID NO: 85)<br>VH:<br>EVQLVESGGGLVKPGGSLRLSCAASGFTFSR<br>YNMNWVRQAPGKGLEWVSSISTSSNYIYYA<br>DSVKGRFTFSRDNAKNSLDLQMSGLRAEDT<br>AIYYCTRGWGPFDYWGQGTLVTVSS (SEQ ID NO: 107)<br>VH DNA sequence (SEQ ID NO: 108) | CDR 1: RARQSIGTAIH (SEQ ID NO: 86)<br>CDR 2: YASESIS (SEQ ID NO: 87)<br>CDR 3: QQSGSWPYT (SEQ ID NO: 88)<br>VL:<br>DIQMTQSPSSLSASVGDRVTITCRARQSIGTAIHW<br>YQQKPGKAPKLLIKYASESISGVPSRFSGSGSGTD<br>FTLTISSLQPEDFATYYCQQSGSWPYTFGQGTKL<br>EIK (SEQ ID NO: 109)<br>VL DNA sequence (SEQ ID NO: 110) |
| CD3B376 | CDR 1: GDSVFNNNAAWS (SEQ ID NO: 193)<br>CDR 2: RTYYRSKWLYD (SEQ ID NO: 194)<br>CDR 3: GYSSSFDY (SEQ ID NO: 195)<br>VH:<br>QVQLQQSGPRLVRPSQTLSLTCAISGDSVFN<br>NNAAWSWIRQSPSRGLEWLGRTYYRSKWL<br>YDYAVSVKSRITVNPDTSRNQFTLQLNSVTP<br>EDTALYYCARGYSSSFDYWGQGTLVTVSS<br>(SEQ ID NO: 196)<br>Heavy chain:<br>QVQLQQSGPRLVRPSQTLSLTCAISGDSVFN<br>NNAAWSWIRQSPSRGLEWLGRTYYRSKWL<br>YDYAVSVKSRITVNPDTSRNQFTLQLNSVTP<br>EDTALYYCARGYSSSFDYWGQGTLVTVSSA<br>STKGPSVFPLAPSSKSTSGGT AALGCLVKDY<br>FPEPVTVSWNSGALTSGVHTFPAVLQSSGLY<br>SLSSVVTVPSSSLGTQTYICNVNHKPSNTKV<br>DKKVEPKSCDKTHTCPPCPAPEAAGGPSVFL<br>FPPKPKDTLMISRTPEVTCVVVSVSHEDPEV<br>KFNWYVDGVEVHNAKTKPREEQYNSTYRV<br>VSVLTVLHQDWLNGKEYKCKVSNKALPAPI<br>EKTISKAKGQPREPQVYTLPPSREEMTKNQV<br>SLSCAVKGFYPSDIAVEWESNGQPENNYKT<br>TPPVLDSDGSFFLVSKLTVDKSRWQQGNVF<br>SCSVMHEALHNRFTQKSLSLSPGK (SEQ ID NO: 197) | CDR 1: TGTSSNIGTYKFVS (SEQ ID NO: 198)<br>CDR 2: EVSKRPS (SEQ ID NO: 199)<br>CDR 3: VSYAGSGTLL (SEQ ID NO: 200)<br>VL:<br>QSALTQPASVSGSPGQSITISCTGTSSNIGTYKFVS<br>WYQQHPDKAPKVLLYEVSKRPSGVSSRFSGSKS<br>GNTASLTISGLQAEDQADYHCVSYAGSGTLLFG<br>GGTKLTVL (SEQ ID NO: 201)<br><br>Light chain:<br>QSALTQPASVSGSPGQSITISCTGTSSNIGTYKFVS<br>WYQQHPDKAPKVLLYEVSKRPSGVSSRFSGSKS<br>GNTASLTISGLQAEDQADYHCVSYAGSGTLLFG<br>GGTKLTVLGQPKAAPSVTLFPPSSEELQANKATL<br>VCLISDFYPGAVTVAWKADSSPVKAGVETTTPS<br>KQSNNKYAASSYLSLTPEQWKSHRSYSCQVTHE<br>GSTVEKTVAPTECS (SEQ ID NO: 202) |
| CD3B219 | CDR 1: TYAMN (SEQ ID NO: 203)<br>CDR 2: RIRSKYNNYATYYAASVKG (SEQ ID NO: 204)<br>CDR 3: HGNFGNSYVSWFAY (SEQ ID NO: 205)<br>VH:<br>EVQLVESGGGLVQPGGSLRLSCAASGFTFNT<br>YAMNWVRQAPGKGLEWVARIRSKYNNYA<br>TYYAASVKGRFTISRDDSKNSLYLQMNSLK<br>TEDTAVYYCARHGNFGNSYVSWFAYWGQG<br>TLVTVSS (SEQ ID NO: 206)<br>Heavy chain:<br>EVQLVESGGGLVQPGGSLRLSCAASGFTFNT<br>YAMNWVRQAPGKGLEWVARIRSKYNNYATYY<br>AASVKGRFTISRDDSKNSLYLQMNSLKTEDT<br>AVYYCARHGNFGNSYVSWFAYWGQGTLVTVS<br>SASTKGPSVFPLAPCSRSTSESTAALGCLVK<br>DYFPEPVTVSWNSGALTSGVHTFPAVLQSSG<br>LYSLSSVVTVPSSSLGTKTYTCNVDHKPSNT<br>KVDKRVESKYGPPCPPCPAPEAAGGPSVFLF<br>PPKPKDTLMISRTPEVTCVVVDVSQEDPEVQ<br>FNWYVDGVEVHNAKTKPREEQFNSTYRVVSV<br>LTVLHQDWLNGKEYKCKVSNKGLPSSIEKTI | CDR 1: RSSTGAVTTSNYAN (SEQ ID NO: 208)<br>CDR 2: GTNKRAP (SEQ ID NO: 209)<br>CDR 3: ALWYSNLWV (SEQ ID NO: 210)<br>VL:<br>QTVVTQEPSLTVSPGGTVTLTCRSSTGAVTTSNY<br>ANWVQQKPGQAPRGLIGGTNKRAPGTPARFSGS<br>LLGGKAALTLSGVQPEDEAEYYCALWYSNLWV<br>FGGGTKLTVL (SEQ ID NO: 211)<br><br>Light chain:<br>QTVVTQEPSLTVSPGGTVTLTCRSSTGAVTTSNY<br>ANWVQQKPGQAPRGLIGGTNKRAPGTPARFSGS<br>LLGGKAALTLSGVQPEDEAEYYCALWYSNLWV<br>FGGGTKLTVLGQPKAAPSVTLFPPSSEELQANKA<br>TLVCLISDFYPGAVTVAWKADSSPVKAGVETTTP<br>SKQSNNKYAASSYLSLTPEQWKSHRSYSCQVTH<br>EGSTVEKTVAPTECS (SEQ ID NO: 212) |

TABLE 3-continued

Heavy chain and light chain CDR, VH, and VL sequences of exemplary CD3-specific antibodies and antigen-binding fragments

| ID | Heavy Chain | Light Chain |
|---|---|---|
| | SKAKGQPREPQVYTLPPSQEEMTKNQVSLTCL<br>VKGFYPSDIAVEWESNGQPENNYKTTPPVLDS<br>DGSFLLYSKLTVDKSRWQEGNVFSCSVMHEAL<br>HNHYTQKSLSLSLGK<br>(SEQ ID NO: 207) | |

Characteristics of some CD3-specific antibodies or antigen-binding fragments may be found in e.g., U.S. Pat. Nos. 10,562,968 and 10,072,088, United States Published Application US2019/0382481, the content of each of which is herein incorporated by reference in its entirety.

In some embodiments, the CD3-binding arm comprises a heavy chain variable domain comprising a CDR1, a CDR2, and a CDR3 of any one of the antibodies described in Table 3. In some embodiments, the CD3-binding arm comprises a light chain variable domain comprising a CDR1, a CDR2, and a CDR3 of any one of the antibodies described in Table 3. In some embodiments, the CD3-binding arm comprises a heavy chain variable domain comprising a CDR1, a CDR2, and a CDR3 of any one of the antibodies described in Table 3 and a light chain variable domain comprising a CDR1, a CDR2, and a CDR3 of any one of the antibodies described in Table 3. In some embodiments, the CD3-binding arm competes for binding to CD3 with an antibody or antigen-binding comprising a heavy chain comprising a CDR1, a CDR2, and a CDR3 of any one of the antibodies described in Table 3 and a light chain comprising a CDR1, a CDR2, and a CDR3 of any one of the antibodies described in Table 3.

In some embodiments, the CD3-binding arm comprises a heavy chain comprising a CDR1, a CDR2, and a CDR3 of any one of the antibodies described in Table 3. In some embodiments, the CD3-binding arm comprises a light chain comprising a CDR1, a CDR2, and a CDR3 of any one of the antibodies described in Table 3. In some embodiments, the CD3-binding arm comprises a heavy chain comprising a CDR1, a CDR2, and a CDR3 of any one of the antibodies described in Table 3 and a light chain comprising a CDR1, a CDR2, and a CDR3 of any one of the antibodies described in Table 3.

In some embodiments, the CD3-binding arm comprises a heavy chain CDR1 comprising SEQ ID NO: 76, a heavy chain CDR2 comprising SEQ ID NO: 77, and a heavy chain CDR3 comprising SEQ ID NO: 78. In some embodiments, the CD3-binding arm comprises a heavy chain CDR1 comprising SEQ ID NO: 76, a heavy chain CDR2 comprising SEQ ID NO: 77, a heavy chain CDR3 comprising SEQ ID NO: 78, a light chain CDR1 comprising SEQ ID NO: 79, a light chain CDR2 comprising SEQ ID NO: 80, and a light chain CDR3 comprising SEQ ID NO: 81. The CD3-binding arm may comprise human framework sequences. In some embodiments, the CD3-binding arm comprises a heavy chain variable domain substantially the same as, or identical to, SEQ ID NO: 97. In some embodiments, the CD3-binding arm comprises a heavy chain variable domain substantially the same as, or identical to, SEQ ID NO: 97 and a light chain variable domain substantially the same as, or identical to, SEQ ID NO: 99. In some embodiments, the CD3-binding arm comprises a heavy chain variable domain that is encoded by a nucleotide sequence substantially the same as, or identical to, SEQ ID NO: 98. In some embodiments, the CD3-binding arm comprises a heavy chain variable domain that is encoded by a nucleotide sequence substantially the same as, or identical to, SEQ ID NO: 98 and a light chain variable domain that is encoded by a nucleotide sequence substantially the same as, or identical to, SEQ ID NO: 100.

In some embodiments, the CD3-binding arm comprises a heavy chain CDR1 comprising SEQ ID NO: 76, a heavy chain CDR2 comprising SEQ ID NO: 77, and a heavy chain CDR3 comprising SEQ ID NO: 75. In some embodiments, the CD3-binding arm comprises a heavy chain CDR1 comprising SEQ ID NO: 76, a heavy chain CDR2 comprising SEQ ID NO: 77, a heavy chain CDR3 comprising SEQ ID NO: 75, a light chain CDR1 comprising SEQ ID NO: 79, a light chain CDR2 comprising SEQ ID NO: 80, and a light chain CDR3 comprising SEQ ID NO: 81. The CD3-binding arm may comprise human framework sequences. In some embodiments, the CD3-binding arm comprises a heavy chain variable domain substantially the same as, or identical to, SEQ ID NO: 101. In some embodiments, the CD3-binding arm comprises a heavy chain variable domain substantially the same as, or identical to, SEQ ID NO: 101 and a light chain variable domain substantially the same as, or identical to, SEQ ID NO: 99. In some embodiments, the CD3-binding arm comprises a heavy chain variable domain that is encoded by a nucleotide sequence substantially the same as, or identical to, SEQ ID NO: 102. In some embodiments, the CD3-binding arm comprises a heavy chain variable domain that is encoded by a nucleotide sequence substantially the same as, or identical to, SEQ ID NO: 102 and a light chain variable domain that is encoded by a nucleotide sequence substantially the same as, or identical to, SEQ ID NO: 100.

In some embodiments, the CD3-binding arm comprises a heavy chain CDR1 comprising SEQ ID NO: 76, a heavy chain CDR2 comprising SEQ ID NO: 77, and a heavy chain CDR3 comprising SEQ ID NO: 78. In some embodiments, the CD3-binding arm comprises a heavy chain CDR1 comprising SEQ ID NO: 76, a heavy chain CDR2 comprising SEQ ID NO: 77, a heavy chain CDR3 comprising SEQ ID NO: 78, a light chain CDR1 comprising SEQ ID NO: 79, a light chain CDR2 comprising SEQ ID NO: 80, and a light chain CDR3 comprising SEQ ID NO: 81. The CD3-binding arm may comprise human framework sequences. In some embodiments, the CD3-binding arm comprises a heavy chain variable domain substantially the same as, or identical to, SEQ ID NO: 103. In some embodiments, the CD3-binding arm comprises a heavy chain variable domain substantially the same as, or identical to, SEQ ID NO: 103 and a light chain variable domain substantially the same as, or identical to, SEQ ID NO: 99. In some embodiments, the CD3-binding arm comprises a heavy chain variable domain that is encoded by a nucleotide sequence substantially the same as, or identical to, SEQ ID NO: 104. In some embodiments, the CD3-binding arm comprises a heavy chain variable domain that is encoded by a nucleotide sequence substantially the same as, or identical to, SEQ ID NO: 104 and a light chain variable domain that is encoded by a nucleotide sequence substantially the same as, or identical to, SEQ ID NO: 100.

In some embodiments, the CD3-binding arm comprises a heavy chain CDR1 comprising SEQ ID NO: 76, a heavy chain CDR2 comprising SEQ ID NO: 77, and a heavy chain CDR3 comprising SEQ ID NO: 82. In some embodiments, the CD3-binding arm comprises a heavy chain CDR1 comprising SEQ ID NO: 76, a heavy chain CDR2 comprising SEQ ID NO: 77, a heavy chain CDR3 comprising SEQ ID NO: 82, a light chain CDR1 comprising SEQ ID NO: 79, a light chain CDR2 comprising SEQ ID NO: 80, and a light chain CDR3 comprising SEQ ID NO: 81. The CD3-binding arm may comprise human framework sequences. In some embodiments, the CD3-binding arm comprises a heavy chain variable domain substantially the same as, or identical to, SEQ ID NO: 105. In some embodiments, the CD3-binding arm comprises a heavy chain variable domain substantially the same as, or identical to, SEQ ID NO: 105 and a light chain variable domain substantially the same as, or identical to, SEQ ID NO: 99. In some embodiments, the CD3-binding arm comprises a heavy chain variable domain that is encoded by a nucleotide sequence substantially the same as, or identical to, SEQ ID NO: 106. In some embodiments, the CD3-binding arm comprises a heavy chain variable domain that is encoded by a nucleotide sequence substantially the same as, or identical to, SEQ ID NO: 106 and a light chain variable domain that is encoded by a nucleotide sequence substantially the same as, or identical to, SEQ ID NO: 100.

In some embodiments, the CD3-binding arm comprises a heavy chain CDR1 comprising SEQ ID NO: 83, a heavy chain CDR2 comprising SEQ ID NO: 84, and a heavy chain CDR3 comprising SEQ ID NO: 85. In some embodiments, the CD3-binding arm comprises a heavy chain CDR1 comprising SEQ ID NO: 83, a heavy chain CDR2 comprising SEQ ID NO: 84, a heavy chain CDR3 comprising SEQ ID NO: 85, a light chain CDR1 comprising SEQ ID NO: 86, a light chain CDR2 comprising SEQ ID NO: 87, and a light chain CDR3 comprising SEQ ID NO: 88. The CD3-binding arm may comprise human framework sequences. In some embodiments, the CD3-binding arm comprises a heavy chain variable domain substantially the same as, or identical to, SEQ ID NO: 107. In some embodiments, the CD3-binding arm comprises a heavy chain variable domain substantially the same as, or identical to, SEQ ID NO: 107 and a light chain variable domain substantially the same as, or identical to, SEQ ID NO: 109. In some embodiments, the CD3-binding arm comprises a heavy chain variable domain that is encoded by a nucleotide sequence substantially the same as, or identical to, SEQ ID NO: 108. In some embodiments, the CD3-binding arm comprises a heavy chain variable domain that is encoded by a nucleotide sequence substantially the same as, or identical to, SEQ ID NO: 108 and a light chain variable domain that is encoded by a nucleotide sequence substantially the same as, or identical to, SEQ ID NO: 110.

In some embodiments, the CD3-binding arm comprises a heavy chain CDR1 comprising SEQ ID NO: 193, a heavy chain CDR2 comprising SEQ ID NO: 194, and a heavy chain CDR3 comprising SEQ ID NO: 195. In some embodiments, the CD3-binding arm comprises a heavy chain CDR1 comprising SEQ ID NO: 193, a heavy chain CDR2 comprising SEQ ID NO: 194, a heavy chain CDR3 comprising SEQ ID NO: 195, a light chain CDR1 comprising SEQ ID NO: 198, a light chain CDR2 comprising SEQ ID NO: 199, and a light chain CDR3 comprising SEQ ID NO: 200. The CD3-binding arm may comprise human framework sequences. In some embodiments, the CD3-binding arm comprises a heavy chain variable domain substantially the same as, or identical to, SEQ ID NO: 196. In some embodiments, the CD3-binding arm comprises a heavy chain variable domain substantially the same as, or identical to, SEQ ID NO: 196 and a light chain variable domain substantially the same as, or identical to, SEQ ID NO: 201.

In some embodiments, the CD3-binding arm comprises a heavy chain CDR1 comprising SEQ ID NO: 203, a heavy chain CDR2 comprising SEQ ID NO: 204, and a heavy chain CDR3 comprising SEQ ID NO: 205. In some embodiments, the CD3-binding arm comprises a heavy chain CDR1 comprising SEQ ID NO: 203, a heavy chain CDR2 comprising SEQ ID NO: 204, a heavy chain CDR3 comprising SEQ ID NO: 205, a light chain CDR1 comprising SEQ ID NO: 208, a light chain CDR2 comprising SEQ ID NO: 209, and a light chain CDR3 comprising SEQ ID NO: 210. The CD3-binding arm may comprise human framework sequences. In some embodiments, the CD3-binding arm comprises a heavy chain variable domain substantially the same as, or identical to, SEQ ID NO: 206. In some embodiments, the CD3-binding arm comprises a heavy chain variable domain substantially the same as, or identical to, SEQ ID NO: 206 and a light chain variable domain substantially the same as, or identical to, SEQ ID NO: 211.

In some embodiments, the CDRs of the heavy chain and/or the light chain are derived from known anti-CD3 antibodies, such as, for example, muromonab-CD3 (OKT3), otelixizumab (TRX4), teplizumab (MGA031), visilizumab (Nuvion), TR-66 or X35-3, VIT3, BMA030 (BW264/56), CLB-T3/3, CRIS7, YTH12.5, Fl 11-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1 and WT-31.

In some embodiments, the CD3-binding arm is IgG, or a derivative thereof. In some embodiments, the CD3-binding arm is IgG1, IgG2, IgG3, or IgG4. In some embodiments where in the CD3-binding arm has an IgG4 isotype, it contains S228P, L234A, L235A, F405L, and R409K substitution(s) in its Fc region. In some embodiments, the antibodies or antigen-binding fragments bind CD3ε on primary human T cells. In some embodiments, the antibodies or antigen-binding fragments bind CD3ε on primary cynomolgus T cells. In some embodiments, the antibodies or antigen-binding fragments bind CD3ε on primary human and cynomolgus T cells. In some embodiments, the antibodies or antigen-binding fragments activate primary human CD3+ T cells. In some embodiments, the antibodies or antigen-binding fragments activate primary cynomolgus CD4+ T cells.

In some embodiments, the multispecific antibodies described herein may adopt any format which has been described in the art for multispecific antibodies. In some embodiments, the multispecific antibodies described herein is constructed based on a bispecific antibody format. This can be achieved by adding a third antigen-binding arm to a bispecific antibody. Different formats of bispecific antibodies have been described and were recently reviewed by Chames and Baty (2009) Curr Opin Drug Disc Dev 12: 276. In some embodiments, the multispecific antibody comprises a bispecific antibody which is a diabody, a cross-body, or a bispecific antibody obtained via a controlled Fab arm exchange as those described in the present disclosure.

In some embodiments, the multispecific antibodies include IgG-like molecules with complementary CH3 domains to force heterodimerization; recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

In some embodiments, IgG-like molecules with complementary CH3 domains molecules include the Triomab/Quadroma (Trion Pharma/Fresenius Biotech), the Knobs-into-Holes (Genentech), CrossMAbs (Roche) and the electrostatically-matched (Amgen), the LUZ-Y (Genentech), the Strand Exchange Engineered Domain body (SEEDbody) (EMD Serono), the Biclonic (Merus), the DuoBody (Genmab A/S), and other asymmetric mutations (e.g., Zymeworks).

In some embodiments, recombinant IgG-like dual targeting molecules include Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer).

In some embodiments, IgG fusion molecules include Dual Variable Domain (DVD)-Ig (Abbott), IgG-like Bispecific (InnClone/Eli Lilly), Ts2Ab (MedImmune/AZ) and BsAb (Zymogenetics), HERCULES (Biogen Idec) and TvAb (Roche).

In some embodiments, Fc fusion molecules include to ScFv/Fc Fusions (Academic Institution), SCORPION (Emergent BioSolutions/Trubion, Zymogenetics/BMS), Dual Affinity Retargeting Technology (Fc-DART) (MacroGenics) and Dual(ScFv).sub.2-Fab (National Research Center for Antibody Medicine—China).

In some embodiments, Fab fusion bispecific antibodies include F(ab)2 (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech). ScFv-, diabody-based and domain antibodies include but are not limited to Bispecific T Cell Engager (BiTE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

Full length multispecific antibodies of the present disclosure may be generated for example using Fab arm exchange (or half molecule exchange) between two mono specific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent mono specific antibodies are reduced. The resulting free cysteines of one of the parent monospecific antibodies form an inter heavy-chain disulfide bond with cysteine residues of a second parent mono specific antibody molecule and simultaneously CH3 domains of the parent antibodies release and reform by dissociation-association. The CH3 domains of the Fab arms may be engineered to favor heterodimerization over homodimerization. The resulting product is a bispecific antibody having two Fab arms or half molecules which each bind a distinct epitope, e.g., an epitope on CD79b (or CD20) and an epitope on CD3. A third antigen-binding arm can be then introduced to the bispecific antibody, for example, to the C-terminus of the first heavy chain or second heavy chain, which can bind to a third epitope, e.g., CD20 (or CD79b).

"Homodimerization" as used herein refers to an interaction of two heavy chains having identical CH3 amino acid sequences. "Homodimer" as used herein refers to an antibody having two heavy chains with identical CH3 amino acid sequences.

"Heterodimerization" as used herein refers to an interaction of two heavy chains having non-identical CH3 amino acid sequences. "Heterodimer" as used herein refers to an antibody having two heavy chains with non-identical CH3 amino acid sequences.

The "knob-in-hole" strategy (see, e.g., PCT Intl. Publ. No. WO 2006/028936) may be used to generate full length multispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V (EU numbering).

In some embodiments of the multispecific antibody or multispecific binding fragment described herein, one of the Fc domains comprise mutations T366S, L368A and Y407V and the other Fc domain comprises mutation T366W. In some embodiments, the Fc domain of the first heavy chain portion (HC1) of the first antigen binding arm (e.g., CD79b binding arm) comprises mutations T366S, L368A and Y407V, and the Fc domain of the second heavy chain portion (HC2) of the second antigen binding arm and/or third antigen-binding arm (e.g., the CD3/CD20 binding arm of the trispecific antibody, or CD3 binding arm of the bispecific antibody) comprises mutation T366W. In some embodiments, the Fc domain of the HC2 of the second antigen-binding arm and/or third antigen-binding arm (e.g., the CD3/CD20 binding arm of the trispecific antibody, or CD3 binding arm in the bispecific antibody) comprises mutations T366S, L368A and Y407V, and the Fc domain of the HC1 of the first antigen-binding arm (e.g., CD79b binding arm) comprises mutation T366W.

Other strategies such as promoting heavy chain heterodimerization using electrostatic interactions by substituting positively charged residues at one CH3 surface and negatively charged residues at a second CH3 surface may be used, as described in US Pat. Publ. No. US2010/0015133; US Pat. Publ. No. US2009/0182127; US Pat. Publ. No. US2010/028637 or US Pat. Publ. No. US2011/0123532. In other strategies, heterodimerization may be promoted by the following substitutions (expressed as modified position in the first CH3 domain of the first heavy chain/modified position in the second CH3 domain of the second heavy chain): L351Y_F405AY407V/T394W, T3661_K392M_T394W/F405A_Y407V, T366L_K392M_T394W/F405A_Y407V, L351Y_Y407A/ T366A_K409F, L351Y_Y407A/T366V K409F Y407A/ T366A_K409F, or T350V_L351Y_F405A_Y407V/ T350V_T366L_K392L_T394W as described in U.S. Pat. Publ. No. US2012/0149876 or U.S. Pat. Publ. No. US2013/0195849 (Zymeworks).

In addition to methods described above, multispecific antibodies of the invention may be generated in vitro in a cell-free environment by introducing asymmetrical mutations in the CH3 regions of two mono specific homodimeric antibodies and forming the multispecific heterodimeric antibody from two parent monospecific homodimeric antibodies in reducing conditions to allow disulfide bond isomerization according to methods described in Inti. Pat. Publ. No. WO2011/131746. In the methods, the first monospecific bivalent antibody (e.g., anti-CD79b antibody) and the second monospecific bivalent antibody (e.g., anti-CD3 antibody) are engineered to have certain substitutions at the CH3 domain that promotes heterodimer stability; the antibodies are incubated together under reducing conditions sufficient to allow the cysteines in the hinge region to undergo disulfide bond isomerization; thereby generating the multispecific antibody by Fab arm exchange. The incubation conditions may optimally be restored to non-reducing conditions. Exemplary reducing agents that may be used are 2-mercaptoethylamine (2-MEA), dithiothreitol (DTT), dithioerythritol (DTE), glutathione, tris (2-carboxyethyl) phosphine (TCEP), L-cysteine and beta-mercaptoethanol, preferably a reducing agent selected from the group consisting of: 2-mercaptoethylamine, dithiothreitol and tris (2-carboxyethyl) phosphine. For example, incubation for at least 90 min at a temperature of at least 20° C. in the presence of at least 25 mM 2-MEA or in the presence of at least 0.5 mM dithiothreitol at a pH from 5-8, for example at pH of 7.0 or at pH of 7.4 may be used.

In some embodiments, the multispecific antibodies or antigen-binding fragments are IgG, or derivatives thereof. The IgG class is divided in four isotypes: IgG1, IgG2, IgG3 and IgG4 in humans. They share more than 95% homology in the amino acid sequences of the Fc regions but show major differences in the amino acid composition and structure of the hinge region. The Fc region mediates effector functions, such as antibody-dependent cellular cytotoxicity (ADCC) and complement-dependent cytotoxicity (CDC). In ADCC, the Fc region of an antibody binds to Fc receptors (FcTRs) on the surface of immune effector cells such as natural killers and macrophages, leading to the phagocytosis or lysis of the targeted cells. In CDC, the antibodies kill the targeted cells by triggering the complement cascade at the cell surface. The antibodies described herein include antibodies with the described features of the variable domains in combination with any of the IgG isotypes, including modified versions in which the Fc sequence has been modified to effect different effector functions.

For many applications of therapeutic antibodies, Fc-mediated effector functions are not part of the mechanism of action. These Fc-mediated effector functions can be detrimental and potentially pose a safety risk by causing off-mechanism toxicity. Modifying effector functions can be achieved by engineering the Fc regions to reduce their binding to FcTRs or the complement factors. The binding of IgG to the activating (FcγRI, FcγRIIa, FcγRIIIa and FcγRIIIb) and inhibitory (FcγRIIb) FcTRs or the first component of complement (Clq) depends on residues located in the hinge region and the CH2 domain. Mutations have been introduced in IgG1, IgG2 and IgG4 to reduce or silence Fc functionalities. The antibodies described herein may include these modifications.

In one embodiment, the antibody comprises an Fc region with one or more of the following properties: (a) reduced effector function when compared to the parent Fc; (b) reduced affinity to FcγRI, FcγRIIa, FcγRIIb, FcγRIIIb and/or FcγRIIIa, (c) reduced affinity to FcγRI (d) reduced affinity to FcγRIIa (e) reduced affinity to FcγRIIb, (f) reduced affinity to FcγRIIIb or (g) reduced affinity to FcγRIIIa.

In some embodiments, the antibodies or antigen-binding fragments are IgG, or derivatives thereof, e.g., IgG1, IgG2, IgG3, and IgG4 isotypes. In some embodiments wherein the antibody has an IgG1 isotype, the antibody contains L234A, L235A, D265S and/or K409R substitution(s) in its Fc region. In some embodiments wherein the antibody has an IgG4 isotype, the antibody contains S228P, L234A, and L235A substitutions in its Fc region. The antibodies described herein may include these modifications.

In some embodiments, the Fc domains of one or more of the heavy chain portions (such as HC1 and/or HC2) described herein each comprise one or more mutations selected from L234A, L235A, and D265S. In some embodiments, the Fc domains of the heavy chain portions (such as HC1 and HC2) each comprise mutations L234A, L235A, and D265S.

In some embodiments, the Fc domain of one of the heavy chain portions of a multispecific antibody described herein further comprises one or more mutations which reduce Fc binding to protein A. In some embodiments, the Fc domain of one of the heavy chain portions comprises mutations H435R and/or Y436F. In some embodiments, the Fc domain of the HC2 of the second antigen-binding arm and/or third antigen-binding arm (e.g., CD3/CD20 binding arms in a trispecific antibody, or CD3 binding arm in a bispecific antibody) comprises mutations H435R and/or Y436F.

In various embodiments of a trispecific antibody described herein, the third antigen-binding arm is operatively linked to the first antigen-binding arm or second antigen-binding armvia a linker. In some embodiments, the linker is a peptide linker and may include any naturally occurring amino acid. Exemplary amino acids that may be included into the linker are Gly, Ser Pro, Thr, Glu, Lys, Arg, Ile, Leu, His and The. The linker should have a length that is adequate to link the third antigen-binding arm and the first antigen-binding arm or the second antigen-binding armin such a way that they form the correct conformation relative to one another so that they retain the desired activity, such as binding to a third antigen (e.g., CD3 or CD20).

In some embodiments of a trispecific antibody described herein, the HC1 comprises, from the N- to C-terminus, the VH1 associated with the first antigen-binding arm, a CH1 domain, the Fc domain, a linker, and the third antigen-binding arm.

In some embodiments of a trispecific antibody described herein, the HC2 comprises, from the N- to C-terminus, the second antigen-binding domain, the Fc domain, a linker, and the third antigen-binding arm.

In various embodiments, the scFvs used in multispecific antibodies described herein comprises, from the N- to C-terminus, a VH, a linker, and a VL (VH-L-VL), or the VL, the linker, and the VH (VL-L-VH). In some embodiments, the scFv comprises, from the N- to C-terminus, the VL, the linker, and the VH (VL-L-VH). In some embodiments, the scFv comprises, from the N- to C-terminus, the VH, the linker, and the VH (VL-L-VH).

Linkers used in the present disclosure may be about 5-50 amino acids long. In some embodiments, the linker is about 10-40 amino acids long. In some embodiments, the linker is about 10-35 amino acids long. In some embodiments, the linker is about 10-30 amino acids long. In some embodiments, the linker is about 10-25 amino acids long. In some embodiments, the linker is about 10-20 amino acids long. In some embodiments, the linker is about 15-20 amino acids long. In some embodiments, the linker is 6 amino acids long. In some embodiments, the linker is 7 amino acids long. In some embodiments, the linker is 8 amino acids long. In some embodiments, the linker is 9 amino acids long. In some embodiments, the linker is 10 amino acids long. In some embodiments, the linker is 11 amino acids long. In some embodiments, the linker is 12 amino acids long. In some embodiments, the linker is 13 amino acids long. In some embodiments, the linker is 14 amino acids long. In some embodiments, the linker is 15 amino acids long. In some embodiments, the linker is 16 amino acids long. In some embodiments, the linker is 17 amino acids long. In some embodiments, the linker is 18 amino acids long. In some embodiments, the linker is 19 amino acids long. In some embodiments, the linker is 20 amino acids long. In some embodiments, the linker is 21 amino acids long. In some embodiments, the linker is 22 amino acids long. In some embodiments, the linker is 23 amino acids long. In some embodiments, the linker is 24 amino acids long. In some embodiments, the linker is 25 amino acids long. In some embodiments, the linker is 26 amino acids long. In some embodiments, the linker is 27 amino acids long. In some embodiments, the linker is 28 amino acids long. In some embodiments, the linker is 29 amino acids long. In some embodiments, the linker is 30 amino acids long. In some embodiments, the linker is 31 amino acids long. In some embodiments, the linker is 32 amino acids long. In some embodiments, the linker is 33 amino acids long. In some embodiments, the linker is 34 amino acids long. In some embodiments, the linker is 35 amino acids long. In some embodiments, the linker is 36 amino acids long. In some embodiments, the linker is 37 amino acids long. In some embodiments, the linker is 38 amino acids long. In some embodiments, the linker is 39 amino acids long. In some embodiments, the linker is 40 amino acids long. Exemplary linkers that may be used are Gly rich linkers, Gly and Ser containing linkers, Gly and Ala containing linkers, Ala and Ser containing linkers, and other flexible linkers.

Other linker sequences may include portions of immunoglobulin hinge area, CL or CH1 derived from any immunoglobulin heavy or light chain isotype. Exemplary linkers that may be used are shown in Table 4. Additional linkers are described for example in Int. Pat. Publ. No. WO2019/060695.

In some embodiments, the linker comprises the amino acid sequence of SEQ ID NO: 215.

In some embodiments, the linker comprises the amino acid sequence of SEQ ID NO: 216.

In some embodiments, the linker comprises the amino acid sequence of SEQ ID NO: 217.

In some embodiments, the linker comprises the amino acid sequence of SEQ ID NO: 218.

In some embodiments, the linker comprises the amino acid sequence of SEQ ID NO: 219.

In some embodiments, the linker comprises the amino acid sequence of SEQ ID NO: 220.

In some embodiments, the linker comprises the amino acid sequence of SEQ ID NO: 221.

In some embodiments, the linker comprises the amino acid sequence of SEQ ID NO: 222.

In some embodiments, the linker comprises the amino acid sequence of SEQ ID NO: 223.

In some embodiments, the linker comprises the amino acid sequence of SEQ ID NO: 224.

In some embodiments, the linker comprises the amino acid sequence of SEQ ID NO: 225.

In some embodiments, the linker comprises the amino acid sequence of SEQ ID NO: 226.

In some embodiments, the linker comprises the amino acid sequence of SEQ ID NO: 227.

In some embodiments, the linker comprises the amino acid sequence of SEQ ID NO: 228.

In some embodiments, the linker comprises the amino acid sequence of SEQ ID NO: 229.

In some embodiments, the linker comprises the amino acid sequence of SEQ ID NO: 230.

In some embodiments, the linker comprises the amino acid sequence of SEQ ID NO: 231.

In some embodiments, the linker comprises the amino acid sequence of SEQ ID NO: 232.

In some embodiments, the linker comprises the amino acid sequence of SEQ ID NO: 233.

In some embodiments, the linker comprises the amino acid sequence of SEQ ID NO: 234.

In some embodiments, the linker comprises the amino acid sequence of SEQ ID NO: 235.

In some embodiments, the linker comprises the amino acid sequence of SEQ ID NO: 236.

In some embodiments, the linker comprises the amino acid sequence of SEQ ID NO: 237.

In some embodiments, the linker comprises the amino acid sequence of SEQ ID NO: 238.

In some embodiments, the linker comprises the amino acid sequence of SEQ ID NO: 239.

In some embodiments, the linker comprises the amino acid sequence of SEQ ID NO: 240.

In some embodiments, the linker comprises the amino acid sequence of SEQ ID NO: 241.

In some embodiments, the linker comprises the amino acid sequence of SEQ ID NO: 242.

In some embodiments, the linker comprises the amino acid sequence of SEQ ID NO: 243.

In some embodiments, the linker comprises the amino acid sequence of SEQ ID NO: 244.

In some embodiments, the linker comprises the amino acid sequence of SEQ ID NO: 245.

In some embodiments, the linker comprises the amino acid sequence of SEQ ID NO: 246.

In some embodiments, the linker comprises the amino acid sequence of SEQ ID NO: 247.

In some embodiments, the linker comprises the amino acid sequence of SEQ ID NO: 248.

TABLE 4

Exemplary linker sequences

| Linker name | Amino acid sequence | SEQ ID NO: |
|---|---|---|
| Linker 1 | GGSEGKSSGSGSESKSTGGS | 215 |
| Linker 2 | GGGSGGGS | 216 |
| Linker 3 | GGGSGGGSGGGS | 217 |
| Linker 4 | GGGSGGGSGGGSGGGS | 218 |
| Linker 5 | GGGSGGGSGGGSGGGSGGGS | 219 |
| Linker 6 | GGGGSGGGSGGGS | 220 |
| Linker 7 | GGGGSGGGGSGGGGSGGGGS | 221 |
| Linker 8 | GGGGSGGGGSGGGGSGGGGSGGGGS | 222 |
| Linker 9 | GSTSGSGKPGSGEGSTKG | 223 |
| Linker 10 | IRPRAIGGSKPRVA | 224 |
| Linker 11 | GKGGSGKGGSGKGGS | 225 |
| Linker 12 | GGKGSGGKGSGGKGS | 226 |
| Linker 13 | GGGKSGGGKSGGGKS | 227 |
| Linker 14 | GKGKSGKGKSGKGKS | 228 |
| Linker 15 | GGGKSGGKGSGKGGS | 229 |
| Linker 16 | GKPGSGKPGSGKPGS | 230 |
| Linker 17 | GKPGSGKPGSGKPGSGKPGS | 231 |
| Linker 18 | GKGKSGKGKSGKGKSGKGKS | 232 |
| Linker 19 | STAGDTHLGGEDFD | 233 |
| Linker 20 | GEGGSGEGGSGEGGS | 234 |
| Linker 21 | GGEGSGGEGSGGEGS | 235 |
| Linker 22 | GEGESGEGESGEGES | 236 |
| Linker 23 | GGGESGGEGSGEGGS | 237 |
| Linker 24 | GEGESGEGESGEGESGEGES | 238 |
| Linker 25 | GSTSGSGKPGSGEGSTKG | 239 |
| Linker 26 | PRGASKSGSASQTGSAPGS | 240 |
| Linker 27 | GTAAAGAGAAGGAAAGAAG | 241 |
| Linker 28 | GTSGSSGSGSGGSGSGGGG | 242 |
| Linker 29 | GKPGSGKPGSGKPGSGKPGS | 243 |
| Linker 30 | GSGS | 244 |
| Linker 31 | APAPAPAPAP | 245 |
| Linker 32 | APAPAPAPAPAPAPAPAP | 246 |
| Linker 33 | AEAAAKEAAAKEAAAAKEAAAAKEAAAAKAAA | 247 |
| Linker 34 | GGGGSGGGGS | 248 |

In some embodiments, a trispecific antibody, or a trispecific antibody fragment of the present disclosure comprises a CD79b binding arm and a single polypeptide comprising the CD3 and CD2 binding arms (also referenced herein to as CD3/CD20 arm). The CD79b binding arm comprises a heavy chain portion (HC1), and a light chain (LC). The CD3/CD2 binding arm comprises from N to C terminus, a scFv that binds to CD3, heavy chain constant regions CH2 and CH3, and a scFv that binds to CD20. The trispecific molecule disclosed herein can be any one of the antibodies described in Table 5. In some embodiments, a trispecific antibody, or a trispecific antibody fragment of the present disclosure may be encoded by a nucleotide sequence encoding the CD79b arm and/or the CD3/CD20 arm of any one of the antibodies described in Table 5.

Table 5 provides a summary of examples of some CD79b×CD20×CD3 trispecific antibodies described herein:

TABLE 5

Exemplary CD79b × CD20 × CD3 Trispecific antibodies

| ID | HC1/LC (CD79b arm) | HC1 Amino acid sequence SEQ ID NO | HC1 DNA sequence SEQ ID NO | LC Amino acid sequence SEQ ID NO | LC DNA sequence SEQ ID NO | CD3/CD20 arm | CD3/CD20 arm Amino acid sequence SEQ ID NO | CD3/CD20 arm DNA sequence SEQ ID NO |
|---|---|---|---|---|---|---|---|---|
| C923B38 | CD9B374 | 172 | 173 | 174 | 175 | CD3B2030-N106A-scFv-LH-C20B22 | 142 | 143 |
| C923B74 | CD9B330-N31S | 176 | 177 | 178 | 179 | CD3B2030-N106A-scFv-LH-C20B22 | 142 | 143 |
| C923B99 | CD9B643 | 180 | 181 | 182 | 183 | CD3B2030-N106A-scFv-LH-C20B22 | 142 | 143 |
| C923B36 | CD9B374 | 172 | 173 | 174 | 175 | CD3B2089-N106G-scFv-LH-C20B22 | 144 | 145 |
| C923B73 | CD9B330-N31S | 176 | 177 | 178 | 179 | CD3B2089-N106G-scFv-LH-C20B22 | 144 | 145 |

TABLE 5-continued

Exemplary CD79b × CD20 × CD3 Trispecific antibodies

| ID | HC1/LC (CD79b arm) | HC1 Amino acid sequence SEQ ID NO | HC1 DNA sequence SEQ ID NO | LC Amino acid sequence SEQ ID NO | LC DNA sequence SEQ ID NO | CD3/CD20 arm | CD3/CD20 arm Amino acid sequence SEQ ID NO | CD3/CD20 arm DNA sequence SEQ ID NO |
|---|---|---|---|---|---|---|---|---|
| C923B95 | CD9B643 | 180 | 181 | 182 | 183 | CD3B2089-N106G-scFv-LH-C20B22 | 144 | 145 |
| C923B138 | CD9B643 | 180 | 181 | 182 | 188 | CD3W245-scFv LH-C20B22 | 148 | 149 |
| C923B139 | CD9B643 | 180 | 181 | 182 | 188 | CD3B2089-N106G-scFv HL-C20B22 | 150 | 151 |
| C923B140 | CD9B643 | 180 | 181 | 182 | 188 | CD3W245-scFv LH-5O10GL | 152 | 153 |
| C923B141 | CD9B643 | 180 | 181 | 182 | 188 | CD3W245-scFv LH-4A16GL | 154 | 155 |
| C923B142 | CD9B643 | 180 | 181 | 182 | 188 | CD3B2030-N106A-LH scFv-5O10GL | 156 | 157 |
| C923B143 | CD9B643 | 180 | 181 | 182 | 188 | CD3B2030-N106A-LH scFv-4A16GL | 158 | 159 |
| C923B144 | CD9B643 | 180 | 181 | 182 | 188 | CD3B2089-N106G-HL scFv-5O10GL | 160 | 161 |
| C923B145 | CD9B643 | 180 | 181 | 182 | 188 | CD3B2089-N106G-HL scFv-4A16GL | 162 | 163 |
| C923B147 | CD9B643 | 191 | 192 | 182 | 183 | CD3B2030-N106A-LH scFv-4A16GL | 166 | 167 |
| C923B168 | CD9B374 | 172 | 173 | 174 | 175 | CD3W245-scFv LH-C20B648 LH | 168 | 169 |
| C923B169 | CD9B374 | 172 | 173 | 174 | 175 | CD3B2030-N106A-LH-C20B648 LH | 170 | 171 |

Table 5 sets out the internal designation of each antigen-binding arm that is present in the various trispecific antibodies. The CDR sequences of CD79b arms are provided in Table 1; and the CDR sequences of CD3/CD20 arms are provided in Table 3 and Table 2a respectively. Thus, for example, trispecific antibody C923B169 comprises CDRs 1, 2, 3, 4, 5, 6; 77, 76, 75, 79, 80, 81; 121, 122, 123, 124, 119 and 125.

In some embodiments, the HC1 of a CD79b×CD20×CD3 trispecific antibody comprises an amino acid sequence substantially the same as, or identical to, SEQ ID NO: 172, 176, 180, or 191. In some embodiments, the nucleotide sequence encoding the HC 1 of a CD79b×CD20×CD3 trispecific antibody comprises the nucleotide sequence substantially the same as, or identical to, SEQ ID NO: 173, 177, 181, or 192.

In some embodiments, the LC of a CD79b×CD20×CD3 trispecific antibody comprises an amino acid sequence substantially the same as, or identical to, SEQ ID NO: 174, 178 or 182. In some embodiments, the nucleotide sequence encoding the LC of a CD79b×CD20×CD3 trispecific antibody comprises the nucleotide sequence substantially the same as, or identical to, SEQ ID NO: 175, 179, 183 or 188.

In some embodiments, the CD3/CD20 arm of a CD79b×CD20×CD3 trispecific antibody comprises an amino acid sequence substantially the same as, or identical to, SEQ ID NO: 142, 144, 148, 150, 152, 154, 156, 158, 160, 162, 166, 168, or 170. In some embodiments, the nucleotide sequence encoding the CD3/CD20 arm of a CD79b×CD20×CD3 trispecific antibody comprises the nucleotide sequence substantially the same as, or identical to, SEQ ID NO: 143, 145, 149, 151, 153, 155, 157, 159, 161, 163, 167, 169, or 171.

In some embodiments, the HC1 of a CD79b×CD20×CD3 trispecific antibody comprises an amino acid sequence substantially the same as, or identical to, SEQ ID NO: 172 and the LC comprises the amino acid sequence substantially the same as, or identical to, SEQ ID NO: 174. In some embodiments, the nucleotide sequence encoding an HC1 of a CD79b×CD20×CD3 trispecific antibody comprises the nucleotide sequence substantially the same as, or identical to, SEQ ID NO: 173 and the nucleotide sequence encoding an LC comprises the nucleotide sequence substantially the same as, or identical to, SEQ ID NO:175.

In some embodiments, the HC1 of a CD79b×CD20×CD3 trispecific antibody comprises an amino acid sequence substantially the same as, or identical to, SEQ ID NO: 176 and the LC comprises an amino acid sequence substantially the same as, or identical to, SEQ ID NO: 178. In some embodiments, the nucleotide sequence encoding the HC1 of a CD79b×CD20×CD3 trispecific antibody comprises the nucleotide sequence substantially the same as, or identical to, SEQ ID NO: 177 and the nucleotide sequence encoding the LC comprises the nucleotide sequence substantially the same as, or identical to, SEQ ID NO:179.

In some embodiments, the HC1 of a CD79b×CD20×CD3 trispecific antibody comprises an amino acid sequence substantially the same as, or identical to, SEQ ID NO: 180 and the LC comprises an amino acid sequence substantially the same as, or identical to, SEQ ID NO: 182. In some embodiments, the nucleotide sequence encoding the HC1 of a CD79b×CD20×CD3 trispecific antibody comprises the nucleotide sequence substantially the same as, or identical to, SEQ ID NO: 181 and the nucleotide sequence encoding the LC comprises the nucleotide sequence substantially the same as, or identical to, SEQ ID NO:183 or 188.

In some embodiments, the HC1 of a CD79b×CD20×CD3 trispecific antibody comprises an amino acid sequence substantially the same as, or identical to, SEQ ID NO: 191 and the LC comprises an amino acid sequence substantially the same as, or identical to, SEQ ID NO: 182. In some embodiments, the nucleotide sequence encoding the HC1 of a CD79b×CD20×CD3 trispecific antibody comprises the nucleotide sequence substantially the same as, or identical to, SEQ ID NO: 192 and the nucleotide sequence encoding the LC comprises the nucleotide sequence substantially the same as, or identical to, SEQ ID NO:183.

In some embodiments of a CD79b×CD20×CD3 trispecific antibody, the HC1 comprises an amino acid sequence substantially the same as, or identical to, SEQ ID NO: 172, the LC comprises an amino acid sequence substantially the same as, or identical to, SEQ ID NO: 174, and the CD3/CD20 arm comprises an amino acid sequence substantially the same as, or identical to, SEQ ID NO: 142. In some embodiments, the nucleotide sequence encoding the HC1 comprises the nucleotide sequence substantially the same as, or identical to, SEQ ID NO: 173, the nucleotide sequence encoding the LC comprises the nucleotide sequence substantially the same as, or identical to, SEQ ID NO:175, and the nucleotide sequence encoding the CD3/CD20 arm comprises the nucleotide sequence substantially the same as, or identical to, SEQ ID NO: 143.

In some embodiments of a CD79b×CD20×CD3 trispecific antibody, the HC1 comprises an amino acid sequence substantially the same as, or identical to, SEQ ID NO: 176, the LC comprises an amino acid sequence of substantially the same as, or identical to, SEQ ID NO: 178, and the CD3/CD20 arm comprises an amino acid sequence of substantially the same as, or identical to, SEQ ID NO: 142. In some embodiments, the nucleotide sequence encoding the HC1 comprises the nucleotide sequence substantially the same as, or identical to, SEQ ID NO: 177, the nucleotide sequence encoding the LC comprises the nucleotide sequence substantially the same as, or identical to, SEQ ID NO:179, and the nucleotide sequence encoding the CD3/CD20 arm comprises the nucleotide sequence substantially the same as, or identical to, SEQ ID NO: 143.

In some embodiments of a CD79b×CD20×CD3 trispecific antibody, the HC1 comprises an amino acid sequence of substantially the same as, or identical to, SEQ ID NO: 180, the LC comprises an amino acid sequence of substantially the same as, or identical to, SEQ ID NO: 182, and the CD3/CD20 arm comprises an amino acid sequence of substantially the same as, or identical to, SEQ ID NO: 142. In some embodiments, the nucleotide sequence encoding the HC1 comprises the nucleotide sequence substantially the same as, or identical to, SEQ ID NO: 181, the nucleotide sequence encoding the LC comprises the nucleotide sequence substantially the same as, or identical to, SEQ ID NO:183, and the nucleotide sequence encoding the CD3/CD20 arm comprises the nucleotide sequence substantially the same as, or identical to, SEQ ID NO: 143.

In some embodiments of a CD79b×CD20×CD3 trispecific antibody, the HC1 comprises an amino acid sequence of substantially the same as, or identical to, SEQ ID NO: 172, the LC comprises an amino acid sequence of substantially the same as, or identical to, SEQ ID NO: 174, and the CD3/CD20 arm comprises an amino acid sequence of substantially the same as, or identical to, SEQ ID NO: 144. In some embodiments, the nucleotide sequence encoding the HC1 comprises the nucleotide sequence substantially the same as, or identical to, SEQ ID NO: 173, the nucleotide sequence encoding the LC comprises the nucleotide sequence substantially the same as, or identical to, SEQ ID NO:175 and the nucleotide sequence encoding the CD3/CD20 arm comprises the nucleotide sequence substantially the same as, or identical to, SEQ ID NO: 145.

In some embodiments of a CD79b×CD20×CD3 trispecific antibody, the HC1 comprises an amino acid sequence of substantially the same as, or identical to, SEQ ID NO: 176, the LC comprises an amino acid sequence of substantially the same as, or identical to, SEQ ID NO: 178, and the CD3/CD20 arm comprises an amino acid sequence of substantially the same as, or identical to, SEQ ID NO: 144. In some embodiments, the nucleotide sequence encoding the HC1 comprises the nucleotide sequence substantially the same as, or identical to, SEQ ID NO: 177, the nucleotide sequence encoding the LC comprises the nucleotide sequence substantially the same as, or identical to, SEQ ID NO:179 and the nucleotide sequence encoding the CD3/CD20 arm comprises the nucleotide sequence substantially the same as, or identical to, SEQ ID NO: 145.

In some embodiments of a CD79b×CD20×CD3 trispecific antibody, the HC1 comprises an amino acid sequence of substantially the same as, or identical to, SEQ ID NO: 180, the LC comprises an amino acid sequence of substantially the same as, or identical to, SEQ ID NO: 182, and the CD3/CD20 arm comprises an amino acid sequence of substantially the same as, or identical to, SEQ ID NO: 144. In some embodiments, the nucleotide sequence encoding the HC1 comprises the nucleotide sequence substantially the same as, or identical to, SEQ ID NO: 181, the nucleotide sequence encoding the LC comprises the nucleotide sequence substantially the same as, or identical to, SEQ ID NO:183, and the nucleotide sequence encoding the CD3/CD20 arm comprises the nucleotide sequence substantially the same as, or identical to, SEQ ID NO: 145.

In some embodiments of a CD79b×CD20×CD3 trispecific antibody, the HC1 comprises an amino acid sequence of substantially the same as, or identical to, SEQ ID NO: 180, the LC comprises an amino acid sequence of substantially the same as, or identical to, SEQ ID NO: 182, and the CD3/CD20 arm comprises an amino acid sequence of substantially the same as, or identical to, SEQ ID NO: 148. In some embodiments, the nucleotide sequence encoding the HC1 comprises the nucleotide sequence substantially the same as, or identical to, SEQ ID NO: 181, the nucleotide sequence encoding the LC comprises the nucleotide sequence substantially the same as, or identical to, SEQ ID NO:183, and the nucleotide sequence encoding the CD3/

CD20 arm comprises the nucleotide sequence substantially the same as, or identical to, SEQ ID NO: 149.

In some embodiments of a CD79b×CD20×CD3 trispecific antibody, the HC1 comprises an amino acid sequence of substantially the same as, or identical to, SEQ ID NO: 180, the LC comprises an amino acid sequence of substantially the same as, or identical to, SEQ ID NO: 182, and the CD3/CD20 arm comprises an amino acid sequence of substantially the same as, or identical to, SEQ ID NO: 150. In some embodiments, the nucleotide sequence encoding the HC1 comprises the nucleotide sequence substantially the same as, or identical to, SEQ ID NO: 181, the nucleotide sequence encoding the LC comprises the nucleotide sequence substantially the same as, or identical to, SEQ ID NO:188, and the nucleotide sequence encoding the CD3/CD20 arm comprises the nucleotide sequence substantially the same as, or identical to, SEQ ID NO: 151.

In some embodiments of a CD79b×CD20×CD3 trispecific antibody, the HC1 comprises an amino acid sequence of substantially the same as, or identical to, SEQ ID NO: 180, the LC comprises an amino acid sequence of substantially the same as, or identical to, SEQ ID NO: 182, and the CD3/CD20 arm comprises an amino acid sequence of substantially the same as, or identical to, SEQ ID NO: 152. In some embodiments, the nucleotide sequence encoding the HC1 comprises the nucleotide sequence substantially the same as, or identical to, SEQ ID NO: 181, the nucleotide sequence encoding the LC comprises the nucleotide sequence substantially the same as, or identical to, SEQ ID NO:188, and the nucleotide sequence encoding the CD3/CD20 arm comprises the nucleotide sequence substantially the same as, or identical to, SEQ ID NO: 153.

In some embodiments of a CD79b×CD20×CD3 trispecific antibody, the HC1 comprises an amino acid sequence of substantially the same as, or identical to, SEQ ID NO: 180, the LC comprises an amino acid sequence of substantially the same as, or identical to, SEQ ID NO: 182, and the CD3/CD20 arm comprises an amino acid sequence of substantially the same as, or identical to, SEQ ID NO: 154. In some embodiments, the nucleotide sequence encoding the HC1 comprises the nucleotide sequence substantially the same as, or identical to, SEQ ID NO: 181, the nucleotide sequence encoding the LC comprises the nucleotide sequence substantially the same as, or identical to, SEQ ID NO:188, and the nucleotide sequence encoding the CD3/CD20 arm comprises the nucleotide sequence substantially the same as, or identical to, SEQ ID NO: 155.

In some embodiments of a CD79b×CD20×CD3 trispecific antibody, the HC1 comprises an amino acid sequence of substantially the same as, or identical to, SEQ ID NO: 180, the LC comprises an amino acid sequence of substantially the same as, or identical to, SEQ ID NO: 182, and the CD3/CD20 arm comprises an amino acid sequence of substantially the same as, or identical to, SEQ ID NO: 156. In some embodiments, the nucleotide sequence encoding the HC1 comprises the nucleotide sequence substantially the same as, or identical to, SEQ ID NO: 181, the nucleotide sequence encoding the LC comprises the nucleotide sequence substantially the same as, or identical to, SEQ ID NO:188, and the nucleotide sequence encoding the CD3/CD20 arm comprises the nucleotide sequence substantially the same as, or identical to, SEQ ID NO: 157.

In some embodiments of a CD79b×CD20×CD3 trispecific antibody, the HC1 comprises an amino acid sequence of substantially the same as, or identical to, SEQ ID NO: 180, the LC comprises an amino acid sequence of substantially the same as, or identical to, SEQ ID NO: 182, and the CD3/CD20 arm comprises an amino acid sequence of substantially the same as, or identical to, SEQ ID NO: 158. In some embodiments, the nucleotide sequence encoding the HC1 comprises the nucleotide sequence substantially the same as, or identical to, SEQ ID NO: 181, the nucleotide sequence encoding the LC comprises the nucleotide sequence substantially the same as, or identical to, SEQ ID NO:188, and the nucleotide sequence encoding the CD3/CD20 arm comprises the nucleotide sequence substantially the same as, or identical to, SEQ ID NO: 159.

In some embodiments of a CD79b×CD20×CD3 trispecific antibody, the HC1 comprises an amino acid sequence of substantially the same as, or identical to, SEQ ID NO: 180, the LC comprises an amino acid sequence of substantially the same as, or identical to, SEQ ID NO: 182, and the CD3/CD20 arm comprises an amino acid sequence of substantially the same as, or identical to, SEQ ID NO: 160. In some embodiments, the nucleotide sequence encoding the HC1 comprises the nucleotide sequence substantially the same as, or identical to, SEQ ID NO: 181, the nucleotide sequence encoding the LC comprises the nucleotide sequence substantially the same as, or identical to, SEQ ID NO:188, and the nucleotide sequence encoding the CD3/CD20 arm comprises the nucleotide sequence substantially the same as, or identical to, SEQ ID NO: 161.

In some embodiments of a CD79b×CD20×CD3 trispecific antibody, the HC1 comprises an amino acid sequence of substantially the same as, or identical to, SEQ ID NO: 180, the LC comprises an amino acid sequence of substantially the same as, or identical to, SEQ ID NO: 182, and the CD3/CD20 arm comprises an amino acid sequence of substantially the same as, or identical to, SEQ ID NO: 162. In some embodiments, the nucleotide sequence encoding the HC1 comprises the nucleotide sequence substantially the same as, or identical to, SEQ ID NO: 181, the nucleotide sequence encoding the LC comprises the nucleotide sequence substantially the same as, or identical to, SEQ ID NO:188, and the nucleotide sequence encoding the CD3/CD20 arm comprises the nucleotide sequence substantially the same as, or identical to, SEQ ID NO: 163.

In some embodiments of a CD79b×CD20×CD3 trispecific antibody, the HC1 comprises an amino acid sequence of substantially the same as, or identical to, SEQ ID NO: 191, the LC comprises an amino acid sequence of substantially the same as, or identical to, SEQ ID NO: 182, and the CD3/CD20 arm comprises an amino acid sequence of substantially the same as, or identical to, SEQ ID NO: 166. In some embodiments, the nucleotide sequence encoding the HC1 comprises the nucleotide sequence substantially the same as, or identical to, SEQ ID NO: 192, the nucleotide sequence encoding the LC comprises the nucleotide sequence substantially the same as, or identical to, SEQ ID NO:183, and the nucleotide sequence encoding the CD3/CD20 arm comprises the nucleotide sequence substantially the same as, or identical to, SEQ ID NO: 167.

In some embodiments of a CD79b×CD20×CD3 trispecific antibody, the HC1 comprises an amino acid sequence of substantially the same as, or identical to, SEQ ID NO: 172, the LC comprises an amino acid sequence of substantially the same as, or identical to, SEQ ID NO: 174, and the CD3/CD20 arm comprises an amino acid sequence of substantially the same as, or identical to, SEQ ID NO: 168. In some embodiments, the nucleotide sequence encoding the HC1 comprises the nucleotide sequence substantially the same as, or identical to, SEQ ID NO: 173, the nucleotide sequence encoding the LC comprises the nucleotide sequence substantially the same as, or identical to, SEQ ID NO:175, and the nucleotide sequence encoding the CD3/CD20 arm comprises the nucleotide sequence substantially the same as, or identical to, SEQ ID NO: 169.

In some embodiments of a CD79b×CD20×CD3 trispecific antibody, the HC1 comprises an amino acid sequence of substantially the same as, or identical to, SEQ ID NO: 172, the LC comprises an amino acid sequence of substantially the same as, or identical to, SEQ ID NO: 174, and the CD3/CD20 arm comprises an amino acid sequence of substantially the same as, or identical to, SEQ ID NO: 170. In some embodiments, the nucleotide sequence encoding the HC1 comprises the nucleotide sequence substantially the same as, or identical to, SEQ ID NO: 173, the nucleotide sequence encoding the LC comprises the nucleotide sequence substantially the same as, or identical to, SEQ ID NO:175 and the nucleotide sequence encoding the CD3/CD20 arm comprises the nucleotide sequence substantially the same as, or identical to, SEQ ID NO: 171.

In one embodiment, the HC1 of a CD79b×CD20×CD3 trispecific antibody comprises an amino acid sequence substantially the same as, or identical to, SEQ ID NO: 172. In one embodiment, the HC1 of a CD79b×CD20×CD3 trispecific antibody is encoded by a nucleotide sequence substantially the same as, or identical to, SEQ ID NO: 173.

In one embodiment, the LC of a CD79b×CD20×CD3 trispecific antibody comprises an amino acid sequence substantially the same as, or identical to, SEQ ID NO: 174. In one embodiment, the LC of a CD79b×CD20×CD3 trispecific antibody is encoded by a nucleotide sequence substantially the same as, or identical to, SEQ ID NO: 175.

In one embodiment, the CD3/CD20 arm of a CD79b×CD20×CD3 trispecific antibody comprises an amino acid sequence substantially the same as, or identical to, SEQ ID NO: 168. In one embodiment, the CD3/CD20 arm of a CD79b×CD20×CD3 trispecific antibody is encoded by a nucleotide sequence substantially the same as, or identical to, SEQ ID NO: 169.

In one embodiment, the CD3/CD20 arm of a CD79b×CD20×CD3 trispecific antibody comprises an amino acid sequence substantially the same as, or identical to, SEQ ID NO: 170. In one embodiment, the CD3/CD20 arm of a CD79b×CD20×CD3 trispecific antibody is encoded by a nucleotide sequence substantially the same as, or identical to, SEQ ID NO: 171.

In one embodiment, provided herein is an isolated trispecific antibody, or a trispecific binding fragment thereof, comprising:
a) a CD79b binding arm comprising a heavy chain (HC1) and a light chain (LC); and
b) a CD3/CD20 binding arm,
wherein HC1 comprises an amino acid sequence substantially the same as, or identical to, SEQ ID NO: 172, LC comprises an amino acid sequence substantially the same as, or identical to, SEQ ID NO: 174, and the CD3/CD20 binding arm comprises an amino acid sequence substantially the same as, or identical to, SEQ ID NO: 168.

In one embodiment, provided herein is an isolated trispecific antibody, or a trispecific binding fragment thereof, comprising:
a) a CD79b binding arm comprising a heavy chain (HC1) and a light chain (LC); and
b) a CD3/CD20 binding arm,
wherein HC1 comprises the amino acid sequence of SEQ ID NO: 172, LC comprises the amino acid sequence of SEQ ID NO: 174, and the CD3/CD20 binding arm comprises the amino acid sequence of SEQ ID NO: 168.

In one embodiment, provided herein is an isolated trispecific antibody, or a trispecific binding fragment thereof, comprising:
a) a CD79b binding arm comprising a heavy chain (HC1) and a light chain (LC); and
b) a CD3/CD20 binding arm,
wherein HC1 comprises an amino acid sequence substantially the same as, or identical to, SEQ ID NO: 172, LC comprises an amino acid sequence substantially the same as, or identical to, SEQ ID NO: 174, and the CD3/Cd20 binding arm comprises an amino acid sequence substantially the same as, or identical to, SEQ ID NO: 170.

In one embodiment, provided herein is an isolated trispecific antibody, or a trispecific binding fragment thereof, comprising:
a) a CD79b binding arm comprising a heavy chain (HC1) and a light chain (LC); and
b) a CD3/CD20 binding arm,
wherein HC1 comprises the amino acid sequence of SEQ ID NO: 172, LC comprises the amino acid sequence of SEQ ID NO: 174, and the CD3/CD20 binding arm comprises the amino acid sequence of SEQ ID NO: 170.

In one embodiment, the CD79b×CD20×CD3 trispecific antibody is C923B168.

In one embodiment, the CD79b×CD20×CD3 trispecific antibody is C923B169.

In some embodiments, a bispecific antibody, or a bispecific antibody fragment of the present disclosure comprises a CD79b binding arm comprising HC1 and LC, and/or CD3 binding arm of any one of the antibodies described in Table 6. In some embodiments, a bispecific antibody, or a bispecific antibody fragment of the present disclosure may be encoded by a nucleotide sequence encoding an HC1, LC, and/or CD3 binding arm of any one of the antibodies described in Table 6.

Table 6 provides a summary of examples of some CD79b×CD3 bispecific antibodies described herein:

TABLE 6

| | | | | | | | | |
|---|---|---|---|---|---|---|---|---|
| Exemplary CD79b × CD3 bispecific antibodies |||||||||
| ID | HC1/LC (CD79b arm) | HC1 amino acid sequence SEQ ID NO | HC1 DNA sequence SEQ ID NO | LC amino acid sequence SEQ ID NO | LC DNA sequence SEQ ID NO | CD3-arm | CD3 arm amino acid sequence SEQ ID NO | CD3 arm DNA sequence SEQ ID NO |
| 79C3B601 | CD9B374 | 172 | 173 | 174 | 175 | CD3B2030-N106A | 164 | 165 |
| 79C3B646 | CD9B330-N31S | 176 | 177 | 178 | 179 | CD3B2030-N106A | 164 | 165 |

TABLE 6-continued

Exemplary CD79b × CD3 bispecific antibodies

| ID | HC1/LC (CD79b arm) | HC1 amino acid sequence SEQ ID NO | HC1 DNA sequence SEQ ID NO | LC amino acid sequence SEQ ID NO | LC DNA sequence SEQ ID NO | CD3-arm | CD3 arm amino acid sequence SEQ ID NO | CD3 arm DNA sequence SEQ ID NO |
|---|---|---|---|---|---|---|---|---|
| 79C3B651 | CD9B643 | 180 | 181 | 182 | 183 | CD3B2030-N106A | 164 | 165 |
| 79C3B605 | CD9B374 | 172 | 173 | 174 | 175 | CD3B2089-N106G | 189 | 190 |
| 79C3B645 | CD9B330-N31S | 176 | 177 | 178 | 179 | CD3B2089-N106G | 189 | 190 |
| 79C3B650 | CD9B643 | 180 | 181 | 182 | 183 | CD3B2089-N106G | 189 | 190 |

In some embodiments, the HC1 of a CD79b×CD3 bispecific antibody comprises an amino acid sequence substantially the same as, or identical to, SEQ ID NO: 172, 176, or 180. In some embodiments, the nucleotide sequence encoding an HC1 of a CD79b×CD3 bispecific antibody comprises the nucleotide sequence substantially the same as, or identical to, SEQ ID NO: 173, 177, or 181.

In some embodiments, the LC of a CD79b×CD3 bispecific antibody comprises an amino acid sequence substantially the same as, or identical to, SEQ ID NO: 174, 178, or 182. In some embodiments, the nucleotide sequence encoding an LC of a CD79b×CD3 bispecific antibody comprises the nucleotide sequence substantially the same as, or identical to, SEQ ID NO: 175, 179, or 183.

In some embodiments, the CD3 arm of a CD79b×CD3 bispecific antibody comprises an amino acid sequence substantially the same as, or identical to, SEQ ID NO: 164 or 189. In some embodiments, the nucleotide sequence encoding a CD3 arm of a CD79b×CD3 bispecific antibody comprises the nucleotide sequence substantially the same as, or identical to, SEQ ID NO: 165 or 190.

In some embodiments, the HC1 of a CD79b×CD3 bispecific antibody comprises an amino acid sequence substantially the same as, or identical to, SEQ ID NO: 172 and the LC comprises the amino acid sequence substantially the same as, or identical to, SEQ ID NO: 174. In some embodiments, the nucleotide sequence encoding an HC1 of a CD79b×CD3 bispecific antibody comprises the nucleotide sequence substantially the same as, or identical to, SEQ ID NO: 173 and the nucleotide sequence encoding an LC comprises the nucleotide sequence substantially the same as, or identical to, SEQ ID NO:175.

In some embodiments, the HC1 of a CD79b×CD3 bispecific antibody comprises an amino acid sequence substantially the same as, or identical to, SEQ ID NO: 176 and the LC comprises an amino acid sequence substantially the same as, or identical to, SEQ ID NO: 178. In some embodiments, the nucleotide sequence encoding an HC1 of a CD79b×CD3 bispecific antibody comprises the nucleotide sequence substantially the same as, or identical to, SEQ ID NO: 177 and the nucleotide sequence encoding an LC comprises the nucleotide sequence substantially the same as, or identical to, SEQ ID NO:179.

In some embodiments, the HC1 of a CD79b×CD3 bispecific antibody comprises an amino acid sequence substantially the same as, or identical to, SEQ ID NO: 180 and the LC comprises an amino acid sequence substantially the same as, or identical to, SEQ ID NO: 182. In some embodiments, the nucleotide sequence encoding an HC1 of a CD79b×CD3 bispecific antibody comprises the nucleotide sequence substantially the same as, or identical to, SEQ ID NO: 181 and the nucleotide sequence encoding an LC comprises the nucleotide sequence substantially the same as, or identical to, SEQ ID NO:183 or 188.

In some embodiments of a CD79b×CD3 bispecific antibody, the HC1 comprises an amino acid sequence substantially the same as, or identical to, SEQ ID NO: 172, the LC comprises an amino acid sequence substantially the same as, or identical to, SEQ ID NO: 174, and the CD3 arm comprises an amino acid sequence substantially the same as, or identical to, SEQ ID NO: 164. In some embodiments, the nucleotide sequence encoding the HC1 comprises the nucleotide sequence substantially the same as, or identical to, SEQ ID NO: 173, the nucleotide sequence encoding the LC comprises the nucleotide sequence substantially the same as, or identical to, SEQ ID NO:175 and the nucleotide sequence encoding the CD3 arm comprises the nucleotide sequence substantially the same as, or identical to, SEQ ID NO: 165.

In some embodiments of a CD79b×CD3 bispecific antibody, the HC1 comprises an amino acid sequence of substantially the same as, or identical to, SEQ ID NO: 176, the LC comprises an amino acid sequence of substantially the same as, or identical to, SEQ ID NO: 178, and the CD3 arm comprises an amino acid sequence of substantially the same as, or identical to, SEQ ID NO: 164. In some embodiments, the nucleotide sequence encoding the HC1 comprises the nucleotide sequence substantially the same as, or identical to, SEQ ID NO: 177, the nucleotide sequence encoding the LC comprises the nucleotide sequence substantially the same as, or identical to, SEQ ID NO:179, and the nucleotide sequence encoding the CD3 arm comprises the nucleotide sequence substantially the same as, or identical to, SEQ ID NO: 165.

In some embodiments of a CD79b×CD3 bispecific antibody, the HC1 comprises an amino acid sequence of substantially the same as, or identical to, SEQ ID NO: 180, the LC comprises an amino acid sequence of substantially the same as, or identical to, SEQ ID NO: 182, and the CD3 arm comprises an amino acid sequence of substantially the same as, or identical to, SEQ ID NO: 164. In some embodiments, the nucleotide sequence encoding the HC1 comprises the nucleotide sequence substantially the same as, or identical to, SEQ ID NO: 181, the nucleotide sequence encoding the LC comprises the nucleotide sequence substantially the same as, or identical to, SEQ ID NO:183, and the nucleotide sequence encoding the CD3 arm comprises the nucleotide sequence substantially the same as, or identical to, SEQ ID NO: 165.

In some embodiments of a CD79bxCD3 bispecific antibody, the HC1 comprises an amino acid sequence of substantially the same as, or identical to, SEQ ID NO: 172, the LC comprises an amino acid sequence of substantially the same as, or identical to, SEQ ID NO: 174, and the CD3 arm comprises an amino acid sequence of substantially the same as, or identical to, SEQ ID NO: 189. In some embodiments, the nucleotide sequence encoding the HC1 comprises the nucleotide sequence substantially the same as, or identical to, SEQ ID NO: 173, the nucleotide sequence encoding the LC comprises the nucleotide sequence substantially the same as, or identical to, SEQ ID NO:175, and the nucleotide sequence encoding the CD3 arm comprises the nucleotide sequence substantially the same as, or identical to, SEQ ID NO: 190.

In some embodiments of a CD79bxCD3 bispecific antibody, the HC1 comprises an amino acid sequence of substantially the same as, or identical to, SEQ ID NO: 176, the LC comprises an amino acid sequence of substantially the same as, or identical to, SEQ ID NO: 178, and the CD3 arm comprises an amino acid sequence of substantially the same as, or identical to, SEQ ID NO: 189. In some embodiments, the nucleotide sequence encoding the HC1 comprises the nucleotide sequence substantially the same as, or identical to, SEQ ID NO: 177, the nucleotide sequence encoding the LC comprises the nucleotide sequence substantially the same as, or identical to, SEQ ID NO:179, and the nucleotide sequence encoding the CD3 arm comprises the nucleotide sequence substantially the same as, or identical to, SEQ ID NO: 190.

In some embodiments of a CD79bxCD3 bispecific antibody, the HC1 comprises an amino acid sequence of substantially the same as, or identical to, SEQ ID NO: 180, the LC comprises an amino acid sequence of substantially the same as, or identical to, SEQ ID NO: 182, and the CD3 arm comprises an amino acid sequence of substantially the same as, or identical to, SEQ ID NO: 189. In some embodiments, the nucleotide sequence encoding the HC1 comprises the nucleotide sequence substantially the same as, or identical to, SEQ ID NO: 181, the nucleotide sequence encoding the LC comprises the nucleotide sequence substantially the same as, or identical to, SEQ ID NO:183, and the nucleotide sequence encoding the CD3 arm comprises the nucleotide sequence substantially the same as, or identical to, SEQ ID NO: 190.

In addition to the described multispecific antibodies or antigen-binding fragments, also provided are polynucleotide sequences capable of encoding the described multispecific antibodies or antigen-binding fragments. Vectors comprising the described polynucleotides are also provided, as are cells expressing the multispecific antibodies or antigen-binding fragments provided herein. Also described are cells capable of expressing the disclosed vectors. These cells may be mammalian cells (such as 293F cells, CHO cells), insect cells (such as Sf7 cells), yeast cells, plant cells, or bacteria cells (such as *E. coli*). The described antibodies may also be produced by hybridoma cells. The described antibodies may also be recombinantly produced.

Polynucleotides encoding recombinant antigen-binding proteins also are within the scope of the disclosure. In some embodiments, the polynucleotides described (and the peptides they encode) include a leader sequence. Any leader sequence known in the art may be employed. The leader sequence may include, but is not limited to, a restriction site or a translation start site.

The multispecific antibodies or antigen-binding fragments described herein include variants having single or multiple amino acid substitutions, deletions, or additions that retain the biological properties (e.g., binding affinity or immune effector activity) of the described multispecific antibodies or antigen-binding fragments. In the context of the present invention the following notations are, unless otherwise indicated, used to describe a mutation; i) substitution of an amino acid in a given position is written as e.g. K409R which means a substitution of a Lysine in position 409 with an Arginine; and ii) for specific variants the specific three or one letter codes are used, including the codes Xaa and X to indicate any amino acid residue. Thus, the substitution of Arginine for Lysine in position 409 is designated as: K409R, or the substitution of any amino acid residue for Lysine in position 409 is designated as K409X. In case of deletion of Lysine in position 409 it is indicated by K409*. The skilled person may produce variants having single or multiple amino acid substitutions, deletions, or additions.

These variants may include: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies or antigen-binding fragments described herein may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (deletions, mutations, etc.), chemical, and enzymatic techniques, are known to persons having ordinary skill in the art.

The multispecific antibodies or antigen-binding fragments described herein may embody several antibody isotypes, such as IgM, IgD, IgG, IgA and IgE. In some embodiments the antibody isotype is IgG1, IgG2, IgG3, or IgG4 isotype, preferably IgG1 or IgG4 isotype. Antibody or antigen-binding fragment thereof specificity is largely determined by the amino acid sequence, and arrangement, of the CDRs. Therefore, the CDRs of one isotype may be transferred to another isotype without altering antigen specificity. Alternatively, techniques have been established to cause hybridomas to switch from producing one antibody isotype to another (isotype switching) without altering antigen specificity. Accordingly, such antibody isotypes are within the scope of the described antibodies or antigen-binding fragments.

Also provided are vectors comprising the polynucleotides described herein. The vectors can be expression vectors. Recombinant expression vectors containing a sequence encoding a polypeptide of interest are thus contemplated as within the scope of this disclosure. The expression vector may contain one or more additional sequences such as but not limited to regulatory sequences (e.g., promoter, enhancer), a selection marker, and a polyadenylation signal. Vectors for transforming a wide variety of host cells are well known and include, but are not limited to, plasmids, phagemids, cosmids, baculoviruses, bacmids, bacterial artificial chromosomes (BACs), yeast artificial chromosomes (YACs), as well as other bacterial, yeast and viral vectors.

Recombinant expression vectors within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors may be constructed as described by Okayama and Berg, 3 *Mol. Cell. Biol.* 280 (1983).

In some embodiments, the multispecific antibody- or antigen-binding fragment-coding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. In one embodiment, the multispecific antibody or antigen-binding fragment thereof coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like.

Vectors described herein may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene, a puromycin resistance gene, a blasticidin resistance gene), glutamate synthase genes, HSV-TK, HSV-TK derivatives for ganciclovir selection, or bacterial purine nucleoside phosphorylase gene for 6-methylpurine selection (Gadi et al., 7 *Gene Ther.* 1738-1743 (2000)). A nucleic acid sequence encoding a selection marker or the cloning site may be upstream or downstream of a nucleic acid sequence encoding a polypeptide of interest or cloning site.

The vectors described herein may be used to transform various cells with the genes encoding the described antibodies or antigen-binding fragments. For example, the vectors may be used to generate multispecific antibody or antigen-binding fragment-producing cells. Thus, another aspect features host cells transformed with vectors comprising a nucleic acid sequence encoding an antibody or antigen-binding fragment thereof that binds CD79b, CD20, and/or CD3, such as the antibodies or antigen-binding fragments described and exemplified herein.

Numerous techniques are known in the art for the introduction of foreign genes into cells and may be used to construct the recombinant cells for purposes of carrying out the described methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, 29 *Pharmac. Ther.* 69-92 (1985)). Calcium phosphate precipitation and polyethylene glycol (PEG)-induced fusion of bacterial protoplasts with mammalian cells may also be used to transform cells.

Cells suitable for use in the expression of the multispecific antibodies or antigen-binding fragments described herein are preferably eukaryotic cells, more preferably cells of plant, rodent, or human origin, for example but not limited to NSO, CHO, CHOK1, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others. In addition, expression of antibodies may be accomplished using hybridoma cells. Methods for producing hybridomas are well established in the art.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Therapeutic Composition and Methods of Treatment Using Multispecific Antibodies and Multispecific Antigen-Binding Fragments Thereof The multispecific antibodies discussed above, for example the CD79b×CD20×CD3 trispecific antibodies or the CD79b×CD3 bispecific antibodies discussed above, are useful in therapy. In particular, the multispecific antibodies are useful in treating cancer. Also provided herein are therapeutic compositions for the treatment of a hyperproliferative disorder in a mammal which comprises a therapeutically effective amount of a multispecific antibody or multispecific antigen-binding fragment described herein and a pharmaceutically acceptable carrier. In some embodiments, the multispecific antibody is a CD79b×CD20×CD3 trispecific antibody as described herein, or a CD79b×CD20×CD3-trispecific antigen-binding fragment thereof. In some embodiments, the bispecific antibody is a CD79b×CD3 trispecific antibody as described herein, or a CD79b×CD3-bispecific antigen-binding fragment thereof. In one embodiment said pharmaceutical composition is for the treatment of a CD79b and/or CD20-expressing cancer, including (but not limited to) the following: CD79b and/or CD20-expressing B cell cancers, such as B-cell lymphoma, non-Hodgkin lymphoma, diffuse large B-cell lymphoma (DLBCL), a mantle cell lymphoma (MCL), a follicular lymphoma (FL), acute lymphoblastic leukemia (ALL), chronic lymphocytic leukemia (CLL), Waldenström macroglobulinemia (WM), multiple myeloma (MM), mucosa-associated lymphoid tissue (MALT) lymphoma, Hodgkin's lymphoma, Burkitt's lymphoma, hairy-cell leukemia, or Plasmacytoma cells, and other cancers yet to be determined in which CD79b and/or CD20 is expressed. Particular trispecific antibodies that may be used to treat cancer, such as hematological cancer, including the specific cancers discussed above, include antibodies C923B168, and C923B169.

In some embodiments, the CD79b×CD20×CD3 trispecific antibody or binding fragment thereof is utilized for the treatment of diffuse large B-cell lymphoma (DLBCL) including R/R DLBCL.

In some embodiments, the CD79b×CD20×CD3 trispecific antibody or binding fragment thereof is utilized for the treatment of non-Hodgkin lymphoma (including R/R non-Hodgkin lymphoma) such as follicular lymphoma (FL) or marginal zone lymphoma (MZL).

In some embodiments, the CD79b×CD20×CD3 trispecific antibody or binding fragment thereof is utilized for the treatment of mantle cell lymphoma (MCL), including R/R MCL.

In some embodiments, the CD79b×CD20×CD3 trispecific antibody or binding fragment thereof is utilized for the treatment of chronic lymphocytic leukemia (CLL), including R/R CLL.

In some embodiments, the CD79b×CD20×CD3 trispecific antibody or binding fragment thereof is utilized for the treatment of Waldenström macroglobulinemia (WM), including R/R WM.

In some embodiments, the CD79b×CD20×CD3 trispecific antibody or binding fragment thereof is utilized for the treatment Burkitt lymphoma (BL).

In some embodiments, the CD79b×CD20×CD3 trispecific antibody or binding fragment thereof is utilized for the treatment of primary mediastinal b cell lymphoma (PMBCL).

In some embodiments, the CD79b×CD20×CD3 trispecific antibody or binding fragment thereof is utilized for the treatment of nodular lymphomcyte predominant Hodgkin Lymphoma (nLPHL).

In some embodiments, the CD79b×CD20×CD3 trispecific antibody or binding fragment thereof is utilized for the treatment of post-transplantation lymphoproliferative disorders (PTLD).

In some embodiments, the CD79b×CD20×CD3 trispecific antibody or binding fragment thereof is utilized for the treatment of primary central nervous system lymphoma (PCNSL).

In some embodiments, the CD79b×CD20×CD3 trispecific antibody or binding fragment thereof is utilized for autologous and allogeneic stem cell transplantation (autoSCT and alloSCT) as a condition regimen, and as a chemotherapy-free maintenance therapy or proactive prevention of relapse post-SCT with the intention of curing relapsed B-cell lymphoma.

In some embodiments, the CD79b×CD20×CD3 trispecific antibody or binding fragment thereof is utilized for local or topical treatment of cutaneous B-cell lymphoma (including DLBCL Leg type), bronchus-associated lymphoid tissue (BALT) lymphoma, intraocular lymphoma (IOL) including primary intraocular lymphoma (PIOL) or secondary intraocular lymphoma (SIOL) of the B-cell lineage. In these embodiments, the CD79b×CD20×CD3 trispecific antibody or binding fragment thereof may utilize new administration approaches, such as inhaler or nebulizer for BALT lymphoma affecting the lungs.

The pharmaceutical compositions provided herein comprise: a) an effective amount of a multispecific antibody or antibody fragment of the present invention, and b) a pharmaceutically acceptable carrier, which may be inert or physiologically active. In some embodiments, the multispecific antibody is a CD79b×CD20×CD3 trispecific antibody as described herein, or a CD79b×CD20×CD3-trispecific antigen-binding fragment thereof. In some embodiments, the bispecific antibody is a CD79b×CD3 trispecific antibody as described herein, or a CD79b×CD3-bispecific antigen-binding fragment thereof. As used herein, the term "pharmaceutically acceptable carriers" includes any and all solvents, dispersion media, coatings, antibacterial and antifungal agents, and the like that are physiologically compatible. Examples of suitable carriers, diluents and/or excipients include one or more of water, saline, phosphate buffered saline, dextrose, glycerol, ethanol, and the like, as well as any combination thereof. In many cases, it will be preferable to include isotonic agents, such as sugars, polyalcohols, or sodium chloride in the composition. In particular, relevant examples of suitable carrier include: (1) Dulbecco's phosphate buffered saline, pH. about.7.4, containing or not containing about 1 mg/mL to 25 mg/mL human serum albumin, (2) 0.9% saline (0.9% w/v sodium chloride (NaCl)), and (3) 5% (w/v) dextrose; and may also contain an antioxidant such as tryptamine and a stabilizing agent such as Tween 20*.

The compositions of the invention may be in a variety of forms. These include for example liquid, semi-solid, and solid dosage forms, but the preferred form depends on the intended mode of administration and therapeutic application. Typical preferred compositions are in the form of injectable or infusible solutions. The preferred mode of administration is parenteral (e.g. intravenous, intramuscular, intraperitoneal, subcutaneous). In a preferred embodiment, the compositions of the invention are administered intravenously as a bolus or by continuous infusion over a period of time. In another preferred embodiment, they are injected by intramuscular, subcutaneous, intra-articular, intrasynovial, intratumoral, peritumoral, intralesional, or perilesional routes, to exert local as well as systemic therapeutic effects.

Sterile compositions for parenteral administration can be prepared by incorporating the antibody, antibody fragment or antibody conjugate of the present invention in the required amount in the appropriate solvent, followed by sterilization by microfiltration. As solvent or vehicle, there may be used water, saline, phosphate buffered saline, dextrose, glycerol, ethanol, and the like, as well as combination thereof. In many cases, it will be preferable to include isotonic agents, such as sugars, polyalcohol's, or sodium chloride in the composition. These compositions may also contain adjuvants, in particular wetting, isotonizing, emulsifying, dispersing and stabilizing agents. Sterile compositions for parenteral administration may also be prepared in the form of sterile solid compositions which may be dissolved at the time of use in sterile water or any other injectable sterile medium.

The multispecific antibody or antibody fragment may also be orally administered. As solid compositions for oral administration, tablets, pills, powders (gelatin capsules, sachets) or granules may be used. In these compositions, the active ingredient according to the invention is mixed with one or more inert diluents, such as starch, cellulose, sucrose, lactose or silica, under an argon stream. These compositions may also comprise substances other than diluents, for example one or more lubricants such as magnesium stearate or talc, a coloring, a coating (sugar-coated tablet) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavoring or stabilizing products.

The doses depend on the desired effect, the duration of the treatment and the route of administration used; they are generally between 5 mg and 1000 mg per day orally for an adult with unit doses ranging from 1 mg to 250 mg of active substance. In general, the doctor will determine the appropriate dosage depending on the age, weight and any other factors specific to the subject to be treated.

Also provided herein are methods for killing a CD79b and/or CD20+ cell by administering to a patient in need thereof a multispecific antibody which binds said CD79b and/or CD20 and is able to recruit T cells to kill said CD79b and/or CD20+ cell (i.e., T cell redirection). Any of the multispecific antibodies or antibody fragments of the invention may be used therapeutically. For example, in one embodiment the CD79b×CD20×CD3-multispecific antibody may be used therapeutically to treat cancer in a subject.

In a preferred embodiment, multispecific antibodies or antibody fragments of the invention are used for the treatment of a hyperproliferative disorder in a mammal. In a more preferred embodiment, one of the pharmaceutical compositions disclosed above, and which contains a multispecific antibody or antibody fragment of the invention, is used for the treatment of a hyperproliferative disorder in a mammal. In one embodiment, the disorder is a cancer. In particular, the cancer is a CD79b and/or CD20-expressing cancer, including (but not limited to) the following: CD79b and/or CD20-expressing B-cell cancers, such as B-cell lymphoma, non-Hodgkin lymphoma, diffuse large B-cell lymphoma (DLBCL), a mantle cell lymphoma (MCL), a follicular lymphoma (FL), acute lymphoblastic leukemia (ALL), chronic lymphocytic leukemia (CLL), Waldenström macroglobulinemia (WM), multiple myeloma (MM), mucosa-associated lymphoid tissue (MALT) lymphoma, Hodgkin's lymphoma, Burkitt's lymphoma, hairy-cell leukemia, or Plasmacytoma cells, and other cancers yet to be determined in which CD79b and/or CD20 is expressed. In some embodiments, the CD79b and/or CD20-expressing B-cell cancer treated with the pharmaceutical composition disclosed herein is a relapsed or refractory form of the cancer. In preferred embodiments, the multispecific antibody is a CD79b×CD20×CD3-multispecific antibody as described herein, or a multispecific antigen-binding fragment thereof, and more preferably a CD79b×CD20×CD3-trispecific antibody as described herein, or a CD79b×CD20×CD3-trispecific antigen-binding fragment thereof.

Accordingly, the pharmaceutical compositions of the invention are useful in the treatment or prevention of a variety of cancers, including (but not limited to) the following: a CD79b and/or CD20-expressing cancer, including (but not limited to) the following: CD79b and/or CD20-expressing B-cell cancers, such as B-cell lymphoma, non-Hodgkin lymphoma, diffuse large B-cell lymphoma (DLBCL), a mantle cell lymphoma (MCL), a follicular lymphoma (FL), acute lymphoblastic leukemia (ALL), chronic lymphocytic leukemia (CLL), Waldenström macroglobulinemia (WM), multiple myeloma (MM), mucosa-associated lymphoid tissue (MALT) lymphoma, Hodgkin's lymphoma, Burkitt's lymphoma, hairy-cell leukemia, or Plasmacytoma cells, and other cancers yet to be determined in which CD79b and/or CD20 is expressed. In some embodiments, the CD79b and/or CD20-expressing B-cell cancer treated with the pharmaceutical composition disclosed herein is a relapsed or refractory form of the cancer.

Similarly, further provided herein is a method for inhibiting the growth of selected cell populations comprising contacting CD79b and/or CD20-expressing target cells, or tissue containing such target cells, with an effective amount of a multispecific antibody or antibody fragment of the present invention, either alone or in combination with other cytotoxic or therapeutic agents, in the presence of a peripheral blood mononuclear cell (PBMC). A CD79b×CD20×CD3 antibody that blocks the binding of ligands to CD79b and CD20 may block CD79b- and CD20-mediated signaling and lead to inhibition or cell death of the target cells. In preferred embodiments, the multispecific antibody is a CD79b×CD20×CD3-multispecific antibody as described herein, or a multispecific antigen-binding fragment thereof, and more preferably a CD79b×CD20×CD3-trispecific antibody as described herein, or a CD79b×CD20×CD3-trispecific antigen-binding fragment thereof.

In some embodiments, the methods described herein involving the administration of a multispecific antibody or pharmaceutical composition comprising the same, further involve administering another therapeutic agent. Suitable other therapeutic agents include, without limitation, a chemotherapeutic agent, an anti-CD20 agent, an anti-CD19 agent, an anti-CD22 agent, an anti-CD37 agent, a Bruton's tyrosine kinase (BTK) inhibitor, a mucosa-associated lymphoid tissue lymphoma translocation protein 1 (MALT1) inhibitor, an immunomodulatory imide drug (IMiD), a pro apoptotic B cell lymphoma 2 (Bcl-2) family inhibitor, a phosphoinositide 3-kinase (PI3K) inhibitor, a NFKB-inducing kinase (NIK) inhibitor, an immune checkpoint inhibitor, a CD28 costimulatory bispecific antibody, or a CD137 costimulatory bispecific antibody, or a combination thereof.

In some embodiments, the other therapeutic agent is a chemotherapeutic regimen, such as rituximab-cyclophosphamide-hydroxydaunorubicin-oncovin-prednisone/prednisolone (R-CHOP), rituximab-ifosfamide-carboplatin-etoposide (R-ICE), rituximab-(dose-adjusted) etoposide-prednisolone-oncovin-cyclophosphamidehydroxydaunorubicin (R [DA] EPOCH), rituximab-dexamethasone-high-dose ara C cytarabine-platinol (R-DHAP), rituximab-etoposide-solu-medrol-high-dose ara C cytarabine-platinol (R-ESHAP), bendamustine-rituximab (BR), and lenalidomide+rituximab ($R^2$), Polivy (polatuzumab vedotin)+BR, or Monjuvi (tafasitamab-cxix)+lenalidomide regimens.

In some embodiments, the other therapeutic agent is an anti-CD79b agent (e.g. an anti-CD79b CAR-T therapy), anti-CD20 agent, such as a CD20×CD3 bispecific antibody (e.g., mosunetuzumab, glofitamab, odronextamab, IGM-2323, and epcoritamab). In some embodiments, the other therapeutic agent is an anti-CD19 agent, such as an anti-CD19 antibody (e.g., tafasitamab), an anti-CD19 CAR-T therapy (e.g., Yescarta, Kymriah, and Breyanzi), or an CD20×CD3 bispecific antibody. In some embodiments, the other therapeutic agent is an anti-CD22 agent, such as anti-CD22 antibody (e.g., moxetumomab pasudotox). In some embodiments, the other therapeutic agent is a Bruton's tyrosine kinase (BTK) inhibitor such as ibrutinib, covalent or non-covalent BTK inhibitors.

In some embodiments, the other therapeutic agent is a mucosa-associated lymphoid tissue lymphoma translocation protein 1 (MALT1) inhibitor. In some embodiments, the other therapeutic agent is an immunomodulatory imide drug (IMiD), such as lenalidominde. In some embodiments, the other therapeutic agent is a pro apoptotic B cell lymphoma 2 (Bcl-2) family inhibitor such as venetoclax and a Bcl-2-related protein A1 (BFL-1) inhibitor. In some embodiments, the other therapeutic agent is a phosphoinositide 3-kinase (PI3K) inhibitor, such as parsaclisib, idelalisib and umbralisib. In some embodiments, the other therapeutic agent is an immune checkpoint inhibitor, such as an anti-PD 1 antibody, anti T-cell Ig, TIM-3, T cell immunoreceptor with Ig and ITIM domains [TIGIT], and LAG-3. In some embodiments, the further therapeutic agent is cytarabine, an anthracycline, histamine dihydrochloride, selinexor, tasemetostat or interleukin 2. In some embodiments, the further therapeutic agent is a chemotherapeutic agent. The method for inhibiting the growth of selected cell populations can be practiced in vitro, in vivo, or ex vivo.

Examples of in vitro uses include treatments of autologous bone marrow prior to their transplant into the same patient in order to kill diseased or malignant cells; and prevent graft-versus-host-disease (GVHD); treatments of cell cultures in order to kill all cells except for desired variants that do not express the target antigen; or to kill variants that express undesired antigen. The conditions of non-clinical in vitro use are readily determined by one of ordinary skill in the art.

Examples of clinical ex vivo use are to remove tumor cells from bone marrow prior to autologous transplantation in cancer treatment. Treatment can be carried out as follows. Bone marrow is harvested from the patient or other individual, or a provided sample is used, and then incubated in medium containing serum to which is added the cytotoxic agent of the invention. Concentrations range from about 10 µM to 1 µM, for about 30 min to about 48 hr at about 37° C. The exact conditions of concentration and time of incubation, i.e., the dose, are readily determined by one of ordinary skill in the art. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, a therapeutically effective amount of the multispecific antibody or antigen-binding fragment is administered to a subject in need thereof. For example, the CD79b×CD20×CD3-multispecific antibodies and multispecific antigen-binding fragments thereof may be useful in the treatment of a CD79b and/or CD20-expressing cancer in a subject in need thereof. In some embodiments, the CD79b and/or CD20-expressing cancer is a B-cell cancer, such as diffuse large B-cell lymphoma (DLBCL). In preferred embodiments, the multispecific antibody is a CD79b×CD20×CD3-multispecific antibody as described herein, or a multispecific antigen-binding fragment thereof, and more preferably a CD79b×CD20×CD3-trispecific antibody as described herein, or a CD79b×CD20×CD3-trispecific antigen-binding fragment thereof. In some embodiments, the subject is a mammal, preferably a human. In some embodiments, the multispecific antibody or antigen-binding fragment will be administered as a solution that has been tested for sterility.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage.

The efficient dosages and the dosage regimens for the multispecific antibodies and fragments depend on the disease or condition to be treated and may be determined by one skilled in the art. An exemplary, non-limiting range for a therapeutically effective amount of a compound of the present invention is about 0.001-10 mg/kg, such as about 0.001-5 mg/kg, for example about 0.001-2 mg/kg, such as about 0.001-1 mg/kg, for instance about 0.001, about 0.01, about 0.1, about 1 or about 10 mg/kg.

A physician or veterinarian having ordinary skill in the art may readily determine and prescribe the effective amount of the pharmaceutical composition required. For example, the physician or veterinarian could start doses of the multispecific antibody or fragment employed in the pharmaceutical composition at levels lower than that required in order to achieve the desired therapeutic effect and gradually increase the dosage until the desired effect is achieved. In general, a suitable daily dose of a multispecific antibody of the present invention will be that amount of the compound which is the lowest dose effective to produce a therapeutic effect. Administration may e.g. be parenteral, such as intravenous, intramuscular, intratumoral (e.g., bone marrow) or subcutaneous. In one embodiment, the multispecific antibody or fragment may be administered by infusion in a weekly dosage of calculated by $mg/m^2$. Such dosages can, for example, be based on the mg/kg dosages provided above according to the following: dose (mg/kg)×body weight (e.g., 50-100 kg). Such administration may be repeated, e.g., 1 to 8 times, such as 3 to 5 times. The administration may be performed by continuous infusion over a period of from 2 to 24 hr, such as of from 2 to 12 hr. In one embodiment, the multispecific antibody or fragment may be administered by slow continuous infusion over a long period, such as more than 24 hours, in order to reduce toxic side effects.

In one embodiment, the multispecific antibody or fragment may be administered in a weekly dosage of calculated as a fixed dose for up to eight times, such as from four to six times when given once a week. Such regimen may be repeated one or more times as necessary, for example, after six months or twelve months. Such fixed dosages can, for example, be based on the mg/kg dosages provided above, with a body weight estimate of 50-100 kg. The dosage may be determined or adjusted by measuring the amount of multispecific antibody of the present invention in the blood upon administration by for instance taking out a biological sample and using anti-idiotypic antibodies which target the CD79b and/or CD20 antigen binding arms of the multispecific antibodies of the present invention.

In one embodiment, the multispecific antibody or fragment may be administered by maintenance therapy, such as, e.g., once a week for a period of six months or more.

A multispecific antibody or fragment may also be administered prophylactically in order to reduce the risk of developing cancer, delay the onset of the occurrence of an event in cancer progression, and/or reduce the risk of recurrence when a cancer is in remission.

The multispecific antibodies and fragments thereof as described herein may also be administered in combination therapy, i.e., combined with other therapeutic agents relevant for the disease or condition to be treated. Accordingly, in one embodiment, the antibody-containing medicament is for combination with one or more further therapeutic agent, such as a chemotherapeutic agent, an anti-CD20 agent, an anti-CD19 agent, an anti-CD22 agent, an anti-CD37 agent, a Bruton's tyrosine kinase (BTK) inhibitor, a mucosa-associated lymphoid tissue lymphoma translocation protein 1 (MALT1) inhibitor, an immunomodulatory imide drug (IMiD), a pro apoptotic B cell lymphoma 2 (Bcl-2) family inhibitor, a phosphoinositide 3-kinase (PI3K) inhibitor, a NFKB-inducing kinase (NIK) inhibitor, an immune checkpoint inhibitor, a CD28 costimulatory bispecific antibody, or a CD137 costimulatory bispecific antibody, or a combination thereof. In some embodiments, the other therapeutic agent is a chemotherapeutic regimen, such as rituximab-cyclophosphamide-hydroxydaunorubicin-oncovin-prednisone/prednisolone (R-CHOP), rituximab-ifosfamide-carboplatin-etoposide (R-ICE), rituximab-(dose-adjusted) etoposide-prednisolone-oncovin-cyclophosphamide-hydroxydaunorubicin (R [DA] EPOCH), rituximab-dexamethasone-high-dose ara C cytarabine-platinol (R-DHAP), rituximab-etoposide-solu-medrol-high-dose ara C cytarabine-platinol (R-ESHAP), bendamustine-rituximab (BR), and lenalidomide+rituximab ($R^2$), Polivy (polatuzumab vedotin)+BR, or Monjuvi (tafasitamab-cxix)+lenalidomide regimens. In some embodiments, the other therapeutic agent is an anti-CD79b agent (e.g. an anti-CD79b CAR-T therapy), anti-CD20 agent, such as a CD20×CD3 bispecific antibody (e.g., mosunetuzumab, glofitamab, odronextamab, IGM-2323, and epcoritamab). In some embodiments, the other therapeutic agent is an anti-CD19 agent, such as an anti-CD19 antibody (e.g., tafasitamab), an anti-CD19 CAR-T therapy (e.g., Yescarta, Kymriah, and Breyanzi), or an CD20×CD3 bispecific antibody. In some embodiments, the other therapeutic agent is an anti-CD22 agent, such as anti-CD22 antibody (e.g., moxetumomab pasudotox). In some embodiments, the other therapeutic agent is a Bruton's tyrosine kinase (BTK) inhibitor such as ibrutinib, covalent or non-covalent BTK inhibitors. In some embodiments, the other therapeutic agent is a mucosa-associated lymphoid tissue lymphoma translocation protein 1 (MALT1) inhibitor. In some embodiments, the other therapeutic agent is an immunomodulatory imide drug (IMiD), such as lenalidominde. In some embodiments, the other therapeutic agent is a pro apoptotic B cell lymphoma 2 (Bcl-2) family inhibitor such as venetoclax and a Bcl-2-related protein A1 (BFL-1) inhibitor. In some embodiments, the other therapeutic agent is a phosphoinositide 3-kinase (PI3K) inhibitor, such as parsaclisib, idelalisib and umbralisib. In some embodiments, the other therapeutic agent is an immune checkpoint inhibitor, such as an anti-PD 1 antibody, anti T-cell Ig, TIM-3, T cell immunoreceptor with Ig and ITIM domains [TIGIT], and LAG-3. In some embodiments, the other therapeutic agent is cytarabine, an anthracycline, histamine dihydrochloride, selinexor, tasemetostat or interleukin 2. Such combined administration may be simultaneous, separate or sequential, in any order. For simultaneous administration the agents may be administered as one composition or as separate compositions, as appropriate.

In one embodiment, a method for treating a disorder involving cells expressing CD79b and/or CD20 in a subject, which method comprises administration of a therapeutically effective amount of a multispecific antibody or fragment, such as a CD79b×CD20×CD3 multispecific antibody described herein, and radiotherapy to a subject in need thereof is provided. In one embodiment is provided a method for treating or preventing cancer, which method comprises administration of a therapeutically effective amount of a multispecific antibody or fragment, such as a CD79b×CD20×CD3 antibody described herein, and radiotherapy to a subject in need thereof. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, actinium-225, and indium-111.

Kits

Also provided herein are includes kits, e.g., comprising a described multispecific antibody or antigen-binding fragment thereof and instructions for the use of the antibody or fragments for killing of particular cell types. In preferred embodiments, the multispecific antibody is a CD79b×CD20×CD3-multispecific antibody as described herein, or a multispecific antigen-binding fragment thereof, and more preferably a CD79b×CD20×CD3-trispecific antibody as described herein, or a CD79b×CD20×CD3-trispecific antigen-binding fragment thereof. The instructions may include directions for using the multispecific antibody or antigen-binding fragment thereof in vitro, in vivo or ex vivo.

Typically, the kit will have a compartment containing the multispecific antibody or antigen-binding fragment thereof. The multispecific antibody or antigen-binding fragment thereof may be in a lyophilized form, liquid form, or other form amendable to being included in a kit. The kit may also contain additional elements needed to practice the method described on the instructions in the kit, such a sterilized solution for reconstituting a lyophilized powder, additional agents for combining with the multispecific antibody or antigen-binding fragment thereof prior to administering to a patient, and tools that aid in administering the multispecific antibody or antigen-binding fragment thereof to a patient.

Diagnostic Uses

The multispecific antibodies and fragments described herein may also be used for diagnostic purposes. Thus, also provided are diagnostic compositions comprising a multispecific antibody or fragments as defined herein, and to its use. In preferred embodiments, the multispecific antibody is a CD79b×CD20×CD3-multispecific antibody as described herein, or a multispecific antigen-binding fragment thereof, and more preferably a CD79b×CD20×CD3-trispecific antibody as described herein, or a CD79b×CD20×CD3-trispecific antigen-binding fragment thereof. In one embodiment, the present invention provides a kit for diagnosis of cancer comprising a container comprising a CD79b×CD20×CD3 trispecific antibody, and one or more reagents for detecting binding of the antibody to CD79b and/or CD20. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized. For example, the multispecific antibodies described herein, or antigen-binding fragments thereof, may be labeled with a radiolabel, a fluorescent label, an epitope tag, biotin, a chromophore label, an ECL label, an enzyme, ruthenium, $^{111}$In-DOTA, $^{111}$In-diethylenetriaminepentaacetic acid (DTPA), horseradish peroxidase, alkaline phosphatase and beta-galactosidase, or poly-histidine or similar such labels known in the art.

CD79b-Specific Antibodies

Described herein are isolated antibodies and antigen-binding fragments specific for CD79b. In some embodiments, the CD79b-specific antibodies and antigen-binding fragments bind human CD79b. The general structure of an CD79b-specific antibody molecule may comprise an antigen binding domain, which includes heavy and light chains, and the Fc domain, which serves a variety of functions, including complement fixation and binding antibody receptors.

In some embodiments are provided a CD79b-specific antibody, or an antigen-binding fragment thereof, comprising a heavy chain comprising a CDR1, a CDR2, and a CDR3 of any one of the antibodies described in Table 1a. In some embodiments are provided a CD79b-specific antibody, or an antigen-binding fragment thereof, comprising a heavy chain comprising a CDR1, a CDR2, and a CDR3 of any one of the antibodies described in Table 1a and a light chain comprising a CDR1, a CDR2, and a CDR3 of any one of the antibodies described in Table 1a.

The heavy chain variable domain and light chain variable domain of antibodies discussed in this section are suitable for inclusion in multispecific (e.g., bispecific or trispecific) constructs in which one arm is an anti-CD79b arm. Exemplary trispecific constructs comprising the CD79b-specific antibody, or an antigen-binding fragment thereof, discussed in this section are provided herein.

In some embodiments, the CD79b-specific antibodies and antigen-binding fragments bind human CD79b and cynomolgus monkey CD79b. In some embodiments, the CD79b-specific antibodies and antigen-binding fragments bind human CD79b but not to cynomolgus monkey CD79b. In some embodiments, the CD79b-specific antibodies and antigen-binding fragments bind to an epitope including one or more residues from the CD79b extracellular domain (ECD). In some embodiments, the CD79b-binding arm binds to one or more residues of a polypeptide having the amino acid sequence of SEQ ID NO: 252. In some embodiments, the CD79b-binding arm binds bind to residues 30-42 (SEDRYRNPKGSAC; SEQ ID NO: 253), residues 50-52 (PRF), residues 81-86 (EMENP; SEQ ID NO: 254), and/or residues 144-148 (GFSTL; SEQ ID NO: 255) of human CD79b. Such CD79b-binding arms may bind to CD79b with an affinity of $5\times10^{-7}$M or less, such as $1\times10^{-7}$M or less, $5\times10^{-8}$M or less, $1\times10^{-8}$M or less, $5\times10^{-9}$M or less, $1\times10^{-9}$M, or $5\times10^{-10}$ M or less. In one embodiment, the CD79b-binding arm binds to the CD79b with an affinity of about $1\times10^{-11}$M to $1\times10^{-9}$M. In one embodiment, the CD79b-binding arm binds to the CD79b with an affinity of about $1\times10^{-11}$M, about $2\times10^{-11}$M, about $3\times10^{-11}$M, about $4\times10^{-11}$M, about $5\times10^{-11}$M, about $6\times10^{-11}$M, about $7\times10^{-11}$M, about $8\times10^{-11}$M, about $9\times10^{-11}$M, $1\times10^{-10}$M, about $2\times10^{-10}$M, about $3\times10^{-10}$M, about $4\times10^{-10}$M, about $5\times10^{-10}$ M, about $6\times10^{-10}$M, about $7\times10^{-10}$M, about $8\times10^{-10}$ M, about $9\times10^{-10}$M or about $1\times10^{-9}$M.

The IgG class is divided in four isotypes: IgG1, IgG2, IgG3 and IgG4 in humans. They share more than 95% homology in the amino acid sequences of the Fc regions but show major differences in the amino acid composition and structure of the hinge region. The Fc region mediates effector functions, such as antibody-dependent cellular cytotoxicity (ADCC) and complement-dependent cytotoxicity (CDC). In ADCC, the Fc region of an antibody binds to Fc receptors (FcTRs) on the surface of immune effector cells such as natural killers and macrophages, leading to the phagocytosis or lysis of the targeted cells. In CDC, the antibodies kill the targeted cells by triggering the complement cascade at the cell surface. The antibodies described herein include antibodies with the described features of the variable domains in combination with any of the IgG isotypes, including modified versions in which the Fc sequence has been modified to effect different effector functions.

For many applications of therapeutic antibodies, Fc-mediated effector functions are not part of the mechanism of action. These Fc-mediated effector functions can be detrimental and potentially pose a safety risk by causing off-mechanism toxicity. Modifying effector functions can be achieved by engineering the Fc regions to reduce their binding to FcTRs or the complement factors. The binding of IgG to the activating (FcγRI, FcγRIIa, FcγRIIIa and FcγRIIIb) and inhibitory (FcγRIIb) FcTRs or the first component of complement (C1q) depends on residues located in the hinge region and the CH2 domain. Mutations have been introduced in IgG1, IgG2 and IgG4 to reduce or silence Fc functionalities. The antibodies described herein may include these modifications.

In one embodiment, the antibody comprises an Fc region with one or more of the following properties: (a) reduced effector function when compared to the parent Fc; (b) reduced affinity to FcγRI, FcγRIIa, FcγRIIb, FcγRIIIb and/or FcγRIIIa, (c) reduced affinity to FcγRI (d) reduced affinity to FcγRIIa (e) reduced affinity to FcγRIIb, (f) reduced affinity to FcγRIIIb or (g) reduced affinity to FcγRIIIa.

In some embodiments, the antibodies or antigen-binding fragments are IgG, or derivatives thereof, e.g., IgG1, IgG2, IgG3, and IgG4 isotypes. In some embodiments wherein the antibody has an IgG1 isotype, the antibody contains L234A, L235A, D265S and/or K409R substitutions in its Fc region. In some embodiments wherein the antibody has an IgG4 isotype, the antibody contains K409R, S228P, L234A, and L235A substitutions in its Fc region. The antibodies described herein may include these modifications.

In some embodiments the described antibodies may be capable of inhibiting APRIL binding with a $IC_{50}$ of low nanomolar as measured by ELISA.

In some embodiments the described antibodies bind to CD79b-positive multiple myeloma cell lines.

In addition to the described CD79b-specific antibodies and antigen-binding fragments, also provided are polynucleotide sequences capable of encoding the described antibodies and antigen-binding fragments. Vectors comprising the described polynucleotides are also provided, as are cells expressing the CD79b-specific antibodies or antigen-binding fragments provided herein. Also described are cells capable of expressing the disclosed vectors. These cells may be mammalian cells (such as 293F cells, CHO cells), insect cells (such as Sf7 cells), yeast cells, plant cells, or bacteria cells (such as E. coli). The described antibodies may also be produced by hybridoma cells.

The described CD79b-specific antibodies or antigen-binding fragments include all isotypes, IgA, IgD, IgE, IgG and IgM, and synthetic multimers of the four-chain immunoglobulin structure. The described antibodies or antigen-binding fragments also include the IgY isotype generally found in hen or turkey serum and hen or turkey egg yolk.

The CD79b-specific antibodies and antigen-binding fragments may be derived from any species by recombinant means. For example, the antibodies or antigen-binding fragments may be mouse, rat, goat, horse, swine, bovine, chicken, rabbit, camelid, donkey, human, or chimeric versions thereof. For use in administration to humans, non-human derived antibodies or antigen-binding fragments may be genetically or structurally altered to be less antigenic upon administration to a human patient.

In some embodiments, the antibodies or antigen-binding fragments are chimeric. As used herein, the term "chimeric" refers to an antibody, or antigen-binding fragment thereof, having at least some portion of at least one variable domain derived from the antibody amino acid sequence of a non-human mammal, a rodent, or a reptile, while the remaining portions of the antibody, or antigen-binding fragment thereof, are derived from a human.

In some embodiments, the antibodies are humanized antibodies. Humanized antibodies may be chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody may include at least a portion of an immunoglobulin constant region (Fc), typically that of a human immunoglobulin.

The antibodies or antigen-binding fragments described herein can occur in a variety of forms, but will include one or more of the antibody CDRs shown in Table 1a.

Described herein are recombinant antibodies and antigen-binding fragments that bind to CD79b. In some embodiments, the CD79b-specific antibodies or antigen-binding fragments are human IgG, or derivatives thereof. While the CD79b-specific antibodies or antigen-binding fragments exemplified herein are human, the antibodies or antigen-binding fragments exemplified may be chimerized.

In some embodiments, the antibodies or antigen-binding fragments are IgG, or derivatives thereof, e.g., IgG1, IgG2, IgG3, and IgG4 isotypes. In some embodiments wherein the antibody is of IgG1 isotype, the antibody comprises an IgG1 Fc region (SEQ ID NO: 249).

```
                                   SEQ ID NO: 249
ASTKGPSVFPLAPSSKSTSGGTAALGCLVKDYFPE

PVTVSWNSGALTSGVHTFPAVLQSSGLYSLSSVVT

VPSSSLGTQTYICNVNHKPSNTKVDKKVEPKSCDK

THTCPPCPAPELLGGPSVFLFPPKPKDTLMISRTP

EVTCVVVDVSHEDPEVKFNWYVDGVEVHNAKTKPR

EEQYNSTYRVVSVLTVLHQDWLNGKEYKCKVSNKA

LPAPIEKTISKAKGQPREPQVYTLPPSREEMTKNQ

VSLTCLVKGFYPSDIAVEWESNGQPENNYKTTPPV

LDSDGSFFLYSKLTVDKSRWQQGNVFSCSVMHEAL

HNHYTQKSLSLSPGK
```

In some embodiments wherein the antibody is of IgG1 isotype, the antibody comprises L234A, L235A, and D265S substitutions (underlined) in its Fc region (SEQ ID NO: 250).

```
                                   SEQ ID NO: 250
ASTKGPSVFPLAPSSKSTSGGTAALGCLVKDYFPE

PVTVSWNSGALTSGVHTFPAVLQSSGLYSLSSVVT

VPSSSLGTQTYICNVNHKPSNTKVDKKVEPKSCDK

THTCPPCPAPEAAGGPSVFLFPPKPKDTLMISRTP

EVTCVVVSVSHEDPEVKFNWYVDGVEVHNAKTKPR

EEQYNSTYRVVSVLTVLHQDWLNGKEYKCKVSNKA

LPAPIEKTISKAKGQPREPQVYTLPPSREEMTKNQ

VSLTCLVKGFYPSDIAVEWESNGQPENNYKTTPPV

LDSDGSFFLYSKLTVDKSRWQQGNVFSCSVMHEAL

HNHYTQKSLSLSPGK
```

In some embodiments wherein the antibody is of IgG4 isotype, the antibody comprises S228P, L234A, and L235A substitutions (underlined) in its Fc region (SEQ ID NO: 251).

```
                                   SEQ ID NO: 251
ASTKGPSVFPLAPCSRSTSESTAALGCLVKDYFPE

PVTVSWNSGALTSGVHTFPAVLQSSGLYSLSSVVT

VPSSSLGTKTYTCNVDHKPSNTKVDKRVESKYGPP

CPPCPAPEAAGGPSVFLFPPKPKDTLMISRTPEVT

CVVVDVSQEDPEVQFNWYVDGVEVHNAKTKPREEQ

FNSTYRVVSVLTVLHQDWLNGKEYKCKVSNKGLPS

SIEKTISKAKGQPREPQVYTLPPSQEEMTKNQVSL

TCLVKGFYPSDIAVEWESNGQPENNYKTTPPVLDS

DGSFFLYSRLTVDKSRWQEGNVFSCSVMHEALHNH

YTQKSLSLSLGK
```

The CD79b specific antibodies defined by CDR and/or variable domain sequence discussed in the above paragraphs may include these IgG Fc regions.

Also disclosed are isolated synthetic polynucleotides that encode the antibodies or antigen-binding fragments that bind to CD79b. The isolated polynucleotides capable of encoding the variable domain segments provided herein may be included on the same, or different, vectors to produce antibodies or antigen-binding fragments.

Polynucleotides encoding recombinant antigen-binding proteins also are within the scope of the disclosure. In some embodiments, the polynucleotides described (and the peptides they encode) include a leader sequence. Any leader sequence known in the art may be employed. The leader sequence may include, but is not limited to, a restriction site or a translation start site.

The CD79b-specific antibodies or antigen-binding fragments described herein include variants having single or multiple amino acid substitutions, deletions, or additions that retain the biological properties (e.g., binding affinity or immune effector activity) of the described CD79b-specific antibodies or antigen-binding fragments. In the context of the present invention the following notations are, unless otherwise indicated, used to describe a mutation; i) substitution of an amino acid in a given position is written as e.g. K409R which means a substitution of a Lysine in position 409 with an Arginine; and ii) for specific variants the specific three or one letter codes are used, including the codes Xaa and X to indicate any amino acid residue. Thus, the substitution of Arginine for Lysine in position 409 is designated as: K409R, or the substitution of any amino acid residue for Lysine in position 409 is designated as K409X. In case of deletion of Lysine in position 409 it is indicated by K409*. The skilled person may produce variants having single or multiple amino acid substitutions, deletions, or additions.

These variants may include: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies or antigen-binding fragments described herein may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (deletions, mutations, etc.) chemical, and enzymatic techniques, are known to persons having ordinary skill in the art.

The CD79b-specific antibodies or antigen-binding fragments described herein may embody several antibody isotypes, such as IgM, IgD, IgG, IgA and IgE. In some embodiments the antibody isotype is IgG1, IgG2, IgG3, or IgG4 isotype, preferably IgG1 or IgG4 isotype. Antibody or antigen-binding fragment thereof specificity is largely determined by the amino acid sequence, and arrangement, of the CDRs. Therefore, the CDRs of one isotype may be transferred to another isotype without altering antigen specificity. Alternatively, techniques have been established to cause hybridomas to switch from producing one antibody isotype to another (isotype switching) without altering antigen specificity. Accordingly, such antibody isotypes are within the scope of the described antibodies or antigen-binding fragments.

Also provided are vectors comprising the polynucleotides described herein. The vectors can be expression vectors. Recombinant expression vectors containing a sequence encoding a polypeptide of interest are thus contemplated as within the scope of this disclosure. The expression vector may contain one or more additional sequences such as but not limited to regulatory sequences (e.g., promoter, enhancer), a selection marker, and a polyadenylation signal. Vectors for transforming a wide variety of host cells are well known and include, but are not limited to, plasmids, phagemids, cosmids, baculoviruses, bacmids, bacterial artificial chromosomes (BACs), yeast artificial chromosomes (YACs), as well as other bacterial, yeast and viral vectors.

Recombinant expression vectors within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors may be constructed as described by Okayama and Berg, 3 Mol. Cell. Biol. 280 (1983).

In some embodiments, the antibody- or antigen-binding fragment-coding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. In one embodiment, the CD79b-specific antibody or antigen-binding fragment thereof coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like.

Vectors described herein may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene, a puromycin resistance gene, a blasticidin resistance gene), glutamate synthase genes, HSV-TK, HSV-TK derivatives for ganciclovir selection, or bacterial purine nucleoside phosphorylase gene for 6-methylpurine selection (Gadi et al., 7 *Gene Ther.* 1738-1743 (2000)). A nucleic acid sequence encoding a selection marker or the cloning site may be upstream or downstream of a nucleic acid sequence encoding a polypeptide of interest or cloning site.

The vectors described herein may be used to transform various cells with the genes encoding the described antibodies or antigen-binding fragments. For example, the vectors may be used to generate CD79b-specific antibody or antigen-binding fragment-producing cells. Thus, another aspect features host cells transformed with vectors comprising a nucleic acid sequence encoding an antibody or antigen-binding fragment thereof that binds CD79b, such as the antibodies or antigen-binding fragments described and exemplified herein.

Numerous techniques are known in the art for the introduction of foreign genes into cells and may be used to construct the recombinant cells for purposes of carrying out the described methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, 29 *Pharmac. Ther.* 69-92 (1985)). Calcium phosphate precipitation and polyethylene glycol (PEG)-induced fusion of bacterial protoplasts with mammalian cells may also be used to transform cells.

Cells suitable for use in the expression of the CD79b-specific antibodies or antigen-binding fragments described herein are preferably eukaryotic cells, more preferably cells of plant, rodent, or human origin, for example but not limited to NSO, CHO, CHOK1, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others. In addition, expression of antibodies may be accomplished using hybridoma cells. Methods for producing hybridomas are well established in the art.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Methods of Using CD79b-Specific Antibodies for Treatment

Provided herein are CD79b-specific antibodies or antigen-binding fragments thereof for use in therapy. In particular, these antibodies or antigen-binding fragments may be useful in treating cancer, such as CD79b-expressing cancer. Accordingly, the invention provides a method of treating cancer comprising administering an antibody as described herein, such as CD79b-specific antibodies or antigen-binding fragments. For example, the use may be by interfering with CD79b-receptor interactions or where the antibody is conjugated to a toxin, so targeting the toxin to the CD79b-expressing cancer. In some embodiments CD79b-expressing cancer includes lymphoma, such as diffuse large B-cell lymphoma (DLBCL). The antibodies for use in these methods include those described herein above, for example a CD79b-specific antibody or antigen-binding fragment with the features set out in Table 1a and Table 1b, for example the CDRs or variable domain sequences, and in the further discussion of these antibodies.

In some embodiments described herein, immune effector properties of the CD79b-specific antibodies may be enhanced or silenced through Fc modifications by techniques known to those skilled in the art and described herein. For example, Fc effector functions such as C1q binding, complement dependent cytotoxicity (CDC), antibody-dependent cell-mediated cytotoxicity (ADCC), antibody-dependent cell-mediated phagocytosis (ADCP), down regulation of cell surface receptors (e.g., B cell receptor; BCR), etc. may be provided and/or controlled by modifying residues in the Fc responsible for these activities.

"Antibody-dependent cell-mediated cytotoxicity" or "ADCC" refers to a cell-mediated reaction in which non-specific cytotoxic cells that express Fc receptors (FcRs) (e.g. Natural Killer (NK) cells, neutrophils, and macrophages) recognize bound antibody on a target cell and subsequently cause lysis of the target cell.

The ability of monoclonal antibodies to induce ADCC can be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such mAbs can be achieved using different methods reported to lead to the successful expression of relatively high defucosylated antibodies bearing the biantennary complex-type of Fc oligosaccharides such as control of culture osmolality (Konno et al., Cytotechnology 64:249-65, 2012), application of a variant CHO line Lec13 as the host cell line (Shields et al., J Biol Chem 277:26733-26740, 2002), application of a variant CHO line EB66 as the host cell line (Olivier et al., MAbs; 2(4), 2010; Epub ahead of print; PMID:20562582), application of a rat hybridoma cell line YB2/0 as the host cell line (Shinkawa et al., J Biol Chem 278:3466-3473, 2003), introduction of small interfering RNA specifically against the .alpha. 1,6-fucosyltrasferase (FUT8) gene (Mori et al., Biotechnol Bioeng 88:901-908, 2004), or coexpression of β-1, 4-N-acetylglucosaminyltransferase III and golgi α-mannosidase II or a potent alpha-mannosidase I inhibitor, kifunensine (Ferrara et al., J Biol Chem 281:5032-5036, 2006, Ferrara et al., Biotechnol Bioeng 93:851-861, 2006; Xhou et al., Biotechnol Bioeng 99:652-65, 2008).

In some embodiments described herein, ADCC elicited by the CD79b antibodies may also be enhanced by certain substitutions in the antibody Fc. Exemplary substitutions are for example substitutions at amino acid positions 256, 290, 298, 312, 356, 330, 333, 334, 360, 378 or 430 (residue numbering according to the EU index) as described in U.S. Pat. No. 6,737,056.

Methods of Detecting CD79b

Provided herein are methods for detecting CD79b in a biological sample by contacting the sample with an antibody, or antigen-binding fragment thereof, described herein. As described herein, the sample may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments the described methods include detecting CD79b in a biological sample by contacting the sample with any of the CD79b-specific antibodies or antigen-binding fragments thereof described herein.

In some embodiments the sample may be contacted with more than one of the CD79b-specific antibodies or antigen-binding fragments described herein. For example, a sample may be contacted with a first CD79b-specific antibody, or antigen-binding fragment thereof, and then contacted with a second CD79b-specific antibody, or antigen-binding fragment thereof, wherein the first antibody or antigen-binding fragment and the second antibody or antigen-binding fragment are not the same antibody or antigen-binding fragment. In some embodiments, the first antibody, or antigen-binding fragment thereof, may be affixed to a surface, such as a multiwell plate, chip, or similar substrate prior to contacting the sample. In other embodiments the first antibody, or antigen-binding fragment thereof, may not be affixed, or attached, to anything at all prior to contacting the sample.

The described CD79b-specific antibodies and antigen-binding fragments may be detectably labeled. In some embodiments labeled antibodies and antigen-binding fragments may facilitate the detection CD79b via the methods described herein. Many such labels are readily known to those skilled in the art. For example, suitable labels include, but should not be considered limited to, radiolabels, fluorescent labels, epitope tags, biotin, chromophore labels, ECL labels, or enzymes. More specifically, the described labels include ruthenium, $^{111}$In-DOTA, $^{111}$In-diethylenetriamine-pentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes, Alexafluor® dyes, and the like.

The described CD79b-specific antibodies and antigen-binding fragments may be used in a variety of assays to detect CD79b in a biological sample. Some suitable assays include, but should not be considered limited to, western blot analysis, radioimmunoassay, surface plasmon resonance, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

In some embodiments described herein detection of CD79b-expressing cancer cells in a subject may be used to determine that the subject may be treated with a therapeutic agent directed against CD79b.

CD79b is present at detectable levels in blood and serum samples. Thus, provided herein are methods for detecting CD79b in a sample derived from blood, such as a serum sample, by contacting the sample with an antibody, or antigen-binding fragment thereof, that binds CD79b. The blood sample, or a derivative thereof, may be diluted, fractionated, or otherwise processed to yield a sample upon which the described method may be performed. In some embodiments, CD79b may be detected in a blood sample, or a derivative thereof, by any number of assays known in the art, such as, but not limited to, western blot analysis, radioimmunoassay, surface plasmon resonance, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

Methods for Diagnosing Cancer

Provided herein are methods for diagnosing CD79b-expressing cancer in a subject. In some embodiments CD79b-expressing cancer include lymphomas, such as diffuse large B-cell lymphoma (DLBCL). In some embodiments, as described above, detecting CD79b in a biological sample, such as a blood sample or a serum sample, provides the ability to diagnose cancer in the subject from whom the sample was obtained. Alternatively, in some embodiments other samples such as a histological sample, a fine needle aspirate sample, resected tumor tissue, circulating cells, circulating tumor cells, and the like, may also be used to assess whether the subject from whom the sample was obtained has cancer. In some embodiments, it may already be known that the subject from whom the sample was obtained has cancer, but the type of cancer afflicting the subject may not yet have been diagnosed or a preliminary diagnosis may be unclear, thus detecting CD79b in a biological sample obtained from the subject can allow for, or clarify, diagnosis of the cancer. For example, a subject may be known to have cancer, but it may not be known, or may be unclear, whether the subject's cancer is CD79b-expressing.

In some embodiments the described methods involve assessing whether a subject is afflicted with CD79b-expressing cancer by determining the amount of CD79b that is present in a biological sample derived from the subject; and comparing the observed amount of CD79b with the amount of CD79b in a control, or reference, sample, wherein a difference between the amount of CD79b in the sample derived from the subject and the amount of CD79b in the control, or reference, sample is an indication that the subject is afflicted with a CD79b-expressing cancer. In another embodiment the amount of CD79b observed in a biological sample obtained from a subject may be compared to levels of CD79b known to be associated with certain forms or stages of cancer, to determine the form or stage of the subject's cancer. In some embodiments the amount of CD79b in the sample derived from the subject is assessed by contacting the sample with an antibody, or an antigen-binding fragment thereof, that binds CD79b, such as the CD79b-specific antibodies described herein. The sample assessed for the presence of CD79b may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments CD79b-expressing cancer includes hematological cancer, such as diffuse large B-cell lymphoma (DLBCL). In some embodiments the subject is a human.

In some embodiments the method of diagnosing a CD79b-expressing cancer will involve: contacting a biological sample of a subject with a CD79b-specific antibody, or an antigen-binding fragment thereof (such as those derivable from the antibodies and fragments provided in Table 1a and Table 1b), quantifying the amount of CD79b present in the sample that is bound by the antibody or antigen-binding fragment thereof, comparing the amount of CD79b present in the sample to a known standard or reference sample; and determining whether the subject's CD79b levels fall within the levels of CD79b associated with cancer. In an additional embodiment, the diagnostic method can be followed with an additional step of administering or prescribing a cancer-specific treatment. In another embodiment, the diagnostic method can be followed with an additional step of transmitting the results of the determination to facilitate treatment of the cancer. In some embodiments the cancer-specific treatment may be directed against CD79b-expressing cancers, such as the CD79b×CD3 multispecific antibodies described herein.

In some embodiments the described methods involve assessing whether a subject is afflicted with CD79b-expressing cancer by determining the amount of CD79b present in a blood or serum sample obtained from the subject; and comparing the observed amount of CD79b with the amount of CD79b in a control, or reference, sample, wherein a difference between the amount of CD79b in the sample derived from the subject and the amount of CD79b in the control, or reference, sample is an indication that the subject is afflicted with a CD79b-expressing cancer.

In some embodiments the control, or reference, sample may be derived from a subject that is not afflicted with CD79b-expressing cancer. In some embodiments the control, or reference, sample may be derived from a subject that is afflicted with CD79b-expressing cancer. In some embodiments where the control, or reference, sample is derived from a subject that is not afflicted with CD79b-expressing cancer, an observed increase in the amount of CD79b present in the test sample, relative to that observed for the control or reference sample, is an indication that the subject being assessed is afflicted with CD79b-expressing cancer. In some embodiments where the control sample is derived from a subject that is not afflicted with CD79b-expressing cancer, an observed decrease or similarity in the amount of CD79b present in the test sample, relative to that observed for the control or reference sample, is an indication that the subject being assessed is not afflicted with CD79b-expressing cancer. In some embodiments where the control or reference sample is derived from a subject that is afflicted with CD79b-expressing cancer, an observed similarity in the amount of CD79b present in the test sample, relative to that observed for the control or reference sample, is an indication that the subject being assessed is afflicted with CD79b-expressing cancer. In some embodiments where the control or reference sample is derived from a subject that is afflicted with CD79b-expressing cancer, an observed decrease in the amount of CD79b present in the test sample, relative to that observed for the control or reference sample, is an indication that the subject being assessed is not afflicted with CD79b-expressing cancer.

In some embodiments the amount of CD79b in the sample derived from the subject is assessed by contacting the sample with an antibody, or an antigen-binding fragment thereof, that binds CD79b, such as the antibodies described herein. The sample assessed for the presence of CD79b may be derived from a blood sample, a serum sample, circulating cells, circulating tumor cells, cells that are not tissue associated (i.e., free cells), tissues (e.g., surgically resected tumor tissue, biopsies, including fine needle aspiration), histological preparations, and the like.

In various aspects, the amount of CD79b is determined by contacting the sample with an antibody, or antigen-binding fragment thereof, that binds CD79b. In some embodiments, the sample may be contacted by more than one type of antibody, or antigen-binding fragment thereof, that binds CD79b. In some embodiments, the sample may be contacted by a first antibody, or antigen-binding fragment thereof, that binds CD79b and then contacted by a second antibody, or antigen-binding fragment thereof, that binds CD79b. CD79b-specific antibodies or antigen-binding fragments such as those described herein may be used in this capacity.

Various combinations of the CD79b-specific antibodies and antigen-binding fragments can be used to provide a "first" and "second" antibody or antigen-binding fragment to carry out the described diagnostic methods. In some embodiments CD79b-expressing cancer includes lymphomas, such as diffuse large B-cell lymphoma (DLBCL).

In certain embodiments, the amount of CD79b is determined by western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

In various embodiments of the described diagnostic methods a control or reference sample is used. This sample may be a positive or negative assay control that ensures the assay used is working properly; for example, an assay control of this nature might be commonly used for immunohistochemistry assays. Alternatively, the sample may be a standardized reference for the amount of CD79b in a biological sample from a healthy subject. In some embodiments, the observed CD79b levels of the tested subject may be compared with CD79b levels observed in samples from subjects known to have CD79b-expressing cancer. In some embodiments, the control subject may be afflicted with a particular cancer of interest. In some embodiments, the control subject is known to have early stage cancer, which may or may not be CD79b-expressing cancer. In some embodiments, the control subject is known to have intermediate stage cancer, which may or may not be CD79b-expressing cancer. In some embodiments, the control subject is known to have late stage, which may or may not be CD79b-expressing cancer. In some embodiments, the methods for diagnosing cancer or a disorder are in vitro methods.

Methods for Monitoring Cancer

Provided herein are methods for monitoring CD79b-expressing cancer in a subject. In some embodiments CD79b-expressing cancer includes lymphomas, such as diffuse large B-cell lymphoma (DLBCL). In some embodiments the described methods involve assessing whether CD79b-expressing cancer is progressing, regressing, or remaining stable by determining the amount of CD79b that is present in a test sample derived from the subject; and comparing the observed amount of CD79b with the amount of CD79b in a biological sample obtained, in a similar manner, from the subject at an earlier point in time, wherein a difference between the amount of CD79b in the test sample and the earlier sample provides an indication of whether the cancer is progressing, regressing, or remaining stable. In this regard, a test sample with an increased amount of CD79b, relative to the amount observed for the earlier sample, may indicate progression of a CD79b-expressing cancer. Conversely, a test sample with a decreased amount of CD79b, relative to the amount observed for the earlier sample, may indicate regression of a CD79b-expressing cancer.

Accordingly, a test sample with an insignificant difference in the amount of CD79b, relative to the amount observed for the earlier sample, may indicate a state of stable disease for a CD79b-expressing cancer. In some embodiments the amount of CD79b in a biological sample derived from the subject is assessed by contacting the sample with an antibody, or an antibody fragment thereof, that binds CD79b, such as the antibodies described herein. The sample assessed for the presence of CD79b may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments the subject is a human.

In some embodiments the methods of monitoring a CD79b-expressing cancer will involve: contacting a biological sample of a subject with a CD79b-specific antibody, or antigen-binding fragment thereof (such as those derivable from the antibodies and fragments provided in Table 1a and Table 1b), quantifying the amount of CD79b present in the sample, comparing the amount of CD79b present in the sample to the amount of CD79b determined to be in a biological sample obtained, in a similar manner, from the same subject at an earlier point in time; and determining whether the subject's CD79b level has changed over time. A test sample with an increased amount of CD79b, relative to the amount observed for the earlier sample, may indicate progression of cancer. Conversely, a test sample with a decreased amount of CD79b, relative to the amount observed for the earlier sample, may indicate regression of a CD79b-expressing cancer. Accordingly, a test sample with an insignificant difference in the amount of CD79b, relative to the amount observed for the earlier sample, may indicate a state of stable disease for a CD79b-expressing cancer. In some embodiments, the CD79b levels of the sample may be compared to a known standard or a reference sample, alone or in addition to the CD79b levels observed for a sample assessed at an earlier point in time. In an additional embodiment, the diagnostic method can be followed with an additional step of administering a cancer-specific treatment. In some embodiments the cancer-specific treatment may be directed against CD79b-expressing cancers, such as the CD79b×CD3 multispecific antibodies described herein.

In various aspects, the amount of CD79b is determined by contacting the sample with an antibody, or antigen-binding fragment thereof, that binds CD79b. In some embodiments, the sample may be contacted by more than one type of antibody, or antigen-binding fragment thereof, that binds CD79b. In some embodiments, the sample may be contacted by a first antibody, or antigen-binding fragment thereof, that binds CD79b and then contacted by a second antibody, or antigen-binding fragment thereof, that binds CD79b. Antibodies such as those described herein may be used in this capacity.

Various combinations of the antibodies and antigen-binding fragments described in Table 1a and Table 1b can be used to provide a "first" and "second" antibody or antigen-binding fragment to carry out the described monitoring methods. In some embodiments CD79b-expressing cancer includes a hematological cancer, such as acute myeloid leukemia (AML).

In certain embodiments, the amount of CD79b is determined by western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay. In some embodiments, the monitoring methods are in vitro methods.

Kits for Detecting CD79b

Provided herein are kits for detecting CD79b in a biological sample. These kits include one or more of the CD79b-specific antibodies described herein, or an antigen-binding fragment thereof, and instructions for use of the kit.

The provided CD79b-specific antibody, or antigen-binding fragment, may be in solution; lyophilized; affixed to a substrate, carrier, or plate; or detectably labeled.

The described kits may also include additional components useful for performing the methods described herein. By way of example, the kits may comprise means for obtaining a sample from a subject, a control or reference sample, e.g., a sample from a subject having slowly progressing cancer and/or a subject not having cancer, one or more sample compartments, and/or instructional material which describes performance of a method of the invention and tissue specific controls or standards.

The means for determining the level of CD79b can further include, for example, buffers or other reagents for use in an assay for determining the level of CD79b. The instructions can be, for example, printed instructions for performing the assay and/or instructions for evaluating the level of expression of CD79b.

The described kits may also include means for isolating a sample from a subject. These means can comprise one or more items of equipment or reagents that can be used to obtain a fluid or tissue from a subject. The means for obtaining a sample from a subject may also comprise means for isolating blood components, such as serum, from a blood sample. Preferably, the kit is designed for use with a human subject.

EMBODIMENTS

The disclosure provided herein also provides the following non-limiting embodiments.

1. A trispecific antibody, or a trispecific binding fragment thereof, comprising:
   (a) a first antigen-binding arm comprising a first heavy chain variable domain (VH1) and a first light chain variable domain (VL1);
   (b) a second antigen-binding arm comprising a second heavy chain variable domain (VH2) and a second light chain variable domain (VL2);
   (c) a third antigen-binding arm comprising a third heavy chain variable domain (VH3) and a third light chain variable domain (VL3),
   wherein the first antigen-binding arm binds to an epitope on cluster of differentiation 79B protein (CD79b), the second antigen-binding arm binds to an epitope on cluster of differentiation 3 (CD3), and the third antigen-binding arm binds to an epitope on cluster of differentiation 20 (CD20).

2. The trispecific antibody or trispecific binding fragment of embodiment 1, wherein the VH1 and VL1 of first antigen-binding arm are present in a diabody, a Fab, Fab', a F(ab')2, a Fv, a scFv, a Fd, a disulfide stabilized Fv fragment (dsFv), or a disulfide stabilized diabody (ds diabody), optionally a Fab.
3. The trispecific antibody or trispecific binding fragment of embodiment 1 or 2, wherein the VH2 and VL2 of the second antigen-binding arm are present in a diabody, a Fab, Fab', a F(ab')2, a Fv, a scFv, a Fv, a Fd, a disulfide stabilized Fv fragment (dsFv), or a disulfide stabilized diabody (ds diabody), optionally a scFv.
4. The trispecific antibody or trispecific binding fragment of any one of embodiments 1-3, wherein the VH3 and VL3 of the third antigen-binding arm are present in an antibody fragment, a diabody, a Fab, Fab', a F(ab')2, a Fv, a scFv, a Fd, a disulfide stabilized Fv fragment (dsFv), or a disulfide stabilized diabody (ds diabody), optionally a scFv.
5. The trispecific antibody or trispecific binding fragment of any one of embodiments 1-4, wherein the first antigen-binding arm that binds CD79b comprises:
a) a heavy chain complementarity determining region (HCDR) 1, a HCDR2 and a HCDR3 of the heavy chain variable domain (VH1) of SEQ ID NO: 35 and a light chain complementarity determining region (LCDR) 1, a LCDR2 and a LCDR3 of the light chain variable domain (VL1) of SEQ ID NO: 37;
b) the HCDR1, the HCDR2 and the HCDR3 of the VH1 of SEQ ID NO: 39 and the LCDR1, the LCDR2 and the LCDR3 of the VL1 of SEQ ID NO: 41;
c) the HCDR1, the HCDR2 and the HCDR3 of the VH1 of SEQ ID NO: 43 and the LCDR1, the LCDR2 and the LCDR3 of the VL1 of SEQ ID NO: 41;
d) the HCDR1, the HCDR2 and the HCDR3 of the VH1 of SEQ ID NO: 45 and the LCDR1, the LCDR2 and the LCDR3 of the VL1 of SEQ ID NO: 47;
e) the HCDR1, the HCDR2 and the HCDR3 of the VH1 of SEQ ID NO: 49 and the LCDR1, the LCDR2 and the LCDR3 of the VL1 of SEQ ID NO: 51;
f) the HCDR1, the HCDR2 and the HCDR3 of the VH1 of SEQ ID NO: 39 and the LCDR1, the LCDR2 and the LCDR3 of the VL1 of SEQ ID NO: 53;
g) the HCDR1, the HCDR2 and the HCDR3 of the VH1 of SEQ ID NO: 55 and the LCDR1, the LCDR2 and the LCDR3 of the VL1 of SEQ ID NO: 57;
h) the HCDR1, the HCDR2 and the HCDR3 of the VH1 of SEQ ID NO: 59 and the LCDR1, the LCDR2 and the LCDR3 of the VL1 of SEQ ID NO: 61;
i) the HCDR1, the HCDR2 and the HCDR3 of the VH1 of SEQ ID NO: 63 and the LCDR1, the LCDR2 and the LCDR3 of the VL1 of SEQ ID NO: 65;
j) the HCDR1, the HCDR2 and the HCDR3 of the VH1 of SEQ ID NO: 67 and the LCDR1, the LCDR2 and the LCDR3 of the VL1 of SEQ ID NO: 69; or
k) the HCDR1, the HCDR2 and the HCDR3 of the VH1 of SEQ ID NO: 71 and the LCDR1, the LCDR2 and the LCDR3 of the VL1 of SEQ ID NO: 73.
6. The trispecific antibody or trispecific binding fragment of any one of embodiments 1-5, wherein the first antigen-binding arm that binds CD79b comprises the HCDR1, the HCDR2, the HCDR3, the LCDR1, the LCDR2, and the LCDR3 of:
a) SEQ ID NOs: 1, 2, 3, 4, 5 and 6, respectively;
b) SEQ ID NOs: 13, 8, 9, 10, 11 and 12, respectively;
c) SEQ ID NOs: 7, 8, 9, 10, 11 and 12, respectively;
d) SEQ ID NOs: 14, 15, 16, 17, 5 and 6, respectively;
e) SEQ ID NOs: 18, 8, 19, 20, 21 and 12, respectively;
f) SEQ ID NOs: 22, 23, 24, 25, 5 and 6, respectively;
g) SEQ ID NOs: 22, 26, 27, 28, 5 and 29, respectively; or
h) SEQ ID NOs: 30, 31, 32, 33, 5 and 6, respectively.

7. The trispecific antibody or trispecific binding fragment of any one of embodiments 1-6, wherein the first antigen-binding arm that binds CD79b comprises:
a) the VH1 of SEQ ID NO: 35 and the VL1 of SEQ ID NO: 37;
b) the VH1 of SEQ ID NO: 39 and the VL1 of SEQ ID NO: 41;
c) the VH1 of SEQ ID NO: 43 and the VL1 of SEQ ID NO: 41;
d) the VH1 of SEQ ID NO: 45 and the VL1 of SEQ ID NO: 47;
e) the VH1 of SEQ ID NO: 49 and the VL1 of SEQ ID NO: 51;
f) the VH1 of SEQ ID NO: 39 and the VL1 of SEQ ID NO: 53;
g) the VH1 of SEQ ID NO: 55 and the VL1 of SEQ ID NO: 57;
h) the VH1 of SEQ ID NO: 59 and the VL1 of SEQ ID NO: 61;
i) the VH1 of SEQ ID NO: 63 and the VL1 of SEQ ID NO: 65;
j) the VH1 of SEQ ID NO: 67 and the VL1 of SEQ ID NO: 69; or
i) the VH1 of SEQ ID NO: 71 and the VL1 of SEQ ID NO: 73.
8. The trispecific antibody or trispecific binding fragment of any one of embodiments 1-7, wherein the second antigen-binding arm that binds CD3 comprises:
a) the HCDR1, the HCDR2 and the HCDR3 of the VH2 of SEQ ID NO: 97 and the LCDR1, the LCDR2 and the LCDR3 of the VL2 of SEQ ID NO: 99;
b) the HCDR1, the HCDR2 and the HCDR3 of the VH2 of SEQ ID NO: 101 and the LCDR1, the LCDR2 and the LCDR3 of the VL2 of SEQ ID NO: 99;
c) the HCDR1, the HCDR2 and the HCDR3 of the VH2 of SEQ ID NO: 103 and the LCDR1, the LCDR2 and the LCDR3 of the VL2 of SEQ ID NO: 99;
d) the HCDR1, the HCDR2 and the HCDR3 of the VH2 of SEQ ID NO: 105 and the LCDR1, the LCDR2 and the LCDR3 of the VL2 of SEQ ID NO: 99; or
e) the HCDR1, the HCDR2 and the HCDR3 of the VH2 of SEQ ID NO: 107 and the LCDR1, the LCDR2 and the LCDR3 of the VL2 of SEQ ID NO: 109.
9. The trispecific antibody or trispecific binding fragment of any one of embodiments 1-8, wherein the second antigen-binding arm that binds CD3 comprises the HCDR1, the HCDR2, the HCDR3, the LCDR1, the LCDR2 and the LCDR3 of:
a) SEQ ID NOs: 76, 77, 78, 79, 80 and 81, respectively;
b) SEQ ID NOs: 76, 77, 75, 79, 80 and 81, respectively;
c) SEQ ID NOs: 76, 77, 82, 79, 80 and 81, respectively; or
d) SEQ ID NOs: 83, 84, 85, 86, 87 and 88, respectively.
10. The trispecific antibody or trispecific binding fragment of any one of embodiments 1-9, wherein the second antigen-binding arm that binds CD3 comprises:
a) the VH2 of SEQ ID NO: 97 and the VL2 of SEQ ID NO: 99;
b) the VH2 of SEQ ID NO: 101 and the VL2 of SEQ ID NO: 99;
c) the VH2 of SEQ ID NO: 103 and the VL2 of SEQ ID NO: 99;
d) the VH2 of SEQ ID NO: 105 and the VL2 of SEQ ID NO: 99; or
e) the VH2 of SEQ ID NO: 107 and the VL2 of SEQ ID NO: 109.

11. The trispecific antibody or trispecific binding fragment of any one of embodiments 1-10, wherein the third antigen-binding arm that binds CD20 comprises:
a) the HCDR1, the HCDR2 and the HCDR3 of the VH3 of SEQ ID NO: 126 and the LCDR1, the LCDR2 and the LCDR3 of the VL3 of SEQ ID NO: 128;
b) the HCDR1, the HCDR2 and the HCDR3 of the VH3 of SEQ ID NO: 130 and the LCDR1, the LCDR2 and the LCDR3 of the VL3 of SEQ ID NO: 132;
c) the HCDR1, the HCDR2 and the HCDR3 of the VH3 of SEQ ID NO: 134 and the LCDR1, the LCDR2 and the LCDR3 of the VL3 of SEQ ID NO: 136; or
d) the HCDR1, the HCDR2 and the HCDR3 of the VH3 of SEQ ID NO: 138 and the LCDR1, the LCDR2 and the LCDR3 of the VL3 of SEQ ID NO: 140.

12. The trispecific antibody or trispecific binding fragment of any one of embodiments 1-11, wherein the third antigen-binding arm that binds CD20 comprises the HCDR1, the HCDR2, the HCDR3, the LCDR1, the LCDR2 and the LCDR3 of:
a) SEQ ID NOs: 115, 116, 117, 118, 119 and 120, respectively;
b) SEQ ID NOs: 121, 122, 123, 124, 119 and 125, respectively;
c) SEQ ID NOs: 115, 116, 95, 96, 119 and 125, respectively; or
d) SEQ ID NOs: 121, 116, 123, 124, 119 and 125, respectively.

13. The trispecific antibody or trispecific binding fragment of any one of embodiments 1-12, wherein the third antigen-binding arm that binds CD20 comprises:
a) the VH3 of SEQ ID NO: 126 and the VL3 of SEQ ID NO: 128;
b) the VH3 of SEQ ID NO: 130 and the VL3 of SEQ ID NO: 132;
c) the VH3 of SEQ ID NO: 134 and the VL3 of SEQ ID NO: 136; or
d) the VH3 of SEQ ID NO: 138 and the VL3 of SEQ ID NO: 140.

14. The trispecific antibody or trispecific binding fragment of any one of embodiments 1-4, wherein the first antigen-binding arm that binds CD79b comprises the HCDR1, the HCDR2 and the HCDR3 of the VH1 of SEQ ID NO: 35 and the LCDR1, the LCDR2 and the LCDR3 of the VL1 of SEQ ID NO: 37;
the second antigen-binding arm that binds CD3 comprises the HCDR1, the HCDR2 and the HCDR3 of the VH2 of SEQ ID NO: 107 and the LCDR1, the LCDR2 and the LCDR3 of the VL2 of SEQ ID NO: 109; and
the third antigen-binding arm that binds CD20 comprises the HCDR1, the HCDR2 and the HCDR3 of the VH3 of SEQ ID NO: 130 and the LCDR1, the LCDR2 and the LCDR3 of the VL3 of SEQ ID NO: 132.

15. The trispecific antibody or trispecific binding fragment of any one of embodiments 1-4 and 14, wherein the first antigen-binding arm that binds CD79b comprises the HCDR1, the HCDR2, the HCDR3, the LCDR1, the LCDR2 and the LCDR3 of SEQ ID NOs: 1, 2, 3, 4, 5 and 6, respectively;
the second antigen-binding arm that binds CD3 comprises the HCDR1, the HCDR2, the HCDR3, the LCDR1, the LCDR2 and the LCDR3 of SEQ ID NOs: 83, 84, 85, 86, 87 and 88, respectively; and
the third antigen-binding arm that binds CD20 comprises the HCDR1, the HCDR2, the HCDR3, the LCDR1, the LCDR2 and the LCDR3 of SEQ ID NOs: 121, 122, 123, 124, 119 and 125, respectively.

16. The trispecific antibody or trispecific binding fragment of any one of embodiments 1-4, 14 and 15, wherein the first antigen-binding arm that binds CD79b comprises the VH1 of SEQ ID NO: 35 and the VL1 of SEQ ID NO: 37;
the second antigen-binding arm that binds CD3 comprises the VH2 of SEQ ID NO: 107 and the VL2 of SEQ ID NO: 109; and
the third antigen-binding arm that binds CD20 comprises the VH3 of SEQ ID NO: 130 and the VL3 of SEQ ID NO: 132.

17. The trispecific antibody or trispecific binding fragment of any one of embodiments 1-4, wherein the first antigen-binding arm that binds CD79b comprises the HCDR1, the HCDR2 and the HCDR3 of the VH1 of SEQ ID NO: 35 and the LCDR1, the LCDR2 and the LCDR3 of the VL1 of SEQ ID NO: 37;
the second antigen-binding arm that binds CD3 comprises the HCDR1, the HCDR2 and the HCDR3 of the VH2 of SEQ ID NO: 101 and the LCDR1, the LCDR2 and the LCDR3 of the VL2 of SEQ ID NO: 99; and
the third antigen-binding arm that binds CD20 comprises the HCDR1, the HCDR2 and the HCDR3 of the VH3 of SEQ ID NO: 130 and the LCDR1, the LCDR2 and the LCDR3 of the VL3 of SEQ ID NO: 132.

18. The trispecific antibody or trispecific binding fragment of any one of embodiments 1-4 and 17, wherein the first antigen-binding arm that binds CD79b comprises the HCDR1, the HCDR2, the HCDR3, the LCDR1, the LCDR2 and the LCDR3 of SEQ ID NOs: 1, 2, 3, 4, 5 and 6, respectively;
the second antigen-binding arm that binds CD3 comprises the HCDR1, the HCDR2, the HCDR3, the LCDR1, the LCDR2 and the LCDR3 of SEQ ID NOs: 76, 77, 75, 79, 80 and 81, respectively; and
the third antigen-binding arm that binds CD20 comprises the HCDR1, the HCDR2, the HCDR3, the LCDR1, the LCDR2 and the LCDR3 of SEQ ID NOs: 121, 122, 123, 124, 119 and 125, respectively.

19. The trispecific antibody or trispecific binding fragment of any one of embodiments 1-4, 17, and 18, wherein the first antigen-binding arm that binds CD79b comprises the VH1 of SEQ ID NO: 35 and the VL1 of SEQ ID NO: 37;
the second antigen-binding arm that binds CD3 comprises the VH2 of SEQ ID NO: 101 and the VL2 of SEQ ID NO: 99; and
the third antigen-binding arm that binds CD20 comprises the VH3 of SEQ ID NO: 130 and the VL3 of SEQ ID NO: 132.

20. The trispecific antibody or trispecific binding fragment thereof of any one of embodiments 1-19, wherein the first antigen-binding arm and second antigen-binding arm each comprise a Fragment crystallizable (Fc) domain.

21. The trispecific antibody or trispecific binding fragment thereof of embodiment 20, wherein the Fc domains comprise one or more mutations which promote heterodimerization of the Fc domains.

22. The trispecific antibody or trispecific binding fragment of embodiment 21, wherein the mutations are selected from T366S, L368A, T366W and Y407V (EU numbering).

23. The trispecific antibody or trispecific binding fragment of any one of embodiments 20-22, wherein the Fc domains further comprise one or more mutations which reduce Fc binding to a Fcγ receptor.

24. The trispecific antibody or trispecific binding fragment of embodiment 23, wherein the Fcγ receptor is FcγRI, FcγRIIA, FcγRIIB, FcγRIIIA, and/or FcγRIIIB.
25. The trispecific antibody or trispecific binding fragment of embodiment 23 or 24, wherein the Fc domains comprise one or more mutations selected from L234A, L235A, and D265S (EU numbering).
26. The trispecific antibody or trispecific binding fragment of any one of embodiments 21-25, wherein the Fc domains further comprise one or more mutations which reduce Fc binding to protein A.
27. The trispecific antibody or trispecific binding fragment of embodiment 26, wherein the Fc domain comprises mutations H435R and/or Y436F (EU numbering).
28. The trispecific antibody or trispecific binding fragment of any one of embodiments 1 to 27, wherein the first antigen-binding arm specifically binds to residues 30-42 (SEDRYRNPKGSAC; SEQ ID NO: 253), residues 50-52 (PRF), residues 81-86 (EMENP; SEQ ID NO: 254), and/or residues 144-148 (GFSTL; SEQ ID NO: 255) of human CD79b.
29. The trispecific antibody or trispecific binding fragment of embodiment 28, wherein the first antigen-binding arm specifically binds to CD79b with an affinity of about $1 \times 10^{-11}$-$1 \times 10^{-9}$ M.
30. The trispecific antibody or trispecific binding fragment of any one of embodiments 1 to 29, wherein the second antigen-binding arm specifically binds to residues 54-58 (GSEIL; SEQ ID NO: 257), residues 74-75 (NI), and/or residues 100-105 (PRGSKP; SEQ ID NO: 258) of human CD3ε.
31. A trispecific antibody, or a trispecific binding fragment thereof, comprising a first antigen-binding arm that binds to an epitope on cluster of differentiation 79B protein (CD79b), a second antigen-binding arm that binds to an epitope on cluster of differentiation 3 (CD3), and a third antigen-binding arm that binds to an epitope on cluster of differentiation 20 (CD20),
wherein the first antigen-binding arm comprises a heavy chain (HC1) polypeptide and a light chain (LC) polypeptide; and
wherein the trispecific antibody, or a trispecific binding fragment thereof, comprise a single polypeptide comprising the second antigen-binding arm and the third antigen-binding arm, optionally wherein the trispecific antibody, or trispecific binding fragment thereof is in accordance with any one of embodiments 1-30
32. The trispecific antibody or trispecific binding fragment of embodiment 31, wherein the HC1 of the first antigen-binding arm comprises the amino acid sequence of SEQ ID NO: 172, 176, 180, or 191.
33. The trispecific antibody or trispecific binding fragment of embodiment 32, wherein the LC of the first antigen-binding arm comprises the amino acid sequence of SEQ ID NO: 174, 178 or 182.
34. The trispecific antibody or trispecific binding fragment of any one of embodiment 31-33, wherein
a) the HC1 comprises the amino acid sequence of SEQ ID NO: 172 and the LC comprises the amino acid sequence of SEQ ID NO: 174;
b) the HC1 comprises the amino acid sequence of SEQ ID NO: 176 and the LC comprises the amino acid sequence of SEQ ID NO: 178;
c) the HC1 comprises the amino acid sequence of SEQ ID NO: 180 and the LC comprises the amino acid sequence of SEQ ID NO: 182;
d) the HC1 comprises the amino acid sequence of SEQ ID NO: 191 and the LC comprises the amino acid sequence of SEQ ID NO: 182.
35. The trispecific antibody or trispecific binding fragment of embodiment 34, wherein the polypeptide comprising the second antigen-binding arm and the third antigen-binding arm comprises an the amino acid sequence of SEQ ID NO: 142, 144, 148, 150, 152, 154, 156, 158, 160, 162, 166, 168, or 170.
36. The trispecific antibody or trispecific binding fragment of embodiment 31-35, wherein
a) the first antigen-binding arm comprises an HC1 comprising the amino acid sequence of SEQ ID NO: 172, and LC comprising the amino acid sequence of SEQ ID NO: 174, and the polypeptide comprising the second antigen-binding arm and the third antigen-binding arm comprises the amino acid sequence of SEQ ID NO: 142;
b) the first antigen-binding arm comprises an HC1 comprising the amino acid sequence of SEQ ID NO: 176, the LC comprising the amino acid sequence of SEQ ID NO: 178, and the polypeptide comprising the second antigen-binding arm and the third antigen-binding arm comprises the amino acid sequence of SEQ ID NO: 142;
c) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 142
d) the first antigen-binding arm comprises an HC1 comprising the amino acid sequence of SEQ ID NO: 172, the LC comprising the amino acid sequence of SEQ ID NO: 174, and the polypeptide comprising the second antigen-binding arm and the third antigen-binding arm comprises the amino acid sequence of SEQ ID NO: 144;
e) the first antigen-binding arm comprises an HC1 comprising the amino acid sequence of SEQ ID NO: 176, the LC comprising the amino acid sequence of SEQ ID NO: 178, and the polypeptide comprising the second antigen-binding arm and the third antigen-binding arm comprises the amino acid sequence of SEQ ID NO: 144;
f) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 144;
g) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 148;
h) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 150;

i) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 152;

j) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 154;

k) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 156;

l) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 158;

m) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 160;

n) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 162;

o) the first antigen-binding arm comprises an HC1 comprising the amino acid sequence of SEQ ID NO: 191, the LC comprising the amino acid sequence of SEQ ID NO: 182, and the polypeptide comprising the second antigen-binding arm and the third antigen-binding arm comprises the amino acid sequence of SEQ ID NO: 166;

p) the first antigen-binding arm comprises an HC1 comprising the amino acid sequence of SEQ ID NO: 172, the LC comprising the amino acid sequence of SEQ ID NO: 174, and the polypeptide comprising the second antigen-binding arm and the third antigen-binding arm comprises the amino acid sequence of SEQ ID NO: 168; or q) the first antigen-binding arm comprises an HC1 comprising the amino acid sequence of SEQ ID NO: 172, the LC comprising the amino acid sequence of SEQ ID NO: 174, and the polypeptide comprising the second antigen-binding arm and the third antigen-binding arm comprises the amino acid sequence of SEQ ID NO: 170.

37. The trispecific antibody or trispecific binding fragment of any one of embodiments 31-36, wherein the first antigen-binding arm comprises an HC1 comprising the amino acid sequence of SEQ ID NO: 172, and a LC comprising the amino acid sequence of SEQ ID NO: 174, and the polypeptide comprising the second antigen-binding arm and the third antigen-binding arm comprises the amino acid sequence of SEQ ID NO: 168.

38. The trispecific antibody or trispecific binding fragment of any one of embodiments 31-36, wherein the first antigen-binding arm comprises an HC1 comprising the amino acid sequence of SEQ ID NO: 172, and a LC comprising the amino acid sequence of SEQ ID NO: 174, and the polypeptide comprising the second antigen-binding arm and the third antigen-binding arm comprises the amino acid sequence of SEQ ID NO: 170.

39. The trispecific antibody or trispecific binding fragment of any one of embodiments 1-38, wherein the antibody or antigen-binding fragment thereof is an IgG1, IgG2, IgG3, or IgG4 (human) isotype.

40. The trispecific antibody or trispecific binding fragment of any of embodiments 1-39, wherein the antibody or antigen-binding fragment thereof is an IgG1 (human) isotype.

41. A trispecific antibody, or a trispecific binding fragment thereof, comprising a first antigen-binding arm that binds to an epitope on cluster of differentiation 79B protein (CD79b), a second antigen-binding arm that binds to an epitope on cluster of differentiation 3 (CD3), and a third antigen-binding arm that binds to an epitope on cluster of differentiation 20 (CD20),
wherein the first antigen-binding arm comprises a heavy chain (HC1) polypeptide and a light chain (LC) polypeptide;
wherein the trispecific antibody, or a trispecific binding fragment thereof, comprise a single polypeptide comprising the second antigen-binding arm and the third antigen-binding arm, and
wherein HC1 comprises the amino acid sequence of SEQ ID NO: 172, LC comprises the amino acid sequence of SEQ ID NO: 174, and the single polypeptide comprising the second antigen-binding arm and the third antigen-binding arm comprises the amino acid sequence of SEQ ID NO: 168, optionally wherein the trispecific antibody, or trispecific binding fragment thereof is in accordance with any one of embodiments 1-36

42. A trispecific antibody, or a trispecific binding fragment thereof, comprising a first antigen-binding arm that binds to an epitope on cluster of differentiation 79B protein (CD79b), a second antigen-binding arm that binds to an epitope on cluster of differentiation 3 (CD3), and a third antigen-binding arm that binds to an epitope on cluster of differentiation 20 (CD20),
wherein the first antigen-binding arm comprises a heavy chain (HC1) polypeptide and a light chain (LC) polypeptide;
wherein the trispecific antibody, or a trispecific binding fragment thereof, comprises a single polypeptide comprising the second antigen-binding arm and the third antigen-binding arm, and
wherein HC1 comprises the amino acid sequence of SEQ ID NO: 172, LC comprises the amino acid sequence of SEQ ID NO: 174, and the single polypeptide comprising the second antigen-binding arm and the third antigen-binding arm comprises the amino acid sequence of SEQ ID NO: 170, optionally wherein the trispecific antibody, or trispecific binding fragment thereof is in accordance with any one of embodiments 1-36.

43. A synthetic polynucleotide encoding the trispecific antibody or trispecific binding fragment of any one of embodiments 1 to 30.

44. The synthetic polynucleotide of embodiment 43, wherein the polynucleotide comprises a sequence encoding an antigen-binding arm that binds CD79b, said sequence comprising
a) a VH-encoding sequence of SEQ ID NO: 36 and a VL-encoding sequence of SEQ ID NO: 38 or 213;
b) a VH-encoding sequence of SEQ ID NO: 40 and a VL-encoding sequence of SEQ ID NO: 42;
c) a VH-encoding sequence of SEQ ID NO: 44 and a VL-encoding sequence of SEQ ID NO: 34;
d) a VH-encoding sequence of SEQ ID NO: 46 and a VL-encoding sequence of SEQ ID NO: 48 or 214;
e) a VH-encoding sequence of SEQ ID NO: 50 and a VL-encoding sequence of SEQ ID NO: 52;
f) a VH-encoding sequence of SEQ ID NO: 40 and a VL-encoding sequence of SEQ ID NO: 54;
g) a VH-encoding sequence of SEQ ID NO: 56 and a VL-encoding sequence of SEQ ID NO: 58;
h) a VH-encoding sequence of SEQ ID NO: 60 and a VL-encoding sequence of SEQ ID NO: 62;
i) a VH-encoding sequence of SEQ ID NO: 64 and a VL-encoding sequence of SEQ ID NO: 66;
j) a VH-encoding sequence of SEQ ID NO: 68 and a VL-encoding sequence of SEQ ID NO: 70; or
k) a VH-encoding sequence of SEQ ID NO: 72 and a VL-encoding sequence of SEQ ID NO: 74.

45. The synthetic polynucleotide of embodiment 43 or 44, wherein the polynucleotide comprises a sequence encoding an antigen-binding arm that binds CD3, said sequence comprising
a) a VH-encoding sequence of SEQ ID NO: 98 and a VL-encoding sequence of SEQ ID NO: 100;
b) a VH-encoding sequence of SEQ ID NO: 102 and a VL-encoding sequence of SEQ ID NO: 100;
c) a VH-encoding sequence of SEQ ID NO: 104 and a VL-encoding sequence of SEQ ID NO: 100;
d) a VH-encoding sequence of SEQ ID NO: 106 and a VL-encoding sequence of SEQ ID NO: 100; or
e) a VH-encoding sequence of SEQ ID NO: 108 and a VL-encoding sequence of SEQ ID NO: 110.

46. The synthetic polynucleotide of any one of embodiments 43-45, wherein the polynucleotide comprises a sequence encoding an antigen-binding arm that binds CD20, said sequence comprising:
a) a VH-encoding sequence of SEQ ID NO: 127 and a VL-encoding sequence of SEQ ID NO: 129;
b) a VH-encoding sequence of SEQ ID NO: 131 and a VL-encoding sequence of SEQ ID NO: 133;
c) a VH-encoding sequence of SEQ ID NO: 135 and a VL-encoding sequence of SEQ ID NO: 137; or
d) a VH-encoding sequence of SEQ ID NO: 139 and a VL-encoding sequence of SEQ ID NO: 141.

47. A synthetic polynucleotide encoding the trispecific antibody or trispecific binding fragment of any one of embodiments 31 to 42.

48. The synthetic polynucleotide of embodiment 47, wherein the polynucleotide comprises a sequence encoding an HC1 comprising the nucleotide sequence of SEQ ID NO: 173, 177, 181, or 192.

49. The synthetic polynucleotide of any one of embodiments 47-48, wherein the polynucleotide comprises a sequence encoding a LC comprising the nucleotide sequence of SEQ ID NO: 175, 179, 183 or 188.

50. The synthetic polynucleotide of embodiment any one of embodiments 47-49, comprising
a) an HC1-encoding sequence of SEQ ID NO: 173 and a LC-encoding sequence of SEQ ID NO: 175;
b) an HC1-encoding sequence of SEQ ID NO: 177, and a LC-encoding sequence of SEQ ID NO: 179;
c) an HC1-encoding sequence of SEQ ID NO: 181, and a LC-encoding sequence of SEQ ID NO: 183;
d) an HC1-encoding sequence of SEQ ID NO: 181, and a LC-encoding sequence of SEQ ID NO: 188;
e) an HC1-encoding sequence of SEQ ID NO: 192, and a LC-encoding sequence of SEQ ID NO: 183.

51. The synthetic polynucleotide of any one of embodiments 47-50, wherein the polynucleotide comprises a sequence encoding the single polypeptide comprising the second antigen-binding arm and the third antigen-binding arm, said sequence comprises the nucleotide sequence of SEQ ID NO: 143, 145, 149, 151, 153, 155, 157, 159, 161, 163, 167, 169, or 171.

52. The synthetic polynucleotide of any one of embodiments 47-51, comprising
a) an HC1-encoding sequence of SEQ ID NO: 173, a LC-encoding sequence of SEQ ID NO: 175, and a sequence of SEQ ID NO: 143 which encodes the single polypeptide comprising the second antigen-binding arm and the third antigen-binding arm;
b) an HC1-encoding sequence of SEQ ID NO: 177, a LC-encoding sequence of SEQ ID NO: 179, and a sequence of SEQ ID NO: 143 which encodes the single polypeptide comprising the second antigen-binding arm and the third antigen-binding arm;
c) an HC1-encoding sequence of SEQ ID NO: 181, a LC-encoding sequence of SEQ ID NO: 183, and a sequence of SEQ ID NO: 143 which encodes the single polypeptide comprising the second antigen-binding arm and the third antigen-binding arm;
d) an HC1-encoding sequence of SEQ ID NO: 173, a LC-encoding sequence of SEQ ID NO: 175, and a sequence of SEQ ID NO: 145 which encodes the single polypeptide comprising the second antigen-binding arm and the third antigen-binding arm;
e) an HC1-encoding sequence of SEQ ID NO: 177, a LC-encoding sequence of SEQ ID NO: 179, and a sequence of SEQ ID NO: 145 which encodes the single polypeptide comprising the second antigen-binding arm and the third antigen-binding arm;
f) an HC1-encoding sequence of SEQ ID NO: 181, a LC-encoding sequence of SEQ ID NO: 183, and a sequence of SEQ ID NO: 145 which encodes the single polypeptide comprising the second antigen-binding arm and the third antigen-binding arm;
g) an HC1-encoding sequence of SEQ ID NO: 181, a LC-encoding sequence of SEQ ID NO: 188, and a sequence of SEQ ID NO: 149 which encodes single polypeptide comprising the second antigen-binding arm and the third antigen-binding arm;
h) an HC1-encoding sequence of SEQ ID NO: 181, a LC-encoding sequence of SEQ ID NO: 188, and a sequence of SEQ ID NO: 151 which encodes the single polypeptide comprising the second antigen-binding arm and the third antigen-binding arm;
i) an HC1-encoding sequence of SEQ ID NO: 181, a LC-encoding sequence of SEQ ID NO: 188, and a sequence of SEQ ID NO: 153 which encodes the single polypeptide comprising the second antigen-binding arm and the third antigen-binding arm;

j) an HC1-encoding sequence of SEQ ID NO: 181, a LC-encoding sequence of SEQ ID NO: 188, and a sequence of SEQ ID NO: 155 which encodes the single polypeptide comprising the second antigen-binding arm and the third antigen-binding arm;

k) an HC1-encoding sequence of SEQ ID NO: 181, a LC-encoding sequence of SEQ ID NO: 188, and a sequence of SEQ ID NO: 157 which encodes the single polypeptide comprising the second antigen-binding arm and the third antigen-binding arm;

l) an HC1-encoding sequence of SEQ ID NO: 181, a LC-encoding sequence of SEQ ID NO: 188, and a sequence of SEQ ID NO: 159 which encodes the single polypeptide comprising the second antigen-binding arm and the third antigen-binding arm;

m) an HC1-encoding sequence of SEQ ID NO: 181, a LC-encoding sequence of SEQ ID NO: 188, and a sequence of SEQ ID NO: 161 which encodes the single polypeptide comprising the second antigen-binding arm and the third antigen-binding arm;

n) an HC1-encoding sequence of SEQ ID NO: 181, a LC-encoding sequence of SEQ ID NO: 188, and a sequence of SEQ ID NO: 163 which encodes the single polypeptide comprising the second antigen-binding arm and the third antigen-binding arm;

o) an HC1-encoding sequence of SEQ ID NO: 192, a LC-encoding sequence of SEQ ID NO: 183, and a sequence of SEQ ID NO: 167 which encodes the single polypeptide comprising the second antigen-binding arm and the third antigen-binding arm;

p) an HC1-encoding sequence of SEQ ID NO: 173, a LC-encoding sequence of SEQ ID NO: 175, and a sequence of SEQ ID NO: 169 which encodes the single polypeptide comprising the second antigen-binding arm and the third antigen-binding arm; or q) an HC1-encoding sequence of SEQ ID NO: 173, a LC-encoding sequence of SEQ ID NO: 175, and a sequence of SEQ ID NO: 171 which encodes the single polypeptide comprising the second antigen-binding arm and the third antigen-binding arm.

53. The synthetic polynucleotide of any one of embodiments 47-52, comprising an HC1-encoding sequence of SEQ ID NO: 173, a LC-encoding sequence of SEQ ID NO: 175, and a sequence of SEQ ID NO: 169 which encodes the single polypeptide comprising the second antigen-binding arm and the third antigen-binding arm.

54. The synthetic polynucleotide of any one of embodiments 47-52, comprising an HC1-encoding sequence of SEQ ID NO: 173, a LC-encoding sequence of SEQ ID NO: 175, and a sequence of SEQ ID NO: 171 which encodes the single polypeptide comprising the second antigen-binding arm and the third antigen-binding arm.

55. A synthetic polynucleotide encoding a trispecific antibody, or a trispecific binding fragment thereof, said trispecific antibody or trispecific binding fragment comprising a first antigen-binding arm that binds to an epitope on cluster of differentiation 79B protein (CD79b), a second antigen-binding arm that binds to an epitope on cluster of differentiation 3 (CD3), and a third antigen-binding arm that binds to an epitope on cluster of differentiation 20 (CD20), wherein the first antigen-binding arm comprises a heavy chain (HC1) polypeptide and a light chain (LC) polypeptide, wherein the trispecific antibody, or a trispecific binding fragment thereof, comprise a single polypeptide comprising the second antigen-binding arm and the third antigen-binding arm, and (a) wherein the polynucleotide comprises an HC1-encoding sequence of SEQ ID NO: 173, a LC-encoding sequence of SEQ ID NO: 175, and a sequence of SEQ ID NO: 169 which encodes the single polypeptide comprising the second antigen-binding arm and the third antigen-binding arm; or (b) wherein the polynucleotide comprises an HC1-encoding sequence of SEQ ID NO: 173, a LC-encoding sequence of SEQ ID NO: 175, and a sequence of SEQ ID NO: 171 which encodes the single polypeptide comprising the second antigen-binding arm and the third antigen-binding arm; optionally wherein the polynucleotide is in accordance with any one of embodiments 43-54.

56. A pharmaceutical composition comprising the trispecific antibody or trispecific binding fragment of any one of embodiments 1 to 42, or the polynucleotide of any one of embodiments 43-55, and a pharmaceutically acceptable carrier.

57. The pharmaceutical composition of embodiment 56, wherein the pharmaceutical composition further comprises a second therapeutic agent.

58. The pharmaceutical composition of embodiment 57, wherein the second therapeutic agent comprises a chemotherapeutic agent, anti-CD20 agent, anti-CD19 agent, anti-CD22 agent, Bruton's tyrosine kinase (BTK) inhibitor, mucosa-associated lymphoid tissue lymphoma translocation protein 1 (MALT1) inhibitor, immunomodulatory imide drug (IMiD), pro apoptotic B cell lymphoma 2 (Bcl-2) family inhibitor, phosphoinositide 3-kinase (PI3K) inhibitor, immune checkpoint inhibitor, CD28 costimulatory bispecific antibody, CD137 costimulatory bispecific antibody, or a combination thereof.

59. An isolated cell expressing the trispecific antibody or trispecific binding fragment of any one of embodiments 1 to 42.

60. The cell of embodiment 59 wherein the cell is a hybridoma.

61. The cell of embodiment 59 wherein the antibody is recombinantly produced.

62. A method for treating cancer in a subject in need thereof, said method comprising administering to the subject a therapeutically effective amount of the trispecific antibody or trispecific binding fragment of any one of embodiments 1 to 42, the polynucleotide of any one of embodiments 43-55, or the pharmaceutical composition of any one of embodiments 56-58.

63. The method of embodiment 62, wherein the trispecific antibody or trispecific binding fragment, polynucleotide, or the pharmaceutical composition is administered for a time sufficient to treat the cancer.

64. A method for inhibiting growth or proliferation of a cancer cell, said method comprising administering to said cell an effective amount of the trispecific antibody or trispecific binding fragment of any one of embodiments 1 to 42, the polynucleotide of any one of embodiments 43-55, or the pharmaceutical composition of any one of embodiments 56-58, wherein said effective amount is sufficient to inhibit the growth or proliferation of said cancer cell.

65. The method of embodiment 64, wherein said cancer cell is in a subject and the trispecific antibody or trispecific binding fragment, polynucleotide, or the pharmaceutical composition is administered to the subject.
66. The method of embodiment 65, wherein said administration is conducted ex vivo.
67. A method of redirecting a T cell to CD79b and/or CD20-expressing cancer cells in a subject in need thereof, said method comprising administering to said subject a therapeutically effective amount of the trispecific antibody or trispecific binding fragment of any one of embodiments 1 to 42, the polynucleotide of any one of embodiments 43-55, or the pharmaceutical composition of any one of embodiments 56-58.
68. The method of embodiment 67, wherein the said therapeutically effective amount is sufficient to direct said T cell response to said cancer cells.
69. The method of any one of embodiments 62-68, wherein the cancer is a hematological cancer.
70. The method of embodiment 69 wherein the hematological cancer is a CD79b and/or CD20-expressing B cell cancer.
71. The method of embodiment 70 wherein the CD79b and/or CD20-expressing B cell cancer is a B-cell lymphoma or a non-Hodgkin lymphoma.
72. The method of embodiment 71 wherein the CD79b and/or CD20-expressing B cell cancer is a diffuse large B-cell lymphoma (DLBCL), mantle cell lymphoma (MCL), marginal zone lymphoma (MZL), follicular lymphoma (FL), chronic lymphocytic leukemia (CLL), or Waldenström macroglobulinemia (WM).
73. The method of any one of embodiments 62-72, wherein the cancer is relapsed, refractory, or malignant cancer, or any combination thereof.
74. The method of any one of embodiments 62-73 further comprising administering a second therapeutic agent.
75. The method of embodiment 74 wherein the second therapeutic agent is a surgery, chemotherapy, androgen deprivation therapy or radiation, anti-CD20 agent, anti-CD19 agent, anti-CD22 agent, Bruton's tyrosine kinase (BTK) inhibitor, mucosa-associated lymphoid tissue lymphoma translocation protein 1 (MALT1) inhibitor, immunomodulatory imide drug (IMiD), pro apoptotic B cell lymphoma 2 (Bcl-2) family inhibitor, phosphoinositide 3-kinase (PI3K) inhibitor, immune checkpoint inhibitor, CD28 costimulatory bispecific antibody, CD137 costimulatory bispecific antibody, or any combination thereof.
76. The method of any one of embodiments 62-63, 65 and 67-75, wherein the trispecific antibody or trispecific binding fragment, polynucleotide, or the pharmaceutical composition is administered intravenously, intramuscularly, intraperitoneally, and/or subcutaneously to the subject.
77. The method of any one of embodiments 62-63, 65 and 67-75, wherein the trispecific antibody or trispecific binding fragment, polynucleotide, or the pharmaceutical composition is administered subcutaneously to the subject.
78. A method for generating the trispecific antibody or trispecific binding fragment of any one of embodiments 1 to 42, wherein said method comprises culturing the cell of any one of embodiments 59 to 61 and isolating said trispecific antibody or trispecific binding fragment.
79. A kit comprising (i) the trispecific antibody or trispecific binding fragment of any one of embodiments 1 to 42 and/or the polynucleotide of any one of embodiments 43-55 and (ii) packaging for the same.
80. An antibody, or an antigen-binding fragment thereof, that binds to an epitope on Cluster of Differentiation 79B protein (CD79b), comprising:
a) a heavy chain complementarity determining region (HCDR) 1, a HCDR2 and a HCDR3 of a heavy chain variable domain (VH) of SEQ ID NO: 35 and a light chain complementarity determining region (LCDR) 1, a LCDR2 and a LCDR3 of a light chain variable domain (VL) of SEQ ID NO: 37;
b) the HCDR1, the HCDR2 and the HCDR3 of the VH of SEQ ID NO: 39 and the LCDR1, the LCDR2 and the LCDR3 of the VL of SEQ ID NO: 41;
c) the HCDR1, the HCDR2 and the HCDR3 of the VH of SEQ ID NO: 43 and the LCDR1, the LCDR2 and the LCDR3 of the VL of SEQ ID NO: 41;
d) the HCDR1, the HCDR2 and the HCDR3 of the VH of SEQ ID NO: 45 and the LCDR1, the LCDR2 and the LCDR3 of the VL of SEQ ID NO: 47;
e) the HCDR1, the HCDR2 and the HCDR3 of the VH of SEQ ID NO: 49 and the LCDR1, the LCDR2 and the LCDR3 of the VL of SEQ ID NO: 51;
f) the HCDR1, the HCDR2 and the HCDR3 of the VH of SEQ ID NO: 39 and the LCDR1, the LCDR2 and the LCDR3 of the VL of SEQ ID NO: 53;
g) the HCDR1, the HCDR2 and the HCDR3 of the VH of SEQ ID NO: 55 and the LCDR1, the LCDR2 and the LCDR3 of the VL of SEQ ID NO: 57;
h) the HCDR1, the HCDR2 and the HCDR3 of the VH of SEQ ID NO: 59 and the LCDR1, the LCDR2 and the LCDR3 of the VL of SEQ ID NO: 61;
i) the HCDR1, the HCDR2 and the HCDR3 of the VH of SEQ ID NO: 63 and the LCDR1, the LCDR2 and the LCDR3 of the VL of SEQ ID NO: 65;
j) the HCDR1, the HCDR2 and the HCDR3 of the VH of SEQ ID NO: 67 and the LCDR1, the LCDR2 and the LCDR3 of the VL of SEQ ID NO: 69; or
k) the HCDR1, the HCDR2 and the HCDR3 of the VH of SEQ ID NO: 71 and the LCDR1, the LCDR2 and the LCDR3 of the VL of SEQ ID NO: 73.
81. The antibody or antigen-binding fragment of embodiment 80, comprising the HCDR1, the HCDR2, the HCDR3, the LCDR1, the LCDR2 and the LCDR3 of:
a) SEQ ID NOs: 1, 2, 3, 4, 5 and 6, respectively;
b) SEQ ID NOs: 13, 8, 9, 10, 11 and 12, respectively;
c) SEQ ID NOs: 7, 8, 9, 10, 11 and 12, respectively;
d) SEQ ID NOs: 14, 15, 16, 17, 5 and 6, respectively;
e) SEQ ID NOs: 18, 8, 19, 20, 21 and 12, respectively;
f) SEQ ID NOs: 22, 23, 24, 25, 5 and 6, respectively;
g) SEQ ID NOs: 22, 26, 27, 28, 5 and 29, respectively; or
h) SEQ ID NOs: 30, 31, 32, 33, 5 and 6, respectively.
82. The antibody or antigen-binding fragment of embodiment 80 or 81, comprising
a) the VH of SEQ ID NO: 35 and the VL of SEQ ID NO: 37;
b) the VH of SEQ ID NO: 39 and the VL of SEQ ID NO: 41;
c) the VH of SEQ ID NO: 43 and the VL of SEQ ID NO: 41;
d) the VH of SEQ ID NO: 45 and the VL of SEQ ID NO: 47;
e) the VH of SEQ ID NO: 49 and the VL of SEQ ID NO: 51;
f) the VH of SEQ ID NO: 39 and the VL of SEQ ID NO: 53;
g) the VH of SEQ ID NO: 55 and the VL of SEQ ID NO: 57;

h) the VH of SEQ ID NO: 59 and the VL of SEQ ID NO: 61;
i) the VH of SEQ ID NO: 63 and the VL of SEQ ID NO: 65;
j) the VH of SEQ ID NO: 67 and the VL of SEQ ID NO: 69; or
k) the VH of SEQ ID NO: 71 and the VL of SEQ ID NO: 73.

83. The antibody or antigen-binding fragment of any one of embodiments 80-82, wherein the antibody or antigen-binding fragment specifically binds residues 30-42 (SEDRYRNPKGSAC; SEQ ID NO: 253), residues 50-52 (PRF), residues 81-86 (EMENP; SEQ ID NO: 254), and/or residues 144-148 (GFSTL; SEQ ID NO: 255) of human CD79b.

84. The antibody or antigen-binding fragment of embodiment 83, wherein the antibody or antigen-binding fragment specifically binds to CD79b with an affinity of about $1\times10^{-11}$-$1\times10^{-9}$ M.

85. The antibody or antigen-binding fragment of any one of embodiments 80-84 wherein the antibody or antigen-binding fragment is a human antibody or antigen-binding fragment.

86. The antibody or antigen-binding fragment of any one of embodiments 80 to 85 wherein the antibody or antigen-binding fragment is recombinant.

87. The antigen binding fragment of any one of embodiments 80 to 86 wherein the antigen binding fragment is a diabody, a Fab, Fab', a F(ab')2, a Fv, a scFv, a Fd, a disulfide stabilized Fv fragment (dsFv), or a disulfide stabilized diabody (ds diabody).

88. The antibody or antigen-binding fragment of any one of embodiments 80 to 87 wherein the antibody or antigen-binding fragment thereof is an IgG1, IgG2, IgG3, or IgG4 (human) isotype.

89. The antibody or antigen-binding fragment of any of embodiments 80 to 88, wherein the antibody or antigen-binding fragment thereof is an IgG1 or an IgG4 (human) isotype.

90. A synthetic polynucleotide encoding the antibody or antigen-binding fragment of any one of embodiments 80 to 89.

91. The synthetic polynucleotide of embodiment 90, comprising
a) a VH-encoding sequence of SEQ ID NO: 36 and a VL-encoding sequence of SEQ ID NO: 38 or 213;
b) a VH-encoding sequence of SEQ ID NO: 40 and a VL-encoding sequence of SEQ ID NO: 42;
c) a VH-encoding sequence of SEQ ID NO: 44 and a VL-encoding sequence of SEQ ID NO: 34;
d) a VH-encoding sequence of SEQ ID NO: 46 and a VL-encoding sequence of SEQ ID NO: 48 or 214;
e) a VH-encoding sequence of SEQ ID NO: 50 and a VL-encoding sequence of SEQ ID NO: 52;
f) a VH-encoding sequence of SEQ ID NO: 40 and a VL-encoding sequence of SEQ ID NO: 54;
g) a VH-encoding sequence of SEQ ID NO: 56 and a VL-encoding sequence of SEQ ID NO: 58;
h) a VH-encoding sequence of SEQ ID NO: 60 and a VL-encoding sequence of SEQ ID NO: 62;
i) a VH-encoding sequence of SEQ ID NO: 64 and a VL-encoding sequence of SEQ ID NO: 66;
j) a VH-encoding sequence of SEQ ID NO: 68 and a VL-encoding sequence of SEQ ID NO: 70; or
k) a VH-encoding sequence of SEQ ID NO: 72 and a VL-encoding sequence of SEQ ID NO: 74.

92. A pharmaceutical composition comprising the antibody or antigen-binding fragment of any one of embodiments 80 to 89, or the polynucleotide of embodiment 90 or 91, and a pharmaceutically acceptable carrier.

93. The pharmaceutical composition of embodiment 92, wherein the pharmaceutical composition further comprises a second therapeutic agent.

94. The pharmaceutical composition of embodiment 93, wherein the second therapeutic agent comprises a chemotherapeutic agent, anti-CD20 agent, anti-CD19 agent, anti-CD22 agent, Bruton's tyrosine kinase (BTK) inhibitor, mucosa-associated lymphoid tissue lymphoma translocation protein 1 (MALT1) inhibitor, immunomodulatory imide drug (IMiD), pro apoptotic B cell lymphoma 2 (Bcl-2) family inhibitor, phosphoinositide 3-kinase (PI3K) inhibitor, immune checkpoint inhibitor, CD28 costimulatory bispecific antibody, CD137 costimulatory bispecific antibody, or a combination thereof.

95. An isolated cell expressing the antibody or antigen-binding fragment of any one of embodiments 80-89.

96. The cell of embodiment 95 wherein the cell is a hybridoma.

97. The cell of embodiment 95 wherein the antibody is recombinantly produced.

98. A method for treating cancer in a subject in need thereof, said method comprising administering to the subject a therapeutically effective amount of the antibody or antigen-binding fragment of any one of embodiments 80 to 89 or the polynucleotide of embodiment 90 or 91, or the pharmaceutical composition of any one of embodiments 92-98.

99. The method of embodiment 98, wherein the antibody or antigen-binding fragment or the pharmaceutical composition is administered for a time sufficient to treat the cancer.

100. A method for inhibiting growth or proliferation of a cancer cell, said method comprising administering to said cell an effective amount of the antibody or antigen-binding fragment of any one of embodiments 80 to 89, or the polynucleotide of embodiment 90 or 91, or the pharmaceutical composition of any one of embodiments 92-98, wherein said effective amount is sufficient to inhibit the growth or proliferation of said cancer cell.

101. The method of embodiment 100, wherein said cancer cell is in a subject and the antibody or antigen-binding fragment or the pharmaceutical composition is administered to the subject.

102. The method of embodiment 101, wherein said administration is conducted ex vivo.

103. The method of any one of embodiments 98-102 wherein the cancer is a hematological cancer.

104. The method of embodiment 103 wherein the hematological cancer is a CD79b-expressing B cell cancer.

105. The method of embodiment 104 wherein the CD79b-expressing B cell cancer is a B-cell lymphoma or a non-Hodgkin lymphoma.

106. The method of embodiment 105 wherein the CD79b-expressing B cell cancer is a diffuse large B-cell lymphoma (DLBCL), mantle cell lymphoma (MCL), marginal zone lymphoma (MZL), follicular lymphoma (FL), chronic lymphocytic leukemia (CLL), or Waldenström macroglobulinemia (WM).

107. The method of any one of embodiments 98-106, wherein the cancer is relapsed, refractory, or malignant cancer, or any combination thereof.

108. The method of any one of embodiments 98-107 further comprising administering a second therapeutic agent.

109. The method of embodiment 108 wherein the second therapeutic agent is a surgery, chemotherapy, androgen deprivation therapy or radiation, anti-CD20 agent, anti-CD19 agent, anti-CD22 agent, Bruton's tyrosine kinase (BTK) inhibitor, mucosa-associated lymphoid tissue lymphoma translocation protein 1 (MALT1) inhibitor, immunomodulatory imide drug (IMiD), pro apoptotic B cell lymphoma 2 (Bcl-2) family inhibitor, phosphoinositide 3-kinase (PI3K) inhibitor, immune checkpoint inhibitor, CD28 costimulatory bispecific antibody, CD137 costimulatory bispecific antibody, or any combination thereof.

110. The method of any one of embodiments 98-99, 101 and 103-109, wherein the antibody or antigen-binding fragment, polynucleotide, or the pharmaceutical composition is administered intravenously, intramuscularly, intraperitoneally, and/or subcutaneously to the subject.

111. The method of any one of embodiments 98-99, 101 and 103-110, wherein the antibody or antigen-binding fragment, polynucleotide, or the pharmaceutical composition is administered subcutaneously to the subject.

112. A method for generating the antibody or antigen-binding fragment of any one of embodiments 80 to 89, wherein said method comprises culturing the cell of any one of embodiments 95 to 97 and isolating said antibody or antigen-binding fragment.

113. A kit comprising (i) the antibody or antigen-binding fragment of any one of embodiments 80 to 89 and/or a polynucleotide of embodiment 90 or 91 and (ii) packaging for the same.

114. A bispecific antibody, or a bispecific binding fragment thereof, comprising:
(a) a first antigen-binding arm comprising a first heavy chain variable domain (VH1) and a first light chain variable domain (VL1);
(b) a second antigen-binding arm comprising a second heavy chain variable domain (VH2) and a second light chain variable domain (VL2);
wherein the first antigen-binding arm binds to an epitope on cluster of differentiation 79B protein (CD79b), and the second antigen-binding arm binds to an epitope on is cluster of differentiation 3 (CD3).

115. The bispecific antibody or bispecific binding fragment of any one of embodiments 114, wherein the VH1 and VL1 of first antigen-binding arm are present in a diabody, a Fab, Fab', a F(ab')2, a Fv, a scFv, a Fd, a disulfide stabilized Fv fragment (dsFv), or a disulfide stabilized diabody (ds diabody), optionally a Fab.

116. The bispecific antibody or bispecific binding fragment of embodiment 114-115, wherein the VH2 and VL2 of the second antigen-binding arm are present in a diabody, a Fab, Fab', a F(ab')2, a Fv, a scFv, a Fd, a disulfide stabilized Fv fragment (dsFv), or a disulfide stabilized diabody (ds diabody), optionally a scFv.

117. The bispecific antibody or bispecific binding fragment of any one of embodiments 114-116, wherein the first antigen-binding arm that binds CD79b comprises:
a) a heavy chain complementarity determining region (HCDR) 1, a HCDR2 and a HCDR3 of a heavy chain variable domain (VH) of SEQ ID NO: 35 and a light chain complementarity determining region (LCDR) 1, a LCDR2 and a LCDR3 of a light chain variable domain (VL) of SEQ ID NO: 37;
b) the HCDR1, the HCDR2 and the HCDR3 of the VH of SEQ ID NO: 39 and the LCDR1, the LCDR2 and the LCDR3 of the VL of SEQ ID NO: 41;
c) the HCDR1, the HCDR2 and the HCDR3 of the VH of SEQ ID NO: 43 and the LCDR1, the LCDR2 and the LCDR3 of the VL of SEQ ID NO: 41;
d) the HCDR1, the HCDR2 and the HCDR3 of the VH of SEQ ID NO: 45 and the LCDR1, the LCDR2 and the LCDR3 of the VL of SEQ ID NO: 47;
e) the HCDR1, the HCDR2 and the HCDR3 of the VH of SEQ ID NO: 49 and the LCDR1, the LCDR2 and the LCDR3 of the VL of SEQ ID NO: 51;
f) the HCDR1, the HCDR2 and the HCDR3 of the VH of SEQ ID NO: 39 and the LCDR1, the LCDR2 and the LCDR3 of the VL of SEQ ID NO: 53;
g) the HCDR1, the HCDR2 and the HCDR3 of the VH of SEQ ID NO: 55 and the LCDR1, the LCDR2 and the LCDR3 of the VL of SEQ ID NO: 57;
h) the HCDR1, the HCDR2 and the HCDR3 of the VH of SEQ ID NO: 59 and the LCDR1, the LCDR2 and the LCDR3 of the VL of SEQ ID NO: 61;
i) the HCDR1, the HCDR2 and the HCDR3 of the VH of SEQ ID NO: 63 and the LCDR1, the LCDR2 and the LCDR3 of the VL of SEQ ID NO: 65;
j) the HCDR1, the HCDR2 and the HCDR3 of the VH of SEQ ID NO: 67 and the LCDR1, the LCDR2 and the LCDR3 of the VL of SEQ ID NO: 69; or
k) the HCDR1, the HCDR2 and the HCDR3 of the VH of SEQ ID NO: 71 and the LCDR1, the LCDR2 and the LCDR3 of the VL of SEQ ID NO: 73.

118. The bispecific antibody or bispecific binding fragment of any one of embodiments 114-117, wherein the first antigen-binding arm that binds CD79b comprises the HCDR1, the HCDR2, the HCDR3, the LCDR1, the LCDR2 and the LCDR3 of:
a) SEQ ID NOs: 1, 2, 3, 4, 5 and 6, respectively;
b) SEQ ID NOs: 13, 8, 9, 10, 11 and 12, respectively;
c) SEQ ID NOs: 7, 8, 9, 10, 11 and 12, respectively;
d) SEQ ID NOs: 14, 15, 16, 17, 5 and 6, respectively;
e) SEQ ID NOs: 18, 8, 19, 20, 21 and 12, respectively;
f) SEQ ID NOs: 22, 23, 24, 25, 5 and 6, respectively;
g) SEQ ID NOs: 22, 26, 27, 28, 5 and 29, respectively; or
h) SEQ ID NOs: 30, 31, 32, 33, 5 and 6, respectively.

119. The bispecific antibody or bispecific binding fragment of any one of embodiments 114-118, wherein the first antigen-binding arm that binds CD79b comprises:
a) the VH of SEQ ID NO: 35 and the VL of SEQ ID NO: 37;
b) the VH of SEQ ID NO: 39 and the VL of SEQ ID NO: 41;
c) the VH of SEQ ID NO: 43 and the VL of SEQ ID NO: 41;
d) the VH of SEQ ID NO: 45 and the VL of SEQ ID NO: 47;
e) the VH of SEQ ID NO: 49 and the VL of SEQ ID NO: 51;
f) the VH of SEQ ID NO: 39 and the VL of SEQ ID NO: 53;
g) the VH of SEQ ID NO: 55 and the VL of SEQ ID NO: 57;
h) the VH of SEQ ID NO: 59 and the VL of SEQ ID NO: 61;
i) the VH of SEQ ID NO: 63 and the VL of SEQ ID NO: 65;
j) the VH of SEQ ID NO: 67 and the VL of SEQ ID NO: 69; or k) the VH of SEQ ID NO: 71 and the VL of SEQ ID NO: 73.
120. The bispecific antibody or bispecific binding fragment of any one of embodiments 114-119, wherein the second antigen-binding arm that binds CD3 comprises:
a) the HCDR1, the HCDR2 and the HCDR3 of the VH of SEQ ID NO: 97 and the LCDR1, the LCDR2 and the LCDR3 of the VL of SEQ ID NO: 99;
b) the HCDR1, the HCDR2 and the HCDR3 of the VH of SEQ ID NO: 101 and the LCDR1, the LCDR2 and the LCDR3 of the VL of SEQ ID NO: 99;
c) the HCDR1, the HCDR2 and the HCDR3 of the VH of SEQ ID NO: 103 and the LCDR1, the LCDR2 and the LCDR3 of the VL of SEQ ID NO: 99;
d) the HCDR1, the HCDR2 and the HCDR3 of the VH of SEQ ID NO: 105 and the LCDR1, the LCDR2 and the LCDR3 of the VL of SEQ ID NO: 99; or
e) the HCDR1, the HCDR2 and the HCDR3 of the VH of SEQ ID NO: 107 and the LCDR1, the LCDR2 and the LCDR3 of the VL of SEQ ID NO: 109.
121. The bispecific antibody or bispecific binding fragment of any one of embodiments 114-120, wherein the second antigen-binding arm that binds CD3 comprises the HCDR1, the HCDR2, the HCDR3, the LCDR1, the LCDR2 and the LCDR3 of:
a) SEQ ID NOs: 76, 77, 78, 79, 80 and 81, respectively;
b) SEQ ID NOs: 76, 77, 75, 79, 80 and 81, respectively;
c) SEQ ID NOs: 76, 77, 82, 79, 80 and 81, respectively; or
d) SEQ ID NOs: 83, 84, 85, 86, 87 and 88, respectively.
122. The bispecific antibody or bispecific binding fragment of any one of embodiments 114-121, wherein the second or third antigen-binding arm that binds CD3 comprises:
a) the VH of SEQ ID NO: 97 and the VL of SEQ ID NO: 99;
b) the VH of SEQ ID NO: 101 and the VL of SEQ ID NO: 99;
c) the VH of SEQ ID NO: 103 and the VL of SEQ ID NO: 99;
d) the VH of SEQ ID NO: 105 and the VL of SEQ ID NO: 99; or
e) the VH of SEQ ID NO: 107 and the VL of SEQ ID NO: 109.
123. The bispecific antibody or bispecific binding fragment thereof of any one of embodiments 114-122, the first antigen-binding arm and second antigen-binding arm each comprise a Fragment crystallizable (Fc) domain.
124. The bispecific antibody or bispecific binding fragment of embodiment 123, wherein the Fc domains of the first antigen-binding arm and second antigen-binding arm comprise one or more different mutations which promote heterodimerization of the Fc domains.
125. The bispecific antibody or bispecific binding fragment of embodiment 124, wherein the mutations are selected from T366S, L368A, T366W and Y407V (EU numbering).
126. The bispecific antibody or bispecific binding fragment of any one of embodiments 123-125, wherein the Fc domains of the first antigen-binding arm and/or the second antigen-binding arm further comprise one or more mutations which reduce Fc binding to a Fcγ receptor.
127. The bispecific antibody or bispecific binding fragment of embodiment 126, wherein the Fcγ receptor is FcγRI, FcγRIIA, FcγRIIB, FcγRIIIA, and/or FcγRIIIB.
128. The bispecific antibody or bispecific binding fragment of embodiment 126 or 127, wherein the Fc domains of the first antigen-binding arm and/or the second antigen-binding arm each comprise one or more mutations selected from L234A, L235A, and D265S (EU numbering).
129. The bispecific antibody or bispecific binding fragment of embodiment 128, wherein the Fc domains of the first antigen-binding arm and the second antigen-binding arm each comprise mutations L234A, L235A, and D265S (EU numbering).
130. The bispecific antibody or bispecific binding fragment of any one of embodiments 124-129, wherein the Fc domains of the first antigen-binding arm or the second antigen-binding arm further comprise one or more mutations which reduce Fc binding to protein A.
131. The bispecific antibody or bispecific binding fragment of embodiment 130, wherein the Fc domains of the first antigen-binding arm or the second antigen-binding arm comprise mutations H435R and/or Y436F (EU numbering).
132. The bispecific antibody or bispecific binding fragment of embodiment 131, wherein the Fc domain of the first antigen-binding arm comprises mutations H435R and Y436F (EU numbering).
133. The bispecific antibody or bispecific binding fragment of any one of embodiments 114-132, wherein the first antigen-binding arm specifically binds to residues 30-42 (SEDRYRNPKGSAC; SEQ ID NO: 253), residues 50-52 (PRF), residues 81-86 (EMENP; SEQ ID NO: 254), and/or residues 144-148 (GFSTL; SEQ ID NO: 255) of human CD79b.
134. The bispecific antibody or bispecific binding fragment of embodiment 133, wherein the first antigen-binding arm specifically binds to CD79b with an affinity of about $1\times10^{-11}$-$1\times10^{-9}$ M.
135. The bispecific antibody or bispecific binding fragment of any one of embodiments 114-134, wherein the second antigen-binding arm specifically binds to residues 54-58 (GSEIL; SEQ ID NO: 257), residues 74-75 (NI), and/or residues 100-105 (PRGSKP; SEQ ID NO: 258) of human CD3ε.
136. A bispecific antibody, or a bispecific binding fragment, comprising a first antigen-binding arm that binds to an epitope on cluster of differentiation 79B protein (CD79b), a second antigen-binding arm that binds to an epitope on cluster of differentiation 3 (CD3),
wherein the first antigen-binding arm comprises a heavy chain (HC1) polypeptide and a light chain (LC) polypeptide; and
the second antigen-binding arm comprises a second antigen-binding arm polypeptide.
137. The bispecific antibody or bispecific binding fragment of embodiment 136, wherein the HC1 comprises the amino acid sequence of SEQ ID NO: 172, 176, or 180.
138. The bispecific antibody or bispecific binding fragment of embodiment 136 or 137, wherein the LC comprises the amino acid sequence of SEQ ID NO: 174, 178, or 182.
139. The bispecific antibody or bispecific binding fragment of any one of embodiments 136-138, wherein
a) the HC1 comprises the amino acid sequence of SEQ ID NO: 172 and the LC comprises the amino acid sequence of SEQ ID NO: 174;

b) the HC1 comprises the amino acid sequence of SEQ ID NO: 176 and the LC comprises the amino acid sequence of SEQ ID NO: 178;
c) the HC1 comprises the amino acid sequence of SEQ ID NO: 180 and the LC comprises the amino acid sequence of SEQ ID NO: 182.
140. The bispecific antibody or bispecific binding fragment of any one of embodiments 136-139, wherein the second antigen-binding arm polypeptide comprises the amino acid sequence of SEQ ID NO: 164 or 189.
141. The bispecific antibody or bispecific binding fragment of any one of embodiments 136-140, wherein
a) the HC1 comprises the amino acid sequence of SEQ ID NO: 172, the LC comprises the amino acid sequence of SEQ ID NO: 174, and the second antigen-binding arm polypeptide comprises the amino acid sequence of SEQ ID NO: 164;
b) the HC1 comprises the amino acid sequence of SEQ ID NO: 176, the LC comprises the amino acid sequence of SEQ ID NO: 178, and the second antigen-binding arm polypeptide comprises the amino acid sequence of SEQ ID NO: 164;
c) the HC1 comprises the amino acid sequence of SEQ ID NO: 180, the LC comprises the amino acid sequence of SEQ ID NO: 182, and the second antigen-binding arm polypeptide comprises the amino acid sequence of SEQ ID NO: 164;
d) the HC1 comprises the amino acid sequence of SEQ ID NO: 172, the LC comprises the amino acid sequence of SEQ ID NO: 174, and the second antigen-binding arm polypeptide comprises the amino acid sequence of SEQ ID NO: 189;
e) the HC1 comprises the amino acid sequence of SEQ ID NO: 176, the LC comprises the amino acid sequence of SEQ ID NO: 178, and the second antigen-binding arm polypeptide comprises the amino acid sequence of SEQ ID NO: 189; or
f) the HC1 comprises the amino acid sequence of SEQ ID NO: 180, the LC comprises the amino acid sequence of SEQ ID NO: 182, and the second antigen-binding arm polypeptide comprises the amino acid sequence of SEQ ID NO: 189.
142. The bispecific antibody or bispecific binding fragment of any one of embodiments 114 to 141, wherein the antibody or antigen-binding fragment thereof is an IgG1, IgG2, IgG3, or IgG4 isotype.
143. The bispecific antibody or bispecific binding fragment of any of embodiments 114 to 142, wherein the antibody or antigen-binding fragment thereof is an IgG1 isotype.
144. An synthetic polynucleotide encoding the bispecific antibody or bispecific binding fragment of any one of embodiments 114 to 135.
145. The synthetic polynucleotide of embodiment 144, wherein the polynucleotide comprises a sequence encoding an antigen-binding arm that binds CD79b, said sequence comprising
a) a VH-encoding sequence of SEQ ID NO: 36 and a VL-encoding sequence of SEQ ID NO: 38 or 213;
b) a VH-encoding sequence of SEQ ID NO: 40 and a VL-encoding sequence of SEQ ID NO: 42;
c) a VH-encoding sequence of SEQ ID NO: 44 and a VL-encoding sequence of SEQ ID NO: 34;
d) a VH-encoding sequence of SEQ ID NO: 46 and a VL-encoding sequence of SEQ ID NO: 48 or 214;
e) a VH-encoding sequence of SEQ ID NO: 50 and a VL-encoding sequence of SEQ ID NO: 52;
f) a VH-encoding sequence of SEQ ID NO: 40 and a VL-encoding sequence of SEQ ID NO: 54;
g) a VH-encoding sequence of SEQ ID NO: 56 and a VL-encoding sequence of SEQ ID NO: 58;
h) a VH-encoding sequence of SEQ ID NO: 60 and a VL-encoding sequence of SEQ ID NO: 62;
i) a VH-encoding sequence of SEQ ID NO: 64 and a VL-encoding sequence of SEQ ID NO: 66;
j) a VH-encoding sequence of SEQ ID NO: 68 and a VL-encoding sequence of SEQ ID NO: 70; or
k) a VH-encoding sequence of SEQ ID NO: 72 and a VL-encoding sequence of SEQ ID NO: 74.
146. The synthetic polynucleotide of embodiment 144 or 145, wherein the polynucleotide comprises a sequence encoding an antigen-binding arm that binds CD3, said sequence comprising
a) a VH-encoding sequence of SEQ ID NO: 98 and a VL-encoding sequence of SEQ ID NO: 100;
b) a VH-encoding sequence of SEQ ID NO: 102 and a VL-encoding sequence of SEQ ID NO: 100;
c) a VH-encoding sequence of SEQ ID NO: 104 and a VL-encoding sequence of SEQ ID NO: 100;
d) a VH-encoding sequence of SEQ ID NO: 106 and a VL-encoding sequence of SEQ ID NO: 100; or
e) a VH-encoding sequence of SEQ ID NO: 108 and a VL-encoding sequence of SEQ ID NO: 110.
147. An synthetic polynucleotide encoding the bispecific antibody or bispecific binding fragment of any one of embodiments 136 to 143.
148. The synthetic polynucleotide of embodiment 147, wherein the polynucleotide comprises a sequence encoding an HC1 comprising the nucleotide sequence of SEQ ID NO: 173, 177, or 181.
149. The synthetic polynucleotide of any one of embodiments 147-148, wherein the polynucleotide comprises a sequence encoding a LC comprising the nucleotide sequence of SEQ ID NO: 175, 179, or 183.
150. The synthetic polynucleotide of any one of embodiments 147-149, comprising
a) an HC1-encoding sequence of SEQ ID NO: 173 and a LC-encoding sequence of SEQ ID NO: 175;
b) an HC1-encoding sequence of SEQ ID NO: 177 and a LC-encoding sequence of SEQ ID NO: 179; or
c) an HC1-encoding sequence of SEQ ID NO: 181 and a LC-encoding sequence of SEQ ID NO: 183.
151. The synthetic polynucleotide of any one of embodiments 147-150, wherein the polynucleotide comprises a sequence encoding a second antigen-binding arm polypeptide, said sequence comprising the nucleotide sequence of SEQ ID NO: 165 or 190.
152. The synthetic polynucleotide of any one of embodiments 147-151, comprising
a) an HC1-encoding sequence of SEQ ID NO: 173 and a LC-encoding sequence of SEQ ID NO: 175 and a sequence of SEQ ID NO: 165 encoding a second antigen-binding arm polypeptide;
b) an HC1-encoding sequence of SEQ ID NO: 177 and a LC-encoding sequence of SEQ ID NO: 179 and a sequence of SEQ ID NO: 165 encoding a second antigen-binding arm polypeptide;
c) an HC1-encoding sequence of SEQ ID NO: 181 and a LC-encoding sequence of SEQ ID NO: 183 and a sequence of SEQ ID NO: 165 encoding a second antigen-binding arm polypeptide;
d) an HC1-encoding sequence of SEQ ID NO: 173 and a LC-encoding sequence of SEQ ID NO: 175 and a sequence of SEQ ID NO: 190 encoding a second antigen-binding arm polypeptide;
e) an HC1-encoding sequence of SEQ ID NO: 177 and a LC-encoding sequence of SEQ ID NO: 179 and a sequence of SEQ ID NO: 190 encoding a second antigen-binding arm polypeptide; or
f) an HC1-encoding sequence of SEQ ID NO: 181 and a LC-encoding sequence of SEQ ID NO: 183 and a sequence of SEQ ID NO: 190 encoding a second antigen-binding arm polypeptide.

153. A pharmaceutical composition comprising the bispecific antibody or bispecific binding fragment of any one of embodiments 114 to 143, or the polynucleotide of any one of embodiments 144-152, and a pharmaceutically acceptable carrier.

154. The pharmaceutical composition of embodiment 153, wherein the pharmaceutical composition further comprises a second therapeutic agent.

155. The pharmaceutical composition of embodiment 154, wherein the second therapeutic agent comprises a chemotherapeutic agent, anti-CD20 agent, anti-CD19 agent, anti-CD22 agent, Bruton's tyrosine kinase (BTK) inhibitor, mucosa-associated lymphoid tissue lymphoma translocation protein 1 (MALT1) inhibitor, immunomodulatory imide drug (IMiD), pro apoptotic B cell lymphoma 2 (Bcl-2) family inhibitor, phosphoinositide 3-kinase (PI3K) inhibitor, immune checkpoint inhibitor, CD28 costimulatory bispecific antibody, CD137 costimulatory bispecific antibody, or a combination thereof.

156. An isolated cell expressing the bispecific antibody or bispecific binding fragment of any one of embodiments 114 to 143.

157. The cell of embodiment 156 wherein the cell is a hybridoma.

158. The cell of embodiment 156 wherein the antibody is recombinantly produced.

159. A method for treating cancer in a subject in need thereof, said method comprising administering to the subject a therapeutically effective amount of the bispecific antibody or bispecific binding fragment of any one of embodiments 114 to 143, the polynucleotide of any one of embodiments 144-152, or the pharmaceutical composition of any one of embodiments 153-155.

160. The method of embodiment 159, wherein the bispecific antibody or bispecific binding fragment or the pharmaceutical composition is administered for a time sufficient to treat the cancer.

161. A method for inhibiting growth or proliferation of a cancer cell, said method comprising administering to said cell an effective amount of the bispecific antibody or bispecific binding fragment of any one of embodiments 114 to 143, the polynucleotide of any one of embodiments 144-152, or the pharmaceutical composition of any one of embodiments 153-155, wherein said effective amount is sufficient to inhibit the growth or proliferation of said cancer cell.

162. The method of embodiment 161, wherein said cancer cell is in a subject and the bispecific antibody or bispecific binding fragment or the pharmaceutical composition is administered to the subject.

163. The method of embodiment 161, wherein said administration is conducted ex vivo.

164. A method of redirecting a T cell to CD79b-expressing cancer cells in a subject in need thereof, said method comprising administering to said subject a therapeutically effective amount of the bispecific antibody or bispecific binding fragment of any one of embodiments 114 to 143, the polynucleotide of any one of embodiments 144-152, or the pharmaceutical composition of any one of embodiments 153-155.

165. The method of embodiment 164, wherein the said therapeutically effective amount is sufficient to direct said T cell response to said cancer cells.

166. The method of any one of embodiments 159-165, wherein the cancer is a hematological cancer.

167. The method of embodiment 166 wherein the hematological cancer is a CD79b-expressing B cell cancer.

168. The method of embodiment 167 wherein the CD79b-expressing B cell cancer is a B-cell lymphoma or a non-Hodgkin lymphoma.

169. The method of embodiment 168 wherein the CD79b-expressing B cell cancer is a diffuse large B-cell lymphoma (DLBCL), mantle cell lymphoma (MCL), marginal zone lymphoma (MZL), follicular lymphoma (FL), chronic lymphocytic leukemia (CLL), or Waldenström macroglobulinemia (WM).

170. The method of any one of embodiments 159-169, wherein the cancer is relapsed, refractory, or malignant cancer, or any combination thereof.

171. The method of any one of embodiments 159-169 further comprising administering a second therapeutic agent.

172. The method of embodiment 171 wherein the second therapeutic agent is a surgery, chemotherapy, androgen deprivation therapy or radiation, anti-CD20 agent, anti-CD19 agent, anti-CD22 agent, Bruton's tyrosine kinase (BTK) inhibitor, mucosa-associated lymphoid tissue lymphoma translocation protein 1 (MALT1) inhibitor, immunomodulatory imide drug (IMiD), pro apoptotic B cell lymphoma 2 (Bcl-2) family inhibitor, phosphoinositide 3-kinase (PI3K) inhibitor, immune checkpoint inhibitor, CD28 costimulatory bispecific antibody, CD137 costimulatory bispecific antibody, or any combination thereof.

173. The method of any one of embodiments 159-160, 161 and 163-172, wherein the bispecific antibody or bispecific binding fragment, polynucleotide, or the pharmaceutical composition is administered intravenously, intramuscularly, intraperitoneally, and/or subcutaneously to the subject.

174. The method of any one of embodiments 159-160, 161 and 163-173, wherein the bispecific antibody or bispecific binding fragment, polynucleotide, or the pharmaceutical composition is administered subcutaneously to the subject.

175. A method for generating the bispecific antibody or bispecific binding fragment of any one of embodiments 114 to 143, wherein said method comprises culturing the cell of any one of embodiments 156-158 and isolating said bispecific antibody or bispecific binding fragment.

176. A kit comprising (i) the bispecific antibody or bispecific binding fragment of any one of embodiments 114 to 143 and/or a polynucleotide of any one of embodiments 144-152, and (ii) packaging for the same.

177. A trispecific antibody, or a trispecific binding fragment thereof, comprising:
a) a first heavy chain portion (HC1) comprising a first heavy chain variable domain (VH);
b) a light chain portion (LC) comprising a light chain variable domain (VL); and
c) a second heavy chain portion (HC2) comprising a second VH domain, wherein (i) the HC1 VH and LC VL domains form a first antigen-binding domain that binds a first antigen,
(ii) the HC2 VH domain forms a second antigen-binding domain that binds a second antigen,
(iii) the HC1 or the HC2 further comprise a third VH domain forming a third antigen-binding domain that binds a third antigen,
(iv) the HC1 and HC2 each optionally comprise a Fragment crystallizable (Fc) domain comprising a CH2-CH3 domain; and wherein the first antigen is cluster of differentiation 79B protein (CD79b), and
(v) the second antigen is cluster of differentiation 3 (CD3), and the third antigen is cluster of differentiation 20 (CD20); or
(vi) the second antigen is cluster of differentiation 20 (CD20), and the third antigen is cluster of differentiation 3 (CD3).

178. The trispecific antibody or trispecific binding fragment of embodiment 177, wherein the HC2 comprises the third VH domain forming the third antigen-binding domain that binds the third antigen.

179. The trispecific antibody or trispecific binding fragment of embodiment 177 or 178, wherein the HC2 comprises, from N to C-terminus, the second VH domain forming the second antigen-binding domain, the Fc domain, a first linker (L1), and the third VH domain forming the third antigen-binding domain.

180. The trispecific antibody or trispecific binding fragment of any one of embodiments 177-179, wherein the HC2 comprises the second VH domain forming the the second antigen-binding domain that binds CD3, and the HC2 further comprises the third VH domain forming the third antigen-binding domain that binds CD20.

181. The trispecific antibody or trispecific binding fragment of any one of embodiments 177-180, wherein the HC1 VH and LC VL form an antigen-binding fragment (Fab) comprising the first antigen-binding domain.

182. The trispecific antibody or trispecific binding fragment of any one of embodiments 177-181, wherein the HC2 VH forms a single-chain variable fragment (scFv) comprising the second antigen-binding domain.

183. The trispecific antibody or trispecific binding fragment of any one of embodiments 177-182, wherein the third VH forms a single-chain variable fragment (scFv) comprising the third antigen-binding domain.

184. The trispecific antibody or trispecific binding fragment of any one of embodiments 177-183, wherein the Fc domains of HC1 and HC2 comprise one or more different mutations which promote heterodimerization.

185. The trispecific antibody or trispecific binding fragment of embodiment 184, wherein the Fc domain of the HC1 comprise mutations T366S, L368A and Y407V (EU numbering) and the Fc domain of the HC2 comprises mutation T366W (EU numbering).

186. The trispecific antibody or trispecific binding fragment of embodiment 184, wherein the Fc domain of the HC2 comprise mutations T366S, L368A and Y407V (EU numbering) and the Fc domain of the HC1 comprises mutation T366W (EU numbering).

187. The trispecific antibody or trispecific binding fragment of any one of embodiments 177-186, wherein the Fc domains of HC1 and/or HC2 further comprise one or more mutations which reduce Fc binding to a Fcγ receptor.

188. The trispecific antibody or trispecific binding fragment of embodiment 187, wherein the Fcγ receptor is FcγRI, FcγRIIA, FcγRIIB, FcγRIIIA, and/or FcγRIIIB.

189. The trispecific antibody or trispecific binding fragment of embodiment 187 or 188, wherein the Fc domains of HC1 and/or HC2 each comprise one or more mutations selected from L234A, L235A, and D265S (EU numbering).

190. The trispecific antibody or trispecific binding fragment of embodiment 189, wherein the Fc domains of HC1 and HC2 each comprise mutations L234A, L235A, and D265S (EU numbering).

191. The trispecific antibody or trispecific binding fragment of any one of embodiments 177-190, wherein the Fc domains of HC1 or HC2 further comprise one or more mutations which reduce Fc binding to protein A.

192. The trispecific antibody or trispecific binding fragment of embodiment 191, wherein the Fc domains of HC1 or HC2 comprise mutations H435R and/or Y436F (EU numbering).

193. The trispecific antibody or trispecific binding fragment of embodiment 192, wherein the Fe domain of HC1 comprises mutations H435R and Y436F (EU numbering).

194. The trispecific antibody or trispecific binding fragment of any one of embodiments 179-193, wherein the first linker (L1) comprises any one of the amino acid sequences of SEQ ID NOs: 215-248.

195. The trispecific antibody or trispecific binding fragment of any one of embodiments 179-194, wherein the first linker (L1) comprises the amino acid sequence of GGSEGKSSGSGSESKSTGGS (SEQ ID NO: 215), GGGGSGGGGS (SEQ ID NO: 248) or GGGGSGGGGSGGGGSGGGGS ((G$_4$S)$_4$, SEQ ID NO: 221).

196. An bispecific antibody, or a bispecific binding fragment thereof, comprising:
a) a first heavy chain portion (HC1) comprising a first heavy chain variable domain (VH);
b) a light chain portion (LC) comprising a light chain variable domain (VL); and
c) a second heavy chain portion (HC2) comprising a second VH domain, wherein
(i) the HC1 VH and the LC VL domains form a first antigen-binding domain that binds a first antigen,
(ii) the HC2 VH domain forms a second antigen-binding domain that binds a second antigen,
(iii) the HC1 and HC2 each optionally comprise a Fragment crystallizable (Fc) domain comprising a CH2-CH3 domain; and
wherein the first antigen is cluster of differentiation 79B protein (CD79b), and the second antigen is cluster of differentiation 3 (CD3).

197. The bispecific antibody or bispecific binding fragment of any one of embodiments 196, wherein the HC1 VH and LC VL form an antigen-binding fragment (Fab) comprising the first antigen-binding domain.

198. The bispecific antibody or bispecific binding fragment of embodiment 196-197, wherein the HC2 VH forms a single-chain variable fragment (scFv) comprising the second antigen-binding domain.

199. The bispecific antibody or bispecific binding fragment of any one of embodiments 196-198, wherein the Fe domains of HC1 and HC2 comprise one or more different mutations which promote heterodimerization.

200. The bispecific antibody or bispecific binding fragment of embodiment 199, wherein the Fc domain of the HC1 comprise mutations T366S, L368A and Y407V (EU numbering) and the Fc domain of the HC2 comprises mutation T366W (EU numbering).

201. The bispecific antibody or bispecific binding fragment of embodiment 199, wherein the Fc domain of the HC2 comprise mutations T366S, L368A and Y407V (EU numbering) and the Fc domain of the HC1 comprises mutation T366W (EU numbering).

202. The bispecific antibody or bispecific binding fragment of any one of embodiments 196-201, wherein the Fc domains of HC1 and/or HC2 further comprise one or more mutations which reduce Fc binding to a Fcγ receptor.

203. The bispecific antibody or bispecific binding fragment of embodiment 202, wherein the Fcγ receptor is FcγRI, FcγRIIA, FcγRIIB, FcγRIIIA, and/or FcγRIIIB.

204. The bispecific antibody or bispecific binding fragment of embodiment 202 or 203, wherein the Fc domains of HC1 and/or HC2 each comprise one or more mutations selected from L234A, L235A, and D265S (EU numbering).

205. The bispecific antibody or bispecific binding fragment of embodiment 204, wherein the Fc domains of HC1 and HC2 each comprise mutations L234A, L235A, and D265S (EU numbering).

206. The bispecific antibody or bispecific binding fragment of any one of embodiments 196-205, wherein the Fc domains of HC1 or HC2 further comprise one or more mutations which reduce Fc binding to protein A.

207. The bispecific antibody or bispecific binding fragment of embodiment 206, wherein the Fc domains of HC1 or HC2 comprise mutations H435R and/or Y436F (EU numbering).

208. The bispecific antibody or bispecific binding fragment of embodiment 207, wherein the Fc domain of HC1 comprises mutations H435R and Y436F (EU numbering).

209. The bispecific antibody or bispecific binding fragment of any one of embodiments 196-208, wherein the first antigen-binding domain that binds CD79b comprises:
a) a heavy chain complementarity determining region (HCDR) 1, a HCDR2 and a HCDR3 of a heavy chain variable domain (VH) of SEQ ID NO: 35 and a light chain complementarity determining region (LCDR) 1, a LCDR2 and a LCDR3 of a light chain variable domain (VL) of SEQ ID NO: 37;
b) the HCDR1, the HCDR2 and the HCDR3 of the VH of SEQ ID NO: 39 and the LCDR1, the LCDR2 and the LCDR3 of the VL of SEQ ID NO: 41;
c) the HCDR1, the HCDR2 and the HCDR3 of the VH of SEQ ID NO: 43 and the LCDR1, the LCDR2 and the LCDR3 of the VL of SEQ ID NO: 41;
d) the HCDR1, the HCDR2 and the HCDR3 of the VH of SEQ ID NO: 45 and the LCDR1, the LCDR2 and the LCDR3 of the VL of SEQ ID NO: 47;
e) the HCDR1, the HCDR2 and the HCDR3 of the VH of SEQ ID NO: 49 and the LCDR1, the LCDR2 and the LCDR3 of the VL of SEQ ID NO: 51;
f) the HCDR1, the HCDR2 and the HCDR3 of the VH of SEQ ID NO: 39 and the LCDR1, the LCDR2 and the LCDR3 of the VL of SEQ ID NO: 53;
g) the HCDR1, the HCDR2 and the HCDR3 of the VH of SEQ ID NO: 55 and the LCDR1, the LCDR2 and the LCDR3 of the VL of SEQ ID NO: 57;
h) the HCDR1, the HCDR2 and the HCDR3 of the VH of SEQ ID NO: 59 and the LCDR1, the LCDR2 and the LCDR3 of the VL of SEQ ID NO: 61;
i) the HCDR1, the HCDR2 and the HCDR3 of the VH of SEQ ID NO: 63 and the LCDR1, the LCDR2 and the LCDR3 of the VL of SEQ ID NO: 65;
j) the HCDR1, the HCDR2 and the HCDR3 of the VH of SEQ ID NO: 67 and the LCDR1, the LCDR2 and the LCDR3 of the VL of SEQ ID NO: 69; or
k) the HCDR1, the HCDR2 and the HCDR3 of the VH of SEQ ID NO: 71 and the LCDR1, the LCDR2 and the LCDR3 of the VL of SEQ ID NO: 73.

210. The bispecific antibody or bispecific binding fragment of any one of embodiments 196-209, wherein the first antigen-binding domain that binds CD79b comprises the HCDR1, the HCDR2, the HCDR3, the LCDR1, the LCDR2 and the LCDR3 of:
a) SEQ ID NOs: 1, 2, 3, 4, 5 and 6, respectively;
b) SEQ ID NOs: 13, 8, 9, 10, 11 and 12, respectively;
c) SEQ ID NOs: 7, 8, 9, 10, 11 and 12, respectively;
d) SEQ ID NOs: 14, 15, 16, 17, 5 and 6, respectively;
e) SEQ ID NOs: 18, 8, 19, 20, 21 and 12, respectively;
f) SEQ ID NOs: 22, 23, 24, 25, 5 and 6, respectively;
g) SEQ ID NOs: 22, 26, 27, 28, 5 and 29, respectively; or
h) SEQ ID NOs: 30, 31, 32, 33, 5 and 6, respectively.

211. The bispecific antibody or bispecific binding fragment of any one of embodiments 196-210, wherein the first antigen-binding domain that binds CD79b comprises:
a) the VH of SEQ ID NO: 35 and the VL of SEQ ID NO: 37;
b) the VH of SEQ ID NO: 39 and the VL of SEQ ID NO: 41;
c) the VH of SEQ ID NO: 43 and the VL of SEQ ID NO: 41;
d) the VH of SEQ ID NO: 45 and the VL of SEQ ID NO: 47;
e) the VH of SEQ ID NO: 49 and the VL of SEQ ID NO: 51;
f) the VH of SEQ ID NO: 39 and the VL of SEQ ID NO: 53;
g) the VH of SEQ ID NO: 55 and the VL of SEQ ID NO: 57;
h) the VH of SEQ ID NO: 59 and the VL of SEQ ID NO: 61;
i) the VH of SEQ ID NO: 63 and the VL of SEQ ID NO: 65;
j) the VH of SEQ ID NO: 67 and the VL of SEQ ID NO: 69; or
k) the VH of SEQ ID NO: 71 and the VL of SEQ ID NO: 73.

212. The bispecific antibody or bispecific binding fragment of any one of embodiments 196-211, wherein the second antigen-binding domain that binds CD3 comprises:
a) the HCDR1, the HCDR2 and the HCDR3 of the VH of SEQ ID NO: 97 and the LCDR1, the LCDR2 and the LCDR3 of the VL of SEQ ID NO: 99;
b) the HCDR1, the HCDR2 and the HCDR3 of the VH of SEQ ID NO: 101 and the LCDR1, the LCDR2 and the LCDR3 of the VL of SEQ ID NO: 99;
c) the HCDR1, the HCDR2 and the HCDR3 of the VH of SEQ ID NO: 103 and the LCDR1, the LCDR2 and the LCDR3 of the VL of SEQ ID NO: 99;
d) the HCDR1, the HCDR2 and the HCDR3 of the VH of SEQ ID NO: 105 and the LCDR1, the LCDR2 and the LCDR3 of the VL of SEQ ID NO: 99; or
e) the HCDR1, the HCDR2 and the HCDR3 of the VH of SEQ ID NO: 107 and the LCDR1, the LCDR2 and the LCDR3 of the VL of SEQ ID NO: 109.

213. The bispecific antibody or bispecific binding fragment of any one of embodiments 196-212, wherein the second antigen-binding domain that binds CD3 comprises the HCDR1, the HCDR2, the HCDR3, the LCDR1, the LCDR2 and the LCDR3 of:
   a) SEQ ID NOs: 76, 77, 78, 79, 80 and 81, respectively;
   b) SEQ ID NOs: 76, 77, 75, 79, 80 and 81, respectively;
   c) SEQ ID NOs: 76, 77, 82, 79, 80 and 81, respectively; or
   d) SEQ ID NOs: 83, 84, 85, 86, 87 and 88, respectively.
214. The bispecific antibody or bispecific binding fragment of any one of embodiments 196-213, wherein the second or third antigen-binding domain that binds CD3 comprises:
   a) the VH of SEQ ID NO: 97 and the VL of SEQ ID NO: 99;
   b) the VH of SEQ ID NO: 101 and the VL of SEQ ID NO: 99;
   c) the VH of SEQ ID NO: 103 and the VL of SEQ ID NO: 99;
   d) the VH of SEQ ID NO: 105 and the VL of SEQ ID NO: 99; or
   e) the VH of SEQ ID NO: 107 and the VL of SEQ ID NO: 109.
215. The bispecific antibody or bispecific binding fragment of any one of embodiments 198-214, wherein the scFv comprises, from the N- to C-terminus, a VH, a linker (L) and a VL (VH-L-VL) or the VL, the linker (L) and the VH (VL-L-VH).
216. The bispecific antibody or bispecific binding fragment of any one of embodiments 198-215, wherein the scFv comprises, from the N- to C-terminus, the VL, the linker (L) and the VH (VL-L-VH).
217. The bispecific antibody or bispecific binding fragment of embodiment 215 or 216, wherein the linker (L) comprises any one of amino acid sequence of SEQ ID NOs: 215-248.
218. The bispecific antibody or bispecific binding fragment of any one of embodiments 215-217, wherein the linker (L) comprises an amino acid sequence of GGSEGKSSGSGSESKSTGGS (SEQ ID NO: 215).
219. The bispecific antibody or bispecific binding fragment of any one of embodiments 196-218, wherein the first antigen-binding domain specifically binds to residues 30-42 (SEDRYRNPKGSAC; SEQ ID NO: 253), residues 50-52 (PRF), residues 81-86 (EMENP; SEQ ID NO: 254), and/or residues 144-148 (GFSTL; SEQ ID NO: 255) of human CD79b.
220. The bispecific antibody or bispecific binding fragment of embodiment 219, wherein the first antigen-binding domain specifically binds to CD79b with an affinity of about $1\times10^{-11}$-$1\times10^{-9}$ M.
221. The bispecific antibody or bispecific binding fragment of any one of embodiments 196-220, wherein the second antigen-binding domain specifically binds to residues 54-58 (GSEIL; SEQ ID NO: 257), residues 74-75 (NI), and/or residues 100-105 (PRGSKP; SEQ ID NO: 258) of human CD3ε.
222. The bispecific antibody or bispecific binding fragment of any one of embodiments 196-221, wherein the antibody or antigen-binding fragment thereof is an IgG1, IgG2, IgG3, or IgG4 isotype.
223. The bispecific antibody or bispecific binding fragment of any of embodiments 196-222, wherein the antibody or antigen-binding fragment thereof is an IgG1 isotype.
224. The bispecific antibody or bispecific binding fragment of embodiment 196, wherein the HC1 comprises the amino acid sequence of SEQ ID NO: 172, 176, or 180.
225. The bispecific antibody or bispecific binding fragment of embodiment 196 or 224, wherein the LC comprises the amino acid sequence of SEQ ID NO: 174, 178, or 182.
226. The bispecific antibody or bispecific binding fragment of any one of embodiments 196, 224-225, wherein
   a. the HC1 comprises the amino acid sequence of SEQ ID NO: 172 and the LC comprises the amino acid sequence of SEQ ID NO: 174;
   b. the HC1 comprises the amino acid sequence of SEQ ID NO: 176 and the LC comprises the amino acid sequence of SEQ ID NO: 178;
   c. the HC1 comprises the amino acid sequence of SEQ ID NO: 180 and the LC comprises the amino acid sequence of SEQ ID NO: 182.
227. The bispecific antibody or bispecific binding fragment of any one of embodiments 196, 224-226, wherein the HC2 comprises the amino acid sequence of SEQ ID NO: 164 or 189.
228. The bispecific antibody or bispecific binding fragment of any one of embodiments 196, 224-227, wherein
   a. the HC1 comprises the amino acid sequence of SEQ ID NO: 172, the LC comprises the amino acid sequence of SEQ ID NO: 174, and the HC2 comprises the amino acid sequence of SEQ ID NO: 164;
   b. the HC1 comprises the amino acid sequence of SEQ ID NO: 176, the LC comprises the amino acid sequence of SEQ ID NO: 178, and the HC2 comprises the amino acid sequence of SEQ ID NO: 164;
   c. the HC1 comprises the amino acid sequence of SEQ ID NO: 180, the LC comprises the amino acid sequence of SEQ ID NO: 182, and the HC2 comprises the amino acid sequence of SEQ ID NO: 164;
   d. the HC1 comprises the amino acid sequence of SEQ ID NO: 172, the LC comprises the amino acid sequence of SEQ ID NO: 174, and the HC2 comprises the amino acid sequence of SEQ ID NO: 189;
   e. the HC1 comprises the amino acid sequence of SEQ ID NO: 176, the LC comprises the amino acid sequence of SEQ ID NO: 178, and the HC2 comprises the amino acid sequence of SEQ ID NO: 189; or
   f. the HC1 comprises the amino acid sequence of SEQ ID NO: 180, the LC comprises the amino acid sequence of SEQ ID NO: 182, and the HC2 comprises the amino acid sequence of SEQ ID NO: 189.

The invention can also be defined by the following numbered clauses.

1. A trispecific antibody, or a trispecific binding fragment thereof, comprising:
   a) a first heavy chain (HC1);
   b) a light chain (LC); and
   c) a second heavy chain (HC2),
   wherein
   (i) the HC1 and the LC form a first antigen-binding site that specifically binds a first antigen,
   (ii) the HC2 comprises a second antigen-binding site that specifically binds a second antigen,
   (iii) the HC1 or the HC2 further comprises a third antigen-binding site that specifically binds a third antigen, (iv) the HC1 and HC2 each comprise a Fragment crystallizable (Fc) domain comprising a CH2-CH3 domain; and wherein the first antigen is cluster of differentiation 79B protein (CD79b), and (v) the second antigen is cluster of differentiation 3 (CD3), and the third antigen is cluster of differentiation 20 (CD20); or (vi) the second antigen is cluster of differentiation 20 (CD20), and the third antigen is cluster of differentiation 3 (CD3).

2. The trispecific antibody or trispecific binding fragment of clause 1, wherein the HC2 comprises the third antigen-binding site that specifically binds the third antigen.

3. The trispecific antibody or trispecific binding fragment of clause 2, wherein the HC2 comprises, from N to C-terminus, the second antigen-binding site, the Fc domain, a first linker (L1), and the third antigen-binding site.

4. The trispecific antibody or trispecific binding fragment of any one of clauses 1-3, wherein the HC2 comprises the second antigen-binding site that specifically binds CD3, and the HC2 further comprises the third antigen-binding site that specifically binds CD20.

5. The trispecific antibody or trispecific binding fragment of any one of clauses 1-4, wherein the first antigen-binding site comprises an antigen-binding fragment (Fab).

6. The trispecific antibody or trispecific binding fragment of any one of clauses 1-5, wherein the second antigen-binding site comprises a single-chain variable fragment (scFv).

7. The trispecific antibody or trispecific binding fragment of any one of clauses 1-6, wherein the third antigen-binding site comprises a single-chain variable fragment (scFv).

8. The trispecific antibody or trispecific binding fragment of any one of clauses 1-7, wherein the Fc domains of HC1 and HC2 comprise one or more different mutations which promote heterodimerization.

9. The trispecific antibody or trispecific binding fragment of clause 8, wherein the Fc domain of the HC1 comprise mutations T366S, L368A and Y407V (EU numbering) and the Fc domain of the HC2 comprises mutation T366W (EU numbering).

10. The trispecific antibody or trispecific binding fragment of clause 8, wherein the Fc domain of the HC2 comprise mutations T366S, L368A and Y407V (EU numbering) and the Fc domain of the HC1 comprises mutation T366W (EU numbering).

11. The trispecific antibody or trispecific binding fragment of any one of clauses 1-10, wherein the Fc domains of HC1 and/or HC2 further comprise one or more mutations which reduce Fc binding to a Fcγ receptor.

12. The trispecific antibody or trispecific binding fragment of clause 11, wherein the Fcγ receptor is FcγRI, FcγRIIA, FcγRIIB, FcγRIIIA, and/or FcγRIIIB.

13. The trispecific antibody or trispecific binding fragment of clause 11 or 12, wherein the Fc domains of HC1 and/or HC2 each comprise one or more mutations selected from L234A, L235A, and D265S (EU numbering).

14. The trispecific antibody or trispecific binding fragment of clause 13, wherein the Fc domains of HC1 and HC2 each comprise mutations L234A, L235A, and D265S (EU numbering).

15. The trispecific antibody or trispecific binding fragment of any one of clauses 1-14, wherein the Fc domains of HC1 or HC2 further comprises one or more mutations which reduce Fc binding to protein A.

16. The trispecific antibody or trispecific binding fragment of clause 15, wherein the Fc domains of HC1 or HC2 comprises mutations H435R and/or Y436F (EU numbering).

17. The trispecific antibody or trispecific binding fragment of clause 16, wherein the Fc domain of HC1 comprises mutations H435R and Y436F (EU numbering).

18. The trispecific antibody or trispecific binding fragment of any one of clauses 3-17, wherein the first linker (L1) comprises any one of amino acid sequence of SEQ ID NOs: 215-248.

19. The trispecific antibody or trispecific binding fragment of any one of clauses 3-18, wherein the first linker (L1) comprises the amino acid sequence of GGSEGKSSGSGSESKSTGGS (SEQ ID NO: 215), GGGGSGGGGS (SEQ ID NO: 248) or GGGGSGGGGSGGGGSGGGGS (($G_4S$)$_4$, SEQ ID NO: 221).

20. The trispecific antibody or trispecific binding fragment of any one of clauses 1-19, wherein the first antigen-binding site that specifically binds CD79b comprises:

a) a heavy chain complementarity determining region (HCDR) 1, a HCDR2 and a HCDR3 of a heavy chain variable region (VH) of SEQ ID NO: 35 and a light chain complementarity determining region (LCDR) 1, a LCDR2 and a LCDR3 of a light chain variable region (VL) of SEQ ID NO: 37;

b) the HCDR1, the HCDR2 and the HCDR3 of the VH of SEQ ID NO: 39 and the LCDR1, the LCDR2 and the LCDR3 of the VL of SEQ ID NO: 41;

c) the HCDR1, the HCDR2 and the HCDR3 of the VH of SEQ ID NO: 43 and the LCDR1, the LCDR2 and the LCDR3 of the VL of SEQ ID NO: 41;

d) the HCDR1, the HCDR2 and the HCDR3 of the VH of SEQ ID NO: 45 and the LCDR1, the LCDR2 and the LCDR3 of the VL of SEQ ID NO: 47;

e) the HCDR1, the HCDR2 and the HCDR3 of the VH of SEQ ID NO: 49 and the LCDR1, the LCDR2 and the LCDR3 of the VL of SEQ ID NO: 51;

f) the HCDR1, the HCDR2 and the HCDR3 of the VH of SEQ ID NO: 39 and the LCDR1, the LCDR2 and the LCDR3 of the VL of SEQ ID NO: 53;

g) the HCDR1, the HCDR2 and the HCDR3 of the VH of SEQ ID NO: 55 and the LCDR1, the LCDR2 and the LCDR3 of the VL of SEQ ID NO: 57;

h) the HCDR1, the HCDR2 and the HCDR3 of the VH of SEQ ID NO: 59 and the LCDR1, the LCDR2 and the LCDR3 of the VL of SEQ ID NO: 61;

i) the HCDR1, the HCDR2 and the HCDR3 of the VH of SEQ ID NO: 63 and the LCDR1, the LCDR2 and the LCDR3 of the VL of SEQ ID NO: 65;

j) the HCDR1, the HCDR2 and the HCDR3 of the VH of SEQ ID NO: 67 and the LCDR1, the LCDR2 and the LCDR3 of the VL of SEQ ID NO: 69; or k) the HCDR1, the HCDR2 and the HCDR3 of the VH of SEQ ID NO: 71 and the LCDR1, the LCDR2 and the LCDR3 of the VL of SEQ ID NO: 73.

21. The trispecific antibody or trispecific binding fragment of any one of clauses 1-20, wherein the first antigen-binding site that specifically binds CD79b comprises the HCDR1, the HCDR2, the HCDR3, the LCDR1, the LCDR2 and the LCDR3 of:
   a) SEQ ID NOs: 1, 2, 3, 4, 5 and 6, respectively;
   b) SEQ ID NOs: 13, 8, 9, 10, 11 and 12, respectively;
   c) SEQ ID NOs: 7, 8, 9, 10, 11 and 12, respectively;
   d) SEQ ID NOs: 14, 15, 16, 17, 5 and 6, respectively;
   e) SEQ ID NOs: 18, 8, 19, 20, 21 and 12, respectively;
   f) SEQ ID NOs: 22, 23, 24, 25, 5 and 6, respectively;
   g) SEQ ID NOs: 22, 26, 27, 28, 5 and 29, respectively; or
   h) SEQ ID NOs: 30, 31, 32, 33, 5 and 6, respectively.

22. The trispecific antibody or trispecific binding fragment of any one of clauses 1-21, wherein the first antigen-binding site that specifically binds CD79b comprises:
   a) the VH of SEQ ID NO: 35 and the VL of SEQ ID NO: 37;
   b) the VH of SEQ ID NO: 39 and the VL of SEQ ID NO: 41;
   c) the VH of SEQ ID NO: 43 and the VL of SEQ ID NO: 41;
   d) the VH of SEQ ID NO: 45 and the VL of SEQ ID NO: 47;
   e) the VH of SEQ ID NO: 49 and the VL of SEQ ID NO: 51;
   f) the VH of SEQ ID NO: 39 and the VL of SEQ ID NO: 53;
   g) the VH of SEQ ID NO: 55 and the VL of SEQ ID NO: 57;
   h) the VH of SEQ ID NO: 59 and the VL of SEQ ID NO: 61;
   i) the VH of SEQ ID NO: 63 and the VL of SEQ ID NO: 65;
   j) the VH of SEQ ID NO: 67 and the VL of SEQ ID NO: 69; or
   k) the VH of SEQ ID NO: 71 and the VL of SEQ ID NO: 73.

23. The trispecific antibody or trispecific binding fragment of any one of clauses 1-22, wherein the second or third antigen-binding site that specifically binds CD3 comprises:
   a) the HCDR1, the HCDR2 and the HCDR3 of the VH of SEQ ID NO: 97 and the LCDR1, the LCDR2 and the LCDR3 of the VL of SEQ ID NO: 99;
   b) the HCDR1, the HCDR2 and the HCDR3 of the VH of SEQ ID NO: 101 and the LCDR1, the LCDR2 and the LCDR3 of the VL of SEQ ID NO: 99;
   c) the HCDR1, the HCDR2 and the HCDR3 of the VH of SEQ ID NO: 103 and the LCDR1, the LCDR2 and the LCDR3 of the VL of SEQ ID NO: 99;
   d) the HCDR1, the HCDR2 and the HCDR3 of the VH of SEQ ID NO: 105 and the LCDR1, the LCDR2 and the LCDR3 of the VL of SEQ ID NO: 99; or
   e) the HCDR1, the HCDR2 and the HCDR3 of the VH of SEQ ID NO: 107 and the LCDR1, the LCDR2 and the LCDR3 of the VL of SEQ ID NO: 109.

24. The trispecific antibody or trispecific binding fragment of any one of clauses 1-23, wherein the second or third antigen-binding site that specifically binds CD3 comprises the HCDR1, the HCDR2, the HCDR3, the LCDR1, the LCDR2 and the LCDR3 of:
   a) SEQ ID NOs: 76, 77, 78, 79, 80 and 81, respectively;
   b) SEQ ID NOs: 76, 77, 75, 79, 80 and 81, respectively;
   c) SEQ ID NOs: 76, 77, 82, 79, 80 and 81, respectively; or
   d) SEQ ID NOs: 83, 84, 85, 86, 87 and 88, respectively.

25. The trispecific antibody or trispecific binding fragment of any one of clauses 1-24, wherein the second or third antigen-binding site that specifically binds CD3 comprises:
   a) the VH of SEQ ID NO: 97 and the VL of SEQ ID NO: 99;
   b) the VH of SEQ ID NO: 101 and the VL of SEQ ID NO: 99;
   c) the VH of SEQ ID NO: 103 and the VL of SEQ ID NO: 99;
   d) the VH of SEQ ID NO: 105 and the VL of SEQ ID NO: 99; or
   e) the VH of SEQ ID NO: 107 and the VL of SEQ ID NO: 109.

26. The trispecific antibody or trispecific binding fragment of any one of clauses 1-25, wherein the second or third antigen-binding site that specifically binds CD20 comprises:
   a) the HCDR1, the HCDR2 and the HCDR3 of the VH of SEQ ID NO: 126 and the LCDR1, the LCDR2 and the LCDR3 of the VL of SEQ ID NO: 128;
   b) the HCDR1, the HCDR2 and the HCDR3 of the VH of SEQ ID NO: 130 and the LCDR1, the LCDR2 and the LCDR3 of the VL of SEQ ID NO: 132;
   c) the HCDR1, the HCDR2 and the HCDR3 of the VH of SEQ ID NO: 134 and the LCDR1, the LCDR2 and the LCDR3 of the VL of SEQ ID NO: 136; or
   d) the HCDR1, the HCDR2 and the HCDR3 of the VH of SEQ ID NO: 138 and the LCDR1, the LCDR2 and the LCDR3 of the VL of SEQ ID NO: 140.

27. The trispecific antibody or trispecific binding fragment of any one of clauses 1-26, wherein the second or third antigen-binding site that specifically binds CD20 comprises the HCDR1, the HCDR2, the HCDR3, the LCDR1, the LCDR2 and the LCDR3 of:
   a) SEQ ID NOs: 115, 116, 117, 118, 119 and 120, respectively;
   b) SEQ ID NOs: 121, 122, 123, 124, 119 and 125, respectively;
   c) SEQ ID NOs: 115, 116, 95, 96, 119 and 125, respectively; or
   d) SEQ ID NOs: 121, 116, 123, 124, 119 and 125, respectively.

28. The trispecific antibody or trispecific binding fragment of any one of clauses 1-27, wherein the second or third antigen-binding site that specifically binds CD20 comprises:
   a) the VH of SEQ ID NO: 126 and the VL of SEQ ID NO: 128;
   b) the VH of SEQ ID NO: 130 and the VL of SEQ ID NO: 132;
   c) the VH of SEQ ID NO: 134 and the VL of SEQ ID NO: 136; or
   d) the VH of SEQ ID NO: 138 and the VL of SEQ ID NO: 140.

29. The trispecific antibody or trispecific binding fragment of any one of clauses 1-19, wherein the first antigen-binding site that specifically binds CD79b comprises the HCDR1, the HCDR2 and the HCDR3 of the VH of SEQ ID NO: 35 and the LCDR1, the LCDR2 and the LCDR3 of the VL of SEQ ID NO: 37;
the second antigen-binding site that specifically binds CD3 comprises the HCDR1, the HCDR2 and the HCDR3 of the VH of SEQ ID NO: 107 and the LCDR1, the LCDR2 and the LCDR3 of the VL of SEQ ID NO: 109; and the third antigen-binding site that specifically binds CD20 comprises the HCDR1, the HCDR2 and the HCDR3 of the VH of SEQ ID NO: 130 and the LCDR1, the LCDR2 and the LCDR3 of the VL of SEQ ID NO: 132.

30. The trispecific antibody or trispecific binding fragment of any one of clauses 1-19 and 29, wherein the first antigen-binding site that specifically binds CD79b comprises the HCDR1, the HCDR2, the HCDR3, the LCDR1, the LCDR2 and the LCDR3 of SEQ ID NOs: 1, 2, 3, 4, 5 and 6, respectively;

the second antigen-binding site that specifically binds CD3 comprises the HCDR1, the HCDR2, the HCDR3, the LCDR1, the LCDR2 and the LCDR3 of SEQ ID NOs: 83, 84, 85, 86, 87 and 88, respectively; and the third antigen-binding site that specifically binds CD20 comprises the HCDR1, the HCDR2, the HCDR3, the LCDR1, the LCDR2 and the LCDR3 of SEQ ID NOs: 121, 122, 123, 124, 119 and 125, respectively.

31. The trispecific antibody or trispecific binding fragment of any one of clauses 1-19, 29 and 30, wherein the first antigen-binding site that specifically binds CD79b comprises the VH of SEQ ID NO: 35 and the VL of SEQ ID NO: 37;

the second antigen-binding site that specifically binds CD3 comprises the VH of SEQ ID NO: 107 and the VL of SEQ ID NO: 109; and the third antigen-binding site that specifically binds CD20 comprises the VH of SEQ ID NO: 130 and the VL of SEQ ID NO: 132.

32. The trispecific antibody or trispecific binding fragment of any one of clauses 1-19, wherein the first antigen-binding site that specifically binds CD79b comprises the HCDR1, the HCDR2 and the HCDR3 of the VH of SEQ ID NO: 35 and the LCDR1, the LCDR2 and the LCDR3 of the VL of SEQ ID NO: 37;

the second antigen-binding site that specifically binds CD3 comprises the HCDR1, the HCDR2 and the HCDR3 of the VH of SEQ ID NO: 101 and the LCDR1, the LCDR2 and the LCDR3 of the VL of SEQ ID NO: 99; and the third antigen-binding site that specifically binds CD20 comprises the HCDR1, the HCDR2 and the HCDR3 of the VH of SEQ ID NO: 130 and the LCDR1, the LCDR2 and the LCDR3 of the VL of SEQ ID NO: 132.

33. The trispecific antibody or trispecific binding fragment of any one of clauses 1-19 and 32, wherein the first antigen-binding site that specifically binds CD79b comprises the HCDR1, the HCDR2, the HCDR3, the LCDR1, the LCDR2 and the LCDR3 of SEQ ID NOs: 1, 2, 3, 4, 5 and 6, respectively;

The second antigen-binding site that specifically binds CD3 comprises the HCDR1, the HCDR2, the HCDR3, the LCDR1, the LCDR2 and the LCDR3 of SEQ ID NOs: 76, 77, 75, 79, 80 and 81, respectively; and the third antigen-binding site that specifically binds CD20 comprises the HCDR1, the HCDR2, the HCDR3, the LCDR1, the LCDR2 and the LCDR3 of SEQ ID NOs: 121, 122, 123, 124, 119 and 125, respectively.

34. The trispecific antibody or trispecific binding fragment of any one of clauses 1-19, 32, and 33, wherein the first antigen-binding site that specifically binds CD79b comprises the VH of SEQ ID NO: 35 and the VL of SEQ ID NO: 37;

the second antigen-binding site that specifically binds CD3 comprises the VH of SEQ ID NO: 101 and the VL of SEQ ID NO: 99; and the third antigen-binding site that specifically binds CD20 comprises the VH of SEQ ID NO: 130 and the VL of SEQ ID NO: 132.

35. The trispecific antibody or trispecific binding fragment of any one of clauses 6-34, wherein the scFv comprises, from the N- to C-terminus, a VH, a second linker (L2) and a VL (VH-L2-VL) or the VL, the L2 and the VH (VL-L2-VH).

36. The trispecific antibody or trispecific binding fragment of any one of clauses 6-35, wherein the scFv comprises, from the N- to C-terminus, the VL, the L2 and the VH (VL-L2-VH).

37. The trispecific antibody or trispecific binding fragment of clause 35 or 36, wherein the second linker (L2) comprises any one of amino acid sequence of SEQ ID NOs: 215-248.

38. The trispecific antibody or trispecific binding fragment of any one of clauses 35-37, wherein the L2 comprises an amino acid sequence of GGSEGKSSGSGSESKSTGGS (SEQ ID NO: 215).

39. The trispecific antibody or trispecific antigen-binding fragment of any one of clauses 1 to 38, wherein the first antigen-binding site specifically binds to residues 30-42 (SEDRYRNPKGSAC; SEQ ID NO: 253), residues 50-52 (PRF), residues 81-86 (EMENP; SEQ ID NO: 254), and/or residues 144-148 (GFSTL; SEQ ID NO: 255) of human CD79b.

40. The trispecific antibody or trispecific antigen-binding fragment of clause 39, wherein the first antigen-binding site specifically binds to CD79b with an affinity of about $1\times10^{-11}$-$1\times10^{-9}$ M.

41. The trispecific antibody or trispecific antigen-binding fragment of any one of clauses 1 to 40, wherein the antibody or antigen-binding fragment thereof are of IgG1, IgG2, IgG3, or IgG4 isotype.

42. The trispecific antibody or trispecific antigen-binding fragment of any of clauses 1 to 41 is an IgG1 isotype.

43. The trispecific antibody or trispecific binding fragment of clause 1, wherein the HC1 comprises the amino acid sequence of SEQ ID NO: 172, 176, 180, or 191.

44. The trispecific antibody or trispecific binding fragment of clause 1 or 43, wherein the LC comprises the amino acid sequence of SEQ ID NO: 174, 178 or 182.

45. The trispecific antibody or trispecific binding fragment of any one of clauses 1, 43 and 44, wherein
a) the HC1 comprises the amino acid sequence of SEQ ID NO: 172 and the LC comprises the amino acid sequence of SEQ ID NO: 174;
b) the HC1 comprises the amino acid sequence of SEQ ID NO: 176 and the LC comprises the amino acid sequence of SEQ ID NO: 178;
c) the HC1 comprises the amino acid sequence of SEQ ID NO: 180 and the LC comprises the amino acid sequence of SEQ ID NO: 182;
d) the HC1 comprises the amino acid sequence of SEQ ID NO: 191 and the LC comprises the amino acid sequence of SEQ ID NO: 182.

46. The trispecific antibody or trispecific binding fragment of any one of clauses 1, 43-45, wherein the HC2 comprises the amino acid sequence of SEQ ID NO: 142, 144, 148, 150, 152, 154, 156, 158, 160, 162, 166, 168, or 170.

47. The trispecific antibody or trispecific binding fragment of clause 1, 43-46, wherein
    a) the HC1 comprises the amino acid sequence of SEQ ID NO: 172, the LC comprises the amino acid sequence of SEQ ID NO: 174, and the HC2 comprises the amino acid sequence of SEQ ID NO: 142;
    b) the HC1 comprises the amino acid sequence of SEQ ID NO: 176, the LC comprises the amino acid sequence of SEQ ID NO: 178, and the HC2 comprises the amino acid sequence of SEQ ID NO: 142;
    c) the HC1 comprises the amino acid sequence of SEQ ID NO: 180, the LC comprises the amino acid sequence of SEQ ID NO: 182, and the HC2 comprises the amino acid sequence of SEQ ID NO: 142;
    d) the HC1 comprises the amino acid sequence of SEQ ID NO: 172, the LC comprises the amino acid sequence of SEQ ID NO: 174, and the HC2 comprises the amino acid sequence of SEQ ID NO: 144;
    e) the HC1 comprises the amino acid sequence of SEQ ID NO: 176, the LC comprises the amino acid sequence of SEQ ID NO: 178, and the HC2 comprises the amino acid sequence of SEQ ID NO: 144;
    f) the HC1 comprises the amino acid sequence of SEQ ID NO: 180, the LC comprises the amino acid sequence of SEQ ID NO: 182, and the HC2 comprises the amino acid sequence of SEQ ID NO: 144;
    g) the HC1 comprises the amino acid sequence of SEQ ID NO: 180, the LC comprises the amino acid sequence of SEQ ID NO: 182, and the HC2 comprises the amino acid sequence of SEQ ID NO: 148;
    h) the HC1 comprises the amino acid sequence of SEQ ID NO: 180, the LC comprises the amino acid sequence of SEQ ID NO: 182, and the HC2 comprises the amino acid sequence of SEQ ID NO: 150;
    i) the HC1 comprises the amino acid sequence of SEQ ID NO: 180, the LC comprises the amino acid sequence of SEQ ID NO: 182, and the HC2 comprises the amino acid sequence of SEQ ID NO: 152;
    j) the HC1 comprises the amino acid sequence of SEQ ID NO: 180, the LC comprises the amino acid sequence of SEQ ID NO: 182, and the HC2 comprises the amino acid sequence of SEQ ID NO: 154;
    k) the HC1 comprises the amino acid sequence of SEQ ID NO: 180, the LC comprises the amino acid sequence of SEQ ID NO: 182, and the HC2 comprises the amino acid sequence of SEQ ID NO: 156;
    l) the HC1 comprises the amino acid sequence of SEQ ID NO: 180, the LC comprises the amino acid sequence of SEQ ID NO: 182, and the HC2 comprises the amino acid sequence of SEQ ID NO: 158;
    m) the HC1 comprises the amino acid sequence of SEQ ID NO: 180, the LC comprises the amino acid sequence of SEQ ID NO: 182, and the HC2 comprises the amino acid sequence of SEQ ID NO: 160;
    n) the HC1 comprises the amino acid sequence of SEQ ID NO: 180, the LC comprises the amino acid sequence of SEQ ID NO: 182, and the HC2 comprises the amino acid sequence of SEQ ID NO: 162;
    o) the HC1 comprises the amino acid sequence of SEQ ID NO: 191, the LC comprises the amino acid sequence of SEQ ID NO: 182, and the HC2 comprises the amino acid sequence of SEQ ID NO: 166;
    p) the HC1 comprises the amino acid sequence of SEQ ID NO: 172, the LC comprises the amino acid sequence of SEQ ID NO: 174, and the HC2 comprises the amino acid sequence of SEQ ID NO: 168; or
    q) the HC1 comprises the amino acid sequence of SEQ ID NO: 172, the LC comprises the amino acid sequence of SEQ ID NO: 174, and the HC2 comprises the amino acid sequence of SEQ ID NO: 170.

48. The trispecific antibody or trispecific binding fragment of any one of clause 1, 43-47, wherein the HC1 comprises the amino acid sequence of SEQ ID NO: 172, the LC comprises the amino acid sequence of SEQ ID NO: 174, and the HC2 comprises the amino acid sequence of SEQ ID NO: 168.

49. The trispecific antibody or trispecific binding fragment of clause 1, 43-47, wherein the HC1 comprises the amino acid sequence of SEQ ID NO: 172, the LC comprises the amino acid sequence of SEQ ID NO: 174, and the HC2 comprises the amino acid sequence of SEQ ID NO: 170.

50. A trispecific antibody, or a trispecific binding fragment thereof, comprising:
    a) a first antigen-binding site that specifically binds CD79b,
    b) a second antigen-binding site that specifically binds CD3, and
    c) a third antigen-binding site that specifically binds CD20.

51. The trispecific antibody or trispecific binding fragment of clause 50, wherein the first antigen-binding site that specifically binds CD79b comprises:
    a) the HCDR1, the HCDR2 and the HCDR3 of the VH of SEQ ID NO: 35 and the LCDR1, the LCDR2 and the LCDR3 of the VL of SEQ ID NO: 37;
    b) the HCDR1, the HCDR2 and the HCDR3 of the VH of SEQ ID NO: 39 and the LCDR1, the LCDR2 and the LCDR3 of the VL of SEQ ID NO: 41;
    c) the HCDR1, the HCDR2 and the HCDR3 of the VH of SEQ ID NO: 43 and the LCDR1, the LCDR2 and the LCDR3 of the VL of SEQ ID NO: 41;
    d) the HCDR1, the HCDR2 and the HCDR3 of the VH of SEQ ID NO: 45 and the LCDR1, the LCDR2 and the LCDR3 of the VL of SEQ ID NO: 47;
    e) the HCDR1, the HCDR2 and the HCDR3 of the VH of SEQ ID NO: 49 and the LCDR1, the LCDR2 and the LCDR3 of the VL of SEQ ID NO: 51;
    f) the HCDR1, the HCDR2 and the HCDR3 of the VH of SEQ ID NO: 39 and the LCDR1, the LCDR2 and the LCDR3 of the VL of SEQ ID NO: 53;
    g) the HCDR1, the HCDR2 and the HCDR3 of the VH of SEQ ID NO: 55 and the LCDR1, the LCDR2 and the LCDR3 of the VL of SEQ ID NO: 57;
    h) the HCDR1, the HCDR2 and the HCDR3 of the VH of SEQ ID NO: 59 and the LCDR1, the LCDR2 and the LCDR3 of the VL of SEQ ID NO: 61;
    i) the HCDR1, the HCDR2 and the HCDR3 of the VH of SEQ ID NO: 63 and the LCDR1, the LCDR2 and the LCDR3 of the VL of SEQ ID NO: 65;
    j) the HCDR1, the HCDR2 and the HCDR3 of the VH of SEQ ID NO: 67 and the LCDR1, the LCDR2 and the LCDR3 of the VL of SEQ ID NO: 69; or
    k) the HCDR1, the HCDR2 and the HCDR3 of the VH of SEQ ID NO: 71 and the LCDR1, the LCDR2 and the LCDR3 of the VL of SEQ ID NO: 73.

52. The trispecific antibody or trispecific binding fragment of clause 50 or 51, wherein the first antigen-binding site that specifically binds CD79b comprises the HCDR1, the HCDR2, the HCDR3, the LCDR1, the LCDR2 and the LCDR3 of:
- a) SEQ ID NOs: 1, 2, 3, 4, 5 and 6, respectively;
- b) SEQ ID NOs: 13, 8, 9, 10, 11 and 12, respectively;
- c) SEQ ID NOs: 7, 8, 9, 10, 11 and 12, respectively;
- d) SEQ ID NOs: 14, 15, 16, 17, 5 and 6, respectively;
- e) SEQ ID NOs: 18, 8, 19, 20, 21 and 12, respectively;
- f) SEQ ID NOs: 22, 23, 24, 25, 5 and 6, respectively;
- g) SEQ ID NOs: 22, 26, 27, 28, 5 and 29, respectively; or
- h) SEQ ID NOs: 30, 31, 32, 33, 5 and 6, respectively.

53. The trispecific antibody or trispecific binding fragment of any one of clauses 50-52, wherein the first antigen-binding site that specifically binds CD79b comprises
- a) the VH of SEQ ID NO: 35 and the VL of SEQ ID NO: 37;
- b) the VH of SEQ ID NO: 39 and the VL of SEQ ID NO: 41;
- c) the VH of SEQ ID NO: 43 and the VL of SEQ ID NO: 41;
- d) the VH of SEQ ID NO: 45 and the VL of SEQ ID NO: 47;
- e) the VH of SEQ ID NO: 49 and the VL of SEQ ID NO: 51;
- f) the VH of SEQ ID NO: 39 and the VL of SEQ ID NO: 53;
- g) the VH of SEQ ID NO: 55 and the VL of SEQ ID NO: 57;
- h) the VH of SEQ ID NO: 59 and the VL of SEQ ID NO: 61;
- i) the VH of SEQ ID NO: 63 and the VL of SEQ ID NO: 65;
- j) the VH of SEQ ID NO: 67 and the VL of SEQ ID NO: 69; or
- k) the VH of SEQ ID NO: 71 and the VL of SEQ ID NO: 73.

54. The trispecific antibody or trispecific binding fragment of any one of clauses 50-53, wherein the second antigen-binding site that specifically binds CD3 comprises:
- a) the HCDR1, the HCDR2 and the HCDR3 of the VH of SEQ ID NO: 97 and the LCDR1, the LCDR2 and the LCDR3 of the VL of SEQ ID NO: 99;
- b) the HCDR1, the HCDR2 and the HCDR3 of the VH of SEQ ID NO: 101 and the LCDR1, the LCDR2 and the LCDR3 of the VL of SEQ ID NO: 99;
- c) the HCDR1, the HCDR2 and the HCDR3 of the VH of SEQ ID NO: 103 and the LCDR1, the LCDR2 and the LCDR3 of the VL of SEQ ID NO: 99;
- d) the HCDR1, the HCDR2 and the HCDR3 of the VH of SEQ ID NO: 105 and the LCDR1, the LCDR2 and the LCDR3 of the VL of SEQ ID NO: 99; or
- e) the HCDR1, the HCDR2 and the HCDR3 of the VH of SEQ ID NO: 107 and the LCDR1, the LCDR2 and the LCDR3 of the VL of SEQ ID NO: 109.

55. The trispecific antibody or trispecific binding fragment of any one of clauses 50-54, wherein the second antigen-binding site that specifically binds CD3 comprises:
- a) SEQ ID NOs: 76, 77, 78, 79, 80 and 81, respectively;
- b) SEQ ID NOs: 76, 77, 75, 79, 80 and 81, respectively;
- c) SEQ ID NOs: 76, 77, 82, 79, 80 and 81, respectively; or
- d) SEQ ID NOs: 83, 84, 85, 86, 87 and 88, respectively.

56. The trispecific antibody or trispecific binding fragment of any one of clauses 50-55, wherein the second antigen-binding site that specifically binds CD3 comprises
- a) the VH of SEQ ID NO: 97 and the VL of SEQ ID NO: 99;
- b) the VH of SEQ ID NO: 101 and the VL of SEQ ID NO: 99;
- c) the VH of SEQ ID NO: 103 and the VL of SEQ ID NO: 99;
- d) the VH of SEQ ID NO: 105 and the VL of SEQ ID NO: 99; or
- e) the VH of SEQ ID NO: 107 and the VL of SEQ ID NO: 109.

57. The trispecific antibody or trispecific binding fragment of any one of clauses 50-56, wherein the third antigen-binding site that specifically binds CD20 comprises:
- a) the HCDR1, the HCDR2 and the HCDR3 of the VH of SEQ ID NO: 126 and the LCDR1, the LCDR2 and the LCDR3 of the VL of SEQ ID NO: 128;
- b) the HCDR1, the HCDR2 and the HCDR3 of the VH of SEQ ID NO: 130 and the LCDR1, the LCDR2 and the LCDR3 of the VL of SEQ ID NO: 132;
- c) the HCDR1, the HCDR2 and the HCDR3 of the VH of SEQ ID NO: 134 and the LCDR1, the LCDR2 and the LCDR3 of the VL of SEQ ID NO: 136;
- d) the HCDR1, the HCDR2 and the HCDR3 of the VH of SEQ ID NO: 138 and the LCDR1, the LCDR2 and the LCDR3 of the VL of SEQ ID NO: 140.

58. The trispecific antibody or trispecific binding fragment of any one of clauses 50-57, wherein the third antigen-binding site that specifically binds CD20 comprises:
- a) SEQ ID NOs: 115, 116, 117, 118, 119 and 120, respectively;
- b) SEQ ID NOs: 121, 122, 123, 124, 119 and 125, respectively;
- c) SEQ ID NOs: 115, 116, 95, 96, 119 and 125, respectively; or
- d) SEQ ID NOs: 121, 116, 123, 124, 119 and 125, respectively.

59. The trispecific antibody or trispecific binding fragment of any one of clauses 50-58, wherein the third antigen-binding site that specifically binds CD20 comprises
- a) the VH of SEQ ID NO: 126 and the VL of SEQ ID NO: 128;
- b) the VH of SEQ ID NO: 130 and the VL of SEQ ID NO: 132;
- c) the VH of SEQ ID NO: 134 and the VL of SEQ ID NO: 136; or
- d) the VH of SEQ ID NO: 138 and the VL of SEQ ID NO: 140.

60. The trispecific antibody or trispecific binding fragment of any one of clauses 50-59, comprising a first antigen-binding site that specifically binds CD79b comprising the HCDR1, the HCDR2 and the HCDR3 of the VH of SEQ ID NO: 35 and the LCDR1, the LCDR2 and the LCDR3 of the VL of SEQ ID NO: 37; a second antigen-binding site that specifically binds CD3 comprising the HCDR1, the HCDR2 and the HCDR3 of the VH of SEQ ID NO: 107 and the LCDR1, the LCDR2 and the LCDR3 of the VL of SEQ ID NO: 109; and a third antigen-binding site that specifically binds CD20 comprising the HCDR1, the HCDR2 and the HCDR3 of the VH of SEQ ID NO: 130 and the LCDR1, the LCDR2 and the LCDR3 of the VL of SEQ ID NO: 132.

61. The trispecific antibody or trispecific binding fragment of any one of clauses 50-60, comprising a first antigen-binding site that specifically binds CD79b comprising the HCDR1, the HCDR2, the HCDR3, the LCDR1, the LCDR2 and the LCDR3 of SEQ ID NOs: 1, 2, 3, 4, 5 and 6, respectively;
a second antigen-binding site that specifically binds CD3 comprising the HCDR1, the HCDR2, the HCDR3, the LCDR1, the LCDR2 and the LCDR3 of SEQ ID NOs: 83, 84, 85, 86, 87 and 88, respectively; and
a third antigen-binding site that specifically binds CD20 comprising the HCDR1, the HCDR2, the HCDR3, the LCDR1, the LCDR2 and the LCDR3 of SEQ ID NOs: 121, 122, 123, 124, 119 and 125, respectively.

62. The trispecific antibody or trispecific binding fragment of any one of clauses 50-61, comprising a first antigen-binding site that specifically binds CD79b comprising the VH of SEQ ID NO: 35 and the VL of SEQ ID NO: 37;
a second antigen-binding site that specifically binds CD3 comprising the VH of SEQ ID NO: 107 and the VL of SEQ ID NO: 109; and
a third antigen-binding site that specifically binds CD20 comprising the VH of SEQ ID NO: 130 and the VL of SEQ ID NO: 132.

63. The trispecific antibody or trispecific binding fragment of any one of clauses 50-59, comprising a first antigen-binding site that specifically binds CD79b comprising the HCDR1, the HCDR2 and the HCDR3 of the VH of SEQ ID NO: 35 and the LCDR1, the LCDR2 and the LCDR3 of the VL of SEQ ID NO: 37;
a second antigen-binding site that specifically binds CD3 comprising the HCDR1, the HCDR2 and the HCDR3 of the VH of SEQ ID NO: 101 and the LCDR1, the LCDR2 and the LCDR3 of the VL of SEQ ID NO: 99; and
a third antigen-binding site that specifically binds CD20 comprising the HCDR1, the HCDR2 and the HCDR3 of the VH of SEQ ID NO: 130 and the LCDR1, the LCDR2 and the LCDR3 of the VL of SEQ ID NO: 132.

64. The trispecific antibody or trispecific binding fragment of any one of clauses 50-59, and 63, comprising a first antigen-binding site that specifically binds CD79b comprising the HCDR1, the HCDR2, the HCDR3, the LCDR1, the LCDR2 and the LCDR3 of SEQ ID NOs: 1, 2, 3, 4, 5 and 6, respectively;
a second antigen-binding site that specifically binds CD3 comprising the HCDR1, the HCDR2, the HCDR3, the LCDR1, the LCDR2 and the LCDR3 of SEQ ID NOs: 76, 77, 75, 79, 80 and 81, respectively; and
a third antigen-binding site that specifically binds CD20 comprising the HCDR1, the HCDR2, the HCDR3, the LCDR1, the LCDR2 and the LCDR3 of SEQ ID NOs: 121, 122, 123, 124, 119 and 125, respectively.

65. The trispecific antibody or trispecific binding fragment of any one of clauses 50-59, 63 and 64, comprising a first antigen-binding site that specifically binds CD79b comprising the VH of SEQ ID NO: 35 and the VL of SEQ ID NO: 37;
a second antigen-binding site that specifically binds CD3 comprising the VH of SEQ ID NO: 101 and the VL of SEQ ID NO: 99; and
a third antigen-binding site that specifically binds CD20 comprising the VH of SEQ ID NO: 130 and the VL of SEQ ID NO: 132.

66. The antibody or antigen-binding fragment of any one of clauses 50-65, wherein the first antigen-binding site specifically binds to residues 30-42 (SEDRYRNPKGSAC; SEQ ID NO: 253), residues 50-52 (PRF), residues 81-86 (EMENP; SEQ ID NO: 254), and/or residues 144-148 (GFSTL; SEQ ID NO: 255) of human CD79b.

67. The antibody or antigen-binding fragment of clause 66, wherein the first antigen-binding site specifically binds to CD79b with an affinity of about $1 \times 10^{-11}$-$1 \times 10^{-9}$ M.

68. The antibody or antigen-binding fragment of any one of clauses 50-67, wherein the antibody or antigen-binding fragment thereof are of IgG1, IgG2, IgG3, or IgG4 isotype.

69. The antibody or antigen-binding fragment of any of clauses 50-68 is an IgG1 isotype.

70. A trispecific antibody, or a trispecific binding fragment thereof, comprising:
a) a first heavy chain (HC1);
b) a light chain (LC); and
c) a second heavy chain (HC2),
wherein HC1 comprises the amino acid sequence of SEQ ID NO: 172, LC comprises the amino acid sequence of SEQ ID NO: 174, and the HC2 comprises the amino acid sequence of SEQ ID NO: 168.

71. A trispecific antibody, or a trispecific binding fragment thereof, comprising:
a) a first heavy chain (HC1);
b) a light chain (LC); and
c) a second heavy chain (HC2),
wherein HC1 comprises the amino acid sequence of SEQ ID NO: 172, LC comprises the amino acid sequence of SEQ ID NO: 174, and the HC2 comprises the amino acid sequence of SEQ ID NO: 170.

72. A synthetic polynucleotide encoding the trispecific antibody or trispecific binding fragment of any one of clauses 1 to 71.

73. The synthetic polynucleotide of clause 72, wherein the polynucleotide comprises a sequence encoding an antigen-binding site that specifically binds CD79b, said sequence comprising
a) a VH-encoding sequence of SEQ ID NO: 36 and a VL-encoding sequence of SEQ ID NO: 38 or 213;
b) a VH-encoding sequence of SEQ ID NO: 40 and a VL-encoding sequence of SEQ ID NO: 42;
c) a VH-encoding sequence of SEQ ID NO: 44 and a VL-encoding sequence of SEQ ID NO: 34;
d) a VH-encoding sequence of SEQ ID NO: 46 and a VL-encoding sequence of SEQ ID NO: 48 or 214;
e) a VH-encoding sequence of SEQ ID NO: 50 and a VL-encoding sequence of SEQ ID NO: 52;
f) a VH-encoding sequence of SEQ ID NO: 40 and a VL-encoding sequence of SEQ ID NO: 54;
g) a VH-encoding sequence of SEQ ID NO: 56 and a VL-encoding sequence of SEQ ID NO: 58;
h) a VH-encoding sequence of SEQ ID NO: 60 and a VL-encoding sequence of SEQ ID NO: 62;
i) a VH-encoding sequence of SEQ ID NO: 64 and a VL-encoding sequence of SEQ ID NO: 66;

j) a VH-encoding sequence of SEQ ID NO: 68 and a VL-encoding sequence of SEQ ID NO: 70; or
k) a VH-encoding sequence of SEQ ID NO: 72 and a VL-encoding sequence of SEQ ID NO: 74.

74. The synthetic polynucleotide of clause 72 or 73, wherein the polynucleotide comprises a sequence encoding an antigen-binding site that specifically binds CD3, said sequence comprising
   a) a VH-encoding sequence of SEQ ID NO: 98 and a VL-encoding sequence of SEQ ID NO: 100;
   b) a VH-encoding sequence of SEQ ID NO: 102 and a VL-encoding sequence of SEQ ID NO: 100;
   c) a VH-encoding sequence of SEQ ID NO: 104 and a VL-encoding sequence of SEQ ID NO: 100;
   d) a VH-encoding sequence of SEQ ID NO: 106 and a VL-encoding sequence of SEQ ID NO: 100; or
   e) a VH-encoding sequence of SEQ ID NO: 108 and a VL-encoding sequence of SEQ ID NO: 110.

75. The synthetic polynucleotide of any one of clauses 72-74, wherein the polynucleotide comprises a sequence encoding an antigen-binding site that specifically binds CD20, said sequence comprising:
   a) a VH-encoding sequence of SEQ ID NO: 127 and a VL-encoding sequence of SEQ ID NO: 129;
   b) a VH-encoding sequence of SEQ ID NO: 131 and a VL-encoding sequence of SEQ ID NO: 133;
   c) a VH-encoding sequence of SEQ ID NO: 135 and a VL-encoding sequence of SEQ ID NO: 137; or
   d) a VH-encoding sequence of SEQ ID NO: 139 and a VL-encoding sequence of SEQ ID NO: 141.

76. The synthetic polynucleotide of any one of clauses 72-75, wherein the polynucleotide comprises a sequence encoding an HC1 comprising the nucleotide sequence of SEQ ID NO: 173, 177, 181, or 192.

77. The synthetic polynucleotide of any one of clauses 72-76, wherein the polynucleotide comprises a sequence encoding a LC comprising the nucleotide sequence of SEQ ID NO: 175, 179, 183 or 188.

78. The synthetic polynucleotide of clause any one of clauses 72-77, comprising
   a) an HC1-encoding sequence of SEQ ID NO: 173 and a LC-encoding sequence of SEQ ID NO: 175;
   b) an HC1-encoding sequence of SEQ ID NO: 177, and a LC-encoding sequence of SEQ ID NO: 179;
   c) an HC1-encoding sequence of SEQ ID NO: 181, and a LC-encoding sequence of SEQ ID NO: 183;
   d) an HC1-encoding sequence of SEQ ID NO: 181, and a LC-encoding sequence of SEQ ID NO: 188;
   e) an HC1-encoding sequence of SEQ ID NO: 192, and a LC-encoding sequence of SEQ ID NO: 183.

79. The synthetic polynucleotide of any one of clauses 72-78, wherein the polynucleotide comprises a sequence encoding an HC2 comprising the nucleotide sequence of SEQ ID NO: 143, 145, 149, 151, 153, 155, 157, 159, 161, 163, 167, 169, or 171.

80. The synthetic polynucleotide of any one of clauses 72-79, comprising
   a) an HC1-encoding sequence of SEQ ID NO: 173, a LC-encoding sequence of SEQ ID NO: 175, and an HC2-encoding sequence of SEQ ID NO: 143;
   b) an HC1-encoding sequence of SEQ ID NO: 177, a LC-encoding sequence of SEQ ID NO: 179, and an HC2-encoding sequence of SEQ ID NO: 143;
   c) an HC1-encoding sequence of SEQ ID NO: 181, a LC-encoding sequence of SEQ ID NO: 183, and an HC2-encoding sequence of SEQ ID NO: 143;
   d) an HC1-encoding sequence of SEQ ID NO: 173, a LC-encoding sequence of SEQ ID NO: 175, and an HC2-encoding sequence of SEQ ID NO: 145;
   e) an HC1-encoding sequence of SEQ ID NO: 177, a LC-encoding sequence of SEQ ID NO: 179, and an HC2-encoding sequence of SEQ ID NO: 145;
   f) an HC1-encoding sequence of SEQ ID NO: 181, a LC-encoding sequence of SEQ ID NO: 183, and an HC2-encoding sequence of SEQ ID NO: 145;
   g) an HC1-encoding sequence of SEQ ID NO: 181, a LC-encoding sequence of SEQ ID NO: 188, and an HC2-encoding sequence of SEQ ID NO: 149;
   h) an HC1-encoding sequence of SEQ ID NO: 181, a LC-encoding sequence of SEQ ID NO: 188, and an HC2-encoding sequence of SEQ ID NO: 151;
   i) an HC1-encoding sequence of SEQ ID NO: 181, a LC-encoding sequence of SEQ ID NO: 188, and an HC2-encoding sequence of SEQ ID NO: 153;
   j) an HC1-encoding sequence of SEQ ID NO: 181, a LC-encoding sequence of SEQ ID NO: 188, and an HC2-encoding sequence of SEQ ID NO: 155;
   k) an HC1-encoding sequence of SEQ ID NO: 181, a LC-encoding sequence of SEQ ID NO: 188, and an HC2-encoding sequence of SEQ ID NO: 157;
   l) an HC1-encoding sequence of SEQ ID NO: 181, a LC-encoding sequence of SEQ ID NO: 188, and an HC2-encoding sequence of SEQ ID NO: 159;
   m) an HC1-encoding sequence of SEQ ID NO: 181, a LC-encoding sequence of SEQ ID NO: 188, and an HC2-encoding sequence of SEQ ID NO: 161;
   n) an HC1-encoding sequence of SEQ ID NO: 181, a LC-encoding sequence of SEQ ID NO: 188, and an HC2-encoding sequence of SEQ ID NO: 163;
   o) an HC1-encoding sequence of SEQ ID NO: 192, a LC-encoding sequence of SEQ ID NO: 183, and an HC2-encoding sequence of SEQ ID NO: 167;
   p) an HC1-encoding sequence of SEQ ID NO: 173, a LC-encoding sequence of SEQ ID NO: 175, and an HC2-encoding sequence of SEQ ID NO: 169; or q) an HC1-encoding sequence of SEQ ID NO: 173, a LC-encoding sequence of SEQ ID NO: 175, and an HC2-encoding sequence of SEQ ID NO: 171.

81. The synthetic polynucleotide of any one of clauses 72-80, comprising an HC1-encoding sequence of SEQ ID NO: 173, a LC-encoding sequence of SEQ ID NO: 175, and an HC2-encoding sequence of SEQ ID NO: 169.

82. The synthetic polynucleotide of any one of clauses 72-80, comprising an HC1-encoding sequence of SEQ ID NO: 173, a LC-encoding sequence of SEQ ID NO: 175, and an HC2-encoding sequence of SEQ ID NO: 171.

83. A synthetic polynucleotide encoding a trispecific antibody, or a trispecific binding fragment thereof, said trispecific antibody or trispecific binding fragment comprising:
   a) a first heavy chain (HC1);
   b) a light chain (LC); and
   c) a second heavy chain (HC2),
   wherein the polynucleotide comprises an HC1-encoding sequence of SEQ ID NO: 173, a LC-encoding sequence of SEQ ID NO: 175, and an HC2-encoding sequence of SEQ ID NO: 169.

84. A synthetic polynucleotide encoding a trispecific antibody, or a trispecific binding fragment thereof, said trispecific antibody or trispecific binding fragment comprising:

a) a first heavy chain (HC1);
b) a light chain (LC); and
c) a second heavy chain (HC2),
wherein the polynucleotide comprises an HC1-encoding sequence of SEQ ID NO: 173, a LC-encoding sequence of SEQ ID NO: 175, and an HC2-encoding sequence of SEQ ID NO: 171.

85. A pharmaceutical composition comprising the trispecific antibody or trispecific binding fragment of any one of clauses 1 to 71, or the polynucleotide of any one of clauses 72-84, and a pharmaceutically acceptable carrier.

86. An isolated cell expressing the trispecific antibody or trispecific binding fragment of any one of clauses 1 to 71.

87. The cell of clause 86 wherein the cell is a hybridoma.

88. The cell of clause 86 wherein the antibody is recombinantly produced.

89. A method for treating cancer in a subject in need thereof, said method comprising administering to the subject a therapeutically effective amount of the trispecific antibody or trispecific binding fragment of any one of clauses 1 to 71, the polynucleotide of any one of clauses 72-84, or the pharmaceutical composition of clause 85.

90. The method of clause 89, wherein the trispecific antibody or trispecific binding fragment, polynucleotide, or the pharmaceutical composition is administered for a time sufficient to treat the cancer.

91. A method for inhibiting growth or proliferation of a cancer cell, said method comprising administering to said cell an effective amount of the trispecific antibody or trispecific binding fragment of any one of clauses 1 to 71, the polynucleotide of any one of clauses 72-84, or the pharmaceutical composition of clause 85, wherein said effective amount is sufficient to inhibit the growth or proliferation of said cancer cell.

92. The method of clause 91, wherein said cancer cell is in a subject and the trispecific antibody or trispecific binding fragment, polynucleotide, or the pharmaceutical composition is administered to the subject.

93. The method of clause 92, wherein said administration is conducted ex vivo.

94. A method of redirecting a T cell to CD79b and/or CD20-expressing cancer cells in a subject in need thereof, said method comprising administering to said subject a therapeutically effective amount of the trispecific antibody or trispecific binding fragment of any one of clauses 1 to 71, the polynucleotide of any one of clauses 72-84, or the pharmaceutical composition of clause 85.

95. The method of clause 94, wherein the said therapeutically effective amount is sufficient to direct said T cell response to said cancer cells.

96. The method of any one of clauses 89-95, wherein the cancer is a hematological cancer.

97. The method of clause 96 wherein the hematological cancer is a CD79b and/or CD20-expressing B cell cancer.

98. The method of clause 97 wherein the CD79b and/or CD20-expressing B cell cancer is a B-cell lymphoma or a non-Hodgkin lymphoma.

99. The method of clause 98 wherein the CD79b and/or CD20-expressing B cell cancer is a diffuse large B-cell lymphoma (DLBCL), mantle cell lymphoma (MCL), marginal zone lymphoma (MZL), or follicular lymphoma (FL).

100. The method of any one of clauses 89-99, wherein the cancer is relapsed, refractory, or malignant cancer, or any combination thereof.

101. The method of any one of clauses 89-100 further comprising administering a second therapeutic agent.

102. The method of clause 101 wherein the second therapeutic agent is a surgery, chemotherapy, androgen deprivation therapy or radiation, or any combination thereof.

103. A method for generating the trispecific antibody or trispecific binding fragment of any one of clauses 1 to 71, wherein said method comprises culturing the cell of any one of clauses 86 to 88 and isolating said trispecific antibody or trispecific binding fragment.

104. A kit comprising (i) the trispecific antibody or trispecific binding fragment of any one of clauses 1 to 71 and/or the polynucleotide of any one of clauses 72-84 and (ii) packaging for the same.

105. An antibody, or an antigen-binding fragment thereof, that binds specifically to Cluster of Differentiation 79B protein (CD79b), comprising:
a) a heavy chain complementarity determining region (HCDR) 1, a HCDR2 and a HCDR3 of a heavy chain variable region (VH) of SEQ ID NO: 35 and a light chain complementarity determining region (LCDR) 1, a LCDR2 and a LCDR3 of a light chain variable region (VL) of SEQ ID NO: 37;
b) the HCDR1, the HCDR2 and the HCDR3 of the VH of SEQ ID NO: 39 and the LCDR1, the LCDR2 and the LCDR3 of the VL of SEQ ID NO: 41;
c) the HCDR1, the HCDR2 and the HCDR3 of the VH of SEQ ID NO: 43 and the LCDR1, the LCDR2 and the LCDR3 of the VL of SEQ ID NO: 41;
d) the HCDR1, the HCDR2 and the HCDR3 of the VH of SEQ ID NO: 45 and the LCDR1, the LCDR2 and the LCDR3 of the VL of SEQ ID NO: 47;
e) the HCDR1, the HCDR2 and the HCDR3 of the VH of SEQ ID NO: 49 and the LCDR1, the LCDR2 and the LCDR3 of the VL of SEQ ID NO: 51;
f) the HCDR1, the HCDR2 and the HCDR3 of the VH of SEQ ID NO: 39 and the LCDR1, the LCDR2 and the LCDR3 of the VL of SEQ ID NO: 53;
g) the HCDR1, the HCDR2 and the HCDR3 of the VH of SEQ ID NO: 55 and the LCDR1, the LCDR2 and the LCDR3 of the VL of SEQ ID NO: 57;
h) the HCDR1, the HCDR2 and the HCDR3 of the VH of SEQ ID NO: 59 and the LCDR1, the LCDR2 and the LCDR3 of the VL of SEQ ID NO: 61;
i) the HCDR1, the HCDR2 and the HCDR3 of the VH of SEQ ID NO: 63 and the LCDR1, the LCDR2 and the LCDR3 of the VL of SEQ ID NO: 65;
j) the HCDR1, the HCDR2 and the HCDR3 of the VH of SEQ ID NO: 67 and the LCDR1, the LCDR2 and the LCDR3 of the VL of SEQ ID NO: 69; or
k) the HCDR1, the HCDR2 and the HCDR3 of the VH of SEQ ID NO: 71 and the LCDR1, the LCDR2 and the LCDR3 of the VL of SEQ ID NO: 73.

106. The antibody or antigen-binding fragment of clause 105, comprising the HCDR1, the HCDR2, the HCDR3, the LCDR1, the LCDR2 and the LCDR3 of:
a) SEQ ID NOs: 1, 2, 3, 4, 5 and 6, respectively;
b) SEQ ID NOs: 13, 8, 9, 10, 11 and 12, respectively;
c) SEQ ID NOs: 7, 8, 9, 10, 11 and 12, respectively;
d) SEQ ID NOs: 14, 15, 16, 17, 5 and 6, respectively;
e) SEQ ID NOs: 18, 8, 19, 20, 21 and 12, respectively;
f) SEQ ID NOs: 22, 23, 24, 25, 5 and 6, respectively;

g) SEQ ID NOs: 22, 26, 27, 28, 5 and 29, respectively; or
h) SEQ ID NOs: 30, 31, 32, 33, 5 and 6, respectively.

107. The antibody or antigen-binding fragment of clause 105 or 106, comprising
  a) the VH of SEQ ID NO: 35 and the VL of SEQ ID NO: 37;
  b) the VH of SEQ ID NO: 39 and the VL of SEQ ID NO: 41;
  c) the VH of SEQ ID NO: 43 and the VL of SEQ ID NO: 41;
  d) the VH of SEQ ID NO: 45 and the VL of SEQ ID NO: 47;
  e) the VH of SEQ ID NO: 49 and the VL of SEQ ID NO: 51;
  f) the VH of SEQ ID NO: 39 and the VL of SEQ ID NO: 53;
  g) the VH of SEQ ID NO: 55 and the VL of SEQ ID NO: 57;
  h) the VH of SEQ ID NO: 59 and the VL of SEQ ID NO: 61;
  i) the VH of SEQ ID NO: 63 and the VL of SEQ ID NO: 65;
  j) the VH of SEQ ID NO: 67 and the VL of SEQ ID NO: 69; or
  k) the VH of SEQ ID NO: 71 and the VL of SEQ ID NO: 73.

108. The antibody or antigen-binding fragment of any one of clauses 105-107, wherein the antibody or antigen-binding fragment specifically binds residues 30-42 (SEDRYRNPKGSAC; SEQ ID NO: 253), residues 50-52 (PRF), residues 81-86 (EMENP; SEQ ID NO: 254), and/or residues 144-148 (GFSTL; SEQ ID NO: 255) of human CD79b.

109. The antibody or antigen-binding fragment of clause 108, wherein the antibody or antigen-binding fragment specifically binds to CD79b with an affinity of about $1\times10^{-11}$-$1\times10^{-9}$ M.

110. The antibody or antigen-binding fragment of any one of clauses 105-109 wherein the antibody or antigen-binding fragment is a human antibody or antigen-binding fragment.

111. The antibody or antigen-binding fragment of any one of clauses 105 to 110 wherein the antibody or antigen-binding fragment is recombinant.

112. The antigen binding fragment of any one of clauses 105 to 111 wherein the antigen binding fragment is a Fab fragment, a Fab2 fragment, a scFv, a (scFv)2, a Fv, a Fd, a dAb or a VHH.

113. The antibody or antigen-binding fragment of any one of clauses 105 to 112 wherein the antibody or antigen-binding fragment thereof are of IgG1, IgG2, IgG3, or IgG4 isotype.

114. The antibody or antigen-binding fragment of any of clauses 105 to 113 is an IgG1 or an IgG4 isotype.

115. A synthetic polynucleotide encoding the antibody or antigen-binding fragment of any one of clauses 105 to 114.

116. The synthetic polynucleotide of clause 115, comprising
  a) a VH-encoding sequence of SEQ ID NO: 36 and a VL-encoding sequence of SEQ ID NO: 38 or 213;
  b) a VH-encoding sequence of SEQ ID NO: 40 and a VL-encoding sequence of SEQ ID NO: 42;
  c) a VH-encoding sequence of SEQ ID NO: 44 and a VL-encoding sequence of SEQ ID NO: 34;
  d) a VH-encoding sequence of SEQ ID NO: 46 and a VL-encoding sequence of SEQ ID NO: 48 or 214;
  e) a VH-encoding sequence of SEQ ID NO: 50 and a VL-encoding sequence of SEQ ID NO: 52;
  f) a VH-encoding sequence of SEQ ID NO: 40 and a VL-encoding sequence of SEQ ID NO: 54;
  g) a VH-encoding sequence of SEQ ID NO: 56 and a VL-encoding sequence of SEQ ID NO: 58;
  h) a VH-encoding sequence of SEQ ID NO: 60 and a VL-encoding sequence of SEQ ID NO: 62;
  i) a VH-encoding sequence of SEQ ID NO: 64 and a VL-encoding sequence of SEQ ID NO: 66;
  j) a VH-encoding sequence of SEQ ID NO: 68 and a VL-encoding sequence of SEQ ID NO: 70; or
  k) a VH-encoding sequence of SEQ ID NO: 72 and a VL-encoding sequence of SEQ ID NO: 74.

117. A pharmaceutical composition comprising the antibody or antigen-binding fragment of any one of clauses 105 to 114, or the polynucleotide of clause 115 or 116, and a pharmaceutically acceptable carrier.

118. An isolated cell expressing the antibody or antigen-binding fragment of any one of clauses 105 to 114.

119. The cell of clause 118 wherein the cell is a hybridoma.

120. The cell of clause 118 wherein the antibody is recombinantly produced.

121. A method for treating cancer in a subject in need thereof, said method comprising administering to the subject a therapeutically effective amount of the antibody or antigen-binding fragment of any one of clauses 105 to 114 or the polynucleotide of clause 115 or 116, or the pharmaceutical composition of clause 117.

122. The method of clause 121, wherein the antibody or antigen-binding fragment or the pharmaceutical composition is administered for a time sufficient to treat the cancer.

123. A method for inhibiting growth or proliferation of a cancer cell, said method comprising administering to said cell an effective amount of the antibody or antigen-binding fragment of any one of clauses 105 to 114, or the polynucleotide of clause 115 or 116, or the pharmaceutical composition of clause 117, wherein said effective amount is sufficient to inhibit the growth or proliferation of said cancer cell.

124. The method of clause 123, wherein said cancer cell is in a subject and the antibody or antigen-binding fragment or the pharmaceutical composition is administered to the subject.

125. The method of clause 124, wherein said administration is conducted ex vivo.

126. The method of any one of clauses 121-125 wherein the cancer is a hematological cancer.

127. The method of clause 126 wherein the hematological cancer is a CD79b-expressing B cell cancer.

128. The method of clause 127 wherein the CD79b-expressing B cell cancer is a B-cell lymphoma or a non-Hodgkin lymphoma.

129. The method of clause 128 wherein the CD79b-expressing B cell cancer is a diffuse large B-cell lymphoma (DLBCL), mantle cell lymphoma (MCL), marginal zone lymphoma (MZL), or follicular lymphoma (FL).

130. The method of any one of clauses 121-125, wherein the cancer is relapsed, refractory, or malignant cancer, or any combination thereof.

131. The method of any one of clauses 121-130 further comprising administering a second therapeutic agent.

132. The method of clause 131 wherein the second therapeutic agent is a surgery, chemotherapy, androgen deprivation therapy or radiation, or any combination thereof.

133. A method for generating the antibody or antigen-binding fragment of any one of clauses 105 to 114, wherein said method comprises culturing the cell of any one of clauses 118 to 120 and isolating said antibody or antigen-binding fragment.

134. A kit comprising (i) the antibody or antigen-binding fragment of any one of clauses 105 to 114 and/or a polynucleotide of clause 115 or 116 and (ii) packaging for the same.

135. An bispecific antibody, or a bispecific binding fragment thereof, comprising:
a) a first heavy chain (HC1);
b) a light chain (LC); and
c) a second heavy chain (HC2),
wherein
(i) the HC1 and the LC form a first antigen-binding site that specifically binds a first antigen,
(ii) the HC2 comprises a second antigen-binding site that specifically binds a second antigen,
(iii) the HC1 and HC2 each comprise a Fragment crystallizable (Fc) domain comprising a CH2-CH3 domain; and
wherein the first antigen is cluster of differentiation 79B protein (CD79b), and the second antigen is cluster of differentiation 3 (CD3).

136. The bispecific antibody or bispecific binding fragment of any one of clauses 135, wherein the first antigen-binding site comprises an antigen-binding fragment (Fab).

137. The bispecific antibody or bispecific binding fragment of clause 135-136, wherein the second antigen-binding site comprises a single-chain variable fragment (scFv).

138. The bispecific antibody or bispecific binding fragment of any one of clauses 135-137, wherein the Fc domains of HC1 and HC2 comprise one or more different mutations which promote heterodimerization.

139. The bispecific antibody or bispecific binding fragment of clause 138, wherein the Fc domain of the HC1 comprise mutations T366S, L368A and Y407V (EU numbering) and the Fc domain of the HC2 comprises mutation T366W (EU numbering).

140. The bispecific antibody or bispecific binding fragment of clause 138, wherein the Fc domain of the HC2 comprise mutations T366S, L368A and Y407V (EU numbering) and the Fc domain of the HC1 comprises mutation T366W (EU numbering).

141. The bispecific antibody or bispecific binding fragment of any one of clauses 135-140, wherein the Fc domains of HC1 and/or HC2 further comprise one or more mutations which reduce Fc binding to a Fcγ receptor.

142. The bispecific antibody or bispecific binding fragment of clause 141, wherein the Fcγ receptor is FcγRI, FcγRIIA, FcγRIIB, FcγRIIIA, and/or FcγRIIIB.

143. The bispecific antibody or bispecific binding fragment of clause 141 or 142, wherein the Fc domains of HC1 and/or HC2 each comprise one or more mutations selected from L234A, L235A, and D265S (EU numbering).

144. The bispecific antibody or bispecific binding fragment of clause 143, wherein the Fc domains of HC1 and HC2 each comprise mutations L234A, L235A, and D265S (EU numbering).

145. The bispecific antibody or bispecific binding fragment of any one of clauses 135-144, wherein the Fc domains of HC1 or HC2 further comprises one or more mutations which reduce Fc binding to protein A.

146. The bispecific antibody or bispecific binding fragment of clause 145, wherein the Fc domains of HC1 or HC2 comprises mutations H435R and/or Y436F (EU numbering).

147. The bispecific antibody or bispecific binding fragment of clause 146, wherein the Fc domain of HC1 comprises mutations H435R and Y436F (EU numbering).

148. The bispecific antibody or bispecific binding fragment of any one of clauses 135-147, wherein the first antigen-binding site that specifically binds CD79b comprises:
a) a heavy chain complementarity determining region (HCDR) 1, a HCDR2 and a HCDR3 of a heavy chain variable region (VH) of SEQ ID NO: 35 and a light chain complementarity determining region (LCDR) 1, a LCDR2 and a LCDR3 of a light chain variable region (VL) of SEQ ID NO: 37;
b) the HCDR1, the HCDR2 and the HCDR3 of the VH of SEQ ID NO: 39 and the LCDR1, the LCDR2 and the LCDR3 of the VL of SEQ ID NO: 41;
c) the HCDR1, the HCDR2 and the HCDR3 of the VH of SEQ ID NO: 43 and the LCDR1, the LCDR2 and the LCDR3 of the VL of SEQ ID NO: 41;
d) the HCDR1, the HCDR2 and the HCDR3 of the VH of SEQ ID NO: 45 and the LCDR1, the LCDR2 and the LCDR3 of the VL of SEQ ID NO: 47;
e) the HCDR1, the HCDR2 and the HCDR3 of the VH of SEQ ID NO: 49 and the LCDR1, the LCDR2 and the LCDR3 of the VL of SEQ ID NO: 51;
f) the HCDR1, the HCDR2 and the HCDR3 of the VH of SEQ ID NO: 39 and the LCDR1, the LCDR2 and the LCDR3 of the VL of SEQ ID NO: 53;
g) the HCDR1, the HCDR2 and the HCDR3 of the VH of SEQ ID NO: 55 and the LCDR1, the LCDR2 and the LCDR3 of the VL of SEQ ID NO: 57;
h) the HCDR1, the HCDR2 and the HCDR3 of the VH of SEQ ID NO: 59 and the LCDR1, the LCDR2 and the LCDR3 of the VL of SEQ ID NO: 61;
i) the HCDR1, the HCDR2 and the HCDR3 of the VH of SEQ ID NO: 63 and the LCDR1, the LCDR2 and the LCDR3 of the VL of SEQ ID NO: 65;
j) the HCDR1, the HCDR2 and the HCDR3 of the VH of SEQ ID NO: 67 and the LCDR1, the LCDR2 and the LCDR3 of the VL of SEQ ID NO: 69; or
k) the HCDR1, the HCDR2 and the HCDR3 of the VH of SEQ ID NO: 71 and the LCDR1, the LCDR2 and the LCDR3 of the VL of SEQ ID NO: 73.

149. The bispecific antibody or bispecific binding fragment of any one of clauses 135-148, wherein the first antigen-binding site that specifically binds CD79b comprises the HCDR1, the HCDR2, the HCDR3, the LCDR1, the LCDR2 and the LCDR3 of:
a) SEQ ID NOs: 1, 2, 3, 4, 5 and 6, respectively;
b) SEQ ID NOs: 13, 8, 9, 10, 11 and 12, respectively;
c) SEQ ID NOs: 7, 8, 9, 10, 11 and 12, respectively;
d) SEQ ID NOs: 14, 15, 16, 17, 5 and 6, respectively;
e) SEQ ID NOs: 18, 8, 19, 20, 21 and 12, respectively;
f) SEQ ID NOs: 22, 23, 24, 25, 5 and 6, respectively;

g) SEQ ID NOs: 22, 26, 27, 28, 5 and 29, respectively; or
h) SEQ ID NOs: 30, 31, 32, 33, 5 and 6, respectively.
150. The bispecific antibody or bispecific binding fragment of any one of clauses 135-149, wherein the first antigen-binding site that specifically binds CD79b comprises:
a) the VH of SEQ ID NO: 35 and the VL of SEQ ID NO: 37;
b) the VH of SEQ ID NO: 39 and the VL of SEQ ID NO: 41;
c) the VH of SEQ ID NO: 43 and the VL of SEQ ID NO: 41;
d) the VH of SEQ ID NO: 45 and the VL of SEQ ID NO: 47;
e) the VH of SEQ ID NO: 49 and the VL of SEQ ID NO: 51;
f) the VH of SEQ ID NO: 39 and the VL of SEQ ID NO: 53;
g) the VH of SEQ ID NO: 55 and the VL of SEQ ID NO: 57;
h) the VH of SEQ ID NO: 59 and the VL of SEQ ID NO: 61;
i) the VH of SEQ ID NO: 63 and the VL of SEQ ID NO: 65;
j) the VH of SEQ ID NO: 67 and the VL of SEQ ID NO: 69; or
k) the VH of SEQ ID NO: 71 and the VL of SEQ ID NO: 73.
151. The bispecific antibody or bispecific binding fragment of any one of clauses 135-150, wherein the second antigen-binding site that specifically binds CD3 comprises:
a) the HCDR1, the HCDR2 and the HCDR3 of the VH of SEQ ID NO: 97 and the LCDR1, the LCDR2 and the LCDR3 of the VL of SEQ ID NO: 99;
b) the HCDR1, the HCDR2 and the HCDR3 of the VH of SEQ ID NO: 101 and the LCDR1, the LCDR2 and the LCDR3 of the VL of SEQ ID NO: 99;
c) the HCDR1, the HCDR2 and the HCDR3 of the VH of SEQ ID NO: 103 and the LCDR1, the LCDR2 and the LCDR3 of the VL of SEQ ID NO: 99;
d) the HCDR1, the HCDR2 and the HCDR3 of the VH of SEQ ID NO: 105 and the LCDR1, the LCDR2 and the LCDR3 of the VL of SEQ ID NO: 99; or
e) the HCDR1, the HCDR2 and the HCDR3 of the VH of SEQ ID NO: 107 and the LCDR1, the LCDR2 and the LCDR3 of the VL of SEQ ID NO: 109.
152. The bispecific antibody or bispecific binding fragment of any one of clauses 135-151, wherein the second antigen-binding site that specifically binds CD3 comprises the HCDR1, the HCDR2, the HCDR3, the LCDR1, the LCDR2 and the LCDR3 of:
a) SEQ ID NOs: 76, 77, 78, 79, 80 and 81, respectively;
b) SEQ ID NOs: 76, 77, 75, 79, 80 and 81, respectively;
c) SEQ ID NOs: 76, 77, 82, 79, 80 and 81, respectively; or
d) SEQ ID NOs: 83, 84, 85, 86, 87 and 88, respectively.
153. The bispecific antibody or bispecific binding fragment of any one of clauses 135-152, wherein the second or third antigen-binding site that specifically binds CD3 comprises:
a) the VH of SEQ ID NO: 97 and the VL of SEQ ID NO: 99;
b) the VH of SEQ ID NO: 101 and the VL of SEQ ID NO: 99;
c) the VH of SEQ ID NO: 103 and the VL of SEQ ID NO: 99;
d) the VH of SEQ ID NO: 105 and the VL of SEQ ID NO: 99; or
e) the VH of SEQ ID NO: 107 and the VL of SEQ ID NO: 109.
154. The bispecific antibody or bispecific binding fragment of any one of clauses 137-153, wherein the scFv comprises, from the N- to C-terminus, a VH, a linker (L) and a VL (VH-L-VL) or the VL, the linker (L) and the VH (VL-L-VH).
155. The bispecific antibody or bispecific binding fragment of any one of clauses 137-154, wherein the scFv comprises, from the N- to C-terminus, the VL, the linker (L) and the VH (VL-L-VH).
156. The bispecific antibody or bispecific binding fragment of clause 154 or 155, wherein the linker (L) comprises any one of amino acid sequence of SEQ ID NOs: 215-248.
157. The bispecific antibody or bispecific binding fragment of any one of clauses 154-156, wherein the linker (L) comprises an amino acid sequence of GGSEGKSSGSGSESKSTGGS (SEQ ID NO: 215).
158. The bispecific antibody or bispecific antigen-binding fragment of any one of clauses 154-157, wherein the first antigen-binding site specifically binds to residues 30-42 (SEDRYRNPKGSAC; SEQ ID NO: 253), residues 50-52 (PRF), residues 81-86 (EMENP; SEQ ID NO: 254), and/or residues 144-148 (GFSTL; SEQ ID NO: 255) of human CD79b.
159. The bispecific antibody or bispecific antigen-binding fragment of clause 158, wherein the first antigen-binding site specifically binds to CD79b with an affinity of about $1 \times 10^{-11}$-$1 \times 10^{-9}$ M.
160. The bispecific antibody or bispecific antigen-binding fragment of any one of clauses 154-159, wherein the antibody or antigen-binding fragment thereof are of IgG1, IgG2, IgG3, or IgG4 isotype.
161. The bispecific antibody or bispecific antigen-binding fragment of any of clauses 154-160 is an IgG1 isotype.
162. The bispecific antibody or bispecific binding fragment of clause 154, wherein the HC1 comprises the amino acid sequence of SEQ ID NO: 172, 176, or 180.
163. The bispecific antibody or bispecific binding fragment of clause 154 or 162, wherein the LC comprises the amino acid sequence of SEQ ID NO: 174, 178, or 182.
164. The bispecific antibody or bispecific binding fragment of any one of clauses 154, 162-163, wherein
a) the HC1 comprises the amino acid sequence of SEQ ID NO: 172 and the LC comprises the amino acid sequence of SEQ ID NO: 174;
b) the HC1 comprises the amino acid sequence of SEQ ID NO: 176 and the LC comprises the amino acid sequence of SEQ ID NO: 178;
c) the HC1 comprises the amino acid sequence of SEQ ID NO: 180 and the LC comprises the amino acid sequence of SEQ ID NO: 182.
165. The bispecific antibody or bispecific binding fragment of any one of clauses 154, 162-164, wherein the HC2 comprises the amino acid sequence of SEQ ID NO: 164 or 189.
166. The bispecific antibody or bispecific binding fragment of any one of clauses 154, 162-165, wherein
a) the HC1 comprises the amino acid sequence of SEQ ID NO: 172, the LC comprises the amino acid sequence of SEQ ID NO: 174, and the HC2 comprises the amino acid sequence of SEQ ID NO: 164;
b) the HC1 comprises the amino acid sequence of SEQ ID NO: 176, the LC comprises the amino acid sequence of SEQ ID NO: 178, and the HC2 comprises the amino acid sequence of SEQ ID NO: 164;
c) the HC1 comprises the amino acid sequence of SEQ ID NO: 180, the LC comprises the amino acid sequence of SEQ ID NO: 182, and the HC2 comprises the amino acid sequence of SEQ ID NO: 164;
d) the HC1 comprises the amino acid sequence of SEQ ID NO: 172, the LC comprises the amino acid sequence of SEQ ID NO: 174, and the HC2 comprises the amino acid sequence of SEQ ID NO: 189;
e) the HC1 comprises the amino acid sequence of SEQ ID NO: 176, the LC comprises the amino acid sequence of SEQ ID NO: 178, and the HC2 comprises the amino acid sequence of SEQ ID NO: 189; or
f) the HC1 comprises the amino acid sequence of SEQ ID NO: 180, the LC comprises the amino acid sequence of SEQ ID NO: 182, and the HC2 comprises the amino acid sequence of SEQ ID NO: 189.

167. An bispecific antibody, or a bispecific binding fragment thereof, comprising a first antigen-binding site that specifically binds CD79b and a second antigen-binding site that specifically binds CD3.

168. The bispecific antibody or bispecific binding fragment of clause 167, wherein the first antigen-binding site that specifically binds CD79b comprises:
a) the HCDR1, the HCDR2 and the HCDR3 of the VH of SEQ ID NO: 35 and the LCDR1, the LCDR2 and the LCDR3 of the VL of SEQ ID NO: 37;
b) the HCDR1, the HCDR2 and the HCDR3 of the VH of SEQ ID NO: 39 and the LCDR1, the LCDR2 and the LCDR3 of the VL of SEQ ID NO: 41;
c) the HCDR1, the HCDR2 and the HCDR3 of the VH of SEQ ID NO: 43 and the LCDR1, the LCDR2 and the LCDR3 of the VL of SEQ ID NO: 41;
d) the HCDR1, the HCDR2 and the HCDR3 of the VH of SEQ ID NO: 45 and the LCDR1, the LCDR2 and the LCDR3 of the VL of SEQ ID NO: 47;
e) the HCDR1, the HCDR2 and the HCDR3 of the VH of SEQ ID NO: 49 and the LCDR1, the LCDR2 and the LCDR3 of the VL of SEQ ID NO: 51;
f) the HCDR1, the HCDR2 and the HCDR3 of the VH of SEQ ID NO: 39 and the LCDR1, the LCDR2 and the LCDR3 of the VL of SEQ ID NO: 53;
g) the HCDR1, the HCDR2 and the HCDR3 of the VH of SEQ ID NO: 55 and the LCDR1, the LCDR2 and the LCDR3 of the VL of SEQ ID NO: 57;
h) the HCDR1, the HCDR2 and the HCDR3 of the VH of SEQ ID NO: 59 and the LCDR1, the LCDR2 and the LCDR3 of the VL of SEQ ID NO: 61;
i) the HCDR1, the HCDR2 and the HCDR3 of the VH of SEQ ID NO: 63 and the LCDR1, the LCDR2 and the LCDR3 of the VL of SEQ ID NO: 65;
j) the HCDR1, the HCDR2 and the HCDR3 of the VH of SEQ ID NO: 67 and the LCDR1, the LCDR2 and the LCDR3 of the VL of SEQ ID NO: 69; or
k) the HCDR1, the HCDR2 and the HCDR3 of the VH of SEQ ID NO: 71 and the LCDR1, the LCDR2 and the LCDR3 of the VL of SEQ ID NO: 73.

169. The bispecific antibody or bispecific binding fragment of clause 167 or 168, wherein the first antigen-binding site that specifically binds CD79b comprises the HCDR1, the HCDR2, the HCDR3, the LCDR1, the LCDR2 and the LCDR3 of:
a) SEQ ID NOs: 1, 2, 3, 4, 5 and 6, respectively;
b) SEQ ID NOs: 13, 8, 9, 10, 11 and 12, respectively;
c) SEQ ID NOs: 7, 8, 9, 10, 11 and 12, respectively;
d) SEQ ID NOs: 14, 15, 16, 17, 5 and 6, respectively;
e) SEQ ID NOs: 18, 8, 19, 20, 21 and 12, respectively;
f) SEQ ID NOs: 22, 23, 24, 25, 5 and 6, respectively;
g) SEQ ID NOs: 22, 26, 27, 28, 5 and 29, respectively; or
h) SEQ ID NOs: 30, 31, 32, 33, 5 and 6, respectively.

170. The bispecific antibody or bispecific binding fragment of any one of clauses 167-169, wherein the first antigen-binding site that specifically binds CD79b comprises:
a) the VH of SEQ ID NO: 35 and the VL of SEQ ID NO: 37;
b) the VH of SEQ ID NO: 39 and the VL of SEQ ID NO: 41;
c) the VH of SEQ ID NO: 43 and the VL of SEQ ID NO: 41;
d) the VH of SEQ ID NO: 45 and the VL of SEQ ID NO: 47;
e) the VH of SEQ ID NO: 49 and the VL of SEQ ID NO: 51;
f) the VH of SEQ ID NO: 39 and the VL of SEQ ID NO: 53;
g) the VH of SEQ ID NO: 55 and the VL of SEQ ID NO: 57;
h) the VH of SEQ ID NO: 59 and the VL of SEQ ID NO: 61;
i) the VH of SEQ ID NO: 63 and the VL of SEQ ID NO: 65;
j) the VH of SEQ ID NO: 67 and the VL of SEQ ID NO: 69; or
k) the VH of SEQ ID NO: 71 and the VL of SEQ ID NO: 73.

171. The bispecific antibody or bispecific binding fragment of any one of clauses 167-170, wherein the second antigen-binding site that specifically binds CD3 comprises:
a) the HCDR1, the HCDR2 and the HCDR3 of the VH of SEQ ID NO: 97 and the LCDR1, the LCDR2 and the LCDR3 of the VL of SEQ ID NO: 99;
b) the HCDR1, the HCDR2 and the HCDR3 of the VH of SEQ ID NO: 101 and the LCDR1, the LCDR2 and the LCDR3 of the VL of SEQ ID NO: 99;
c) the HCDR1, the HCDR2 and the HCDR3 of the VH of SEQ ID NO: 103 and the LCDR1, the LCDR2 and the LCDR3 of the VL of SEQ ID NO: 99;
d) the HCDR1, the HCDR2 and the HCDR3 of the VH of SEQ ID NO: 105 and the LCDR1, the LCDR2 and the LCDR3 of the VL of SEQ ID NO: 99; or
e) the HCDR1, the HCDR2 and the HCDR3 of the VH of SEQ ID NO: 107 and the LCDR1, the LCDR2 and the LCDR3 of the VL of SEQ ID NO: 109.

172. The bispecific antibody or bispecific binding fragment of any one of clauses 167-171, wherein the second antigen-binding site that specifically binds CD3 comprises:
a) SEQ ID NOs: 76, 77, 78, 79, 80 and 81, respectively;
b) SEQ ID NOs: 76, 77, 75, 79, 80 and 81, respectively;
c) SEQ ID NOs: 76, 77, 82, 79, 80 and 81, respectively; or
d) SEQ ID NOs: 83, 84, 85, 86, 87 and 88, respectively.

173. The bispecific antibody or bispecific binding fragment of any one of clauses 167-172, wherein the second antigen-binding site that specifically binds CD3 comprises
  a) the VH of SEQ ID NO: 97 and the VL of SEQ ID NO: 99;
  b) the VH of SEQ ID NO: 101 and the VL of SEQ ID NO: 99;
  c) the VH of SEQ ID NO: 103 and the VL of SEQ ID NO: 99;
  d) the VH of SEQ ID NO: 105 and the VL of SEQ ID NO: 99; or
  e) the VH of SEQ ID NO: 107 and the VL of SEQ ID NO: 109.
174. The bispecific antibody or bispecific antigen-binding fragment of any one of clauses 167-173, wherein the first antigen-binding site specifically binds to residues 30-42 (SEDRYRNPKGSAC; SEQ ID NO: 253), residues 50-52 (PRF), residues 81-86 (EMENP; SEQ ID NO: 254), and/or residues 144-148 (GFSTL; SEQ ID NO: 255) of human CD79b.
175. The bispecific antibody or bispecific antigen-binding fragment of clause 174, wherein the first antigen-binding site specifically binds to CD79b with an affinity of about $1\times10^{-11}$-$1\times10^{-9}$ M.
176. The bispecific antibody or bispecific antigen-binding fragment of any one of clauses 167 to 175, wherein the antibody or antigen-binding fragment thereof are of IgG1, IgG2, IgG3, or IgG4 isotype.
177. The bispecific antibody or bispecific antigen-binding fragment of any of clauses 167 to 176 is an IgG1 isotype.
178. An synthetic polynucleotide encoding the bispecific antibody or bispecific binding fragment of any one of clauses 167 to 177.
179. The synthetic polynucleotide of clause 178, wherein the polynucleotide comprises a sequence encoding an antigen-binding site that specifically binds CD79b, said sequence comprising
  a) a VH-encoding sequence of SEQ ID NO: 36 and a VL-encoding sequence of SEQ ID NO: 38 or 213;
  b) a VH-encoding sequence of SEQ ID NO: 40 and a VL-encoding sequence of SEQ ID NO: 42;
  c) a VH-encoding sequence of SEQ ID NO: 44 and a VL-encoding sequence of SEQ ID NO: 34;
  d) a VH-encoding sequence of SEQ ID NO: 46 and a VL-encoding sequence of SEQ ID NO: 48 or 214;
  e) a VH-encoding sequence of SEQ ID NO: 50 and a VL-encoding sequence of SEQ ID NO: 52;
  f) a VH-encoding sequence of SEQ ID NO: 40 and a VL-encoding sequence of SEQ ID NO: 54;
  g) a VH-encoding sequence of SEQ ID NO: 56 and a VL-encoding sequence of SEQ ID NO: 58;
  h) a VH-encoding sequence of SEQ ID NO: 60 and a VL-encoding sequence of SEQ ID NO: 62;
  i) a VH-encoding sequence of SEQ ID NO: 64 and a VL-encoding sequence of SEQ ID NO: 66;
  j) a VH-encoding sequence of SEQ ID NO: 68 and a VL-encoding sequence of SEQ ID NO: 70; or
  k) a VH-encoding sequence of SEQ ID NO: 72 and a VL-encoding sequence of SEQ ID NO: 74.
180. The synthetic polynucleotide of clause 178 or 179, wherein the polynucleotide comprises a sequence encoding an antigen-binding site that specifically binds CD3, said sequence comprising
  a) a VH-encoding sequence of SEQ ID NO: 98 and a VL-encoding sequence of SEQ ID NO: 100;
  b) a VH-encoding sequence of SEQ ID NO: 102 and a VL-encoding sequence of SEQ ID NO: 100;
  c) a VH-encoding sequence of SEQ ID NO: 104 and a VL-encoding sequence of SEQ ID NO: 100;
  d) a VH-encoding sequence of SEQ ID NO: 106 and a VL-encoding sequence of SEQ ID NO: 100; or
  e) a VH-encoding sequence of SEQ ID NO: 108 and a VL-encoding sequence of SEQ ID NO: 110.
181. The synthetic polynucleotide of any one of clauses 178-180, wherein the polynucleotide comprises a sequence encoding an HC1 comprising the nucleotide sequence of SEQ ID NO: 173, 177, or 181.
182. The synthetic polynucleotide of any one of clauses 178-181, wherein the polynucleotide comprises a sequence encoding a LC comprising the nucleotide sequence of SEQ ID NO: 175, 179, or 183.
183. The synthetic polynucleotide of any one of clauses 178-182, comprising
  a) an HC1-encoding sequence of SEQ ID NO: 173 and a LC-encoding sequence of SEQ ID NO: 175;
  b) an HC1-encoding sequence of SEQ ID NO: 177 and a LC-encoding sequence of SEQ ID NO: 179; or
  c) an HC1-encoding sequence of SEQ ID NO: 181 and a LC-encoding sequence of SEQ ID NO: 183.
184. The synthetic polynucleotide of any one of clauses 178-183, wherein the polynucleotide comprises a sequence encoding an HC2 comprising the nucleotide sequence of SEQ ID NO: 165 or 190.
185. The synthetic polynucleotide of any one of clauses 178-184, comprising
  a) an HC1-encoding sequence of SEQ ID NO: 173 and a LC-encoding sequence of SEQ ID NO: 175 and an HC2-encoding sequence of SEQ ID NO: 165;
  b) an HC1-encoding sequence of SEQ ID NO: 177 and a LC-encoding sequence of SEQ ID NO: 179 and an HC2-encoding sequence of SEQ ID NO: 165;
  c) an HC1-encoding sequence of SEQ ID NO: 181 and a LC-encoding sequence of SEQ ID NO: 183 and an HC2-encoding sequence of SEQ ID NO: 165;
  d) an HC1-encoding sequence of SEQ ID NO: 173 and a LC-encoding sequence of SEQ ID NO: 175 and an HC2-encoding sequence of SEQ ID NO: 190;
  e) an HC1-encoding sequence of SEQ ID NO: 177 and a LC-encoding sequence of SEQ ID NO: 179 and an HC2-encoding sequence of SEQ ID NO: 190; or
  f) an HC1-encoding sequence of SEQ ID NO: 181 and a LC-encoding sequence of SEQ ID NO: 183 and an HC2-encoding sequence of SEQ ID NO: 190.
186. A pharmaceutical composition comprising the bispecific antibody or bispecific binding fragment of any one of clauses 154 to 177, or the polynucleotide of any one of clauses 178-185, and a pharmaceutically acceptable carrier.
187. An isolated cell expressing the bispecific antibody or bispecific binding fragment of any one of clauses 154 to 177.
188. The cell of clause 187 wherein the cell is a hybridoma.
189. The cell of clause 187 wherein the antibody is recombinantly produced.
190. A method for treating cancer in a subject in need thereof, said method comprising administering to the subject a therapeutically effective amount of the bispecific antibody or bispecific binding fragment of any one of clauses 154 to 177, the polynucleotide of any one of clauses 178-185, or the pharmaceutical composition of clause 186.

191. The method of clause 190, wherein the bispecific antibody or bispecific binding fragment or the pharmaceutical composition is administered for a time sufficient to treat the cancer.
192. A method for inhibiting growth or proliferation of a cancer cell, said method comprising administering to said cell an effective amount of the bispecific antibody or bispecific binding fragment of any one of clauses 154 to 177, the polynucleotide of any one of clauses 178-185, or the pharmaceutical composition of clause 186, wherein said effective amount is sufficient to inhibit the growth or proliferation of said cancer cell.
193. The method of clause 192, wherein said cancer cell is in a subject and the bispecific antibody or bispecific binding fragment or the pharmaceutical composition is administered to the subject.
194. The method of clause 193, wherein said administration is conducted ex vivo.
195. A method of redirecting a T cell to CD79b-expressing cancer cells in a subject in need thereof, said method comprising administering to said subject a therapeutically effective amount of the bispecific antibody or bispecific binding fragment of any one of clauses 154 to 177, the polynucleotide of any one of clauses 178-185, or the pharmaceutical composition of clause 186.
196. The method of clause 195, wherein the said therapeutically effective amount is sufficient to direct said T cell response to said cancer cells.
197. The method of any one of clauses 190-196, wherein the cancer is a hematological cancer.
198. The method of clause 197 wherein the hematological cancer is a CD79b-expressing B cell cancer.
199. The method of clause 198 wherein the CD79b-expressing B cell cancer is a B-cell lymphoma or a non-Hodgkin lymphoma.
200. The method of clause 199 wherein the CD79b-expressing B cell cancer is a diffuse large B-cell lymphoma (DLBCL), mantle cell lymphoma (MCL), marginal zone lymphoma (MZL), or follicular lymphoma (FL).
201. The method of any one of clauses 190-200, wherein the cancer is relapsed, refractory, or malignant cancer, or any combination thereof.
202. The method of any one of clauses 190-201 further comprising administering a second therapeutic agent.
203. The method of clause 202 wherein the second therapeutic agent is a surgery, chemotherapy, androgen deprivation therapy or radiation, or any combination thereof.
204. A method for generating the bispecific antibody or bispecific binding fragment of any one of clauses 154 to 177, wherein said method comprises culturing the cell of any one of clauses 187-189 and isolating said bispecific antibody or bispecific binding fragment.
205. A kit comprising (i) the bispecific antibody or bispecific binding fragment of any one of clauses 154 to 177 and/or a polynucleotide of any one of clauses 178-185, and (ii) packaging for the same.

EXAMPLES

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

Example 1: Target Validation

B-cell non-Hodgkin lymphoma (B-NHL) tumor cells express B-cell-related antigens (i.e., CD20, CD22, CD79b, and CD19) on their cell surfaces at heterogeneous levels. As these antigens are expressed exclusively in the B-cell lineage, and not in other cell lineages or tissues, antibody therapies targeting these antigens have been actively developed in patients with B-NHL.

CD79b is expressed on the surface of B cells from pre-B through memory B-cell stage and, in cancer, is highly expressed in mantle cell lymphoma (MCL), diffuse large B-cell lymphoma (DLBCL), follicular lymphoma (FL), and marginal zone lymphoma (MZL). While CD79b expression is low in chronic lymphocytic leukemia (CLL), increased CD79b surface expression correlates with acalabrutinib resistance in patients with CLL (13).

Figure 9A:
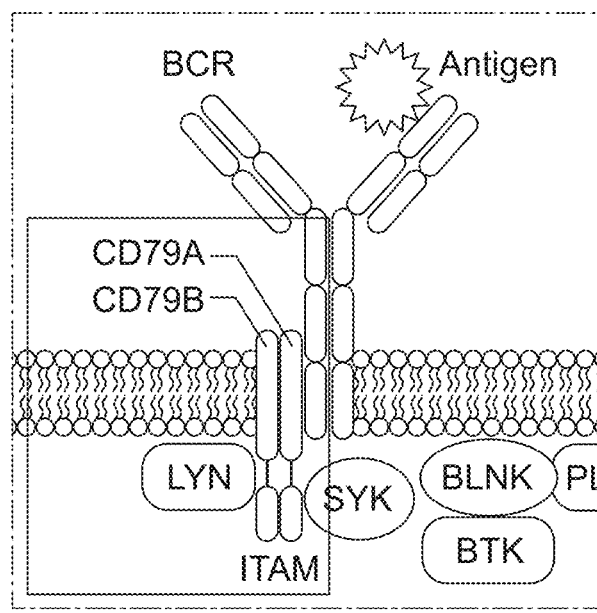
FIGS. 9A-9C. CD79b and CD20 structure.

CD79b (also known as immunoglobulin [Ig]-β or B29) forms a disulfide-linked heterodimer with CD79a (also known as Ig-α or MB-1), and in association with membrane-bound immunoglobulins (mIgs), forms the B-cell receptor (BCR). The CD79 heterodimer constitutes the signaling component of the BCR (FIG. 9A). Upon antigen recognition, specific tyrosine residues within the cytoplasmic immunoreceptor tyrosine-based activation motif (ITAM) domain of CD79a/b are phosphorylated by Src-family tyrosine kinases (e.g., LYN, FYN, BLK), which leads to the recruitment and activation of SH2-containing tyrosine kinases (e.g., Syk) and initiation of the signaling cascades that control B-cell immune responses. BCR signaling regulates a variety of functions in mature B cells, such as signal transduction in response to antigen stimulation, processing, and presentation. CD79b mutations, identified in approximately 30% of activated B cell (ABC) DLBCLs and 3% of germinal center B cell (GCB) DLBCL, while CD79a mutations are less common, ranging from 2.9% to 4% of cases ABC DLBCL (14). CD79b mutations have been described as oncogenic drivers in DLBCL by leading to constitutive activation of the nuclear factor kappa-light-chain-enhancer of activated B cells (NF-κB) pathway. In addition, a large proportion of DLBCL tumors are dependent on CD79b expression for survival, independent of its mutational status (15-17). Therefore, CD79b is an attractive target for a T-cell redirection approach, as the development of resistance to CD79b-targeted agents through antigen loss may be less likely.

Figure 9B:
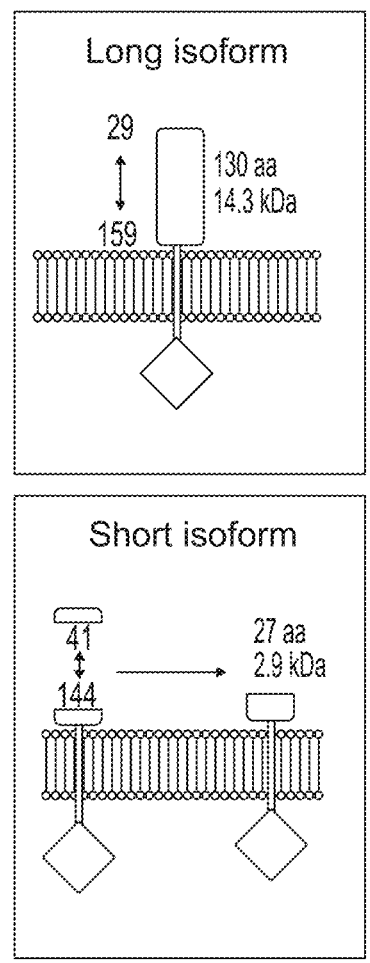

The CD79b protein consists of 229 amino acids characterized by an extracellular domain (ECD) containing a signal peptide, a V-type Ig-like domain, a transmembrane (TM) domain, and an ITAM-containing cytoplasmic domain (FIG. 9A). Two splice isoforms of CD79b exist (FIG. 9B), with the long CD79b isoform being the prominent form in DLBCL. The truncated CD79b isoform lacks a portion of the ECD that contains the cysteine residues involved in the interaction with Igs to stabilize its TM portion and promote BCR surface expression. It is detected at very low expression in DLBCL tumors, and when present in Burkitt lymphomas it is not efficiently transported to the plasma membrane (18). CD79b shares very little homology with CD79a as shown by FASTA analysis (i.e., 29% identity). Moreover, sequence alignment of CD79b orthologues revealed that while the TM and the intracellular domain of CD79b are highly conserved among various species, the sequence homology of the ECD is significantly lower (Table 46).

Figure 9C:
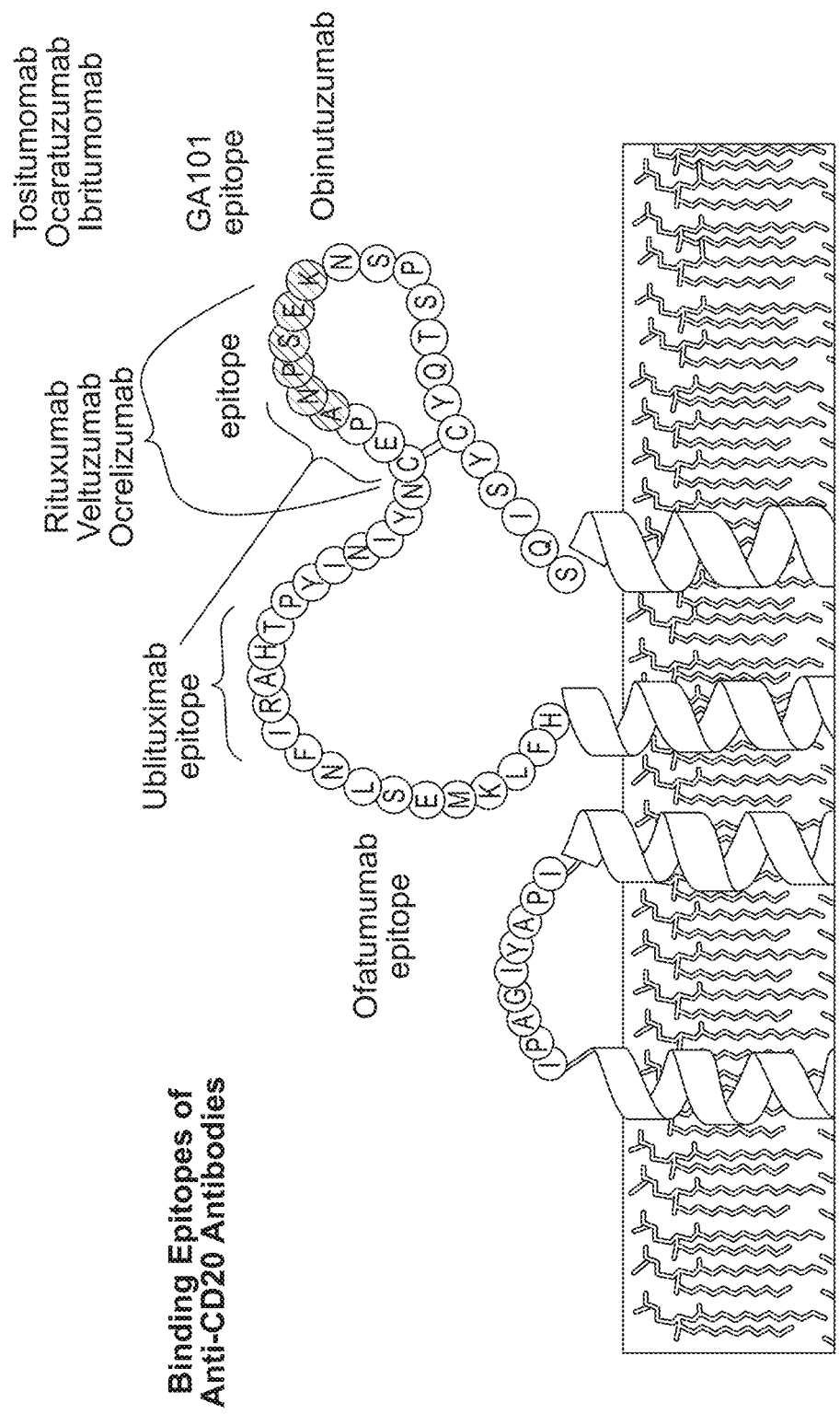

CD20 is a transmembrane protein of the membrane-spanning 4-domain family A (MS4A) protein family involved in B-cell activation and differentiation. CD20 is expressed on all mature B-cells and most B-NHL tumors (21). The CD20 protein consists of 4 hydrophobic TM domains, 1 intracellular domain, and 2 ECDs (large and small loops) with both N- and C-termini residing within the cytosol (FIG. 9C) (22). While 3 different transcripts of CD20 have been identified, they are all translated into identical full-length CD20 protein. Moreover, other alternative transcripts have been identified in malignant B cells alongside CD20 full-length protein, but these truncated forms represent only a very minor fraction of total CD20 protein (<5%; 23). It has been proposed that they might impair binding of anti-CD20 monoclonal antibodies (mAbs) in cellular models (23,24). Epstein-Barr virus (EBV) transformation might modify the CD20 splicing profile and contribute to generation of CD20 variant transcripts (23). Three different phosphorylation patterns of CD20 have been identified, and CD20 phosphorylation was reported to be higher in proliferating malignant than in resting B cells (25). CD20 is organized in the plasma membrane as multimeric molecular complexes with other cell-surface and cytoplasmic proteins involved in BCR-activated calcium entry and contributing to signal transduction and B-cell proliferation (26).

The CD79b and CD20 proteins are specific to the B-cell lineage and their pattern of expression is closely similar to that of some of the most common B-cell antigens, starting from early committed B-cell progenitors (early pre-B stage) until mature B-cell stage. Both proteins are undetectable in terminally differentiated plasma cells.

Figure 10:
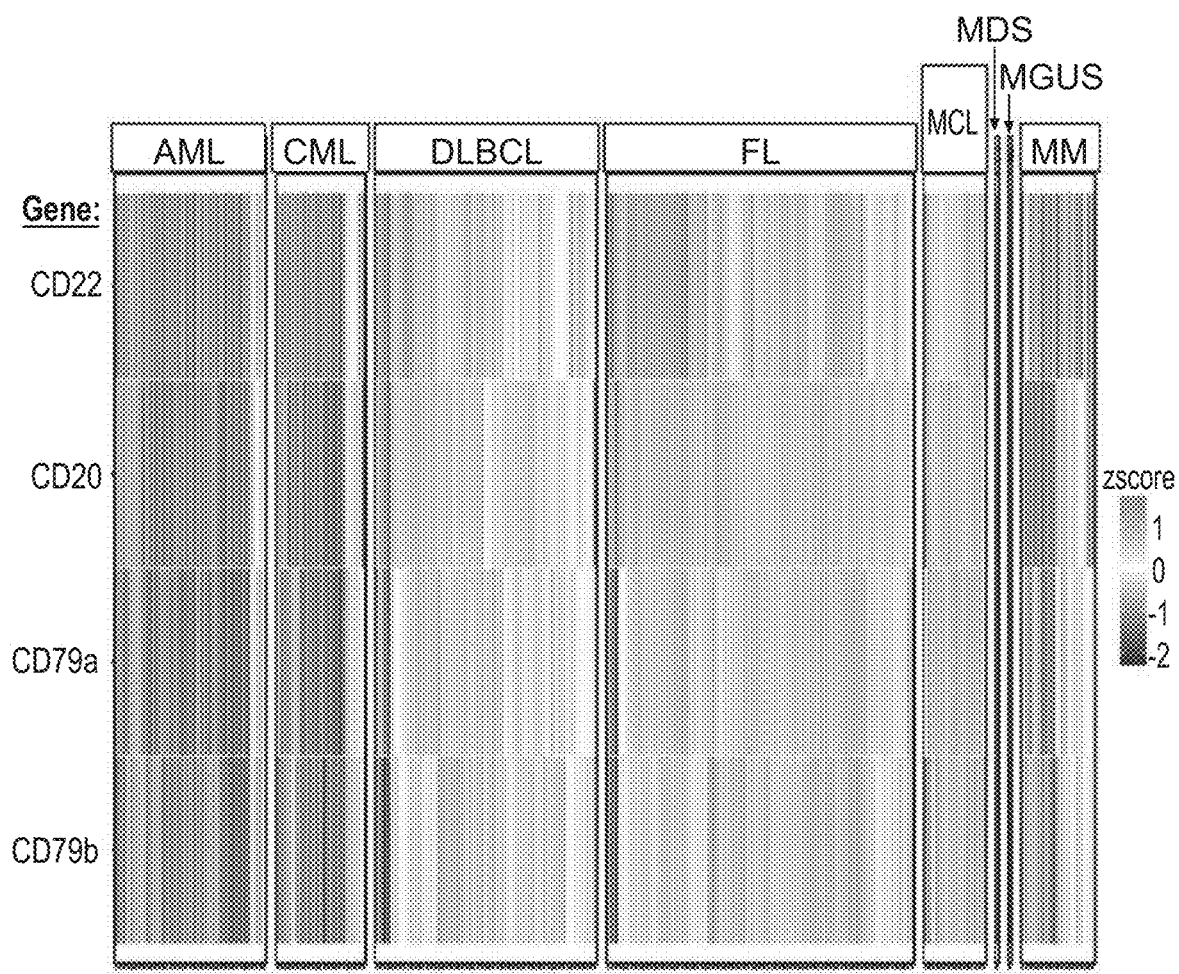
FIG. 10. CD79b and CD20 B-cell marker expression in cancer (mRNA levels). AML, acute myeloid leukemia; CD, cluster of differentiation; CML, chronic myelogenous leukemia; DLBCL, diffused large B cell lymphoma; FL, follicular lymphoma; MCL, mantle cell lymphoma; MDS, myelodysplastic syndrome; MGUS, monoclonal gammopathy of undetermined significance; MM, multiple myeloma. InforMe database was used to quantitate the relative mRNA levels of CD22, MS4A1 (CD20), CD79a, and CD79b across hematological malignancies using the GeneLogic Heme Plus 2.0 data set. mRNA levels are expressed as z score, which describes the expression of a gene relative to the average across all of the samples. The darker the color the lower the z-score (corresponding to lower expression), the lighter the color the higher z-score (corresponding to higher gene expression). Based on this heat map, high expression of CD79b and CD20 was detected in DLBCL, FL, and MCL, but not in AML, MDS, MGUS, CML, MM.

In cancer, CD79b and CD20 were found to be highly expressed in several B-NHL such as DLBCL, FL, and MCL (FIG. 10).

Figure 11A:
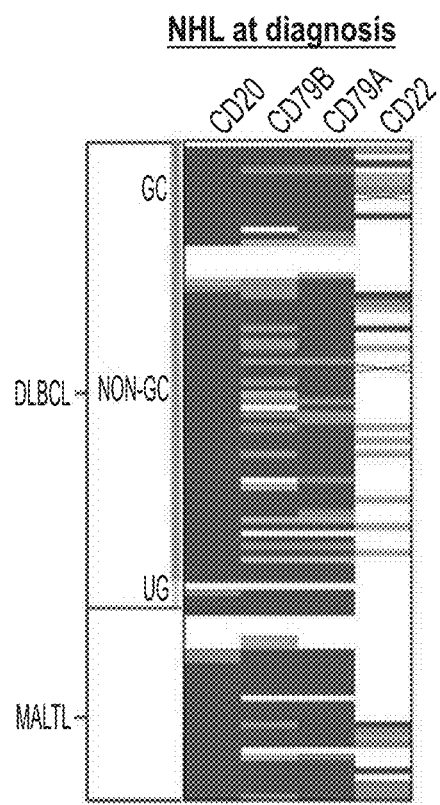
FIGS. 11A-11C. B-cell marker expression in FFPE tumor sections derived from B NHL patients (IHC) and cell lines. CD20, CD79b, CD79a, CD22 IHC staining performed on samples from B-NHL patient at (FIG. 11A) diagnosis or (FIG. 11B) relapse. B-NHL, B-cell non-Hodgkin lymphoma; CD, cluster of differentiation; FFPE, formalin-fixed, paraffin-embedded; GC, germinal center; IHC, immunohistochemistry; MALTL, mucosa-associated lymphoid tissue lymphoma; NHL, non-Hodgkin lymphoma; NON-GC, non-germinal center; R-CHOP, rituximab-cyclophosphamide-hydroxydaunorubicin-oncovin-prednisone/prednisolone regimen; R/R, relapsed/refractory.
Figure 11B:
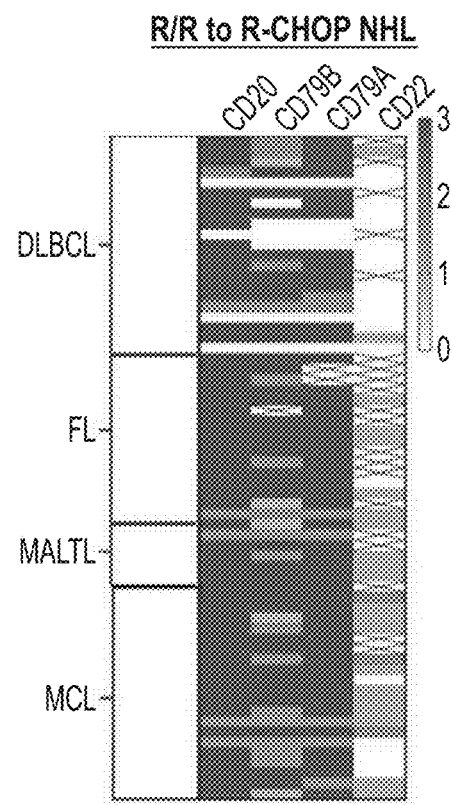
Figure 11C:
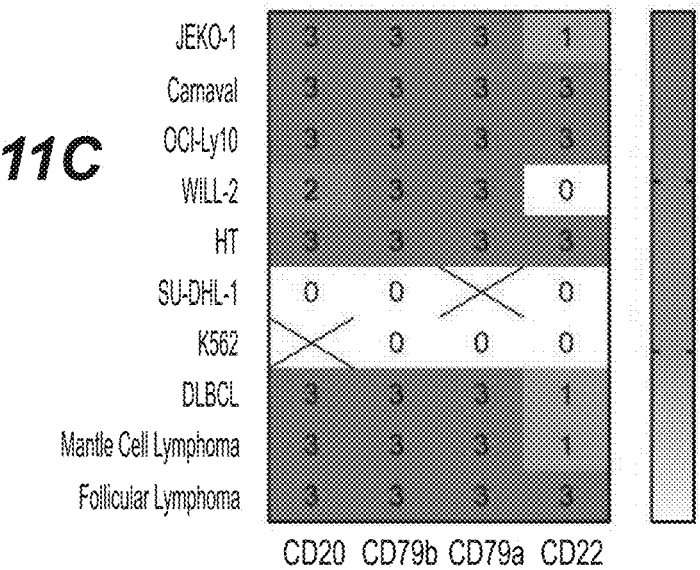

To confirm the expression of the targets of interest at the protein level, CD20, CD79b, CD79a, and CD22 immunohistochemistry (IHC) staining of formalin-fixed, paraffin-embedded (FFPE) tumor sections derived from B-NHL patients collected at diagnosis (FIG. 11A) or patients R/R to rituximab-cyclophosphamide-hydroxydaunorubicin-oncovin-prednisone/prednisolone regimen (R-CHOP; FIG. 11B) was performed. Expression of both CD20 and CD79b was confirmed across samples. Intensity of CD79b expression was more variable as compared to CD20. However, underlying IHC detection limitations of the anti-CD79b antibody should be taken into consideration interpreting these data, especially in cases when CD79a is expressed, which requires CD79b for efficient cell surface expression.

While the IHC results show high CD20 expression across B-NHL, recent reports showed that several CD20 gene mutations resulting in loss of CD20 expression were detected in patient samples at clinical progression on CD20× CD3 bispecifics, suggesting potential target-antigen-dependent disease escape (27). These data overall support the hypothesis that dual targeting should provide a therapeutic benefit for a broad patient population. Given the expression profile of targeted tumor antigens and reported tumor dependency on CD79b expression, combined targeting of CD79b with CD20 might provide an inflection point in the management of B-cell malignancies.

Example 2: Immunization Protocol and V Gene Recovery of CD79b Binders

The following protocol was used to prepare CD79b monoclonal antibodies (mAbs).

AB239

A human immunoglobulin transgenic mouse strain (Ablexis®; AlivaMab, LLC.) was used to develop human CD79b monoclonal antibodies. The Ablexis® mice contained a chimeric human/mouse IgH locus (comprising of 32 human V alleles, 27 human D alleles and 6 human J alleles in natural configuration linked to the mouse $C_H$ locus) together with fully human IgL locus (comprising of 18 Vκ alleles and 5 Jκ alleles and/or 29 $V_\lambda$ alleles and 7 $J_\lambda$ alleles linked to appropriate mouse Cλ or Cκ). Accordingly, the mice contained an inactivated endogenous Ig locus, and in response to immunization, the introduced human heavy and light chain transgenes undergo class switching and somatic mutation to generate high affinity human IgG monoclonal antibodies. The preparation and use of Ablexis®, and the genomic modifications carried by such mice, is described in U.S. Patent Pub. No. 2013/0167256.

When immunized with recombinant human CD79b (rhCD79b), this transgenic mouse produced human IgG antibodies specific to human CD79b.

For HYB650, the immunization strategy in Ablexis® kappa mice included repetitive immunizations multiple sites+intraperitoneal (RIMMS+IP) injections of rhCD79b (R&D Cas 9687-CD Lot: TLS021805A) in CL413 (InvivoGen cat #vac-c1413-5) (days 42, 49, and 56) or Sigma (Sigma, Catalog S6322) (days 72, 79, 86, and 114). On day 129, after sufficient titers were reached, mice were given a final boost of rhCD79b (R&D Cas 9687-CD Lot: TLS021805A)+CL413 (InvivoGen cat #vac-c1413-5)+ CD40 (R&D cat #MAB440; lot: AHY181704A) 7 days prior to sorting. Spleens and mandibular, accessory mandibular, superficial parotid, proper axillary, accessory axillary, sub-iliac, sciatic, popliteal, gastric, pancreaticodoudenal, jejunal, and medial iliac lymph nodes were harvested and antigen-positive B cells were isolated by Fluorescence-activated cell sorting (FACS). Ten 384-well plates of sorted B cell supernatants were screened by cell-based MSD to identify mAbs with specific binding to human CD79b expressing SU-DHL-10 cells (CD79a/b expressing primary cell lines, AG000002270). Positive clones were sequenced, cloned and expressed in small scale.

AB241

A human immunoglobulin transgenic mouse strain (Ablexis®; AlivaMab, LLC.) was used to develop human CD79b monoclonal antibodies. The Ablexis® mice contained a chimeric human/mouse IgH locus (comprising of 32 human V alleles, 27 human D alleles and 6 human J alleles in natural configuration linked to the mouse $C_H$ locus) together with fully human IgL locus (comprising of 18 Vκ alleles and 5 Jκ alleles and/or 29 $V_\lambda$ alleles and 7 $J_\lambda$ alleles linked to appropriate mouse Cλ or Cκ). Accordingly, the mice contained an inactivated endogenous Ig locus, and in response to immunization, the introduced human heavy and light chain transgenes undergo class switching and somatic mutation to generate high affinity human IgG monoclonal antibodies. The preparation and use of Ablexis®, and the genomic modifications carried by such mice, is described in U.S. Patent Pub. No. 2013/0167256.

When immunized with recombinant human CD79b (rhCD79b), this transgenic mouse produced human IgG antibodies specific to human CD79b.

For HYB649, the immunization strategy in Ablexis® kappa mice consisted of RIMMS+IP injections rhCD79b (R&D Cas 9687-CD Lot: TLS021805A) in sigma adjuvant (Sigma, Catalog S6322) (days 0, 8, 13, and 20). On day 31, after sufficient titers were reached, mice were given a final boost of rhCD79b (R&D Cas 9687-CD Lot: TLS021805A)+ anti-msCD40 (R&D cat #MAB440; lot: AHY181704A) 4 days prior to fusion. Spleens and mandibular, accessory mandibular, superficial parotid, proper axillary, accessory axillary, subiliac, sciatic, popliteal, gastric, pancreaticodoudenal, jejunal, and medial iliac lymph nodes were harvested and used to generate hybridomas. Sixty plates of hybridoma supernatants were screened by cell-based MSD to identify mAbs which exhibited binding to rhCD79b. After further confirmatory screenings, hybridoma supernatants from both screens that exhibited binding specific to human CD79b expressing SU-DHL-4 & SU-DHL-10 cells (CD79a/b expressing primary cell lines, AG000002269 & AG000002270, respectively) were sequenced, cloned and expressed in small scale.

V Region Cloning

B-cells were lysed in RealTime Ready Cell Lysis Buffer (Roche) and the B cell lysate was used directly for cDNA synthesis using the Smarter cDNA synthesis kit (Clontech, Mount View, CA). To facilitate cDNA synthesis, oligodT was used to prime reverse transcription of all messenger RNAs followed by "5' capping" with a Smarter IIA oligonucleotide. Subsequent amplification of the VH and VL fragments was performed using a 2-step PCR amplification using 5' primers targeting the Smarter IIA cap and 3' primers targeting consensus regions in CH1. Briefly, each 50 μl PCR reaction consists of 10 μM of forward and reverse primer mixes, 25 μl of PrimeStar Max DNA polymerase premix (Clontech), 2 μl of unpurified cDNA, and 21 μl of double-distilled $H_2O$. The cycling program starts at 94° C. for 3 min, followed by 35 cycles (94° C. for 10 Sec, 55° C. for 1 min, 68° C. for 1 min), and ends at 72° C. for 7 min. The second round PCR was performed with VL and VH 2nd round primers containing 15 bp complementary extensions that "overlap" respective regions in their respective Lonza mother vector (VH and VL). Second round PCR was performed with the following program: 94° C. for 3 min; 35 cycles (94° C. for 10 Sec, 65° C. for 1 min, 72° C. for 1 min), and ends at 72° C. for 7 min. In-Fusion® HD Cloning Kit (Clonetech, U.S.A.) was used for directional cloning of VL gene into Lonza huIgK or Lambda vector and VH gene into Lonza huIgG1 vector. To facilitate In-Fusion® HD Cloning, PCR products were treated with Cloning Enhancer before In-Fusion HD Cloning. Cloning and transformation were performed according to manufacturer's protocol (Clonetech, U.S.A.). Mini-prep DNAs were subjected to Sanger sequencing to confirm that complete V-gene fragments were obtained. The DNA plasmid DNA or glycerol stocks were sequenced at GENEWIZ using pre-designed primers to obtain v-region sequences. The resulting .abi files of V-region sequences were collected and analyzed by a Sanger V-region sequence analysis program. All V genes were cloned into the Lonza-based expression vector carrying the appropriate constant region of the desired human antibody isotype IgG1 AAS. A total of 147 antibodies were successfully cloned and proceeded for further characterization from Ablexis Mice.

Example 3: Expression and Purification of Bispecific CD79b×CD3 and Trispecific CD79b×CD20×CD3 Antibodies The CD79b×CD3 bispecific antibody (bsAb) is an immunoglobulin (Ig) G1 bispecific antibody that can bind simultaneously or individually to the cluster of differentiation (CD) 3 receptor complex on T lymphocytes and to CD79b on B lymphocytes. The CD79b×CD20×CD3 trispecific antibody is an immunoglobulin (Ig) G1 trispecific antibody that can bind simultaneously or individually to the CD3 receptor complex on T lymphocytes, and to the CD20 receptor complex on B lymphocytes and to the CD79b receptor complex on B lymphocytes. The antibody has mutations which reduce Fc binding to a Fcγ receptor and heterodimerization has been enhanced using the knobs-in-holes platform mutations. The trispecific antibody was developed to evaluate the therapeutic potential of dual targeting CD20 and CD79b for T cell redirection. An illustration of an exemplary CD79b×CD20×CD3 antibody is depicted in FIG. 1.

The antibodies were expressed in ExpiCHO-S™ cells (ThermoFisher Scientific; Waltham, MA, Cat #A29127) by transient transfection with purified plasmid DNA following the manufacturer's recommendations. Briefly, ExpiCHO-S™ cells were maintained in suspension in ExpiCHO™ expression medium (ThermoFisher Scientific, Cat #A29100) in an orbital shaking incubator set at 37° C., 8% $CO_2$ and 125 RPM. The cells were passaged and diluted prior to transfection to $6.0 \times 10^6$ cells per ml, maintaining cell viability at 99.0% or better. Transient transfections were done using the ExpiFectamine™ CHO transfection kit (ThermoFisher Scientific, Cat #A29131). For each ml of diluted cells to be transfected, 0.5 microgram of bispecific encoding DNA (HC1:HC2:LC=1:2:2) and 0.5 microgram of pAdVAntage DNA (Promega, Cat #E1711) was used and diluted into OptiPRO™ SFM complexation medium. ExpiFectamine™ CHO reagent was used at a 1:4 ratio (v/v, DNA:reagent) and diluted into OptiPRO™. The diluted DNA and transfection reagent were combined for one minute, allowing DNA/lipid complex formation, and then added to the cells. After overnight incubation, ExpiCHO™ feed and ExpiFectamine™ CHO enhancers were added to the cells as per the manufacturer's Standard protocol. Cells were incubated with orbital shaking (125 rpm) at 37° C. for seven days prior to harvesting the culture broth. The culture supernatant from the transiently transfected ExpiCHO-S™ cells was clarified by centrifugation (30 min, 3000 rcf) followed by filtration (0.2 μm PES membrane, Corning; Corning, NY).

The filtered cell culture supernatant was loaded onto a pre-equilibrated (1×DPBS, pH 7.2) MabSelect Sure Protein A column (GE Healthcare) using an AKTAXpress chromatography system. After loading, the column was washed with 10 column volumes of 1×DPBS, pH7.2. The protein was eluted with 10 column volumes of 0.1 M sodium (Na)-Acetate, pH 3.5. Protein fractions were neutralized immediately by the addition of 2.5 M Tris HC1, pH 7.2 to 20% (v/v) of the elution fraction volume. Peak fractions were pooled and loaded onto a CH1 column (Thermofisher). After loading, the column was washed with 10 column volumes of 1×DPBS, pH7.2. The protein was eluted with 10 column volumes of 0.1 M sodium (Na)-Acetate, pH 3.5. Protein fractions were partially neutralized by the addition of 2.5 M Tris HC1, pH 7.2 to 15% (v/v) of the final volume. The high molecular weight species were removed by preparative size exclusion chromatography (SEC) using Superdex 200 (GE Healthcare). Post sample injection, the column was developed with 1×DPBS and the major peak fractions were pooled, dialyzed into 10 mM Histidine, pH6.5 and filtered (0.2 m).

The concentration of purified protein was determined by absorbance at 280 nm on a Dropsense spectrophotometer. The quality of the purified protein was assessed by cSDS and analytical size exclusion HPLC (Agilent HPLC system).

The endotoxin level was measured using a turbidometric LAL assay (Pyrotell®-T, Associates of Cape Cod; Falmouth, MA).

Example 4: Bispecific and Trispecific Antibodies Binding Characterization Binding of Bispecific CD79×CD3 Antibodies on CD79+ Target Cells The binding affinity of the CD79b binding arm of the CD79×CD3 bispecific molecules were assessed using cell lines that were validated by flow cytometry to have different endogenous expression levels of CD79b on the cell surface, shown in Table 7.

TABLE 7

CD79b Antigen Density of B Lymphoma Cell Lines

| Cell Line | Cell Type | CD79b Antigen Density (Antigen Number/cell) |
| --- | --- | --- |
| HBL-1 | Diffuse large B-cell lymphoma line | 429,649 |
| OCI-LY-10 | Diffuse large B-cell lymphoma line | 38,885 |
| CARNAVAL | Diffuse large B-cell lymphoma line | 98,176 |
| WILL2 | Diffuse large B-cell lymphoma line | 3,824 |

Diffuse large B-cell lymphoma cell lines were incubated for 1 hour with CD79b×CD3 test molecules 79C3B646, 79C3B651, and 79C3B601 (1 uM starting concentration at 1:3 serial dilutions) at 37° C. All cells were washed with BD stain buffer (BD Biosciences; Cat #554657), centrifuged at 1200 RPM for 3 mins, with supernatant discarded. Cells were then stained for 20 minutes at 4° C. with BD stain buffer containing AlexaFluor 647 labeled anti-human IgG secondary antibody (Jackson Immuno; Cat #109-606-098) at a 1:200 dilution along with Aqua Fixable Live/Dead stain (Invitrogen; Cat #L34957) at a 1:400 dilution. All cells were washed with BD stain buffer (BD Biosciences; Cat #554657), centrifuged at 1200 RPM for 3 minutes, with supernatant discarded. Cells were analyzed using Intellicyt (Sartorius) flow cytometer and mean fluorescent intensity (MFI) was generated using Forcyt software (Sartorius). MFI was graphed and EC50 values generated using GraphPad PRISM v.8. Dose response curves were generated by transforming the x axis values using the formula x=lox. Data were then graphed using non-linear regression curve fit analysis "log(agonist) vs. response-variable slope (four parameter)".

All CD79b×CD3 molecules showed good binding on cell lines expressing endogenous CD79b on the cell surface, with the CD79b binding arm of construct 79C3B651 showing the highest binding affinity across all tested cell lines, shown in FIGS. 2A-2D and Table 8.

TABLE 8

CD79bxCD3 Bispecifics Cell Binding EC50 Values

| | HBL-1 EC50 (nM) | OCI-LY10 EC50 (nM) | Carnaval EC50 (nM) | WILL-2 EC50 (nM) |
| --- | --- | --- | --- | --- |
| 79C3B646 | 97 | undetermined | 44 | undetermined |
| 79C3B651 | 15 | undetermined | 12 | undetermined |
| 79C3B601 | 48 | undetermined | 89 | undetermined |

Note:
For OCI-Ly10 and WILL-2 cell lines, antibody binding did not reach the plateau and therefore EC50 value could not be determined. On Table 8, the EC50 column is listed it as "undetermined" for these cell lines.

Binding of Trispecific CD79×CD20×CD3 Antibodies on CD79b+ and CD20+ Target Cells The Binding Affinity of the CD79b Binding Arm of the CD79×CD20×CD3 Trispecific molecules as well as control CD79b×CD3 and Null×CD20×CD3 were assessed using cell lines that were validated by flow cytometry to have different endogenous expression levels of CD79b and CD20 on the cell surface, shown in Table 9.

TABLE 9

CD79b and CD20 Antigen Density of B Lymphoma Cell Lines

| Cell Line | Cell Type | CD79b Antigen Density (Antigen Number/cell) | CD20 Antigen Density (Antigen Number/cell) |
| --- | --- | --- | --- |
| HBL-1 | Diffuse large B-cell lymphoma line | 429,649 | 73,467 |
| OCI-LY-10 | Diffuse large B-cell lymphoma line | 38,885 | 67,352 |
| CARNAVAL | Diffuse large B-cell lymphoma line | 98,176 | 118,789 |
| WILL2 | Diffuse large B-cell lymphoma line | 3,824 | 314 |

Diffuse large B-cell lymphoma cell lines were incubated for 1 hour with CD79b×CD20×CD3 test molecules C923B74, C923B99, and C923B38; CD79×CD3 test molecules 79C3B646, 79C3B651, and 79C3B601 and Null× CD20×CD3 control molecule C923B98 (1 µM starting concentration at 1:3 serial dilutions) at 37° C. All cells were washed with BD stain buffer (BD Biosciences; Cat #554657), centrifuged at 1200 RPM for 3 minutes, with supernatant discarded. Cells were then stained for 20 minutes at 4° C. with BD stain buffer containing AlexaFluor 647 labeled anti-human IgG secondary antibody (Jackson Immuno; Cat #109-606-098) at a 1:200 dilution along with Aqua Fixable Live/Dead stain (Invitrogen; Cat #L34957) at a 1:400 dilution. All cells were washed with BD stain buffer (BD Biosciences; Cat #554657), centrifuged at 1200 RPM for 3 mins, with supernatant discarded. Cells were analyzed using Intellicyt (Sartorius) flow cytometer and mean fluorescent intensity (MFI) was generated using Forcyt software (Sartorius). MFI was graphed and EC50 values generated using GraphPad PRISM v.8. Dose response curves were generated by transforming the x axis values using the formula x=lox. Data was then graphed using non-linear regression curve fit analysis "log(agonist) vs. response-variable slope (four parameter)".

All CD79b×CD20×CD3 molecules showed good binding on cell lines expressing endogenous CD79b and CD20 on the cell surface, with some trispecific constructs showing better binding affinity across cell lines when compared to binding of CD79b×CD3 and CD20×CD3 control molecules, shown in FIGS. 3A-3D and Table 10. The CD79b binding arm of trispecific construct C923B99 showed the highest binding affinity across all tested cell lines, shown in FIGS. 3A-3D and Table 10.

TABLE 10

CD79bxCD20xCD3 Trispecific Cell Binding EC50 Values

| | HBL-1 EC50 (nM) | OCI-LY10 EC50 (nM) | Carnaval EC50 (nM) | WILL-2 EC50 (nM) |
| --- | --- | --- | --- | --- |
| C923B38 | 43 | 12 | 16 | undetermined |
| C923B74 | 52 | 66 | 23 | undetermined |
| C923B99 | 8 | 2 | 6 | undetermined |

TABLE 10-continued

CD79bxCD20xCD3 Trispecific Cell Binding EC50 Values

|  | HBL-1 EC50 (nM) | OCI-LY10 EC50 (nM) | Carnaval EC50 (nM) | WILL-2 EC50 (nM) |
|---|---|---|---|---|
| 79C3B646 | 97 | undetermined | 44 | undetermined |
| 79C3B651 | 15 | undetermined | 12 | undetermined |
| 79C3B601 | 48 | undetermined | 89 | undetermined |
| C923B98 | undetermined | undetermined | Undetermined | undetermined |

Note:
"Undetermined" signifies that antibody binding did not reach the plateau and therefore EC50 value could not be determined.

Kinetic Cell Binding of Bispecific CD79×CD3 Antibodies on CD79+ Target Cells

The binding kinetics of the CD79b binding arm of the CD79×CD3 bispecific molecules were assessed over a time course using cell lines that were validated by flow cytometry to have different endogenous expression levels of CD79b on the cell surface, shown in Table 11.

TABLE 11

CD79b Antigen Density of B Lymphoma Cell Lines

| Cell Line | Cell Type | CD79b Antigen Density (Antigen Number/cell) |
|---|---|---|
| HBL-1 | Diffuse large B-cell lymphoma line | 429,649 |
| OCI-LY10 | Diffuse large B-cell lymphoma line | 38,885 |
| CARNAVAL | Diffuse large B-cell lymphoma line | 98,176 |

Diffuse large B-cell lymphoma cell lines were incubated for 1, 3, 24, and 48 hours with CD79b×CD3 test molecules 79C3B646, 79C3B651, and 79C3B601 (300 nM, 60 nM, 12 nM) at 37° C. At each time point, cells were washed with BD stain buffer (BD Biosciences; Cat #554657), centrifuged at 1200 RPM for 3 mins, with supernatant discarded. Cells were then stained for 30 minutes at 4° C. with BD stain buffer containing AlexaFluor 647 labeled anti-human IgG secondary antibody (Jackson Immuno; Cat #109-606-098) at a 1:200 dilution. All cells were washed with BD stain buffer (BD Biosciences; Cat #554657), centrifuged at 1200 RPM for 3 mins, with supernatant discarded. Cells were resuspended in 50 ul of FACS buffer containing a 1:1000 dilution of Cytox Green viability dye (Invitrogen, Cat #S34860). Cells were analyzed using Intellicyt (Sartorius) flow cytometer and mean fluorescent intensity (MFI) was generated using Forcyt software (Sartorius). MFI was graphed and EC50 values generated using GraphPad PRISM v.8.

All CD79b×CD3 bispecific constructs showed steady CD79b binding kinetics with minimal loss of signal over time, as shown in FIGS. 4A-4I. 79C3B651 showed superior binding kinetics and the least amount of signal loss over time, shown in FIGS. 4A-4I.

Kinetic Cell Binding of Trispecific CD79×CD20×CD3 Antibodies on CD79b+ and CD20+ Target Cells The binding kinetics of the CD79b and CD20 binding arms of the CD79×CD20×CD3 trispecific molecules were assessed over a time course using cell lines that were validated by flow cytometry to have different endogenous expression levels of CD79b and CD20 on the cell surface, shown in Table 12.

TABLE 12

CD79b and CD20 Antigen Density of B Lymphoma Cell Lines

| Cell Line | Cell Type | CD79b Antigen Density (Antigen Number/cell) | CD20 Antigen Density (Antigen Number/cell) |
|---|---|---|---|
| HBL-1 | Diffuse large B-cell lymphoma line | 429,649 | 73,467 |
| OCI-LY-10 | Diffuse large B-cell lymphoma line | 38,885 | 67,352 |
| CARNAVAL | Diffuse large B-cell lymphoma line | 98,176 | 118,789 |

Diffuse large B-cell lymphoma cell lines were incubated for 1, 3, 24, and 48 hours with CD79b×CD20×CD3 test molecules C923B74, C923B99, and C923B38; CD79×CD3 test molecules 79C3B646, 79C3B651, and 79C3B601 and Null×CD20×CD3 control molecule C923B98 (300 nM, 60 nM, 12 nM) at 37° C. At each time point, cells were washed with BD stain buffer (BD Biosciences; Cat #554657), centrifuged at 1200 RPM for 3 mins, with supernatant discarded. Cells were then stained for 30 minutes at 4° C. with BD stain buffer containing AlexaFluor 647 labeled anti-human IgG secondary antibody (Jackson Immuno; Cat #109-606-098) at a 1:200 dilution. All cells were washed with BD stain buffer (BD Biosciences; Cat #554657), centrifuged at 1200 RPM for 3 mins, with supernatant discarded. Cells were resuspended in 50 ul of FACS buffer containing a 1:1000 dilution of Cytox Green viability dye (Invitrogen, Cat #S34860). Cells were analyzed using Intellicyt (Sartorius) flow cytometer and mean fluorescent intensity (MFI) was generated using Forcyt software (Sartorius). MFI was graphed and EC50 values generated using GraphPad PRISM v.8.

All CD79b×CD20×CD3 bispecific constructs showed steady CD79b binding kinetics with minimal loss of signal over time, shown in FIGS. 5A-5I. Trispecific construct C923B99 and bispecific construct 79C3B651, which both have the same CD79b and CD20 binding arms, showed superior binding kinetics and the least amount of signal loss over time, shown in FIGS. 5A-5I.

Binding of Bispecific CD79×CD3 Antibodies and Trispecific CD79×CD20×CD3 Antibodies on Pan T-Cells Binding of the CD3 arm of CD79×CD3 bispecific and CD79b×CD20×CD3 trispecific constructs was assessed using cryo-preserved, negatively selected, primary human CD3+ pan T cells. Primary human CD3+ pan T cells from four different donors were incubated for 1 hour with CD79b×CD20×CD3 test molecules C923B74, C923B99, and C923B38 or CD79×CD3 test molecules 79C3B646, 79C3B651 (1 uM starting concentration at 1:3 serial dilutions) at 37° C. All cells were washed with BD stain buffer (BD Biosciences; Cat #554657), centrifuged at 1200 RPM for 3 mins, with supernatant discarded. Cells were then stained for 20 minutes at 4° C. with BD stain buffer containing AlexaFluor 647 labeled anti-human IgG secondary antibody (Jackson Immuno; Cat #109-606-098) at a 1:300 dilution. All cells were washed with BD stain buffer (BD Biosciences; Cat #554657), centrifuged at 1200 RPM for 3 mins, with supernatant discarded. Cells were resuspended in 50 ul of FACS buffer containing a 1:1000 dilution of Cytox Green viability dye (Invitrogen, Cat #S34860). Cells were analyzed using Intellicyt (Sartorius) flow cytometer and mean fluorescent intensity (MFI) was generated using Forcyt software (Sartorius). MFI was graphed using GraphPad PRISM v.8. Dose response curves were generated by transforming the x axis values using the formula x=lox. Data was then graphed using non-linear regression curve fit analysis "log(agonist) vs. response-variable slope (four parameter)".

All CD79b×CD20×CD3 and CD79b×CD3 molecules showed moderate binding on all donor Pan T cells expressing endogenous CD3 on the cell surface, shown in FIGS. 6A-6D.

Example 5: Functional Characterization: Antagonistic Activity of CD79×CD3 Bispecific and CD79×CD20×CD3 Trispecific Antibodies Bispecific CD79×CD3 and Trispecific CD79×CD20×CD3 Mediated Cytotoxicity Against CD79B⁺ and CD79B⁻ Target Cells mKATE2 DLBCL target cells were maintained in complete RPMI (ThermoFisher, catalog #11875093)1640 media containing 10% heat inactivated fetal bovine serum. Prior to the assay, antibodies were made at 3-fold serial dilutions in the at RPMI 1640 media containing 10% heat inactivated fetal bovine serum, at 4-fold expected final concentration. A volume of 50 µL of medium-diluted bsAb or trispecific Ab in each well of a 96-well plate were further diluted into 200 µL by adding a mix of target and effector cell suspension. The target cell lines were harvested by centrifuge at 400×g for 5 min, washed one time with phenol red-free RPMI 1640 media, counted and suspended in fresh complete phenol red-free RPMI 1640 media at 1×10$^6$ cells/mL. Healthy donor T cells (isolated by CD3-negative selection provided by Discovery Life Sciences) were thawed in complete phenol red-free media (RPMI 1640 media containing 10% heat inactivated fetal bovine serum), counted and suspended in fresh complete phenol red-free RPMI 1640 media at 1×10$^6$ cells/mL. Target cells and T cells were mixed to obtain 5:1 effector to target cell ratio. Cell suspension was added to antibody dilution wells according to plate layout (150 µL/well).

After mixing target and T cells with corresponding bsAb dilution, 80 µL from each well, containing 200 µl with 10000 target and 50000 T cells, were dispensed in a 384 well plate, in duplicate. Plates were sealed using a Breathe-Easy membrane seal. Next, co-cultures were placed in an IncuCyte ZOOM live-content imaging system, and images were automatically acquired in both phase and fluorescence channels every 6 hours for 3 to 6 days with a 4× objective lens (single whole well image). IncuCyte Zoom software was used to detect target cells based on mKATE2 expression using optimized process definition parameters. To measure the amount of target cells/well, the total red area was quantified, and raw values were exported in Excel (Microsoft Office). To quantify cancer cell killing over time, the average values for each replicate were pasted in Prism (GraphPad; version 7 for PC). Expansion indexes (EI) per timepoint were calculated by dividing value at Tx by T0. Growth inhibition (GI) was calculated by normalizing each timepoint to the value of the untreated well average at that timepoint. From the GI values, area under the curve (AUC) values were derived for each condition. After normalizing the AUC to the untreated control (target with effector), antibody concentrations were plotted against the AUC values as a dose response. EC50 values were generated using GraphPad PRISM v.8. Dose response curves were generated by transforming the x axis values using the formula x=lox. Data was then graphed using non-linear regression curve fit analysis "log(agonist) vs. response-variable slope (four parameter)".

CD79b×CD3 bispecific antibodies (79C3B645, 79C3B646, 79C3B601, 79C3B605, 79C3B650, 79C3B651) and CD79b×CD20×CD3 trispecific antibodies (C923B73, C923B74, C923B36, C923B38, C923B99, C923B95) were evaluated for cytotoxicity on HBL1 and OCI-Ly10 cells. IC50 (pM) values are listed in Table 13, Table 14, Table 15, and Table 16.

TABLE 13

HBL-1 killing Incucyte (Average of 2 independent experiments)

| Protein ID | CD79b | CD20 | CD3 | IC50 (pM) |
|---|---|---|---|---|
| 79C3B645 | CD9B330 | NA | CD3B2089 | 7189.0 |
| 79C3B646 | CD9B330 | NA | CD3B2030 | 257.4 |
| C923B73 | CD9B330 | C20B22 | CD3B2089 | 6805.0 |
| C923B74 | CD9B330 | C20B22 | CD3B2030 | 346.3 |
| 79C3B605 | CD9B374 | NA | CD3B2089 | 29549.0 |
| 79C3B601 | CD9B374 | NA | CD3B2030 | 203.9 |
| C923B36 | CD9B374 | C20B22 | CD3B2089 | 31040.0 |
| C923B38 | CD9B374 | C20B22 | CD3B2030 | 301.2 |
| 79C3B650 | CD9B643 | NA | CD3B2089 | 43314.0 |
| 79C3B651 | CD9B643 | NA | CD3B2030 | 32.5 |
| C923B95 | CD9B643 | C20B22 | CD3B2089 | 4891.0 |
| C923B99 | CD9B643 | C20B22 | CD3B2030 | 69.2 |

NA = Not Applicable

TABLE 14

OCI-Ly10 killing Incucyte (Average of 2 independent experiments)

| Protein ID | CD79b | CD20 | CD3 | IC50 (nM) |
|---|---|---|---|---|
| 79C3B645 | CD9B330 | NA | CD3B2089 | 18.0 |
| 79C3B646 | CD9B330 | NA | CD3B2030 | 18.3 |
| C923B73 | CD9B330 | C20B22 | CD3B2089 | 132.4 |
| C923B74 | CD9B330 | C20B22 | CD3B2030 | 25.6 |
| 79C3B605 | CD9B374 | NA | CD3B2089 | 54.3 |
| 79C3B601 | CD9B374 | NA | CD3B2030 | 11.7 |
| C923B36 | CD9B374 | C20B22 | CD3B2089 | 42.0 |
| C923B38 | CD9B374 | C20B22 | CD3B2030 | 8.0 |
| 79C3B650 | CD9B643 | NA | CD3B2089 | 7.0 |
| 79C3B651 | CD9B643 | NA | CD3B2030 | 4.7 |
| C923B95 | CD9B643 | C20B22 | CD3B2089 | 14.8 |
| C923B99 | CD9B643 | C20B22 | CD3B2030 | 5.6 |

NA = Not Applicable

TABLE 15

CARNAVAL killing (Incucyte)

| Protein ID | CD79b | CD20 | CD3 | IC50 (nM) |
|---|---|---|---|---|
| 79C3B646 | CD9B330 | NA | CD3B2030 | 1.393 |
| C923B74 | CD9B330 | C20B22 | CD3B2030 | 0.741 |
| 79C3B601 | CD9B374 | NA | CD3B2030 | 1.645 |
| C923B38 | CD9B374 | C20B22 | CD3B2030 | 0.465 |
| C923B99 | CD9B643 | C20B22 | CD3B2030 | 0.285 |

TABLE 16

Daudi killing (Incucyte)

| Protein ID | CD79b | CD20 | CD3 | IC50 (nM) |
|---|---|---|---|---|
| 79C3B646 | CD9B330 | NA | CD3B2030 | 0.597 |
| C923B74 | CD9B330 | C20B22 | CD3B2030 | 0.100 |
| 79C3B601 | CD9B374 | NA | CD3B2030 | 0.406 |
| C923B38 | CD9B374 | C20B22 | CD3B2030 | 0.071 |
| C923B99 | CD9B643 | C20B22 | CD3B2030 | <Conc tested |

NA = Not Applicable

FACS T Cell Killing Data on Panel of Target Positive (CD79b+ and CD20+) and Target Negative (CD79B− and CD20−) Cell Lines Functional activity of the CD79b×CD3 bispecific and CD79b×CD20×CD3 trispecific constructs was assessed at 72 hr time point in an in vitro T cell killing assay by flow cytometry using cell lines that were validated by flow cytometry to have different endogenous expression levels of CD79b and CD20 on the cell surface, shown in Table 17.

TABLE 17

CD79b and CD20 Antigen Density of B Lymphoma Cell Lines

| Cell Line | Cell Type | CD79b Antigen Density (Antigen Number/cell) | CD20 Antigen Density (Antigen Number/cell) |
|---|---|---|---|
| HBL-1 | Diffuse large B-cell lymphoma line | 429,649 | 73,467 |
| OCI-LY10 | Diffuse large B-cell lymphoma line | 38,885 | 67,352 |
| CARNAVAL | Diffuse large B-cell lymphoma line | 98,176 | 118,789 |
| K562 | Chronic myelogenous leukemia | 0 | 0 |
| HEL | Erythroleukemia | 0 | 0 |

Target cancer cells were maintained in complete RPMI 1640 (ThermoFisher, catalog #11875093) media containing 10% heat inactivated fetal bovine serum. Prior to the assay, antibodies were made at 3-fold serial dilutions in RPMI 1640 media containing 10% heat inactivated fetal bovine serum, at 4-fold expected final concentration. A volume of 50 µL of medium-diluted bispecific or trispecific Ab in each well of a 96-well plate were further diluted into 200 µL by adding a mix of target and effector cell suspension. The target cell lines were harvested by centrifuge at 400×g for 5 min, washed one time with RPMI 1640 media. Target cancer cells were stain targets with CellTrace CFSE (ThermoFisher; Cat #: C34554) diluted 1/5000. Healthy donor T cells (isolated by CD3-negative selection provided by Discovery Life Sciences) were thawed in complete media (RPMI 1640 media containing 10% heat inactivated fetal bovine serum), counted and suspended in fresh complete phenol red-free RPMI 1640 media at $1\times10^6$ cells/mL. Target cells and T cells were mixed to obtain 5:1 effector to target cell ratio. Cell suspension was added to plate layout (150 µL/well). Cells were incubated for 72 hours with CD79b×CD3 or CD79b×CD20× CD3 test molecules (100 nM starting concentration at 1:3 serial dilutions) at 37° C. All cells were washed with BD stain buffer (BD Biosciences; Cat #554657), centrifuged at 1200 RPM for 3 minutes, with supernatant discarded. Cells were stained for 15 minutes at room temperature with Fixable Live/Dead stain (ThermoFisher; Cat #65-0865-14) at a 1:1000 dilution. All cells were washed with BD stain buffer (BD Biosciences; Cat #554657), centrifuged at 1200 RPM for 3 mins, with supernatant discarded. Cells were then stained for 30 minutes at 4° C. with BD stain buffer containing flow panel antibodies (Table 18), antibodies amount added as listed in the table. All cells were washed with BD stain buffer (BD Biosciences; Cat #554657), centrifuged at 1200 RPM for 3 mins, with supernatant discarded. Cells were analyzed using FACS Lyric (BD) flow cytometer and percent of cancer cell killing was generated using Cytobank. Percent of cancer cell killing was graphed and 9C50 values generated using GraphPad PRISM v.8. Dose response curves were generated by transforming the x axis values using the formula x=1ox. Data was then graphed using non-linear regression curve fit analysis "log(inhibitor) vs. response-variable slope (four parameter)".

TABLE 18

Flow Panel Antibodies for T cell killing Assay

| Antibody Name | Conjugated Fluorophore | Vendor | Catalog Number | LOT Number: | Amount added per well (µl) |
|---|---|---|---|---|---|
| CD4 | V500 | BD Biosciences | 560768 | 9340575 | 2 µ/well |
| CD8 | PerCPCy5.5 | BD Biosciences | 560662 | 9290508 | 2 µl/well |
| CD69 | PE | BD Biosciences | 560968 | 9049603 | 10 µl/well |
| CD25 | BV421 | BD Biosciences | 562443 | 10302 | 2 µl/well |

Figure 7A:
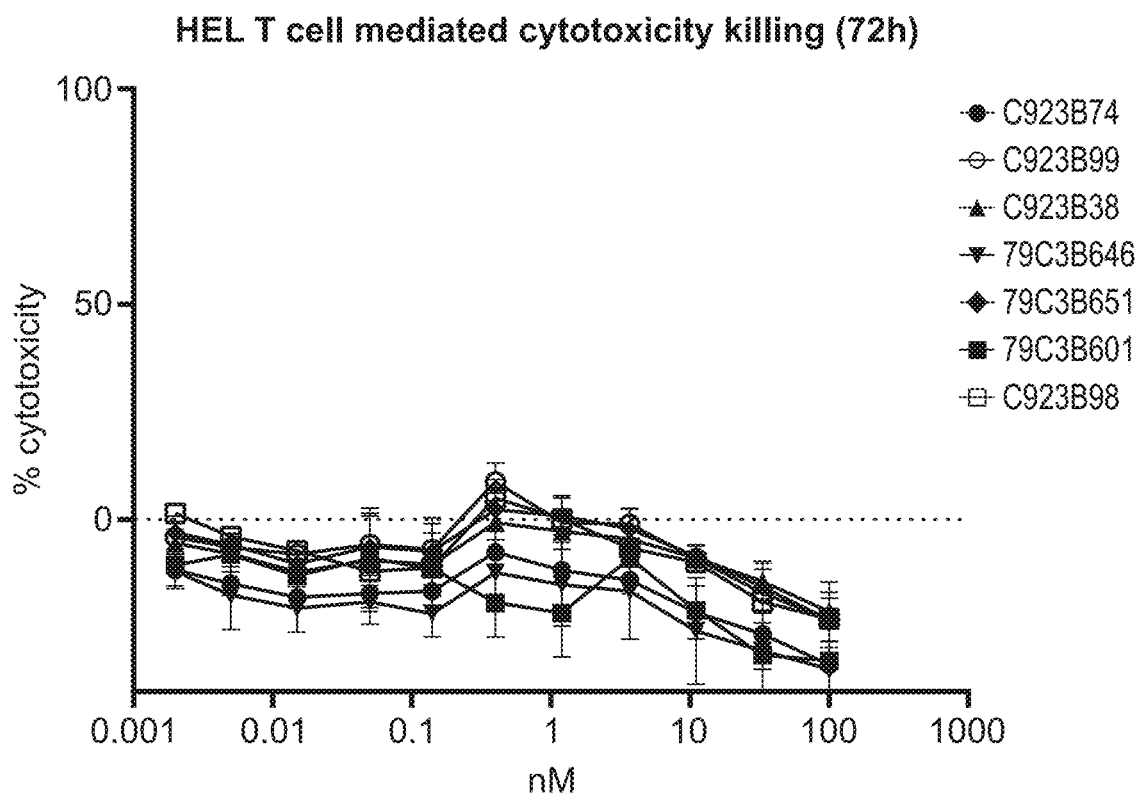
FIGS. 7A-7B. T cell cytotoxicity of CD79b×CD20×CD3 trispecific antibodies and CD79b×CD3 bispecific antibodies. Cytotoxicity of the selected antibodies in the HEL T-cell line (FIG. 7A). Cytotoxicity of the selected antibodies in the K562 T-cell line (FIG. 7B). Shaded circles correspond to the trispecific antibody C923B74; clear circles correspond to the trispecific antibody C923B99; triangles correspond to the trispecific antibody C923B38; inverted triangles correspond to the 79C3B646 bsAb; diamonds correspond to 79C3B651 bsAb; black squares correspond to the 79C3B601 bsAb; and white squares correspond to C923B98 bsAb.
Figure 7B:
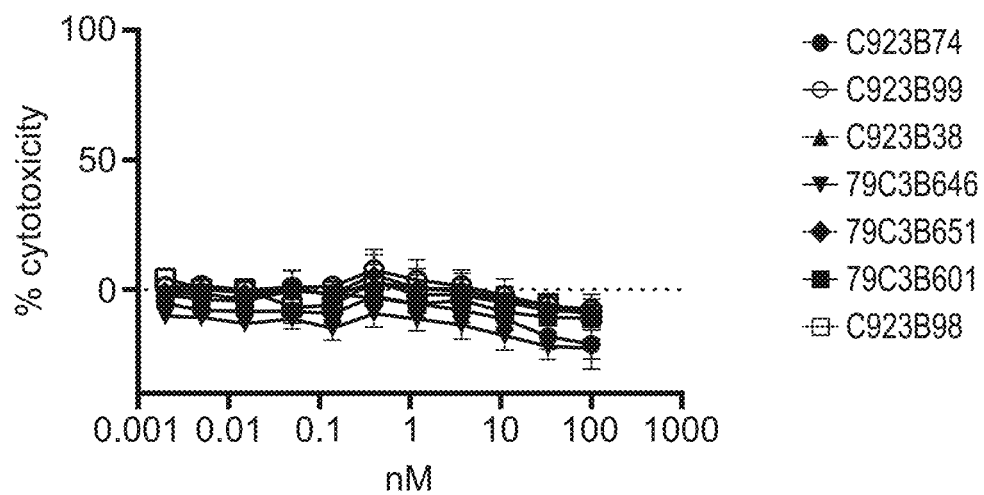

CD79b×CD20×CD3 trispecific mediated more potent cytotoxicity as compared to bispecific constructs in CD79b- and CD20-target positive cell lines. >C50 (pM) values are listed in Table 19. No killing has been observed in target negative cell lines (FIG. 7A-7B).

TABLE 19

Killing of target positive (CARNAVAL, OCI-Ly10) cell lines (FACS).

| Protein ID | CD79b | CD20 | CD3 | CARNAVAL IC50 (nM)* | HBL-1 IC50 (nM) | OCI-LY10 IC50 (nM)** |
|---|---|---|---|---|---|---|
| 79C3B646 | CD9B330 | NA | CD3B2030 | 0.29 | 0.73 | >100 nM |
| C923B74 | CD9B330 | C20B22 | CD3B2030 | 0.35 | 2.42 | 24.19 |
| 79C3B601 | CD9B374 | NA | CD3B2030 | NA | 2.86 | >100 nM |
| C923B38 | CD9B374 | C20B22 | CD3B2030 | 0.33 | 2.71 | 48.59 |
| 79C3B651 | CD9B643 | NA | CD3B2030 | 0.25 | 2.20 | >100 nM |
| C923B99 | CD9B643 | C20B22 | CD3B2030 | 0.17 | 1.68 | 16.95 |

NA = not applicable
*average values of T cell mediated killing from 3 independent T cell donors
**average values of T cell mediated killing from 4 independent T cell donors Bispecific CD79b×CD3 Mediated Cytotoxicity Against Autologous B-Cells Functional activity of the CD79b×CD3 bispecific constructs was assessed in an in vitro autologous B cell depletion assay. This functional assay utilizes PBMCs to focus on the killing of primary B cells as well as T cell activation on donor matched primary cells. Cryo-preserved PBMCs from 3 different human donors were incubated for 72 hours with CD79b×CD3 test molecules 79C3B646, 79C3B651, and 79C3B601 (300 nM starting concentration at 1:3 serial dilutions) at 37° C. All cells were washed with BD stain buffer (BD Biosciences; Cat #554657), centrifuged at 1200 RPM for 3 minutes, with supernatant discarded. Cells were stained for 10 minutes at room temperature with BD stain buffer containing Fc blocking agent (Accurate Chemical and Scientific Corp; Cat #NB309) and Near IR Fixable Live/Dead stain (Invitrogen; Cat #L10119) at a 1:400 dilution. All cells were washed with BD stain buffer (BD Biosciences; Cat #554657), centrifuged at 1200 RPM for 3 mins, with supernatant discarded. Cells were then stained for 30 minutes at 4° C. with BD stain buffer containing flow panel antibodies (Table 20) at a 1:100 dilution. All cells were washed with BD stain buffer (BD Biosciences; Cat #554657), centrifuged at 1200 RPM for 3 mins, with supernatant discarded. Cells were analyzed using Intellicyt (Sartorius) flow cytometer and mean fluorescent intensity (MFI) was generated using Forcyt software (Sartorius). MFI was graphed and EC50 values generated using GraphPad PRISM v.8. Dose response curves were generated by transforming the x axis values using the formula x=lox. Data was then graphed using non-linear regression curve fit analysis "log (agonist) vs. response-variable slope (four parameter)".

TABLE 20

Flow Panel Antibodies for Autologous B Cell Depletion Assay

| Antibody Name | Conjugated Fluorophore | Vendor | Catalog Number |
|---|---|---|---|
| Anti-human CD25 | BV650 | BD Biosciences | 563719 |
| Anti-Human CD4 | BV510 | Biolegend | 317444 |
| Anti-Human CD8 | PE-Cy7 | Biolegend | 301012 |
| Anti-Human CD20 | PE | Biolegend | 302306 |
| Anti-Human CD11c | AF647 | BD Biosciences | 565911 |
| Anti-Human CD2 | BV605 | BD Biosciences | 740391 |

Figure 8A:
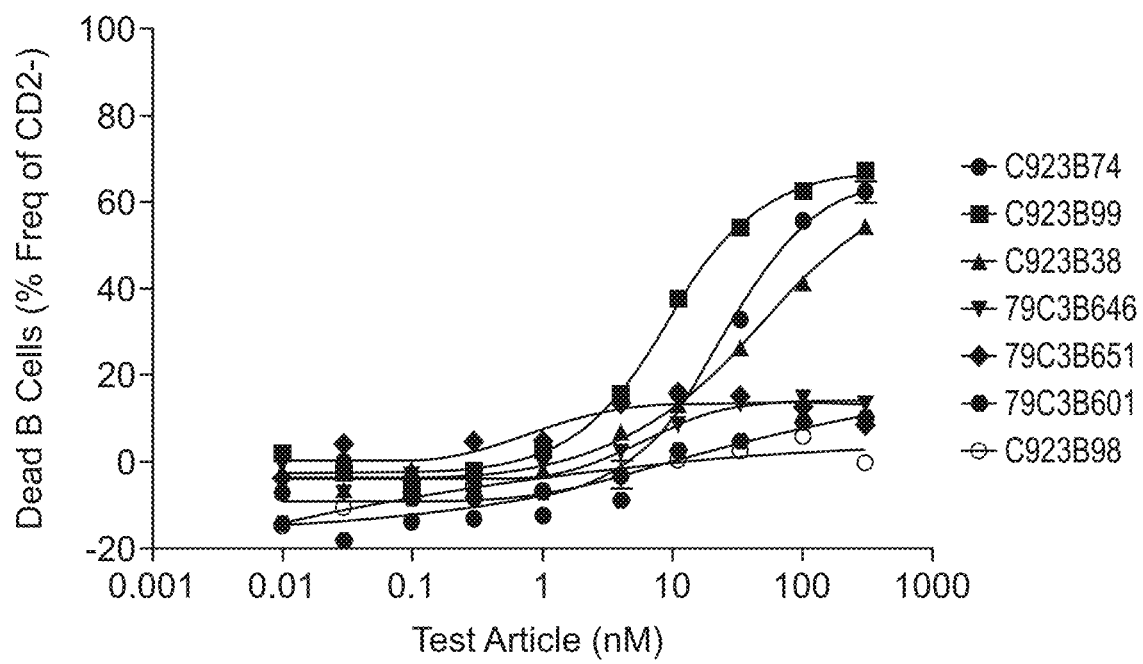

CD79b×CD3 bispecific constructs showed a maximum drug mediated cytotoxicity of 20 percent with low levels of $CD4^+$ and $CD8^+$ T cell activation as demonstrated by CD25 expression on these T cell subsets, as shown in FIGS. 8A-8C. The CD79b×CD20×CD3 trispecific has a synergistic effect on drug mediated cytotoxicity when compared to control molecules as shown in Table 21.

Example 6: Biophysical Characterization

Binding Affinity by SPR

General Protocol for SPR Affinity Assessment: Affinity assessment of the bispecific and trispecific constructs against human CD79b were measured using recombinantly expressed extracellular domain of CD79b short and long isoforms (CD9W7.001 and CD9W8.001, respectively) by Surface Plasmon Resonance (SPR) using a Biacore 8k SPR system (Biacore) at 25° C. in HBSP+ buffer. Cross-reactivity of the same antibody panel was also assessed against cyno and mouse antigens (CD9W1.001 and CD9W105.001, respectively). Briefly, a C1 sensor chip was immobilized with anti-human Fc (target immobilization levels of >400 RU) using vendor recommended amino coupling protocol. The test antibodies were captured through immobilized anti-Fc and was followed by the injection of different CD79b constructs at different concentration series (human CD79b short and long isoforms: 30 nM-0.37 nM at 3-fold dilutions; cyno and mouse CD79b: 3000 nM-37 nM at 3-fold dilutions). The association and dissociation phases were measured for 2 or 3 minutes and 30 minutes, respectively. Binding of the trispecifics (C923B168 and C923B169) to CD3 was tested by injecting CD3W220.001 at 100 nM-1.23 nM at 3-fold dilutions, with association and dissociation phases were measured for 3 min and 15 min, respectively (CD79b-00478).

The raw binding sensorgrams were processed using Biacore Insight software (Biacore) by double-referencing and the processed sensorgrams were analyzed for cross-reactivity and fitted to a 1:1 Langmuir model to obtain on-rates, off-rates and affinities.

SPR Binding Results: As shown in Table 22 and Table 23, 5he bispecific and trispecific antibodies bound to the human CD79b long isoform (hu CD79b long) with affinities from 0.02-0.06 nM, and to the CD79b short isoform (hu CD79b short) with affinities between 0.27-0.64 nM. The antibody panel showed very poor cross-reactivity to cyno CD79b (KD estimated >3000 nM) or did not bind to mouse CD79b. C923B168 binds recombinant CD3 antigen with an affinity of 0.5 nM. No quantitative kinetics/affinities were reported for those with complex kinetic binding profiles using the specified antigens, as noted in the summary tables below.

TABLE 21

CD79b × CD20 × CD3 EC50 Values and Maximum Cytotoxicity

| Construct Name | CD79b Arm | CD20 Arm | CD3 Arm | Donor 1 | | Donor 2 | | Donor 3 | |
|---|---|---|---|---|---|---|---|---|---|
| | | | | EC50 (nM) | $C_{max}$ | EC50 (nM) | $C_{max}$ | EC50 (nM) | $C_{max}$ |
| C923B74 | B330-Fab | C20B22 scFv | CD3B2030 | 78 | 34% | 23 | 66% | UD* | 40% |
| 79C3B646 | N/A | | CD3B2030 | 40 | 9% | 6 | 14% | 8 | 35% |
| C23B98 | N/A | C20B22 scFv | CD3B2030 | UD* | 11% | UD* | 5% | 88 | 52% |
| C923B99 | B543-Fab | C20B22 scFv | CD3B2030 | UD* | 35% | 9 | 67% | 23 | 66% |
| 79C3B651 | N/A | | CD3B2030 | UD* | 5% | UD* | 13% | 17 | 34% |
| C23B98 | N/A | C20B22 scFv | CD3B2030 | UD* | 11% | UD* | 5% | 88 | 52% |
| C923B38 | B374-Fab | C20B22 scFv | CD3B2030 | 1 | 24% | 50 | 60% | UD* | 50% |
| 79C3B601 | N/A | | CD3B2030 | UD* | 10% | UD* | 10% | 20 | 32% |
| C23B98 | N/A | C20B22 scFv | CD3B2030 | UD* | 11% | UD* | 5% | 88 | 52% |

*Undetermined

TABLE 22

Binding affinities for bispecific antibody constructs

| Name | KD to hu CD79b long (M) | KD to hu CD79b short (M) | KD to hu CD3 (M) |
|---|---|---|---|
| 79C3B601 | 4.6E−11 | 5.6E−10 | n.d** |
| 79C3B646 | 2.2E−11 | 5.8E−10 | n.d** |
| 79C3B651 | 5.2E−11 | 3.5E−10 | n.d** |
| 79C3B605 | n.d* | n.d* | n.d** |
| 79C3B645 | n.d* | n.d* | n.d** |
| 79C3B650 | n.d* | n.d* | n.d** |

*samples not submitted for SPR binding analysis
**Affinities for CD3 not determined due to complex SPR binding profiles observed for Cris7b derived CD3 antibodies (historically observed results).

TABLE 23

Binding affinities for trispecific antibody constructs

| Name | KD to hu CD79b long (M) | KD to hu CD79b short (M) | KD to hu CD20 (M) | KD to hu CD3 (M) |
|---|---|---|---|---|
| C923B38 | 6.5E−11 | 6.4E−10 | n.d** | n.d** |
| C923B74 | 2.3E−11 | 3.9E−10 | n.d** | n.d** |
| C923B99 | 4.0E−11 | 2.7E−10 | n.d** | n.d** |
| C923B36 | n.d* | n.d* | n.d** | n.d** |
| C923B73 | n.d* | n.d* | n.d** | n.d** |
| C923B95 | n.d* | n.d* | n.d** | n.d** |
| C923B168 | 1.92E−10 | n.d* | n.d** | 4.96E−10 |
| C923B169 | 1.64E−10 | n.d* | n.d** | n.d** |

*samples not submitted for SPR binding analysis
**Affinities for CD20 or CD3 not determined due to SPR constraints with CD20 nanodiscs or complex binding profiles observed for Cris7b derived CD3 antibodies (historically observed results)

Binding Epitope by HDX-MS

The CD79b epitopes bound by trispecific molecules CD9B374 and CD9B643 were mapped by Hydrogen Deuterium Exchange Mass Spectrometry (HDX-MS) according to the following protocol.

General Procedure for HDX-MS Data Acquisition. HDX-MS sample preparation was performed with automated HDx system (LEAP Technologies, Morrisville, NC). The columns and pump were: protease, protease type XIII (protease from *Aspergillus saitoi*, type XIII)/pepsin column (w/w, 1:1; 2.1×30 mm) (NovaBioAssays Inc., Woburn, MA); trap, ACQUITY UPLC BEH C18 VanGuard Pre-column (2.1×5 mm) (Waters, Milford, MA), analytical, Accucore C18 (2.1× 100 mm) (Thermo Fisher Scientific, Waltham, MA); and LC pump, VH-P10-A (Thermo Fisher Scientific). The loading pump (from the protease column to the trap column) was set at 600 µL/min with 0.1% aqueous formic acid. The gradient pump (from the trap column to the analytical column) was set from 9% to 35% acetonitrile in 0.1% aqueous formic acid in 20 min at 100 µL/min.

MS Data Acquisition. Mass spectrometric analyses were carried out using an LTQ™ Orbitrap Fusion Lumos mass spectrometer (Thermo Fisher Scientific) with the capillary temperature at 275° C., resolution 120,000, and mass range (m/z) 300-1,800.

HDX-MS Data Extraction. BioPharma Finder 3.0 (Thermo Fisher Scientific) was used for the peptide identification of non-deuterated samples prior to the HDX experiments. HDExaminer version 2.5 (Sierra Analytics, Modesto, CA) was used to extract centroid values from the MS raw data files for the HDX experiments.

HDX-MS Data Analysis. The extracted HDX-MS data were further analyzed in Excel. All exchange time points (at pH 6.4 or pH 7.4 at 3.2° C.) were converted to the equivalent time points at pH 7.4 and 23° C.

Results

HDX-MS analysis of CD9B374 and CD9B643 indicate binding to a nearly identical, conformational epitope of CD79 made up of residues 30-42 (SEDRYRNPKGSAC; SEQ ID NO: 253), 50-52 (PRF), 81-86 (EMENP; SEQ ID NO: 254), and 144-148 (GFSTL; SEQ ID NO: 255). The residue numbers are those of CD79B_Human (P40259).

Thermal Stability of Trispecific CD79b×CD20×CD3 Antibodies by DSC and DSF

The thermal stability of C923B168 and C923B169 was determined by Differential Scanning Calorimetry (DSC) and differential scanning fluorimetry (DSF).

In this characterization, Tonset and Tagg were determined by DSF and the other thermal stability transitions of Tms were determined by DSC. As shown in Table 24, C923B168 and C923B169 have good thermal stability with Tonset >61° C. and Tm1>65° C.

TABLE 24

Transition temperatures for trispecific CD79b × CD20 × CD3 antibodies

| Sample ID | Tonset °C. | σ | Tm1 °C. | σ | Tm2 °C. | σ | Tm3 °C. | σ | Tagg °C. | σ |
|---|---|---|---|---|---|---|---|---|---|---|
| C923B168.008 | 61.3 | 0.15 | 65.5 | 0.03 | 73.5 | 0.18 | 77.3 | 0.07 | 73.8 | 0.37 |
| C923B169.008 | 61.7 | 0.07 | 68.4 | 0.03 | 75.1 | 0.44 | 77.7 | 0.21 | 74.2 | 0.5 |

Example 7: Functional Characterization of CD79×CD20×CD3 Trispecific Antibodies

Binding of Trispecific CD79b×CD20×CD3 Antibodies to Pan T-Cells

Binding of the CD3 arm of CD79b×CD20×CD3 trispecific constructs was assessed using cryo-preserved, negatively selected, primary human CD3+ pan T cells. Primary human CD3+ pan T cells from three different donors were incubated for 1 hour with CD79b×CD20×CD3 test molecules C923B169 and C923B168 (1 uM starting concentration at 1:3 serial dilutions) at 37° C. All cells were washed with BD stain buffer (BD Biosciences; Cat #554657), centrifuged at 1200 RPM for 3 mins, with supernatant discarded. Cells were then stained for 20 minutes at 4° C. with BD stain buffer containing AlexaFluor 647 labeled anti-human IgG secondary antibody (Jackson Immuno; Cat #109-606-098) at a 1:300 dilution. All cells were washed with BD stain buffer (BD Biosciences; Cat #554657), centrifuged at 1200 RPM for 3 mins, with supernatant discarded. Cells were resuspended in 50 ul of FACS buffer containing a 1:1000 dilution of Cytox Green viability dye (Invitrogen, Cat #S34860). Cells were analyzed using Intellicyt (Sartorius) flow cytometer and mean fluorescent intensity (MFI) was generated using Forcyt software (Sartorius). MFI was graphed using GraphPad PRISM v.8. Dose response curves were generated by transforming the x axis values using the formula x=lox. Data was then graphed using non-linear regression curve fit analysis "log(agonist) vs. response-variable slope (four parameter)".

All CD79b×CD20×CD3 molecules showed binding on all donor Pan T cells expressing endogenous CD3 on the cell surface, shown in Table 25.

TABLE 25

C923B169 and C923B168 CD79b × CD20 × CD3 binding to Pan CD3 T cells.

| Construct Name | Pan T cell binding, EC50 (nM) | | | Pan T cell max binding, MFI (×10$^6$) | | |
|---|---|---|---|---|---|---|
| | Donor 1 | Donor 2 | Donor 3 | Donor 1 | Donor 2 | Donor 3 |
| C923B168 | 125 | 91 | 97 | 1.3 | 1.0 | 1.0 |
| C923B169 | UD* | UD* | UD* | 0.1 | 0.03 | 0.04 |

UD* = undetermined

FACS T Cell Killing Data on Panel of Target Positive (CD79b$^+$ and CD20$^+$) Cell Lines Functional activity of the CD79b×CD20×CD3 trispecific constructs was assessed at 48 and 72 hr time point in an in vitro T cell killing assay by flow cytometry using cell lines that were validated by flow cytometry to have different endogenous expression levels of CD79b and CD20 on the cell surface, shown in Table 26.

TABLE 26

CD79b and CD20 Antigen Density of B Lymphoma Cell Lines

| Cell Line | Cell Type | CD79b Antigen Density (Antigen Number/cell) | CD20 Antigen Density (Antigen Number/cell) |
|---|---|---|---|
| OCI-LY10 | Diffuse large B-cell lymphoma line | 38,885 | 67,352 |
| CARNAVAL | Diffuse large B-cell lymphoma line | 98,176 | 118,789 |
| JEKO-1 | Mantle cell lymphoma | 280,000 | 50,000 |

Target cancer cells were maintained in complete RPMI-1640 (ThermoFisher, catalog #11875093) media containing 10% heat inactivated fetal bovine serum. Prior to the assay, antibodies were made at 3-fold serial dilutions in RPMI 1640 media containing 10% heat inactivated fetal bovine serum, at 4-fold expected final concentration. A volume of 50 µL of medium-diluted bispecific or trispecific Ab in each well of a 96-well plate were further diluted into 200 µL by adding a mix of target and effector cell suspension. The target cell lines were harvested by centrifuge at 400×g for 5 min, washed one time with RPMI 1640 media. Target cancer cells were stain targets with CellTrace CFSE (ThermoFisher; Cat #: C34554) diluted 1/5000. Healthy donor T cells (isolated by CD3-negative selection provided by Discovery Life Sciences) were thawed in complete media (RPMI 1640 media containing 10% heat inactivated fetal bovine serum), counted and suspended in fresh complete phenol red-free RPMI 1640 media at 1×10$^6$ cells/mL. Target cells and T cells were mixed to obtain 5:1 effector to target cell ratio. Cell suspension was added to antibody dilution wells according to plate layout (150 µL/well). Cells were incubated for 48 and 72 hours with CD79b×CD20×CD3 test molecules C923B169 and C923B168 (100 nM starting concentration at 1:3 serial dilutions) at 37° C. All cells were washed with BD stain buffer (BD Biosciences; Cat #554657), centrifuged at 1200 RPM for 3 minutes, with supernatant discarded. Cells were stained for 15 minutes at room temperature with Fixable Live/Dead stain (ThermoFisher; Cat #65-0865-14) at a 1:1000 dilution. All cells were washed with BD stain buffer (BD Biosciences; Cat #554657), centrifuged at 1200 RPM for 3 mins, with supernatant discarded. Cells were then stained for 30 minutes at 4° C. with BD stain buffer containing flow panel antibodies (Table 27), antibodies amount added as listed in the table. All cells were washed with BD stain buffer (BD Biosciences; Cat #554657), centrifuged at 1200 RPM for 3 mins, with supernatant discarded. Cells were analyzed using FACS Lyric (BD) flow cytometer and percent of cancer cell killing was generated using Cytobank. Percent of cancer cell killing was graphed and IC50 values generated using GraphPad PRISM v.8. Dose response curves were generated by transforming the x axis values using the formula x=lox. Data was then graphed using non-linear regression curve fit analysis "log(inhibitor) vs. response-variable slope (four parameter)".

TABLE 27

Flow Panel Antibodies for T cell killing Assay

| Antibody Name | Conjugated Fluorophore | Vendor | Catalog Number | LOT Number: | Amount added per well (µl) |
|---|---|---|---|---|---|
| CD4 | V500 | BD Biosciences | 560768 | 9340575 | 2 µl/well |
| CD8 | PerCPCy5.5 | BD Biosciences | 560662 | 9290508 | 2 µl/well |
| CD69 | PE | BD Biosciences | 560968 | 9049603 | 10 µl/well |
| CD25 | BV421 | BD Biosciences | 562443 | 10302 | 2 µl/well |

CD79b × CD20 × CD3 trispecific mediated potent cytotoxicity. IC50 (nM) values and Max killing values are listed in Table 28 and Table 29.

TABLE 28

C923B169 and C923B168 CD79b × CD20 × CD3 killing of target positive (CARNAVAL, OCI-Ly10, JEK0-1) cell lines (FACS) at 48 hours. IC50 (nM) and percent of maximal killing are listed in the table. Average values from 2 independent T cell donors.

| Protein ID | Killing CARNAVAL 1:1 48 hr | | Killing CARNAVAL 5:1 48 hr | | Killing JEKO-1 1:1 48 hr | | Killing JEKO-1 5:1 48 hr | | Killing OCI-Ly10 1:1 48 hr | | Killing OCI-Ly10 5:1 48 hr | |
|---|---|---|---|---|---|---|---|---|---|---|---|---|
| | IC50 | Max | IC50 | Max | IC50 | Max | IC50 | Max | IC50 | Max | IC50 | Max |
| C923B169 | 110.3 | 49.7% | 0.179 | 87.2% | 27.307 | 60.8% | 0.027 | 93.5% | >100 | 22.2% | >100 | 19.7% |
| C923B168 | 13.6 | 58.8% | 0.012 | 95.0% | 7.466 | 65.3% | 0.002 | 96.7% | >100 | 25.1% | >100 | 29.8% |

TABLE 29

C923B169 and C923B168 CD79b × CD20 × CD3 killing of target positive (CARNAVAL, OCI-Ly10, JEKO-1) cell lines (FACS) at 72 hours. IC50 (nM) and percent of maximal killing are listed in the table. Average values from 2 independent T cell donors.

| | Killing CARNAVAL; 1:1 72 hr | | Killing CARNAVAL; 5:1 72 hr | | Killing JEKO-1; 1:1 72 hr | | Killing JEKO-1; 5:1 72 hr | | Killing OCI-Ly10; 1:1 72 hr | | Killing OCI-Ly10; 5:1 72 hr | |
|---|---|---|---|---|---|---|---|---|---|---|---|---|
| Protein ID | IC50 | Max | IC50 | Max | IC50 | Max | IC50 | Max | IC50 | Max | IC50 | Max |
| C923B169 | 50.15 | 66.8% | 0.026 | 98.3% | 0.087 | 82.2 | 0.003 | 99.4% | >100 | 43.5% | 24.58 | 70.0% |
| C923B168 | 15.53 | 75.9% | 0.003 | 99.3% | 0.010 | 85.8% | 0.001 | 99.6% | 0.81 | 61.0% | 0.51 | 90.7% |

C923B169 and C923B168 CD79b×CD20×CD3 Mediated Cytotoxicity Against Autologous B-Cells Functional activity of the C923B169 and C923B168 CD79b×CD20×CD3 constructs was assessed in an in vitro autologous B cell depletion assay. This functional assay utilizes PBMCs to focus on the killing of primary B cells as well as T cell activation on donor matched primary cells. Cryo-preserved PBMCs from 3 different human donors were incubated for 72 hours with CD79b×CD20×CD3 test molecules C923B169 and C923B168 (300 nM starting concentration at 1:3 serial dilutions) at 37° C. All cells were washed with BD stain buffer (BD Biosciences; Cat #554657), centrifuged at 1200 RPM for 3 minutes, with supernatant discarded. Cells were stained for 10 minutes at room temperature with BD stain buffer containing Fc blocking agent (Accurate Chemical and Scientific Corp; Cat #NB309) and Near IR Fixable Live/Dead stain (Invitrogen; Cat #L10119) at a 1:400 dilution. All cells were washed with BD stain buffer (BD Biosciences; Cat #554657), centrifuged at 1200 RPM for 3 mins, with supernatant discarded. Cells were then stained for 30 minutes at 4° C. with BD stain buffer containing flow panel antibodies (Table 30) at a 1:100 dilution. All cells were washed with BD stain buffer (BD Biosciences; Cat #554657), centrifuged at 1200 RPM for 3 mins, with supernatant discarded. Cells were analyzed using Intellicyt (Sartorius) flow cytometer. EC50 values generated using GraphPad PRISM v.8. Dose response curves were generated by transforming the x axis values using the formula x=lox. Data was then graphed using non-linear regression curve fit analysis "log(agonist) vs. response-variable slope (four parameter)".

TABLE 30

Flow Panel Antibodies for Autologous B Cell Depletion Assay

| Antibody Name | Conjugated Fluorophore | Vendor | Catalog Number |
|---|---|---|---|
| Anti-human CD25 | BV650 | BD Biosciences | 563719 |
| Anti-Human CD4 | BV510 | Biolegend | 317444 |
| Anti-Human CD8 | PE-Cy7 | Biolegend | 301012 |
| Anti-Human CD20 | PE | Biolegend | 302306 |
| Anti-Human CD11c | AF647 | BD Biosciences | 565911 |
| Anti-Human CD2 | BV605 | BD Biosciences | 740391 |

CD79b×CD20×CD3 C923B169 and C923B168 constructs showed a maximum drug mediated cytotoxicity of 69-95 percent (Table 31) with low levels of CD4 and CD8$^+$ T cell activation as demonstrated by CD25 expression on these T cell subsets.

TABLE 31

C923B169 and C923B168 CD79b × CD20 × CD3 killing of B cell in the primary autologous B cell depletion assay at 72 hours. EC50 (nM) and percent of maximal killing are listed in the table. Values from 3 independent T cell donors listed.

| | D329465 | | D198013 | | D221837 | | Average values | |
|---|---|---|---|---|---|---|---|---|
| Name | EC50 (nM) | Max Kill (%) | EC50 (nM) | Max Kill (%) | EC50 (nM) | Max Kill (%) | EC50 (nM) | Max Kill (%) |
| C923B168 | 0.1 | 69 | 0.02 | 92 | 0.1 | 95 | 0.07 | 84 |
| C923B169 | 2.0 | 69 | 1.70 | 92 | 6.30 | 81 | 2.80 | 80 |

Example 8: C9231B169

The trispecific antibody C923B169 (CD9B374 Fab× C20B648 LH scFv×CD3B2030 N106A LH scFv) is a fully human IgG1 trispecific mAb that simultaneously binds to the epsilon subunit of the CD3 TCR complex (i.e., CD3ε; Uniprot ID P07766), and to CD79b (i.e., B-cell antigen receptor complex-associated protein β chain; Uniprot ID P40259) and CD20 (i.e., B-lymphocyte antigen CD20; Uniprot ID P11836) on tumor cells. The antibody features mutations of L234A, L235A, and D265S (AAS) in the constant region (i.e., fragment crystallizable [Fc]) to abolish interaction with Fc receptors. Heterodimerization is enhanced using the knobs-into-holes platform mutations. The molecule comprises an anti-CD3ε single-chain variable fragment (scFv) fused onto the N-terminus of the 'knob' Fc region (i.e., T366W) and an anti-CD20 scFv attached to the C-terminus of the Fc. The 'hole' chain (i.e., T366S, L368A, Y407V) features an anti-CD79b fragment antigen-binding (Fab) and contains 'RF' mutations (i.e., H435R, Y436F) to disrupt Protein A binding of monomeric and homodimerized hole chains (mutations numbered according to EU numbering).

Table 32 provides recombinant antigen binding, species cross-reactivity, CD79b and CD3 epitope identification, Fc receptor binding, and biophysical intrinsic property attributes for C923B169. The trispecific molecule C923B224 (SEQ ID NO: 263) was generated. C923B224 is identical to C923B169 with an added Histidine at the C-terminus of HC1 (SEQ ID NO: 260) The biophysical characteristics for C923B224 were essentially similar to C923B169.

Biophysical Assessment of C923B169

TABLE 32

List of biophysical assessments and results for C923B169.

| mAb TMP characteristic | Result | Comments |
|---|---|---|
| Binding | | |
| Binding affinity (SPR) | Human CD79b: $K_D$ = 0.16 nM; CD3: no quantitative results by SPR due to biphasic profile; Antigens: CD9W7.001 and CD3W220.001 | CD20 binding: the Acro-biotinylated CD20 antigen had little to no measurable activity due to technical challenge. Affinity binding was assessed using cell-based method on CARNAVAL cells instead, with $EC_{50}$ determined to be 2.1 nM for Fab and 16 nM for scFv. Binding may be repeated on target KO cells upon further cell line validation. CD3 binding: weak binding to CD3 protein was detected, but $K_D$ could not be determined due to lack of fit of the binding curve. Affinity binding was further evaluated on pan T cells (see details below) |
| Cross-reactivity of the CD9B374 binder | Cyno CD79b: weak binding, $K_D$ estimated >3 μM; Mouse CD79b: no binding (up to 3 μM antigen concentration) | Binding data were collected from C923B38 containing the same CD79b Fab arm |
| FcRn binding (SPR) | pH 6.0: hu FcRn $K_D$ = 890 nM; cyno FcRn $K_D$ = 818 nM | Rapid dissociation at pH 7.4 |
| Serum interference (Octet) | No significant change in association rate to bt-CD79b and bt-CD3 in 50% human serum; $k_a$ buffer/$k_a$ serum <2.0 | The Acro-biotinylated CD20 antigen had little to no measurable activity due to technical challenge. |
| CD79b binding epitope | Epitope encompassing residues of P40259 at segments 30-42 (SEDRYRNPKGSAC; SEQ ID NO: 253), 50-52 (PRF), 81-86 (EMENP; SEQ ID NO: 254), and 144-148 (GFSTL; SEQ ID NO: 255) | The residue numbers correspond to P40259 (CD79B_Human); the CD79b construct used for the epitope mapping was CD9W7 |
| CD3 binding epitope | Epitope encompassing residues of P07766 at segments 54-58 (GSEIL; SEQ ID NO: 257), 74-75 (NI), and 100-105 (PRGSKP; SEQ ID NO: 258) | The residue numbers correspond to P07766 (CD3E_Human); similar to OKT3's epitope; the CD3 construct used for the epitope mapping was CD3W220 |
| Protein characterization | | |
| Intact trispecific Ab mass, release (MS) | 156,308.2 Da | N/A |
| Glycoform profile (MS) | Typical IgG1 profile with main glycoform G0F/G0F | N/A |
| Level of homodimer(s) (MS) | None detected | N/A |
| Levels of other product-related impurities (MS) | None detected | N/A |
| N-link gly (non-Fc) (MS) | None predicted nor detected | N/A |
| O-link gly sites (MS) | None detected | N/A |
| Glycation (% relative abundance) (MS) | CD79b HC: 13.8%; CD79b LC: 6.0%; CD3 HC: 32.2% | N/A |
| Free Cys (MS) | None predicted nor detected | N/A |
| N-terminal elongation/truncation (MS) | None detected | N/A |
| Conformational stability (DSC) | $T_{m1}$ = 68.4° C.; $T_{m2}$ = 75.1° C.; $T_{m3}$ = 77.7° C. | Measured in 10 mM L-histidine pH 6.5 |
| % Purity (2-step purification) (AUC) | >94% Monomer (monomer presents 2 peaks in AUC, most likely due to conformational isoforms) | Measured in 10 mM L-histidine pH 6.5 |

TABLE 32-continued

List of biophysical assessments and results for C923B169.

| mAb TMP characteristic | Result | Comments |
| --- | --- | --- |
| Serum stability (SEC-FDS) | ~0.5% increase in HMW and LMW after 7-day incubation at 37° C. | Assessed by SEC using Alexa488-labeled C923B169 |
| IgG interactions (SPR) | No IgG interactions detected | N/A |
| Non-specific binding | No non-specific binding detected | N/A |
| Isoelectric point (cIEF) | pI = 8.44; % acidic/main/basic peak area: 35.5/58.5/6.0 | N/A |
| Relative hydrophobicity (aHIC) | Relatively low/medium hydrophobicity (HI = 0.67) | N/A |
| Viscosity | 6.1 cP | Determined at 100 mg/mL in 10 mM L-histidine pH 6.5 with 0.04% PS20 |
| 2-week high concentration stability (4 and 40° C., target 150 mg/mL in 10 mM L-histidine buffer with 0.04% PS20 and 50 mg/mL in PBS) | | |
| Concentratability and % recovery in L-histidine | Sample was concentrated to 162 mg/mL with 84% recovery | Determined in 10 mM L-histidine pH 6.5 with 0.04% PS20 |
| Concentratability and % recovery in PBS | Sample was concentrated to 65 mg/mL with 90.5% recovery | Determined in PBS |
| % Monomer (initial) (AUC) | 96.4% | Determined in 10 mM L-histidine pH 6.5 with 0.04% PS20 |
| % Monomer 2 weeks, 4° C. (AUC) | 95.5% | Determined in 10 mM L-histidine pH 6.5 with 0.04% PS20 |
| % Monomer 2 weeks, 40° C. (AUC) | 63.7% | Determined in 10 mM L-histidine pH 6.5 with 0.04% PS20 |
| Chemical (PTM) and physical stability | | |
| Intact MS after forced degradation (MS) | Trace losses from N- and C-terminus of both HCs seen under high pH stress, while a trace loss of the C-terminal domain of HC1 scFv was also observed under physiological stress. | Observed fragmentation is insignificant due to very low levels detected. |
| Size after forced degradation (aSEC) | Samples maintained >97.0% monomer under stressing conditions, except for: Thermal: 30.3% aggregate at 162 mg/mL in L-histidine and 14.7% aggregates at 65 mg/mL in PBS after 2 weeks at 40° C.; High pH: 1.5% aggregates and ~16.6% fragment after 1 week at pH 8.5 37° C. | N/A |
| Purity forced degradation (R and NR GXII) | All stressed samples maintained >95% intact, expect high pH sample (~27.5% LMW) | N/A |
| Basal oxidation level | 2.4% M95 (CD9B374 LC CDR3); 3.0% in M98 (CD9B374 LC CDR3); <1.2% for all other CDR residues | N/A |
| Met/Trp oxidation under stress ($H_2O_2$) | 3.3% in M95 (CD9B374 LC CDR3); 89.8% in M94 (CD9B374 LC CDR3) along with a 3.3-fold weaker binding affinity but no changes in % activity | N/A |
| Basal deamidation level | <0.1% in CDRs | N/A |
| Deamidation under stress (pH 8.5) | No significant change | N/A |
| Basal isomerization level | <1% in CDRs | N/A |
| Isomerization under stress (pH 5) | No significant change | N/A |

Ab, antibody; aHIC, analytical hydrophobic interaction chromatography; aSEC, analytical size-exclusion chromatography; AUC, analytical ultracentrifugation; bt, biotinylated; CD, cluster of differentiation; CDR, complementarity determining region; cIEF, capillary isoelectric focusing; cyno, cynomolgus monkey; Cys, cysteine; DSC, differential scanning calorimetry; $EC_{50}$, 50% effective concentration; Fab, fragment antigen-binding; Fc, fragment crystallizable; FcRn, neonatal Fc receptor; FDS, fluorescence detection system; gly, glycosylation; HC, heavy chain; HMW, higher molecular weight; hu, human; Ig, immunoglobulin; $k_a$, association constant; $K_D$, equilibrium dissociation constant; KO, knock out; LC, light chain; LMW, lower molecular weight; mAb, monoclonal antibody; Met, methionine; MS, mass spectrometry; N/A, not assessed; NR GXII, non-reduced capillary electrophoresis; PBS, phosphate-buffered saline; pI, isoelectric point; PS20, Polysorbate 20; ref, reference; R GXII, reduced capillary electrophoresis; scFv, single-chain variable fragment; SEC, size-exclusion chromatography; SPR, surface plasmon resonance; $T_m$, melting temperature; TMP, target medicinal product; Trp, tryptophan.

Target Arm and CD3 Arm Binding Characterization of C923B169
Endogenous Tumor Cell Line Binding of C923B169

Figure 12A:
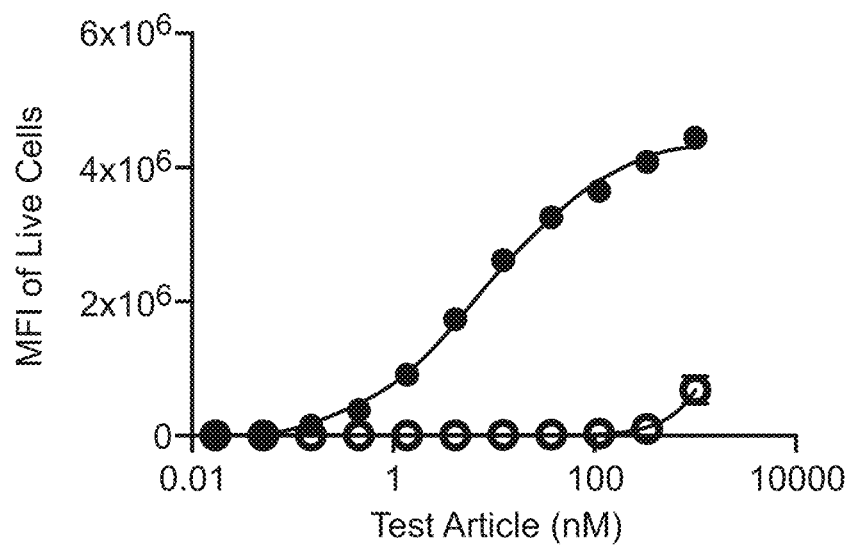
FIGS. 12A-12B. Exemplary binding profiles of C923B169 on CARNAVAL and OCI Ly10 cell lines after 1 hour 37° C. incubation.
Figure 12B:
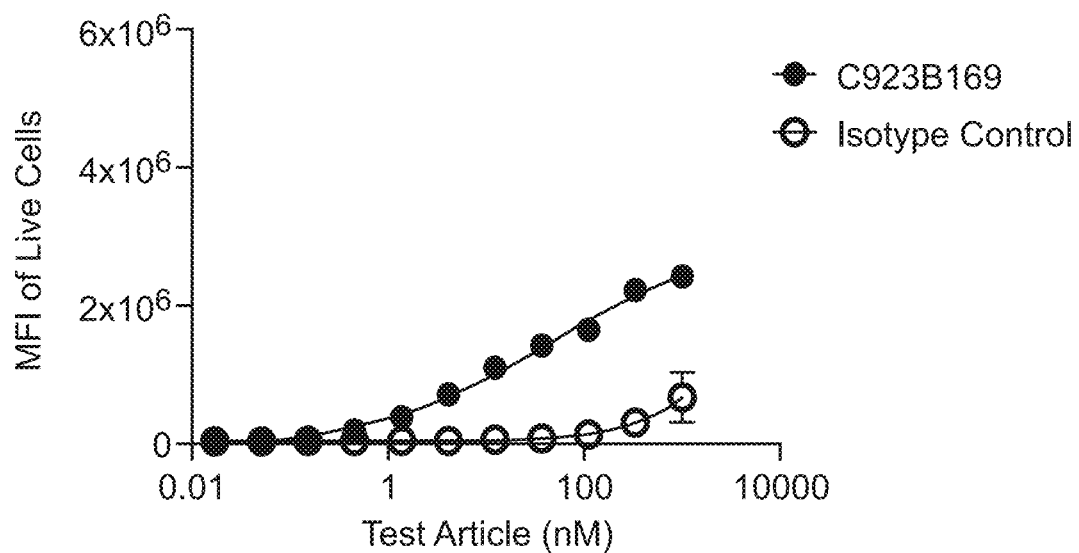
Figures 26A, 26B:
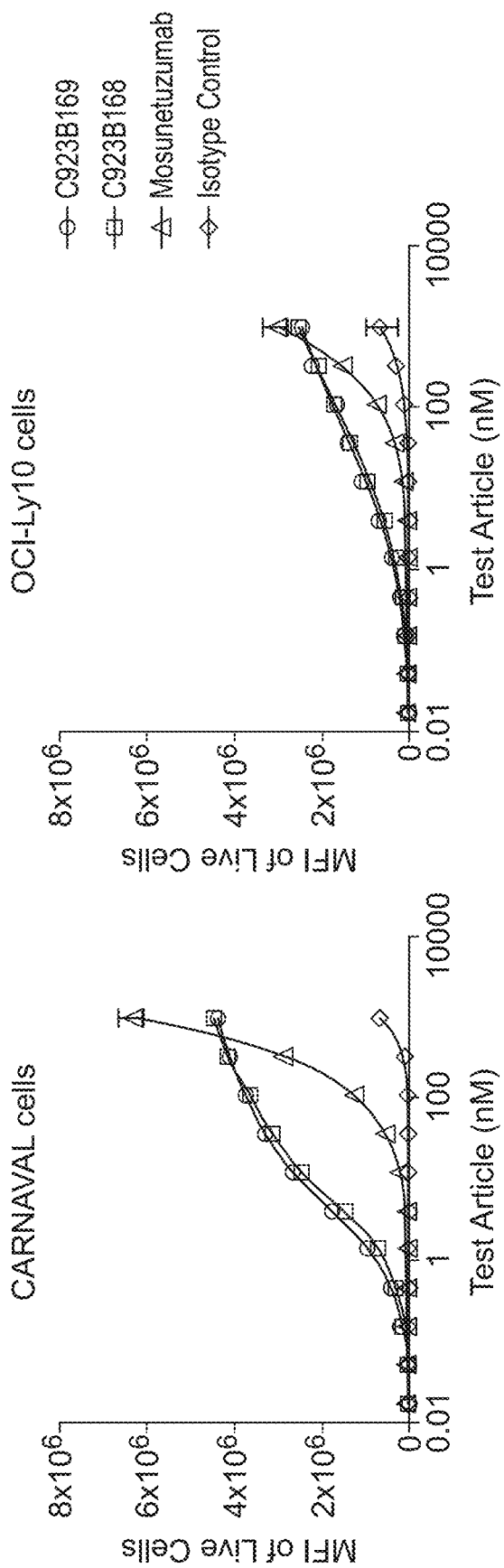
FIGS. 26A-26B. Binding profiles of C923B169, C923B168, and mosunetuzumab after 1-hour 37° C. incubation with CARNAVAL (FIG. 26A) and OCI-Ly10 (FIG. 26B) cell lines. MFI, mean fluorescence intensity.

Flow cytometry was used to evaluate the CD79b and CD20 arm binding of C923B169 in vitro. C923B169 and isotype were tested on a panel of endogenous cell lines of varying CD79b and CD20 receptor densities after 1-hour 37° C. incubation. C923B169 showed good binding on cell lines expressing endogenous CD79b and CD20 on the cell surface at a range of antigen densities (FIGS. 12A-12B, Table 33). C923B169 also illustrated better binding potency compared to mosunetuzumab (see FIGS. 26A-26B, Table 34).

TABLE 33

Calculated receptor counts and $EC_x$ values for endogenous tumor cell line binding.

| Cell lines | CD79b receptor count | CD20 receptor count | Type of cell line | Cell binding $EC_{20}$, $EC_{50}$, and $EC_{90}$ values (nM) | | |
|---|---|---|---|---|---|---|
| | | | | $EC_{20}$ | $EC_{50}$ | $EC_{90}$ |
| CARNAVAL | 165,541 | 429,801 | DH DLBCL | 1 | 8 | 216 |
| Jeko-1 | 617,117 | 334,371 | MCL | 1.6 | 20.3 | 1,098 |
| WILL-2 | 4,304 | 756 | DH DLBCL | I | I | I |
| OCI-Ly10 | 63,633 | 424,335 | ABC DLBCL | 2.3 | 43.4 | 4,791 |
| SU-DHL1 | −438 | −919 | ALCL | NA | NA | NA |
| K562 | −546 | −1,309 | CML | NA | NA | NA |

ABC, activated B-cell; ALCL, anaplastic large-cell lymphoma; B-NHL, B-cell non-Hodgkin lymphoma; CD, cluster of differentiation; CML, chronic myelogenous leukemia; DH, double-hit; DLBCL, diffuse large B-cell lymphoma; $EC_x$, x % effective concentration; I, indeterminate; MCL, mantle cell lymphoma; NA, not assessed; PE, phycoerythrin.
CD79b and CD20 receptor density results in CD79b and CD20 receptor positive B-NHL cell lines were evaluated. CD79b expression was determined by flow cytometry using a PE-labeled commercial antibody (human CD79B-PE clone # SN8; BD Bioscience #335833), CD20 expression was determined by flow cytometry using a PE-labeled commercial antibody (human CD79B-PE clone # 2H7; BD Bioscience #555623), and receptor counts were calculated using the Quantum Simply cellular kit (Bangslabs #815). $EC_{20}$, $EC_{50}$, and $EC_{90}$ values for endogenous tumor cell binding were assessed.

TABLE 34

Calculated cell binding $EC_{20}$, $EC_{50}$, and $EC_{90}$ values (nM) for CARNAVAL and OCI-Ly10 binding.

| | C923B169 | | | C923B168 | | | Mosunetuzumab | | |
|---|---|---|---|---|---|---|---|---|---|
| | $EC_{20}$ | $EC_{50}$ | $EC_{90}$ | $EC_{20}$ | $EC_{50}$ | $EC_{90}$ | $EC_{20}$ | $EC_{50}$ | $EC_{90}$ |
| CARNAVAL | 1.0 | 8.0 | 216.0 | 1.0 | 11.0 | 267.0 | I | I | I |
| OCI-Ly10 | 2.3 | 43.4 | 4,791.0 | 4.0 | 55.0 | 5,000.0 | I | I | I |

$EC_x$, x % effective concentration; I, indeterminate.

Figure 13A:
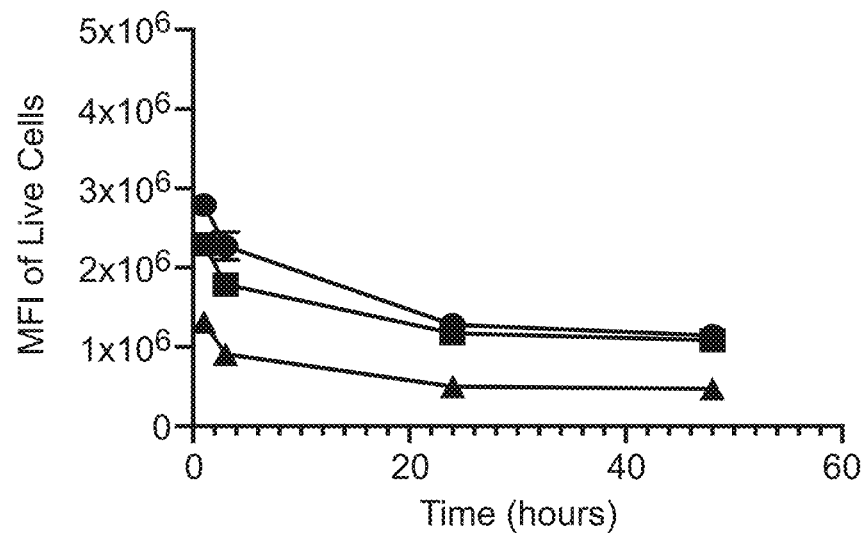
FIGS. 13A-13B. Exemplary kinetic binding profiles of C923B169 on CARNAVAL and OCI Ly10 cell lines throughout 48 hours 37° C. incubation.
Figure 13B:
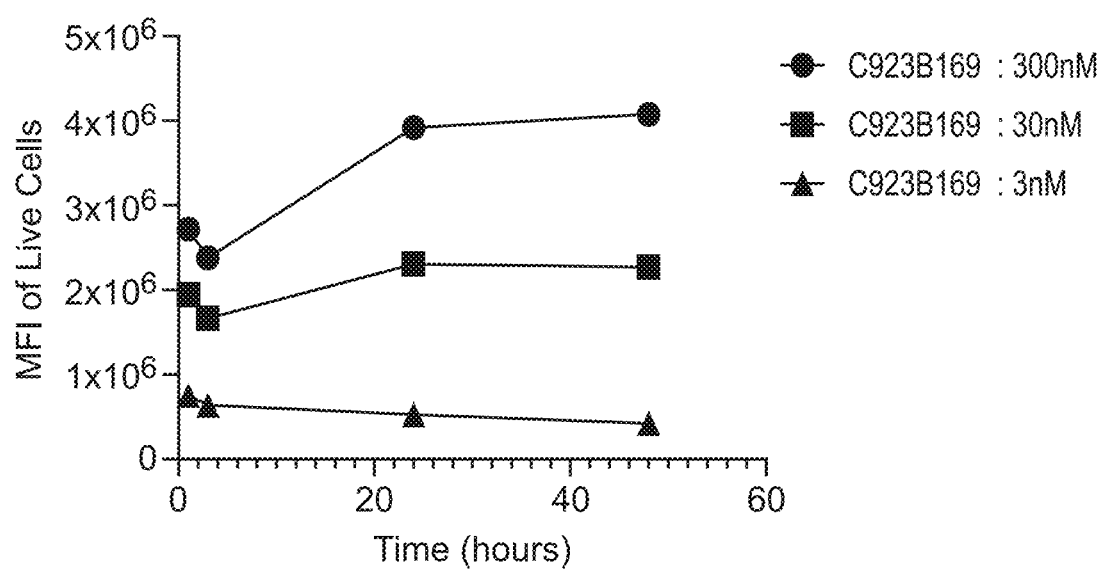
Figure 14A:
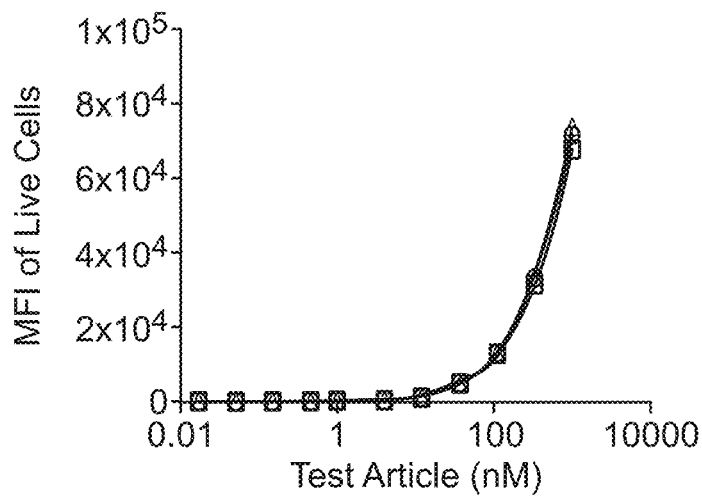
FIGS. 14A-14C. Binding profiles of C923B169 of primary T cells from 3 donors after 1 hour 37° C. incubation.
Figure 14B:
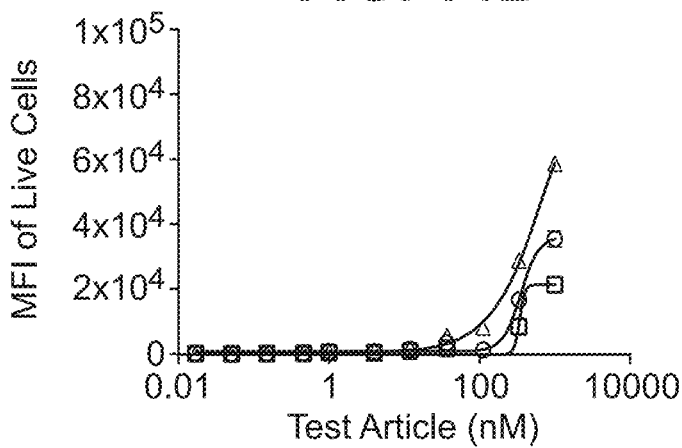
Figure 14C:
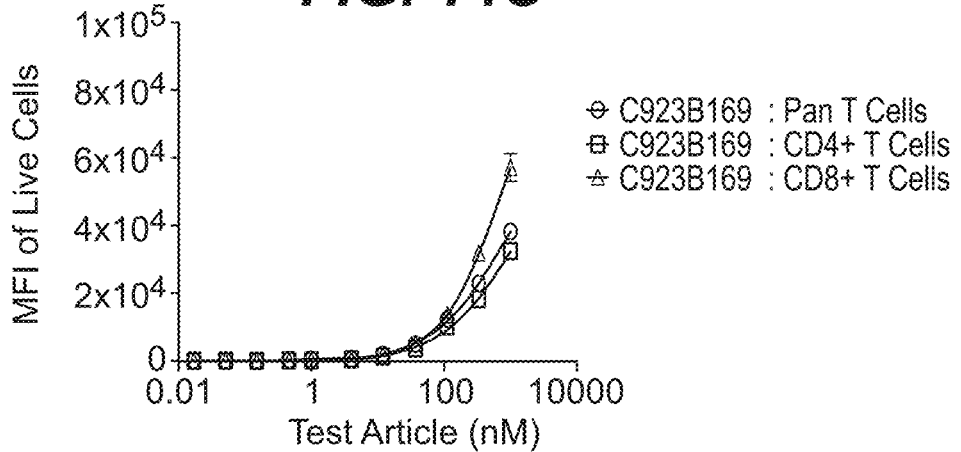

Flow cytometry was used to evaluate the CD79b and CD20 arm binding kinetic of C923B169 in vitro. C923B169 and isotype were tested in parallel on CARNAVAL, OCI-Ly10, and WILL-2 (data not shown) cell lines at 300, 30, and 3 nM throughout 48-hour 37° C. incubation. C923B169 showed stable binding profiles at all tested concentrations to tumor cell lines co-expressing endogenous CD79b and CD20 on the cell surface (FIGS. 13A-13B). C923B169 also illustrated superior tumor arm binding stability compared to mosunetuzumab (see FIGS. 27A-27D).

Primary T-Cell Binding of C923B169

Flow cytometry was used to evaluate the CD3 arm binding of C923B169 to CD3+ pan T cells from 3 different healthy human donors. C923B169 and isotype were tested after 1-hour 37° C. incubation in pan T cells. C923B169 showed consistent binding profiles across primary T-cell populations expressing endogenous CD3 on the cell surface (FIGS.

TABLE 35

Max MFI values for primary T-cell binding of C923B169.

| | Mean of Max MFI ± SD (×$10^5$) |
|---|---|
| Pan T-cell binding | 0.5 ± 0.2 |
| CD4+ T-cell binding | 0.4 ± 0.2 |
| CD8+ T-cell binding | 0.6 ± 0.1 |

Max, maximum; MFI, mean fluorescence intensity; SD, standard deviation.

TABLE 36

Max MFI values for primary T-cell binding.

| | Mean Max MFI ± SD (×$10^6$) | | |
|---|---|---|---|
| | C923B169 | C923B168 | Mosunetuzumab |
| Pan T-cell binding | 0.05 ± 0.02 | 0.87 ± 0.39 | 0.13 ± 0.06 |
| CD4+ T-cell binding | 0.04 ± 0.02 | 1.30 ± 0.30 | 0.23 ± 0.11 |
| CD8+ T-cell binding | 0.06 ± 0.01 | 1.13 ± 0.15 | 0.23 ± 0.05 |

Max, maximum; MFI, mean fluorescence intensity; SD, standard deviation.
C923B168 has an $EC_{50}$ value of 104 ± 18 nM.

In conclusion, C923B169 is a fully human trispecific mAb targeting the TCR CD3 with 1 binding arm and tumor cell surface antigens CD79b or CD20 with the remaining 2 binding domains. C923B169 showed acceptable intrinsic biophysical properties and bound to all tested CD79b- and CD20-expressing cell lines. Binding profiles and reported EC values were dependent on cell surface antigen density. C923B169 showed stable tumor cell binding profiles over 48 hours. C923B169 also showed measurable, low-affinity binding to primary human T cells expressing CD3 on the cell surface.

Example 9: Therapeutic Pharmacology

C923B169-Induced T-Cell-Mediated Cytotoxicity of B-Cell Lymphoma Lines In Vitro

Figure 15A:
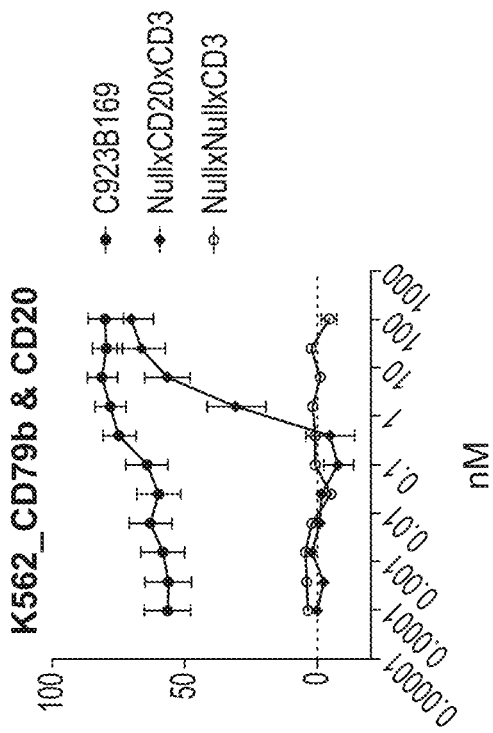
FIGS. 15A-15C. Therapeutic efficacy (in vitro cytotoxicity assay) comparing CD79b×CD20×CD3 (C923B169) to single-antigen Null×CD20×CD3 engagement. Cancer cell killing was assessed over time using Incucyte technology after coculture of pan CD3 T cells with K562 cancer cells expressing CD79b or CD20 or CD79b/CD20 at 5:1 E:T ratio. AUC calculation of (FIG. 15A) K562 CD79b$^+$, (FIG. 15B) K562 CD20$^+$, and (FIG. 15C) K562 CD79b$^+$/CD20$^+$ cancer cell growth inhibition over time as determined by mKate2$^+$/GFP$^+$ area per well was done over 6-day time frame. After normalizing the AUC to the untreated control (target with effector), antibody concentrations were plotted against the AUC values as a dose response. EC$_{50}$ values were generated using GraphPad PRISM v.9. AUC, area under the curve; EC50, 50% effective concentration; E:T ratio, effector-to-target ratio.
Figure 15B:
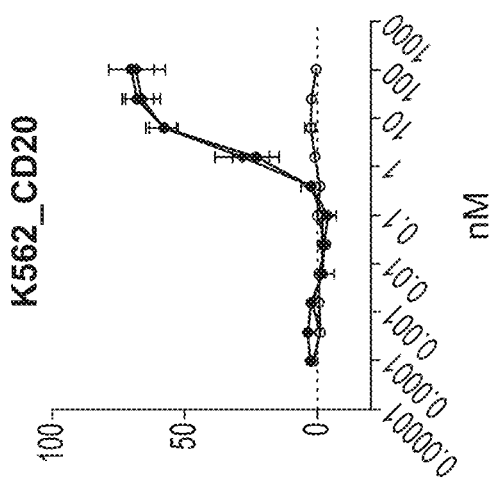
Figure 15C:
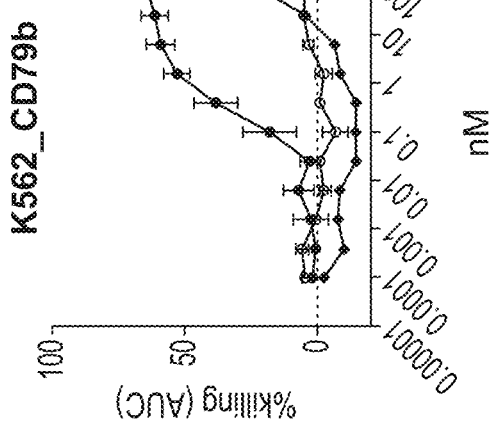
Figures 16G, 16H:
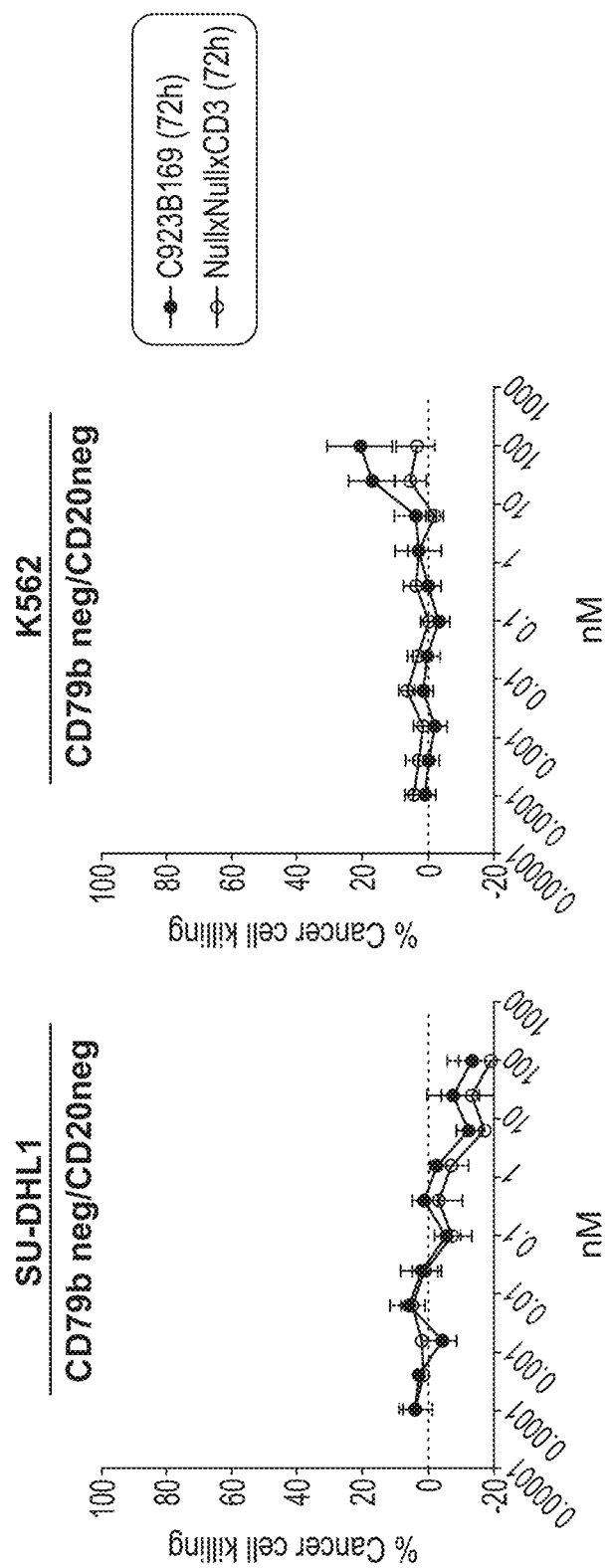

To validate that CD79b×CD20×CD3 trispecific antibodies could target cancer cells expressing CD79b or CD20 only, as well as to show that increased efficacy is observed when both antigens are present, K562 models either overexpressing CD79b (FIG. 15A) or CD20 (FIG. 15B) alone, or both targets together, were generated (FIG. 15C). Using long-term assays, T-cell-mediated cytotoxicity was assessed in presence of C923B169 or matched Null×CD20×CD3 control. In the K562 CD79b overexpression model, cytotoxicity was only observed with C923B169 while the matched Null×CD20×CD3 antibody was inactive (FIG. 15A, Table 37). In the K562 CD20 overexpression model, C923B169 and the matched Null×CD20×CD3 control showed overlapping activity (FIG. 15B, Table 37). When both CD79b and CD20 antigens were present in the K562 CD79b/CD20 overexpression model, a clear benefit of using C923B169 was observed as compared to the CD20-targeting antibody resulting in ~100-fold 50% effective concentration ($EC_{50}$) shifts, confirming an avidity effect (FIG. 15C, Table 37). High expression levels of CD79b and CD20 in the K562 isogenic models may contribute to the strong avidity effect observed. No cytotoxicity was observed when using the K562 parental cells (see FIG. 16H) in a 72-hour fluorescence activated cell sorting (FACS) cytotoxicity assay.

TABLE 37

EC50 values (nM) for long-term Incucyte cytotoxicity of CD79b/CD20 isogenic K562 cell lines.

|  | K562 CD79b | K562 CD20 | K562 CD79b&CD20 |
|---|---|---|---|
| C923B169 | 1.04 | 4.08 | <0.0001 |
| Null×CD20×CD3 | >100 | 3.58 | 3.19 |
| Null×Null×CD3 | >100 | >100 | >100 |

$EC_{50}$, 50% effective concentration.

To assess the cytotoxicity potential of C923B169 in B-NHL models in vitro, a FACS-based approach was utilized to measure tumor cell viability in the presence of test compound and purified human pan T cells. Selected B-cell lymphoma cell lines, expressing varying levels of CD79b and CD20 representing DLBCL and MCL, were used to assess efficacy. SU-DHL-1 (anaplastic large cell lymphoma) and K562 (chronic myelogenous leukemia [CML]) cells were used as target-negative cell lines (Table 33 lists the receptor density values across a panel of cell lines). HT (GCB DLBCL) cells are reported to express low levels of CD79b and medium levels of CD20. Confirmation of HT receptor density measurement is currently ongoing. Naïve $CD3^+$ pan T cells from healthy donors were combined with individual cell lines at a 5:1 effector-to-target (E:T) ratio and treated with varying concentrations of C923B169 for either 48 or 72 hours. C923B169 was able to elicit cytotoxicity of $CD79b^+/CD20^+$ cell lines after 48 and 72 hours, but not of the $CD79b^-/CD20^-$ cell lines (FIGS. 16A-16H). A Null× Null×CD3 negative control antibody had no to minimal effect on cytotoxicity; minimal effects were observed in some cellular models at the top concentration tested (i.e., 100 nM). The up-and-down behavior of the curve observed for target-negative cell line SU-DHL1 across all antibodies tested, including Null×Null×CD3 control antibodies, was clearly attributed to a FACS technical acquisition issue.

To assess the impact of increased target burden on the cytotoxicity potential of C923B169 in vitro, a FACS-based approach was utilized to measure tumor cell viability in the presence of treatment and purified human pan $CD3^+$ T cells at a 1:1 E:T ratio for either 48 or 72 hours. Both maximum cytotoxicity and $EC_{50}$ values of C923B169 were decreased and increased, respectively, at a 1:1 ratio in comparison to a 5:1 ratio (Table 38).

TABLE 38

C923B169-induced T-cell-directed cytotoxicity: $EC_{50}$ and maximum cytotoxicity values with different cancer cell lines at different E:T ratios at 48 and 72 hours.

| | 48 hours: mean values | | | | | 72 hours: mean values | | | | |
|---|---|---|---|---|---|---|---|---|---|---|
| | JEKO-1 | CARNAVAL | OCI-Ly10 | HT | WILL-2 | JEKO-1 | CARNAVAL | OCI-Ly10 | HT | WILL-2 |
| | E:T ratio 5:1 | | | | | | | | | |
| $EC_{50}$ (nM) | 0.149 | 0.237 | 2.221 | 4.186 | NE | 0.0092 | 0.092 | 27.042 | 2.016 | 31.971 |
| Max kill (%) | 90.8 | 78.4 | 31.0 | 59.1 | NE | 99.0 | 98.5 | 81.8 | 86.8 | 95.5 |
| | E:T ratio 1:1 | | | | | | | | | |
| EC50 (nM) | 0.588 | 0.658 | 94.462* | NA | NA | 0.155 | 0.536 | 16.54 | NA | NA |
| Max kill (%) | 65.8 | 35.0 | 62.8* | NA | NA | 85.9 | 77.8 | 49.3 | NA | NA |

$EC_{50}$, 50% effective concentration; E:T ratio, effector-to-target ratio; Max kill, maximum cytotoxicity; NA, not assessed; NE, not estimable with the NLME statistical model; NLME, non-linear mixed effects;
*high variability across tested donors.

Values are representative of 5 to 6 individual healthy donors. Data from independent experiments were pooled and represented as mean. A NLME model was used for $EC_{50}$ value estimation across the donors. Separate NLME models were fit for each time point, treatment, and titration. The NLME model was used to estimate dose-response profile, using the 4 parameters of the standard 4-parameter logistic regression model as the fixed effects (minimum, maximum, slope, $logEC_{50}$) and using donor as a random effect. $EC_{50}$ values were derived from this model, along with donor-specific $EC_{50}$ using post-hoc estimation. Results are reported on the original scale. All analyses were performed in R Version 4.0.3.

C923B169-Mediated T-Cell Activation In Vitro

To assess the level of T-cell activation in the cytotoxicity assays described above, CD25 expression was measured on T cells in the same assays. T cells activation was induced in the presence of C923B169 only when incubated with CD79b$^+$/CD20$^+$ cell lines, but not in the presence of the CD79b$^-$/CD20$^-$ cell lines, demonstrating the specificity of T-cell activation (FIGS. 17A-17B). SU-DHL1 is a T-cell lymphoma with reported constitutive expression of interleukin (IL)-2 receptor (CD25) and secretion of IL-2 (36). This SU-DHL1 intrinsic feature corresponds to higher basal CD25 levels in T cells in coculture with this particular cell line independent of CD3 redirection antibody presence. C923B169 did not contribute to further increase in the level of T-cell activation in SU-DHL1 cells. Similarly, a negative control Null×Null×CD3 antibody did not induce significant T-cell activation in any of the cell lines.

The impact of lower E:T ratio on T-cell activation was also assessed, by measuring CD25 expression on T cells. EC$_{50}$ values for T-cell activation were similar for most of the cell lines at 1:1 and 5:1 E:T ratios in the presence of C923B169 (Table 39).

TABLE 39

C923B169-induced CD8 T-cell activation: EC$_{50}$ values from T-cell cytotoxicity assays with different cancer cell lines at different E:T ratios at 48 and 72 hours.

| E:T ratio | 48 hours: mean values | | | | | 72 hours: mean values | | | | |
|---|---|---|---|---|---|---|---|---|---|---|
| | JEKO-1 | CARNAVAL | OCI-Ly10 | HT | WILL-2 | JEKO-1 | CARNAVAL | OCI-Ly10 | HT | WILL-2 |
| 5:1 | 0.097 | 0.465 | 3.925 | 1.648 | 5.048 | 0.068 | 0.185 | 2.386 | 0.638 | 12.651 |
| 1:1 | 0.099 | 0.207 | 0.295 | NA | NA | 0.098 | 0.107 | 0.386 | NA | NA |

EC$_{50}$, 50% effective concentration; E:T ratio, effector-to-target ratio; NA, not assessed.

Values are representative of 5 to 6 individual healthy donors. A non-linear mixed effect model was used to estimate dose-response using the 4 parameters of standard 4-parameter logistic regression model as fixed (minimum, maximum, slope, and logEC$_{50}$) and using donor as a random effect. EC$_{50}$ (nM) values were derived using post-hoc estimation. Data from independent experiments were pooled and represented as mean.

Impact of Longer Incubation on C923B169 Cytotoxicity of CARNAVAL and OCI-Ly10 Cells As the limited time frame of in vitro assays might not reflect the potency of CD3 redirectors specifically with low CD3 affinity, long-term cytotoxic effects of C923B169 were assessed. To this end, CD3$^+$ T cells were cocultured with red fluorescent protein (RFP)-expressing CARNAVAL or OCI-Ly10 target cells at 2 different E:T ratios (i.e., 5:1 and 1:1). Cancer cell proliferation/viability was assessed for 2, 3, and 6 days taking advantage of the Incucyte technology by measuring over time the RFP$^+$ area in each well. The area under the curve (AUC) was calculated to evaluate cancer cell growth over the indicated time. EC$_{20}$, EC$_{30}$, and EC$_{50}$ values were calculated over specific time frames (Table 40). In almost all conditions analyzed, the EC$_{20}$, EC$_{30}$, and EC$_{50}$ values decreased over prolonged time, indicative of increased long-term potency.

TABLE 40

C923B169-induced T-cell-directed kinetic cytotoxicity (Incucyte) values of CARNAVAL and OCI-Ly10 cells at different E:T ratios after 2, 3, and 6 days.

| E:T ratio | EC$_x$ | OCI-Ly10 | | | CARNAVAL | | |
|---|---|---|---|---|---|---|---|
| | | 2 days Model est. (nM): mean | 3 days Model est. (nM): mean | 6 days Model est. (nM): mean | 2 days Model est. (nM): mean | 3 days Model est. (nM): mean | 6 days Model est. (nM): mean |
| 5:1 | EC$_{20}$ | 3.74 | 1.01 | 0.33 | 1.79 | 1.22 | 1.02 |
| | EC$_{30}$ | 32.59 | 2.65 | 0.61 | 3.10 | 1.45 | 1.06 |
| | EC$_{50}$ | >100 | >100 | 1.98 | >100 | 2.90 | 1.16 |
| 1:1 | EC$_{20}$ | >100 | 3.42 | 2.07 | 0.60 | 0.22 | 0.10 |
| | EC$_{30}$ | >100 | 16.37 | 3.50 | 1.36 | 0.49 | 0.18 |
| | EC$_{50}$ | >100 | >100 | 17.14 | >100 | 5.02 | 0.44 |

EC$_x$, x % effective concentration; est., estimated; E:T ratio, effector-to-target ratio; RFP, red fluorescent protein.

Cytotoxicity to cancer cells was assessed over time using Incucyte technology after coculture of T cells with RFP-expressing CD79b$^+$/CD20$^+$ cancer cells at the indicated E:T ratios. Average EC$_x$ values from 2 independent donor over specific time are listed in the table.

Figure 18:
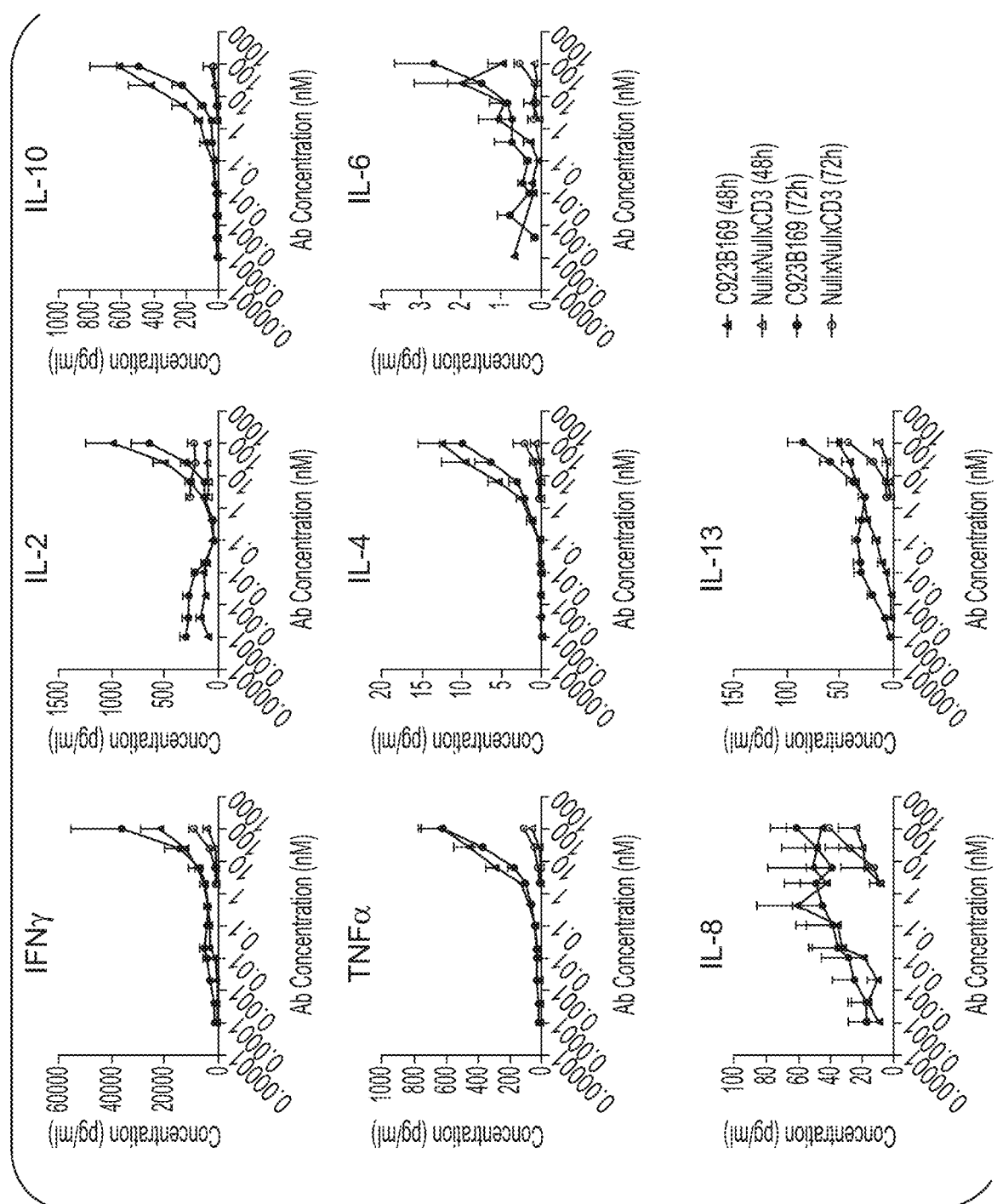
FIG. 18. C923B169-induced inflammatory cytokines in vitro in the presence of CARNAVAL cells at a 5:1 E:T ratio at 48 and 72 hours. CFSE-labeled CARNAVAL cells were added to CD3 T cells at 5:1 E:T ratio for 48 or 72 hours with increasing concentrations of C923B169. Supernatant was analyzed for inflammatory cytokines using MSD Proinflammatory kit (MSD K15049D). Values are averages of 6 individual healthy donors. Graphing of data was done in GraphPad Prism 9. Data from independent experiments were pooled and represented as mean±SEM. Ab, antibody; CFSE, carboxyfluorescein succinimidyl ester; E:T ratio, effector-to-target ratio; IFN, interferon; IL, interleukin; MSD, Meso Scale Discovery; SEM, standard error of the mean; TNF, tumor necrosis factor.
Figure 23:
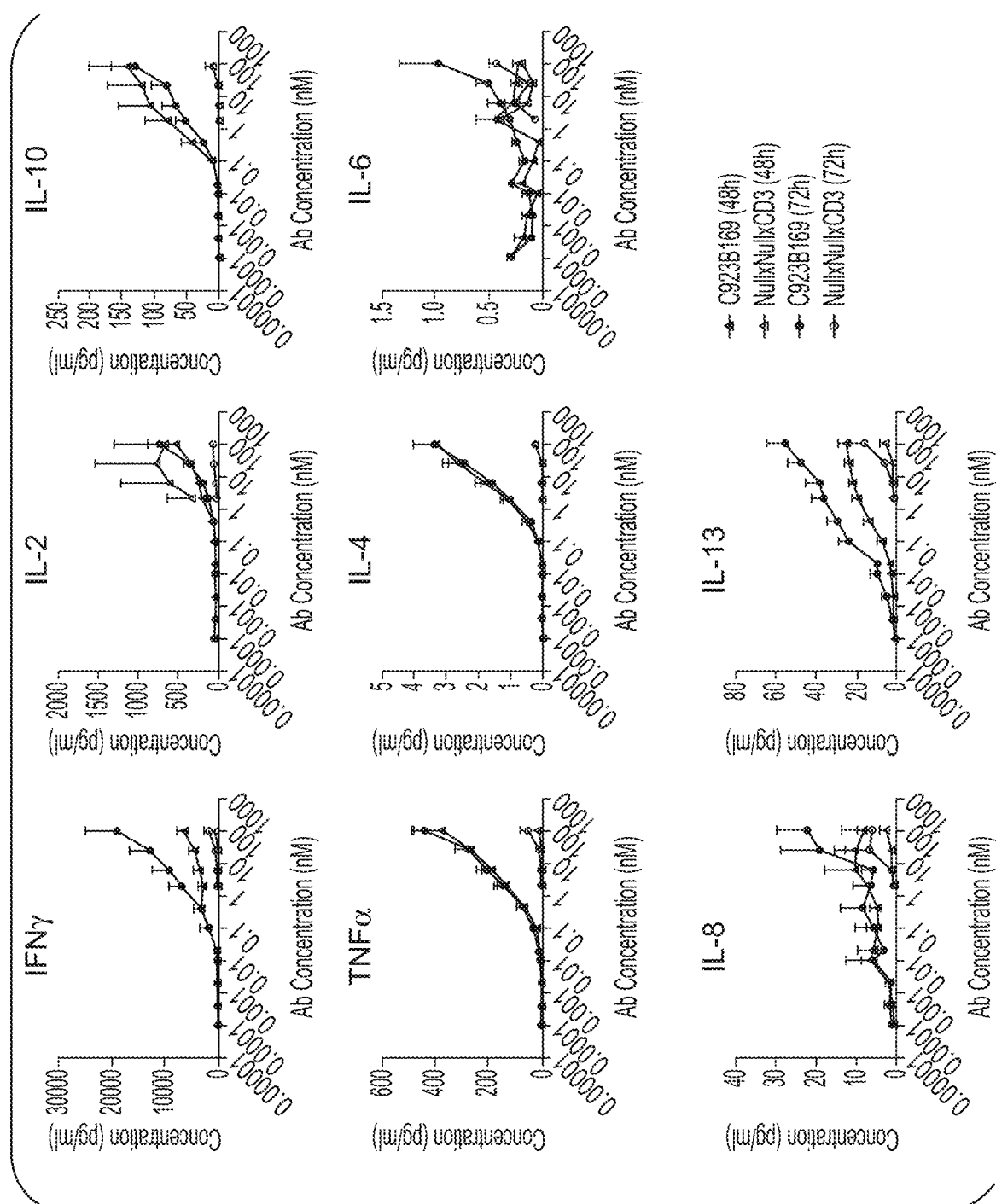
FIG. 23. C923B169-induced inflammatory cytokines in vitro in the presence of CARNAVAL cells at a 1:1 E:T ratio at 48 and 72 hours. CFSE-labeled CARNAVAL cells were added to CD3 T cells at 1:1 E:T ratio for 48 or 72 hours with increasing concentrations of C923B169. Supernatant was analyzed for inflammatory cytokines using MSD Proinflammatory kit (MSD K15049D). Values are averages of 6 individual healthy donors. Graphing of data was done in GraphPad Prism 9. Data from independent experiments were pooled and represented as mean±SEM. Ab, antibody; CFSE, carboxyfluorescein succinimidyl ester; E:T ratio, effector-to-target ratio; IFN, interferon; IL, interleukin; MSD, Meso Scale Discovery; SEM, standard error of the mean; TNF, tumor necrosis factor.
Figure 24:
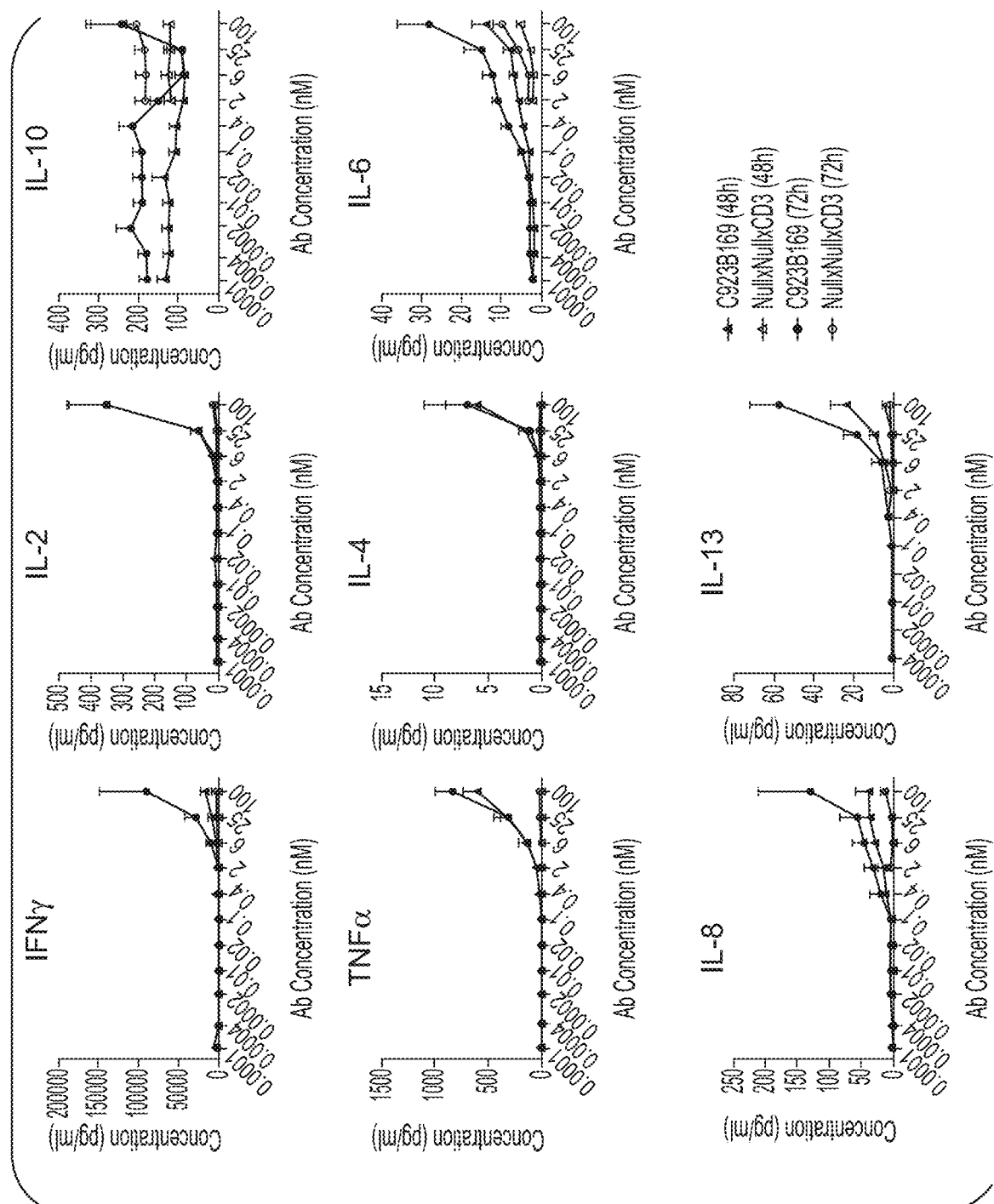
FIG. 24. C923B169-induced inflammatory cytokines in vitro in the presence of OCI-Ly10 cells at a 5:1 E:T ratio at 48 and 72 hours. CFSE-labeled OCI-Ly10 cells were added to CD3 T cells at 5:1 E:T ratio for 48 or 72 hours with increasing concentrations of C923B169. Supernatant was analyzed for inflammatory cytokines using MSD Proinflammatory kit (MSD K15049D). Values are averages of 6 individual healthy donors. Graphing of data was done in GraphPad Prism 9. Data from independent experiments were pooled and represented as mean±SEM. OCI-Ly10 cells downstream of NF-κB secrete IL-10. As C923B169 mediates CD79b antagonistic effect on OCI-Ly10 cancer cell (see Example 9), yet in the cancer cell and T-cell coculture system it mediates IL-10 cytokines secretion from T cells. The effect observed on IL-10 cytokine in this coculture system is a balance between the antagonistic effect of C923B169 on OCI-Ly10 cancer cells versus effect of C923B169 on T-cell-mediated cytokine secretion. Ab, antibody; CD, cluster of differentiation; CFSE, carboxyfluorescein succinimidyl ester; E:T ratio, effector-to-target ratio; IFN, interferon; IL, interleukin; MSD, Meso Scale Discovery; NF-κB, nuclear factor kappa-light-chain-enhancer of activated B cells; SEM, standard error of the mean; TNF, tumor necrosis factor.
Figure 25:
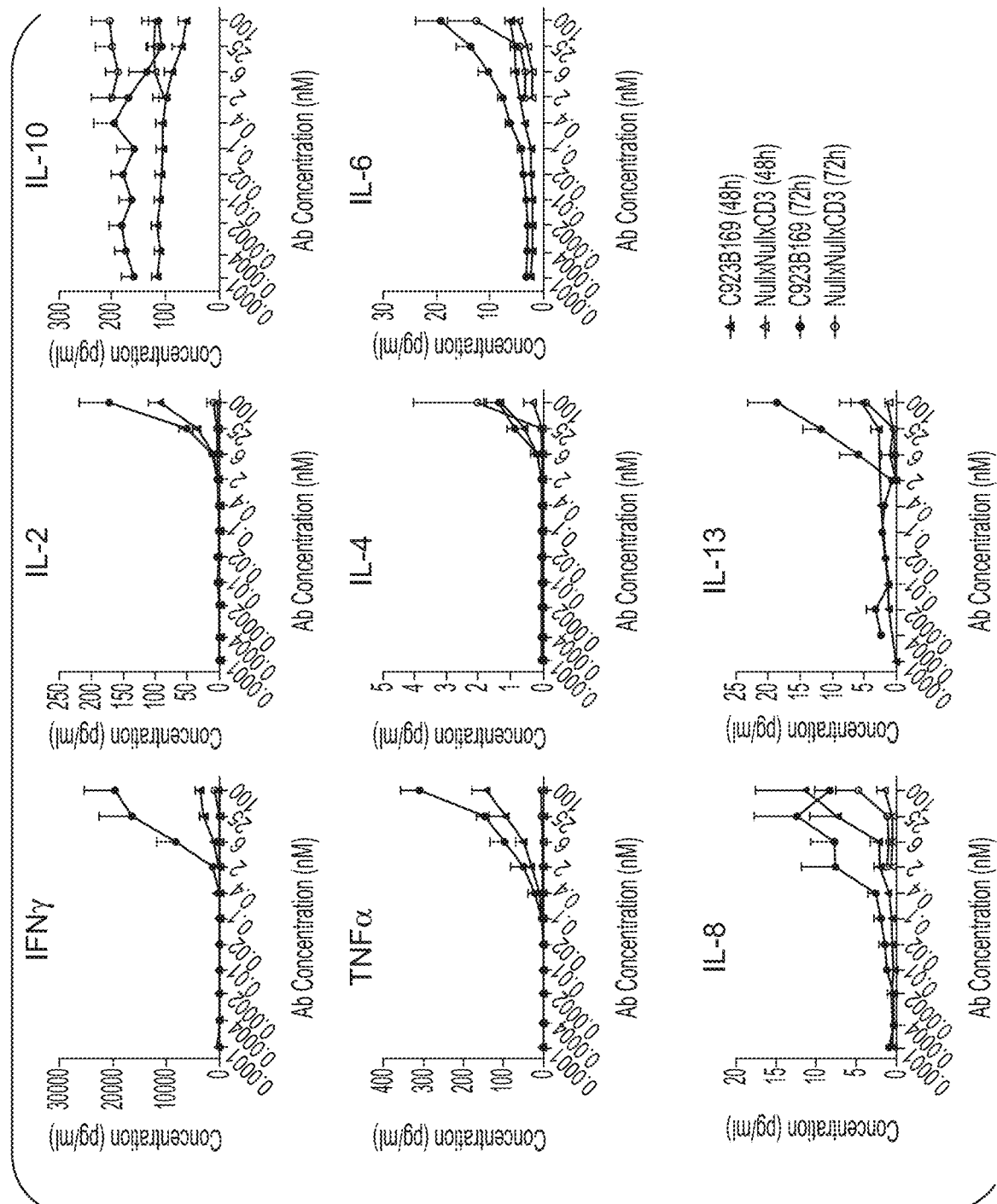
FIG. 25. C923B169-induced inflammatory cytokines in vitro in the presence of OCI-Ly10 cells at a 1:1 E:T ratio at 48 and 72 hours. CFSE-labeled OCI-Ly10 cells were added to CD3 T cells at 1:1 E:T ratio for 48 or 72 hours with increasing concentrations of C923B169. Supernatant was analyzed for inflammatory cytokines using MSD Proinflammatory kit (MSD K15049D). Values are averages of 6 individual healthy donors. Graphing of data was done in GraphPad Prism 9. Data from independent experiments were pooled and represented as mean±SEM. OCI-Ly10 cells downstream of NF-κB secrete IL-10. As C923B169 mediates CD79b antagonistic effect on OCI-Ly10 cancer cell (see Example 9), yet in the cancer cell and T-cell coculture system it mediates IL-10 cytokines secretion from T cells. The effect observed on IL-10 cytokine in this coculture system is a balance between the antagonistic effect of C923B169 on OCI-Ly10 cancer cells versus effect of C923B169 on T-cell-mediated cytokine secretion. Ab, antibody; CFSE, carboxyfluorescein succinimidyl ester; E:T ratio, effector-to-target ratio; IFN, interferon; IL, interleukin; MSD, Meso Scale Discovery; NF-κB, nuclear factor kappa-light-chain-enhancer of activated B cells; SEM, standard error of the mean; TNF, tumor necrosis factor.
Figure 28A:
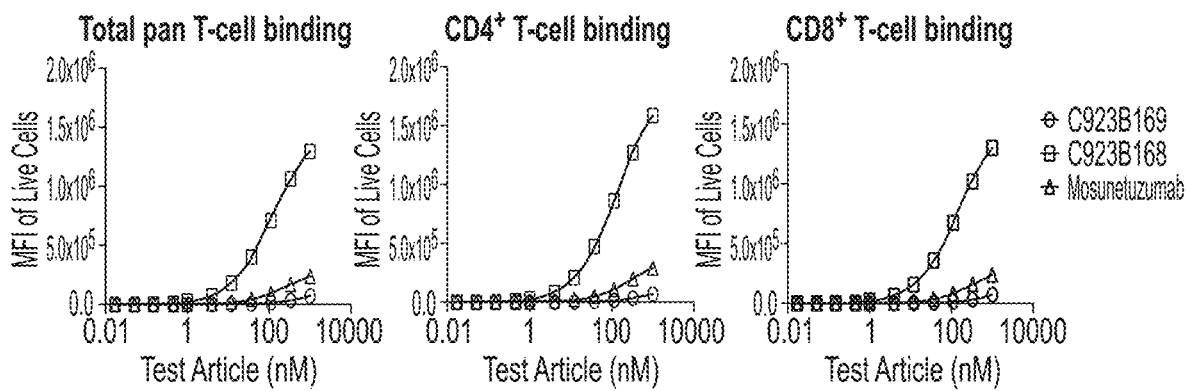
FIGS. 28A-28C. Primary T-cell binding profiles of C923B169, C923B168, and mosunetuzumab in Donor D327645 (FIG. 28A), Donor D198013 (FIG. 28B), and Donor D221837 (FIG. 28C). MFI, mean fluorescence intensity.
Figure 28B:
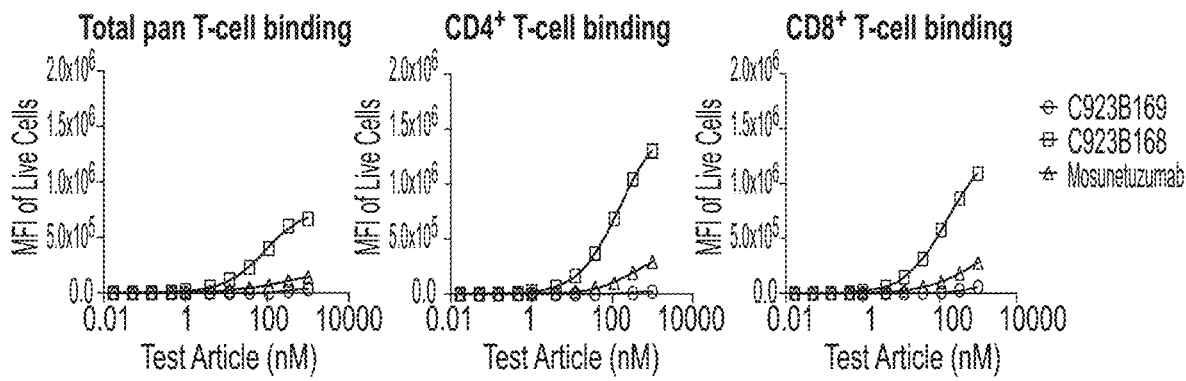
Figure 28C:
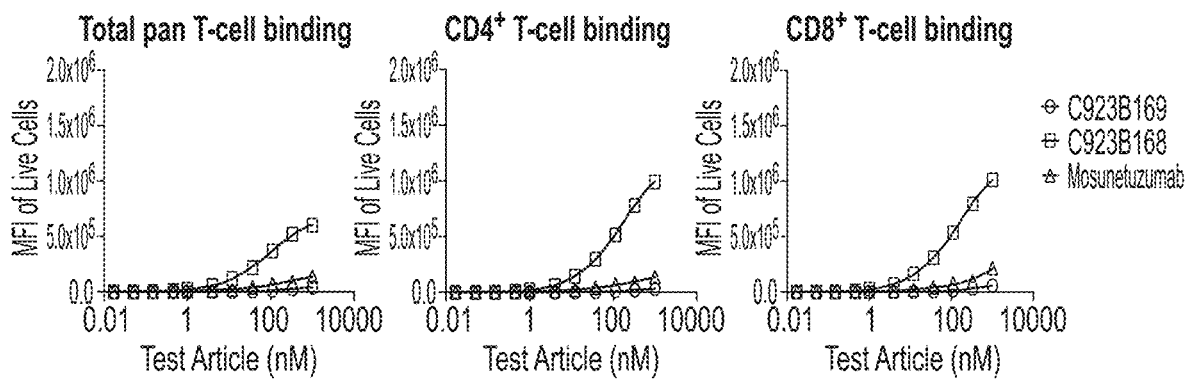
Figure 29:
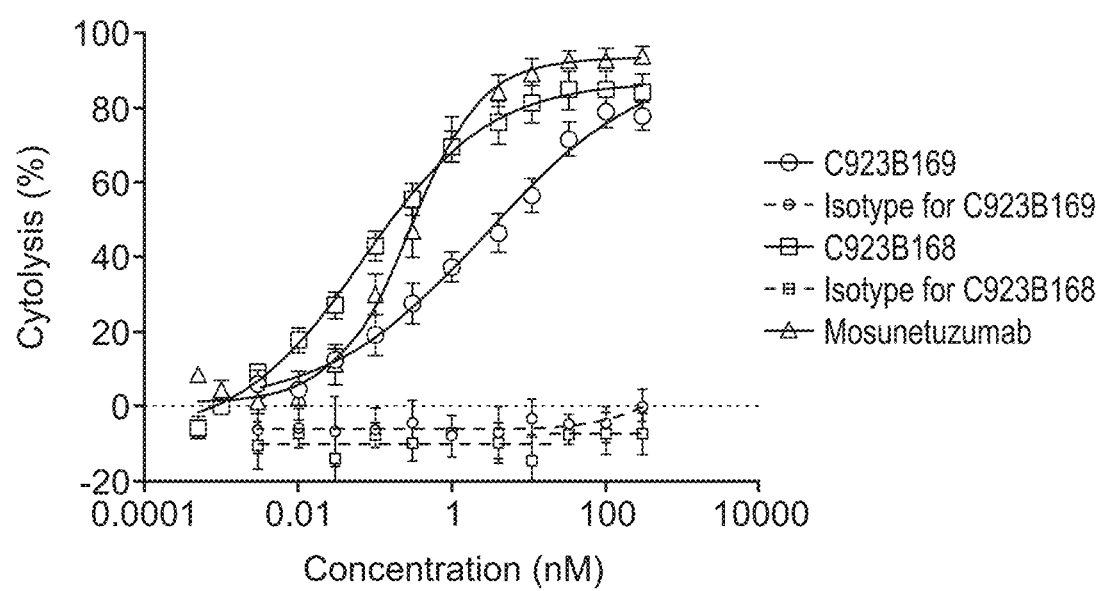
FIG. 29. Autologous B-cell depletion assay showing cytotoxicity of C923B169, C923B168, and mosunetuzumab against B cells.

C923B169-Induced Cytokine Release in the Presence of CARNAVAL and OCI-Ly10 Cell Lines at 5:1 and 1:1 Effector-to-Target Ratio To further characterize T-cell activation induced by C923B169, supernatants from the in vitro cytotoxicity assay were analyzed for cytokine levels using a Meso Scale Discovery (MSD) enzyme-linked immunosorbent assay (ELISA) Proinflammatory Panel 1. Overview of the data for T-cell-mediated cytokine release to CARNAVAL cells at an E:T ratio of 5:1 are shown in FIG. 18 and the $EC_{50}$ and corresponding maximal cytokine values are shown in Table 41. Similar results were obtained for assessment of cytokines at lower 1:1 E:T ratio and during OCI-Ly10 T-cell-mediated cytotoxicity at both 1:1 and 5:1 E:T ratio (see FIGS. 23-25, Tables 42-43). As hypothesized, weak engagement of CD3 resulted in T-cell activation with lower cytokine release across tested cell lines in in vitro T-cell cytotoxicity assays as compared to the trispecific C923B168, which has medium affinity for CD3 (pan T-cell binding $EC_{50}=104\pm18$ nM), and mosunetuzumab (see FIGS. 28A-28C, Table 44).

TABLE 41

C923B169-induced inflammatory cytokines in the presence of CARNAVAL and OCI-Ly10 cells at different E:T ratios at 48 and 72 hours ($EC_{50}$ [nM] and maximal cytokine release [pg/mL] values)).

| | | 48-hour incubation | | | |
| | | CARNAVAL | | OCI-Ly10 | |
| | | E:T ratio | | | |
| Cytokine | Value | 1:1 | 5:1 | 1:1 | 5:1 |
|---|---|---|---|---|---|
| IFN-γ | $EC_{50}$ | 2.097 | NE | 36.339 | 55.646 |
| | Max value | 4,213.3 | NE | 5,630.8 | 16,564.2 |
| IL-1β | $EC_{50}$ | NE | NE | ND | ND |
| | Max value | NE | NE | ND | ND |
| IL-2 | $EC_{50}$ | 2.871 | 15.516 | 62.195 | >100* |
| | Max value | 386.8 | 747.7 | 105.0 | 461.7 |
| IL-4 | $EC_{50}$ | 1.894 | 7.946 | NE | NE |
| | Max value | 2.1 | 11.1 | NE | NE |
| IL-8 | $EC_{50}$ | NE | NE | 15.050 | 1.944 |
| | Max value | NE | NE | 5.3 | 19.1 |
| IL-6 | $EC_{50}$ | NE | NE | 1.251 | NE |
| | Max value | NE | NE | 5.5 | NE |
| IL-10 | $EC_{50}$ | 1.047 | >100* | NE | NE |
| | Max value | 81.0 | 1,173.8 | NE | NE |
| IL-13 | $EC_{50}$ | 0.429 | 3.392 | NE | NE |
| | Max value | 0.2 | 42.5 | NE | NE |
| TNF-α | $EC_{50}$ | 2.158 | 60.226 | >100* | >100* |
| | Max value | 282.0 | 980.4 | 234.6 | 1,310.3 |

| | 72-hour incubation | | | |
| | CARNAVAL | | OCI-Ly10 | |
| | E:T ratio | | | |
| Cytokine | 1:1 | 5:1 | 1:1 | 5:1 |
|---|---|---|---|---|
| IFN-γ | 1.571 | 48.338 | 13.744 | 85.887 |
| | 12,185.5 | 30,242.4 | 16,383.0 | 59,934.1 |
| IL-1β | NE | NE | ND | ND |
| | NE | NE | ND | ND |
| IL-2 | >100* | >100* | >100* | >100* |
| | 1,005.3 | 1,468.5 | 0.1 | 1,253.9 |
| IL-4 | 14.044 | 37.367 | NE | NE |
| | 3.0 | 11.1 | NE | NE |
| IL-8 | NE | NE | >100* | 1.878 |
| | NE | NE | 23.2 | 32.8 |
| IL-6 | NE | NE | 8.545 | NE |
| | NE | NE | 17.1 | NE |
| IL-10 | 0.939 | >100* | NE | NE |
| | 67.2 | 223,016.3 | NE | NE |
| IL-13 | 0.202 | 17.497 | NE | NE |
| | 42.9 | 77.3 | NE | NE |
| TNF-α | 10.573 | >100* | 33.971 | >100* |
| | 397.0 | 2,382.7 | 344.8 | 3,143.2 |

CFSE, carboxyfluorescein succinimidyl ester; $EC_{50}$, 50% effective concentration; E:T ratio, effector-to-target ratio; IFN, interferon; IL, interleukin; MSD, Meso Scale Discovery; Max value, maximal cytokine release value; ND; not detectable in 5 out of 6 donors; NE, not estimable; TNF, tumor necrosis factor.
CFSE-labeled CARNAVAL cells were added to CD3 T cells at 5:1 or 1:1 E:T ratio for either 48 or 72 hours with increasing concentrations of C923B169. Supernatants were analyzed for inflammatory cytokines using a custom MSD Proinflammatory kit (MSD K15049D). Values are representative of 6 individual healthy donors. $EC_{50}$ estimates come from a non-linear mixed effects model and standard 4-parameter logistic regression model as the fixed effects (minimum, maximum, slope, and log$EC_{50}$) and using donor as a random effect. $EC_{50}$ values could not be estimated for cytokines for which non-sigmoidal or decreasing response was observed and were listed in the table as NE. The model was fit using log-transformed data, estimates of interest were back-transformed to the original scale for reporting.
*$EC_{50}$ values estimated to be higher than highest tested concentration.

TABLE 42

C923B169-induced lower levels of inflammatory cytokines as compared to C923B168 and mosunetuzumab (MSCB782.001) in the presence of CARNAVAL and OCI-Ly10 cells at different E:T ratios at 48 and 72 hours ($EC_{50}$ values [nM]).

|  |  | 48 hour incubation | | | | 72 hour incubation | | | |
|---|---|---|---|---|---|---|---|---|---|
|  |  | CARNAVAL | | OCI-Ly10 | | CARNAVAL | | OCI-Ly10 | |
|  |  | | | | E:T | | | | |
| Cytokine | Antibody | 1:1 | 5:1 | 1:1 | 5:1 | 1:1 | 5:1 | 1:1 | 5:1 |
| IFN-γ | C923B169 | 2.097 | NE | 36.339 | 55.646 | 1.571 | 48.338 | 13.744 | 85.887 |
|  | C923B168 | 0.451 | 0.774 | 0.522 | 3.642 | 25.541 | 4.864 | 1.244 | 3.263 |
|  | Mosunetuzumab | 0.201 | 14.483 | 0.174 | 0.639 | 0.625 | >100* | 0.367 | 0.931 |
| IL-2 | C923B169 | 2.871 | 15.516 | 62.195 | >100* | >100* | >100* | >100* | >100* |
|  | C923B168 | 1.520 | 1.160 | >100* | 77.461 | 2.123 | 2.588 | 28.409 | 26.548 |
|  | Mosunetuzumab | 0.794 | 1.094 | 1.464 | 6.430 | 4.947 | 2.035 | 3.457 | 9.436 |
| TNF-α | C923B169 | 2.158 | 60.226 | >100* | >100* | 10.573 | >100* | 33.971 | >100* |
|  | C923B168 | 0.292 | 1.774 | 7.505 | 10.138 | 1.359 | 2.090 | 5.349 | 11.121 |
|  | Mosunetuzumab | 0.362 | 1.398 | 0.549 | 1.944 | 2.840 | 2.790 | 0.629 | 1.711 |

$EC_{50}$, 50% effective concentration; E:T ratio, effector-to-target ratio; IFN, interferon; IL, interleukin; NE, not estimable; TNF, tumor necrosis factor.
Values are representative of 5 to 6 individual healthy donors. A non-linear mixed effect model was used to estimate dose-response using the 4 parameters of standard 4-parameter logistic regression model as fixed (minimum, maximum, slope, and $logEC_{50}$) and using donor as a random effect. $EC_{50}$ (nM) values were derived using post-hoc estimation. Data from independent experiments were pooled and represented as mean.
*$EC_{50}$ values estimated to be higher than highest tested concentration.

TABLE 43

Comparison of C923B169-induced CD8 T-cell activation as compared to C923B168 and mosunetuzumab (MSCB782.001): $EC_{50}$ values of CD8 T-cell activation from T-cell cytotoxicity assays with different cancer cell lines at different E:T ratios at 48 and 72 hours.

|  | 48 hours: mean values | | | | | 72 hours: mean values | | | | |
|---|---|---|---|---|---|---|---|---|---|---|
|  | JEKO-1 | CARNAVAL | OCI-Ly10 | HT | WILL-2 | JEKO-1 | CARNAVAL | OCI-Ly10 | HT | WILL-2 |
|  | | | E:T ratio 5:1 | | | | | | | |
| C923B169 | 0.097 | 0.465 | 3.925 | 1.648 | 5.048 | 0.068 | 0.185 | 2.386 | 0.638 | 12.651 |
| C923B168 | 0.051 | 1.901 | 2.346 | 0.859 | 0.885 | 0.020 | 0.079 | 0.815 | 0.451 | 2.288 |
| Mosunetuzumab | 0.043 | 0.038 | 0.256 | 0.148 | 1.237 | 0.019 | 0.021 | 0.120 | 0.078 | 1.268 |
|  | | | E:T ratio 1:1 | | | | | | | |
| C923B169 | 0.099 | 0.207 | 0.295 | NA | NA | 0.098 | 0.107 | 0.386 | NA | NA |
| C923B168 | 0.021 | 0.063 | 0.141 | NA | NA | 0.031 | 0.032 | 0.087 | NA | NA |
| Mosunetuzumab | 0.022 | 0.053 | 0.045 | NA | NA | 0.021 | 0.013 | 0.035 | NA | NA |

$EC_{50}$, 50% effective concentration; E:T ratio, effector-to-target ratio; NA, not assessed.
Values are representative of 5 to 6 individual healthy donors. A non-linear mixed effect model was used to estimate dose-response using the 4 parameters of standard 4-parameter logistic regression model as fixed (minimum, maximum, slope, and $logEC_{50}$) and using donor as a random effect. $EC_{50}$ (nM) values were derived using post-hoc estimation. Data from independent experiments were pooled and represented as mean.

TABLE 44

Max MFI values for primary T-cell binding.

| | Mean Max MFI ± SD (×10⁶) | | |
|---|---|---|---|
| | C923B169 | C923B168 | Mosunetuzumab |
| Pan T-cell binding | 0.05 ± 0.02 | 0.87 ± 0.39 | 0.13 ± 0.06 |
| CD4⁺ T-cell binding | 0.04 ± 0.02 | 1.30 ± 0.30 | 0.23 ± 0.11 |
| CD8⁺ T-cell binding | 0.06 ± 0.01 | 1.13 ± 0.15 | 0.23 ± 0.05 |

Max, maximum; MFI, mean fluorescence intensity; SD, standard deviation.
C923B168 has an $EC_{50}$ value of 104 ± 18 nM.

C923B169-Induced T-Cell-Mediated Cytotoxicity of Primary B Cells in the Autologous Setting (B-Cell Depletion Assay)

Figure 19:
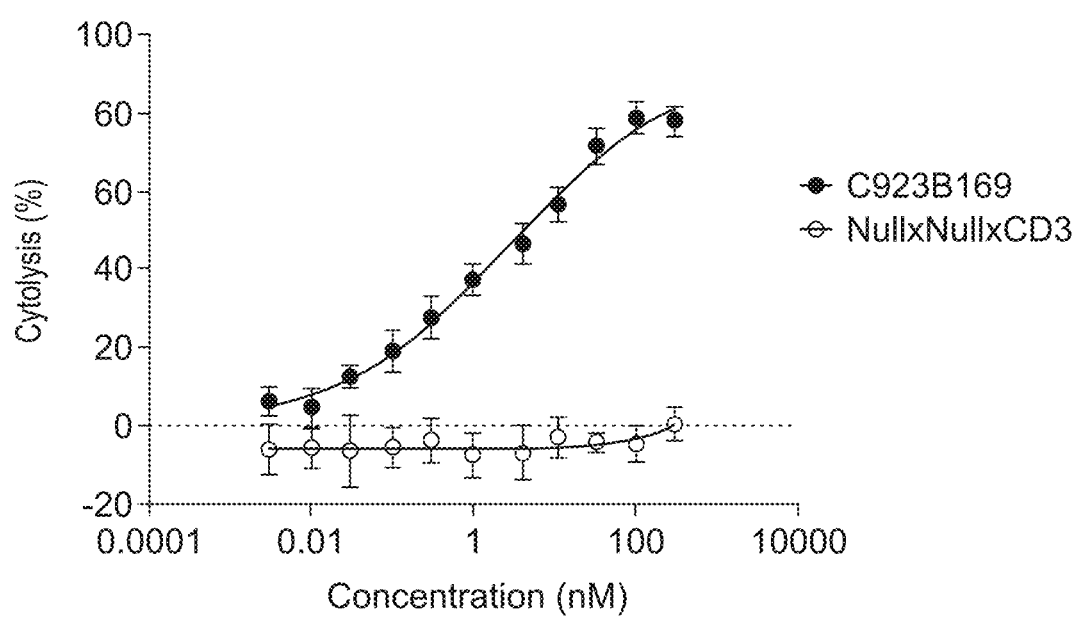
FIG. 19. Autologous B cell depletion assay showing cytotoxicity of C923B169 on primary target B cells.
Figure 20A:
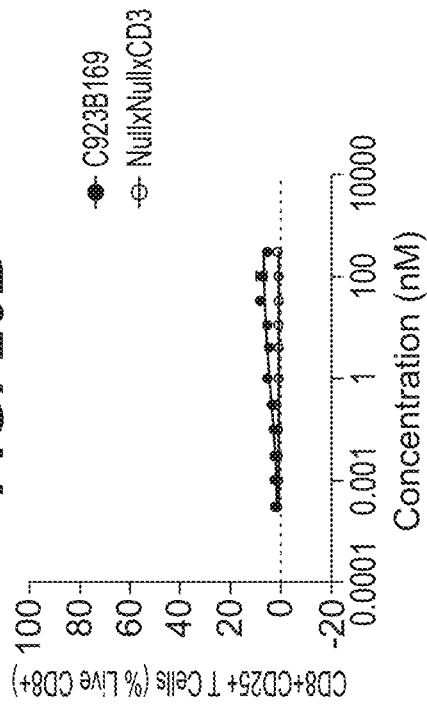
FIGS. 20A-20D. Autologous B-cell depletion assay showing T-cell activation profiles with C923B169 treatment.
Figure 20B:
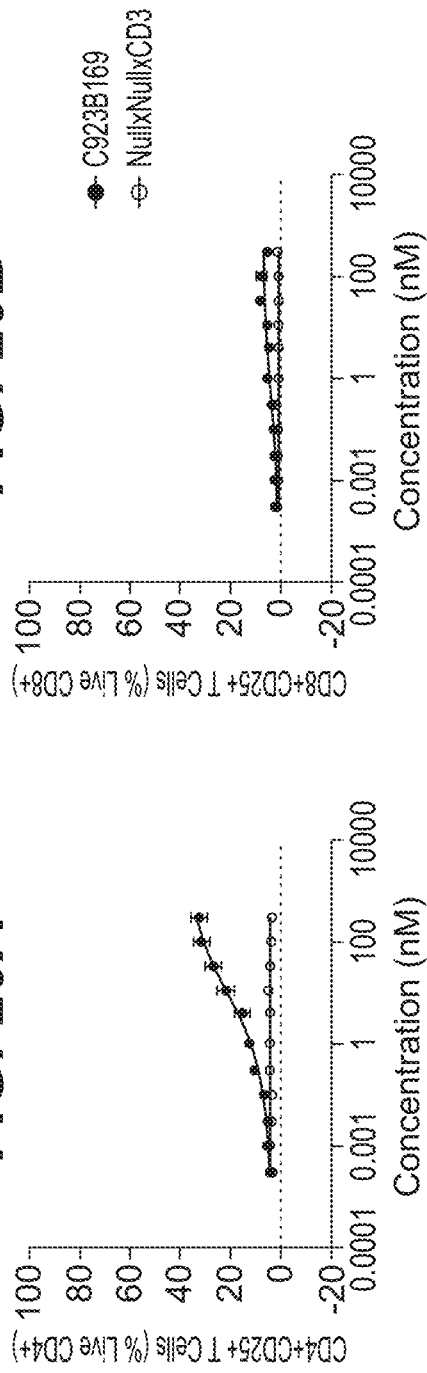
Figure 20C:
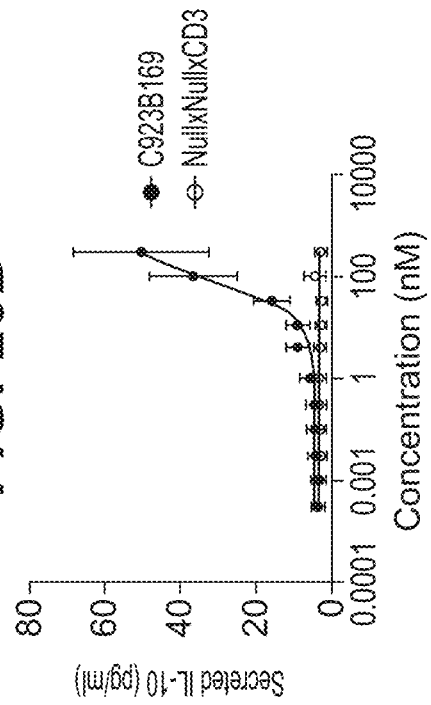
Figure 20D:
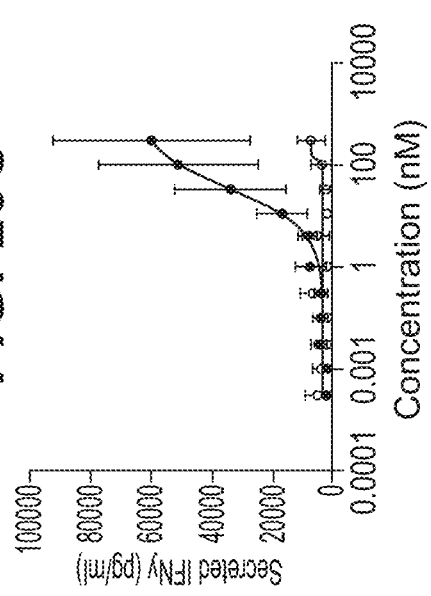

The cytotoxicity of C923B169 against autologous B cells was evaluated with peripheral blood mononuclear cells (PBMCs) from 3 different normal human donors. C923B169 was incubated with PBMCs from each donor for 72 hours at 37° C., followed by the assessment of cytotoxic and T-cell activation effectiveness. The E:T ratio of the individual donors was 1:1 for donor D327645, 1:1 for donor D198013, and 1:2 for donor D221837. C923B169 showed robust cytotoxicity of autologous B cells (FIG. 19), with an $EC_{50}$ value of 3.3±2.6 nM and a maximum cytotoxicity value of 81%±11%. T-cell activation with lower levels of secreted cytokines than for mosunetuzumab were measured, showing the desired T-cell profiles for C923B169 (FIGS. 20A-20D; see FIG. 29, FIGS. 30A-30D, Table 45).

TABLE 45

Autologous B-cell depletion assay calculated $EC_{50}$ values and maximum cytotoxicity.

| | D329465 | | D198013 | | D221837 | |
|---|---|---|---|---|---|---|
| | $EC_{50}$ (nM) | Max kill (%) | $EC_{50}$ (nM) | Max kill (%) | $EC_{50}$ (nM) | Max kill (%) |
| C923B169 | 2.0 | 69 | 1.70 | 92 | 6.30 | 81 |
| C923B168 | 0.1 | 69 | 0.02 | 88 | 0.1 | 95 |
| Mosunetuzumab | 0.2 | 86 | 0.2 | 97 | 0.5 | 98 |

$EC_x$, x % effective concentration; Max kill, maximum cytotoxicity.

Antagonistic Activity of C923B169

Figure 21:
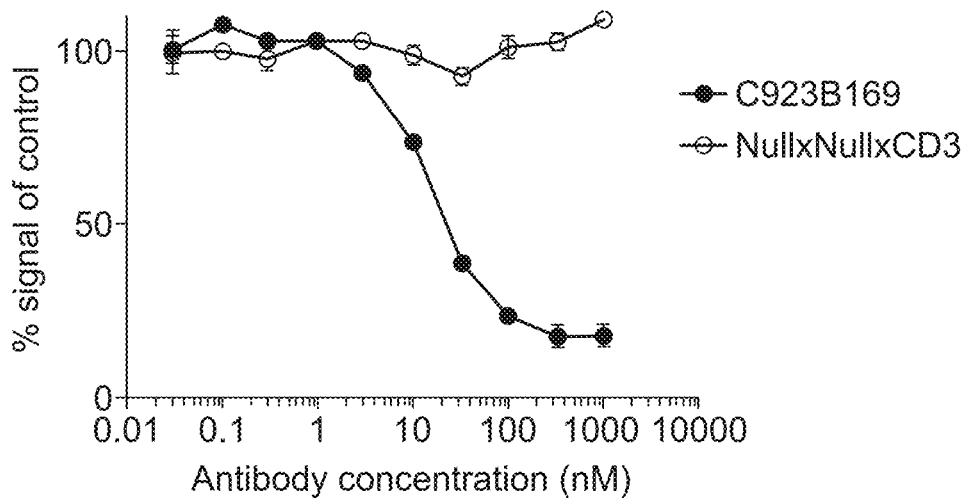
FIG. 21. C923B169-induced antagonism of IL 10 secretion. C923B169 was added at a range of concentrations to activated B cell DLBCL cell line (OCI Ly10) for 24 hours to assess the effect on IL 10 secretion. IL 10 levels were normalized to untreated control cells and expressed as percent.

Phosphorylation of CD79a and CD79b initiates BCR signaling. One of the prominent downstream signaling pathways engaged after BCR stimulation is the classical NF-κB pathway, which is frequently activated in ABC DLBCL due to oncogenic mutations in CD79a/b or caspase recruitment domain family member 11 (CARD11). NF-κB signaling regulates the expression of multiple cytokines, including IL-10. Secretion of IL-10 by CD79b mutant OCI-Ly10 (ABC DLBCL) cells was measured using a MSD assay. Inhibition of NF-κB signaling by C923B169 resulted in a decrease of IL-10 secretion indicative of antagonistic activity of C923B169 (FIG. 21). The $EC_{50}$ value of C923B169 was 15.43 nM.

C923B169-Induced T-Cell-Mediated Cytotoxicity of B-Cell Lymphoma Xenografts In Vivo The antitumor efficacy of C923B169 was evaluated in SC human double-hit (DH) DLBCL CARNAVAL (Study A) and human ABC DLBCL OCI-Ly10 xenografts (Study B) in T-cell-humanized mice. For all studies, female NSG (i.e., non-obese diabetic [NOD] severe combined immunodeficiency [scid] or NOD.Cg $Prkdc^{scid}$ $Il2rg^{tm1Wjl}$/SzJ) mice (Charles River Labs, Lyon, France) were used to provide a suitable host for reconstituting a human immune system using human donor CD3+ pan T cells. Mice were inoculated with $1\times10^6$ CARNAVAL or OCI-Ly10 lymphoma tumor cells SC prior to T-cell engraftment. The implant day was designated as Day 0 of the study.

Expanded human pan T cells were inoculated intraperitoneally (IP) into NSG mice to humanize the immune system. Humanization of mice with CD3-expressing T cells provided effector cells to facilitate C923B169-mediated cytotoxicity to human CD79b/CD20-expressing tumor cells. T-cell-humanized mice were given Fc block IP and intravenous immunoglobulin (IVIg) IP at least 30 minutes prior to C923B169 dosing to correct for the low Ig environment in NSG mice.

Figure 22A:
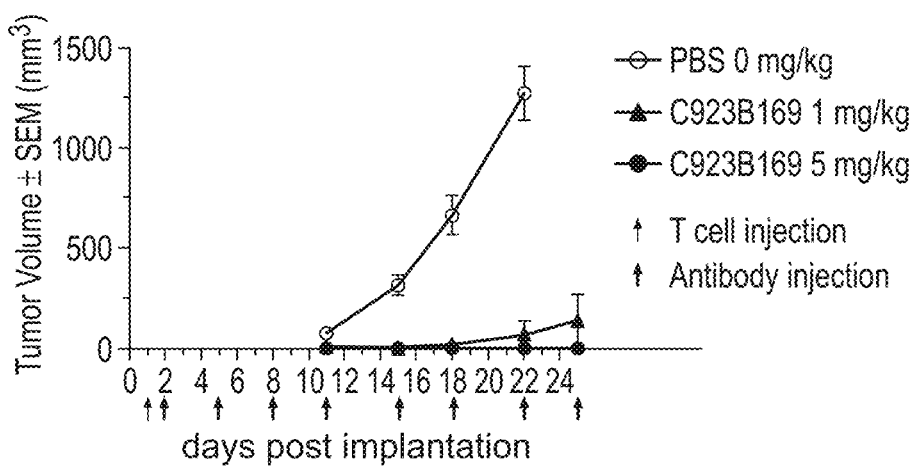
FIGS. 22A-22B. Antitumor efficacy of C923B169 in subcutaneous CARNAVAL xenografts (FIG. 22A) and OCI Ly10 xenograft (FIG. 22B) in T cell-humanized NSG mice. T cell-humanized (T cell injection indicated by grey arrow) NOD scid gamma or NOD.Cg Prkdc$^{scid}$ Il2rg$^{tm1Wjl}$/SzJ (NSG) mice injected SC with (FIG. 22A) CARNAVAL tumors or (FIG. 22B) OCI Ly10 tumors were dosed intraperitoneally (IP) with C923B169 at 1 and 5 mg/kg for CARNAVAL model or at 3 and 10 mg/kg for OCI Ly10 model (dosing indicated by black arrows). Tumor volume was measured twice weekly and results presented as the mean tumor volume±SEM for each group. Data graphically represented for each group with >66% of mice remaining. PBS, phosphate-buffered saline.

Efficacy Study A (FIG. 22A) served as a tumor growth prevention study. NSG mice were randomly assigned into groups of 10 animals, implanted SC with CARNAVAL cells, humanized with pan T cells on Day 1 post cell implantation and treated with C923B169 IP from Day 2 post cell implantation onwards at 1 and 5 mg/kg twice weekly for a total of 8 doses. Percent tumor growth inhibition (TGI) of SC CARNAVAL xenografts was calculated on Day 22 post tumor implantation, when >66% of control animals remained on study. Statistically significant TGI was observed with C923B169 at 1 and 5 mg/kg resulting in 94.6% (p<0.0001) and 100% (p<0.0001) TGI, respectively, as compared with vehicle-treated controls (phosphate-buffered saline [PBS]).

Figure 22B:
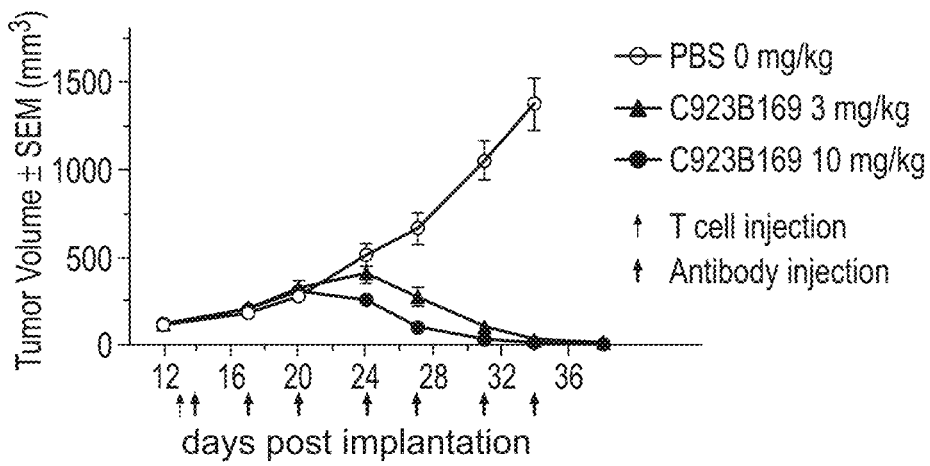

In efficacy Study B (FIG. 22B), NSG mice were randomized into groups of 10 animals and humanized with T cells 13 days post OCI-Ly10 SC cell implantation with starting tumor volumes averaging 108 mm³. IP treatment with 3 and 10 mg/kg of C923B169 per animal was initiated on Day 14 post OCI-Ly10 cell implantation twice weekly for a total of 7 doses. Percent ΔTGI of SC OCI-Ly10 xenografts was calculated on Day 34 post tumor implantation, when >66% of control animals remained on study. Statistically significant ΔTGI was observed with C923B169 at 3 and 10 mg/kg resulting in 94.6% (p<0.0001) and 100% (p<0.0001) ΔTGI, respectively, as compared with vehicle-treated controls (PBS). Tumor regression as compared to initial tumor burden of SC OCI-Ly10 xenografts was evaluated on Day 34 and 38 (i.e., 3 days post final dose). Tumor regression was observed with C923B169 at 3 and 10 mg/kg resulting in 69.1% (p<0.001) and 86.6% (p<0.001) tumor regression, respectively, at Day 34, progressing to almost complete tumor regression of 91.2% (p<0.001) and 98.1% (p<0.001) respectively, at Day 38 compared to initial tumor burden.

In both studies, treatment with C923B169 at 1 or 5 mg/kg (for Study A up to Day 25) and 3 or 10 mg/kg (for Study B up to Day 38) did not show signs of body weight loss or other signs of gross toxicity. First signs of graft-versus-host disease (GvHD)-related morbidity due to the humanization with T cells was observed on Day 38 in Study B, but not in Study A.

Taken together, the in vitro and in vivo results presented above document C923B169's ability to induce potent and antigen-specific cytotoxicity to cancer cells and tumor regression.

In vitro, C923B169 led to cytotoxicity to cancer cells in a broad panel of NHL cell models showing different levels of CD79b and CD20 surface expression, both in long- and short-term assays. No impact on cancer cell viability of target-negative cell lines was observed. Moreover, B-cell depletion was observed in the autologous system in presence of C923B169. T-cell activation with lower cytokine secretion were observed across the in vitro T-cell cytotoxicity assays as compared to the trispecific C923B168, which has medium affinity to CD3, and mosunetuzumab. This is in line with the weak engagement of CD3 by C923B169.

In vivo, C923B169 prevented tumor growth in the CARNAVAL xenograft model and induced potent tumor regression in the OCI-Ly10 xenograft model.

Example 10: Minimal Target-Related Risks Associated with CD79b×CD20×CD3 Trispecific Antibody Normal Tissue Expression With T-cell-engaging antibodies, on-target/off-tumor toxicity has been identified as a risk in cases where expression of the targeted tumor antigen(s) is not restricted to the tumor. Data in the public domain on CD79b- and CD20-related immune cell and tissue expression were reviewed (results further described below). Furthermore, CD79b expression using IHC on FFPE tissue microarrays (TMAs) was also assessed and CD79b positivity was found to be limited to mononuclear cells consistent with lymphocytes. IHC for CD20 expression was not conducted due to the consistent view from available clinical data for multiple marketed CD20-targeted cytolytic therapeutics.

Figure 31:
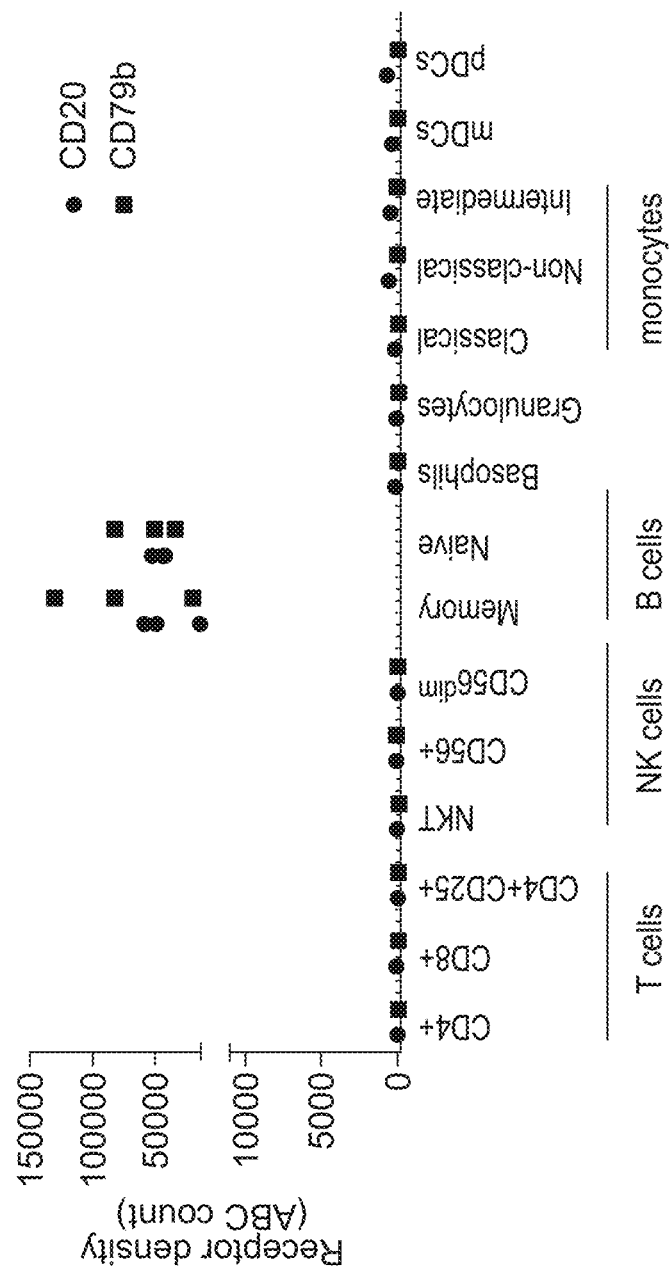
FIG. 31. CD79b and CD20 expression profile in peripheral blood. CD79b and CD20 receptor density results in several immune cell populations were evaluated in whole blood derived from 3 different healthy donors. CD79b expression was determined by flow cytometry using a PE-labeled commercial antibody (human CD79B-PE clone #SN8, BD Bioscience #335833), CD20 expression was determined by flow cytometry using a PE-labeled commercial antibody (human CD20-PE clone #2H7, BD Bioscience #555623), and receptor counts were calculated using the Quantum Simply cellular kit (Bangslabs #815). NKT, natural killer T cell; mDC, myeloid dendritic cell; pDC, plasmacytoid dendritic cell; PE, phycoerythrin.

By IHC, CD79b positivity was found to be limited to mononuclear cells consistent with lymphocytes. To confirm B-cell-lineage-specific expression of CD79b and CD20, receptor density was measured on peripheral blood cells derived from 3 different healthy human donors (FIG. 31). The results confirmed that CD79b and CD20 expression are detectable only on B cells as already suggested by the RNA sequencing (RNA-seq) analysis of CD79b performed on 21 distinct purified immune cell subsets isolated from individual peripheral blood samples.

Based on these data, there is a low risk of on-target/off-tumor toxicity for C923B169 beyond B-cell aplasia due to the restricted expression of CD79b and/or CD20 on cells of the B-cell lineage.

CD79b Tissue Expression

CD79 is a disulfide-linked heterodimer of CD79a and CD79b and constitutes the signaling component of the BCR (19). CD79b is restrictively expressed on the surface of B cells from pre-B to memory B-cell stage and is overexpressed in DLBCL, FL, and MCL, and numerous other B-cell neoplasms (37).

A comprehensive in silico evaluation of CD79b tissue expression was performed based on public and proprietary database and literature searches. CD79b mRNA expression was detected in lymphoid organs, gastrointestinal, immune stem and progenitor cells, and myeloid cells. CD79b protein expression was observed in bone marrow, lymph nodes, spleen, and tonsil (using RNA-seq [CAGE; FANTOM5; Blueprint; Human Proteome Map]). Literature indicates the presence of CD79b-positive staining for most B cells present in peripheral blood and lymphoid tissue (38-40). Although there is 1 literature report of aberrant CD79b T-cell reactivity (41), CD79b protein expression on T cells was not detected by in-house in silico analysis or flow cytometry. In fact, receptor density on non-B immune cells appeared negligible/absent (FIG. 31).

Figure 32:
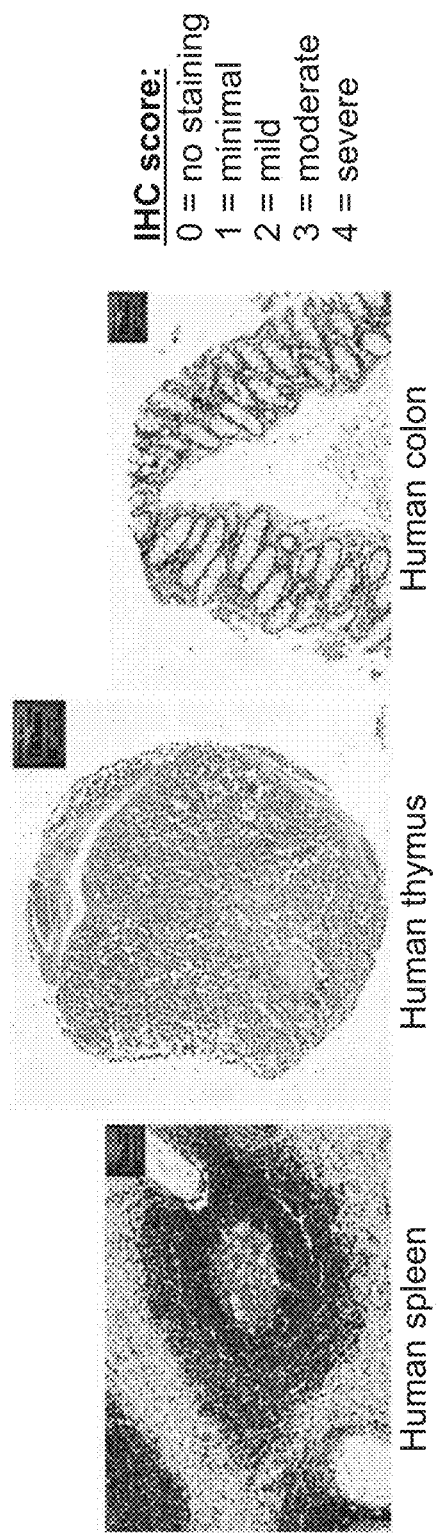
FIG. 32. CD79b expression profile in normal tissues. Photomicrographs of CD79b immunohistochemistry (IHC)-stained core biopsies from an formalin-fixed, paraffin-embedded (FFPE) human normal tissue microarray (TMA). Strong positive staining of mononuclear cells was present (CD79b antibody: CST rabbit mAb clone D7V2F; 0.15 μg/mL).

In an IHC study using core biopsies from FFPE human normal TMA, CD79b$^+$ staining was restricted to mononuclear cells consistent with B cells (FIG. 32). The distribution pattern of CD79b$^+$ IHC-positive cells within tissues was consistent with B cells based on positive cells located primarily in follicular structures in lymph node, spleen, and tonsil. CD79b$^+$ mononuclear cell staining in other tissues (ie, small intestine, colon, thymus, bone marrow, breast, lung, esophagus, salivary gland, uterus, cervix, skin) was consistent with resident lymphocytes or lymphoid infiltrates. Non-B-cell subsets of lymphocytes or mononuclear cells cannot be excluded based solely on distribution patterns. However, in peripheral blood, only B cells were CD79b$^+$ (FIG. 31).

Similar results were achieved upon IHC staining of an FFPE cynomolgus monkey normal tissue TMA. Detection of mRNA or protein (Human Proteome Map) in tissues is consistent with the presence of resident or circulating B-cell populations as demonstrated by the IHC on human normal TMA. Detection of mRNA on myeloid cells was not demonstrated at the protein level based on the peripheral blood immunophenotyping.

CD20 Tissue Expression

CD20 is a transmembrane protein restricted to the surface of B cells. Like CD79b, a comprehensive in silico evaluation of CD20 tissue expression analysis was performed. The results for CD20 are similar to CD79b with presence of CD20 mRNA restricted to B cells in lymphoid organs, gastrointestinal (ileum, stomach mucosa, rectum), gall bladder and selected T cells (using RNA-seq [CAGE; FANTOM5; Blueprint; Human Proteome Map]). Literature indicates the presence of CD20$^+$ staining for most B cells present in peripheral blood and lymphoid tissue (38-40).

Determination of expression of CD20 was not performed using in-house IHC given the available literature regarding CD20 B-cell-restricted expression in normal tissue (42-45), and over a decade of anti-CD20 cytolytic therapy in numerous cancers and other diseases including NHL, Burkitt lymphoma, FL, CLL (46), relapsing multiple sclerosis, systemic lupus erythematosus, rheumatoid arthritis, and others (47), have not identified on-target/off-tumor toxicity beyond the B-cell lineage. In addition, T-cell depletion has not been reported with B-cell cytolytic therapies. Furthermore, treatment of cynomolgus monkeys with rituximab was well tolerated and exhibited depletion of peripheral blood B cells (48); and knockout of CD20 in the mouse did not impact B-cell development or function (49).

Related to expression on T cells, limited expression of CD20 on memory myelin-specific CD8$^+$ T-cells has been directly implicated in multiple sclerosis pathogenesis in addition to its role in B cells. Notably, reconstitution of CD20$^+$ T cells occurs more rapidly than CD20$^+$ B cells (50,51).

It can be concluded, based upon the information detailed above, that any on-target/off-tumor toxicity for C923B169 is expected to be limited to normal B cells.

Example 11: Binding Characteristics of the CD3, CD79b and CD20 Binding Arms

Detailed below are the evaluations conducted to determine binding characteristics of the CD3 binding arm and the TAA (i.e., CD79b and CD20) binding arms.

CD3 Binding Arm

The CD3 binder used in C923B169, CD3B2030, binds to CD3 on the surface of human, but not of cynomolgus monkey, peripheral blood T cells.

CD3B2030 (tested as a NullxCD3 or NullxNullxCD3, 79C3B615 and C923B175, respectively) was assessed by flow cytometry for binding to cynomolgus monkey and human peripheral blood T cells. The results indicated that CD3B2030 does not bind cynomolgus monkey T cells unlike the positive control anti-CD3 clone SP34, which is cross-reactive with cynomolgus monkey CD3. As expected, CD3B2030 did bind to human peripheral blood T cells at a similar frequency as the positive control.

CD79b Binding Arm

The CD79b-targeting arm demonstrated low (equilibrium dissociation constant [$K_D$] estimated >3 µM) binding to the long CD79b isoform for the cynomolgus monkey protein representing >4-log weaker affinity compared to human, while no binding was observed to mouse CD79b by SPR (Table 32).

As detailed in Table 46, CD79b amino acid percentage identity and similarity across orthologue species is moderately conserved across mammalian species. The low binding/lack of binding is in accordance with the low sequence alignment between human and these nonclinical species at the targeted domain.

TABLE 46

CD79b extracellular domain (ECD) percent identity
and similarity across orthologue species.

|  | Mouse | Rat | Rhesus monkey | Cynomolgus monkey | Marmoset | Dog | Rabbit | Guinea Pig |
|---|---|---|---|---|---|---|---|---|
| Identity | 53.3 | 53.0 | 76.7 | 76.7 | 70.5 | 66.4 | 52.9 | 63.0 |
| Similarity | 71.4 | 73.3 | 85.7 | 85.7 | 80.3 | 78.6 | 69.9 | 78.5 |

These results are similar to polatuzumab vedotin, which was also not cross-reactive to CD79b despite only 3 amino acid difference at the binding epitope between the human and cynomolgus monkey (61).

CD20 Binding Arm

In a flow cytometry study with a CD20 binder (i.e., C20B680 LH scFv, tested as the IgG1 Fc fusion protein C923B192), binding was observed to both human and cynomolgus monkey B cells. Additionally, C20B648 bound to a similar frequency of cell surface CD20 on human and cynomolgus monkey B cells, further confirming cross-reactivity to cynomolgus monkeys.

As detailed in Table 47, CD20 amino acid percentage identity of the ECD across orthologue species is moderately to highly conserved across mammalian species. The high degree of binding as assessed by flow cytometry to non-human primates is in accordance with the high sequence alignment between human and these nonclinical species at the targeted domain.

TABLE 47

CD20 extracellular domain (ECD) percent identity
matrix across orthologue species.

|  | Mouse | Rat | Rhesus monkey | Cynomolgus monkey | Marmoset | Dog | Rabbit | Guinea Pig |
|---|---|---|---|---|---|---|---|---|
| Identity | 68.9 | 68.9 | 95.6 | 97.8 | 86.7 | 68.9 | 80.0 | 71.1 |

The biophysical assessment for the CD20 binding arm indicated little to no measurable affinity to recombinant human CD20 as full binding curve could not be generated.

Example 12: Potential C923B169 Off-Target Toxicity

CD9B374 has a low risk for off-target effects based on selective binding and functional activity. There are 2 splice isoforms of CD79b (FIG. 9B), with the long isoform being the prominent form in DLBCL. Specific to the CD79b counterpart in the B-cell receptor, CD79a, low homology exists between the ECD binding regions (Table 47).

To characterize the potential off-target binding of the tumor-antigen-targeting arms of C923B169, namely, CD9B374 (anti-CD79b mAb) and C20B648 LH scFv (anti-CD20 scFv, tested as an Fc fusion, C923B192), the bivalent molecules were evaluated for binding on a human plasma membrane protein array (Retrogenix) in 2 separate non-GLP studies.

Assessment for Off-Target Binding

CD79b

The CD79b binder (CD9B374, IgG1) when screened for binding against fixed HEK293 cells individually expressing a library of 5,475 full-length human plasma membrane and cell-surface-tethered human secreted proteins and 371 heterodimers, was determined to bind specifically to its primary target, CD79b with strong intensity when expressed alone or as part of a heterodimer with CD79a. CD9B374 did not bind CD79a expressed alone on HEK293 cells. No off-target interactions were identified, demonstrating the target specificity of the CD79b binding domain contained in C923B169.

CD20

The CD20 binder (C20B680 LH scFv, tested as an IgG1 Fc fusion protein, C923B192) when screened for binding against fixed HEK293 cells individually expressing a library of 5,681 full-length human plasma membrane and cell-surface-tethered human secreted proteins and 371 heterodimers, was determined to bind specifically to its primary target, CD20, with strong intensity. No off-target interactions were identified, demonstrating the target specificity of the CD20 binding domain contained in C923B169.

Assessment for Off-Target Functional Activity

Functional selectivity of C923B169 in TAA⁻ cell lines

The antigen specificity of C923B169 was further characterized in an in vitro functional assay using a panel of 6 cancer cell lines that lack expression of CD79b and CD20, but by transcriptomics are predicted to express >50% of the known cell surface proteins. In coculture studies with healthy donor-derived T cells, C923B169 was able to induce antibody-dependent, T-cell-mediated cytokine release of granzyme B, interferon (IFN)-γ, tumor necrosis factor (TNF)-α, and IL-2 when added to cocultures with target cells that express CD79b and CD20 (i.e., CARNAVAL) but no release (or negligible levels) with cell lines that do not express the target antigens. These data support the antigen specificity of C923B169 to CD79b and CD20 and demonstrate a lack of off-target T-cell activation, as measured by cytokine release.

Example 13: Pharmacokinetics in Preclinical Species

Pharmacokinetics in Mouse Efficacious Model

Figure 33:
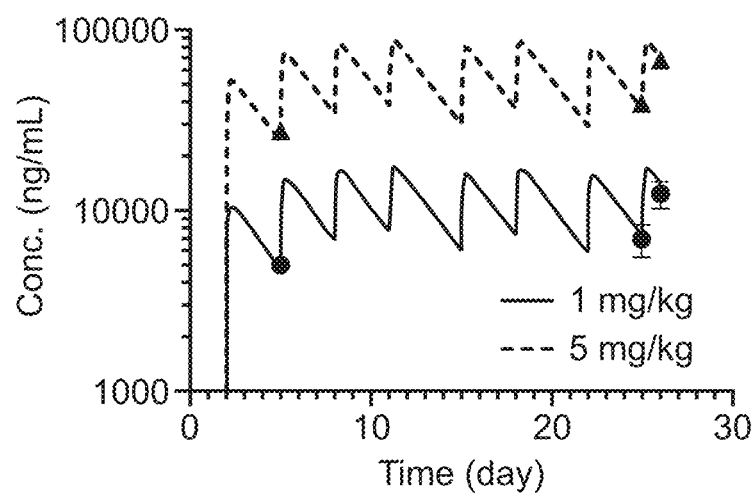
FIG. 33. Mean (standard deviation) serum concentration-time profiles following repeated dosing of 1 or 5 mg/kg C923B169 in CARNAVAL-bearing xenograft mice (n=10/group).

Serum samples were collected from NSG mice bearing SC tumor of the CARNAVAL cell line. Serum concentrations of C923B169 at 72 hours post first dose, 1 hour before and 24 hours post the final dose (Study A) following every 3 or 4 days dosing were fitted using a 2-compartment model to characterize the mouse PK. PK parameters (i.e., plasma clearance [CL], volume of the central compartment [Vc], and volume of the peripheral compartment [Vp]) were estimated for C923B169 by fixing the distribution clearance (Q) to an experience value obtained from a previous study. Data analysis was performed using Monolix 2018R2 (Lixoft®). Model fitting is shown in FIG. 33. Mild serum drug accumulation was observed in mice following repeated dosing at 1 or 5 mg/kg. The observed plasma concentration immediately prior to next administration ($C_{trough}$) was approximately 7,000 and 40,000 ng/mL at 1 and 5 mg/kg, respectively. The results are used in PK/PD correlation in the mouse models.

Pharmacokinetics in Monkey and Minipig

The PK of C923B169 is being studied in cynomolgus monkeys and Göttingen minipigs.

Figure 34:
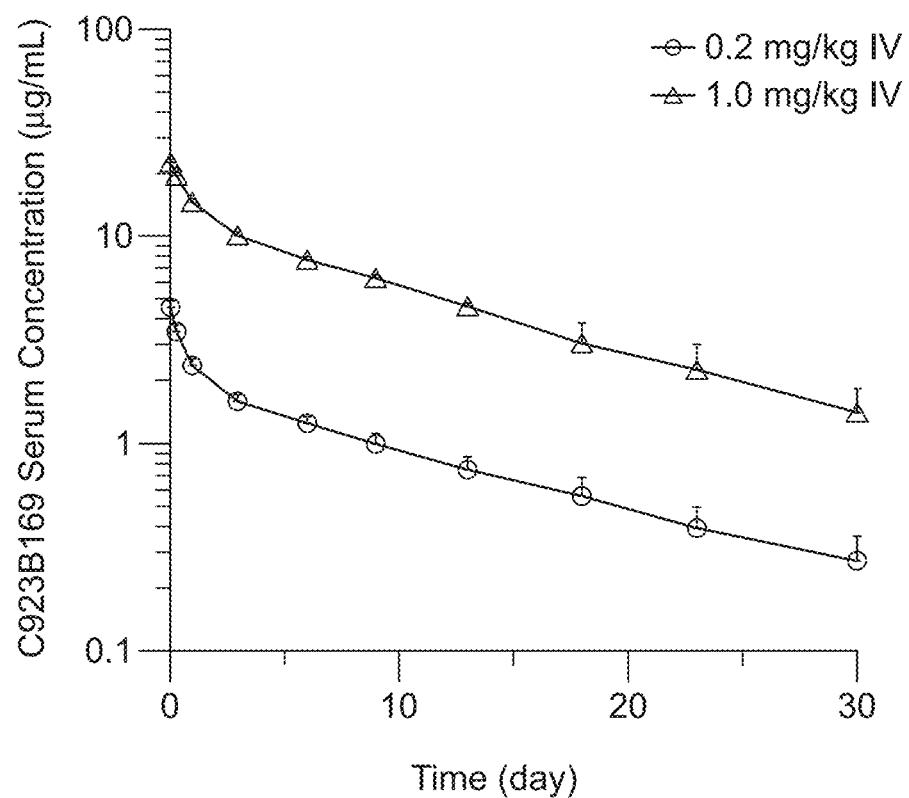
FIG. 34. Preliminary C923B169 PK results in cyno monkeys.

In the monkey study, C923B169 was administered as a single dose at 0.2 and 1.0 mg/kg intravenously (IV; as 0.2 and 1 mg/mL in 10 mM histidine, pH 6.5 dosing formulations). Serum samples were collected for 30 days. Preliminary PK results in cyno monkeys are shown in FIG. 34 and Table 48.

Serum C923B169 concentrations were below the lowest quantifiable concentration in all samples collected prior to the dose administration in C923B169-treated IV and SC groups.

Following a single IV administration of C923B169, serum C923B169 concentrations decreased from the first post-dose collection (0.04 day) through $T_{last}$ (14 or 32 days post-dose). Mean clearance, volume of distribution and terminal half-life following single IV administration of C923B169 at 1 mg/kg was found to be 6.18 mL/kg/day, 95.64 mL/kg, and 11.29 days, respectively.

Following a single SC administration of C923B169, serum C923B169 concentrations were quantifiable from 0.04 to 45 days post-dose. Mean serum C923B169 concentrations reached the $C_{max}$ at 1-4 days post-dose and then decreased through $T_{last}$. Terminal half-life following single SC administration C923B169 at 1 mg/kg was estimated to be 11.42 days and was comparable to that of IV adminis-

TABLE 48

Summary of PK results in cyno monkeys

| C923B169 | N = 3 | $C_{max}$ (µg/mL) | $AUC_{last}$ (µg · day/mL) | $AUC_{inf}$ (µg · day/mL) | CL (mL/day/kg) | $V_z$ (mL/kg) | $T_{1/2}$ (day) |
|---|---|---|---|---|---|---|---|
| 0.2 mg/kg | Mean | 4.51 | 26.04 | 30.64 | 6.66 | 109.73 | 11.59 |
| IV | SD | 0.42 | 3.39 | 5.46 | 1.10 | 11.28 | 1.82 |
| 1.0 mg/kg | Mean | 22.88 | 156.21 | 178.70 | 5.65 | 88.07 | 10.83 |
| IV | SD | 1.54 | 15.24 | 22.88 | 0.68 | 9.69 | 0.80 |

In the minipig study, C923B169 was administered as a single dose at 1.0 mg/kg IV or SC (as 3.39 mg/mL in 10 mM histidine, pH 6.5 dosing formulation) to four male minipigs per study group. The dose was given on study Day 1. Serum samples are collected for up to 45 days. For quantification of C923B169 concentrations, the lowest quantifiable concentration in a sample was 0.08 µg/mL (lower limit of quantification×minimum required dilution).

Figure 35:
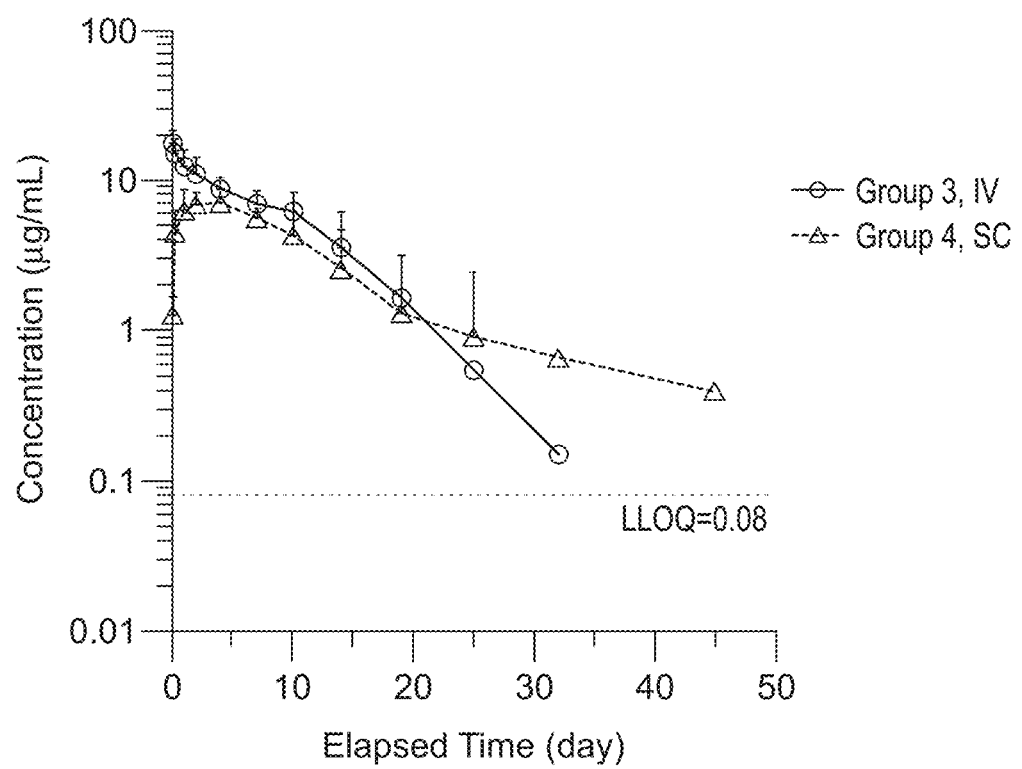
FIG. 35. Mean (SD) serum C923B169 concentration-time profiles following a single intravenous (IV) or subcutaneous (SC) dose of 1 mg/kg of C923B169 in male minipigs. Data points with concentrations below the lowest quantifiable concentration are not shown in the graph.
Figure 36:
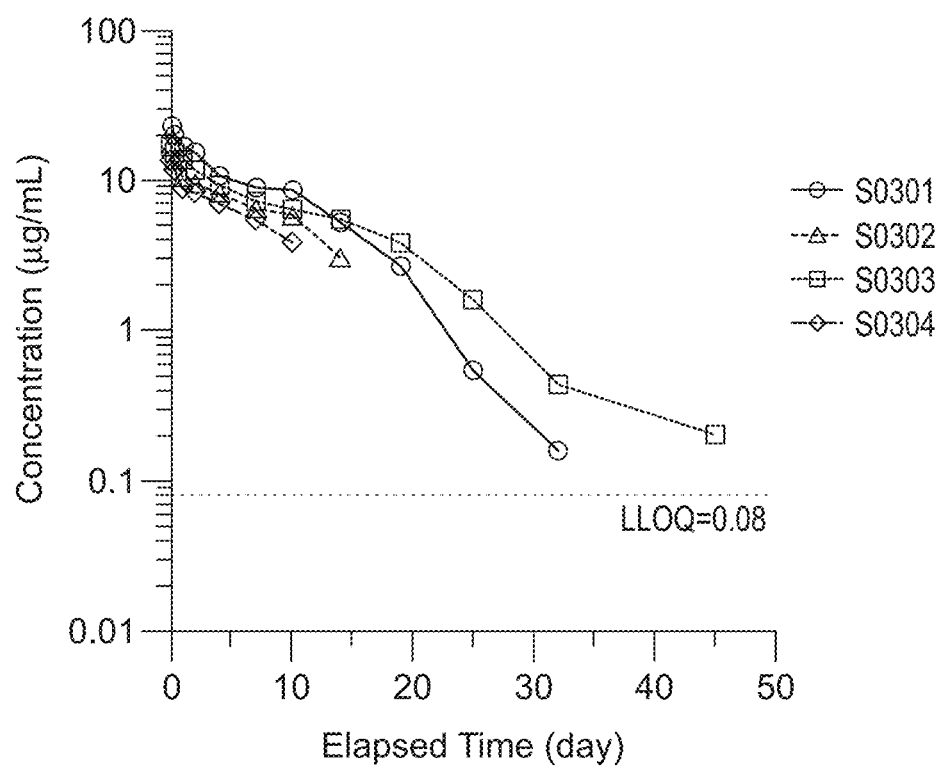
FIG. 36. Individual serum C923B169 concentration-time profiles following a single IV dose of 1 mg/kg of C923B169 in male minipigs (Group 3). Data points with concentrations below the lowest quantifiable concentration are not shown in the graph.
Figure 37:
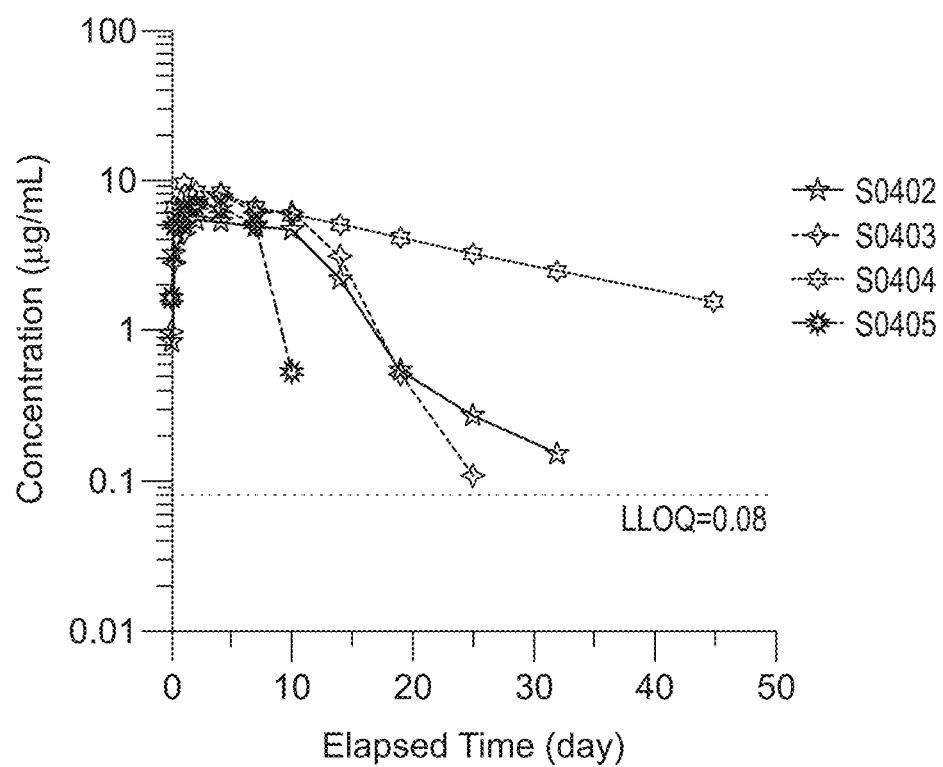
FIG. 37. Individual serum C923B169 concentration-time profiles following single SC dose of 1 mg/kg of C923B169 in male minipigs (Group 4). Data points with concentrations below the lowest quantifiable concentration are not shown in the graph.

Individual and mean (SD) PK parameters of C923B169 following single IV or SC dose are summarized in Table 49. Mean (SD) serum concentrations of C923B169 versus time for male minipigs are illustrated in FIG. 35. Individual serum concentrations of C923B169 versus time for male minipigs are illustrated in FIG. 36 and FIG. 37.

tration (11.29 days) at similar dose level. The SC bioavailability was estimated as 79% by comparing $AUC_{inf}$ following a single SC and IV dose.

An aberrant decrease in serum C923B169 concentrations were observed in most of the animals from the IV and SC dosing groups, which were likely due to the impact of anti-drug antibodies (ADA); however, ADA was not assayed in the study.

The quantifiable serum C923B169 concentrations that were likely impacted by ADA development were not used in the calculation of $AUC_{inf}$, CL, $V_z$ and $T_{1/2}$ (Table 50 and Table 51).

TABLE 49

Individual and mean (SD) serum C923B169 PK parameters following a single IV or SC dose of C923B169 at 1 mg/kg in male minipigs

| Group | ID | $C_{max}$ (µg/mL) | $T_{max}$ (day) | $AUC_{last}$ (µg · day/mL) | $T_{last}$ (day) | $AUC_{inf}$ (µg · day/mL) | CL (mL/day/kg) | $V_z$ (mL/kg) | $T_{1/2}$ (day) |
|---|---|---|---|---|---|---|---|---|---|
| Group 3 | S0301 | 22.59 | — | 174.02 | 32.00 | 204.48 | 4.89 | 78.00 | 11.06 |
| IV | S0302 | 17.56 | — | 98.23 | 14.00 | 184.40[a] | 5.42 | 100.73 | 12.87 |
|  | S0303 | 16.70 | — | 166.74 | 45.00 | 188.25 | 5.31 | 105.01 | 13.70 |
|  | S0304 | 13.54 | — | 66.64 | 10.00 | 109.94[a] | 9.10 | 98.82 | 7.53 |
|  | Mean | 17.60 | — | 126.41 | 25.25 | 171.77 | 6.18 | 95.64 | 11.29 |
|  | SD | 3.75 | — | 52.47 | 16.28 | 42.13 | 1.96 | 12.04 | 2.74 |
| Group 4 | S0402 | 5.39 | 2.00 | 71.50 | 32.00 | 78.59 | — | — | 8.36 |
| SC | S0403 | 8.27 | 4.00 | 90.38 | 25.00 | 102.10 | — | — | 7.04 |
|  | S0404 | 9.50 | 1.00 | 186.17 | 45.00 | 228.60 | — | — | 18.87 |
|  | S0405 | 7.01 | 2.00 | 49.23 | 10.00 | NR[b] | — | — | NR[b] |
|  | Mean | 7.54 | 2.25 | 99.32 | 28.00 | 136.43 | — | — | 11.42 |
|  | SD | 1.76 | 1.26 | 60.29 | 14.58 | 80.68 | — | — | 6.49 |

[a]Extrapolated AUC was larger than 20% for all animals.
[b]Not applicable due to poorly characterized terminal phase and has been excluded from the calculation of the mean data.

TABLE 50

Individual and mean (SD) serum C923B169 concentrations (μg/ml) following a single IV dose of 1 mg/kg of C923B169 in male minipigs (Group 3)

| Protocol Time | Time (day) | S0301 | S0302 | S0303 | S0304 | Mean | SD |
|---|---|---|---|---|---|---|---|
| Predose | 0 | <0.08 | <0.08 | <0.08 | <0.08 | <0.08 | NR |
| 1 hr | 0.04 | 22.59 | 17.56 | 16.70 | 13.54 | 17.60 | 3.75 |
| 6 hr | 0.25 | 20.03 | 13.62 | 15.28 | 11.28 | 15.05 | 3.70 |
| 24 hr | 1 | 16.42 | 10.60 | 13.97 | 8.73 | 12.43 | 3.43 |
| 48 hr | 2 | 15.26 | 9.42 | 11.51 | 8.11 | 11.08 | 3.12 |
| 96 hr | 4 | 10.58 | 8.18 | 9.32 | 7.03 | 8.78 | 1.52 |
| 168 hr | 7 | 8.97 | 6.39 | 7.18 | 5.45 | 7.00 | 1.49 |
| 240 hr | 10 | 8.76 | 5.92 | 6.42 | 3.88 | 6.24 | 2.01 |
| 336 hr | 14 | 5.45 | 3.11* | 5.64 | <0.08 | 3.55 | 2.63 |
| 456 hr | 19 | 2.69* | <0.08 | 3.87 | <0.08 | 1.64 | NR |
| 600 hr | 25 | 0.55* | <0.08 | 1.60* | <0.08 | 0.54 | NR |
| 768 hr | 32 | 0.16* | <0.08 | 0.44* | <0.08 | 0.15 | NR |
| 1080 hr | 45 | <0.08 | <0.08 | 0.20* | <0.08 | <0.08 | NR |

*The time points were not used for the calculation of $AUC_{inf}$, CL, $V_z$ and $T_{1/2}$ due to possible ADA impact.

TABLE 51

Individual and mean (SD) serum C923B169 concentrations (μg/ml) following a single SC dose of 1 mg/kg of C923B169 in male minipigs (Group 4)

| Protocol Time | Time (day) | S0402 | S0403 | S0404 | S0405 | Mean | SD |
|---|---|---|---|---|---|---|---|
| Predose | 0 | <0.08 | <0.08 | <0.08 | <0.08 | <0.08 | <0.08 |
| 1 hr | 0.04 | 0.84 | 0.98 | 1.60 | 1.67 | 1.27 | 0.42 |
| 6 hr | 0.25 | 3.24 | 2.81 | 6.76 | 5.14 | 4.49 | 1.82 |
| 24 hr | 1 | 4.74 | 4.38 | 9.50 | 6.84 | 6.36 | 2.35 |
| 48 hr | 2 | 5.39 | 6.92 | 8.47 | 7.01 | 6.95 | 1.26 |
| 96 hr | 4 | 5.27 | 8.27 | 8.24 | 6.51 | 7.07 | 1.45 |
| 168 hr | 7 | 4.82 | 6.06 | 6.70 | 5.18 | 5.69 | 0.85 |
| 240 hr | 10 | 4.68 | 6.19 | 5.90 | 0.53 | 4.32 | 2.62 |
| 336 hr | 14 | 2.22 | 3.13 | 5.07 | <0.08 | 2.60 | 2.10 |
| 456 hr | 19 | 0.55* | 0.51* | 4.09 | <0.08 | 1.29 | 1.89 |
| 600 hr | 25 | 0.27* | 0.11* | 3.24 | <0.08 | 0.90 | 1.56 |
| 768 hr | 32 | 0.15* | <0.08 | 2.47 | <0.08 | 0.66 | NR |
| 1080 hr | 45 | <0.08 | <0.08 | 1.57 | <0.08 | 0.39 | NR |

*The time points were not used for the calculation of $AUC_{inf}$, CL, $V_z$ and $T_{1/2}$ due to possible ADA impact.

The ADA development may impact the evaluation of bioavailability; however the extent of impact could not be concluded.

Pharmacokinetic/Pharmacodynamic Analysis

A full characterization of the in vitro and in vivo PK/PD relationship of C923B169 is performed using relevant in vitro potency data and in vivo dose-efficacy relationship from the mouse efficacy model. The PK results from the ongoing PK and SC bioavailability evaluation in monkeys and minipigs are the basis of human efficacious dose projection.

REFERENCES

1. Kochenderfer, J. N. et al. Chemotherapy-refractory diffuse large B-cell lymphoma and indolent B-cell malignancies can be effectively treated with autologous T cells expressing an anti-CD19 chimeric antigen receptor. *J Clin Oncol* 33, 540-549 (2015).
2. Schuster, S. J. et al. Chimeric Antigen Receptor T Cells in Refractory B-Cell Lymphomas. *N Engl J Med* 377, 2545-2554 (2017).
3. Shalabi, H. et al. Sequential loss of tumor surface antigens following chimeric antigen receptor T-cell therapies in diffuse large B-cell lymphoma. *Haematologica* 103, e215-e218 (2018).
4. Sotillo, E. et al. Convergence of Acquired Mutations and Alternative Splicing of CD19 Enables Resistance to CART-19 Immunotherapy. *Cancer Discov* 5, 1282-1295 (2015).
5. Packard, T. A. & Cambier, J. C. B lymphocyte antigen receptor signaling: initiation, amplification, and regulation. *F1000 Prime Rep* 5, 40 (2013).
6. Puri, K. D., Di Paolo, J. A. & Gold, M. R. B-cell receptor signaling inhibitors for treatment of autoimmune inflammatory diseases and B-cell malignancies. *Int Rev Immunol* 32, 397-427 (2013).
7. Polson, A. G. et al. Antibody-drug conjugates targeted to CD79 for the treatment of non-Hodgkin lymphoma. *Blood* 110, 616-623 (2007).
8. Palanca-Wessels, M. C. A. et al. Safety and activity of the anti-CD79B antibody-drug conjugate polatuzumab vedotin in relapsed or refractory B-cell non-Hodgkin lymphoma and chronic lymphocytic leukaemia: a phase 1 study. *The Lancet Oncology* 16, 704-715 (2015).
9. Astsaturov, I. A. et al. Differential expression of B29 (CD79b) and mb-1 (CD79a) proteins in acute lymphoblastic leukaemia. *Leukemia* 10, 769-773 (1996).
10. Foster L H, Lum L G. Treatment of hematological malignancies with T cell redirected bispecific antibodies: current status and future needs. Expert Opin Biol Ther. 2019; 19(7):707-720. doi:10.1080/14712598.2019.1604672

11. Dufner V, Sayehli C M, Chatterjee M, et al. Long-term outcome of patients with relapsed/refractory B-cell non-Hodgkin lymphoma treated with blinatumomab. Blood Adv. 2019; 3(16):2491-2498. doi:10.1182/bloodadvances.2019000025
12. Burt R, Warcel D, Fielding A K. Blinatumomab, a bispecific B-cell and T-cell engaging antibody, in the treatment of B-cell malignancies. Hum Vaccin Immunother. 2019; 15(3):594-602. doi:10.1080/21645515.2018.1540828
13. Bibikova E, Law B, Clevenger T, et al. High surface expression of CD49d (VLA-4) and CD79b correlates with acalabrutinib resistance in patients with chronic lymphocytic leukemia (CLL). Blood. 2019; 134(Supplement_1):2571. doi: 10.1182/blood-2019-128872
14. Visco C, Tanasi I, Quaglia F M, Ferrarini I, Fraenza C, Krampera M. Oncogenic mutations of MYD88 and CD79b in diffuse large B-cell lymphoma and implications for clinical practice. Cancers (Basel). 2020; 12(10):2913. Published 2020 Oct. 10. doi:10.3390/cancers12102913
15. Davis R E, Ngo V N, Lenz G, et al. Chronic active B-cell-receptor signalling in diffuse large B-cell lymphoma. Nature. 2010; 463(7277):88-92. doi:10.1038/nature08638
16. Phelan J D, Young R M, Webster D E, et al. A multiprotein supercomplex controlling oncogenic signalling in lymphoma. Nature. 2018; 560(7718):387-391. doi:10.1038/s41586-018-0290-0
17. He X, Klasener K, Iype J M, et al. Continuous signaling of CD79b and CD19 is required for the fitness of Burkitt lymphoma B cells. EMBO J. 2018; 37(11):e97980. doi:10.15252/embj.201797980
18. Cragg M S, Chan H T, Fox M D, et al. The alternative transcript of CD79b is overexpressed in B-CLL and inhibits signaling for apoptosis. Blood. 2002; 100(9):3068-3076. doi:10.1182/blood.V100.9.3068
19. Burger J A, Wiestner A. Targeting B cell receptor signalling in cancer: preclinical and clinical advances. Nat Rev Cancer. 2018; 18(3):148-167. doi:10.1038/nrc.2017.121
20. Klein C, Lammens A, Schafer W, et al. Epitope interactions of monoclonal antibodies targeting CD20 and their relationship to functional properties. MAbs. 2013; 5(1):22-33. doi:10.4161/mabs.22771
21. Scheuplein R J. Permeability of the skin: a review of major concepts. Curr Probl Dermatol. 1978; 7:172-186. doi:10.1159/000401285
22. Eon Kuek L, Leffler M, Mackay G A, Hulett M D. The MS4A family: counting past 1, 2 and 3. Immunol Cell Biol. 2016; 94(1):11-23. doi:10.1038/icb.2015.48
23. Gamonet C, Bole-Richard E, Delherme A, et al. New CD20 alternative splice variants: molecular identification and differential expression within hematological B cell malignancies [published correction appears in Exp Hematol Oncol. 2015; 5:10]. Exp Hematol Oncol. 2016; 5:7. Published 2016 Mar. 1. doi:10.1186/s40164-016-0036-3
24. Henry C, Deschamps M, Rohrlich P S, et al. Identification of an alternative CD20 transcript variant in B-cell malignancies coding for a novel protein associated to rituximab resistance. Blood. 2010; 115(12):2420-2429. doi:10.1182/blood-2009-06-229112
25. Tedder T F, Schlossman S F. Phosphorylation of the B1 (CD20) molecule by normal and malignant human B lymphocytes. J Biol Chem. 1988; 263(20):10009-10015.
26. Bubien J K, Zhou L J, Bell P D, Frizzell R A, Tedder T F. Transfection of the CD20 cell surface molecule into ectopic cell types generates a Ca2+ conductance found constitutively in B lymphocytes. J Cell Biol. 1993; 121(5):1121-1132. doi:10.1083/jcb.121.5.1121
27. Brouwer-Visser J, Fiaschi N, Deering R P, et al. Baseline biomarkers of T-cell function correlate with clinical responses to odronextamab (REGN1979), and loss of CD20 target antigen expression identified as a mechanism of treatment resistance. $62^{nd}$ ASH Annual Meeting and Exposition. Dec. 5-8, 2020; Abstract 2108. Available from: https://ash.confex.com/ash/2020/webprogram/Paper137499.html. Accessed: 3 Jun. 2021.
28. Salvaris R, Ong J, Gregory G P. Bispecific Antibodies: A review of development, clinical efficacy and toxicity in B-cell lymphomas. J Pers Med. 2021; 11(5):355. Published 2021 Apr. 29. doi:10.3390/jpm11050355
29. American Cancer Society. Non-Hodgkin lymphoma [internet]. Atlanta, GA: ACS; 2018. Available from: https://www.cancer.org/cancer/non-hodgkin-lymphoma/about/key-statistics.html. Accessed: 17 *May* 2021.
30. Evans A G, Rothberg P G, Burack W R, et al. Evolution to plasmablastic lymphoma evades CD19-directed chimeric antigen receptor T cells. Br J Haematol. 2015; 171(2):205-209. doi:10.1111/bjh.13562
31. Porter D L, Levine B L, Kalos M, Bagg A, June C H. Chimeric antigen receptor-modified T cells in chronic lymphoid leukemia [published correction appears in N Engl J Med. 2016 Mar. 10; 374(10):998]. N Engl J Med. 2011; 365(8):725-733. doi:10.1056/NEJMoa1103849
32. Shalabi H, Kraft I L, Wang H W, et al. Sequential loss of tumor surface antigens following chimeric antigen receptor T-cell therapies in diffuse large B-cell lymphoma. Haematologica. 2018; 103(5):e215-e218. doi:10.3324/haematol.2017.183459
33. Fry T J, Shah N N, Orentas R J, et al. CD22-targeted CAR T cells induce remission in B-ALL that is naïve or resistant to CD19-targeted CAR immunotherapy. Nat Med. 2018; 24(1):20-28. doi:10.1038/nm.4441
34. Majzner R G, Mackall C L. Tumor antigen escape from CAR T-cell therapy. Cancer Discov. 2018; 8(10):1219-1226. doi:10.1158/2159-8290.CD-18-0442
35. Decision Resource Group. Non-Hodgkin's lymphoma and chronic lymphocytic leukemia. Burlington, MA: Decision Resources Group; November 2019.
36. Ito M, Zhao N, Zeng Z, Zhou X, Chang C C, Zu Y. Interleukin-2 functions in anaplastic large cell lymphoma cells through augmentation of extracellular signal-regulated kinases 1/2 activation. Int J Biomed Sci. 2011; 7(3):181-190.
37. Chu P G, Arber D A. CD79: a review. Appl Immunohistochem Mol Morphol. 2001; 9(2):97-106. doi:10.1097/00129039-200106000-00001
38. Guisado Vasco P, Villar Rodriguez J L, Ibanez Martinez J, Gonzalez Campora R, Galera Davidson H. Immunohistochemical organization patterns of the follicular dendritic cells, myofibroblasts and macrophages in the human spleen—new considerations on the pathological diagnosis of splenectomy pieces. Int J Clin Exp Pathol. 2009; 3(2):189-202. Published 2009 Dec. 10.
39. Tomita A. Genetic and Epigenetic Modulation of CD20 Expression in B-Cell Malignancies: molecular mechanisms and significance to rituximab resistance. J Clin Exp Hematop. 2016; 56(2):89-99. doi:10.3960/jslrt.56.89
40. Zuccolo J, Deng L, Unruh T L, et al. Expression of MS4A and TMEM176 genes in human B lymphocytes. Front Immunol. 2013; 4:195. Published 2013 Jul. 15. doi:10.3389/fimmu.2013.00195
41. Jahn L, Hombrink P, Hassan C, et al. Therapeutic targeting of the BCR-associated protein CD79b in a TCR-based approach is hampered by aberrant expression of CD79b. Blood. 2015; 125(6):949-958. doi:10.1182/blood-2014-07-587840

42. Middleton O, Wheadon H, Michie A. Classical complement pathway. In: Ratcliffe M J H, ed. Encyclopedia of immunobiology, 1st ed. New York, NY: Elsevier; 2016: Volume 2. doi:10.1016/B978-0-12-374279-7.02014-2

43. Ajina R, et al. Cancer Immunotherapy. In: Chackalamannil S, Rotella D, Ward S, eds. Comprehensive medicinal chemistry III, 3' ed. New York, NY: Elsevier; 2017: Volume 6. doi:10.1016/B978-0-12-409547-2.12426-62017

44. Naeim F, Rao P N, Song S X, Phan R T. Chapter 2: principles of Immunophenotyping. In: Naeim F, Rao P N, Song S X, Phan R T, eds. Atlas of hematopathology: morphology, immunophenotype, cytogenetics, and molecular approaches, 2nd ed. Cambridge, MA: Academic Press; 2018. doi:10.1016/B978-0-12-809843-1.00002-4

45. Uchida J, Lee Y, Hasegawa M, et al. Mouse CD20 expression and function. Int Immunol. 2004; 16(1):119-129. doi:10.1093/intimm/dxh009

46. Klasener K, Jellusova J, Andrieux G, et al. CD20 as a gatekeeper of the resting state of human B cells. Proc Natl Acad Sci USA. 2021; 118(7):e2021342118. doi:10.1073/pnas.2021342118

47. Lee D S W, Rojas O L, Gommerman J L. B cell depletion therapies in autoimmune disease: advances and mechanistic insights. Nat Rev Drug Discov. 2021; 20(3):179-199. doi:10.1038/s41573-020-00092-2

48. Schröder C, Azimzadeh A M, Wu G, Price J O, Atkinson J B, Pierson R N. Anti-CD20 treatment depletes B-cells in blood and lymphatic tissue of cynomolgus monkeys. Transpl Immunol. 2003; 12(1):19-28. doi:10.1016/S0966-3274(03)00059-5

49. O'Keefe T L, Williams G T, Davies S L, Neuberger M S. Mice carrying a CD20 gene disruption. Immunogenetics. 1998; 48(2):125-132. doi:10.1007/s002510050412

50. Sabatino J J Jr, Wilson M R, Calabresi P A, Hauser S L, Schneck J P, Zamvil S S. Anti-CD20 therapy depletes activated myelin-specific CD8$^+$ T cells in multiple sclerosis. Proc Natl Acad Sci USA. 2019; 116(51):25800-25807. doi:10.1073/pnas.1915309116

51. Waisman A, Ebering A. Unraveling the T-B tangle in anti-CD20 multiple sclerosis therapy. Proc Natl Acad Sci USA. 2019; 116(51):25376-25377. doi:10.1073/pnas.1919044116

52. Lu T, Gibiansky L, Li X, et al. Exposure-safety and exposure-efficacy analyses of polatuzumab vedotin in patients with relapsed or refractory diffuse large B-cell lymphoma. Leuk Lymphoma. 2020; 61(12):2905-2914. doi:10.1080/10428194.2020.1795154

53. Arcari A, Chiappella A, Spina M, et al. Safety and efficacy of rituximab plus bendamustine in relapsed or refractory diffuse large B-cell lymphoma patients: an Italian retrospective multicenter study. Leuk Lymphoma. 2016; 57(8):1823-1830. doi:10.3109/10428194.2015.1106536

54. Gea-Banacloche J C. Rituximab-associated infections. Semin Hematol. 2010; 47(2):187-198. doi:10.1053/j.seminhematol.2010.01.002

55. Sacco K A, Abraham R S. Consequences of B-cell-depleting therapy: hypogammaglobulinemia and impaired B-cell reconstitution. Immunotherapy. 2018; 10(8):713-728. doi:10.2217/imt-2017-0178

56. Kelesidis T, Daikos G, Boumpas D, Tsiodras S. Does rituximab increase the incidence of infectious complications? A narrative review. Int J Infect Dis. 2011; 15(1): e2-e16. doi:10.1016/j.ijid.2010.03.025

57. Kusumoto S, Arcaini L, Hong X, et al. Risk of HBV reactivation in patients with B-cell lymphomas receiving obinutuzumab or rituximab immunochemotherapy. Blood. 2019; 133(2):137-146. doi:10.1182/blood-2018-04-848044

58. Klein C, Jamois C, Nielsen T. Anti-CD20 treatment for B-cell malignancies: current status and future directions. Expert Opin Biol Ther. 2021; 21(2):161-181. doi: 10.1080/14712598.2020.1822318

59. International Council for Harmonisation of Technical Requirements for Pharmaceuticals for Human Use. ICH S6(R1) Guideline: Preclinical safety evaluation of biotechnology-derived pharmaceuticals; July 1997/Addendum R1 incorporated June 2011 [internet]. Geneva, Switzerland: ICH; 2011. Available from: https://database.ich.org/sites/default/files/S6_R1_Guideline_0.pdf. Accessed: 19 May 2021.

60. Singh A, Dees S, Grewal I S. Overcoming the challenges associated with CD3$^+$ T-cell redirection in cancer. Br J Cancer. 2021; 124(6):1037-1048. doi:10.1038/s41416-020-01225-5

61. Li D, Lee D, Dere R C, et al. Evaluation and use of an anti-cynomolgus monkey CD79b surrogate antibody-drug conjugate to enable clinical development of polatuzumab vedotin. Br J Pharmacol. 2019; 176(19): 3805-3818. doi:10.1111/bph.14784

62. Li J, Piskol R, Ybarra R, et al. CD3 bispecific antibody-induced cytokine release is dispensable for cytotoxic T cell activity. Sci Transl Med. 2019; 11(508):eaax8861. doi:10.1126/scitranslmed.aax8861

63. Leong S R, Sukumaran S, Hristopoulos M, et al. An anti-CD3/anti-CLL-1 bispecific antibody for the treatment of acute myeloid leukemia. Blood. 2017; 129(5): 609-618. doi:10.1182/blood-2016-08-735365

64. Jain T, Litzow M R. Management of toxicities associated with novel immunotherapy agents in acute lymphoblastic leukemia. Ther Adv Hematol. 2020; 11:2040620719899897. Published 2020 Jan. 20. doi: 10.1177/2040620719899897

65. Bargou R, Leo E, Zugmaier G, et al. Tumor regression in cancer patients by very low doses of a T cell-engaging antibody. Science. 2008; 321(5891):974-977. doi: 10.1126/science.1158545

66. Klinger M, Brandl C, Zugmaier G, et al. Immunopharmacologic response of patients with B-lineage acute lymphoblastic leukemia to continuous infusion of T cell-engaging CD19/CD3-bispecific BiTE antibody blinatumomab. Blood. 2012; 119(26):6226-6233. doi: 10.1182/blood-2012-01-400515

67. Nagele V, Kratzer A, Zugmaier G, et al. Changes in clinical laboratory parameters and pharmacodynamic markers in response to blinatumomab treatment of patients with relapsed/refractory ALL. Exp Hematol Oncol. 2017; 6:14. Published 2017 May 18. doi:10.1186/s40164-017-0074-5

68. Kamphorst A O, Wieland A, Nasti T, et al. Rescue of exhausted CD8 T cells by PD-1-targeted therapies is CD28-dependent. Science. 2017; 355(6332):1423-1427. doi:10.1126/science.aaf0683

69. Verma V, Shrimali R K, Ahmad S, et al. PD-1 blockade in subprimed CD8 cells induces dysfunctional PD-1+ CD38hi cells and anti-PD-1 resistance [published correction appears in Nat Immunol. 2019 Sep. 24:]. Nat Immunol. 2019; 20(9):1231-1243. doi:10.1038/s41590-019-0441-y 70. Guo B, Zhang L, Chiorazzi N, Rothstein T L. IL-4 rescues surface IgM expression in chronic lymphocytic leukemia. Blood. 2016; 128(4):553-562. doi:10.1182/blood-2015-11-682997
71. Aguilar-Hernandez M M, Blunt M D, Dobson R, et al. IL-4 enhances expression and function of surface IgM in CLL cells. Blood. 2016; 127(24):3015-3025. doi:10.1182/blood-2015-11-682906
72. Jacoby E, Nguyen S M, Fountaine T J, et al. CD19 CAR immune pressure induces B-precursor acute lymphoblastic leukaemia lineage switch exposing inherent leukaemic plasticity. Nat Commun. 2016; 7:12320. Published 2016 Jul. 27. doi:10.1038/ncommsi2320
73. Köhnke T, Krupka C, Tischer J, Knösel T, Subklewe M. Increase of PD-L1 expressing B-precursor ALL cells in a patient resistant to the CD19/CD3-bispecific T cell engager antibody blinatumomab. J Hematol Oncol. 2015; 8:111. Published 2015 Oct. 8. doi:10.1186/si3045-015-0213-6
74. Kobold S, Pantelyushin S, Rataj F, Vom Berg J. Rationale for combining bispecific T cell activating antibodies with checkpoint blockade for cancer therapy. Front Oncol. 2018; 8:285. Published 2018 Jul. 25. doi:10.3389/fonc.2018.00285

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

LIST OF SEQUENCES

| Name | Sequence | ID |
|---|---|---|
| CD79b Ab VH-CDR1 | GASISSFYWS | SEQ ID NO: 1 |
| CD79b Ab VH-CDR2 | RISPSGKTN | SEQ ID NO: 2 |
| CD79b Ab VH-CDR3 | GEYSGTYSYSFDV | SEQ ID NO: 3 |
| CD79b Ab VL-CDR1 | RSSESLLDSEDGNTYLD | SEQ ID NO: 4 |
| CD79b Ab VL-CDR2 | TLSYRAS | SEQ ID NO: 5 |
| CD79b Ab VL-CDR3 | MQRMEFPLT | SEQ ID NO: 6 |
| CD79b Ab VH-CDR1 | GDSVSSNSATWN | SEQ ID NO: 7 |
| CD79b Ab VH-CDR2 | RTYYRSKWYND | SEQ ID NO: 8 |
| CD79b Ab VH-CDR3 | VDIAFDY | SEQ ID NO: 9 |
| CD79b Ab VL-CDR1 | SGSSSNIGNHGVN | SEQ ID NO: 10 |
| CD79b Ab VL-CDR2 | NDDLLPS | SEQ ID NO: 11 |
| CD79b Ab VL-CDR3 | AAWDDSLNGVV | SEQ ID NO: 12 |
| CD79b Ab VH-CDR1 | GDSVSNNSATWN | SEQ ID NO: 13 |
| CD79b Ab VH-CDR1 | GVSISNYYWS | SEQ ID NO: 14 |
| CD79b Ab VH-CDR2 | RISPSGRTN | SEQ ID NO: 15 |
| CD79b Ab VH-CDR3 | GEYSGTYSYSFDI | SEQ ID NO: 16 |
| CD79b Ab VL-CDR1 | RSSQSLFDSDDGNTYLD | SEQ ID NO: 17 |
| CD79b Ab VH-CDR1 | GDSVSSNSAAWN | SEQ ID NO: 18 |
| CD79b Ab VH-CDR3 | VNTTFDY | SEQ ID NO: 19 |
| CD79b Ab VL-CDR1 | SGSSSNIGKNAVS | SEQ ID NO: 20 |
| CD79b Ab VL-CDR2 | SDDLLSS | SEQ ID NO: 21 |
| CD79b Ab VH-CDR1 | GASISSYYWS | SEQ ID NO: 22 |
| CD79b Ab VH-CDR2 | RISNTGRTN | SEQ ID NO: 23 |
| CD79b Ab VH-CDR3 | GEYSGTFSYGFDI | SEQ ID NO: 24 |
| CD79b Ab VL-CDR1 | RSSLSLLDSDDGKIYLD | SEQ ID NO: 25 |
| CD79b Ab VH-CDR2 | RIYSNGNIN | SEQ ID NO: 26 |
| CD79b Ab VH-CDR3 | GEYSGDFSYSFDI | SEQ ID NO: 27 |
| CD79b Ab VL-CDR1 | RSSQSLLDSDDGNTYLD | SEQ ID NO: 28 |
| CD79b Ab VL-CDR3 | MQRIEFPLT | SEQ ID NO: 29 |

-continued

CD79b Ab VH-CDR1
SEQ ID NO: 30
GGSISNYYWS

CD79b Ab VH-CDR2
SEQ ID NO: 31
RIFYSGKTN

CD79b Ab VH-CDR3
SEQ ID NO: 32
GEYSGEYSYSFDI

CD79b Ab VL-CDR1
SEQ ID NO: 33
RSSQSLLDSDDGNTYVD

CD79b Ab VL
SEQ ID NO: 34
CAGACAGTGGTCACCCAGCCTCCATCTGTGTCTGAGGCCCCTAGA

CAGAGAGTGACCATCTCCTGCTCCGGCTCCTCCTCCAACATCGGC

AATCATGGCGTGAACTGGTATCAGCAGCTGCCCGGCAAGGCTCCC

AAACTGCTGATCTACAACGACGACCTGCTGCCTTCTGGCGTGTCC

GACAGATTCTCCGGCTCTACCTCTGGCACCTCTGGATCCCTGGCT

ATCTCTGGCCTGCAGTCTGAGGACGAGGCCGACTACTATTGTGCC

GCCTGGGACGATTCTCTGAACGGCGTTGTGTTTGGCGGAGGCACC

AAGCTGACAGTGTTG

CD79b Ab VH
SEQ ID NO: 35
QVQLQESGPGLVKPSETLSLTCSVSGASISSFYWSWIRQPADEGL

EWIGRISPSGKTNYIPSLKSRIIMSLDASKNQFSLRLNSVTAADT

AMYYCARGEYSGTYSYSFDVWGQGTMVTVSS

CD79b Ab VH
SEQ ID NO: 36
CAGGTTCAGCTGCAAGAGTCTGGTCCTGGCCTGGTCAAGCCTTCC

GAGACACTGTCTCTGACCTGCTCTGTGTCCGGCGCCTCCATCTCT

TCCTTCTACTGGTCCTGGATCCGGCAGCCTGCTGACGAAGGACTG

GAATGGATCGGCCGGATCAGCCCTTCTGGCAAGACCAACTACATC

CCCAGCCTGAAGTCCCGGATCATCATGTCCCTGGACGCCTCCAAG

AACCAGTTCTCCCTGCGGCTGAACTCTGTGACCGCTGCCGATACC

GCCATGTACTACTGTGCCAGAGGCGAGTACTCCGGCACCTACTCC

TACAGCTTTGACGTGTGGGGACAAGGCACCATGGTCACAGTTTCT

TCT

CD79b Ab VL
SEQ ID NO: 37
DIVMTQSPLSLSVTPGEPASISCRSSESLLDSEDGNTYLDWFLQK

PGQSPQLLIYTLSYRASGVPDRFSGSGSDTDFTLHISSLEAEDVG

LYYCMQREFPLTFGQGTKVEIK

CD79b Ab VL
SEQ ID NO: 38
GACATCGTGATGACCCAGTCTCCACTGAGCCTGTCTGTGACACCT

GGCGAGCCTGCCTCCATCTCCTGTAGATCTTCTGAGTCCCTGCTG

GACAGCGAGGACGGCAATACCTACCTGGACTGGTTCCTGCAGAAG

CCCGGACAGTCTCCTCAGCTGCTGATCTACACCCTGTCCTACAGA

GCCTCTGGCGTGCCCGATAGATTCTCCGGCTCTGGCTCTGACACC

GACTTTACCCTGCACATCTCCAGCCTGGAAGCCGAGGATGTGGGC

CTGTACTACTGTATGCAGCGGATGGAATTTCCCCTGACCTTCGGC

CAGGGCACCAAGGTGGAAATCAAG

CD79b Ab VH
SEQ ID NO: 39
QVQLQQSGPGLVKPSQTLSLTCAISGDSVSNNSATWNWIRQSPSR

GLEWLGRTYYRSKWYNDYTVSVKSRITINPDTSKNQFSLQLNSVT

PEDTAVYYCTRVDIAFDYWGQGTLVTVSS

CD79b Ab VH
SEQ ID NO: 40
CAAGTGCAACTGCAGCAGTCTGGCCCTGGACTGGTCAAGCCTTCT

CAGACCCTGTCTCTGACCTGCGCCATCTCCGGCGACTCCGTGTCC

AACAACTCCGCTACCTGGAACTGGATCAGACAGTCCCCTTCCAGA

GGCCTGGAATGGCTGGGCAGAACCTACTACCGGTCCAAGTGGTAC

AACGACTACACCGTGTCCGTGAAGTCCCGGATCACCATCAACCCT

GATACCTCTAAGAACCAGTTCTCCCTGCAACTGAACTCTGTGACC

CCTGAGGACACCGCCGTGTACTACTGCACCAGAGTGGACATCGCC

TTCGACTACTGGGGCCAGGGCACCCTGGTGACCGTGTCTAGC

CD79b Ab VL
SEQ ID NO: 41
QTVVTQPPSVSEAPRQRVTISCSGSSSNIGNHGVNWYQQLPGKAP

KLLIYNDDLLPSGVSDRFSGSTSGTSGSLAISGLQSEDEADYYCA

AWDDSLNGVVFGGGTKLTVL

CD79b Ab VL
SEQ ID NO: 42
CAGACTGTGGTGACTCAGCCACCCTCGGTGTCTGAAGCCCCCAGG

CAGAGGGTCACCATCTCCTGTTCTGGAAGTAGCTCCAACATCGGA

AATCATGGTGTAAACTGGTACCAGCAGCTCCCAGGAAAGGCTCCC

AAACTCCTCATCTATAATGATGATCTGCTGCCCTCAGGGGTCTCT

GACCGATTCTCTGGCTCCACGTCTGGCACCTCAGGTTCCCTGGCC

ATCAGTGGGCTCCAGTCTGAGGATGAGGCTGATTATTACTGTGCA

GCATGGGATGACAGCCTGAATGGTGTGGTATTCGGCGGAGGGACT

AAACTGACCGTCCTA

CD79b Ab VH
SEQ ID NO: 43
QVQLQQSGPGLVKPSQTLSLTCAISGDSVSSNSATWNWIRQSPSR

GLEWLGRTYYRSKWYNDYTVSVKSRITINPDTSKNQFSLQLNSVT

PEDTAVYYCTRVDIAFDYWGQGTLVTVSS

CD79b Ab VH
SEQ ID NO: 44
CAGGTTCAGCTGCAGCAGTCTGGCCCTGGACTGGTCAAGCCCTCT

CAGACCCTGTCTCTGACCTGTGCCATCTCCGGCGACTCCGTGTCC

TCTAATTCTGCCACCTGGAACTGGATCCGGCAGTCCCCTAGTAGA

GGCCTGGAATGGCTGGGCAGAACCTACTACCGGTCCAAGTGGTAC

AACGACTACACCGTGTCCGTGAAGTCCCGGATCACCATCAATCCC

GACACCTCCAAGAACCAGTTCTCCCTGCAGCTCAACAGCGTGACC

CCTGAGGATACCGCCGTGTACTACTGCACCAGAGTGGATATCGCC

TTCGACTACTGGGGCCAGGGCACACTGGTTACCGTTTCTTCT

CD79b Ab VH
SEQ ID NO: 45
QVQLQESGPGLVKPSQTLSLTCTVSGVSISNYYWSWIRQPPGKGL

EWIGRISPSGRTNYNPSLKSRVTMSLDASKNQFSLKLSSVTAADT

AVYYCARGEYSGTYSYSFDIWGQGTMVTVSS

CD79b Ab VH
SEQ ID NO: 46
CAGGTTCAGCTGCAAGAGTCTGGCCCTGGCCTGGTCAAGCCCTCT

CAGACCCTGTCTCTGACCTGTACCGTGTCCGGCGTGTCCATCTCC

AACTACTACTGGTCCTGGATCCGGCAGCCTCCTGGCAAAGGACTG

GAATGGATCGGCCGCATCTCTCCTTCTGGTCGCACCAACTACAAC

CCCAGCCTGAAAAGCAGAGTGACCATGTCTCTGGACGCCTCCAAG

AACCAGTTCTCCCTGAAGCTGTCCTCCGTGACCGCTGCTGATACC

GCCGTGTACTACTGTGCCAGAGGCGAGTACTCCGGCACCTACTCC

TACAGCTTCGACATCTGGGGCCAGGGCACCATGGTCACAGTCTCT

TCT

CD79b Ab VL
SEQ ID NO: 47
DIQMTQSPSSLSASVGDRVTITCRSSQSLFDSDDGNTYLDWFQQK

PGQSPKLLIQTLSYRASGVPSRFSGSGSGTDFTLTISSLQPEDFA

TYYCMQRMEFPLTFGGGTKVEIK

CD79b Ab VL
SEQ ID NO: 48
GACATCCAGATGACCCAGTCTCCATCCTCTCTGTCCGCCTCTGTG

GGCGACAGAGTGACCATCACCTGTCGGTCCTCTCAGTCCCTGTTC

GACTCTGACGACGGCAACACCTACCTGGACTGGTTCCAGCAGAAG

CCCGGCCAGTCTCCTAAGCTGCTGATCCAGACACTGTCCTACAGA

GCCTCTGGCGTGCCCTCCAGATTTTCCGGCTCTGGCTCTGGCACC

GACTTTACCCTGACAATCTCCAGCCTGCAGCCTGAGGACTTCGCC

ACCTACTACTGTATGCAGCGGATGGAATTTCCCCTGACCTTCGGC

GGAGGCACCAAGGTGGAAATCAAG

CD79b Ab VH
SEQ ID NO: 49
EVQLVESGPGLVKPSQTLSLTCAISGDSVSSNSAAWNWIRQSPSR

GLEWLGRTYYRSKWYNDYAVSVRSRITINPDTSKNQFSLQLNSVT

PEDTAVYFCTRVNTTFDYWGQGTLVTVSS

CD79b Ab VH
SEQ ID NO: 50
GAAGTGCAACTGGTGGAATCTGGCCCTGGACTGGTGAAGCCTTCT

CAGACCCTGTCTCTGACCTGCGCCATCTCCGGCGACTCCGTGTCC

TCCAACTCTGCCGCCTGGAACTGGATCAGACAGTCCCCTTCCAGA

GGCCTGGAATGGCTGGGCAGAACCTACTACAGATCCAAGTGGTAC

AACGACTACGCCGTGTCTGTGCGGTCCCGGATCACCATCAACCCT

GACACCTCTAAGAACCAGTTCTCCCTGCAACTGAACTCCGTGACC

CCTGAGGACACCGCCGTGTACTTCTGCACCAGAGTGAACACCACC

TTCGACTACTGGGGCCAGGGCACCCTGGTCACCGTGTCCTCT

CD79b Ab VL
SEQ ID NO: 51
QSVLTQPPSVSEAPRQRVTISCSGSSSNIGKNAVSWYQQLPGKAP

KLLIHSDDLLSSGVSDRFSGSQSGTSASLAISGLQSEDEADYYCA

AWDDSLNGVVFGGGTKLTVL

CD79b Ab VL
SEQ ID NO: 52
CAGTCTGTGCTGACTCAGCCACCCTCGGTGTCTGAAGCCCCCAGG

CAGAGGGTCACCATCTCCTGTTCTGGAAGTAGCTCCAACATCGGA

AAAAATGCTGTAAGCTGGTACCAGCAGCTCCCAGGAAAGGCTCCC

AAACTCCTCATCCATTCTGATGATCTGCTGTCCTCAGGGGTCTCT

GACCGATTCTCTGGCTCCCAGTCTGGCACCTCAGCCTCCCTGGCC

ATCAGTGGGCTCCAGTCCGAGGATGAGGCTGATTATTACTGTGCA

GCATGGGATGACAGCCTGAATGGTGTGGTATTCGGCGGAGGGACT

AAACTGACCGTCCTA

CD79b Ab VL
SEQ ID NO: 53
QLVLTQPPSVSEAPRQRVTISCSGSSSNIGNHGVNWYQQLPGKAP

KLLIYNDDLLPSGVSDRFSGSTSGTSGSLAISGLQSEDEADYYCA

AWDDSLNGVVFGGGTKLTVL

CD79b Ab VL
SEQ ID NO: 54
CAGCTTGTGCTGACTCAGCCACCCTCGGTGTCTGAAGCCCCCAGG

CAGAGGGTCACCATCTCCTGTTCTGGAAGTAGCTCCAACATCGGA

AATCATGGTGTAAACTGGTACCAGCAGCTCCCAGGAAAGGCTCCC

AAACTCCTCATCTATAATGATGATCTGCTGCCCTCAGGGGTCTCT

GACCGATTCTCTGGCTCCACGTCTGGCACCTCAGGTTCCCTGGCC

ATCAGTGGGCTCCAGTCTGAGGATGAGGCTGATTATTACTGTGCA

GCATGGGATGACAGCCTGAATGGTGTGGTATTCGGCGGAGGGACT

AAACTGACCGTCCTA

CD79b Ab VH
SEQ ID NO: 55
QVQLQQSGPGLVKPSQTLSLTCAISGDSVSNNSATWNWIRQSPSR

GLEWLGRTYYRSKWYNDYTVSVKSRITINPDTSKNQFSLQLNSVT

PEDTAVYYCTRVDIAFDYWGQGTTVTVSS

CD79b Ab VH
SEQ ID NO: 56
CAAGTGCAACTGCAGCAGTCTGGCCCTGGCCTGGTGAAGCCTTCT

CAGACCCTGTCTCTGACCTGCGCCATCTCCGGCGACTCCGTGTCC

AACAACTCTGCTACCTGGAACTGGATCAGACAGTCCCCTTCCAGA

GGCCTGGAATGGCTGGGCAGAACCTACTACAGATCCAAGTGGTAC

AACGACTACACCGTGTCTGTGAAGTCCCGGATCACCATCAACCCC

GATACCTCTAAGAACCAGTTCTCCCTGCAACTGAACTCCGTGACC

CCTGAGGACACCGCCGTGTACTACTGCACCAGAGTGGACATCGCC

TTCGACTACTGGGGCCAGGGCACCACCGTGACAGTGTCCTCC

CD79b Ab VL

```
QSALTQPPSVSEAPRQRVTISCSGSSSNIGNHGVNWYQQLPGKAP
KLLIYNDDLLPSGVSDRFSGSTSGTSGSLAISGLQSEDEADYYCA
AWDDSLNGVVFGGGTKLTVL
```

CD79b Ab VL
SEQ ID NO: 58
```
CAGTCTGCCCTGACTCAGCCACCCTCGGTGTCTGAAGCCCCCAGG
CAGAGGGTCACCATCTCCTGTTCTGGAAGTAGCTCCAACATCGGA
AATCATGGTGTAAACTGGTACCAGCAGCTCCCAGGAAAGGCTCCC
AAACTCCTCATCTATAATGATGATCTGCTGCCCTCAGGGGTCTCT
GACCGATTCTCTGGCTCCACGTCTGGCACCTCAGGTTCCCTGGCC
ATCAGTGGGCTCCAGTCTGAGGATGAGGCTGATTATTACTGTGCA
GCATGGGATGACAGCCTGAATGGTGTGGTATTCGGCGGAGGGACC
AAGCTGACCGTCCTA
```

CD79b Ab VH
SEQ ID NO: 59
```
QVQLVQSGPGLVKPSETLSLICTVSGASISSYYWSWIRQPAGKGL
EWLGRISNTGRTNYNPSLKSRVTMSSDTSKNQFSLKLRSVTAADT
AVYYCARGEYSGTFSYGFDIWGQGTMVTVSS
```

CD79b Ab VH
SEQ ID NO: 60
```
CAAGTGCAGTTGGTACAGTCTGGTCCCGGGCTTGTAAAGCCTTCT
GAAACATTGAGCCTGATATGCACCGTCTCCGGTGCCAGTATAAGT
AGTTATTACTGGTCATGGATCCGTCAGCCCGCAGGTAAAGGCTTG
GAGTGGTTGGGAAGGATTAGTAATACTGGACGAACCAATTACAAT
CCTTCCCTGAAGAGTCGTGTTACCATGAGTAGTGATACCAGCAAG
AACCAGTTCTCACTTAAATTGAGGTCCGTGACCGCCGCTGACACC
GCTGTCTACTACTGTGCTCGCGGAGAGTATTCAGGAACCTTTTCA
TACGGGTTCGATATTTGGGGCCAGGGGACAATGGTTACTGTGAGT
TCA
```

CD79b Ab VL
SEQ ID NO: 61
```
EIVLTQSPLSLSVTPGEPASISCRSSLSLLDSDDGKIYLDWYLQR
PGQSPQLLIQTLSYRASGVPDRFSGSGSGTDHTLKISRVEAEDVG
VYYCMQRMEFPLTFGGGTKLEIK
```

CD79b Ab VL
SEQ ID NO: 62
```
GAAATTGTGTTGACACAGTCTCCACTCTCCCTGTCCGTCACCCCT
GGAGAGCCGGCCTCCATCTCCTGCAGGTCTAGTCTGAGCCTCTTG
GATAGTGATGATGGAAAAATCTATTTGGACTGGTACCTGCAGAGG
CCAGGGCAGTCTCCACAGCTCCTGATCCAGACGCTTTCCTATCGG
GCCTCTGGAGTCCCAGACAGGTTCAGTGGCAGTGGGTCAGGCACT
GATCACACACTGAAAATCAGCAGGGTGGAGGCTGAGGATGTTGGA
GTTTATTACTGCATGCAACGTATGGAGTTTCCGCTCACTTTCGGC
GGAGGGACCAAGCTGGAGATCAAA
```

CD79b Ab VH
SEQ ID NO: 63
```
QVQLQESGPGLVKPSETLSLTCSVSGASISSYYWSWIRQPAGKGL
EWIGRIYSNGNINYHSSLKRRVTMSVDTSKNQFSLKLNAVTAADT
AVYYCARGEYSGDFSYSFDIWGQGTMVTVSS
```

CD79b Ab VH
SEQ ID NO: 64
```
CAAGTACAGCTTCAAGAGTCCGGGCCAGGTCTCGTTAAGCCATCC
GAAACTCTGTCACTTACTTGTTCAGTCTCAGGAGCTTCAATTTCT
TCATATTACTGGTCCTGGATTCGTCAACCAGCCGGCAAAGGTTTG
GAGTGGATAGGCCGGATATATTCAAATGGAAATATCAACTACCAC
TCATCCCTTAAACGTAGGGTTACAATGAGTGTGGATACCTCTAAG
AATCAGTTCAGTTTGAAATTGAATGCTGTCACCGCCGCTGACACC
GCAGTCTATTATTGTGCCAGAGGCGAATACAGTGGTGACTTCTCA
TATAGCTTTGACATTTGGGGTCAGGGAACAATGGTCACAGTGAGT
TCC
```

CD79b Ab VL
SEQ ID NO: 65
```
DIVMTQSPLSLPVTPGEPASISCRSSQSLLDSDDGNTYLDWFLQK
PGQSPQLLIYTLSYRASGVPDRFSGSGSGTDFTLKISRVEAEDVG
IYYCMQRIEFPLTFGGGTKVEIK
```

CD79b Ab VL
SEQ ID NO: 66
```
GATATTGTGATGACTCAGTCTCCACTCTCCCTGCCCGTCACCCCT
GGAGAGCCGGCCTCCATCTCCTGCAGGTCTAGTCAGAGCCTCTTG
GATAGTGATGATGGAAACACCTATTTGGACTGGTTCCTGCAGAAG
CCAGGGCAGTCTCCACAGCTCCTGATCTATACGCTTTCCTATCGG
GCCTCTGGAGTCCCAGACAGGTTCAGTGGCAGTGGGTCAGGCACG
GATTTCACACTGAAAATCAGCAGGGTGGAGGCTGAGGATGTTGGA
ATTTATTACTGCATGCAACGTATAGAGTTTCCGCTCACTTTCGGC
GGAGGGACCAAGGTGGAAATCAAA
```

CD79b Ab VH
SEQ ID NO: 67
```
QVQLQQSGPGLVRPSETLALTCSVSGVSISNYYWSWIRQPAGRGL
EWIGRISPSGRTNYNTSLKSRGTMSLDASKNQFSLKVNSVTAADT
AVYYCARGEYSGTYSYSFDIWGQGTMVTVSS
```

CD79b Ab VH
SEQ ID NO: 68
```
CAAGTTCAGCTTCAACAATCTGGTCCAGGTCTCGTAAGACCATCA
GAAACATTGGCTCTTACATGCTCTGTTAGTGGTGTGTCAATCAGT
AACTATTACTGGTCCTGGATCCGCCAACCTGCTGGCCGTGGGCTC
GAATGGATCGGACGAATCTCACCTAGCGGTAGGACAAATTACAAC
ACTTCCCTTAAATCACGAGGGACAATGAGCCTCGACGCATCAAAG
AACCAGTTCAGCCTTAAAGTAAACTCCGTTACCGCAGCAGATACT
```

```
GCAGTCTACTATTGTGCCAGGGGTGAATATTCAGGAACATATTCC

TATTCTTTTGACATTTGGGGCCAGGGAACCATGGTAACAGTGAGT

TCA

CD79b Ab VL
                                        SEQ ID NO: 69
DIVMTQTPLSLPVTPGEPASISCRSSQSLFDSDDGNTYLDWFLQK

PGQSPQLLIQTLSYRASGVPDRFSGSGSGTDFTLKISRVEADDVG

VYYCMQRMEFPLTFGGGTKLEIK

CD79b Ab VL
                                        SEQ ID NO: 70
GATATTGTGATGACTCAGACTCCACTCTCTCTGCCCGTCACCCCT

GGAGAACCGGCCTCCATCTCCTGCAGGTCTAGTCAGAGCCTCTTT

GATAGTGATGATGGAAACACCTATTTGGACTGGTTCCTGCAGAAG

CCAGGGCAGTCTCCACAGCTCCTAATCCAAACGCTTTCCTATCGG

GCCTCTGGAGTCCCAGACAGGTTCAGTGGCAGTGGGTCAGGCACC

GATTTCACACTGAAAATCAGCAGGGTGGAGGCTGATGATGTTGGA

GTTTATTACTGCATGCAACGTATGGAGTTTCCGCTCACTTTCGGC

GGAGGGACCAAGCTGGAGATCAAA

CD79b Ab VH
                                        SEQ ID NO: 71
QVQLQESGPGLVKPSETLSLTCSVSGGSISNYYWSWIRQPAGKGL

EWIGRIFYSGKTNYNSSLKSRVTMSADTSKNQFSLKLSSVTAADT

AVYYCARGEYSGEYSYSFDIWGQGTTVTVSS

CD79b Ab VH
                                        SEQ ID NO: 72
CAGGTACAACTTCAGGAGAGCGGCCCAGGTTTGGTTAAACCAAGT

GAAACCTTGTCACTTACCTGTTCCGTGTCAGGTGGGTCAATAAGC

AATTACTACTGGTCCTGGATTAGACAACCTGCTGGAAAGGGGCTT

GAATGGATCGGGAGGATATTCTACTCAGGGAAGACAAACTACAAT

AGTAGCCTCAAGTCCAGGGTGACCATGTCCGCTGATACTTCCAAG

AATCAATTTAGCCTTAAATTGTCCTCCGTTACAGCCGCTGATACC

GCAGTGTACTACTGTGCAAGAGGTGAGTACAGTGGCGAATACTCA

TATTCCTTTGACATCTGGGGTCAGGGCACTACTGTGACTGTTTCA

TCT

CD79b Ab VL
                                        SEQ ID NO: 73
EIVMTQSPLSLPVTPGEPASISCRSSQSLLDSDDGNTYVDWFLQK

PGQSPQLLIYTLSYRASGVPDRFSGSGSDTDFTLKISRVEAEDVG

IYYCMQRMEFPLTFGGGTKVEIK

CD79b Ab VL
                                        SEQ ID NO: 74
GAAATAGTGATGACGCAGTCTCCACTCTCCCTGCCCGTCACCCCT

GGAGAGCCGGCCTCCATTTCCTGCCGGTCTAGTCAGAGCCTCTTG

GATAGTGATGATGGAAACACCTATGTGGACTGGTTCCTGCAGAAG

CCAGGGCAGTCTCCACAACTCCTGATCTATACGCTTTCCTATCGG

GCCTCTGGAGTCCCAGACAGGTTCAGTGGCAGTGGGTCAGACACT

GATTTCACACTGAAAATCAGCAGGGTGGAGGCTGAAGATGTTGGA
```

```
ATTTATTACTGCATGCAACGTATGGAGTTTCCGCTCACTTTCGGC

GGAGGGACCAAGGTGGAGATCAAA

CD3 Ab VH-CDR3
                                        SEQ ID NO: 75
PQVHYDYAGFPY

CD3 Ab VH-CDR1
                                        SEQ ID NO: 76
GYTFTRSTMH

CD3 Ab VH-CDR2
                                        SEQ ID NO: 77
YINPSSAYTN

CD3 Ab VH-CDR3
                                        SEQ ID NO: 78
PQVHYDYNGFPY

CD3 Ab VL-CDR1
                                        SEQ ID NO: 79
SASSSVSYMN

CD3 Ab VL-CDR2
                                        SEQ ID NO: 80
DSSKLAS

CD3 Ab VL-CDR3
                                        SEQ ID NO: 81
QQWSRNPPT

CD3 Ab VH-CDR3
                                        SEQ ID NO: 82
PQVHYDYGGFPY

CD3 Ab VH-CDR1
                                        SEQ ID NO: 83
GFTFSRYNMN

CD3 Ab VH-CDR2
                                        SEQ ID NO: 84
SISTSSNYIY

CD3 Ab VH-CDR3
                                        SEQ ID NO: 85
GWGPFDY

CD3 Ab VL-CDR1
                                        SEQ ID NO: 86
RARQSIGTAIH

CD3 Ab VL-CDR2
                                        SEQ ID NO: 87
YASESIS

CD3 Ab VL-CDR3
                                        SEQ ID NO: 88
QQSGSWPYT

CD3 Ab VH-CDR1
                                        SEQ ID NO: 89
GFTFSSYAMS

CD3 Ab VH-CDR2
                                        SEQ ID NO: 90
AISGSGGSTY

CD3 Ab VH-CDR3
                                        SEQ ID NO: 91
YDGIYGELDF

CD3 Ab VL-CDR1
                                        SEQ ID NO: 92
RAS QSISSYLN

CD3 Ab VL-CDR2
                                        SEQ ID NO: 93
AASSLQS
```

CD3 Ab VL-CDR3
QQSYSTPLT
SEQ ID NO: 94

CD20 Ab VH-CDR3
VYYGSNYWYFDV
SEQ ID NO: 95

CD20 Ab VL-CDR1
RASSSVSYMH
SEQ ID NO: 96

CD3 Ab VH
SEQ ID NO: 97
QVQLVQSGAEVKKPGSSVKVSCKASGYTFTRSTMHWVKQAPGQGL
EWIGYINPSSAYTNYNQKFQGRVTLTADKSTSTAYMELSSLRSED
TAVYYCASPQVHYDYNGFPYWGQGTLVTVSS

CD3 Ab VH
SEQ ID NO: 98
CAGGTTCAGCTGGTTCAGTCTGGCGCCGAAGTGAAGAAACCTGGC
TCCTCCGTCAAGGTGTCCTGCAAGGCTTCCGGCTACACCTTTACC
AGATCCACCATGCACTGGGTCAAACAGGCTCCAGGACAAGGCTTG
GAGTGGATCGGCTACATCAACCCCAGCTCCGCCTACACCAACTAC
AACCAGAAATTCCAGGGCAGAGTCACCCTCACCGCCGACAAGTCT
ACCTCCACCGCCTACATGAACTGTCCAGCCTGAGATCTGAGGAC
ACCGCCGTGTACTACTGCGCCAGCCCTCAGGTGCACTACGACTAC
AACGGCTTCCCTTATTGGGGCCAGGGCACCCTGGTTACCGTTTCT
TCT

CD3 Ab VL
SEQ ID NO: 99
EIVLTQSPATLSASPGERVTLSCSASSSVSYMNWYQQKPGQAPRR
WIYDSSKLASGVPARFSGSGSGRDYTLTISSLEPEDFAVYYCQQW
SRNPPTFGGGTKVEIK

CD3 Ab VL
SEQ ID NO: 100
GAGATCGTGCTGACCCAGTCTCCTGCCACACTGAGTGCTTCTCCA
GGCGAGAGAGTGACCCTGTCCTGCTCCGCTTCCTCCTCCGTGTCC
TACATGAACTGGTATCAGCAGAAGCCCGGCCAGGCTCCTCGGAGA
TGGATCTACGACTCTTCCAAGCTGGCCTCTGGTGTGCCAGCCAGA
TTTTCTGGCTCTGGCTCCGGCAGAGACTATACCCTGACCATCTCC
AGCCTGGAACCTGAGGACTTCGCCGTGTACTACTGCCAGCAGTGG
TCTAGGAACCCTCCTACCTTTGGCGGAGGCACCAAGGTGGAAATC
AAG

CD3 Ab VH
SEQ ID NO: 101
QVQLVQSGAEVKKPGSSVKVSCKASGYTFTRSTMHWVKQAPGQGL
EWIGYINPSSAYTNYNQKFQGRVTLTADKSTSTAYMELSSLRSED
TAVYYCASPQVHYDYAGFPYWGQGTLVTVSS

CD3 Ab VH
SEQ ID NO: 102
CAGGTTCAACTGGTTCAGTCTGGCGCCGAAGTGAAGAAACCTGGC
TCCTCCGTCAAGGTGTCCTGCAAGGCTTCCGGCTACACCTTTACC
AGATCCACCATGCACTGGGTCAAGCAGGCCCCTGGACAAGGCTTG
GAGTGGATCGGCTACATCAACCCCAGCTCCGCCTACACCAACTAC
AACCAGAAATTCCAGGGCAGAGTGACCCTGACCGCCGACAAGTCT
ACCTCCACCGCCTACATGAACTGTCCAGCCTGAGATCTGAGGAC
ACCGCCGTGTACTACTGCGCCTCTCCTCAGGTCCACTACGACTAC
GCCGGCTTTCCTTATTGGGCCAGGGCACACTGGTCACCGTTTCT
TCT

CD3 Ab VH
SEQ ID NO: 103
QVQLVQSGAEVKKPGSSVKVSCKASGYTFTRSTMHWVRQAPGQGL
EWMGYINPSSAYTNYAQKFQGRVTLTADKSTSTAYMELSSLRSED
TAVYYCASPQVHYDYNGFPYWGQGTLVTVSS

CD3 Ab VH
SEQ ID NO: 104
CAGGTTCAGCTGGTTCAGTCTGGCGCCGAAGTGAAGAAACCTGGC
TCCTCCGTCAAGGTGTCCTGCAAGGCTTCCGGCTACACCTTTACC
AGATCCACCATGCACTGGGTCCGACAGGCTCCAGGCCAAGGCTTG
GAGTGGATGGGCTACATCAACCCCAGCTCCGCCTACACCAACTAC
GCCCAGAAATTCCAGGGCAGAGTCACCCTCACCGCCGACAAGTCT
ACCTCCACCGCCTACATGAACTGTCCAGCCTGAGATCTGAGGAC
ACCGCCGTGTACTACTGCGCCAGCCCTCAGGTGCACTACGACTAC
AACGGCTTCCCTTATTGGGGCCAGGGCACCCTGGTTACCGTTTCT
TCT

CD3 Ab VH
SEQ ID NO: 105
QVQLVQSGAEVKKPGSSVKVSCKASGYTFTRSTMHWVRQAPGQGL
EWMGYINPSSAYTNYAQKFQGRVTLTADKSTSTAYMELSSLRSED
TAVYYCASPQVHYDYGGFPYWGQGTLVTVSS

CD3 Ab VH
SEQ ID NO: 106
CAGGTTCAACTGGTTCAGTCTGGCGCCGAAGTGAAGAAACCTGGC
TCCTCCGTGAAAGTGTCCTGCAAGGCTTCCGGCTACACTTTTACC
AGATCCACCATGCACTGGGTCCGACAGGCTCCAGGACAAGGCTTG
GAGTGGATGGGCTACATCAACCCCAGCTCCGCCTACACCAACTAC
GCCCAGAAATTCCAGGGCAGAGTGACCCTGACCGCCGACAAGTCT
ACCTCCACCGCCTACATGAACTGTCCAGCCTGAGATCTGAGGAC
ACCGCCGTGTACTACTGCGCTTCTCCTCAGGTGCACTACGACTAC
GGCGGCTTTCCTTATTGGGGCCAGGGCACACTGGTCACCGTTTCT
TCT

CD3 Ab VH
SEQ ID NO: 107
EVQLVESGGGLVKPGGSLRLSCAASGFTFSRYNMNWVRQAPGKGL
EWVSSISTSSNYIYYADSVKGRFTFSRDNAKNSLDLQMSGLRAED
TAIYYCTRGWGPFDYWGQGTLVTVSS

-continued

CD3 Ab VH
                                              SEQ ID NO: 108
GAGGTGCAACTGGTGGAGTCTGGGGGAGGCCTGGTCAAGCCTGGG

GGGTCCCTGAGACTCTCCTGTGCAGCCTCTGGATTCACCTTCAGT

AGATATAACATGAACTGGGTCCGCCAGGCTCCAGGGAAGGGGCTG

GAGTGGGTCTCATCCATTAGTACTAGTAGTAATTACATATACTAC

GCAGACTCAGTGAAGGGCCGATTCACCTTCTCCAGAGACAACGCC

AAGAACTCACTGGATCTGCAAATGAGCGGCCTGAGAGCCGAGGAC

ACGGCTATTTATTACTGTACGAGAGGCTGGGGGCCTTTTGACTAC

TGGGGCCAGGGAACCCTGGTCACCGTCTCCTCA

CD3 Ab VL
                                              SEQ ID NO: 109
DIQMTQSPSSLSASVGDRVTITCRARQSIGTAIHWYQQKPGKAPK

LLIKYASESISGVPSRFSGSGSGTDFTLTISSLQPEDFATYYCQQ

SGSWPYTFGQGTKLEIK

CD3 Ab VL
                                              SEQ ID NO: 110
GACATACAAATGACACAATCACCCTCTTCTCTTTCTGCAAGCGTT

GGCGACCGTGTCACTATCACTTGTCGAGCCCGCCAGTCCATAGGT

ACTGCCATTCACTGGTATCAACAGAAGCCTGGCAAGGCTCCCAAA

CTCCTGATTAAGTATGCCAGCGAGAGCATTTCCGGCGTACCTTCA

AGATTTTCCGGCTCCGGTAGTGGGACAGATTTCACTCTCACTATA

TCTAGCCTCCAACCAGAAGATTTCGCCACTTACTACTGTCAACAA

TCAGGTTCATGGCCTTACACTTTCGGCCAGGGGACAAAATTGGAG

ATCAAG

CD3 Ab VH
                                              SEQ ID NO: 111
EVQLLESGGGLVQPGGSLRLSCAASGFTFSSYAMSWVRQAPGKGL

EWVSAISGSGGSTYYADSVKGRFTISRDNSKNTLYLQMNSLRAED

TAVYYCAKYDGIYGELDFWGQGTLVTVSS

CD3 Ab VH
                                              SEQ ID NO: 112
GAGGTGCAGTTGCTGGAGTCCGGGGGTGGACTCGTACAACCTGGA

GGTTCTCTGCGGTTGTCCTGTGCTGCCAGCGGATTCACATTTTCC

TCTTATGCCATGTCCTGGGTACGTCAAGCACCCGGCAAAGGACTT

GAGTGGGTCTCCGCTATCAGTGGTTCAGGGGGATCAACCTACTAT

GCTGATAGTGTTAAGGGCGTTTTACCATCTCAAGAGACAACTCC

AAGAACACCCTGTACCTGCAGATGAACTCACTCCGCGCCGAGGAT

ACAGCAGTTTACTACTGTGCTAAGTATGACGGCATTTACGGCGAA

CTGGACTTTTGGGGACAGGGGACCTTGGTCACAGTCTCCAGC

CD3 Ab VL
                                              SEQ ID NO: 113
DIQMTQSPSSLSASVGDRVTITCRASQSISSYLNWYQQKPGKAPK

LLIYAASSLQSGVPSRFSGSGSGTDFTLTISSLQPEDFATYYCQQ

SYSTPLTFGQGTKVEIK

CD3 Ab VL
                                              SEQ ID NO: 114
GATATTCAGATGACTCAGAGCCCCTCTTCACTGAGTGCCTCAGTA

GGGGATCGTGTGACTATCACCTGTCGTGCTTCCCAAAGCATCTCC

TCATATTTGAACTGGTACCAGCAGAAGCCAGGCAAGGCACCCAAA

CTGCTGATTTACGCCGCCAGTTCTCTCCAGAGTGGCGTTCCCAGC

CGTTTCTCAGGTTCTGGATCTGGTACCGATTTCACATTGACCATA

TCATCCCTCCAGCCTGAGGACTTCGCCACCTACTATTGCCAACAG

TCATATTCTACTCCACTTACATTCGGCCAGGGCACCAAGGTGGAA

ATTAAG

CD20 Ab VH-CDR1
                                              SEQ ID NO: 115
GYTFTSYNMH

CD20 Ab VH-CDR2
                                              SEQ ID NO: 116
AIYPGNGDTS

CD20 Ab VH-CDR3
                                              SEQ ID NO: 117
STYYGGDWYFNV

CD20 Ab VL-CDR1
                                              SEQ ID NO: 118
RAS S SVSYIH

CD20 Ab VL-CDR2
                                              SEQ ID NO: 119
ATSNLAS

CD20 Ab VL-CDR3
                                              SEQ ID NO: 120
QQWTSNPPT

CD20 Ab VH-CDR1
                                              SEQ ID NO: 121
GYTFSSYNMH

CD20 Ab VH-CDR2
                                              SEQ ID NO: 122
AIYPGAGDTS

CD20 Ab VH-CDR3
                                              SEQ ID NO: 123
SNYYGSSGWYFDV

CD20 Ab VL-CDR1
                                              SEQ ID NO: 124
RASLSVSSMH

CD20 Ab VL-CDR3
                                              SEQ ID NO: 125
QQWIFNPPT

CD20 Ab VH
                                              SEQ ID NO: 126
QVQLVQSGAEVKKPGSSVKVSCKASGYTFTSYNMHWVRQAPGQGL

EWMGAIYPGNGDTSYAQKFQGRVTITADKSTSTAYMELSSLRSED

TAVYYCARSTYYGGDWYFNVWGQGTLVTVSS

CD20 Ab VH
                                              SEQ ID NO: 127
CAGGTTCAGCTGGTTCAGTCTGGTGCCGAAGTGAAGAAACCTGGC

TCCTCCGTGAAAGTGTCCTGCAAGGCTTCCGGCTACACTTTTACC

AGCTACAACATGCACTGGGTCCGACAGGCCCCTGGACAAGGATTG

```
-continued
GAATGGATGGGCGCTATCTACCCCGGCAACGGCGATACCTCTTAC
GCCCAGAAATTCCAGGGCAGAGTGACCATCACCGCCGACAAGTCT
ACCTCCACCGCCTACATGGAACTGTCCAGCCTGAGATCTGAGGAC
ACCGCCGTGTACTACTGCGCCCGGTCTACCTATTATGGCGGCGAC
TGGTACTTCAACGTGTGGGGCCAGGGAACCCTGGTCACAGTCTCT
TCT
```

CD20 Ab VL  
SEQ ID NO: 128  
AIQLTQSPSSLSASVGDRVTITCRASSSVSYIHWFQQKPGKAPKP
LIYATSNLASGVPSRFSGSGSGTDFTLTISSLQPEDFATYYCQQW
TSNPPTFGQGTKLEIK

CD20 Ab VL  
SEQ ID NO: 129  
```
GCCATTCAGCTGACCCAGTCTCCATCCTCTCTGTCCGCCTCTGTG
GGCGACAGAGTGACAATTACCTGCCGGGCCTCCTCCTCCGTGTCC
TACATCCATTGGTTCCAGCAGAAGCCCGGCAAGGCCCCTAAGCCT
CTGATCTACGCCACCTCCAATCTGGCCTCTGGCGTGCCCTCCAGA
TTTTCCGGATCTGGCTCTGGAACCGACTTTACCCTGACAATCTCC
AGCCTGCAGCCTGAGGACTTCGCCACCTACTACTGTCAGCAGTGG
ACCAGCAATCCTCCTACCTTTGGCCAGGGCACCAAGCTGGAAATC
AAG
```

CD20 Ab VH  
SEQ ID NO: 130  
QVQLVQSGAEVKKPGSSVKVSCKASGYTFSSYNMHWVRQAPGQGL
EWMGAIYPGAGDTSYAQKFQGRVTITADESTSTAYMELSSLRSED
TAVYYCARSNYYGSSGWYFDVWGKGTTVTVSS

CD20 Ab VH  
SEQ ID NO: 131  
```
CAGGTTCAACTGGTTCAGTCTGGCGCCGAAGTGAAGAAACCTGGC
TCCTCCGTGAAGGTGTCCTGCAAGGCTTCCGGCTACACCTTCTCC
AGCTACAACATGCACTGGGTCCGACAGGCCCCTGGACAAGGATTG
GAATGGATGGGCGCTATCTACCCTGGCGCTGGCGATACCTCTTAC
GCCCAGAAATTCCAGGGCAGAGTGACCATCACCGCCGACGAGTCT
ACCTCCACCGCCTACATGGAACTGTCCAGCCTGAGATCTGAGGAC
ACCGCCGTGTACTACTGCGCCCGGTCTAATTACTACGGCTCCAGC
GGCTGGTACTTCGACGTGTGGGGAAAGGGCACCACCGTGACAGTC
TCTTCT
```

CD20 Ab VL  
SEQ ID NO: 132  
EIVLTQSPATLSLSPGERATLSCRASLSVSSMHWYQQKPGQAPRL
LIYATSNLASGIPARFSGSGSGTDFTLTISSLEPEDFAVYYCQQW
IFNPPTFGGGTKVEIK

CD20 Ab VL  
SEQ ID NO: 133  
```
GAGATCGTGCTGACCCAGTCTCCAGCCACACTGTCACTGTCTCCA
GGCGAGAGAGCTACCCTGTCCTGTAGAGCCTCTCTGTCCGTGTCC
TCCATGCACTGGTATCAGCAGAAGCCTGGACAGGCCCCTCGGCTG
```

-continued
```
CTGATCTACGCTACCTCTAATCTGGCCAGCGGTATCCCCGCCAGA
TTTTCTGGTTCTGGCTCTGGCACCGACTTTACCCTGACCATCTCC
AGCCTGGAACCTGAGGACTTCGCCGTGTACTACTGCCAGCAGTGG
ATCTTCAACCCTCCTACCTTTGGCGGAGGCACCAAGGTGGAAATC
AAG
```

CD20 Ab VH  
SEQ ID NO: 134  
QAYLQQSGAELVRPGASVKMSCKASGYTFTSYNMHWVKQTPRQGL
EWIGAIYPGNGDTSYNQKFKGKATLTVDKSSSTAYMQLSSLTSED
SAVYFCARVYYGSNYWYFDVWGTGTTVTVSS

CD20 Ab VH  
SEQ ID NO: 135  
```
CAAGCATATCTGCAACAGAGCGGAGCTGAGCTGGTTCGGCCTGGC
GCCTCTGTAAAAATGAGTTGCAAGGCCAGTGGTTATACATTCACA
TCATATAATATGCACTGGGTAAAGCAAACTCCCCGACAGGGGCTT
GAATGGATTGGCGCAATCTATCCCGGCAATGGGGATACATCCTAC
AATCAGAAATTCAAGGGCAAGGCAACACTGACCGTTGACAAATCC
TCATCAACAGCCTACATGCAGCTCAGTTCCCTCACTAGCGAAGAT
TCTGCTGTGTATTTCTGTGCAAGGGTGTATTATGGTTCTAATTAC
TGGTATTTCGATGTTTGGGGAACCGGAACTACCGTAACTGTTTCT
AGC
```

CD20 Ab VL  
SEQ ID NO: 136  
QIVLSQSPAILSASPGEKVTMTCRASSSVSYMHWYQQKPGSSPQV
WIYATSNLASGVPVRFSGSGSGTSYSLTISRVEAEDTATYYCQQW
IFNPPTFGSGTKLEIR

CD20 Ab VL  
SEQ ID NO: 137  
```
CAAATAGTCCTTTCACAGTCCCCAGCTATTCTTTCAGCCTCTCCC
GGTGAAAAGGTTACAATGACCTGCCGGGCAAGCTCCAGTGTCTCA
TATATGCACTGGTACCAACAAAAACCTGGCAGTAGTCCTCAGGTG
TGGATCTACGCTACAAGCAATCTCGCTTCCGGGGTTCCCGTGAGG
TTTAGCGGAAGCGGGTCTGGAACTAGTTATTCCTTGACAATTAGT
CGGGTTGAAGCCGAGGACACCGCCACTTACTATTGCCAACAGTGG
ATATTCAATCCACCCACCTTCGGTTCAGGTACCAAGCTCGAAATC
CGT
```

CD20 Ab VH  
SEQ ID NO: 138  
QAYLQQSGAELVRPGASVKMSCKTSGYTFSSYNMHWVKQTPRQAL
EWIGAIYPGNGDTSYNQKFKGKATLTVDKSSSTAYMQLSSLTSED
SAVYFCTRSNYYGSSGWYFDVWGTGTTVTVSS

CD20 Ab VH  
SEQ ID NO: 139  
```
CAAGCCTATCTTCAACAATCTGGGGCTGAGCTTGTCCGGCCAGGA
GCCTCCGTCAAAATGAGCTGCAAAACCTCAGGTTATACTTTTAGT
AGCTATAACATGCATTGGGTAAAACAAACCCCCCGACAAGCATTG
```

```
GAGTGGATAGGGGCCATATACCCCGGCAATGGAGACACAAGTTAC
AACCAGAAGTTTAAAGGCAAAGCTACACTCACAGTTGACAAATCC
TCAAGTACTGCTTATATGCAACTCTCCTCTCTCACTTCCGAAGAC
AGTGCCGTATATTTTTGCACTCGGTCCAATTACTATGGATCTAGT
GGCTGGTACTTTGACGTTTGGGGCACTGGGACAACTGTTACAGTG
TCCAGC
```

CD20 Ab VL
SEQ ID NO: 140
```
QIVLSQSPAILSASPGEKVTMTCRASLSVSSMHWYQQKPGSSPKP
WIYATSNLASGVPARFSGSGSGTSYSLTISRVEAEDAATYYCQQW
IFNPPTFGGGTKLEIK
```

CD20 Ab VL
SEQ ID NO: 141
```
CAGATTGTCCTGAGCCAATCCCCAGCAATTCTGAGTGCTAGCCCT
GGAGAGAAGGTAACAATGACTTGTCGGGCATCCCTTAGCGTCTCA
TCCATGCATTGGTATCAACAAAAGCCAGGTTCATCTCCAAAACCC
TGGATTTACGCTACATCTAACCTGGCATCTGGGGTGCCTGCCAGA
TTTAGTGGATCTGGTTCCGGCACATCATATTCCCTTACAATCAGC
CGAGTGGAAGCCGAGGATGCTGCAACCTATTACTGTCAACAATGG
ATATTTAACCCTCCCACCTTTGGGGGTGGGACTAAACTCGAAATC
AAG
``` trispecific Ab CD3-CD20 arm
SEQ ID NO: 142
```
EIVLTQSPATLSASPGERVTLSCSASSSVSYMNWYQQKPGQAPRR
WIYDSSKLASGVPARFSGSGSGRDYTLTISSLEPEDFAVYYCQQW
SRNPPTFGGGTKVEIKGGSEGKSSGSGSESKSTGGSQVQLVQSGA
EVKKPGSSVKVSCKASGYTFTRSTMHWVKQAPGQGLEWIGYINPS
SAYTNYNQKFQGRVTLTADKSTSTAYMELSSLRSEDTAVYYCASP
QVHYDYAGFPYWGQGTLVTVSSEPKSSDKTHTCPPCPAPEAAGGP
SVFLFPPKPKDTLMISRTPEVTCVVVSVSHEDPEVKFNWYVDGVE
VHNAKTKPREEQYNSTYRVVSVLTVLHQDWLNGKEYKCKVSNKAL
PAPIEKTISKAKGQPREPQVYTLPPSREEMTKNQVSLWCLVKGFY
PSDIAVEWESNGQPENNYKTTPPVLDSDGSFFLYSKLTVDKSRWQ
QGNVFSCSVMHEALHNHYTQKSLSLSPGKGGSEGKSSGSGSESKS
TGGSAIQLTQSPSSLSASVGDRVTITCRASSSVSYIHWFQQKPGK
APKPLIYATSNLASGVPSRFSGSGSGTDFTLTISSLQPEDFATYY
CQQWTSNPPTFGQGTKLEIKGGSEGKSSGSGSESKSTGGSQVQLV
QSGAEVKKPGSSVKVSCKASGYTFTSYNMHWVRQAPGQGLEWMGA
IYPGNGDTSYAQKFQGRVTITADKSTSTAYMELSSLRSEDTAVYY
CARSTYYGGDWYFNVWGQGTLVTVSS
``` trispecific Ab CD3-CD20 arm
SEQ ID NO: 143
```
GAGATCGTGCTGACCCAGTCTCCTGCCACACTGAGTGCTTCTCCA
GGCGAGAGAGTGACCCTGTCCTGCTCCGCTTCCTCCTCCGTGTCC
TACATGAACTGGTATCAGCAGAAGCCCGGCCAGGCTCCTCGGAGA
TGGATCTACGACTCTTCCAAGCTGGCCTCTGGTGTGCCAGCCAGA
TTTTCTGGCTCTGGCTCCGGCAGAGACTATACCCTGACCATCTCC
AGCCTGGAACCTGAGGACTTCGCCGTGTACTACTGCCAGCAGTGG
TCTAGGAACCCTCCTACCTTTGGCGGAGGCACCAAGGTGGAAATC
AAGGGCGGATCTGAGGGAAAGTCCAGCGGCTCCGGCAGCGAAAGC
AAGTCCACCGGCGGAAGCCAGGTTCAACTGGTTCAGTCTGGCGCC
GAAGTGAAGAAACCTGGCTCCTCCGTCAAGGTGTCCTGCAAGGCT
TCCGGCTACACCTTTACCAGATCCACCATGCACTGGGTCAAGCAG
GCCCCTGGACAAGGCTTGGAGTGGATCGGCTACATCAACCCCAGC
TCCGCCTACACCAACTACAACCAGAAATTCCAGGGCAGAGTGACC
CTGACCGCCGACAAGTCTACCTCCACCGCCTACATGGAACTGTCC
AGCCTGAGATCTGAGGACACCGCCGTGTACTACTGCGCCTCTCCT
CAGGTCCACTACGACTACGCCGGCTTTCCTTATTGGGGCCAGGGC
ACACTGGTCACCGTTTCTTCTGAGCCCAAATCTAGCGACAAAACT
CACACATGCCCACCGTGCCCAGCACCTGAAGCCGCCGGGGGACCG
TCAGTCTTCCTCTTCCCCCCAAAACCCAAGGACACCCTCATGATC
TCCCGGACCCCTGAGGTCACATGCGTGGTGGTGAGCGTGAGCCAC
GAAGACCCTGAGGTCAAGTTCAACTGGTACGTGGACGGCGTGGAG
GTGCATAATGCCAAGACAAAGCCGCGGGAGGAGCAGTACAACAGC
ACGTACCGTGTGGTCAGCGTCCTCACCGTCCTGCACCAGGACTGG
CTGAATGGCAAGGAGTACAAGTGCAAGGTGTCGAACAAAGCCCTC
CCAGCCCCCATCGAGAAAACCATCTCCAAAGCCAAAGGGCAGCCC
CGAGAACCACAGGTGTACACCCTGCCCCCATCCCGGGAGGAGATG
ACCAAGAACCAGGTCAGCCTGTGGTGCCTGGTCAAAGGCTTCTAT
CCCAGCGACATCGCCGTGGAGTGGGAGAGCAATGGGCAGCCGGAG
AACAACTACAAGACCACGCCTCCCGTGCTGGACTCCGACGGCTCC
TTCTTCCTCTACAGCAAGCTCACCGTGGACAAGAGCAGATGGCAG
CAGGGGAACGTCTTCTCATGCTCCGTGATGCATGAGGCTCTGCAC
AACCACTACACGCAGAAGTCTCTCTCCCTGTCTCCGGGAAAAGGA
GGGAGCGAGGGAAAGTCCAGCGGAAGCGGCTCTGAGTCCAAATCC
ACCGGAGGGAGCGCCATTCAGCTGACCCAGTCTCCATCCTCTCTG
TCCGCCTCTGTGGGCGACAGAGTGACAATTACCTGCCGGGCCTCC
TCCTCCGTGTCCTACATCCATTGGTTCCAGCAGAAGCCCGGCAAG
GCCCCTAAGCCTCTGATCTACGCCACCTCCAATCTGGCCTCTGGC
GTGCCCTCCAGATTTTCCGGATCTGGCTCTGGAACCGACTTTACC
CTGACAATCTCCAGCCTGCAGCCTGAGGACTTCGCCACCTACTAC
TGTCAGCAGTGGACCAGCAATCCTCCTACCTTTGGCCAGGGCACC
AAGCTGGAAATCAAGGGCGGCTCCGAGGGCAAGAGCAGCGGCAGC
GGCAGCGAGAGCAAGAGCACCGGCGGCAGCCAGGTTCAGCTGGTT
CAGTCTGGTGCCGAAGTGAAGAAACCTGGCTCCTCCGTGAAAGTG
```

-continued

```
TCCTGCAAGGCTTCCGGCTACACTTTTACCAGCTACAACATGCAC
TGGGTCCGACAGGCCCCTGGACAAGGATTGGAATGGATGGGCGCT
ATCTACCCCGGCAACGGCGATACCTCTTACGCCCAGAAATTCCAG
GGCAGAGTGACCATCACCGCCGACAAGTCTACCTCCACCGCCTAC
ATGGAACTGTCCAGCCTGAGATCTGAGGACACCGCCGTGTACTAC
TGCGCCCGGTCTACCTATTATGGCGGCGACTGGTACTTCAACGTG
TGGGGCCAGGGAACCCTGGTCACAGTCTCTTCT
``` trispecific Ab CD3-CD20 arm

SEQ ID NO: 144

```
EIVLTQSPATLSASPGERVTLSCSASSSVSYMNWYQQKPGQAPRR
WIYDSSKLASGVPARFSGSGSGRDYTLTISSLEPEDFAVYYCQQW
SRNPPTFGGGTKVEIKGGSEGKSSGSGSESKSTGGSQVQLVQSGA
EVKKPGSSVKVSCKASGYTFTRSTMHWVRQAPGQGLEWMGYINPS
SAYTNYAQKFQGRVTLTADKSTSTAYMELSSLRSEDTAVYYCASP
QVHYDYGGFPYWGQGTLVTVSSEPKSSDKTHTCPPCPAPEAAGGP
SVFLFPPKPKDTLMISRTPEVTCVVVSVSHEDPEVKFNWYVDGVE
VHNAKTKPREEQYNSTYRVVSVLTVLHQDWLNGKEYKCKVSNKAL
PAPIEKTISKAKGQPREPQVYTLPPSREEMTKNQVSLWCLVKGFY
PSDIAVEWESNGQPENNYKTTPPVLDSDGSFFLYSKLTVDKSRWQ
QGNVFSCSVMHEALHNHYTQKSLSLSPGKGGSEGKSSGSGSESKS
TGGSAIQLTQSPSSLSASVGDRVTITCRASSSVSYIHWFQQKPGK
APKPLIYATSNLASGVPSRFSGSGSGTDFTLTISSLQPEDFATYY
CQQWTSNPPTFGQGTKLEIKGGSEGKSSGSGSESKSTGGSQVQLV
QSGAEVKKPGSSVKVSCKASGYTFTSYNMHWVRQAPGQGLEWMGA
IYPGNGDTSYAQKFQGRVTITADKSTSTAYMELSSLRSEDTAVYY
CARSTYYGGDWYFNVWGQGTLVTVSS
``` trispecific Ab CD3-CD20 arm

SEQ ID NO: 145

```
GAGATCGTGCTGACCCAGTCTCCTGCCACACTGAGTGCTTCTCCA
GGCGAGAGAGTGACCCTGTCCTGCTCCGCTTCCTCCTCCGTGTCC
TACATGAACTGGTATCAGCAGAAGCCCGGCCAGGCTCCTCGGAGA
TGGATCTACGACTCTTCCAAGCTGGCCTCTGGTGTGCCAGCCAGA
TTTTCTGGCTCTGGCTCCGGCAGAGACTATACCCTGACCATCTCC
AGCCTGGAACCTGAGGACTTCGCCGTGTACTACTGCCAGCAGTGG
TCTAGGAACCCTCCTACCTTTGGCGGAGGCACCAAGGTGGAAATC
AAGGGCGGATCTGAGGGAAAGTCCAGCGGCTCCGGCAGCGAAAGC
AAGTCCACCGGCGGAAGCCAGGTCAACTGGTTCAGTCTGGCGCC
GAAGTGAAGAAACCTGGCTCCTCCGTGAAAGTGTCCTGCAAGGCT
TCCGGCTACACTTTTACCAGATCCACCATGCACTGGGTCCGACAG
GCTCCAGGACAAGGCTTGGAGTGGATGGGCTACATCAACCCCAGC
TCCGCCTACACCAACTACGCCCAGAAATTCCAGGGCAGAGTGACC
CTGACCGCCGACAAGTCTACCTCCACCGCCTACATGGAACTGTCC
AGCCTGAGATCTGAGGACACCGCCGTGTACTACTGCGCTTCTCCT
```

-continued

```
CAGGTGCACTACGACTACGGCGGCTTTCCTTATTGGGGCCAGGGC
ACACTGGTCACCGTTTCTTCTGAGCCCAAATCTAGCGACAAAACT
CACACACATGCCCACCGTGCCCAGCACCTGAAGCCGCCGGGGGACCG
TCAGTCTTCCTCTTCCCCCCAAAACCCAAGGACACCCTCATGATC
TCCCGGACCCCTGAGGTCACATGCGTGGTGGTGAGCGTGAGCCAC
GAAGACCCTGAGGTCAAGTTCAACTGGTACGTGGACGGCGTGGAG
GTGCATAATGCCAAGACAAAGCCGCGGGAGGAGCAGTACAACAGC
ACGTACCGTGTGGTCAGCGTCCTCACCGTCCTGCACCAGGACTGG
CTGAATGGCAAGGAGTACAAGTGCAAGGTGTCGAACAAAGCCCTC
CCAGCCCCCATCGAGAAAACCATCTCCAAAGCCAAAGGGCAGCCC
CGAGAACCACAGGTGTACACCCTGCCCCCATCCCGGGAGGAGATG
ACCAAGAACCAGGTCAGCCTGTGGTGCCTGGTCAAAGGCTTCTAT
CCCAGCGACATCGCCGTGGAGTGGGAGAGCAATGGGCAGCCGGAG
AACAACTACAAGACCACGCCTCCCGTGCTGGACTCCGACGGCTCC
TTCTTCCTCTACAGCAAGCTCACCGTGGACAAGAGCAGATGGCAG
CAGGGGAACGTCTTCTCATGCTCCGTGATGCATGAGGCTCTGCAC
AACCACTACACGCAGAAGTCTCTCTCCCTGTCTCCGGGAAAAGGA
GGGAGCGAGGGAAAGTCCAGCGGAAGCGGCTCTGAGTCCAAATCC
ACCGGAGGGAGCGCCATTCAGCTGACCCAGTCTCCATCCTCTCTG
TCCGCCTCTGTGGGCGACAGAGTGACAATTACCTGCCGGGCCTCC
TCCTCCGTGTCCTACATCCATTGGTTCCAGCAGAAGCCCGGCAAG
GCCCCTAAGCCTCTGATCTACGCCACCTCCAATCTGGCCTCTGGC
GTGCCCTCCAGATTTTCCGGATCTGGCTCTGGAACCGACTTTACC
CTGACAATCTCCAGCCTGCAGCCTGAGGACTTCGCCACCTACTAC
TGTCAGCAGTGGACCAGCAATCCTCCTACCTTTGGCCAGGGCACC
AAGCTGGAAATCAAGGGCGGCTCCGAGGGCAAGAGCAGCGGCAGC
GGCAGCGAGAGCAAGAGCACCGGCGGCAGCCAGGTTCAGCTGGTT
CAGTCTGGTGCCGAAGTGAAGAAACCTGGCTCCTCCGTGAAAGTG
TCCTGCAAGGCTTCCGGCTACACTTTTACCAGCTACAACATGCAC
TGGGTCCGACAGGCCCCTGGACAAGGATTGGAATGGATGGGCGCT
ATCTACCCCGGCAACGGCGATACCTCTTACGCCCAGAAATTCCAG
GGCAGAGTGACCATCACCGCCGACAAGTCTACCTCCACCGCCTAC
ATGGAACTGTCCAGCCTGAGATCTGAGGACACCGCCGTGTACTAC
TGCGCCCGGTCTACCTATTATGGCGGCGACTGGTACTTCAACGTG
TGGGGCCAGGGAACCCTGGTCACAGTCTCTTCT
``` trispecific Ab CD3-CD20 arm

SEQ ID NO: 146

```
DIQMTQSPSSLSASVGDRVTITCRASQSISSYLNWYQQKPGKAPK
LLIYAASSLQSGVPSRFSGSGSGTDFTLTISSLQPEDFATYYCQQ
SYSTPLTFGQGTKVEIKGGSEGKSSGSGSESKSTGGSEVQLLESG
GGLVQPGGSLRLSCAASGFTFSSYAMSWVRQAPGKGLEWVSAISG
```

SGGSTYYADSVKGRFTISRDNSKNTLYLQMNSLRAEDTAVYYCAK
YDGIYGELDFWGQGTLVTVSSEPKSSDKTHTCPPCPAPEAAGGPS
VFLFPPKPKDTLMISRTPEVTCVVVSVSHEDPEVKFNWYVDGVEV
HNAKTKPREEQYNSTYRVVSVLTVLHQDWLNGKEYKCKVSNKALP
APIEKTISKAKGQPREPQVYTLPPSREEMTKNQVSLWCLVKGFYP
SDIAVEWESNGQPENNYKTTPPVLDSDGSFFLYSKLTVDKSRWQQ
GNVFSCSVMHEALHNHYTQKSLSLSPGKGGGGSGGGGSAIQLTQS
PSSLSASVGDRVTITCRASSSVSYIHWFQQKPGKAPKPLIYATSN
LASGVPSRFSGSGSGTDFTLTISSLQPEDFATYYCQQWTSNPPTF
GQGTKLEIKGGSEGKSSGSGSESKSTGGSQVQLVQSGAEVKKPGS
SVKVSCKASGYTFTSYNMHWVRQAPGQGLEWMGAIYPGNGDTSYA
QKFQGRVTITADKSTSTAYMELSSLRSEDTAVYYCARSTYYGGDW
YFNVWGQGTLVTVSS trispecific Ab CD3-CD20 arm
SEQ ID NO: 147
GATATTCAGATGACTCAGAGCCCCTCTTCACTGAGTGCCTCAGTA
GGGGATCGTGTGACTATCACCTGTCGTGCTTCCCAAAGCATCTCC
TCATATTTGAACTGGTACCAGCAGAAGCCAGGCAAGGCACCCAAA
CTGCTGATTTACGCCGCCAGTTCTCTCCAGAGTGGCGTTCCCAGC
CGTTTCTCAGGTTCTGGATCTGGTACCGATTTCACATTGACCATA
TCATCCCTCCAGCCTGAGGACTTCGCCACCTACTATTGCAACAG
TCATATTCTACTCCACTTACATTCGGCCAGGGCACCAAGGTGGAA
ATTAAGGGCGGCTCCGAGGGCAAGAGCAGCGGCAGCGGCAGCGAG
AGCAAGAGCACCGGCGGCAGCGAGGTGCAGTTGCTGGAGTCCGGG
GGTGGACTCGTACAACCTGGAGGTTCTCTGCGGTTGTCCTGTGCT
GCCAGCGGATTCACATTTTCCTCTTATGCCATGTCCTGGGTACGT
CAAGCACCCGGCAAAGGACTTGAGTGGGTCTCCGCTATCAGTGGT
TCAGGGGGATCAACCTACTATGCTGATAGTGTTAAGGGGCGTTTT
ACCATCTCAAGAGACAACTCCAAGAACACCCTGTACCTGCAGATG
AACTCACTCCGCGCCGAGGATACAGCAGTTTACTACTGTGCTAAG
TATGACGGCATTTACGGCGAACTGGACTTTTGGGGACAGGGGACC
TTGGTCACAGTCTCCAGCGAGCCCAAATCTAGCGACAAAACTCAC
ACATGTCCACCGTGCCCAGCACCTGAAGCAGCAGGGGGACCGTCA
GTCTTCCTCTTCCCCCCAAAACCCAAGGACACCCTCATGATCTCC
CGGACCCCTGAGGTCACATGCGTGGTGGTGAGCGTGAGCCACGAA
GACCCTGAGGTCAAGTTCAACTGGTACGTGGACGGCGTGGAGGTG
CATAATGCCAAGACAAAGCCGCGGGAGGAGCAGTACAACAGCACG
TACCGTGTGGTCAGCGTCCTCACCGTCCTGCACCAGGACTGGCTG
AATGGCAAGGAGTACAAGTGCAAGGTCTCCAACAAAGCCCTCCCA
GCCCCCATCGAGAAAACCATCTCCAAAGCCAAAGGGCAGCCCCGA
GAACCACAGGTGTACACCCTGCCCCCATCCCGGGAGGAGATGACC
AAGAACCAGGTCAGCCTGTGGTGCCTGGTCAAAGGCTTCTATCCC AGCGACATCGCCGTGGAGTGGGAGAGCAATGGGCAGCCGGAGAAC
AACTACAAGACCACGCCTCCCGTGCTGGACTCCGACGGCTCCTTC
TTCCTCTACAGCAAGCTCACCGTGGACAAGTCTAGATGGCAGCAG
GGGAACGTCTTCTCATGCTCCGTGATGCATGAGGCTCTGCACAAC
CACTACACGCAGAAGAGCCTCTCCCTGTCTCCGGGTAAAGGAGGC
GGAGGGAGTGGCGGGGGAGGCTCTGCAATCCAACTAACTCAAAGT
CCAAGTAGTCTGTCTGCTTCCGTGGGCGACAGAGTGACAATCACC
TGTAGAGCCTCCAGCAGCGTCTCCTACATCCACTGGTTCCAGCAA
AAACCTGGCAAGGCCCCTAAGCCTCTGATCTACGCCACCTCCAAC
CTGGCCTCTGGCGTGCCCTCTCGGTTCTCCGGCTCTGGCTCCGGA
ACCGACTTCACCCTGACCATCTCCAGCCTGCAGCCTGAGGATTTT
GCTACCTACTACTGCCAGCAGTGGACCTCTAACCCTCCAACATTC
GGCCAGGGCACCAAGCTGGAAATCAAGGGCGGCTCCGAGGGCAAG
AGCAGCGGCAGCGGCAGCGAGAGCAAGAGCACCGGCGGCAGCCAA
GTGCAATTAGTGCAAAGTGGTGCAGAAGTCAAGAAGCCTGGAAGC
TCCGTGAAAGTGTCCTGCAAGGCCTCTGGCTACACCTTTACCTCC
TACAACATGCACTGGGTGCGGCAGGCTCCTGGCCAGGGCCTGGAG
TGGATGGGCGCTATCTACCCCGGCAACGGCGATACCTCTTACGCC
CAGAAGTTCCAGGGCAGAGTGACCATCACCGCCGACAAGTCCACA
TCTACAGCCTACATGGAACTGTCCTCCCTGCGGTCCGAGGACACC
GCTGTGTACTATTGTGCCAGATCTACCTACTACGGCGGCGACTGG
TACTTCAACGTGTGGGGCCAAGGAACCCTGGTGACCGTGTCTAGC trispecific Ab CD3-CD20 arm
SEQ ID NO: 148
DIQMTQSPSSLSASVGDRVTITCRARQSIGTAIHWYQQKPGKAPK
LLIKYASESISGVPSRFSGSGSGTDFTLTISSLQPEDFATYYCQQ
SGSWPYTFGQGTKLEIKGGSEGKSSGSGSESKSTGGSEVQLVESG
GGLVKPGGSLRLSCAASGFTFSRYNMNWVRQAPGKGLEWVSSIST
SSNYIYYADSVKGRFTFSRDNAKNSLDLQMSGLRAEDTAIYYCTR
GWGPFDYWGQGTLVTVSSEPKSSDKTHTCPPCPAPEAAGGPSVFL
FPPKPKDTLMISRTPEVTCVVVSVSHEDPEVKFNWYVDGVEVHNA
KTKPREEQYNSTYRVVSVLTVLHQDWLNGKEYKCKVSNKALPAPI
EKTISKAKGQPREPQVYTLPPSREEMTKNQVSLWCLVKGFYPSDI
AVEWESNGQPENNYKTTPPVLDSDGSFFLYSKLTVDKSRWQQGNV
FSCSVMHEALHNHYTQKSLSLSPGKGGGGSGGGGSAIQLTQSPSS
LSASVGDRVTITCRASSSVSYIHWFQQKPGKAPKPLIYATSNLAS
GVPSRFSGSGSGTDFTLTISSLQPEDFATYYCQQWTSNPPTFGQG
TKLEIKGGSEGKSSGSGSESKSTGGSQVQLVQSGAEVKKPGSSVK
VSCKASGYTFTSYNMHWVRQAPGQGLEWMGAIYPGNGDTSYAQKF
QGRVTITADKSTSTAYMELSSLRSEDTAVYYCARSTYYGGDWYFN
VWGQGTLVTVSS trispecific Ab CD3-CD20 arm
SEQ ID NO: 149
GACATACAAATGACACAATCACCCTCTTCTCTTTCTGCAAGCGTT
GGCGACCGTGTCACTATCACTTGTCGAGCCCGCCAGTCCATAGGT
ACTGCCATTCACTGGTATCAACAGAAGCCTGGCAAGGCTCCCAAA
CTCCTGATTAAGTATGCCAGCGAGAGCATTTCCGGCGTACCTTCA
AGATTTTCCGGCTCCGGTAGTGGGACAGATTTCACTCTCACTATA
TCTAGCCTCCAACCAGAAGATTTCGCCACTTACTACTGTCAACAA
TCAGGTTCATGGCCTTACACTTTCGGCCAGGGGACAAAATTGGAG
ATCAAGGGCGGCTCCGAGGGCAAGAGCAGCGGCAGCGGCAGCGAG
AGCAAGAGCACCGGCGGCAGCGAGGTGCAACTGGTGGAGTCTGGG
GGAGGCCTGGTCAAGCCTGGGGGGTCCCTGAGACTCTCCTGTGCA
GCCTCTGGATTCACCTTCAGTAGATATAACATGAACTGGGTCCGC
CAGGCTCCAGGGAAGGGGCTGGAGTGGGTCTCATCCATTAGTACT
AGTAGTAATTACATATACTACGCAGACTCAGTGAAGGGCCGATTC
ACCTTCTCCAGAGACAACGCCAAGAACTCACTGGATCTGCAAATG
AGCGGCCTGAGAGCCGAGGACACGGCTATTTATTACTGTACGAGA
GGCTGGGGGCCTTTTGACTACTGGGGCCAGGGAACCCTGGTCACC
GTCTCCTCAGAGCCCAAATCTAGCGACAAAACTCACACATGTCCA
CCGTGCCCAGCACCTGAAGCAGCAGGGGACCGTCAGTCTTCCTC
TTCCCCCCAAAACCCAAGGACACCCTCATGATCTCCCGGACCCCT
GAGGTCACATGCGTGGTGGTGAGCGTGAGCCACGAAGACCCTGAG
GTCAAGTTCAACTGGTACGTGGACGGCGTGGAGGTGCATAATGCC
AAGACAAAGCCGCGGGAGGAGCAGTACAACAGCACGTACCGTGTG
GTCAGCGTCCTCACCGTCCTGCACCAGGACTGGCTGAATGGCAAG
GAGTACAAGTGCAAGGTCTCCAACAAAGCCCTCCCAGCCCCCATC
GAGAAAACCATCTCCAAAGCCAAAGGGCAGCCCCGAGAACCACAG
GTGTACACCCTGCCCCCATCCCGGGAGGAGATGACCAAGAACCAG
GTCAGCCTGTGGTGCCTGGTCAAAGGCTTCTATCCCAGCGACATC
GCCGTGGAGTGGGAGAGCAATGGGCAGCCGGAGAACAACTACAAG
ACCACGCCTCCCGTGCTGGACTCCGACGGCTCCTTCTTCCTCTAC
AGCAAGCTCACCGTGGACAAGTCTAGATGGCAGCAGGGGAACGTC
TTCTCATGCTCCGTGATGCATGAGGCTCTGCACAACCACTACACG
CAGAAGAGCCTCTCCCTGTCTCCGGGTAAAGGAGGCGGAGGGAGT
GGCGGGGGAGGCTCTGCAATCCAACTAACTCAAAGTCCAAGTAGT
CTGTCTGCTTCCGTGGGCGACAGAGTGACAATCACCTGTAGAGCC
TCCAGCAGCGTCTCCTACATCCACTGGTTCCAGCAAAAACCTGGC
AAGGCCCCTAAGCCTCTGATCTACGCCACCTCCAACCTGGCCTCT
GGCGTGCCCTCTCGGTTCTCCGGCTCTGGCTCCGGAACCGACTTC
ACCCTGACCATCTCCAGCCTGCAGCCTGAGGATTTTGCTACCTAC
TACTGCCAGCAGTGGACCTCTAACCCTCCAACATTCGGCCAGGGC
ACCAAGCTGGAAATCAAGGGCGGCTCCGAGGGCAAGAGCAGCGGC
AGCGGCAGCGAGAGCAAGAGCACCGGCGGCAGCCAAGTGCAATTA
GTGCAAAGTGGTGCAGAAGTCAAGAAGCCTGGAAGCTCCGTGAAA
GTGTCCTGCAAGGCCTCTGGCTACACCTTTACCTCCTACAACATG
CACTGGGTGCGGCAGGCTCCTGGCCAGGGCCTGGAGTGGATGGGC
GCTATCTACCCCGGCAACGGCGATACCTCTTACGCCCAGAAGTTC
CAGGGCAGAGTGACCATCACCGCCGACAAGTCCACATCTACAGCC
TACATGGAACTGTCCTCCCTGCGGTCCGAGGACACCGCTGTGTAC
TATTGTGCCAGATCTACCTACTACGGCGGCGACTGGTACTTCAAC
GTGTGGGGCCAAGGAACCCTGGTGACCGTGTCTAGC trispecific Ab CD3-CD20 arm
SEQ ID NO: 150
QVQLVQSGAEVKKPGSSVKVSCKASGYTFTRSTMHWVRQAPGQGL
EWMGYINPSSAYTNYAQKFQGRVTLTADKSTSTAYMELSSLRSED
TAVYYCASPQVHYDYGGFPYWGQGTLVTVSSGGSEGKSSGSGSES
KSTGGSEIVLTQSPATLSASPGERVTLSCSASSSVSYMNWYQQKP
GQAPRRWIYDSSKLASGVPARFSGSGSGRDYTLTISSLEPEDFAV
YYCQQWSRNPPTFGGGTKVEIKEPKSSDKTHTCPPCPAPEAAGGP
SVFLFPPKPKDTLMISRTPEVTCVVVSVSHEDPEVKFNWYVDGVE
VHNAKTKPREEQYNSTYRVVSVLTVLHQDWLNGKEYKCKVSNKAL
PAPIEKTISKAKGQPREPQVYTLPPSREEMTKNQVSLWCLVKGFY
PSDIAVEWESNGQPENNYKTTPPVLDSDGSFFLYSKLTVDKSRWQ
QGNVFSCSVMHEALHNHYTQKSLSLSPGKGGGGSGGGGSAIQLTQ
SPSSLSASVGDRVTITCRASSSVSYIHWFQQKPGKAPKPLIYATS
NLASGVPSRFSGSGSGTDFTLTISSLQPEDFATYYCQQWTSNPPT
FGQGTKLEIKGGSEGKSSGSGSESKSTGGSQVQLVQSGAEVKKPG
SSVKVSCKASGYTFTSYNMHWVRQAPGQGLEWMGAIYPGNGDTSY
AQKFQGRVTITADKSTSTAYMELSSLRSEDTAVYYCARSTYYGGD
WYFNVWGQGTLVTVSS trispecific Ab CD3-CD20 arm
SEQ ID NO: 151
CAGGTGCAGCTGGTGCAGAGCGGCGCCGAGGTGAAGAAGCCTGGC
AGCAGCGTGAAGGTGAGCTGTAAGGCCAGCGGCTACACTTTCACT
AGGAGCACTATGCACTGGGTGAGGCAGGCCCCTGGCCAGGGCCTG
GAGTGGATGGGCTACATCAATCCTAGCAGCGCCTACACTAATTAC
GCCCAGAAGTTCCAGGGCAGGGTGACTCTGACTGCCGATAAGAGC
ACTAGCACTGCCTACATGGAGCTGAGCAGCCTGAGGAGCGAGGAT
ACTGCCGTGTACTACTGTGCCAGCCCTCAGGTGCACTACGATTAC
GGCGGCTTCCCTTACTGGGGCCAGGGCACTCTGGTGACTGTGAGC
AGCGGCGGCTCCGAGGGCAAGAGCAGCGGCAGCGGCAGCGAGAGC
AAGAGCACCGGCGGCAGCGAGATCGTGCTGACTCAGAGCCCTGCC
ACTCTGAGCGCCAGCCCTGGCGAGAGGGTGACTCTGAGCTGTAGC
GCCAGCAGCAGCGTGAGCTACATGAATTGGTACCAGCAGAAGCCT -continued
```
GGCCAGGCCCCTAGGAGGTGGATCTACGATAGCAGCAAGCTGGCC
AGCGGCGTGCCTGCCAGGTTCAGCGGCAGCGGCAGCGGCAGGGAT
TACACTCTGACTATCAGCAGCCTGGAGCCTGAGGATTTCGCCGTG
TACTACTGTCAGCAGTGGAGCAGGAATCCTCCTACTTTCGGCGGC
GGCACTAAGGTGGAGATCAAGGAGCCCAAATCTAGCGACAAAACT
CACACATGTCCACCGTGCCCAGCACCTGAAGCAGCAGGGGACCG
TCAGTCTTCCTCTTCCCCCCAAAACCCAAGGACACCCTCATGATC
TCCCGGACCCCTGAGGTCACATGCGTGGTGGTGAGCGTGAGCCAC
GAAGACCCTGAGGTCAAGTTCAACTGGTACGTGGACGGCGTGGAG
GTGCATAATGCCAAGACAAAGCCGCGGGAGGAGCAGTACAACAGC
ACGTACCGTGTGGTCAGCGTCCTCACCGTCCTGCACCAGGACTGG
CTGAATGGCAAGGAGTACAAGTGCAAGGTCTCCAACAAAGCCCTC
CCAGCCCCCATCGAGAAAACCATCTCCAAAGCCAAAGGGCAGCCC
CGAGAACCACAGGTGTACACCCTGCCCCCATCCCGGGAGGAGATG
ACCAAGAACCAGGTCAGCCTGTGGTGCCTGGTCAAAGGCTTCTAT
CCCAGCGACATCGCCGTGGAGTGGGAGAGCAATGGGCAGCCGGAG
AACAACTACAAGACCACGCCTCCCGTGCTGGACTCCGACGGCTCC
TTCTTCCTCTACAGCAAGCTCACCGTGGACAAGTCTAGATGGCAG
CAGGGGAACGTCTTCTCATGCTCCGTGATGCATGAGGCTCTGCAC
AACCACTACACGCAGAAGAGCCTCTCCCTGTCTCCGGGTAAAGGA
GGCGGAGGGAGTGGCGGGGAGGCTCTGCAATCCAACTAACTCAA
AGTCCAAGTAGTCTGTCTGCTTCCGTGGGCGACAGAGTGACAATC
ACCTGTAGAGCCTCCAGCAGCGTCTCCTACATCCACTGGTTCCAG
CAAAAACCTGGCAAGGCCCCTAAGCCTCTGATCTACGCCACCTCC
AACCTGGCCTCTGGCGTGCCCTCTCGGTTCTCCGGCTCTGGCTCC
GGAACCGACTTCACCCTGACCATCTCCAGCCTGCAGCCTGAGGAT
TTTGCTACCTACTACTGCCAGCAGTGGACCTCTAACCCTCCAACA
TTCGGCCAGGGCACCAAGCTGGAAATCAAGGGCGGCTCCGAGGGC
AAGAGCAGCGGCAGCGGCAGCGAGAGCAAGAGCACCGGCGGCAGC
CAAGTGCAATTAGTGCAAAGTGGTGCAGAAGTCAAGAAGCCTGGA
AGCTCCGTGAAAGTGTCCTGCAAGGCCTCTGGCTACACCTTTACC
TCCTACAACATGCACTGGGTGCGGCAGGCTCCTGGCCAGGGCCTG
GAGTGGATGGGCGCTATCTACCCCGGCAACGGCGATACCTCTTAC
GCCCAGAAGTTCCAGGGCAGAGTGACCATCACCGCCGACAAGTCC
ACATCTACAGCCTACATGAACTGTCCTCCCTGCGGTCCGAGGAC
ACCGCTGTGTACTATTGTGCCAGATCTACCTACTACGGCGGCGAC
TGGTACTTCAACGTGTGGGGCCAAGGAACCCTGGTGACCGTGTCT
AGC
```
trispecific Ab CD3-CD20 arm
SEQ ID NO: 152
```
DIQMTQSPSSLSASVGDRVTITCRARQSIGTAIHWYQQKPGKAPK
LLIKYASESISGVPSRFSGSGSGTDFTLTISSLQPEDFATYYCQQ
```

-continued
```
SGSWPYTFGQGTKLEIKGGSEGKSSGSGSESKSTGGSEVQLVESG
GGLVKPGGSLRLSCAASGFTFSRYNMNWVRQAPGKGLEWVSSIST
SSNYIYYADSVKGRFTFSRDNAKNSLDLQMSGLRAEDTAIYYCTR
GWGPFDYWGQGTLVTVSSEPKSSDKTHTCPPCPAPEAAGGPSVFL
FPPKPKDTLMISRTPEVTCVVVSVSHEDPEVKFNWYVDGVEVHNA
KTKPREEQYNSTYRVVSVLTVLHQDWLNGKEYKCKVSNKALPAPI
EKTISKAKGQPREPQVYTLPPSREEMTKNQVSLWCLVKGFYPSDI
AVEWESNGQPENNYKTTPPVLDSDGSFFLYSKLTVDKSRWQQGNV
FSCSVMHEALHNHYTQKSLSLSPGKGGGGSGGGGSQIVLSQSPAI
LSASPGEKVTMTCRASSSVSYMHWYQQKPGSSPQVWIYATSNLAS
GVPVRFSGSGSGTSYSLTISRVEAEDTATYYCQQWIFNPPTFGSG
TKLEIRGGSEGKSSGSGSESKSTGGSQAYLQQSGAELVRPGASVK
MSCKASGYTFTSYNMHWVKQTPRQGLEWIGAIYPGNGDTSYNQKF
KGKATLTVDKSSSTAYMQLSSLTSEDSAVYFCARVYYGSNYWYFD
VWGTGTTVTVSS
```
trispecific Ab CD3-CD20 arm
SEQ ID NO: 153
```
GACATACAAATGACACAATCACCCTCTTCTCTTTCTGCAAGCGTT
GGCGACCGTGTCACTATCACTTGTCGAGCCCGCCAGTCCATAGGT
ACTGCCATTCACTGGTATCAACAGAAGCCTGGCAAGGCTCCCAAA
CTCCTGATTAAGTATGCCAGCGAGAGCATTTCCGGCGTACCTTCA
AGATTTTCCGGCTCCGGTAGTGGGACAGATTTCACTCTCACTATA
TCTAGCCTCCAACCAGAAGATTTCGCCACTTACTACTGTCAACAA
TCAGGTTCATGGCCTTACACTTTCGGCCAGGGGACAAAATTGGAG
ATCAAGGGCGGCTCCGAGGGCAAGAGCAGCGGCAGCGGCAGCGAG
AGCAAGAGCACCGGCGGCAGCGAGGTGCAACTGGTGGAGTCTGGG
GGAGGCCTGGTCAAGCCTGGGGGGTCCCTGAGACTCTCCTGTGCA
GCCTCTGGATTCACCTTCAGTAGATATAACATGAACTGGGTCCGC
CAGGCTCCAGGGAAGGGGCTGGAGTGGGTCTCATCCATTAGTACT
AGTAGTAATTACATATACTACGCAGACTCAGTGAAGGGCCGATTC
ACCTTCTCCAGAGACAACGCCAAGAACTCACTGGATCTGCAAATG
AGCGGCCTGAGAGCCGAGGACACGGCTATTTATTACTGTACGAGA
GGCTGGGGGCCTTTTGACTACTGGGGCCAGGGAACCCTGGTCACC
GTCTCCTCAGAGCCCAAATCTAGCGACAAAACTCACACATGTCCA
CCCGTGCCCAGCACCTGAAGCAGCAGGGGACCGTCAGTCTTCCTC
TTCCCCCCAAAACCCAAGGACACCCTCATGATCTCCCGGACCCCT
GAGGTCACATGCGTGGTGGTGAGCGTGAGCCACGAAGACCCTGAG
GTCAAGTTCAACTGGTACGTGGACGGCGTGGAGGTGCATAATGCC
AAGACAAAGCCGCGGGAGGAGCAGTACAACAGCACGTACCGTGTG
GTCAGCGTCCTCACCGTCCTGCACCAGGACTGGCTGAATGGCAAG
GAGTACAAGTGCAAGGTCTCCAACAAAGCCCTCCCAGCCCCCATC
```

```
GAGAAAACCATCTCCAAAGCCAAAGGGCAGCCCCGAGAACCACAG
GTGTACACCCTGCCCCCATCCCGGGAGGAGATGACCAAGAACCAG
GTCAGCCTGTGGTGCCTGGTCAAAGGCTTCTATCCCAGCGACATC
GCCGTGGAGTGGGAGAGCAATGGGCAGCCGGAGAACAACTACAAG
ACCACGCCTCCCGTGCTGGACTCCGACGGCTCCTTCTTCCTCTAC
AGCAAGCTCACCGTGGACAAGTCTAGATGGCAGCAGGGGAACGTC
TTCTCATGCTCCGTGATGCATGAGGCTCTGCACAACCACTACACG
CAGAAGAGCCTCTCCCTGTCTCCGGGTAAAGGAGGCGGAGGGAGT
GGCGGGGGAGGCTCTCAAATAGTCCTTTCACAGTCCCCAGCTATT
CTTTCAGCCTCTCCCGGTGAAAAGGTTACAATGACCTGCCGGGCA
AGCTCCAGTGTCTCATATATGCACTGGTACCAACAAAAACCTGGC
AGTAGTCCTCAGGTGTGGATCTACGCTACAAGCAATCTCGCTTCC
GGGGTTCCCGTGAGGTTTAGCGGAAGCGGGTCTGGAACTAGTTAT
TCCTTGACAATTAGTCGGGTGAAGCCGAGGACACCGCCACTTAC
TATTGCCAACAGTGGATATTCAATCCACCCACCTTCGGTTCAGGT
ACCAAGCTCGAAATCCGTGGCGGCTCCGAGGGCAAGAGCAGCGGC
AGCGGCAGCGAGAGCAAGAGCACCGGCGGCAGCCAAGCATATCTG
CAACAGAGCGGAGCTGAGCTGGTTCGGCCTGGCGCCTCTGTAAAA
ATGAGTTGCAAGGCCAGTGGTTATACATTCACATCATATAATATG
CACTGGGTAAAGCAAACTCCCCGACAGGGGCTTGAATGGATTGGC
GCAATCTATCCCGGCAATGGGATACATCCTACAATCAGAAATTC
AAGGGCAAGGCAACACTGACCGTTGACAAATCCTCATCAACAGCC
TACATGCAGCTCAGTTCCCTCACTAGCGAAGATTCTGCTGTGTAT
TTCTGTGCAAGGGTGTATTATGGTTCTAATTACTGGTATTTCGAT
GTTTGGGGAACCGGAACTACCGTAACTGTTTCTAGC
``` trispecific Ab CD3-CD20 arm

SEQ ID NO: 154

DIQMTQSPSSLSASVGDRVTITCRARQSIGTAIHWYQQKPGKAPK
LLIKYASESISGVPSRFSGSGSGTDFTLTISSLQPEDFATYYCQQ
SGSWPYTFGQGTKLEIKGGSEGKSSGSGSESKSTGGSEVQLVESG
GGLVKPGGSLRLSCAASGFTFSRYNMNWVRQAPGKGLEWVSSIST
SSNYIYYADSVKGRFTFSRDNAKNSLDLQMSGLRAEDTAIYYCTR
GWGPFDYWGQGTLVTVSSEPKSSDKTHTCPPCPAPEAAGGPSVFL
FPPKPKDTLMISRTPEVTCVVVSVSHEDPEVKFNWYVDGVEVHNA
KTKPREEQYNSTYRVVSVLTVLHQDWLNGKEYKCKVSNKALPAPI
EKTISKAKGQPREPQVYTLPPSREEMTKNQVSLWCLVKGFYPSDI
AVEWESNGQPENNYKTTPPVLDSDGSFFLYSKLTVDKSRWQQGNV
FSCSVMHEALHNHYTQKSLSLSPGKGGGGSGGGGSQIVLSQSPAI
LSASPGEKVTMTCRASLSVSSMHWYQQKPGSSPKPWIYATSNLAS
GVPARFSGSGSGTSYSLTISRVEAEDAATYYCQQWIFNPPTFGGG
TKLEIKGGSEGKSSGSGSESKSTGGSQAYLQQSGAELVRPGASVK
MSCKTSGYTFSSYNMHWVKQTPRQALEWIGAIYPGNGDTSYNQKF

KGKATLTVDKSSSTAYMQLSSLTSEDSAVYFCTRSNYYGSSGWYF
DVWGTGTTVTVSS trispecific Ab CD3-CD20 arm

SEQ ID NO: 155

```
GACATACAAATGACACAATCACCCTCTTCTCTTTCTGCAAGCGTT
GGCGACCGTGTCACTATCACTTGTCGAGCCCGCCAGTCCATAGGT
ACTGCCATTCACTGGTATCAACAGAAGCCTGGCAAGGCTCCCAAA
CTCCTGATTAAGTATGCCAGCGAGAGCATTTCCGGCGTACCTTCA
AGATTTTCCGGCTCCGGTAGTGGGACAGATTTCACTCTCACTATA
TCTAGCCTCCAACCAGAAGATTTCGCCACTTACTACTGTCAACAA
TCAGGTTCATGGCCTTACACTTTCGGCCAGGGGACAAAATTGGAG
ATCAAGGGCGGCTCCGAGGGCAAGAGCAGCGGCAGCGGCAGCGAG
AGCAAGAGCACCGGCGGCAGCGAGGTGCAACTGGTGGAGTCTGGG
GGAGGCCTGGTCAAGCCTGGGGGGTCCCTGAGACTCTCCTGTGCA
GCCTCTGGATTCACCTTCAGTAGATATAACATGAACTGGGTCCGC
CAGGCTCCAGGGAAGGGGCTGGAGTGGGTCTCATCCATTAGTACT
AGTAGTAATTACATATACTACGCAGACTCAGTGAAGGGCCGATTC
ACCTTCTCCAGAGACAACGCCAAGAACTCACTGGATCTGCAAATG
AGCGGCCTGAGAGCCGAGGACACGGCTATTTATTACTGTACGAGA
GGCTGGGGGCCTTTTGACTACTGGGGCCAGGGAACCCTGGTCACC
GTCTCCTCAGAGCCCAAATCTAGCGACAAAACTCACACATGTCCA
CCGTGCCCAGCACCTGAAGCAGCAGGGGACCGTCAGTCTTCCTC
TTCCCCCCAAAACCCAAGGACACCCTCATGATCTCCCGGACCCCT
GAGGTCACATGCGTGGTGGTGAGCGTGAGCCACGAAGACCCCTGAG
GTCAAGTTCAACTGGTACGTGGACGGCGTGGAGGTGCATAATGCC
AAGACAAAGCCGCGGGAGGAGCAGTACAACAGCACGTACCGTGTG
GTCAGCGTCCTCACCGTCCTGCACCAGGACTGGCTGAATGGCAAG
GAGTACAAGTGCAAGGTCTCCAACAAAGCCCTCCCAGCCCCCATC
GAGAAAACCATCTCCAAAGCCAAAGGGCAGCCCCGAGAACCACAG
GTGTACACCCTGCCCCCATCCCGGGAGGAGATGACCAAGAACCAG
GTCAGCCTGTGGTGCCTGGTCAAAGGCTTCTATCCCAGCGACATC
GCCGTGGAGTGGGAGAGCAATGGGCAGCCGGAGAACAACTACAAG
ACCACGCCTCCCGTGCTGGACTCCGACGGCTCCTTCTTCCTCTAC
AGCAAGCTCACCGTGGACAAGTCTAGATGGCAGCAGGGGAACGTC
TTCTCATGCTCCGTGATGCATGAGGCTCTGCACAACCACTACACG
CAGAAGAGCCTCTCCCTGTCTCCGGGTAAAGGAGGCGGAGGGAGT
GGCGGGGGAGGCTCTCAGATTGTCCTGAGCCAATCCCCAGCAATT
CTGAGTGCTAGCCCTGGAGAAGGTAACAATGACTTGTCGGGCA
TCCCTTAGCGTCTCATCCATGCATTGGTATCAACAAAAGCCAGGT
TCATCTCCAAAACCCTGGATTTACGCTACATCTAACCTGGCATCT
GGGGTGCCTGCCAGATTTAGTGGATCTGGTTCCGGCACATCATAT
```

-continued

TCCCTTACAATCAGCCGAGTGGAAGCCGAGGATGCTGCAACCTAT

TACTGTCAACAATGGATATTTAACCCTCCCACCTTTGGGGGTGGG

ACTAAACTCGAAATCAAGGGCGGCTCCGAGGGCAAGAGCAGCGGC

AGCGGCAGCGAGAGCAAGAGCACCGGCGGCAGCCAAGCCTATCTT

CAACAATCTGGGGCTGAGCTTGTCCGGCCAGGAGCCTCCGTCAAA

ATGAGCTGCAAAACCTCAGGTTATACTTTTAGTAGCTATAACATG

CATTGGGTAAAACAAACCCCCCGACAAGCATTGGAGTGGATAGGG

GCCATATACCCCGGCAATGGAGACACAAGTTACAACCAGAAGTTT

AAAGGCAAAGCTACACTCACAGTTGACAAATCCTCAAGTACTGCT

TATATGCAACTCTCCTCTCTCACTTCCGAAGACAGTGCCGTATAT

TTTTGCACTCGGTCCAATTACTATGGATCTAGTGGCTGGTACTTT

GACGTTTGGGGCACTGGGACAACTGTTACAGTGTCCAGC trispecific Ab CD3-CD20 arm

SEQ ID NO: 156

EIVLTQSPATLSASPGERVTLSCSASSSVSYMNWYQQKPGQAPRR

WIYDSSKLASGVPARFSGSGSGRDYTLTISSLEPEDFAVYYCQQW

SRNPPTFGGGTKVEIKGGSEGKSSGSGSESKSTGGSQVQLVQSGA

EVKKPGSSVKVSCKASGYTFTRSTMHWVKQAPGQGLEWIGYINPS

SAYTNYNQKFQGRVTLTADKSTSTAYMELSSLRSEDTAVYYCASP

QVHYDYAGFPYWGQGTLVTVSSEPKSSDKTHTCPPCPAPEAAGGP

SVFLFPPKPKDTLMISRTPEVTCVVVSVSHEDPEVKFNWYVDGVE

VHNAKTKPREEQYNSTYRVVSVLTVLHQDWLNGKEYKCKVSNKAL

PAPIEKTISKAKGQPREPQVYTLPPSREEMTKNQVSLWCLVKGFY

PSDIAVEWESNGQPENNYKTTPPVLDSDGSFFLYSKLTVDKSRWQ

QGNVFSCSVMHEALHNHYTQKSLSLSPGKGGGGSGGGGSQIVLSQ

SPAILSASPGEKVTMTCRASSSVSYMHWYQQKPGSSPQVWIYATS

NLASGVPVRFSGSGSGTSYSLTISRVEAEDTATYYCQQWIFNPPT

FGSGTKLEIRGGSEGKSSGSGSESKSTGGSQAYLQQSGAELVRPG

ASVKMSCKASGYTFTSYNMHWVKQTPRQGLEWIGAIYPGNGDTSY

NQKFKGKATLTVDKSSSTAYMQLSSLTSEDSAVYFCARVYYGSNY

WYFDVWGTGTTVTVSS trispecific Ab CD3-CD20 arm

SEQ ID NO: 157

GAGATCGTGCTGACTCAGAGCCCTGCCACTCTGAGCGCCAGCCCT

GGCGAGAGGGTGACTCTGAGCTGTAGCGCCAGCAGCAGCGTGAGC

TACATGAATTGGTACCAGCAGAAGCCTGGCCAGGCCCCTAGGAGG

TGGATCTACGATAGCAGCAAGCTGGCCAGCGGCGTGCCTGCCAGG

TTCAGCGGCAGCGGCAGCGGCAGGGATTACACTCTGACTATCAGC

AGCCTGGAGCCTGAGGATTTCGCCGTGTACTACTGTCAGCAGTGG

AGCAGGAATCCTCCTACTTTCGGCGGCGGCACTAAGGTGGAGATC

AAGGGCGGCTCCGAGGGCAAGAGCAGCGGCAGCGGCAGCGAGAGC

AAGAGCACCGGCGGCAGCCAGGTGCAGCTGGTGCAGAGCGGCGCC

GAGGTGAAGAAGCCTGGCAGCAGCGTGAAGGTGAGCTGTAAGGCC

-continued

AGCGGCTACACTTTCACTAGGAGCACTATGCACTGGGTGAAGCAG

GCCCCTGGCCAGGGCCTGGAGTGGATCGGCTACATCAATCCTAGC

AGCGCCTACACTAATTACAATCAGAAGTTCCAGGGCAGGGTGACT

CTGACTGCCGATAAGAGCACTAGCACTGCCTACATGGAGCTGAGC

AGCCTGAGGAGCGAGGATACTGCCGTGTACTACTGTGCCAGCCCT

CAGGTGCACTACGATTACGCCGGCTTCCCTTACTGGGGCCAGGGC

ACTCTGGTGACTGTGAGCAGCGAGCCCAAATCTAGCGACAAAACT

CACACATGTCCACCGTGCCCAGCACCTGAAGCAGCAGGGGACCG

TCAGTCTTCCTCTTCCCCCCAAAACCCAAGGACACCCTCATGATC

TCCCGGACCCCTGAGGTCACATGCGTGGTGGTGAGCGTGAGCCAC

GAAGACCCTGAGGTCAAGTTCAACTGGTACGTGGACGGCGTGGAG

GTGCATAATGCCAAGACAAAGCCGCGGGAGGAGCAGTACAACAGC

ACGTACCGTGTGGTCAGCGTCCTCACCGTCCTGCACCAGGACTGG

CTGAATGGCAAGGAGTACAAGTGCAAGGTCTCCAACAAAGCCCTC

CCAGCCCCCATCGAGAAAACCATCTCCAAAGCCAAAGGGCAGCCC

CGAGAACCACAGGTGTACACCCTGCCCCCATCCCGGGAGGAGATG

ACCAAGAACCAGGTCAGCCTGTGGTGCCTGGTCAAAGGCTTCTAT

CCCAGCGACATCGCCGTGGAGTGGGAGAGCAATGGGCAGCCGGAG

AACAACTACAAGACCACGCCTCCCGTGCTGGACTCCGACGGCTCC

TTCTTCCTCTACAGCAAGCTCACCGTGGACAAGTCTAGATGGCAG

CAGGGGAACGTCTTCTCATGCTCCGTGATGCATGAGGCTCTGCAC

AACCACTACACGCAGAAGAGCCTCTCCCTGTCTCCGGGTAAAGGA

GGCGGAGGGAGTGGCGGGGGAGGCTCTCAAATAGTCCTTTCACAG

TCCCCAGCTATTCTTTCAGCCTCTCCCGGTGAAAAGGTTACAATG

ACCTGCCGGGCAAGCTCCAGTGTCTCATATATGCACTGGTACCAA

CAAAAACCTGGCAGTAGTCCTCAGGTGTGGATCTACGCTACAAGC

AATCTCGCTTCCGGGGTTCCCGTGAGGTTTAGCGGAAGCGGGTCT

GGAACTAGTTATTCCTTGACAATTAGTCGGGTTGAAGCCGAGGAC

ACCGCCACTTACTATTGCCAACAGTGGATATTCAATCCACCCACC

TTCGGTTCAGGTACCAAGCTCGAAATCCGTGGCGGCTCCGAGGGC

AAGAGCAGCGGCAGCGGCAGCGAGAGCAAGAGCACCGGCGGCAGC

CAAGCATATCTGCAACAGAGCGGAGCTGAGCTGGTTCGGCCTGGC

GCCTCTGTAAAAATGAGTTGCAAGGCCAGTGGTTATACATTCACA

TCATATAATATGCACTGGGTAAAGCAAACTCCCCGACAGGGGCTT

GAATGGATTGCGCAATCTATCCCGGCAATGGGGATACATCCTAC

AATCAGAAATTCAAGGGCAAGGCAACACTGACCGTTGACAAATCC

TCATCAACAGCCTACATGCAGCTCAGTTCCCTCACTAGCGAAGAT

TCTGCTGTGTATTTCTGTGCAAGGGTGTATTATGGTTCTAATTAC

TGGTATTTCGATGTTTGGGGAACCGGAACTACCGTAACTGTTTCT

AGC

Ab CD3-CD20 arm
SEQ ID NO: 158 trispecific
EIVLTQSPATLSASPGERVTLSCSASSSVSYMNWYQQKPGQAPRR
WIYDSSKLASGVPARFSGSGSGRDYTLTISSLEPEDFAVYYCQQW
SRNPPTFGGGTKVEIKGGSEGKSSGSGSESKSTGGSQVQLVQSGA
EVKKPGSSVKVSCKASGYTFTRSTMHWVKQAPGQGLEWIGYINPS
SAYTNYNQKFQGRVTLTADKSTSTAYMELSSLRSEDTAVYYCASP
QVHYDYAGFPYWGQGTLVTVSSEPKSSDKTHTCPPCPAPEAAGGP
SVFLFPPKPKDTLMISRTPEVTCVVVSVSHEDPEVKFNWYVDGVE
VHNAKTKPREEQYNSTYRVVSVLTVLHQDWLNGKEYKCKVSNKAL
PAPIEKTISKAKGQPREPQVYTLPPSREEMTKNQVSLWCLVKGFY
PSDIAVEWESNGQPENNYKTTPPVLDSDGSFFLYSKLTVDKSRWQ
QGNVFSCSVMHEALHNHYTQKSLSLSPGKGGGGSGGGGSQIVLSQ
SPAILSASPGEKVTMTCRASLSVSSMHWYQQKPGSSPKPWIYATS
NLASGVPARFSGSGSGTSYSLTISRVEAEDAATYYCQQWIFNPPT
FGGGTKLEIKGGSEGKSSGSGSESKTGGSQAYLQQSGAELVRPG
ASVKMSCKTSGYTFSSYNMHWVKQTPRQALEWIGAIYPGNGDTSY
NQKFKGKATLTVDKSSSTAYMQLSSLTSEDSAVYFCTRSNYYGSS
GWYFDVWGTGTTVTVSS trispecific Ab CD3-CD20 arm
SEQ ID NO: 159
GAGATCGTGCTGACTCAGAGCCCTGCCACTCTGAGCGCCAGCCCT
GGCGAGAGGGTGACTCTGAGCTGTAGCGCCAGCAGCAGCGTGAGC
TACATGAATTGGTACCAGCAGAAGCCTGGCCAGGCCCCTAGGAGG
TGGATCTACGATAGCAGCAAGCTGGCCAGCGGCGTGCCTGCCAGG
TTCAGCGGCAGCGGCAGCGGCAGGGATTACACTCTGACTATCAGC
AGCCTGGAGCCTGAGGATTTCGCCGTGTACTACTGTCAGCAGTGG
AGCAGGAATCCTCCTACTTTCGGCGGCGGCACTAAGGTGGAGATC
AAGGGCGGCTCCGAGGGCAAGAGCAGCGGCAGCGGCAGCGAGAGC
AAGAGCACCGGCGGCAGCCAGGTGCAGCTGGTGCAGAGCGGCGCC
GAGGTGAAGAAGCCTGGCAGCAGCGTGAAGGTGAGCTGTAAGGCC
AGCGGCTACACTTTCACTAGGAGCACTATGCACTGGGTGAAGCAG
GCCCCTGGCCAGGGCCTGGAGTGGATCGGCTACATCAATCCTAGC
AGCGCCTACACTAATTACAATCAGAAGTTCCAGGGCAGGGTGACT
CTGACTGCCGATAAGAGCACTAGCACTGCCTACATGGAGCTGAGC
AGCCTGAGGAGCGAGGATACTGCCGTGTACTACTGTGCCAGCCCT
CAGGTGCACTACGATTACGCCGGCTTCCCTTACTGGGGCCAGGGC
ACTCTGGTGACTGTGAGCAGCGAGCCCAAATCTAGCGACAAAACT
CACACATGTCCACCGTGCCCAGCACCTGAAGCAGCAGGGGGACCG
TCAGTCTTCCTCTTCCCCCCAAAACCCAAGGACACCCTCATGATC
TCCCGGACCCCTGAGGTCACATGCGTGGTGGTGAGCGTGAGCCAC
GAAGACCCTGAGGTCAAGTTCAACTGGTACGTGGACGGCGTGGAG
GTGCATAATGCCAAGACAAAGCCGCGGGAGGAGCAGTACAACAGC ACGTACCGTGTGGTCAGCGTCCTCACCGTCCTGCACCAGGACTGG
CTGAATGGCAAGGAGTACAAGTGCAAGGTCTCCAACAAAGCCCTC
CCAGCCCCCATCGAGAAAACCATCTCCAAAGCCAAAGGGCAGCCC
CGAGAACCACAGGTGTACACCCTGCCCCCATCCCGGGAGGAGATG
ACCAAGAACCAGGTCAGCCTGTGGTGCCTGGTCAAAGGCTTCTAT
CCCAGCGACATCGCCGTGGAGTGGGAGAGCAATGGGCAGCCGGAG
AACAACTACAAGACCACGCCTCCCGTGCTGGACTCCGACGGCTCC
TTCTTCCTCTACAGCAAGCTCACCGTGGACAAGTCTAGATGGCAG
CAGGGGAACGTCTTCTCATGCTCCGTGATGCATGAGGCTCTGCAC
AACCACTACACGCAGAAGAGCCTCTCCCTGTCTCCGGGTAAAGGA
GGCGGAGGGAGTGGCGGGGGAGGCTCTCAGATTGTCCTGAGCCAA
TCCCCAGCAATTCTGAGTGCTAGCCCTGGAGAGAAGGTAACAATG
ACTTGTCGGGCATCCCTTAGCGTCTCATCCATGCATTGGTATCAA
CAAAAGCCAGGTTCATCTCCAAAACCCTGGATTTACGCTACATCT
AACCTGGCATCTGGGGTGCCTGCCAGATTTAGTGGATCTGGTTCC
GGCACATCATATTCCCTTACAATCAGCCGAGTGGAAGCCGAGGAT
GCTGCAACCTATTACTGTCAACAATGGATATTTAACCCTCCCACC
TTTGGGGGTGGGACTAAACTCGAAATCAAGGGCGGCTCCGAGGGC
AAGAGCAGCGGCAGCGGCAGCGAGAGCAAGAGCACCGGCGGCAGC
CAAGCCTATCTTCAACAATCTGGGGCTGAGCTTGTCCGGCCAGGA
GCCTCCGTCAAAATGAGCTGCAAAACCTCAGGTTATACTTTTAGT
AGCTATAACATGCATTGGGTAAAACAAACCCCCCGACAAGCATTG
GAGTGGATAGGGGCCATATACCCCGGCAATGGAGACACAAGTTAC
AACCAGAAGTTTAAAGGCAAAGCTACACTCACAGTTGACAAATCC
TCAAGTACTGCTTATATGCAACTCTCCTCTCTCACTTCCGAAGAC
AGTGCCGTATATTTTTGCACTCGGTCCAATTACTATGGATCTAGT
GGCTGGTACTTTGACGTTTGGGGCACTGGGACAACTGTTACAGTG
TCCAGC trispecific Ab CD3-CD20 arm
SEQ ID NO: 160
QVQLVQSGAEVKKPGSSVKVSCKASGYTFTRSTMHWVRQAPGQGL
EWMGYINPSSAYTNYAQKFQGRVTLTADKSTSTAYMELSSLRSED
TAVYYCASPQVHYDYGGFPYWGQGTLVTVSSGGSEGKSSGSGSES
KSTGGSEIVLTQSPATLSASPGERVTLSCSASSSVSYMNWYQQKP
GQAPRRWIYDSSKLASGVPARFSGSGSGRDYTLTISSLEPEDFAV
YYCQQWSRNPPTFGGGTKVEIKEPKSSDKTHTCPPCPAPEAAGGP
SVFLFPPKPKDTLMISRTPEVTCVVVSVSHEDPEVKFNWYVDGVE
VHNAKTKPREEQYNSTYRVVSVLTVLHQDWLNGKEYKCKVSNKAL
PAPIEKTISKAKGQPREPQVYTLPPSREEMTKNQVSLWCLVKGFY
PSDIAVEWESNGQPENNYKTTPPVLDSDGSFFLYSKLTVDKSRWQ
QGNVFSCSVMHEALHNHYTQKSLSLSPGKGGGGSGGGGSQIVLSQ

```
-continued
SPAILSASPGEKVTMTCRASSSVSYMHWYQQKPGSSPQVWIYATS
NLASGVPVRFSGSGSGTSYSLTISRVEAEDTATYYCQQWIFNPPT
FGSGTKLEIRGGSEGKSSGSGSESKSTGGSQAYLQQSGAELVRPG
ASVKMSCKASGYTFTSYNMHWVKQTPRQGLEWIGAIYPGNGDTSY
NQKFKGKATLTVDKSSSTAYMQLSSLTSEDSAVYFCARVYYGSNY
WYFDVWGTGTTVTVSS trispecific Ab CD3-CD20 arm
                                SEQ ID NO: 161
CAGGTGCAGCTGGTGCAGAGCGGCGCCGAGGTGAAGAAGCCTGGC
AGCAGCGTGAAGGTGAGCTGTAAGGCCAGCGGCTACACTTTCACT
AGGAGCACTATGCACTGGGTGAGGCAGGCCCCTGGCCAGGGCCTG
GAGTGGATGGGCTACATCAATCCTAGCAGCGCCTACACTAATTAC
GCCCAGAAGTTCCAGGGCAGGGTGACTCTGACTGCCGATAAGAGC
ACTAGCACTGCCTACATGGAGCTGAGCAGCCTGAGGAGCGAGGAT
ACTGCCGTGTACTACTGTGCCAGCCCTCAGGTGCACTACGATTAC
GGCGGCTTCCCTTACTGGGGCCAGGGCACTCTGGTGACTGTGAGC
AGCGGCGGCTCCGAGGGCAAGAGCAGCGGCAGCGGCAGCGAGAGC
AAGAGCACCGGCGGCAGCGAGATCGTGCTGACTCAGAGCCCTGCC
ACTCTGAGCGCCAGCCCTGGCGAGAGGGTGACTCTGAGCTGTAGC
GCCAGCAGCAGCGTGAGCTACATGAATTGGTACCAGCAGAAGCCT
GGCCAGGCCCCTAGGAGGTGGATCTACGATAGCAGCAAGCTGGCC
AGCGGCGTGCCTGCCAGGTTCAGCGGCAGCGGCAGCGGCAGGGAT
TACACTCTGACTATCAGCAGCCTGGAGCCTGAGGATTTCGCCGTG
TACTACTGTCAGCAGTGGAGCAGGAATCCTCCTACTTTCGGCGGC
GGCACTAAGGTGGAGATCAAGGAGCCCAAATCTAGCGACAAAACT
CACACATGTCCACCGTGCCCAGCACCTGAAGCAGCAGGGGACCG
TCAGTCTTCCTCTTCCCCCCAAAACCCAAGGACACCCTCATGATC
TCCCGGACCCCTGAGGTCACATGCGTGGTGGTGAGCGTGAGCCAC
GAAGACCCTGAGGTCAAGTTCAACTGGTACGTGGACGGCGTGGAG
GTGCATAATGCCAAGACAAAGCCGCGGGAGGAGCAGTACAACAGC
ACGTACCGTGTGGTCAGCGTCCTCACCGTCCTGCACCAGGACTGG
CTGAATGGCAAGGAGTACAAGTGCAAGGTCTCCAACAAAGCCCTC
CCAGCCCCCATCGAGAAAACCATCTCCAAAGCCAAAGGGCAGCCC
CGAGAACCACAGGTGTACACCCTGCCCCCATCCCGGGAGGAGATG
ACCAAGAACCAGGTCAGCCTGTGGTGCCTGGTCAAAGGCTTCTAT
CCCAGCGACATCGCCGTGGAGTGGGAGAGCAATGGGCAGCCGGAG
AACAACTACAAGACCACGCCTCCCGTGCTGGACTCCGACGGCTCC
TTCTTCCTCTACAGCAAGCTCACCGTGGACAAGTCTAGATGGCAG
CAGGGGAACGTCTTCTCATGCTCCGTGATGCATGAGGCTCTGCAC
AACCACTACACGCAGAAGAGCCTCTCCCTGTCTCCGGGTAAAGGA
GGCGGAGGGAGTGGCGGGGGAGGCTCTCAAATAGTCCTTTCACAG
TCCCCAGCTATTCTTTCAGCCTCTCCCGGTGAAAAGGTTACAATG -continued
ACCTGCCGGGCAAGCTCCAGTGTCTCATATATGCACTGGTACCAA
CAAAAACCTGGCAGTAGTCCTCAGGTGTGGATCTACGCTACAAGC
AATCTCGCTTCCGGGGTTCCCGTGAGGTTTAGCGGAAGCGGGTCT
GGAACTAGTTATTCCTTGACAATTAGTCGGGTTGAAGCCGAGGAC
ACCGCCACTTACTATTGCCAACAGTGGATATTCAATCCACCCACC
TTCGGTTCAGGTACCAAGCTCGAAATCCGTGGCGGCTCCGAGGGC
AAGAGCAGCGGCAGCGGCAGCGAGAGCAAGAGCACCGGCGGCAGC
CAAGCATATCTGCAACAGAGCGGAGCTGAGCTGGTTCGGCCTGGC
GCCTCTGTAAAAATGAGTTGCAAGGCCAGTGGTTATACATTCACA
TCATATAATATGCACTGGGTAAAGCAAACTCCCCGACAGGGGCTT
GAATGGATTGGCGCAATCTATCCCGGCAATGGGGATACATCCTAC
AATCAGAAATTCAAGGGCAAGGCAACACTGACCGTTGACAAATCC
TCATCAACAGCCTACATGCAGCTCAGTTCCCTCACTAGCGAAGAT
TCTGCTGTGTATTTCTGTCAAGGGTGTATTATGGTTCTAATTAC
TGGTATTTCGATGTTTGGGGAACCGGAACTACCGTAACTGTTTCT
AGC trispecific Ab CD3-CD20 arm
                                SEQ ID NO: 162
QVQLVQSGAEVKKPGSSVKVSCKASGYTFTRSTMHWVRQAPGQGL
EWMGYINPSSAYTNYAQKFQGRVTLTADKSTSTAYMELSSLRSED
TAVYYCASPQVHYDYGGFPYWGQGTLVTVSSGGSEGKSSGSGSES
KSTGGSEIVLTQSPATLSASPGERVTLSCSASSSVSYMNWYQQKP
GQAPRRWIYDSSKLASGVPARFSGSGSGRDYTLTISSLEPEDFAV
YYCQQWSRNPPTFGGGTKVEIKEPKSSDKTHTCPPCPAPEAAGGP
SVFLFPPKPKDTLMISRTPEVTCVVVSVSHEDPEVKFNWYVDGVE
VHNAKTKPREEQYNSTYRVVSVLTVLHQDWLNGKEYKCKVSNKAL
PAPIEKTISKAKGQPREPQVYTLPPSREEMTKNQVSLWCLVKGFY
PSDIAVEWESNGQPENNYKTTPPVLDSDGSFFLYSKLTVDKSRWQ
QGNVFSCSVMHEALHNHYTQKSLSLSPGKGGGGSGGGGSQIVLSQ
SPAILSASPGEKVTMTCRASLSVSSMHWYQQKPGSSPKPWIYATS
NLASGVPARFSGSGSGTSYSLTISRVEAEDAATYYCQQWIFNPPT
FGGGTKLEIKGGSEGKSSGSGSESKSTGGSQAYLQQSGAELVRPG
ASVKMSCKTSGYTFSSYNMHWVKQTPRQALEWIGAIYPGNGDTSY
NQKFKGKATLTVDKSSSTAYMQLSSLTSEDSAVYFCTRSNYYGSS
GWYFDVWGTGTTVTVSS trispecific Ab CD3-CD20 arm
                                SEQ ID NO: 163
CAGGTGCAGCTGGTGCAGAGCGGCGCCGAGGTGAAGAAGCCTGGC
AGCAGCGTGAAGGTGAGCTGTAAGGCCAGCGGCTACACTTTCACT
AGGAGCACTATGCACTGGGTGAGGCAGGCCCCTGGCCAGGGCCTG
GAGTGGATGGGCTACATCAATCCTAGCAGCGCCTACACTAATTAC
GCCCAGAAGTTCCAGGGCAGGGTGACTCTGACTGCCGATAAGAGC
```

-continued

```
ACTAGCACTGCCTACATGGAGCTGAGCAGCCTGAGGAGCGAGGAT
ACTGCCGTGTACTACTGTGCCAGCCCTCAGGTGCACTACGATTAC
GGCGGCTTCCCTTACTGGGGCCAGGGCACTCTGGTGACTGTGAGC
AGCGGCGGCTCCGAGGGCAAGAGCAGCGGCAGCGGCAGCGAGAGC
AAGAGCACCGGCGGCAGCGAGATCGTGCTGACTCAGAGCCCTGCC
ACTCTGAGCGCCAGCCCTGGCGAGAGGGTGACTCTGAGCTGTAGC
GCCAGCAGCAGCGTGAGCTACATGAATTGGTACCAGCAGAAGCCT
GGCCAGGCCCCTAGGAGGTGGATCTACGATAGCAGCAAGCTGGCC
AGCGGCGTGCCTGCCAGGTTCAGCGGCAGCGGCAGCGGCAGGGAT
TACACTCTGACTATCAGCAGCCTGGAGCCTGAGGATTTCGCCGTG
TACTACTGTCAGCAGTGGAGCAGGAATCCTCCTACTTTCGGCGGC
GGCACTAAGGTGGAGATCAAGGAGCCCAAATCTAGCGACAAAACT
CACACATGTCCACCGTGCCCAGCACCTGAAGCAGCAGGGGACCG
TCAGTCTTCCTCTTCCCCCCAAAACCCAAGGACACCCTCATGATC
TCCCGGACCCCTGAGGTCACATGCGTGGTGGTGAGCGTGAGCCAC
GAAGACCCTGAGGTCAAGTTCAACTGGTACGTGGACGGCGTGGAG
GTGCATAATGCCAAGACAAAGCCGCGGGAGGAGCAGTACAACAGC
ACGTACCGTGTGGTCAGCGTCCTCACCGTCCTGCACCAGGACTGG
CTGAATGGCAAGGAGTACAAGTGCAAGGTCTCCAACAAAGCCCTC
CCAGCCCCCATCGAGAAAACCATCTCCAAAGCCAAAGGGCAGCCC
CGAGAACCACAGGTGTACACCCTGCCCCCATCCCGGGAGGAGATG
ACCAAGAACCAGGTCAGCCTGTGGTGCCTGGTCAAAGGCTTCTAT
CCCAGCGACATCGCCGTGGAGTGGGAGAGCAATGGGCAGCCGGAG
AACAACTACAAGACCACGCCTCCCGTGCTGGACTCCGACGGCTCC
TTCTTCCTCTACAGCAAGCTCACCGTGGACAAGTCTAGATGGCAG
CAGGGGAACGTCTTCTCATGCTCCGTGATGCATGAGGCTCTGCAC
AACCACTACACGCAGAAGAGCCTCTCCCTGTCTCCGGGTAAAGGA
GGCGGAGGGAGTGGCGGGGGAGGCTCTCAGATTGTCCTGAGCCAA
TCCCCAGCAATTCTGAGTGCTAGCCCTGGAGAGAAGGTAACAATG
ACTTGTCGGGCATCCCTTAGCGTCTCATCCATGCATTGGTATCAA
CAAAAGCCAGGTTCATCTCCAAAACCCTGGATTTACGCTACATCT
AACCTGGCATCTGGGGTGCCTGCCAGATTTAGTGGATCTGGTTCC
GGCACATCATATTCCCTTACAATCAGCCGAGTGGAAGCCGAGGAT
GCTGCAACCTATTACTGTCAACAATGGATATTTAACCCTCCCACC
TTTGGGGGTGGGACTAAACTCGAAATCAAGGGCGGCTCCGAGGGC
AAGAGCAGCGGCAGCGGCAGCGAGAGCAAGAGCACCGGCGGCAGC
CAAGCCTATCTTCAACAATCTGGGGCTGAGCTTGTCCGGCCAGGA
GCCTCCGTCAAAATGAGCTGCAAAACCTCAGGTTATACTTTTAGT
AGCTATAACATGCATTGGGTAAAACAACCCCCCGACAAGCATTG
GAGTGGATAGGGGCCATATACCCCGGCAATGGAGACACAAGTTAC
AACCAGAAGTTTAAAGGCAAAGCTACACTCACAGTTGACAAATCC
```

```
TCAAGTACTGCTTATATGCAACTCTCCTCTCTCACTTCCGAAGAC
AGTGCCGTATATTTTTGCACTCGGTCCAATTACTATGGATCTAGT
GGCTGGTACTTTGACGTTTGGGGCACTGGGACAACTGTTACAGTG
TCCAGC
``` bispecific Ab CD3-arm
SEQ ID NO: 164

```
EIVLTQSPATLSASPGERVTLSCSASSSVSYMNWYQQKPGQAPRR
WIYDSSKLASGVPARFSGSGSGRDYTLTISSLEPEDFAVYYCQQW
SRNPPTFGGGTKVEIKGGSEGKSSGSGSESKSTGGSQVQLVQSGA
EVKKPGSSVKVSCKASGYTFTRSTMHWVKQAPGQGLEWIGYINPS
SAYTNYNQKFQGRVTLTADKSTSTAYMELSSLRSEDTAVYYCASP
QVHYDYAGFPYWGQGTLVTVSSEPKSSDKTHTCPPCPAPEAAGGP
SVFLFPPKPKDTLMISRTPEVTCVVVSVSHEDPEVKFNWYVDGVE
VHNAKTKPREEQYNSTYRVVSVLTVLHQDWLNGKEYKCKVSNKAL
PAPIEKTISKAKGQPREPQVYTLPPSREEMTKNQVSLWCLVKGFY
PSDIAVEWESNGQPENNYKTTPPVLDSDGSFFLYSKLTVDKSRWQ
QGNVFSCSVMHEALHNHYTQKSLSLSPGK
``` bispecific Ab CD3-arm
SEQ ID NO: 165

```
GAGATCGTGCTGACCCAGTCTCCTGCCACACTGAGTGCTTCTCCA
GGCGAGAGAGTGACCCTGTCCTGCTCCGCTTCCTCCTCCGTGTCC
TACATGAACTGGTATCAGCAGAAGCCCGGCCAGGCTCCTCGGAGA
TGGATCTACGACTCTTCCAAGCTGGCCTCTGGTGTGCCAGCCAGA
TTTTCTGGCTCTGGCTCCGGCAGAGACTATACCCTGACCATCTCC
AGCCTGGAACCTGAGGACTTCGCCGTGTACTACTGCCAGCAGTGG
TCTAGGAACCCTCCTACCTTTGGCGGAGGCACCAAGGTGGAAATC
AAGGGCGGATCTGAGGGAAAGTCCAGCGGCTCCGGCAGCGAAAGC
AAGTCCACCGGCGGAAGCCAGGTTCAACTGGTTCAGTCTGGCGCC
GAAGTGAAGAAACCTGGCTCCTCCGTCAAGGTGTCCTGCAAGGCT
TCCGGCTACACCTTTACCAGATCCACCATGCACTGGGTCAAGCAG
GCCCCTGGACAAGGCTTGGAGTGGATCGGCTACATCAACCCCAGC
TCCGCCTACACCAACTACAACCAGAAATTCCAGGGCAGAGTGACC
CTGACCGCCGACAAGTCTACCTCCACCGCCTACATGGAACTGTCC
AGCCTGAGATCTGAGGACACCGCCGTGTACTACTGCGCCTCTCCT
CAGGTCCACTACGACTACGCCGGCTTTCCTTATTGGGCCAGGGC
ACACTGGTCACCGTTTCTTCTGAGCCCAAATCTAGCGACAAAACT
CACACATGCCCACCGTGCCCAGCACCTGAAGCCGCCGGGGACCG
TCAGTCTTCCTCTTCCCCCCAAAACCCAAGGACACCCTCATGATC
TCCCGGACCCCTGAGGTCACATGCGTGGTGGTGAGCGTGAGCCAC
GAAGACCCTGAGGTCAAGTTCAACTGGTACGTGGACGGCGTGGAG
GTGCATAATGCCAAGACAAAGCCGCGGGAGGAGCAGTACAACAGC
ACGTACCGTGTGGTCAGCGTCCTCACCGTCCTGCACCAGGACTGG
```

-continued

CTGAATGGCAAGGAGTACAAGTGCAAGGTGTCGAACAAAGCCCTC
CCAGCCCCCATCGAGAAAACCATCTCCAAAGCCAAAGGGCAGCCC
CGAGAACCACAGGTGTACACCCTGCCCCCATCCCGGGAGGAGATG
ACCAAGAACCAGGTCAGCCTGTGGTGCCTGGTCAAAGGCTTCTAT
CCCAGCGACATCGCCGTGGAGTGGGAGAGCAATGGGCAGCCGGAG
AACAACTACAAGACCACGCCTCCCGTGCTGGACTCCGACGGCTCC
TTCTTCCTCTACAGCAAGCTCACCGTGGACAAGAGCAGATGGCAG
CAGGGGAACGTCTTCTCATGCTCCGTGATGCATGAGGCTCTGCAC
AACCACTACACGCAGAAGTCTCTCTCCCTGTCTCCGGGAAAA trispecific Ab CD3-CD20 arm
SEQ ID NO: 166
EIVLTQSPATLSASPGERVTLSCSASSSVSYMNWYQQKPGQAPRR
WIYDSSKLASGVPARFSGSGSGRDYTLTISSLEPEDFAVYYCQQW
SRNPPTFGGGTKVEIKGGSEGKSSGSGSESKSTGGSQVQLVQSGA
EVKKPGSSVKVSCKASGYTFTRSTMHWVKQAPGQGLEWIGYINPS
SAYTNYNQKFQGRVTLTADKSTSTAYMELSSLRSEDTAVYYCASP
QVHYDYAGFPYWGQGTLVTVSSEPKSSDKTHTCPPCPAPEAAGGP
SVFLFPPKPKDTLMISRTPEVTCVVVSVSHEDPEVKFNWYVDGVE
VHNAKTKPREEQYNSTYRVVSVLTVLHQDWLNGKEYKCKVSNKAL
PAPIEKTISKAKGQPREPQVYTLPPSREEMTKNQVSLSCAVKGFY
PSDIAVEWESNGQPENNYKTTPPVLDSDGSFFLVSKLTVDKSRWQ
QGNVFSCSVMHEALHNRFTQKSLSLSPGKGGGGSGGGGSGGGGSG
GGGSQIVLSQSPAILSASPGEKVTMTCRASLSVSSMHWYQQKPGS
SPKPWIYATSNLASGVPARFSGSGSGTSYSLTISRVEAEDAATYY
CQQWIFNPPTFGGGTKLEIKGGSEGKSSGSGSESKSTGGSQAYLQ
QSGAELVRPGASVKMSCKTSGYTFSSYNMHWVKQTPRQALEWIGA
IYPGNGDTSYNQKFKGKATLTVDKSSSTAYMQLSSLTSEDSAVYF
CTRSNYYGSSGWYFDVWGTGTTVTVSS trispecific Ab CD3-CD20 arm
SEQ ID NO: 167
GAGATCGTGCTGACCCAGTCTCCTGCCACACTGAGTGCTTCTCCA
GGCGAGAGAGTGACCCTGTCCTGCTCCGCTTCCTCCTCCGTGTCC
TACATGAACTGGTATCAGCAGAAGCCCGGCCAGGCTCCTCGGAGA
TGGATCTACGACTCTTCCAAGCTGGCCTCTGGTGTGCCAGCCAGA
TTTTCTGGCTCTGGCTCCGGCAGAGACTATACCCTGACCATCTCC
AGCCTGGAACCTGAGGACTTCGCCGTGTACTACTGCCAGCAGTGG
TCTAGGAACCCTCCTACCTTTGGCGGAGGCACCAAGGTGGAAATC
AAGGGCGGATCTGAGGGAAAGTCCAGCGGCTCCGGCAGCGAAAGC
AAGTCCACCGGCGGAAGCCAGGTTCAACTGGTTCAGTCTGGCGCC
GAAGTGAAGAAACCTGGCTCCTCCGTCAAGGTGTCCTGCAAGGCT
TCCGGCTACACCTTTACCAGATCCACCATGCACTGGGTCAAGCAG
GCCCCTGGACAAGGCTTGGAGTGGATCGGCTACATCAACCCCAGC
TCCGCCTACACCAACTACAACCAGAAATTCCAGGGCAGAGTGACC -continued CTGACCGCCGACAAGTCTACCTCCACCGCCTACATGGAACTGTCC
AGCCTGAGATCTGAGGACACCGCCGTGTACTACTGCGCCTCTCCT
CAGGTCCACTACGACTACGCCGGCTTTCCTTATTGGGGCCAGGGC
ACACTGGTCACCGTTTCTTCTGAGCCCAAATCTAGCGACAAAACT
CACACATGCCCACCGTGCCCAGCACCTGAAGCCGCCGGGGGACCG
TCAGTCTTCCTCTTCCCCCCAAAACCCAAGGACACCCTCATGATC
TCCCGGACCCCTGAGGTCACATGCGTGGTGGTGAGCGTGAGCCAC
GAAGACCCTGAGGTCAAGTTCAACTGGTACGTGGACGGCGTGGAG
GTGCATAATGCCAAGACAAAGCCGCGGGAGGAGCAGTACAACAGC
ACGTACCGTGTGGTCAGCGTCCTCACCGTCCTGCACCAGGACTGG
CTGAATGGCAAGGAGTACAAGTGCAAGGTGTCGAACAAAGCCCTC
CCAGCCCCCATCGAGAAAACCATCTCCAAAGCCAAAGGGCAGCCC
CGAGAACCACAGGTGTACACCCTGCCCCCATCCCGGGAGGAGATG
ACCAAGAACCAGGTCAGCCTGTCCTGCGCCGTCAAAGGCTTCTAT
CCCAGCGACATCGCCGTGGAGTGGGAGAGCAATGGGCAGCCGGAG
AACAACTACAAGACCACGCCTCCCGTGCTGGACTCCGACGGCTCC
TTCTTCCTCGTGAGCAAGCTCACCGTGGACAAGAGCAGATGGCAG
CAGGGGAACGTCTTCTCATGCTCCGTGATGCATGAGGCTCTGCAC
AACCGGTTCACGCAGAAGTCTCTCTCCCTGTCTCCGGGAAAAGGA
GGCGGAGGATCTGGCGGAGGTGGAAGTGGCGGAGGCGGTTCTGGT
GGTGGTGGATCTCAGATCGTGCTGTCTCAGTCTCCAGCTATCCTG
TCTGCTAGCCCTGGCGAGAAAGTGACCATGACCTGTAGAGCCAGC
CTGTCCGTGTCCTCCATGCACTGGTATCAGCAGAAGCCTGGCAGC
TCCCCTAAGCCTTGGATCTACGCCACCTCCAATCTGGCCTCTGGC
GTGCCAGCTAGATTCTCCGGATCTGGCTCCGGCACCTCCTACAGC
CTGACAATCTCCAGAGTGGAAGCCGAGGATGCCGCCACCTACTAC
TGTCAGCAGTGGATCTTCAACCCTCCTACCTTCGGCGGAGGCACC
AAGCTGGAAATCAAGGGAGGGAGCGAGGGAAAGTCCAGCGGAAGC
GGCTCTGAGTCCAAATCCACCGGAGGGAGCCAGGCTTACTTGCAG
CAGTCTGGTGCCGAACTCGTTAGACCTGGAGCCTCCGTGAAGATG
TCCTGCAAGACCTCCGGCTACACCTTCTCCAGCTACAACATGCAC
TGGGTCAAGCAGACCCCTCGGCAGGCTCTGGAATGGATCGGCGCT
ATCTATCCTGGCAACGGCGACACCTCCTACAACCAGAAGTTCAAG
GGCAAAGCTACCCTGACCGTGGACAAGTCCTCCTCCACCGCTTAC
ATGCAGCTGTCCAGCCTGACCTCTGAGGACTCCGCCGTGTACTTC
TGCACCCGGTCTAACTACTACGGCTCCTCCGGCTGGTACTTCGAT
GTGTGGGGAACCGGAACCACCGTGACAGTCTCTTCT trispecific Ab CD3-CD20 arm
SEQ ID NO: 168
DIQMTQSPSSLSASVGDRVTITCRARQSIGTAIHWYQQKPGKAPK
LLIKYASESISGVPSRFSGSGSGTDFTLTISSLQPEDFATYYCQQ

```
SGSWPYTFGQGTKLEIKGGSEGKSSGSGSESKSTGGSEVQLVESG
GGLVKPGGSLRLSCAASGFTFSRYNMNWVRQAPGKGLEWVSSIST
SSNYIYYADSVKGRFTFSRDNAKNSLDLQMSGLRAEDTAIYYCTR
GWGPFDYWGQGTLVTVSSEPKSSDKTHTCPPCPAPEAAGGPSVFL
FPPKPKDTLMISRTPEVTCVVVSVSHEDPEVKFNWYVDGVEVHNA
KTKPREEQYNSTYRVVSVLTVLHQDWLNGKEYKCKVSNKALPAPI
EKTISKAKGQPREPQVYTLPPSREEMTKNQVSLWCLVKGFYPSDI
AVEWESNGQPENNYKTTPPVLDSDGSFFLYSKLTVDKSRWQQGNV
FSCSVMHEALHNHYTQKSLSLSPGKGGGGSGGGGSGGGGSGGGGS
EIVLTQSPATLSLSPGERATLSCRASLSVSSMHWYQQKPGQAPRL
LIYATSNLASGIPARFSGSGSGTDFTLTISSLEPEDFAVYYCQQW
IFNPPTFGGGTKVEIKGGSEGKSSGSGSESKSTGGSQVQLVQSGA
EVKKPGSSVKVSCKASGYTFSSYNMHWVRQAPGQGLEWMGAIYPG
AGDTSYAQKFQGRVTITADESTSTAYMELSSLRSEDTAVYYCARS
NYYGSSGWYFDVWGKGTTVTVSS
``` trispecific Ab CD3-CD20 arm
SEQ ID NO: 169
```
GACATCCAGATGACCCAGTCTCCATCCTCTCTGTCCGCCTCTGTG
GGCGACAGAGTGACCATTACCTGCCGGGCCAGACAGTCTATCGGC
ACCGCTATCCACTGGTATCAGCAGAAGCCTGGCAAGGCCCCTAAG
CTGCTGATTAAGTACGCCTCCGAGTCCATCTCCGGCGTGCCCTCC
AGATTTTCTGGCTCTGGATCTGGCACCGACTTTACCCTGACAATC
TCCAGCCTGCAGCCTGAGGACTTCGCCACCTACTACTGTCAGCAG
TCCGGCTCTTGGCCTTACACCTTTGGTCAGGGCACCAAGCTGGAA
ATCAAGGGCGGATCTGAGGGAAAGTCCAGCGGCTCCGGCAGCGAA
AGCAAGTCCACCGGCGGAAGCGAGGTGCAGCTGGTTGAATCTGGC
GGAGGACTGGTTAAGCCTGGCGGCTCTCTGAGACTGTCTTGTGCT
GCTTCTGGCTTCACCTTCAGCCGGTACAACATGAACTGGGTCCGA
CAGGCTCCTGGCAAAGGCCTGGAATGGGTGTCCTCCATCTCCACC
TCCAGCAACTACATCTACTACGCCGACTCCGTGAAGGGCAGATTC
ACCTTCTCCAGAGACAACGCCAAGAACTCCCTGGACCTGCAGATG
TCTGGCCTGAGAGCTGAGGACACCGCTATCTACTACTGCACCAGA
GGCTGGGGACCCTTCGATTATTGGGGCCAGGGAACCCTGGTCACC
GTGTCATCTGAGCCCAAATCTAGCGACAAAACTCACACATGCCCA
CCGTGCCCAGCACCTGAAGCCGCCGGGGGACCGTCAGTCTTCCTC
TTCCCCCCAAAACCCAAGGACACCCTCATGATCTCCCGGACCCCT
GAGGTCACATGCGTGGTGGTGAGCGTGAGCCACGAAGACCCTGAG
GTCAAGTTCAACTGGTACGTGGACGGCGTGGAGGTGCATAATGCC
AAGACAAAGCCGCGGGAGGAGCAGTACAACAGCACGTACCGTGTG
GTCAGCGTCCTCACCGTCCTGCACCAGGACTGGCTGAATGGCAAG
GAGTACAAGTGCAAGGTGTCGAACAAAGCCCTCCCAGCCCCCATC
GAGAAAACCATCTCCAAAGCCAAAGGGCAGCCCCGAGAACCACAG
GTGTACACCCTGCCCCCATCCCGGGAGGAGATGACCAAGAACCAG
GTCAGCCTGTGGTGCCTGGTCAAAGGCTTCTATCCCAGCGACATC
GCCGTGGAGTGGGAGAGCAATGGGCAGCCGGAGAACAACTACAAG
ACCACGCCTCCCGTGCTGGACTCCGACGGCTCCTTCTTCCTCTAC
AGCAAGCTCACCGTGGACAAGAGCAGATGGCAGCAGGGGAACGTC
TTCTCATGCTCCGTGATGCATGAGGCTCTGCACAACCACTACACG
CAGAAGTCTCTCTCCCTGTCTCCGGGAAAAGGAGGCGGAGGATCT
GGCGGAGGTGGAAGTGGCGGAGGCGGTTCTGGTGGTGGTGGATCT
GAGATCGTGCTGACCCAGTCTCCAGCCACACTGTCACTGTCTCCA
GGCGAGAGAGCTACCCTGTCCTGTAGAGCCTCTCTGTCCGTGTCC
TCCATGCACTGGTATCAGCAGAAGCCTGGACAGGCCCCTCGGCTG
CTGATCTACGCTACCTCTAATCTGGCCAGCGGTATCCCCGCCAGA
TTTTCTGGTTCTGGCTCTGGCACCGACTTTACCCTGACCATCTCC
AGCCTGGAACCTGAGGACTTCGCCGTGTACTACTGCCAGCAGTGG
ATCTTCAACCCTCCTACCTTTGGCGGAGGCACCAAGGTGGAAATC
AAGGGAGGGAGCGAGGGAAAGTCCAGCGGAAGCGGCTCTGAGTCC
AAATCCACCGGAGGGAGCCAGGTTCAACTGGTTCAGTCTGGCGCC
GAAGTGAAGAAACCTGGCTCCTCCGTGAAGGTGTCCTGCAAGGCT
TCCGGCTACACCTTCTCCAGCTACAACATGCACTGGGTCCGACAG
GCCCCTGGACAAGGATTGGAATGGATGGGCGCTATCTACCCTGGC
GCTGGCGATACCTCTTACGCCCAGAAATTCCAGGGCAGAGTGACC
ATCACCGCCGACGAGTCTACCTCCACCGCCTACATGGAACTGTCC
AGCCTGAGATCTGAGGACACCGCCGTGTACTACTGCGCCCGGTCT
AATTACTACGGCTCCAGCGGCTGGTACTTCGACGTGTGGGGAAAG
GGCACCACCGTGACAGTCTCTTCT
``` trispecific Ab CD3-CD20 arm
SEQ ID NO: 170
```
EIVLTQSPATLSASPGERVTLSCSASSSVSYMNWYQQKPGQAPRR
WIYDSSKLASGVPARFSGSGSGRDYTLTISSLEPEDFAVYYCQQW
SRNPPTFGGGTKVEIKGGSEGKSSGSGSESKSTGGSQVQLVQSGA
EVKKPGSSVKVSCKASGYTFTRSTMHWVKQAPGQGLEWIGYINPS
SAYTNYNQKFQGRVTLTADKSTSTAYMELSSLRSEDTAVYYCASP
QVHYDYAGFPYWGQGTLVTVSSEPKSSDKTHTCPPCPAPEAAGGP
SVFLFPPKPKDTLMISRTPEVTCVVVSVSHEDPEVKFNWYVDGVE
VHNAKTKPREEQYNSTYRVVSVLTVLHQDWLNGKEYKCKVSNKAL
PAPIEKTISKAKGQPREPQVYTLPPSREEMTKNQVSLWCLVKGFY
PSDIAVEWESNGQPENNYKTTPPVLDSDGSFFLYSKLTVDKSRWQ
QGNVFSCSVMHEALHNHYTQKSLSLSPGKGGGGSGGGGSGGGGS
GGGSEIVLTQSPATLSLSPGERATLSCRASLSVSSMHWYQQKPGQ
APRLLIYATSNLASGIPARFSGSGSGTDFTLTISSLEPEDFAVYY
CQQWIFNPPTFGGGTKVEIKGGSEGKSSGSGSESKSTGGSQVQLV
```

-continued

```
QSGAEVKKPGSSVKVSCKASGYTFSSYNMHWVRQAPGQGLEWMGA
IYPGAGDTSYAQKFQGRVTITADESTSTAYMELSSLRSEDTAVYY
CARSNYYGSSGWYFDVWGKGTTVTVSS
``` trispecific Ab CD3-CD20 arm
SEQ ID NO: 171

```
GAGATCGTGCTGACCCAGTCTCCTGCCACACTGAGTGCTTCTCCA
GGCGAGAGAGTGACCCTGTCCTGCTCCGCTTCCTCCTCCGTGTCC
TACATGAACTGGTATCAGCAGAAGCCCGGCCAGGCTCCTCGGAGA
TGGATCTACGACTCTTCCAAGCTGGCCTCTGGTGTGCCAGCCAGA
TTTTCTGGCTCTGGCTCCGGCAGAGACTATACCCTGACCATCTCC
AGCCTGGAACCTGAGGACTTCGCCGTGTACTACTGCCAGCAGTGG
TCTAGGAACCCTCCTACCTTTGGCGGAGGCACCAAGGTGGAAATC
AAGGGCGGATCTGAGGGAAAGTCCAGCGGCTCCGGCAGCGAAAGC
AAGTCCACCGGCGGAAGCCAGGTTCAACTGGTTCAGTCTGGCGCC
GAAGTGAAGAAACCTGGCTCCTCCGTCAAGGTGTCCTGCAAGGCT
TCCGGCTACACCTTTACCAGATCCACCATGCACTGGGTCAAGCAG
GCCCCTGGACAAGGCTTGGAGTGGATCGGCTACATCAACCCCAGC
TCCGCCTACACCAACTACAACCAGAAATTCCAGGGCAGAGTGACC
CTGACCGCCGACAAGTCTACCTCCACCGCCTACATGGAACTGTCC
AGCCTGAGATCTGAGGACACCGCCGTGTACTACTGCGCCTCTCCT
CAGGTCCACTACGACTACGCCGGCTTTCCTTATTGGGGCCAGGGC
ACACTGGTCACCGTTTCTTCTGAGCCCAAATCTAGCGACAAAACT
CACACATGCCCACCGTGCCCAGCACCTGAAGCCGCCGGGGGACCG
TCAGTCTTCCTCTTCCCCCCAAAACCCAAGGACACCCTCATGATC
TCCCGGACCCCTGAGGTCACATGCGTGGTGGTGAGCGTGAGCCAC
GAAGACCCTGAGGTCAAGTTCAACTGGTACGTGGACGGCGTGGAG
GTGCATAATGCCAAGACAAAGCCGCGGGAGGAGCAGTACAACAGC
ACGTACCGTGTGGTCAGCGTCCTCACCGTCCTGCACCAGGACTGG
CTGAATGGCAAGGAGTACAAGTGCAAGGTGTCGAACAAAGCCCTC
CCAGCCCCCATCGAGAAAACCATCTCCAAAGCCAAAGGGCAGCCC
CGAGAACCACAGGTGTACACCCTGCCCCCATCCCGGGAGGAGATG
ACCAAGAACCAGGTCAGCCTGTGGTGCCTGGTCAAAGGCTTCTAT
CCCAGCGACATCGCCGTGGAGTGGGAGAGCAATGGGCAGCCGGAG
AACAACTACAAGACCACGCCTCCCGTGCTGGACTCCGACGGCTCC
TTCTTCCTCTACAGCAAGCTCACCGTGGACAAGAGCAGATGGCAG
CAGGGGAACGTCTTCTCATGCTCCGTGATGCATGAGGCTCTGCAC
AACCACTACACGCAGAAGTCTCTCTCCCTGTCTCCGGGAAAAGGA
GGCGGAGGATCTGGCGGAGGTGGAAGTGGCGGAGGCGGTTCTGGT
GGTGGTGGATCTGAGATCGTGCTGACCCAGTCTCCAGCCACACTG
TCACTGTCTCCAGGCGAGAGAGCTACCCTGTCCTGTAGAGCCTCT
CTGTCCGTGTCCTCCATGCACTGGTATCAGCAGAAGCCTGGACAG
GCCCCTCGGCTGCTGATCTACGCTACCTCTAATCTGGCCAGCGGT
```

-continued

```
ATCCCCGCCAGATTTTCTGGTTCTGGCTCTGGCACCGACTTTACC
CTGACCATCTCCAGCCTGGAACCTGAGGACTTCGCCGTGTACTAC
TGCCAGCAGTGGATCTTCAACCCTCCTACCTTTGGCGGAGGCACC
AAGGTGGAAATCAAGGGCGGAGGCGAGGGAAAGTCCAGCGGAAGC
GGCTCTGAGTCCAAATCCACCGGAGGGAGCCAGGTTCAACTGGTT
CAGTCTGGCGCCGAAGTGAAGAAACCTGGCTCCTCCGTGAAGGTG
TCCTGCAAGGCTTCCGGCTACACCTTCTCCAGCTACAACATGCAC
TGGGTCCGACAGGCCCCTGGACAAGGATTGGAATGGATGGGCGCT
ATCTACCCTGGCGCTGGCGATACCTCTTACGCCCAGAAATTCCAG
GGCAGAGTGACCATCACCGCCGACGAGTCTACCTCCACCGCCTAC
ATGGAACTGTCCAGCCTGAGATCTGAGGACACCGCCGTGTACTAC
TGCGCCCGGTCTAATTACTACGGCTCCAGCGGCTGGTACTTCGAC
GTGTGGGGAAAGGGCACCACCGTGACAGTCTCTTCT
``` trispecific/bispecific Ab CD79b arm HC
SEQ ID NO: 172

```
QVQLQESGPGLVKPSETLSLTCSVSGASISSFYWSWIRQPADEGL
EWIGRISPSGKTNYIPSLKSRIIMSLDASKNQFSLRLNSVTAADT
AMYYCARGEYSGTYSYSFDVWGQGTMVTVSSASTKGPSVFPLAPS
SKSTSGGTAALGCLVKDYFPEPVTVSWNSGALTSGVHTFPAVLQS
SGLYSLSSVVTVPSSSLGTQTYICNVNHKPSNTKVDKKVEPKSCD
KTHTCPPCPAPEAAGGPSVFLFPPKPKDTLMISRTPEVTCVVVSV
SHEDPEVKFNWYVDGVEVHNAKTKPREEQYNSTYRVVSVLTVLHQ
DWLNGKEYKCKVSNKALPAPIEKTISKAKGQPREPQVYTLPPSRE
EMTKNQVSLSCAVKGFYPSDIAVEWESNGQPENNYKTTPPVLDSD
GSFFLVSKLTVDKSRWQQGNVFSCSVMHEALHNRFTQKSLSLSPG
K
``` trispecific/bispecific Ab CD79b arm HC
SEQ ID NO: 173

```
CAGGTTCAGCTGCAAGAGTCTGGTCCTGGCCTGGTCAAGCCTTCC
GAGACACTGTCTCTGACCTGCTCTGTGTCCGGCGCCTCCATCTCT
TCCTTCTACTGGTCCTGGATCCGGCAGCCTGCTGACGAAGGACTG
GAATGGATCGGCCGGATCAGCCCTTCTGGCAAGACCAACTACATC
CCCAGCCTGAAGTCCCGGATCATCATGTCCCTGGACGCCTCCAAG
AACCAGTTCTCCCTGCGGCTGAACTCTGTGACCGCTGCCGATACC
GCCATGTACTACTGTGCCAGAGGCGAGTACTCCGGCACCTACTCC
TACAGCTTTGACGTGTGGGGACAAGGCACCATGGTCACAGTTTCT
TCTGCCTCCACCAAGGGCCCATCGGTCTTCCCCCTGGCACCCTCC
TCCAAGAGCACCTCTGGGGGCACAGCGGCCCTGGGCTGCCTGGTC
AAGGACTACTTCCCCGAACCGGTGACGGTGTCGTGGAACTCAGGC
GCCCTGACCAGCGGCGTGCACACCTTCCCGGCTGTCCTACAGTCC
TCAGGACTCTACTCCCTCAGCAGCGTGGTGACCGTGCCCTCCAGC
AGCTTGGGCACCCAGACCTACATCTGCAACGTGAATCACAAGCCC
```

-continued

AGCAACACCAAGGTGGACAAGAAAGTTGAGCCCAAATCTTGTGAC

AAAACTCACACATGCCCACCGTGCCCAGCACCTGAAGCCGCCGGG

GGACCGTCAGTCTTCCTCTTCCCCCCAAAACCCAAGGACACCCTC

ATGATCTCCCGGACCCCTGAGGTCACATGCGTGGTGGTGAGCGTG

AGCCACGAAGACCCTGAGGTCAAGTTCAACTGGTACGTGGACGGC

GTGGAGGTGCATAATGCCAAGACAAAGCCGCGGGAGGAGCAGTAC

AACAGCACGTACCGTGTGGTCAGCGTCCTCACCGTCCTGCACCAG

GACTGGCTGAATGGCAAGGAGTACAAGTGCAAGGTGTCGAACAAA

GCCCTCCCAGCCCCCATCGAGAAAACCATCTCCAAAGCCAAAGGG

CAGCCCCGAGAACCACAGGTGTACACCCTGCCCCCATCCCGGGAG

GAGATGACCAAGAACCAGGTCAGCCTGTCCTGCGCCGTCAAAGGC

TTCTATCCCAGCGACATCGCCGTGGAGTGGGAGAGCAATGGGCAG

CCGGAGAACAACTACAAGACCACGCCTCCCGTGCTGGACTCCGAC

GGCTCCTTCTTCCTCGTGAGCAAGCTCACCGTGGACAAGAGCAGA

TGGCAGCAGGGGAACGTCTTCTCATGCTCCGTGATGCATGAGGCT

CTGCACAACCGGTTCACGCAGAAGTCTCTCTCCCTGTCTCCGGGA

AAA trispecific/bispecific Ab CD79b arm LC

SEQ ID NO: 174
DIVMTQSPLSLSVTPGEPASISCRSSESLLDSEDGNTYLDWFLQK

PGQSPQLLIYTLSYRASGVPDRFSGSGSDTDFTLHISSLEAEDVG

LYYCMQRMEFPLTFGQGTKVEIKRTVAAPSVFIFPPSDEQLKSGT

ASVVCLLNNFYPREAKVQWKVDNALQSGNSQESVTEQDSKDSTYS

LSSTLTLSKADYEKHKVYACEVTHQGLSSPVTKSFNRGEC trispecific/bispecific Ab CD79b arm LC

SEQ ID NO: 175
GACATCGTGATGACCCAGTCTCCACTGAGCCTGTCTGTGACACCT

GGCGAGCCTGCCTCCATCTCCTGTAGATCTTCTGAGTCCCTGCTG

GACAGCGAGGACGGCAATACCTACCTGGACTGGTTCCTGCAGAAG

CCCGGACAGTCTCCTCAGCTGCTGATCTACACCCTGTCCTACAGA

GCCTCTGGCGTGCCCGATAGATTCTCCGGCTCTGGCTCTGACACC

GACTTTACCCTGCACATCTCCAGCCTGGAAGCCGAGGATGTGGGC

CTGTACTACTGTATGCAGCGGATGGAATTTCCCCTGACCTTCGGC

CAGGGCACCAAGGTGGAAATCAAGCGCACCGTGGCCGCCCCTAGC

GTGTTTATCTTCCCTCCTCGGATGAGCAGCTTAAGTCAGGCACC

GCATCCGTGGTCTGCCTGCTCAACAACTTCTACCCGAGGGAAGCC

AAAGTGCAGTGGAAAGTGGACAACGCGCTCCAGTCGGGAAACTCC

CAGGAGTCCGTGACCGAACAGGACTCCAAGGACAGCACTTATTCC

CTGTCCTCCACTCTGACGCTGTCAAAGGCCGACTACGAGAAGCAC

AAGGTCTACGCCTGCGAAGTGACCCATCAGGGGCTTTCCTCGCCC

GTGACTAAGAGCTTCAATCGGGGCGAATGC

-continued trispecific/bispecific Ab CD79b arm HC

SEQ ID NO: 176
QVQLQQSGPGLVKPSQTLSLTCAISGDSVSSNSATWNWIRQSPSR

GLEWLGRTYYRSKWYNDYTVSVKSRITINPDTSKNQFSLQLNSVT

PEDTAVYYCTRVDIAFDYWGQGTLVTVSSASTKGPSVFPLAPSSK

STSGGTAALGCLVKDYFPEPVTVSWNSGALTSGVHTFPAVLQSSG

LYSLSSVVTVPSSSLGTQTYICNVNHKPSNTKVDKKVEPKSCDKT

HTCPPCPAPEAAGGPSVFLFPPKPKDTLMISRTPEVTCVVVSVSH

EDPEVKFNWYVDGVEVHNAKTKPREEQYNSTYRVVSVLTVLHQDW

LNGKEYKCKVSNKALPAPIEKTISKAKGQPREPQVYTLPPSREEM

TKNQVSLSCAVKGFYPSDIAVEWESNGQPENNYKTTPPVLDSDGS

FFLVSKLTVDKSRWQQGNVFSCSVMHEALHNRFTQKSLSLSPGK trispecific/bispecific Ab CD79b arm HC

SEQ ID NO: 177
CAGGTTCAGCTGCAGCAGTCTGGCCCTGGACTGGTCAAGCCCTCT

CAGACCCTGTCTCTGACCTGTGCCATCTCCGGCGACTCCGTGTCC

TCTAATTCTGCCACCTGGAACTGGATCCGGCAGTCCCCTAGTAGA

GGCCTGGAATGGCTGGGCAGAACCTACTACCGGTCCAAGTGGTAC

AACGACTACACCGTGTCCGTGAAGTCCCGGATCACCATCAATCCC

GACACCTCCAAGAACCAGTTCTCCCTGCAGCTCAACAGCGTGACC

CCTGAGGATACCGCCGTGTACTACTGCACCAGAGTGGATATCGCC

TTCGACTACTGGGGCCAGGGCACACTGGTTACCGTTTCTTCTGCC

TCCACCAAGGGCCCATCGGTCTTCCCCCTGGCACCCTCCTCCAAG

AGCACCTCTGGGGGCACAGCGGCCCTGGGCTGCCTGGTCAAGGAC

TACTTCCCCGAACCGGTGACGGTGTCGTGGAACTCAGGCGCCCTG

ACCAGCGGCGTGCACACCTTCCCGGCTGTCCTACAGTCCTCAGGA

CTCTACTCCCTCAGCAGCGTGGTGACCGTGCCCTCCAGCAGCTTG

GGCACCCAGACCTACATCTGCAACGTGAATCACAAGCCCAGCAAC

ACCAAGGTGGACAAGAAAGTTGAGCCCAAATCTTGTGACAAAACT

CACACATGCCCACCGTGCCCAGCACCTGAAGCCGCCGGGGACCG

TCAGTCTTCCTCTTCCCCCCAAAACCCAAGGACACCCTCATGATC

TCCCGGACCCCTGAGGTCACATGCGTGGTGGTGAGCGTGAGCCAC

GAAGACCCTGAGGTCAAGTTCAACTGGTACGTGGACGGCGTGGAG

GTGCATAATGCCAAGACAAAGCCGCGGGAGGAGCAGTACAACAGC

ACGTACCGTGTGGTCAGCGTCCTCACCGTCCTGCACCAGGACTGG

CTGAATGGCAAGGAGTACAAGTGCAAGGTGTCGAACAAAGCCCTC

CCAGCCCCCATCGAGAAAACCATCTCCAAAGCCAAAGGGCAGCCC

CGAGAACCACAGGTGTACACCCTGCCCCCATCCCGGGAGGAGATG

ACCAAGAACCAGGTCAGCCTGTCCTGCGCCGTCAAAGGCTTCTAT

CCCAGCGACATCGCCGTGGAGTGGGAGAGCAATGGGCAGCCGGAG

-continued
AACAACTACAAGACCACGCCTCCCGTGCTGGACTCCGACGGCTCC
TTCTTCCTCGTGAGCAAGCTCACCGTGGACAAGAGCAGATGGCAG
CAGGGGAACGTCTTCTCATGCTCCGTGATGCATGAGGCTCTGCAC
AACCGGTTCACGCAGAAGTCTCTCTCCCTGTCTCCGGGAAAA trispecific/bispecific Ab CD79b arm LC
SEQ ID NO: 178
QTVVTQPPSVSEAPRQRVTISCSGSSSNIGNHGVNWYQQLPGKAP
KLLIYNDDLLPSGVSDRFSGSTSGTSGSLAISGLQSEDEADYYCA
AWDDSLNGVVFGGGTKLTVLGQPKAAPSVTLFPPSSEELQANKAT
LVCLISDFYPGAVTVAWKADSSPVKAGVETTTPSKQSNNKYAASS
YLSLTPEQWKSHRSYSCQVTHEGSTVEKTVAPTECS trispecific/bispecific Ab CD79b arm LC
SEQ ID NO: 179
CAGACAGTGGTCACCCAGCCTCCATCTGTGTCTGAGGCCCCTAGA
CAGAGAGTGACCATCTCCTGCTCCGGCTCCTCCTCCAACATCGGC
AATCATGGCGTGAACTGGTATCAGCAGCTGCCCGGCAAGGCTCCC
AAACTGCTGATCTACAACGACGACCTGCTGCCTTCTGGCGTGTCC
GACAGATTCTCCGGCTCTACCTCTGGCACCTCTGGATCCCTGGCT
ATCTCTGGCCTGCAGTCTGAGGACGAGGCCGACTACTATTGTGCC
GCCTGGGACGATTCTCTGAACGGCGTTGTGTTTGGCGGAGGCACC
AAGCTGACAGTGTTGGGACAGCCTAAGGCAGCCCCCTCCGTGACC
CTGTTCCCGCCATCATCCGAAGAACTGCAGGCCAACAAGGCCACG
CTCGTGTGCCTGATTTCCGACTTCTACCCGGGGGCCGTGACTGTG
GCCTGGAAGGCAGACTCAAGCCCTGTGAAGGCTGGCGTCGAGACT
ACCACCCCGTCGAAGCAATCCAACAACAAATACGCGGCGTCCAGC
TACCTGAGCCTGACCCCTGAGCAGTGGAAATCCCACCGGTCCTAC
TCGTGCCAAGTCACCCACGAGGGATCCACTGTGGAAAAGACCGTG
GCGCCGACTGAGTGTTCC trispecific/bispecific Ab CD79b arm HC
SEQ ID NO: 180
QVQLQESGPGLVKPSQTLSLTCTVSGVSISNYYWSWIRQPPGKGL
EWIGRISPSGRTNYNPSLKSRVTMSLDASKNQFSLKLSSVTAADT
AVYYCARGEYSGTYSYSFDIWGQGTMVTVSSASTKGPSVFPLAPS
SKSTSGGTAALGCLVKDYFPEPVTVSWNSGALTSGVHTFPAVLQS
SGLYSLSSVVTVPSSSLGTQTYICNVNHKPSNTKVDKKVEPKSCD
KTHTCPPCPAPEAAGGPSVFLFPPKPKDTLMISRTPEVTCVVVSV
SHEDPEVKFNWYVDGVEVHNAKTKPREEQYNSTYRVVSVLTVLHQ
DWLNGKEYKCKVSNKALPAPIEKTISKAKGQPREPQVYTLPPSRE
EMTKNQVSLSCAVKGFYPSDIAVEWESNGQPENNYKTTPPVLDSD
GSFFLVSKLTVDKSRWQQGNVFSCSVMHEALHNRFTQKSLSLSPG
K trispecific/bispecific Ab CD79b arm HC
SEQ ID NO: 181
CAGGTTCAGCTGCAAGAGTCTGGCCCTGGCCTGGTCAAGCCCTCT
CAGACCCTGTCTCTGACCTGTACCGTGTCCGGCGTGTCCATCTCC -continued
AACTACTACTGGTCCTGGATCCGGCAGCCTCCTGGCAAAGGACTG
GAATGGATCGGCCGCATCTCTCCTTCTGGTCGCACCAACTACAAC
CCCAGCCTGAAAAGCAGAGTGACCATGTCTCTGGACGCCTCCAAG
AACCAGTTCTCCCTGAAGCTGTCCTCCGTGACCGCTGCTGATACC
GCCGTGTACTACTGTGCCAGAGGCGAGTACTCCGGCACCTACTCC
TACAGCTTCGACATCTGGGGCCAGGGCACCATGGTCACAGTCTCT
TCTGCCTCCACCAAGGGCCCATCGGTCTTCCCCCTGGCACCCTCC
TCCAAGAGCACCTCTGGGGGCACAGCGGCCCTGGGCTGCCTGGTC
AAGGACTACTTCCCCGAACCGGTGACGGTGTCGTGGAACTCAGGC
GCCCTGACCAGCGGCGTGCACACCTTCCCGGCTGTCCTACAGTCC
TCAGGACTCTACTCCCTCAGCAGCGTGGTGACCGTGCCCTCCAGC
AGCTTGGGCACCCAGACCTACATCTGCAACGTGAATCACAAGCCC
AGCAACACCAAGGTGGACAAGAAAGTTGAGCCCAAATCTTGTGAC
AAAACTCACACATGCCCACCGTGCCCAGCACCTGAAGCCGCCGGG
GGACCGTCAGTCTTCCTCTTCCCCCCAAAACCCAAGGACACCCTC
ATGATCTCCCGGACCCCTGAGGTCACATGCGTGGTGGTGAGCGTG
AGCCACGAAGACCCTGAGGTCAAGTTCAACTGGTACGTGGACGGC
GTGGAGGTGCATAATGCCAAGACAAAGCCGCGGGAGGAGCAGTAC
AACAGCACGTACCGTGTGGTCAGCGTCCTCACCGTCCTGCACCAG
GACTGGCTGAATGGCAAGGAGTACAAGTGCAAGGTGTCGAACAAA
GCCCTCCCAGCCCCCATCGAGAAAACCATCTCCAAAGCCAAAGGG
CAGCCCCGAGAACCACAGGTGTACACCCTGCCCCCATCCCGGGAG
GAGATGACCAAGAACCAGGTCAGCCTGTCCTGCGCCGTCAAAGGC
TTCTATCCCAGCGACATCGCCGTGGAGTGGGAGAGCAATGGGCAG
CCGGAGAACAACTACAAGACCACGCCTCCCGTGCTGGACTCCGAC
GGCTCCTTCTTCCTCGTGAGCAAGCTCACCGTGGACAAGAGCAGA
TGGCAGCAGGGGAACGTCTTCTCATGCTCCGTGATGCATGAGGCT
CTGCACAACCGGTTCACGCAGAAGTCTCTCTCCCTGTCTCCGGGA
AAA trispecific/bispecific Ab CD79b arm LC
SEQ ID NO: 182
DIQMTQSPSSLSASVGDRVTITCRSSQSLFDSDDGNTYLDWFQQK
PGQSPKLLIQTLSYRASGVPSRFSGSGSGTDFTLTISSLQPEDFA
TYYCMQRMEFPLTFGGGTKVEIKRTVAAPSVFIFPPSDEQLKSGT
ASVVCLLNNFYPREAKVQWKVDNALQSGNSQESVTEQDSKDSTYS
LSSTLTLSKADYEKHKVYACEVTHQGLSSPVTKSFNRGEC trispecific/bispecific Ab CD79b arm LC
SEQ ID NO: 183
GACATCCAGATGACCCAGTCTCCATCCTCTCTGTCCGCCTCTGTG
GGCGACAGAGTGACCATCACCTGTCGGTCCTCTCAGTCCCTGTTC
GACTCTGACGACGGCAACACCTACCTGGACTGGTTCCAGCAGAAG
CCCGGCCAGTCTCCTAAGCTGCTGATCCAGACACTGTCCTACAGA

```
GCCTCTGGCGTGCCCTCCAGATTTTCCGGCTCTGGCTCTGGCACC
GACTTTACCCTGACAATCTCCAGCCTGCAGCCTGAGGACTTCGCC
ACCTACTACTGTATGCAGCGGATGGAATTTCCCCTGACCTTCGGC
GGAGGCACCAAGGTGGAAATCAAGCGCACCGTGGCCGCCCCTAGC
GTGTTTATCTTCCCTCCCTCGGATGAGCAGCTTAAGTCAGGCACC
GCATCCGTGGTCTGCCTGCTCAACAACTTCTACCCGAGGGAAGCC
AAAGTGCAGTGGAAAGTGGACAACGCGCTCCAGTCGGGAAACTCC
CAGGAGTCCGTGACCGAACAGGACTCCAAGGACAGCACTTATTCC
CTGTCCTCCACTCTGACGCTGTCAAAGGCCGACTACGAGAAGCAC
AAGGTCTACGCCTGCGAAGTGACCCATCAGGGGCTTTCCTCGCCC
GTGACTAAGAGCTTCAATCGGGGCGAATGC
``` trispecific/bispecific Ab CD79b arm HC
SEQ ID NO: 184
```
QITLKESGPTLVKPTQTLTLTCTFSGFSLSTSGMGVSWIRQPPGK
ALEWLAHIYWDDDKRYNPSLKSRLTITKDTSKNQVVLTMTNMDPV
DTATYYCARLYGFTYGFAYWGQGTLVTVSSASTKGPSVFPLAPSS
KSTSGGTAALGCLVKDYFPEPVTVSWNSGALTSGVHTFPAVLQSS
GLYSLSSVVTVPSSSLGTQTYICNVNHKPSNTKVDKKVEPKSCDK
THTCPPCPAPEAAGGPSVFLFPPKPKDTLMISRTPEVTCVVVSVS
HEDPEVKFNWYVDGVEVHNAKTKPREEQYNSTYRVVSVLTVLHQD
WLNGKEYKCKVSNKALPAPIEKTISKAKGQPREPQVYTLPPSREE
MTKNQVSLSCAVKGFYPSDIAVEWESNGQPENNYKTTPPVLDSDG
SFFLVSKLTVDKSRWQQGNVFSCSVMHEALHNRFTQKSLSLSPGK
``` trispecific/bispecific Ab CD79b arm HC
SEQ ID NO: 185
```
CAGATCACTCTGAAAGAGTCCGGCCCAACACTGGTCAAGCCTACC
CAGACACTCACACTGACCTGTACCTTCAGCGGATTTTCTCTGTCC
ACCTCTGGCATGGGCGTGTCTTGGATCAGACAGCCTCCTGGCAAG
GCCCTGGAATGGCTGGCTCACATCTACTGGGACGATGACAAGCGG
TACAACCCCAGCCTGAAGTCCCGGCTGACCATCACCAAGGACACC
TCCAAGAACCAAGTGGTGCTGACCATGACCAACATGGACCCTGTG
GATACCGCTACCTACTACTGCGCCAGACTGTACGGCTTCACCTAT
GGCTTCGCCTACTGGGGCCAGGGCACCCTGGTGACCGTGTCCTCT
GCCTCCACCAAGGGCCCATCGGTCTTCCCCCTGGCACCCTCCTCC
AAGAGCACCTCTGGGGGCACAGCGGCCCTGGGCTGCCTGGTCAAG
GACTACTTCCCCGAACCGGTGACGGTGTCGTGGAACTCAGGCGCC
CTGACCAGCGGCGTGCACACCTTCCCGGCTGTCCTACAGTCCTCA
GGACTCTACTCCCTCAGCAGCGTGGTGACCGTGCCCTCCAGCAGC
TTGGGCACCCAGACCTACATCTGCAACGTGAATCACAAGCCCAGC
AACACCAAGGTGGACAAGAAAGTTGAGCCCAAATCTTGTGACAAA
ACTCACACATGCCCACCGTGCCCAGCACCTGAAGCCGCGGGGGA
CCGTCAGTCTTCCTCTTCCCCCCAAAACCCAAGGACACCCTCATG
ATCTCCCGGACCCCTGAGGTCACATGCGTGGTGGTGAGCGTGAGC
CACGAAGACCCTGAGGTCAAGTTCAACTGGTACGTGGACGGCGTG
GAGGTGCATAATGCCAAGACAAAGCCGCGGGAGGAGCAGTACAAC
AGCACGTACCGTGTGGTCAGCGTCCTCACCGTCCTGCACCAGGAC
TGGCTGAATGGCAAGGAGTACAAGTGCAAGGTGTCGAACAAAGCC
CTCCCAGCCCCCATCGAGAAAACCATCTCCAAAGCCAAAGGGCAG
CCCCGAGAACCACAGGTGTACACCCTGCCCCCATCCCGGGAGGAG
ATGACCAAGAACCAGGTCAGCCTGTCCTGCGCCGTCAAAGGCTTC
TATCCCAGCGACATCGCCGTGGAGTGGGAGAGCAATGGGCAGCCG
GAGAACAACTACAAGACCACGCCTCCCGTGCTGGACTCCGACGGC
TCCTTCTTCCTCGTGAGCAAGCTCACCGTGGACAAGAGCAGATGG
CAGCAGGGGAACGTCTTCTCATGCTCCGTGATGCATGAGGCTCTG
CACAACCGGTTCACGCAGAAGTCTCTCTCCCTGTCTCCGGGAAAA
``` trispecific/bispecific Ab CD79b arm LC
SEQ ID NO: 186
```
DIVMTQSPDSLAVSLGERATINCRASQSVDYNGISYMHWYQQKPG
QPPKLLIYAASNPESGVPDRFSGSGSGTDFTLTISSLQAEDVAVY
YCQQIIEDPWTFGQGTKVEIKRTVAAPSVFIFPPSDEQLKSGTAS
VVCLLNNFYPREAKVQWKVDNALQSGNSQESVTEQDSKDSTYSLS
STLTLSKADYEKHKVYACEVTHQGLSSPVTKSFNRGEC
``` trispecific/bispecific Ab CD79b arm LC
SEQ ID NO: 187
```
GATATTGTGATGACCCAGTCCCCCGATTCTCTCGCTGTCTCTCTG
GGCGAACGGGCTACAATCAACTGTAGGGCTTCACAGTCTGTCGAC
TACAACGGCATCTCTTACATGCATTGGTACCAGCAGAAACCTGGA
CAGCCACCAAAACTCCTCATCTACGCCGCTTCCAATCCTGAATCT
GGCGTGCCCGACCGATTTTCCGGATCCGGCTCTGGCACCGACTTT
ACACTCACTATTAGTAGCCTCCAGGCCGAGGATGTGGCCGTGTAC
TACTGTCAGCAGATCATCGAGGATCCTTGGACATTTGGACAGGGA
ACCAAAGTGGAGATCAAACGTACGGTGGCTGCACCATCTGTCTTC
ATCTTCCCGCCATCTGATGAGCAGTTGAAATCTGGAACTGCCTCT
GTTGTGTGCCTGCTGAATAACTTCTATCCCAGAGAGGCCAAAGTA
CAGTGGAAGGTGGATAACGCCCTCCAATCGGGTAACTCCCAGGAG
AGTGTCACAGAGCAGGACAGCAAGGACAGCACCTACAGCCTCAGC
AGCACCCTGACGCTGAGCAAAGCAGACTACGAGAAACACAAAGTC
TACGCCTGCGAAGTCACCCATCAGGGCCTGAGCTCGCCCGTCACA
AAGAGCTTCAACAGGGGAGAGTGT
``` trispecific/bispecific Ab CD79b arm LC
SEQ ID NO: 188
```
GACATCCAGATGACCCAGAGCCCTAGCAGCCTGAGCGCCAGCGTG
GGCGACAGAGTGACCATTACCTGCAGAAGCAGCCAGAGCCTGTTC
GACAGCGACGACGGCAATACCTACCTGGACTGGTTCCAGCAGAAG
CCTGGCCAGAGCCCTAAGCTGCTGATCCAGACCCTGAGCTACAGA
```

```
GCCAGCGGCGTGCCTAGCAGATTCTCCGGCAGCGGCTCCGGCACC
GACTTCACCCTGACCATCAGCAGCCTGCAGCCTGAGGACTTCGCC
ACCTACTACTGCATGCAGAGAATGGAGTTCCCTCTGACCTTCGGC
GGCGGCACCAAGGTGGAGATCAAGCGTACGGTGGCTGCACCATCT
GTCTTCATCTTCCCGCCATCTGATGAGCAGTTGAAATCTGGAACT
GCCTCTGTTGTGTGCCTGCTGAATAACTTCTATCCCAGAGAGGCC
AAAGTACAGTGGAAGGTGGATAACGCCCTCCAATCGGGTAACTCC
CAGGAGAGTGTCACAGAGCAGGACAGCAAGGACAGCACCTACAGC
CTCAGCAGCACCCTGACGCTGAGCAAAGCAGACTACGAGAAACAC
AAAGTCTACGCCTGCGAAGTCACCCATCAGGGCCTGAGCTCGCCC
GTCACAAAGAGCTTCAACAGGGGAGAGTGT
bispecific Ab CD3 arm
                             SEQ ID NO: 189
EIVLTQSPATLSASPGERVTLSCSASSSVSYMNWYQQKPGQAPRR
WIYDSSKLASGVPARFSGSGSGRDYTLTISSLEPEDFAVYYCQQW
SRNPPTFGGGTKVEIKGGSEGKSSGSGSESKSTGGSQVQLVQSGA
EVKKPGSSVKVSCKASGYTFTRSTMHWVRQAPGQGLEWMGYINPS
SAYTNYAQKFQGRVTLTADKSTSTAYMELSSLRSEDTAVYYCASP
QVHYDYGGFPYWGQGTLVTVSSEPKSSDKTHTCPPCPAPEAAGGP
SVFLFPPKPKDTLMISRTPEVTCVVVSVSHEDPEVKFNWYVDGVE
VHNAKTKPREEQYNSTYRVVSVLTVLHQDWLNGKEYKCKVSNKAL
PAPIEKTISKAKGQPREPQVYTLPPSREEMTKNQVSLWCLVKGFY
PSDIAVEWESNGQPENNYKTTPPVLDSDGSFFLYSKLTVDKSRWQ
QGNVFSCSVMHEALHNHYTQKSLSLSPGK
bispecific Ab CD3 arm
                             SEQ ID NO: 190
GAGATCGTGCTGACCCAGTCTCCTGCCACACTGAGTGCTTCTCCA
GGCGAGAGAGTGACCCTGTCCTGCTCCGCTTCCTCCTCCGTGTCC
TACATGAACTGGTATCAGCAGAAGCCCGGCCAGGCTCCTCGGAGA
TGGATCTACGACTCTTCCAAGCTGGCCTCTGGTGTGCCAGCCAGA
TTTTCTGGCTCTGGCTCCGGCAGAGACTATACCCTGACCATCTCC
AGCCTGGAACCTGAGGACTTCGCCGTGTACTACTGCCAGCAGTGG
TCTAGGAACCCTCCTACCTTTGGCGGAGGCACCAAGGTGGAAATC
AAGGGCGGATCTGAGGGAAAGTCCAGCGGCTCCGGCAGCGAAAGC
AAGTCCACCGGCGGAAGCCAGGTTCAACTGGTTCAGTCTGGCGCC
GAAGTGAAGAAACCTGGCTCCTCCGTGAAAGTGTCCTGCAAGGCT
TCCGGCTACACTTTTACCAGATCCACCATGCACTGGGTCCGACAG
GCTCCAGGACAAGGCTTGGAGTGGATGGGCTACATCAACCCCAGC
TCCGCCTACACCAACTACGCCCAGAAATTCCAGGGCAGAGTGACC
CTGACCGCCGACAAGTCTACCTCCACCGCCTACATGGAACTGTCC
AGCCTGAGATCTGAGGACACCGCCGTGTACTACTGCGCTTCTCCT
CAGGTGCACTACGACTACGGCGGCTTTCCTTATTGGGGCCAGGGC
ACACTGGTCACCGTTTCTTCTGAGCCCAAATCTAGCGACAAAACT
```

```
CACACATGCCCACCGTGCCCAGCACCTGAAGCCGCCGGGGGACCG
TCAGTCTTCCTCTTCCCCCCAAAACCCAAGGACACCCTCATGATC
TCCCGGACCCCTGAGGTCACATGCGTGGTGGTGAGCGTGAGCCAC
GAAGACCCTGAGGTCAAGTTCAACTGGTACGTGGACGGCGTGGAG
GTGCATAATGCCAAGACAAAGCCGCGGGAGGAGCAGTACAACAGC
ACGTACCGTGTGGTCAGCGTCCTCACCGTCCTGCACCAGGACTGG
CTGAATGGCAAGGAGTACAAGTGCAAGGTGTCGAACAAAGCCCTC
CCAGCCCCCATCGAGAAAACCATCTCCAAAGCCAAAGGGCAGCCC
CGAGAACCACAGGTGTACACCCTGCCCCCATCCCGGGAGGAGATG
ACCAAGAACCAGGTCAGCCTGTGGTGCCTGGTCAAAGGCTTCTAT
CCCAGCGACATCGCCGTGGAGTGGGAGAGCAATGGGCAGCCGGAG
AACAACTACAAGACCACGCCTCCCGTGCTGGACTCCGACGGCTCC
TTCTTCCTCTACAGCAAGCTCACCGTGGACAAGAGCAGATGGCAG
CAGGGGAACGTCTTCTCATGCTCCGTGATGCATGAGGCTCTGCAC
AACCACTACACGCAGAAGTCTCTCTCCCTGTCTCCGGGAAAA
trispecific/bispecific Ab CD79b arm HC
                                       SEQ ID NO: 191
QVQLQESGPGLVKPSQTLSLTCTVSGVSISNYYWSWIRQPPGKGL
EWIGRISPSGRTNYNPSLKSRVTMSLDASKNQFSLKLSSVTAADT
AVYYCARGEYSGTYSYSFDIWGQGTMVTVSSASTKGPSVFPLAPS
SKSTSGGTAALGCLVKDYFPEPVTVSWNSGALTSGVHTFPAVLQS
SGLYSLSSVVTVPSSSLGTQTYICNVNHKPSNTKVDKKVEPKSCD
KTHTCPPCPAPEAAGGPSVFLFPPKPKDTLMISRTPEVTCVVVSV
SHEDPEVKFNWYVDGVEVHNAKTKPREEQYNSTYRVVSVLTVLHQ
DWLNGKEYKCKVSNKALPAPIEKTISKAKGQPREPQVYTLPPSRE
EMTKNQVSLWCLVKGFYPSDIAVEWESNGQPENNYKTTPPVLDSD
GSFFLYSKLTVDKSRWQQGNVFSCSVMHEALHNHYTQKSLSLSPG
K
trispecific/bispecific Ab CD79b arm HC
                                       SEQ ID NO: 192
CAGGTTCAGCTGCAAGAGTCTGGCCCTGGCCTGGTCAAGCCCTCT
CAGACCCTGTCTCTGACCTGTACCGTGTCCGGCGTGTCCATCTCC
AACTACTACTGGTCCTGGATCCGGCAGCCTCCTGGCAAGGACTG
GAATGGATCGGCCGCATCTCTCCTTCTGGTCGCACCAACTACAAC
CCCAGCCTGAAAAGCAGAGTGACCATGTCTCTGGACGCCTCCAAG
AACCAGTTCTCCCTGAAGCTGTCCTCCGTGACCGCTGCTGATACC
GCCGTGTACTACTGTGCCAGAGGCGAGTACTCCGGCACCTACTCC
TACAGCTTCGACATCTGGGGCCAGGGCACCATGGTCACAGTCTCT
TCTGCCTCCACCAAGGGCCCATCGGTCTTCCCCCTGGCACCCTCC
TCCAAGAGCACCTCTGGGGGCACAGCGGCCCTGGGCTGCCTGGTC
AAGGACTACTTCCCCGAACCGGTGACGGTGTCGTGGAACTCAGGC
GCCCTGACCAGCGGCGTGCACACCTTCCCGGCTGTCCTACAGTCC
```

```
TCAGGACTCTACTCCCTCAGCAGCGTGGTGACCGTGCCCTCCAGC
AGCTTGGGCACCCAGACCTACATCTGCAACGTGAATCACAAGCCC
AGCAACACCAAGGTGGACAAGAAAGTTGAGCCCAAATCTTGTGAC
AAAACTCACACATGCCCACCGTGCCCAGCACCTGAAGCCGCCGGG
GGACCGTCAGTCTTCCTCTTCCCCCCAAAACCCAAGGACACCCTC
ATGATCTCCCGGACCCCTGAGGTCACATGCGTGGTGGTGAGCGTG
AGCCACGAAGACCCTGAGGTCAAGTTCAACTGGTACGTGGACGGC
GTGGAGGTGCATAATGCCAAGACAAAGCCGCGGGAGGAGCAGTAC
AACAGCACGTACCGTGTGGTCAGCGTCCTCACCGTCCTGCACCAG
GACTGGCTGAATGGCAAGGAGTACAAGTGCAAGGTGTCGAACAAA
GCCCTCCCAGCCCCCATCGAGAAAACCATCTCCAAAGCCAAAGGG
CAGCCCCGAGAACCACAGGTGTACACCCTGCCCCCATCCCGGGAG
GAGATGACCAAGAACCAGGTCAGCCTGTGGTGCCTGGTCAAAGGC
TTCTATCCCAGCGACATCGCCGTGGAGTGGGAGAGCAATGGGCAG
CCGGAGAACAACTACAAGACCACGCCTCCCGTGCTGGACTCCGAC
GGCTCCTTCTTCCTCTACAGCAAGCTCACCGTGGACAAGAGCAGA
TGGCAGCAGGGGAACGTCTTCTCATGCTCCGTGATGCATGAGGCT
CTGCACAACCACTACACGCAGAAGTCTCTCTCCCTGTCTCCGGGA
AAA
```

CD3 arm VH-CDR 1
SEQ ID NO: 193
GDSVFNNNAAWS

CD3 arm VH-CDR 2
SEQ ID NO: 194
RTYYRSKWLYD

CD3 arm VH-CDR 3
SEQ ID NO: 195
GYSSSFDY

CD3 arm VH
SEQ ID NO: 196
QVQLQQSGPRLVRPSQTLSLTCAISGDSVFNNNAAWSWIRQSPSR
GLEWLGRTYYRSKWLYDYAVSVKSRITVNPDTSRNQFTLQLNSVT
PEDTALYYCARGYSSSFDYWGQGTLVTVSS CD3 arm Heavy chain
SEQ ID NO: 197
QVQLQQSGPRLVRPSQTLSLTCAISGDSVFNNNAAWSWIRQSPSR
GLEWLGRTYYRSKWLYDYAVSVKSRITVNPDTSRNQFTLQLNSVT
PEDTALYYCARGYSSSFDYWGQGTLVTVSSASTKGPSVFPLAPSS
KSTSGGTAALGCLVKDYFPEPVTVSWNSGALTSGVHTFPAVLQSS
GLYSLSSVVTVPSSSLGTQTYICNVNHKPSNTKVDKKVEPKSCDK
THTCPPCPAPEAAGGPSVFLFPPKPKDTLMISRTPEVTCVVVSVS
HEDPEVKFNWYVDGVEVHNAKTKPREEQYNSTYRVVSVLTVLHQD
WLNGKEYKCKVSNKALPAPIEKTISKAKGQPREPQVYTLPPSREE
MTKNQVSLSCAVKGFYPSDIAVEWESNGQPENNYKTTPPVLDSDG
SFFLVSKLTVDKSRWQQGNVFSCSVMHEALHNRFTQKSLSLSPGK CD3 arm VL-CDR 1
SEQ ID NO: 198
TGTSSNIGTYKFVS CD3 arm VL-CDR 2
SEQ ID NO: 199
EVSKRPS CD3 arm VL-CDR 3
SEQ ID NO: 200
VSYAGSGTLL CD3 arm VL
SEQ ID NO: 201
QSALTQPASVSGSPGQSITISCTGTSSNIGTYKFVSWYQQHPDKA
PKVLLYEVSKRPSGVSSRFSGSKSGNTASLTISGLQAEDQADYHC
VSYAGSGTLLFGGGTKLTVL CD3 arm Light chain
SEQ ID NO: 202
QSALTQPASVSGSPGQSITISCTGTSSNIGTYKFVSWYQQHPDKA
PKVLLYEVSKRPSGVSSRFSGSKSGNTASLTISGLQAEDQADYHC
VSYAGSGTLLFGGGTKLTVLGQPKAAPSVTLFPPSSEELQANKAT
LVCLISDFYPGAVTVAWKADSSPVKAGVETTTPSKQSNNKYAASS
YLSLTPEQWKSHRSYSCQVTHEGSTVEKTVAPTECS CD3 arm VH-CDR 1
SEQ ID NO: 203
TYAMN CD3 arm VH-CDR 2
SEQ ID NO: 204
MRSKYNNYATYYAASVKG CD3 arm VH-CDR 3
SEQ ID NO: 205
HGNFGNSYVSWFAY CD3 arm VH
SEQ ID NO: 206
EVQLVESGGGLVQPGGSLRLSCAASGFTFNTYAMNWVRQAPGKGL
EWVARIRSKYNNYATYYAASVKGRFTISRDDSKNSLYLQMNSLKT
EDTAVYYCARHGNFGNSYVSWFAYWGQGTLVTVSS CD3 arm Heavy chain
SEQ ID NO: 207
EVQLVESGGGLVQPGGSLRLSCAASGFTFNTYAMNWVRQAPGKGL
EWVARIRSKYNNYATYYAASVKGRFTISRDDSKNSLYLQMNSLKT
EDTAVYYCARHGNFGNSYVSWFAYWGQGTLVTVSSASTKGPSVFP
LAPCSRSTSESTAALGCLVKDYFPEPVTVSWNSGALTSGVHTFPA
VLQSSGLYSLSSVVTVPSSSLGTKTYTCNVDHKPSNTKVDKRVES
KYGPPCPPCPAPEAAGGPSVFLFPPKPKDTLMISRTPEVTCVVVD
VSQEDPEVQFNWYVDGVEVHNAKTKPREEQFNSTYRVVSVLTVLH
QDWLNGKEYKCKVSNKGLPSSIEKTISKAKGQPREPQVYTLPPSQ
EEMTKNQVSLTCLVKGFYPSDIAVEWESNGQPENNYKTTPPVLDS
DGSFFLYSKLTVDKSRWQEGNVFSCSVMHEALHNHYTQKSLSLSL
GK CD3 arm VL-CDR 1
SEQ ID NO: 208
RSSTGAVTTSNYAN CD3 arm VL-CDR 2

-continued

GTNKRAP

CD3 arm VL-CDR 3

SEQ ID NO: 210
ALWYSNLWV

CD3 arm VL

SEQ ID NO: 211
QTVVTQEPSLTVSPGGTVTLTCRSSTGAVTTSNYANWVQQKPGQA

PRGLIGGTNKRAPGTPARFSGSLLGGKAALTLSGVQPEDEAEYYC

ALWYSNLWVFGGGTKLTVL

CD3 arm Light chain

SEQ ID NO: 212
QTVVTQEPSLTVSPGGTVTLTCRSSTGAVTTSNYANWVQQKPGQA

PRGLIGGTNKRAPGTPARFSGSLLGGKAALTLSGVQPEDEAEYYC

ALWYSNLWVFGGGTKLTVLGQPKAAPSVTLFPPSSEELQANKATL

VCLISDFYPGAVTVAWKADSSPVKAGVETTTPSKQSNNKYAASSY

LSLTPEQWKSHRSYSCQVTHEGSTVEKTVAPTECS

CD79b Ab VL DNA

SEQ ID NO: 213
GATATTGTGATGACTCAGTCTCCACTCTCCCTGTCCGTCACCCCT

GGAGAGCCGGCCTCCATCTCCTGCAGGTCTAGTGAGAGCCTCTTG

GATAGTGAAGATGGAAACACCTATTTGGACTGGTTCCTGCAGAAG

CCAGGGCAGTCTCCTCAGCTCCTGATCTATACGCTTTCCTATCGG

GCCTCTGGAGTCCCAGACAGGTTCAGTGGCAGTGGGTCGGACACT

GATTTCACACTGCACATCAGCAGTCTGGAGGCTGAGGATGTTGGA

CTTTATTACTGCATGCAACGTATGGAGTTTCCGCTCACTTTCGGC

CAAGGGACCAAGGTGGAAATCAAA

CD79b Ab VL DNA

SEQ ID NO: 214
GACATCCAGATGACCCAGAGCCCTAGCAGCCTGAGCGCCAGCGTG

GGCGACAGAGTGACCATTACCTGCAGAAGCAGCCAGAGCCTGTTC

GACAGCGACGACGGCAATACCTACCTGGACTGGTTCCAGCAGAAG

CCTGGCCAGAGCCCTAAGCTGCTGATCCAGACCCTGAGCTACAGA

GCCAGCGGCGTGCCTAGCAGATTCTCCGGCAGCGGCTCCGGCACC

GACTTCACCCTGACCATCAGCAGCCTGCAGCCTGAGGACTTCGCC

ACCTACTACTGCATGCAGAGAATGGAGTTCCCTCTGACCTTCGGC

GGCGGCACCAAGGTGGAGATCAAG

Linker 1

SEQ ID NO: 215
GGSEGKS S GS GSESKSTGGS

Linker 2

SEQ ID NO: 216
GGGSGGGS

Linker 3

SEQ ID NO: 217
GGGSGGGSGGGS

Linker 4

SEQ ID NO: 218
GGGSGGGSGGGSGGGS

Linker 5

SEQ ID NO: 219
GGGSGGGSGGGSGGGSGGGS

Linker 6

SEQ ID NO: 220
GGGGSGGGGSGGGGS

Linker 7

SEQ ID NO: 221
GGGGSGGGGSGGGGSGGGGS

Linker 8

SEQ ID NO: 222
GGGGSGGGGSGGGGSGGGGSGGGGS

Linker 9

SEQ ID NO: 223
GSTS GS GKPGS GEGSTKG

Linker 10

SEQ ID NO: 224
IRPRAIGGSKPRVA

Linker 11

SEQ ID NO: 225
GKGGSGKGGSGKGGS

Linker 12

SEQ ID NO: 226
GGKGSGGKGSGGKGS

Linker 13

SEQ ID NO: 227
GGGKSGGGKSGGGKS

Linker 14

SEQ ID NO: 228
GKGKSGKGKSGKGKS

Linker 15

SEQ ID NO: 229
GGGKSGGKGSGKGGS

Linker 16

SEQ ID NO: 230
GKPGSGKPGSGKPGS

Linker 17

SEQ ID NO: 231
GKPGSGKPGSGKPGSGKPGS

Linker 18

SEQ ID NO: 232
GKGKSGKGKSGKGKSGKGKS

Linker 19

SEQ ID NO: 233
STAGDTHLGGEDFD

Linker 20

SEQ ID NO: 234
GEGGSGEGGSGEGGS

Linker 21

SEQ ID NO: 235
GGEGSGGEGSGGEGS

Linker 22

SEQ ID NO: 236
GEGESGEGESGEGES

Linker 23

SEQ ID NO: 237
GGGESGGEGSGEGGS

-continued

```
Linker 24
                                    SEQ ID NO: 238
GEGESGEGESGEGESGEGES Linker 25
                                    SEQ ID NO: 239
GSTS GS GKPGS GEGSTKG Linker 26
                                    SEQ ID NO: 240
PRGASKSGSASQTGSAPGS Linker 27
                                    SEQ ID NO: 241
GTAAAGAGAAGGAAAGAAG Linker 28
                                    SEQ ID NO: 242
GTSGSSGSGSGGSGSGGGG Linker 29
                                    SEQ ID NO: 243
GKPGSGKPGSGKPGSGKPGS Linker 30
                                    SEQ ID NO: 244
GSGS Linker 31
                                    SEQ ID NO: 245
APAPAPAPAP Linker 32
                                    SEQ ID NO: 246
APAPAPAPAPAPAPAPAPAP Linker 33
                                    SEQ ID NO: 247
AEAAAKEAAAKEAAAAKEAAAAKEAAAAKAAA Linker 34
                                    SEQ ID NO: 248
GGGGSGGGGS IgG-1
                                    SEQ ID NO: 249
ASTKGPSVFPLAPSSKSTSGGTAALGCLVKDYFPEPVTVSWNSGA

LTSGVHTFPAVLQSSGLYSLSSVVTVPSSSLGTQTYICNVNHKPS

NTKVDKKVEPKSCDKTHTCPPCPAPELLGGPSVFLFPPKPKDTLM

ISRTPEVTCVVVDVSHEDPEVKFNWYVDGVEVHNAKTKPREEQYN

STYRVVSVLTVLHQDWLNGKEYKCKVSNKALPAPIEKTISKAKGQ

PREPQVYTLPPSREEMTKNQVSLTCLVKGFYPSDIAVEWESNGQP

ENNYKTTPPVLDSDGSFFLYSKLTVDKSRWQQGNVFSCSVMHEAL

HNHYTQKSLSLSPGK

IgG-1
                                    SEQ ID NO: 250
ASTKGPSVFPLAPSSKSTSGGTAALGCLVKDYFPEPVTVSWNSGA

LTSGVHTFPAVLQSSGLYSLSSVVTVPSSSLGTQTYICNVNHKPS

NTKVDKKVEPKSCDKTHTCPPCPAPEAAGGPSVFLFPPKPKDTLM

ISRTPEVTCVVVDVSHEDPEVKFNWYVDGVEVHNAKTKPREEQYN

STYRVVSVLTVLHQDWLNGKEYKCKVSNKALPAPIEKTISKAKGQ

PREPQVYTLPPSREEMTKNQVSLTCLVKGFYPSDIAVEWESNGQP

ENNYKTTPPVLDSDGSFFLYSKLTVDKSRWQQGNVFSCSVMHEAL

HNHYTQKSLSLSPGK

IgG4
                                    SEQ ID NO: 251
ASTKGPSVFPLAPCSRSTSESTAALGCLVKDYFPEPVTVSWNSGA

LTSGVHTFPAVLQSSGLYSLSSVVTVPSSSLGTKTYTCNVDHKPS

NTKVDKRVESKYGPPCPPCPAPEAAGGPSVFLFPPKPKDTLMISR

TPEVTCVVVDVSQEDPEVQFNWYVDGVEVHNAKTKPREEQFNSTY

RVVSVLTVLHQDWLNGKEYKCKVSNKGLPSSIEKTISKAKGQPRE

PQVYTLPPSQEEMTKNQVSLTCLVKGFYPSDIAVEWESNGQPENN

YKTTPPVLDSDGSFFLYSRLTVDKSRWQEGNVFSCSVMHEALHNH

YTQKSLSLSLGK

CD79b
                                    SEQ ID NO: 252
MARLALSPVPSHWMVALLLLLSAEPVPAARSEDRYRNPKGSACSR

IWQSPRFIARKRGFTVKMHCYMNSASGNVSWLWKQEMDENPQQLK

LEKGRMEESQNESLATLTIQGIRFEDNGIYFCQQKCNNTSEVYQG

CGTELRVMGFSTLAQLKQRNTLKDGIIMIQTLLIILFIIVPIFLL

LDKDDSKAGMEEDHTYEGLDIDQTATYEDIVTLRTGEVKWSVGEH

PGQE

CD79b epitope
                                    SEQ ID NO: 253
SEDRYRNPKGS AC

CD79b epitope
                                    SEQ ID NO: 254
EMENP

CD79b epitope
                                    SEQ ID NO: 255
GFSTL

CD3 epitope
                                    SEQ ID NO: 256
QDGNEEMGGITQTP

CD3 E epitope
                                    SEQ ID NO: 257
GSEIL

CD3 E epitope
                                    SEQ ID NO: 258
PRGSKP

C923B169
                                    SEQ ID NO: 259
EIVLTQSPATLSASPGERVTLSCSASSSVSYMNWYQQKPGQAPRRW

IYDSSKLASGVPARFSGSGSGRDYTLTISSLEPEDFAVYYCQQWS

RNPPTFGGGTKVEIKGGSEGKSSGSGSESKSTGGSQVQLVQSGAE

VKKPGSSVKVSCKASGYTFTRSTMHWVKQAPGQGLEWIGYINPSS

AYTNYNQKFQGRVTLTADKSTSTAYMELSSLRSEDTAVYYCASPQ

VHYDYAGFPYWGQGTLVTVSSEPKSSDKTHTCPPCPAPEAAGGPS

VFLFPPKPKDTLMISRTPEVTCVVVSVSHEDPEVKFNWYVDGVEV

HNAKTKPREEQYNSTYRVVSVLTVLHQDWLNGKEYKCKVSNKALP

APIEKTISKAKGQPREPQVYTLPPSREEMTKNQVSLWCLVKGFYP

SDIAVEWESNGQPENNYKTTPPVLDSDGSFFLYSKLTVDKSRWQQ

GNVFSCSVMHEALHNHYTQKSLSLSPGKGGGGSGGGGSGGGGSGG

GGSEIVLTQSPATLSLSPGERATLSCRASLSVSVSMHWYQQKPGQ
```

APRLLIYATSNLASGIPARFSGSGSGTDFTLTIS
SLEPEDFAVYYCQQWIFNPPTFGGGTKVEIKGGSEGKSSGSGSES
KSTGGSQVQLVQSGAEVKKPGSSVKVSCKASGYTFSSYNMHWVRQ
APGQGLEWMGAIYPGAGDTSYAQKFQGRVTITADESTSTAYMELS
SLRSEDTAVYYCARSNYYGSSGWYFDVVVGKGTTVTVSSQVQLQE
SGPGLVKPSETLSLTCSVSGASISSFYWSWIRQPADEGLEWIGRI
SPSGKTNYEPSLKSRIIMSLDASKNQFSLRLNSVTAADTAMYYCA
RGEYSGTYSYSFDVWGQGTMVTVSSASTKGPSVFPLAPSSKSTSG
GTAALGCLVKDYFPEPVTVSWNSGALTSGVHTFPAVLQSSGLYSL
SSVVTVPSSSLGTQTYTCNVNHKPSNTKVDKKVEPKSCDKTHTCP
PCPAPEAAGGPSVFLFPPKPKDTLMISRTPEVTCVVVSVSHEDPE
VKFNWYVDGVEVHNAKTKPREEQYNSTYRVVSVLTVLHQDWLNGK
EYKCKVSNKALPAPIEKTISICAKGQPREPQVYTLPPSREEMTKN
QVSLSCAVKGFYPSDIAVEWESNGQPENNYKTTPPVLDSDGSFFL
VSKLTVDKSRWQQGNVFSCSVMMEALHNRFTQKSLSLSPGKDIVM
TQSPLSLSVTPGEPASISCRSSESLLDSEDGNTYLDWFLQKPGQS
PQLLIYTLSYRASGVPDRFSGSGSDTDFTLHISSLEAEDVGLYYC
MQRMEFPLTFGQGTKVEIKRTVAAPSVFIFPPSDEQLKSGTASVV
CLLNNFYPREAKVQWKVDNALQSGNSQESVTEQDSKDSTYSLSST
LTLSKADYEKHKVYACEVTHQGLSSPVTKSFNRGEC

C923B224 HC1
SEQ ID NO: 260
EIVLTQSPAT LSASPGERVT LSCSASSSVS
YMNWYQQKPG QAPRRWIYDS SKLASGVPAR
FSGSGSGRDY TLTISSLEPE DFAVYYCQQW
SRNPPTFGGG TKVEIKGGSE GKSSGSGSES
KSTGGSQVQL VQSGAEVKKP GSSVKVSCKA
SGYTFTRSTM HWVKQAPGQG LEWIGYINPS
SAYTNYNQKF QGRVTLTADK STSTAYMELS
SLRSEDTAVY YCASPQVHYD YAGFPYWGQG
TLVTVSSEPK SSDKTHTCPP CPAPEAAGGP
SVFLFPPKPK DTLMISRTPE VTCVVVSVSH
EDPEVKFNWY VDGVEVHNAK TKPREEQYNS
TYRVVSVLTV LHQDWLNGKE YKCKVSNKAL
PAPIEKTISK AKGQPREPQV YTLPPSREEM
TKNQVSLWCL VKGFYPSDIA VEWESNGQPE
NNYKTTPPVL DSDGSFFLYS KLTVDKSRWQ
QGNVFSCSVM HEALHNHYTQ KSLSLSPGKG
GGGSGGGGSG GGGSGGGGSE IYLTQSPATL
SLSPGERATL SCRASLSVSS MHWYQQKPGQ
APRLLIYATS NLASGIPARF SGSGSGTDFT

LTISSLEPED FAVYYCQ QW1FNPPTFGGGT
KVEIKGGSEG KSSGSGSESK STGGSQVQLV
QSGAEVKKPG SSVKVSCKAS GYTFSSYNMH
WVRQAPGQGL EWMGAIYPGA GDTSYAQKFQ
GRVTITADES TSTAYMELSS LRSEDTAVYY
CARSNYYGSS GWYFDVWGKG TTVTVSSH

C923B224 HC2
SEQ ID NO: 261
QVQLQESGPGLVKPSETLSLTCSVSGASISSFYWSWIRQPADEGL
EWIGRISPSGKTNYIPSLKSRIIMSLDASKNQFSLRLNSVTAADT
AMYYCARGEYSGTYSYSFDVWGQGIMVTVSSASTKGPSVFPLAPS
SKSTSGGTAALGCLVKDYFPEPVTV
SWNSGALTSGVIITFPAVLQSSGLYSLSSVVTVPSSSLGTQTYIC
NVNHKPSNTKVDKKVEPKSCDKTHTCPPCPAPEAAGGPSVFLFPP
KPKDTLMISRTPEVTCVVVSVSHEDPEVKFNWYVDGVEVHNAKTK
PREEQYNSTYRVVSVLTVLHQDWLNGKEYKCKVSNKALPAPIEKT
ISKAKGQPREPQVYTLPPSREEMTKNQVSLSCAVKGFYPSDIAVE
WESNGQPENNYKTTPPVLDSDGSFFLVSKLTVDKSRWQQGNVFSC
SVMHEALHNRFTQKSLSLSPGK

C923B224 LC
SEQ ID NO: 262
DIVMTQSPLSLSVTPGEPASISCRSSESLLDSEDGNTYLDWFLQK
PGQSPQLLIYTLSYRASGVPDRFSGSGSDTDFTLHISSLEAEDVG
LYYCMQRMEFPLTFGQGTKVEIKRTVAAPSVFIEPPSDEQLKSGT
ASVVCLLNNFYPREAKVQWKVDNALQSGNSQESVTEQDSKDSTYS
LSSTLTLSKADYEKHKVYACEWHQGLSSPVTKSFNRGEC

C923B224
SEQ ID NO: 263
EIVLTQSPATLSASPGERVTLSCSASSSVSYMNWYQQKPGQAPRR
WIYDSSKLASGVPARFSGSGSGRDYTLTISSLEPEDFAVYYCQQW
SRNPPTFGGGTKVEIKGGSEGKSSGSGSESKSTGGSQVQLVQSGA
EVKKPGSSVKVSCKASGYTFTRSTMHWVKQAPGQGLEWIGYINPS
SAYTNYNQKFQGRVTLTADKSTSTAYMELSSLRSEDTAVYYCASP
QVHYDYAGFPYWGQGTLVTVSSEPK SSDKTHTCPPCPAPEAAGGP
SVFLFPPKPKDTLMISRTPEVTCVVVSVSHEDPEVKFNVVYVDGV
EVHNAKTKPREEQYNSTYRVVSVLTVLHQDWLNGKEYKCKVSNKK
ALPAPIEKTISKAKGQPREPQVYTLPPSREEMTKNQVSLWCLVKG
FYPSDIAVEWESNGQPENNYKTTPPVLDSDGSFFLYSKLTVDKSR
WQQGNVFSCSVMHEALHNHYTQKSLSLSPGKGGGGSGGGGSGGGG
SGGGGSEIVLTQSPATLSLSPGERATLSCRASLVSSMHWYQQKPG
QAPRLLIYATSNLASGIPARFSGSGSGTDFTLTISSLEPEDFAVY
YCQQWI FNPPTFGGGT KVEIKGGSEG KSSGSGSESKSTGGSQ
VQLVQSGAEVKKPGSSVKVSCKASGYTFSSYNMHWVRQAPGQGLE
WMGAIYPGAGDTSYAQKFQGRVTITADESTSTAYMELSSLRSEDTA

-continued

VYYCARSNYYGSSGWYFDVWGKGTTVTVSSHQVQLQESGPGLVKPS

ETLSLTCSVSGASISSFYWSWIRQPADEGLEWIGRISPSGKTNYIP

SLKSRIIMSLDASKNQFSLRLNSVTAADTAMYYCARGEYSGTYSY

SFDVWGQGTMVTVSSASTKGPSVFPLAPSSKSTSGGTAALGCLVK

DYFPEPVTVSWNSGALTSGVHTFPAVLQSSGLYSLSSVVTVPSSS

LGTQTYICNVNHKPSNTKVDKKVEPKSCDKTHTCPPCPAPEAAGG

PSVFLFPPKPKDTLMISRTPEVTCVVVSVSHEDPEVKFNWYVDGV

EVHNAKTKPREEQYNSTYRVVSVLTVLHQDWLNGKEYKCKVSNKA

LPAPIEKTISKAKGQPREPQVYTLPPSREEMTKNQVSLSCAVKGF

YPSDIAVEWESNGQPENNYKTTPPVLDSDGSFFLVSKLTVDKSRW

QQGNVFSCSVMHEALHNRFTQKSLSLSPGKDIVMTQSPLSLSVTP

-continued

GEPASISCRSSESLLDSEDGNTYLDWFLQKPGQSPQLLIYTLSYR

ASGVPDRFSGS GSDTDFTLHI SSLEAEDVGLYYCMQRMEFPLTF

GQGTKVEIKRTVAAPSVFIFPPSDEQLKSGTASVVCLLNNFYPREA

KVQWKVDNALQSGNSQESVTEQDSKDSTYSLSSTLTLSKADYEKH

KVYAGEVTHQGLSSPVTKSFNRGEC

SEQ ID NO: 264

IPAGIYAPI

SEQ ID NO: 265

His Phe Leu Lys Met Glu Ser Leu Asn Phe Ile

Arg Ala His Thr Pro Tyr Ile Asn Ile Tyr Asn

Cys Glu Pro Ala Asn Pro Ser Glu Lys Asn Ser

Pro Ser Thr Gln Tyr Cys Tyr Ser Ile Gln Ser

---

We claim:

1. A trispecific antibody, or a trispecific binding fragment thereof, comprising:
    (a) a first antigen-binding arm comprising a first heavy chain variable domain (VH1) and a first light chain variable domain (VL1),
    wherein the VH1 and VL1 comprise the HCDR1, the HCDR2, the HCDR3, the LCDR1, the LCDR2, and the LCDR3 of:
      a) SEQ ID NOs: 1, 2, 3, 4, 5 and 6, respectively;
      b) SEQ ID NOs: 13, 8, 9, 10, 11 and 12, respectively;
      c) SEQ ID NOs: 7, 8, 9, 10, 11 and 12, respectively;
      d) SEQ ID NOs: 14, 15, 16, 17, 5 and 6, respectively;
      e) SEQ ID NOs: 18, 8, 19, 20, 21 and 12, respectively;
      f) SEQ ID NOs: 22, 23, 24, 25, 5 and 6, respectively;
      g) SEQ ID NOs: 22, 26, 27, 28, 5 and 29, respectively; or
      h) SEQ ID NOs: 30, 31, 32, 33, 5 and 6, respectively;
    (b) a second antigen-binding arm comprising a second heavy chain variable domain (VH2) and a second light chain variable domain (VL2),
    wherein the VH2 and VL2 comprise the HCDR1, the HCDR2, the HCDR3, the LCDR1, the LCDR2, and the LCDR3 of:
      a) SEQ ID NOs: 76, 77, 78, 79, 80 and 81, respectively;
      b) SEQ ID NOs: 76, 77, 75, 79, 80 and 81, respectively;
      c) SEQ ID NOs: 76, 77, 82, 79, 80 and 81, respectively; or
      d) SEQ ID NOs: 83, 84, 85, 86, 87 and 88, respectively;
    (c) a third antigen-binding arm comprising a third heavy chain variable domain (VH3) and a third light chain variable domain (VL3),
    wherein the VH3 and VL3 comprise the HCDR1, the HCDR2, the HCDR3, the LCDR1, the LCDR2, and the LCDR3 of:
      a) SEQ ID NOs: 115, 116, 117, 118, 119 and 120, respectively;
      b) SEQ ID NOs: 121, 122, 123, 124, 119 and 125, respectively;
      c) SEQ ID NOs: 115, 116, 95, 96, 119 and 125, respectively; or
      d) SEQ ID NOs: 121, 116, 123, 124, 119 and 125, respectively,
    wherein the first antigen-binding arm binds to an epitope on cluster of differentiation 79B protein (CD79b), the second antigen-binding arm binds to an epitope on cluster of differentiation 3 (CD3), and the third antigen-binding arm binds to an epitope on cluster of differentiation 20 (CD20).

2. The trispecific antibody or trispecific binding fragment of claim 1, wherein the first antigen-binding arm that binds CD79b comprises:
    a) the VH1 of SEQ ID NO: 35 and the VL1 of SEQ ID NO: 37;
    b) the VH1 of SEQ ID NO: 39 and the VL1 of SEQ ID NO: 41;
    c) the VH1 of SEQ ID NO: 43 and the VL1 of SEQ ID NO: 41;
    d) the VH1 of SEQ ID NO: 45 and the VL1 of SEQ ID NO: 47;
    e) the VH1 of SEQ ID NO: 49 and the VL1 of SEQ ID NO: 51;
    f) the VH1 of SEQ ID NO: 39 and the VL1 of SEQ ID NO: 53;
    g) the VH1 of SEQ ID NO: 55 and the VL1 of SEQ ID NO: 57;
    h) the VH1 of SEQ ID NO: 59 and the VL1 of SEQ ID NO: 61;
    i) the VH1 of SEQ ID NO: 63 and the VL1 of SEQ ID NO: 65;
    j) the VH1 of SEQ ID NO: 67 and the VL1 of SEQ ID NO: 69; or a) the VH1 of SEQ ID NO: 71 and the VL1 of SEQ ID NO: 73.

3. The trispecific antibody or trispecific binding fragment of claim 1, wherein the second antigen-binding arm that binds CD3 comprises:
   a) the VH2 of SEQ ID NO: 97 and the VL2 of SEQ ID NO: 99;
   b) the VH2 of SEQ ID NO: 101 and the VL2 of SEQ ID NO: 99;
   c) the VH2 of SEQ ID NO: 103 and the VL2 of SEQ ID NO: 99;
   d) the VH2 of SEQ ID NO: 105 and the VL2 of SEQ ID NO: 99; or
   e) the VH2 of SEQ ID NO: 107 and the VL2 of SEQ ID NO: 109.

4. The trispecific antibody or trispecific binding fragment of claim 1, wherein the third antigen-binding arm that binds CD20 comprises:
   a) the VH3 of SEQ ID NO: 126 and the VL3 of SEQ ID NO: 128;
   b) the VH3 of SEQ ID NO: 130 and the VL3 of SEQ ID NO: 132;
   c) the VH3 of SEQ ID NO: 134 and the VL3 of SEQ ID NO: 136; or
   d) the VH3 of SEQ ID NO: 138 and the VL3 of SEQ ID NO: 140.

5. The trispecific antibody or trispecific binding fragment of claim 1, wherein the first antigen-binding arm that binds CD79b comprises the HCDR1, the HCDR2 and the HCDR3 of the VH1 of SEQ ID NO: 35 and the LCDR1, the LCDR2 and the LCDR3 of the VL1 of SEQ ID NO: 37;
   the second antigen-binding arm that binds CD3 comprises the HCDR1, the HCDR2 and the HCDR3 of the VH2 of SEQ ID NO: 107 and the LCDR1, the LCDR2 and the LCDR3 of the VL2 of SEQ ID NO: 109; and
   the third antigen-binding arm that binds CD20 comprises the HCDR1, the HCDR2 and the HCDR3 of the VH3 of SEQ ID NO: 130 and the LCDR1, the LCDR2 and the LCDR3 of the VL3 of SEQ ID NO: 132.

6. The trispecific antibody or trispecific binding fragment of claim 1, wherein the first antigen-binding arm that binds CD79b comprises the HCDR1, the HCDR2, the HCDR3, the LCDR1, the LCDR2 and the LCDR3 of SEQ ID NOs: 1, 2, 3, 4, 5 and 6, respectively;
   the second antigen-binding arm that binds CD3 comprises the HCDR1, the HCDR2, the HCDR3, the LCDR1, the LCDR2 and the LCDR3 of SEQ ID NOs: 83, 84, 85, 86, 87 and 88, respectively; and
   the third antigen-binding arm that binds CD20 comprises the HCDR1, the HCDR2, the HCDR3, the LCDR1, the LCDR2 and the LCDR3 of SEQ ID NOs: 121, 122, 123, 124, 119 and 125, respectively.

7. The trispecific antibody or trispecific binding fragment of claim 1, wherein the first antigen-binding arm that binds CD79b comprises the VH1 of SEQ ID NO: 35 and the VL1 of SEQ ID NO: 37;
   the second antigen-binding arm that binds CD3 comprises the VH2 of SEQ ID NO: 107 and the VL2 of SEQ ID NO: 109; and
   the third antigen-binding arm that binds CD20 comprises the VH3 of SEQ ID NO: 130 and the VL3 of SEQ ID NO: 132.

8. The trispecific antibody or trispecific binding fragment of claim 1, wherein the first antigen-binding arm that binds CD79b comprises the HCDR1, the HCDR2 and the HCDR3 of the VH1 of SEQ ID NO: 35 and the LCDR1, the LCDR2 and the LCDR3 of the VL1 of SEQ ID NO: 37;
   the second antigen-binding arm that binds CD3 comprises the HCDR1, the HCDR2 and the HCDR3 of the VH2 of SEQ ID NO: 101 and the LCDR1, the LCDR2 and the LCDR3 of the VL2 of SEQ ID NO: 99; and
   the third antigen-binding arm that binds CD20 comprises the HCDR1, the HCDR2 and the HCDR3 of the VH3 of SEQ ID NO: 130 and the LCDR1, the LCDR2 and the LCDR3 of the VL3 of SEQ ID NO: 132.

9. The trispecific antibody or trispecific binding fragment of claim 1, wherein the first antigen-binding arm that binds CD79b comprises the HCDR1, the HCDR2, the HCDR3, the LCDR1, the LCDR2 and the LCDR3 of SEQ ID NOs: 1, 2, 3, 4, 5 and 6, respectively;
   the second antigen-binding arm that binds CD3 comprises the HCDR1, the HCDR2, the HCDR3, the LCDR1, the LCDR2 and the LCDR3 of SEQ ID NOs: 76, 77, 75, 79, 80 and 81, respectively; and
   the third antigen-binding arm that binds CD20 comprises the HCDR1, the HCDR2, the HCDR3, the LCDR1, the LCDR2 and the LCDR3 of SEQ ID NOs: 121, 122, 123, 124, 119 and 125, respectively.

10. The trispecific antibody or trispecific binding fragment of claim 1, wherein the first antigen-binding arm that binds CD79b comprises the VH1 of SEQ ID NO: 35 and the VL1 of SEQ ID NO: 37;
    the second antigen-binding arm that binds CD3 comprises the VH2 of SEQ ID NO: 101 and the VL2 of SEQ ID NO: 99; and
    the third antigen-binding arm that binds CD20 comprises the VH3 of SEQ ID NO: 130 and the VL3 of SEQ ID NO: 132.

11. The trispecific antibody or trispecific binding fragment of claim 1, wherein the first antigen-binding arm and second antigen-binding arm comprise a Fragment crystallizable (Fc) domain, and where in the Fc domain comprises one or more mutations selected from T366S, L368A, T366W and Y407V according to EU numbering.

12. The trispecific antibody or trispecific binding fragment of claim 11, wherein the Fc domains further comprise one or more mutations which reduce Fc binding to a Fcγ receptor, and wherein the one or more mutations are selected from L234A, L235A, and D265S according to EU numbering.

13. The trispecific antibody or trispecific binding fragment of claim 11, wherein the Fc domain further comprises mutations H435R and/or Y436F according to EU numbering.

14. The trispecific antibody or trispecific binding fragment of claim 1, wherein the first antigen-binding arm comprises a heavy chain (HC1) polypeptide and a light chain (LC) polypeptide; and wherein the trispecific antibody, or a trispecific binding fragment thereof, comprises a single polypeptide comprising the second antigen-binding arm and the third antigen-binding arm wherein,
    a) the first antigen-binding arm comprises an HC1 comprising the amino acid sequence of SEQ ID NO: 172, and LC comprising the amino acid sequence of SEQ ID NO: 174, and the polypeptide comprising the second antigen-binding arm and the third antigen-binding arm comprises the amino acid sequence of SEQ ID NO: 142;
    b) the first antigen-binding arm comprises an HC1 comprising the amino acid sequence of SEQ ID NO: 176, the LC comprising the amino acid sequence of SEQ ID NO: 178, and the polypeptide comprising the second antigen-binding arm and the third antigen-binding arm comprises the amino acid sequence of SEQ ID NO: 142;

c) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 142 d) the first antigen-binding arm comprises an HC1 comprising the amino acid sequence of SEQ ID NO: 172, the LC comprising the amino acid sequence of SEQ ID NO: 174, and the polypeptide comprising the second antigen-binding arm and the third antigen-binding arm comprises the amino acid sequence of SEQ ID NO: 144;

e) the first antigen-binding arm comprises an HC1 comprising the amino acid sequence of SEQ ID NO: 176, the LC comprising the amino acid sequence of SEQ ID NO: 178, and the polypeptide comprising the second antigen-binding arm and the third antigen-binding arm comprises the amino acid sequence of SEQ ID NO: 144;

f) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 144;

g) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 148;

h) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 150;

i) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 152;

j) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 154;

k) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 156;

l) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 158;

m) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 160;

n) the first antigen-binding arm comprises an HC1 comprising the amino acid sequence of SEQ ID NO: 180, the LC comprising the amino acid sequence of SEQ ID NO: 182, and the polypeptide comprising the second antigen-binding arm and the third antigen-binding arm comprises the amino acid sequence of SEQ ID NO: 162;

o) the first antigen-binding arm comprises an HC1 comprising the amino acid sequence of SEQ ID NO: 191, the LC comprising the amino acid sequence of SEQ ID NO: 182, and the polypeptide comprising the second antigen-binding arm and the third antigen-binding arm comprises the amino acid sequence of SEQ ID NO: 166;

p) the first antigen-binding arm comprises an HC1 comprising the amino acid sequence of SEQ ID NO: 172, the LC comprising the amino acid sequence of SEQ ID NO: 174, and the polypeptide comprising the second antigen-binding arm and the third antigen-binding arm comprises the amino acid sequence of SEQ ID NO: 168; or q) the first antigen-binding arm comprises an HC1 comprising the amino acid sequence of SEQ ID NO: 172, the LC comprising the amino acid sequence of SEQ ID NO: 174, and the polypeptide comprising the second antigen-binding arm and the third antigen-binding arm comprises the amino acid sequence of SEQ ID NO: 170.

15. A synthetic polynucleotide encoding a polypeptide comprising a trispecific antibody or a trispecific binding fragment thereof, wherein the trispecific antibody or the trispecific binding fragment thereof comprises a first antigen-binding arm comprising a heavy chain (HC1) polypeptide and a light chain (LC) polypeptide, and a single polypeptide comprising a second antigen-binding arm and a third antigen-binding arm, wherein the polynucleotide comprises:

a) an HC1-encoding sequence of SEQ ID NO: 173, a LC-encoding sequence of SEQ ID NO: 175, and a sequence of SEQ ID NO: 143 which encodes the single polypeptide comprising the second antigen-binding arm and the third antigen-binding arm;

b) an HC1-encoding sequence of SEQ ID NO: 177, a LC-encoding sequence of SEQ ID NO: 179, and a sequence of SEQ ID NO: 143 which encodes the single polypeptide comprising the second antigen-binding arm and the third antigen-binding arm;

c) an HC1-encoding sequence of SEQ ID NO: 181, a LC-encoding sequence of SEQ ID NO: 183, and a sequence of SEQ ID NO: 143 which encodes the single polypeptide comprising the second antigen-binding arm and the third antigen-binding arm;

d) an HC1-encoding sequence of SEQ ID NO: 173, a LC-encoding sequence of SEQ ID NO: 175, and a sequence of SEQ ID NO: 145 which encodes the single polypeptide comprising the second antigen-binding arm and the third antigen-binding arm;
e) an HC1-encoding sequence of SEQ ID NO: 177, a LC-encoding sequence of SEQ ID NO: 179, and a sequence of SEQ ID NO: 145 which encodes the single polypeptide comprising the second antigen-binding arm and the third antigen-binding arm;
f) an HC1-encoding sequence of SEQ ID NO: 181, a LC-encoding sequence of SEQ ID NO: 183, and a sequence of SEQ ID NO: 145 which encodes the single polypeptide comprising the second antigen-binding arm and the third antigen-binding arm;
g) an HC1-encoding sequence of SEQ ID NO: 181, a LC-encoding sequence of SEQ ID NO: 188, and a sequence of SEQ ID NO: 149 which encodes the single polypeptide comprising the second antigen-binding arm and the third antigen-binding arm;
h) an HC1-encoding sequence of SEQ ID NO: 181, a LC-encoding sequence of SEQ ID NO: 188, and a sequence of SEQ ID NO: 151 which encodes the single polypeptide comprising the second antigen-binding arm and the third antigen-binding arm;
i) an HC1-encoding sequence of SEQ ID NO: 181, a LC-encoding sequence of SEQ ID NO: 188, and a sequence of SEQ ID NO: 153 which encodes the single polypeptide comprising the second antigen-binding arm and the third antigen-binding arm;
j) an HC1-encoding sequence of SEQ ID NO: 181, a LC-encoding sequence of SEQ ID NO: 188, and a sequence of SEQ ID NO: 155 which encodes the single polypeptide comprising the second antigen-binding arm and the third antigen-binding arm;
k) an HC1-encoding sequence of SEQ ID NO: 181, a LC-encoding sequence of SEQ ID NO: 188, and a sequence of SEQ ID NO: 157 which encodes the single polypeptide comprising the second antigen-binding arm and the third antigen-binding arm;
l) an HC1-encoding sequence of SEQ ID NO: 181, a LC-encoding sequence of SEQ ID NO: 188, and a sequence of SEQ ID NO: 159 which encodes the single polypeptide comprising the second antigen-binding arm and the third antigen-binding arm;
m) an HC1-encoding sequence of SEQ ID NO: 181, a LC-encoding sequence of SEQ ID NO: 188, and a sequence of SEQ ID NO: 161 which encodes the single polypeptide comprising the second antigen-binding arm and the third antigen-binding arm;
n) an HC1-encoding sequence of SEQ ID NO: 181, a LC-encoding sequence of SEQ ID NO: 188, and a sequence of SEQ ID NO: 163 which encodes the single polypeptide comprising the second antigen-binding arm and the third antigen-binding arm;
o) an HC1-encoding sequence of SEQ ID NO: 192, a LC-encoding sequence of SEQ ID NO: 183, and a sequence of SEQ ID NO: 167 which encodes the single polypeptide comprising the second antigen-binding arm and the third antigen-binding arm;
p) an HC1-encoding sequence of SEQ ID NO: 173, a LC-encoding sequence of SEQ ID NO: 175, and a sequence of SEQ ID NO: 169 which encodes the single polypeptide comprising the second antigen-binding arm and the third antigen-binding arm; or
q) an HC1-encoding sequence of SEQ ID NO: 173, a LC-encoding sequence of SEQ ID NO: 175, and a sequence of SEQ ID NO: 171 which encodes the single polypeptide comprising the second antigen-binding arm and the third antigen-binding arm.

16. A pharmaceutical composition comprising the trispecific antibody or trispecific binding fragment of claim 1 and a pharmaceutically acceptable carrier.

17. An isolated cell expressing the trispecific antibody or trispecific binding fragment of claim 1.

18. A method for treating cancer in a subject in need thereof, said method comprising administering to the subject a therapeutically effective amount of the trispecific antibody or trispecific binding fragment of claim 1.

19. An antibody, or an antigen-binding fragment thereof, that binds to an epitope on Cluster of Differentiation 79B protein (CD79b), comprising the HCDR1, the HCDR2, the HCDR3, the LCDR1, the LCDR2 and the LCDR3 of:
a) SEQ ID NOs: 1, 2, 3, 4, 5 and 6, respectively;
b) SEQ ID NOs: 13, 8, 9, 10, 11 and 12, respectively;
c) SEQ ID NOs: 7, 8, 9, 10, 11 and 12, respectively;
d) SEQ ID NOs: 14, 15, 16, 17, 5 and 6, respectively;
e) SEQ ID NOs: 18, 8, 19, 20, 21 and 12, respectively;
f) SEQ ID NOs: 22, 23, 24, 25, 5 and 6, respectively;
g) SEQ ID NOs: 22, 26, 27, 28, 5 and 29, respectively; or
h) SEQ ID NOs: 30, 31, 32, 33, 5 and 6, respectively.

20. The antibody or antigen-binding fragment of claim 19 comprising
a) the VH of SEQ ID NO: 35 and the VL of SEQ ID NO: 37;
b) the VH of SEQ ID NO: 39 and the VL of SEQ ID NO: 41;
c) the VH of SEQ ID NO: 43 and the VL of SEQ ID NO: 41;
d) the VH of SEQ ID NO: 45 and the VL of SEQ ID NO: 47;
e) the VH of SEQ ID NO: 49 and the VL of SEQ ID NO: 51;
f) the VH of SEQ ID NO: 39 and the VL of SEQ ID NO: 53;
g) the VH of SEQ ID NO: 55 and the VL of SEQ ID NO: 57;
h) the VH of SEQ ID NO: 59 and the VL of SEQ ID NO: 61;
i) the VH of SEQ ID NO: 63 and the VL of SEQ ID NO: 65;
j) the VH of SEQ ID NO: 67 and the VL of SEQ ID NO: 69; or
k) the VH of SEQ ID NO: 71 and the VL of SEQ ID NO: 73.

21. A synthetic polynucleotide encoding the antibody or antigen-binding fragment comprising
a) a VH-encoding sequence of SEQ ID NO: 36 and a VL-encoding sequence of SEQ ID NO: 38 or 213;
b) a VH-encoding sequence of SEQ ID NO: 40 and a VL-encoding sequence of SEQ ID NO: 42;
c) a VH-encoding sequence of SEQ ID NO: 44 and a VL-encoding sequence of SEQ ID NO: 34;
d) a VH-encoding sequence of SEQ ID NO: 46 and a VL-encoding sequence of SEQ ID NO: 48 or 214;
e) a VH-encoding sequence of SEQ ID NO: 50 and a VL-encoding sequence of SEQ ID NO: 52;
f) a VH-encoding sequence of SEQ ID NO: 40 and a VL-encoding sequence of SEQ ID NO: 54;
g) a VH-encoding sequence of SEQ ID NO: 56 and a VL-encoding sequence of SEQ ID NO: 58;
h) a VH-encoding sequence of SEQ ID NO: 60 and a VL-encoding sequence of SEQ ID NO: 62;
i) a VH-encoding sequence of SEQ ID NO: 64 and a VL-encoding sequence of SEQ ID NO: 66;
j) a VH-encoding sequence of SEQ ID NO: 68 and a VL-encoding sequence of SEQ ID NO: 70; or k) a VH-encoding sequence of SEQ ID NO: 72 and a VL-encoding sequence of SEQ ID NO: 74.

22. A pharmaceutical composition comprising the antibody or antigen-binding fragment of claim 19 and a pharmaceutically acceptable carrier.

23. An isolated cell expressing the antibody or antigen-binding fragment of any one of claim 19.

24. A method for treating cancer in a subject in need thereof, said method comprising administering to the subject a therapeutically effective amount of the antibody or antigen-binding fragment of claim 19.

25. A bispecific antibody, or a bispecific binding fragment thereof, comprising:
   (a) a first antigen-binding arm comprising a first heavy chain variable domain (VH1) and a first light chain variable domain (VL1);
   wherein the VH1 and VL1 comprise the HCDR1, the HCDR2, the HCDR3, the LCDR1, the LCDR2, and the LCDR3 of:
      a) SEQ ID NOs: 1, 2, 3, 4, 5 and 6, respectively;
      b) SEQ ID NOs: 13, 8, 9, 10, 11 and 12, respectively;
      c) SEQ ID NOs: 7, 8, 9, 10, 11 and 12, respectively;
      d) SEQ ID NOs: 14, 15, 16, 17, 5 and 6, respectively;
      e) SEQ ID NOs: 18, 8, 19, 20, 21 and 12, respectively;
      f) SEQ ID NOs: 22, 23, 24, 25, 5 and 6, respectively;
      g) SEQ ID NOs: 22, 26, 27, 28, 5 and 29, respectively; or
      h) SEQ ID NOs: 30, 31, 32, 33, 5 and 6, respectively,
   (b) a second antigen-binding arm comprising a second heavy chain variable domain (VH2) and a second light chain variable domain (VL2);
   wherein the VH2 and VL2 comprise the HCDR1, the HCDR2, the HCDR3, the LCDR1, the LCDR2, and the LCDR3 of:
      a) SEQ ID NOs: 76, 77, 78, 79, 80 and 81, respectively;
      b) SEQ ID NOs: 76, 77, 75, 79, 80 and 81, respectively;
      c) SEQ ID NOs: 76, 77, 82, 79, 80 and 81, respectively; or
      d) SEQ ID NOs: 83, 84, 85, 86, 87 and 88, respectively,
   wherein the first antigen-binding arm binds to an epitope on cluster of differentiation 79B protein (CD79b), and the second antigen-binding arm binds to an epitope on is cluster of differentiation 3 (CD3).

26. The bispecific antibody or bispecific binding fragment of claim 25, wherein the first antigen-binding arm that binds CD79b comprises:
   a) the VH of SEQ ID NO: 35 and the VL of SEQ ID NO: 37;
   b) the VH of SEQ ID NO: 39 and the VL of SEQ ID NO: 41;
   c) the VH of SEQ ID NO: 43 and the VL of SEQ ID NO: 41;
   d) the VH of SEQ ID NO: 45 and the VL of SEQ ID NO: 47;
   e) the VH of SEQ ID NO: 49 and the VL of SEQ ID NO: 51;
   f) the VH of SEQ ID NO: 39 and the VL of SEQ ID NO: 53;
   g) the VH of SEQ ID NO: 55 and the VL of SEQ ID NO: 57;
   h) the VH of SEQ ID NO: 59 and the VL of SEQ ID NO: 61;
   i) the VH of SEQ ID NO: 63 and the VL of SEQ ID NO: 65;
   j) the VH of SEQ ID NO: 67 and the VL of SEQ ID NO: 69; or
   k) the VH of SEQ ID NO: 71 and the VL of SEQ ID NO: 73.

27. The bispecific antibody or bispecific binding fragment of claim 25, wherein the second antigen-binding arm that binds CD3 comprises:
   a) the VH of SEQ ID NO: 97 and the VL of SEQ ID NO: 99;
   b) the VH of SEQ ID NO: 101 and the VL of SEQ ID NO: 99;
   c) the VH of SEQ ID NO: 103 and the VL of SEQ ID NO: 99;
   d) the VH of SEQ ID NO: 105 and the VL of SEQ ID NO: 99; or
   c) the VH of SEQ ID NO: 107 and the VL of SEQ ID NO: 109.

28. The bispecific antibody or bispecific binding fragment of claim 25, wherein the first antigen-binding arm and second antigen-binding arm comprise a Fragment crystallizable (Fc) domain, and where in the Fc domain comprises one or more mutations selected from T366S, L368A, T366W and Y407V according to EU numbering.

29. The bispecific antibody or bispecific binding fragment of claim 28, wherein the Fc domains of the first antigen-binding arm and/or second antigen-binding arm further comprise one or more mutations which reduce Fc binding to a Fcγ receptor, and wherein the Fc domains of the first antigen-binding arm and/or second antigen-binding arm each comprise one or more mutations selected from L234A, L235A, and D265S according to EU numbering.

30. The bispecific antibody or bispecific binding fragment of claim 28, wherein the Fc domains of the first antigen-binding arm or second antigen-binding arm further comprise mutations H435R and/or Y436F according to EU numbering.

31. A bispecific antibody, or a bispecific binding fragment, comprising a first antigen-binding arm that binds to an epitope on cluster of differentiation 79B protein (CD79b), a second antigen-binding arm that binds to an epitope on cluster of differentiation 3 (CD3), wherein the first antigen-binding arm comprises a heavy chain (HC1) polypeptide and a light chain (LC) polypeptide; and the second antigen-binding arm comprises a second antigen-binding arm polypeptide, wherein
   a) the HC1 comprises the amino acid sequence of SEQ ID NO: 172, the LC comprises the amino acid sequence of SEQ ID NO: 174, and the second antigen-binding arm polypeptide comprises the amino acid sequence of SEQ ID NO: 164;
   b) the HC1 comprises the amino acid sequence of SEQ ID NO: 176, the LC comprises the amino acid sequence of SEQ ID NO: 178, and the second antigen-binding arm polypeptide comprises the amino acid sequence of SEQ ID NO: 164;
   c) the HC1 comprises the amino acid sequence of SEQ ID NO: 180, the LC comprises the amino acid sequence of SEQ ID NO: 182, and the second antigen-binding arm polypeptide comprises the amino acid sequence of SEQ ID NO: 164;
   d) the HC1 comprises the amino acid sequence of SEQ ID NO: 172, the LC comprises the amino acid sequence of SEQ ID NO: 174, and the second antigen-binding arm polypeptide comprises the amino acid sequence of SEQ ID NO: 189;
   e) the HC1 comprises the amino acid sequence of SEQ ID NO: 176, the LC comprises the amino acid sequence of SEQ ID NO: 178, and the second antigen-binding arm polypeptide comprises the amino acid sequence of SEQ ID NO: 189; or f) the HC1 comprises the amino acid sequence of SEQ ID NO: 180, the LC comprises the amino acid sequence of SEQ ID NO: 182, and the second antigen-binding arm polypeptide comprises the amino acid sequence of SEQ ID NO: 189.

32. A synthetic polynucleotide encoding a polypeptide comprising a bispecific antibody or a bispecific binding fragment thereof, wherein the bispecific antibody or the bispecific binding fragment thereof comprises a first antigen-binding arm comprising a heavy chain (HC1) polypeptide and a light chain (LC) polypeptide, and a second antigen-binding arm polypeptide, wherein the polynucleotide comprises:

a) an HC1-encoding sequence of SEQ ID NO: 173 and a LC-encoding sequence of SEQ ID NO: 175 and a sequence of SEQ ID NO: 165 encoding the second antigen-binding arm polypeptide;

b) an HC1-encoding sequence of SEQ ID NO: 177 and a LC-encoding sequence of SEQ ID NO: 179 and a sequence of SEQ ID NO: 165 encoding the second antigen-binding arm polypeptide;

c) an HC1-encoding sequence of SEQ ID NO: 181 and a LC-encoding sequence of SEQ ID NO: 183 and a sequence of SEQ ID NO: 165 encoding the second antigen-binding arm polypeptide;

d) an HC1-encoding sequence of SEQ ID NO: 173 and a LC-encoding sequence of SEQ ID NO: 175 and a sequence of SEQ ID NO: 190 encoding the second antigen-binding arm polypeptide;

e) an HC1-encoding sequence of SEQ ID NO: 177 and a LC-encoding sequence of SEQ ID NO: 179 and a sequence of SEQ ID NO: 190 encoding the second antigen-binding arm polypeptide; or f) an HC1-encoding sequence of SEQ ID NO: 181 and a LC-encoding sequence of SEQ ID NO: 183 and a sequence of SEQ ID NO: 190 encoding the second antigen-binding arm polypeptide.

33. A pharmaceutical composition comprising the bispecific antibody or bispecific binding fragment of claim 25, and a pharmaceutically acceptable carrier.

34. An isolated cell expressing the bispecific antibody or bispecific binding fragment of claim 25.

35. A method for treating cancer in a subject in need thereof, said method comprising administering to the subject a therapeutically effective amount of the bispecific antibody or bispecific binding fragment of claim 25.

* * * * *

SEQUENCE LISTING

```
<160> NUMBER OF SEQ ID NOS: 265

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Ala Ser Ile Ser Ser Phe Tyr Trp Ser
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ile Ser Pro Ser Gly Lys Thr Asn
1               5

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Glu Tyr Ser Gly Thr Tyr Ser Tyr Ser Phe Asp Val
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 4

Arg Ser Ser Glu Ser Leu Leu Asp Ser Glu Asp Gly Asn Thr Tyr Leu
1               5                   10                  15

Asp

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Leu Ser Tyr Arg Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Gln Arg Met Glu Phe Pro Leu Thr
1               5

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Asp Ser Val Ser Ser Asn Ser Ala Thr Trp Asn
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Thr Tyr Tyr Arg Ser Lys Trp Tyr Asn Asp
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Asp Ile Ala Phe Asp Tyr
1               5

<210> SEQ ID NO 10
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Gly Ser Ser Ser Asn Ile Gly Asn His Gly Val Asn
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asn Asp Asp Leu Leu Pro Ser
1               5

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Ala Trp Asp Asp Ser Leu Asn Gly Val Val
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Asp Ser Val Ser Asn Asn Ser Ala Thr Trp Asn
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Val Ser Ile Ser Asn Tyr Tyr Trp Ser
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15
```

```
Arg Ile Ser Pro Ser Gly Arg Thr Asn
1               5

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Glu Tyr Ser Gly Thr Tyr Ser Tyr Ser Phe Asp Ile
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ser Ser Gln Ser Leu Phe Asp Ser Asp Asp Gly Asn Thr Tyr Leu
1               5                   10                  15
Asp

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Asp Ser Val Ser Ser Asn Ser Ala Ala Trp Asn
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Val Asn Thr Thr Phe Asp Tyr
1               5

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Gly Ser Ser Ser Asn Ile Gly Lys Asn Ala Val Ser
1               5                   10

<210> SEQ ID NO 21
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 21

Ser Asp Asp Leu Leu Ser Ser
1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Ala Ser Ile Ser Ser Tyr Tyr Trp Ser
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Ile Ser Asn Thr Gly Arg Thr Asn
1               5

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Glu Tyr Ser Gly Thr Phe Ser Tyr Gly Phe Asp Ile
1               5                   10

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ser Ser Leu Ser Leu Leu Asp Ser Asp Gly Lys Ile Tyr Leu
1               5                   10                  15

Asp

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26
```

Arg Ile Tyr Ser Asn Gly Asn Ile Asn
1               5

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Glu Tyr Ser Gly Asp Phe Ser Tyr Ser Phe Asp Ile
1               5                   10

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Ser Ser Gln Ser Leu Leu Asp Ser Asp Asp Gly Asn Thr Tyr Leu
1               5                   10                  15
Asp

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Met Gln Arg Ile Glu Phe Pro Leu Thr
1               5

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gly Ser Ile Ser Asn Tyr Tyr Trp Ser
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Ile Phe Tyr Ser Gly Lys Thr Asn
1               5

<210> SEQ ID NO 32
<211> LENGTH: 13
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 32

Gly Glu Tyr Ser Gly Glu Tyr Ser Tyr Ser Phe Asp Ile
1               5                   10

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ser Ser Gln Ser Leu Leu Asp Ser Asp Asp Gly Asn Thr Tyr Val
1               5                   10                  15

Asp

<210> SEQ ID NO 34
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
cagacagtgg tcacccagcc tccatctgtg tctgaggccc ctagacagag agtgaccatc      60
tcctgctccg gctcctcctc caacatcggc aatcatggcg tgaactggta tcagcagctg     120
cccggcaagg ctcccaaact gctgatctac aacgacgacc tgctgccttc tggcgtgtcc     180
gacagattct ccggctctac ctctggcacc tctggatccc tggctatctc tggcctgcag     240
tctgaggacg aggccgacta ctattgtgcc gcctgggacg attctctgaa cggcgttgtg     300
tttggcggag gcaccaagct gacagtgttg                                      330

<210> SEQ ID NO 35
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Ser Phe
                20                  25                  30

Tyr Trp Ser Trp Ile Arg Gln Pro Ala Asp Glu Gly Leu Glu Trp Ile
            35                  40                  45

Gly Arg Ile Ser Pro Ser Gly Lys Thr Asn Tyr Ile Pro Ser Leu Lys
        50                  55                  60

Ser Arg Ile Ile Met Ser Leu Asp Ala Ser Lys Asn Gln Phe Ser Leu
65                  70                  75                  80

Arg Leu Asn Ser Val Thr Ala Ala Asp Thr Ala Met Tyr Tyr Cys Ala
                85                  90                  95

Arg Gly Glu Tyr Ser Gly Thr Tyr Ser Tyr Ser Phe Asp Val Trp Gly

```
              100                 105                 110

Gln Gly Thr Met Val Thr Val Ser Ser
        115                 120

<210> SEQ ID NO 36
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
caggttcagc tgcaagagtc tggtcctggc ctggtcaagc cttccgagac actgtctctg      60
acctgctctg tgtccggcgc ctccatctct tccttctact ggtcctggat ccggcagcct     120
gctgacgaag gactggaatg gatcggccgg atcagccctt ctggcaagac caactacatc     180
cccagcctga gtcccggat catcatgtcc ctggacgcct ccaagaacca gttctccctg     240
cggctgaact ctgtgaccgc tgccgatacc gccatgtact actgtgccag aggcgagtac     300
tccggcacct actcctacag ctttgacgtg tggggacaag gcaccatggt cacagtttct     360
tct                                                                    363

<210> SEQ ID NO 37
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Val Met Thr Gln Ser Pro Leu Ser Leu Ser Val Thr Pro Gly
1               5                   10                  15

Glu Pro Ala Ser Ile Ser Cys Arg Ser Ser Glu Ser Leu Leu Asp Ser
            20                  25                  30

Glu Asp Gly Asn Thr Tyr Leu Asp Trp Phe Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Asp Thr Asp Phe Thr Leu His
65                  70                  75                  80

Ile Ser Ser Leu Glu Ala Glu Asp Val Gly Leu Tyr Tyr Cys Met Gln
                85                  90                  95

Arg Met Glu Phe Pro Leu Thr Phe Gly Gln Gly Thr Lys Val Glu Ile
            100                 105                 110

Lys

<210> SEQ ID NO 38
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gacatcgtga tgacccagtc tccactgagc ctgtctgtga cacctggcga gcctgcctcc      60
atctcctgta gatcttctga gtccctgctg gacagcgagg acggcaatac ctacctggac     120
```

-continued

```
tggttcctgc agaagcccgg acagtctcct cagctgctga tctacacccct gtcctacaga    180 gcctctggcg tgcccgatag attctccggc tctggctctg acaccgactt taccctgcac    240
atctccagcc tggaagccga ggatgtgggc ctgtactact gtatgcagcg gatggaattt    300
cccctgacct tcggccaggg caccaaggtg gaaatcaag                           339
```

<210> SEQ ID NO 39
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Asn Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Thr
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Thr Arg Val Asp Ile Ala Phe Asp Tyr Trp Gly Gln Gly
            100                 105                 110

Thr Leu Val Thr Val Ser Ser
        115
```

<210> SEQ ID NO 40
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
caagtgcaac tgcagcagtc tggccctgga ctggtcaagc cttctcagac cctgtctctg    60
acctgcgcca tctccggcga ctccgtgtcc aacaactccg ctacctggaa ctggatcaga    120
cagtcccctt ccagaggcct ggaatggctg ggcagaacct actaccggtc aagtggtac    180 aacgactaca ccgtgtccgt gaagtccggg atcaccatca accctgatac ctctaagaac    240
cagttctccc tgcaactgaa ctctgtgacc cctgaggaca ccgccgtgta ctactgcacc    300
agagtggaca tcgccttcga ctactggggc cagggcaccc tggtgaccgt gtctagc      357
```

<210> SEQ ID NO 41
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Gln Thr Val Val Thr Gln Pro Pro Ser Val Ser Glu Ala Pro Arg Gln
1               5                   10                  15
```

Arg Val Thr Ile Ser Cys Ser Gly Ser Ser Asn Ile Gly Asn His
            20                  25                  30

Gly Val Asn Trp Tyr Gln Gln Leu Pro Gly Lys Ala Pro Lys Leu Leu
        35                  40                  45

Ile Tyr Asn Asp Asp Leu Leu Pro Ser Gly Val Ser Asp Arg Phe Ser
50                  55                  60

Gly Ser Thr Ser Gly Thr Ser Gly Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110

<210> SEQ ID NO 42
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
cagactgtgg tgactcagcc accctcggtg tctgaagccc ccaggcagag ggtcaccatc     60
tcctgttctg gaagtagctc caacatcgga aatcatggtg taaactggta ccagcagctc    120
ccaggaaagg ctcccaaact cctcatctat aatgatgatc tgctgccctc agggggtctct   180 gaccgattct ctggctccac gtctggcacc tcaggttccc tggccatcag tgggctccag    240
tctgaggatg aggctgatta ttactgtgca gcatgggatg acagcctgaa tggtgtggta    300
ttcggcggag ggactaaact gaccgtccta                                     330

<210> SEQ ID NO 43
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Thr
50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Thr Arg Val Asp Ile Ala Phe Asp Tyr Trp Gly Gln Gly
            100                 105                 110

Thr Leu Val Thr Val Ser Ser
        115

<210> SEQ ID NO 44

```
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
caggttcagc tgcagcagtc tggccctgga ctggtcaagc cctctcagac cctgtctctg    60
acctgtgcca tctccggcga ctccgtgtcc tctaattctg ccacctggaa ctggatccgg   120
cagtccccta gtagaggcct ggaatggctg ggcagaacct actaccggtc aagtggtac    180 aacgactaca ccgtgtccgt gaagtcccgg atcaccatca atcccgacac ctccaagaac   240
cagttctccc tgcagctcaa cagcgtgacc cctgaggata ccgccgtgta ctactgcacc   300
agagtggata tcgccttcga ctactggggc cagggcacac tggttaccgt ttcttct     357

<210> SEQ ID NO 45
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Ile Ser Asn Tyr
            20                  25                  30

Tyr Trp Ser Trp Ile Arg Gln Pro Pro Gly Lys Gly Leu Glu Trp Ile
        35                  40                  45

Gly Arg Ile Ser Pro Ser Gly Arg Thr Asn Tyr Asn Pro Ser Leu Lys
    50                  55                  60

Ser Arg Val Thr Met Ser Leu Asp Ala Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Glu Tyr Ser Gly Thr Tyr Ser Tyr Ser Phe Asp Ile Trp Gly
            100                 105                 110

Gln Gly Thr Met Val Thr Val Ser Ser
        115                 120

<210> SEQ ID NO 46
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
caggttcagc tgcaagagtc tggccctggc ctggtcaagc cctctcagac cctgtctctg    60
acctgtaccg tgtccggcgt gtccatctcc aactactact ggtcctggat ccggcagcct   120
cctggcaaag actggaatg gatcggccgc atctctcctt ctggtcgcac caactacaac   180
cccagcctga aaagcagagt gaccatgtct ctggacgcct ccaagaacca gttctccctg   240
aagctgtcct ccgtgaccgc tgctgatacc gccgtgtact actgtgccag aggcgagtac   300
tccggcacct actcctacag cttcgacatc tggggccagg gcaccatggt cacagtctct   360
```

```
tct                                                             363
```

<210> SEQ ID NO 47
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Phe Asp Ser
            20                  25                  30

Asp Asp Gly Asn Thr Tyr Leu Asp Trp Phe Gln Gln Lys Pro Gly Gln
        35                  40                  45

Ser Pro Lys Leu Leu Ile Gln Thr Leu Ser Tyr Arg Ala Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Met Gln
                85                  90                  95

Arg Met Glu Phe Pro Leu Thr Phe Gly Gly Gly Thr Lys Val Glu Ile
            100                 105                 110

Lys

<210> SEQ ID NO 48
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
gacatccaga tgacccagtc tccatcctct ctgtccgcct ctgtgggcga cagagtgacc      60
atcacctgtc ggtcctctca gtccctgttc gactctgacg acggcaacac ctacctggac    120
tggttccagc agaagcccgg ccagtctcct aagctgctga tccagacact gtcctacaga    180
gcctctggcg tgccctccag attttccggc tctggctctg gcaccgactt taccctgaca    240
atctccagcc tgcagcctga ggacttcgcc acctactact gtatgcagcg gatggaattt    300
cccctgacct cggcggagg caccaaggtg gaaatcaag                             339
```

<210> SEQ ID NO 49
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Glu Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

```
Trp Leu Gly Arg Thr Tyr Tyr Arg Ser Lys Trp Tyr Asn Asp Tyr Ala
    50                  55                  60

Val Ser Val Arg Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Phe Cys Thr Arg Val Asn Thr Thr Phe Asp Tyr Trp Gly Gln Gly
            100                 105                 110

Thr Leu Val Thr Val Ser Ser
            115
```

<210> SEQ ID NO 50
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

```
gaagtgcaac tggtggaatc tggccctgga ctggtgaagc cttctcagac cctgtctctg      60
acctgcgcca tctccggcga ctccgtgtcc tccaactctg ccgcctggaa ctggatcaga     120 cagtccccctt ccagaggcct ggaatggctg ggcagaacct actacagatc caagtggtac   180
aacgactacg ccgtgtctgt gcggtcccgg atcaccatca accctgacac tctctaagaac   240 cagttctccc tgcaactgaa ctccgtgacc cctgaggaca ccgccgtgta cttctgcacc   300
agagtgaaca ccaccttcga ctactggggc cagggcaccc tggtcaccgt gtcctct      357
```

<210> SEQ ID NO 51
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Gln Ser Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Lys Asn
            20                  25                  30

Ala Val Ser Trp Tyr Gln Gln Leu Pro Gly Lys Ala Pro Lys Leu Leu
        35                  40                  45

Ile His Ser Asp Asp Leu Leu Ser Ser Gly Val Ser Asp Arg Phe Ser
    50                  55                  60

Gly Ser Gln Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110
```

<210> SEQ ID NO 52
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
cagtctgtgc tgactcagcc accctcggtg tctgaagccc ccaggcagag ggtcaccatc    60
tcctgttctg gaagtagctc caacatcgga aaaaatgctg taagctggta ccagcagctc   120
ccaggaaagg ctcccaaact cctcatccat tctgatgatc tgctgtcctc aggggtctct   180
gaccgattct ctggctccca gtctggcacc tcagcctccc tggccatcag tgggctccag   240
tccgaggatg aggctgatta ttactgtgca gcatgggatg acagcctgaa tggtgtggta   300
ttcggcggag ggactaaact gaccgtccta                                     330
```

<210> SEQ ID NO 53
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Leu Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn His
            20                  25                  30

Gly Val Asn Trp Tyr Gln Gln Leu Pro Gly Lys Ala Pro Lys Leu Leu
        35                  40                  45

Ile Tyr Asn Asp Asp Leu Leu Pro Ser Gly Val Ser Asp Arg Phe Ser
    50                  55                  60

Gly Ser Thr Ser Gly Thr Ser Gly Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110

<210> SEQ ID NO 54
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

```
cagcttgtgc tgactcagcc accctcggtg tctgaagccc ccaggcagag ggtcaccatc    60
tcctgttctg gaagtagctc caacatcgga aatcatggtg taaactggta ccagcagctc   120
ccaggaaagg ctcccaaact cctcatctat aatgatgatc tgctgccctc aggggtctct   180
gaccgattct ctggctccac gtctggcacc tcaggttccc tggccatcag tgggctccag   240
tctgaggatg aggctgatta ttactgtgca gcatgggatg acagcctgaa tggtgtggta   300
ttcggcggag ggactaaact gaccgtccta                                     330
```

<210> SEQ ID NO 55
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Asn Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Thr
    50                  55                  60

Val Ser Val Lys Ser Arg Ile Thr Ile Asn Pro Asp Thr Ser Lys Asn
65              70                  75                  80

Gln Phe Ser Leu Gln Leu Asn Ser Val Thr Pro Glu Asp Thr Ala Val
                85                  90                  95

Tyr Tyr Cys Thr Arg Val Asp Ile Ala Phe Asp Tyr Trp Gly Gln Gly
            100                 105                 110

Thr Thr Val Thr Val Ser Ser
            115

<210> SEQ ID NO 56
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
caagtgcaac tgcagcagtc tggccctggc ctggtgaagc cttctcagac cctgtctctg      60
acctgcgcca tctccggcga ctccgtgtcc aacaactctg ctacctggaa ctggatcaga     120
cagtccccdt tccagaggcct ggaatggctg ggcagaacct actacagatc caagtggtac     180
aacgactaca ccgtgtctgt gaagtcccgg atcaccatca accccgatac ctctaagaac     240
cagttctccc tgcaactgaa ctccgtgacc cctgaggaca ccgccgtgta ctactgcacc     300
agagtggaca tcgccttcga ctactggggc cagggcacca ccgtgacagt gtcctcc       357

<210> SEQ ID NO 57
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Ser Ala Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn His
            20                  25                  30

Gly Val Asn Trp Tyr Gln Gln Leu Pro Gly Lys Ala Pro Lys Leu Leu
        35                  40                  45

Ile Tyr Asn Asp Asp Leu Leu Pro Ser Gly Val Ser Asp Arg Phe Ser
    50                  55                  60

Gly Ser Thr Ser Gly Thr Ser Gly Ser Leu Ala Ile Ser Gly Leu Gln
65              70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110

<210> SEQ ID NO 58
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
cagtctgccc tgactcagcc accctcggtg tctgaagccc caggcagag  ggtcaccatc    60 tcctgttctg gaagtagctc caacatcgga atcatggtg taaactggta ccagcagctc   120
ccaggaaagg ctcccaaact cctcatctat aatgatgatc tgctgccctc agggtctct   180 gaccgattct ctggctccac gtctggcacc tcaggttccc tggccatcag tgggctccag   240
tctgaggatg aggctgatta ttactgtgca gcatgggatg acagcctgaa tggtgtggta   300
ttcggcggag ggaccaagct gaccgtccta                                     330
```

<210> SEQ ID NO 59
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Gln Val Gln Leu Val Gln Ser Gly Pro Gly Leu Val Lys Pro Ser Glu
1               5                   10                  15

Thr Leu Ser Leu Ile Cys Thr Val Ser Gly Ala Ser Ile Ser Ser Tyr
            20                  25                  30

Tyr Trp Ser Trp Ile Arg Gln Pro Ala Gly Lys Gly Leu Glu Trp Leu
        35                  40                  45

Gly Arg Ile Ser Asn Thr Gly Arg Thr Asn Tyr Asn Pro Ser Leu Lys
    50                  55                  60

Ser Arg Val Thr Met Ser Ser Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg Gly Glu Tyr Ser Gly Thr Phe Ser Tyr Gly Phe Asp Ile Trp Gly
            100                 105                 110

Gln Gly Thr Met Val Thr Val Ser Ser
        115                 120
```

<210> SEQ ID NO 60
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
caagtgcagt tggtacagtc tggtcccggg cttgtaaagc cttctgaaac attgagcctg    60
atatgcaccg tctccggtgc cagtataagt agttattact ggtcatggat ccgtcagccc   120
gcaggtaaag gcttggagtg gttgggaagg attagtaata ctggacgaac caattacaat   180
ccttccctga agagtcgtgt taccatgagt agtgatacca gcaagaacca gttctcactt   240
aaattgaggt ccgtgaccgc cgctgacacc gctgtctact actgtgctcg cggagagtat   300
```

```
tcaggaacct tttcatacgg gttcgatatt tggggccagg ggacaatggt tactgtgagt    360
tca                                                                  363
```

<210> SEQ ID NO 61
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

```
Glu Ile Val Leu Thr Gln Ser Pro Leu Ser Leu Ser Val Thr Pro Gly
1               5                   10                  15

Glu Pro Ala Ser Ile Ser Cys Arg Ser Ser Leu Ser Leu Leu Asp Ser
            20                  25                  30

Asp Asp Gly Lys Ile Tyr Leu Asp Trp Tyr Leu Gln Arg Pro Gly Gln
        35                  40                  45

Ser Pro Gln Leu Leu Ile Gln Thr Leu Ser Tyr Arg Ala Ser Gly Val
    50                  55                  60

Pro Asp Arg Phe Ser Gly Ser Gly Ser Gly Thr Asp His Thr Leu Lys
65                  70                  75                  80

Ile Ser Arg Val Glu Ala Glu Asp Val Gly Val Tyr Tyr Cys Met Gln
                85                  90                  95

Arg Met Glu Phe Pro Leu Thr Phe Gly Gly Gly Thr Lys Leu Glu Ile
            100                 105                 110

Lys
```

<210> SEQ ID NO 62
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
gaaattgtgt tgacacagtc tccactctcc ctgtccgtca cccctggaga gccggcctcc    60
atctcctgca ggtctagtct gagcctcttg gatagtgatg atggaaaaat ctatttggac   120
tggtacctgc agaggccagg gcagtctcca cagctcctga tccagacgct ttcctatcgg   180
gcctctggag tcccagacag gttcagtggc agtgggtcag gcactgatca cacactgaaa   240
atcagcaggg tggaggctga ggatgttgga gtttattact gcatgcaacg tatggagttt   300
ccgctcactt tcggcggagg gaccaagctg gagatcaaa                          339
```

<210> SEQ ID NO 63
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Gln Val Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Ser Tyr
            20                  25                  30
```

Tyr Trp Ser Trp Ile Arg Gln Pro Ala Gly Lys Gly Leu Glu Trp Ile
             35                  40                  45

Gly Arg Ile Tyr Ser Asn Gly Asn Ile Asn Tyr His Ser Ser Leu Lys
 50                  55                  60

Arg Arg Val Thr Met Ser Val Asp Thr Ser Lys Asn Gln Phe Ser Leu
 65                  70                  75                  80

Lys Leu Asn Ala Val Thr Ala Ala Asp Thr Ala Val Tyr Tyr Cys Ala
                 85                  90                  95

Arg Gly Glu Tyr Ser Gly Asp Phe Ser Tyr Ser Phe Asp Ile Trp Gly
                100                 105                 110

Gln Gly Thr Met Val Thr Val Ser Ser
            115                 120

<210> SEQ ID NO 64
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
caagtacagc ttcaagagtc cgggccaggt ctcgttaagc catccgaaac tctgtcactt      60
acttgttcag tctcaggagc ttcaatttct tcatattact ggtcctggat cgtcaacca     120 gccggcaaag gtttggagtg gataggccgg atatattcaa atggaaatat caactaccac     180
tcatccctta aacgtagggt tacaatgagt gtggatacct ctaagaatca gttcagtttg     240
aaattgaatg ctgtcaccgc cgctgacacc gcagtctatt attgtgccag aggcgaatac     300
agtggtgact ctcatatag ctttgacatt tggggtcagg gaacaatggt cacagtgagt     360
tcc                                                                  363

<210> SEQ ID NO 65
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Asp Ser
                 20                  25                  30

Asp Asp Gly Asn Thr Tyr Leu Asp Trp Phe Leu Gln Lys Pro Gly Gln
             35                  40                  45

Ser Pro Gln Leu Leu Ile Tyr Thr Leu Ser Tyr Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Ile Tyr Tyr Cys Met Gln
                 85                  90                  95

Arg Ile Glu Phe Pro Leu Thr Phe Gly Gly Gly Thr Lys Val Glu Ile
                100                 105                 110

Lys

<210> SEQ ID NO 66

```
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
gatattgtga tgactcagtc tccactctcc ctgcccgtca cccctggaga gccggcctcc      60
atctcctgca ggtctagtca gagcctcttg gatagtgatg atggaaacac ctatttggac     120
tggttcctgc agaagccagg gcagtctcca cagctcctga tctatacgct ttcctatcgg     180
gcctctggag tcccagacag gttcagtggc agtgggtcag gcacggattt cacactgaaa     240
atcagcaggg tggaggctga ggatgttgga atttattact gcatgcaacg tatagagttt     300
ccgctcactt tcggcggagg gaccaaggtg gaaatcaaa                            339

<210> SEQ ID NO 67
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Gln Gln Ser Gly Pro Gly Leu Val Arg Pro Ser Glu
1               5                   10                  15

Thr Leu Ala Leu Thr Cys Ser Val Ser Gly Val Ser Ile Ser Asn Tyr
            20                  25                  30

Tyr Trp Ser Trp Ile Arg Gln Pro Ala Gly Arg Gly Leu Glu Trp Ile
        35                  40                  45

Gly Arg Ile Ser Pro Ser Gly Arg Thr Asn Tyr Asn Thr Ser Leu Lys
    50                  55                  60

Ser Arg Gly Thr Met Ser Leu Asp Ala Ser Lys Asn Gln Phe Ser Leu
65                  70                  75                  80

Lys Val Asn Ser Val Thr Ala Ala Asp Thr Ala Val Tyr Tyr Cys Ala
                85                  90                  95

Arg Gly Glu Tyr Ser Gly Thr Tyr Ser Tyr Ser Phe Asp Ile Trp Gly
            100                 105                 110

Gln Gly Thr Met Val Thr Val Ser Ser
        115                 120

<210> SEQ ID NO 68
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
caagttcagc ttcaacaatc tggtccaggt ctcgtaagac catcagaaac attggctctt      60
acatgctctg ttagtggtgt gtcaatcagt aactattact ggtcctggat ccgccaacct     120
gctggccgtg ggctcgaatg gatcggacga atctcaccta gcggtaggac aaattacaac     180
acttccctta atcacgagg acaatgagc ctcgacgcat caaagaacca gttcagcctt      240
aaagtaaact ccgttaccgc agcagatact gcagtctact attgtgccag gggtgaatat     300
tcaggaacat attcctattc ttttgacatt tggggccagg gaaccatggt aacagtgagt     360
``` tca                                                               363

<210> SEQ ID NO 69
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Phe Asp Ser
            20                  25                  30

Asp Asp Gly Asn Thr Tyr Leu Asp Trp Phe Leu Gln Lys Pro Gly Gln
        35                  40                  45

Ser Pro Gln Leu Leu Ile Gln Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Asp Asp Val Gly Val Tyr Tyr Cys Met Gln
                85                  90                  95

Arg Met Glu Phe Pro Leu Thr Phe Gly Gly Gly Thr Lys Leu Glu Ile
            100                 105                 110

Lys

<210> SEQ ID NO 70
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
gatattgtga tgactcagac tccactctct ctgcccgtca cccctggaga accggcctcc      60
atctcctgca ggtctagtca gagcctcttt gatagtgatg atggaaacac ctatttggac     120
tggttcctgc agaagccagg gcagtctcca cagctcctaa tccaaacgct ttcctatcgg     180
gcctctggag tcccagacag gttcagtggc agtgggtcag gcaccgattt cacactgaaa     240
atcagcaggg tggaggctga tgatgttgga gtttattact gcatgcaacg tatggagttt     300
ccgctcactt tcggcggagg gaccaagctg gagatcaaa                            339

<210> SEQ ID NO 71
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Ser Asn Tyr
            20                  25                  30

Tyr Trp Ser Trp Ile Arg Gln Pro Ala Gly Lys Gly Leu Glu Trp Ile
        35                  40                  45

Gly Arg Ile Phe Tyr Ser Gly Lys Thr Asn Tyr Asn Ser Ser Leu Lys
            50                  55                  60

Ser Arg Val Thr Met Ser Ala Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Glu Tyr Ser Gly Glu Tyr Ser Tyr Ser Phe Asp Ile Trp Gly
            100                 105                 110

Gln Gly Thr Thr Val Thr Val Ser Ser
        115                 120

<210> SEQ ID NO 72
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
caggtacaac ttcaggagag cggcccaggt ttggttaaac caagtgaaac cttgtcactt      60
acctgttccg tgtcaggtgg gtcaataagc aattactact ggtcctggat tagacaacct     120
gctggaaagg ggcttgaatg gatcgggagg atattctact cagggaagac aaactacaat     180
agtagcctca gtccagggt gaccatgtcc gctgatactt ccaagaatca atttagcctt      240
aaattgtcct ccgttacagc cgctgatacc gcagtgtact actgtgcaag aggtgagtac     300
agtggcgaat actcatattc ctttgacatc tggggtcagg gcactactgt gactgtttca     360
tct                                                                   363

<210> SEQ ID NO 73
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Val Asp Trp Phe Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Asp Thr Asp Phe Thr Leu Lys
65                  70                  75                  80

Ile Ser Arg Val Glu Ala Glu Asp Val Gly Ile Tyr Tyr Cys Met Gln
                85                  90                  95

Arg Met Glu Phe Pro Leu Thr Phe Gly Gly Gly Thr Lys Val Glu Ile
            100                 105                 110

Lys

<210> SEQ ID NO 74
<211> LENGTH: 339
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 74
gaaatagtga tgacgcagtc tccactctcc ctgcccgtca cccctggaga gccggcctcc      60
atttcctgcc ggtctagtca gagcctcttg gatagtgatg atggaaacac ctatgtggac     120
tggttcctgc agaagccagg gcagtctcca caactcctga tctatacgct ttcctatcgg     180
gcctctggag tcccagacag gttcagtggc agtgggtcag acactgattt cacactgaaa     240
atcagcaggg tggaggctga agatgttgga atttattact gcatgcaacg tatggagttt     300
ccgctcactt tcggcggagg gaccaaggtg gagatcaaa                            339

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Gln Val His Tyr Asp Tyr Ala Gly Phe Pro Tyr
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Tyr Thr Phe Thr Arg Ser Thr Met His
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Tyr Ile Asn Pro Ser Ser Ala Tyr Thr Asn
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Pro Gln Val His Tyr Asp Tyr Asn Gly Phe Pro Tyr
1               5                   10

<210> SEQ ID NO 79
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 79

Ser Ala Ser Ser Ser Val Ser Tyr Met Asn
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asp Ser Ser Lys Leu Ala Ser
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Gln Trp Ser Arg Asn Pro Pro Thr
1               5

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Pro Gln Val His Tyr Asp Tyr Gly Gly Phe Pro Tyr
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Phe Thr Phe Ser Arg Tyr Asn Met Asn
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ser Ile Ser Thr Ser Ser Asn Tyr Ile Tyr
1               5                   10
```

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Trp Gly Pro Phe Asp Tyr
1               5

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Ala Arg Gln Ser Ile Gly Thr Ala Ile His
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Tyr Ala Ser Glu Ser Ile Ser
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Gln Ser Gly Ser Trp Pro Tyr Thr
1               5

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Phe Thr Phe Ser Ser Tyr Ala Met Ser
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 90

Ala Ile Ser Gly Ser Gly Gly Ser Thr Tyr
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Tyr Asp Gly Ile Tyr Gly Glu Leu Asp Phe
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Arg Ala Ser Gln Ser Ile Ser Ser Tyr Leu Asn
1               5                   10

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ala Ala Ser Ser Leu Gln Ser
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Gln Ser Tyr Ser Thr Pro Leu Thr
1               5

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Val Tyr Tyr Gly Ser Asn Tyr Trp Tyr Phe Asp Val
1               5                   10

<210> SEQ ID NO 96
<211> LENGTH: 10
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 96

Arg Ala Ser Ser Ser Val Ser Tyr Met His
1               5                   10

<210> SEQ ID NO 97
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Arg Ser
            20                  25                  30

Thr Met His Trp Val Lys Gln Ala Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Pro Gln Val His Tyr Asp Tyr Asn Gly Phe Pro Tyr Trp Gly
            100                 105                 110

Gln Gly Thr Leu Val Thr Val Ser Ser
        115                 120

<210> SEQ ID NO 98
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
caggttcagc tggttcagtc tggcgccgaa gtgaagaaac ctggctcctc cgtcaaggtg      60
tcctgcaagg cttccggcta cacctttacc agatccacca tgcactgggt caaacaggct     120
ccaggacaag gcttggagtg gatcggctac atcaacccca gctccgccta caccaactac     180
aaccagaaat tccagggcag agtcaccctc accgccgaca gtctacctc caccgcctac      240 atggaactgt ccagcctgag atctgaggac accgccgtgt actactgcgc cagccctcag     300
gtgcactacg actacaacgg cttcccttat tggggccagg gcaccctggt taccgtttct     360
tct                                                                    363

<210> SEQ ID NO 99
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 99

Glu Ile Val Leu Thr Gln Ser Pro Ala Thr Leu Ser Ala Ser Pro Gly
1               5                   10                  15

Glu Arg Val Thr Leu Ser Cys Ser Ala Ser Ser Ser Val Ser Tyr Met
            20                  25                  30

Asn Trp Tyr Gln Gln Lys Pro Gly Gln Ala Pro Arg Trp Ile Tyr
        35                  40                  45

Asp Ser Ser Lys Leu Ala Ser Gly Val Pro Ala Arg Phe Ser Gly Ser
    50                  55                  60

Gly Ser Gly Arg Asp Tyr Thr Leu Thr Ile Ser Ser Leu Glu Pro Glu
65                  70                  75                  80

Asp Phe Ala Val Tyr Tyr Cys Gln Gln Trp Ser Arg Asn Pro Pro Thr
                85                  90                  95

Phe Gly Gly Gly Thr Lys Val Glu Ile Lys
            100                 105

<210> SEQ ID NO 100
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
gagatcgtgc tgacccagtc tcctgccaca ctgagtgctt ctccaggcga gagagtgacc      60
ctgtcctgct ccgcttcctc ctccgtgtcc tacatgaact ggtatcagca aaagcccggc    120
caggctcctc ggagatggat ctacgactct tccaagctgg cctctggtgt gccagccaga    180 tttctggct ctggctccgg cagagactat accctgacca tctccagcct ggaacctgag    240
gacttcgccg tgtactactg ccagcagtgg tctaggaacc ctcctacctt tggcggaggc    300
accaaggtgg aaatcaag                                                  318

<210> SEQ ID NO 101
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Arg Ser
            20                  25                  30

Thr Met His Trp Val Lys Gln Ala Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Pro Gln Val His Tyr Asp Tyr Ala Gly Phe Pro Tyr Trp Gly
            100                 105                 110

Gln Gly Thr Leu Val Thr Val Ser Ser

<210> SEQ ID NO 102
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 102

```
caggttcaac tggttcagtc tggcgccgaa gtgaagaaac ctggctcctc cgtcaaggtg      60
tcctgcaagg cttccggcta cacctttacc agatccacca tgcactgggt caagcaggcc     120
cctggacaag gcttggagtg gatcggctac atcaacccca gctccgccta caccaactac     180
aaccagaaat tccagggcag agtgaccctg accgccgaca gtctacctc caccgcctac      240
atggaactgt ccagcctgag atctgaggac accgccgtgt actactgcgc ctctcctcag     300
gtccactacg actacgccgg ctttccttat tggggccagg gcacactggt caccgtttct     360
tct                                                                   363
```

<210> SEQ ID NO 103
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

```
Gln Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Thr Arg Ser
            20                  25                  30
Thr Met His Trp Val Arg Gln Ala Pro Gly Gln Gly Leu Glu Trp Met
        35                  40                  45
Gly Tyr Ile Asn Pro Ser Ser Ala Tyr Thr Asn Tyr Ala Gln Lys Phe
    50                  55                  60
Gln Gly Arg Val Thr Leu Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Ser Pro Gln Val His Tyr Asp Tyr Asn Gly Phe Pro Tyr Trp Gly
            100                 105                 110
Gln Gly Thr Leu Val Thr Val Ser Ser
        115                 120
```

<210> SEQ ID NO 104
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 104

```
caggttcagc tggttcagtc tggcgccgaa gtgaagaaac ctggctcctc cgtcaaggtg      60
tcctgcaagg cttccggcta cacctttacc agatccacca tgcactgggt ccgacaggct     120
ccaggccaag gcttggagtg gatgggctac atcaacccca gctccgccta caccaactac     180
```

```
gcccagaaat tccagggcag agtcaccctc accgccgaca agtctacctc caccgcctac    240
atggaactgt ccagcctgag atctgaggac accgccgtgt actactgcgc cagccctcag    300
gtgcactacg actacaacgg cttcccttat tggggccagg gcaccctggt taccgtttct    360
tct                                                                  363
```

<210> SEQ ID NO 105
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Arg Ser
            20                  25                  30

Thr Met His Trp Val Arg Gln Ala Pro Gly Gln Gly Leu Glu Trp Met
        35                  40                  45

Gly Tyr Ile Asn Pro Ser Ser Ala Tyr Thr Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Pro Gln Val His Tyr Asp Tyr Gly Gly Phe Pro Tyr Trp Gly
            100                 105                 110

Gln Gly Thr Leu Val Thr Val Ser Ser
        115                 120
```

<210> SEQ ID NO 106
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106

```
caggttcaac tggttcagtc tggcgccgaa gtgaagaaac ctggctcctc cgtgaaagtg    60
tcctgcaagg cttccggcta cactttacc agatccacca tgcactgggt ccgacaggct    120
ccaggacaag gcttggagtg gatgggctac atcaacccca gctccgccta caccaactac    180
gcccagaaat tccagggcag agtgaccctg accgccgaca agtctacctc caccgcctac    240
atggaactgt ccagcctgag atctgaggac accgccgtgt actactgcgc ttctcctcag    300
gtgcactacg actacggcgg cttccttat tggggccagg gcacactggt caccgtttct    360
tct                                                                  363
```

<210> SEQ ID NO 107
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Tyr
            20                  25                  30

Asn Met Asn Trp Val Arg Gln Ala Pro Gly Lys Gly Leu Glu Trp Val
        35                  40                  45

Ser Ser Ile Ser Thr Ser Ser Asn Tyr Ile Tyr Tyr Ala Asp Ser Val
50                  55                  60

Lys Gly Arg Phe Thr Phe Ser Arg Asp Asn Ala Lys Asn Ser Leu Asp
65                  70                  75                  80

Leu Gln Met Ser Gly Leu Arg Ala Glu Asp Thr Ala Ile Tyr Tyr Cys
                85                  90                  95

Thr Arg Gly Trp Gly Pro Phe Asp Tyr Trp Gly Gln Gly Thr Leu Val
            100                 105                 110

Thr Val Ser Ser
            115
```

<210> SEQ ID NO 108
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 108

```
gaggtgcaac tggtggagtc tgggggaggc ctggtcaagc ctggggggtc cctgagactc      60
tcctgtgcag cctctggatt caccttcagt agatataaca tgaactgggt ccgccaggct     120
ccagggaagg gctggagtg gtctcatcc attagtacta gtagtaatta catatactac      180
gcagactcag tgaagggccg attcaccttc tccagagaca acgccaagaa ctcactggat    240
ctgcaaatga gcggcctgag agccgaggac acggctattt attactgtac gagaggctgg    300
gggccttttg actactgggg ccagggaacc ctggtcaccg tctcctca                 348
```

<210> SEQ ID NO 109
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

```
Asp Ile Gln Met Thr Gln Ser Pro Ser Ser Leu Ser Ala Ser Val Gly
1               5                   10                  15

Asp Arg Val Thr Ile Thr Cys Arg Ala Arg Gln Ser Ile Gly Thr Ala
            20                  25                  30

Ile His Trp Tyr Gln Gln Lys Pro Gly Lys Ala Pro Lys Leu Leu Ile
        35                  40                  45

Lys Tyr Ala Ser Glu Ser Ile Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Ser Trp Pro Tyr
                85                  90                  95

Thr Phe Gly Gln Gly Thr Lys Leu Glu Ile Lys
            100                 105
```

<210> SEQ ID NO 110
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
gacatacaaa tgacacaatc accctcttct ctttctgcaa gcgttggcga ccgtgtcact      60
atcacttgtc gagcccgcca gtccataggt actgccattc actggtatca acagaagcct     120
ggcaaggctc ccaaactcct gattaagtat gccagcgaga gcatttccgg cgtaccttca     180
agattttccg gctccggtag tgggacagat ttcactctca ctatatctag cctccaacca     240
gaagatttcg ccacttacta ctgtcaacaa tcaggttcat ggccttacac tttcggccag     300
gggacaaaat tggagatcaa g                                               321

<210> SEQ ID NO 111
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Asp Gly Ile Tyr Gly Glu Leu Asp Phe Trp Gly Gln Gly
            100                 105                 110

Thr Leu Val Thr Val Ser Ser
        115

<210> SEQ ID NO 112
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
gaggtgcagt tgctggagtc cggggggtgga ctcgtacaac ctggaggttc tctgcggttg      60
tcctgtgctg ccagcggatt cacatttttcc tcttatgcca tgtcctgggt acgtcaagca    120
cccggcaaag gacttgagtg ggtctccgct atcagtggtt caggggggatc aacctactat    180 gctgatagtg ttaaggggcg ttttaccatc tcaagagaca actccaagaa caccctgtac    240
ctgcagatga actcactccg cgccgaggat acagcagttt actactgtgc taagtatgac    300

```
ggcatttacg gcgaactgga cttttgggga caggggacct tggtcacagt ctccagc      357
```

<210> SEQ ID NO 113
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105
```

<210> SEQ ID NO 114
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114

```
gatattcaga tgactcagag cccctcttca ctgagtgcct cagtagggga tcgtgtgact      60
atcacctgtc gtgcttccca aagcatctcc tcatatttga actggtacca gcagaagcca     120
ggcaaggcac ccaaactgct gatttacgcc gccagttctc tccagagtgg cgttcccagc     180
cgtttctcag gttctggatc tggtaccgat ttcacattga ccatatcatc cctccagcct     240
gaggacttcg ccacctacta ttgccaacag tcatattcta ctccacttac attcggccag     300
ggcaccaagg tggaaattaa g                                               321
```

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

```
Gly Tyr Thr Phe Thr Ser Tyr Asn Met His
1               5                   10
```

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 116

Ala Ile Tyr Pro Gly Asn Gly Asp Thr Ser
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ser Thr Tyr Tyr Gly Gly Asp Trp Tyr Phe Asn Val
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Ala Ser Ser Val Ser Tyr Ile His
1               5                   10

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ala Thr Ser Asn Leu Ala Ser
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gln Gln Trp Thr Ser Asn Pro Pro Thr
1               5

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Tyr Thr Phe Ser Ser Tyr Asn Met His
1               5                   10

<210> SEQ ID NO 122
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ala Ile Tyr Pro Gly Ala Gly Asp Thr Ser
1               5                   10

<210> SEQ ID NO 123
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ser Asn Tyr Tyr Gly Ser Ser Gly Trp Tyr Phe Asp Val
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Ala Ser Leu Ser Val Ser Ser Met His
1               5                   10

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gln Gln Trp Ile Phe Asn Pro Pro Thr
1               5

<210> SEQ ID NO 126
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Arg Gln Ala Pro Gly Gln Gly Leu Glu Trp Met
        35                  40                  45

Gly Ala Ile Tyr Pro Gly Asn Gly Asp Thr Ser Tyr Ala Gln Lys Phe
    50                  55                  60

Gln Gly Arg Val Thr Ile Thr Ala Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
             85                  90                  95

Ala Arg Ser Thr Tyr Tyr Gly Gly Asp Trp Tyr Phe Asn Val Trp Gly
            100                 105                 110

Gln Gly Thr Leu Val Thr Val Ser Ser
        115                 120

<210> SEQ ID NO 127
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127
caggttcagc tggttcagtc tggtgccgaa gtgaagaaac ctggctcctc cgtgaaagtg      60
tcctgcaagg cttccggcta cactttttacc agctacaaca tgcactgggt ccgacaggcc   120
cctggacaag gattggaatg gatgggcgct atctaccccg caacggcga tacctcttac     180 gcccagaaat tccagggcag agtgaccatc accgccgaca gtctacctc accgcctac      240 atggaactgt ccagcctgag atctgaggac accgccgtgt actactgcgc ccggtctacc   300
tattatggcg gcgactggta cttcaacgtg tggggccagg gaaccctggt cacagtctct   360
tct                                                                  363

<210> SEQ ID NO 128
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Ala Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Ile
            20                  25                  30

His Trp Phe Gln Gln Lys Pro Gly Lys Ala Pro Lys Pro Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Thr Ser Asn Pro Pro Thr
                85                  90                  95

Phe Gly Gln Gly Thr Lys Leu Glu Ile Lys
            100                 105

<210> SEQ ID NO 129
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129
gccattcagc tgacccagtc tccatcctct ctgtccgcct ctgtgggcga cagagtgaca      60
```

```
attacctgcc gggcctcctc ctccgtgtcc tacatccatt ggttccagca gaagcccggc    120
aaggccccta agcctctgat ctacgccacc tccaatctgg cctctggcgt gccctccaga    180
ttttccggat ctggctctgg aaccgacttt accctgacaa tctccagcct gcagcctgag    240
gacttcgcca cctactactg tcagcagtgg accagcaatc ctcctacctt tggccagggc    300
accaagctgg aaatcaag                                                  318
```

<210> SEQ ID NO 130
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Asn Met His Trp Val Arg Gln Ala Pro Gly Gln Gly Leu Glu Trp Met
        35                  40                  45

Gly Ala Ile Tyr Pro Gly Ala Gly Asp Thr Ser Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asn Tyr Tyr Gly Ser Ser Gly Trp Tyr Phe Asp Val Trp
            100                 105                 110

Gly Lys Gly Thr Thr Val Thr Val Ser Ser
        115                 120
```

<210> SEQ ID NO 131
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131

```
caggttcaac tggttcagtc tggcgccgaa gtgaagaaac ctggctcctc cgtgaaggtg     60
tcctgcaagg cttccggcta caccttctcc agctacaaca tgcactgggt ccgacaggcc    120
cctggacaag gattggaatg gatgggcgct atctaccctg gcgctggcga tacctcttac    180
gcccagaaat tccagggcag agtgaccatc accgccgacg agtctacctc caccgcctac    240
atggaactgt ccagcctgag atctgaggac accgccgtgt actactgcgc ccggtctaat    300
tactacggct ccagcggctg gtacttcgac gtgtggggaa agggcaccac cgtgacagtc    360
tcttct                                                              366
```

<210> SEQ ID NO 132
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Leu Ser Val Ser Ser Met
            20                  25                  30

His Trp Tyr Gln Gln Lys Pro Gly Gln Ala Pro Arg Leu Leu Ile Tyr
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ile Phe Asn Pro Pro Thr
                85                  90                  95

Phe Gly Gly Gly Thr Lys Val Glu Ile Lys
            100                 105

<210> SEQ ID NO 133
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133
gagatcgtgc tgacccagtc tccagccaca ctgtcactgt ctccaggcga gagagctacc      60
ctgtcctgta gagcctctct gtccgtgtcc tccatgcact ggtatcagca aaagcctgga     120
caggcccctc ggctgctgat ctacgctacc tctaatctgg ccagcggtat ccccgccaga     180 tttttctggtt ctggctctgg caccgacttt accctgacca tctccagcct ggaacctgag     240
gacttcgccg tgtactactg ccagcagtgg atcttcaacc ctcctacctt tggcggaggc     300
accaaggtgg aaatcaag                                                    318

<210> SEQ ID NO 134
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Val Tyr Tyr Gly Ser Asn Tyr Trp Tyr Phe Asp Val Trp Gly
            100                 105                 110

Thr Gly Thr Thr Val Thr Val Ser Ser

<210> SEQ ID NO 135
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135
caagcatatc tgcaacagag cggagctgag ctggttcggc ctggcgcctc tgtaaaaatg    60
agttgcaagg ccagtggtta tacattcaca tcatataata tgcactgggt aaagcaaact   120
ccccgacagg ggcttgaatg gattggcgca atctatcccg gcaatgggga tacatcctac   180
aatcagaaat tcaagggcaa ggcaacactg accgttgaca atcctcatc aacagcctac    240 atgcagctca gttccctcac tagcgaagat tctgctgtgt atttctgtgc aagggtgtat   300
tatggttcta attactggta tttcgatgtt tggggaaccg gaactaccgt aactgtttct   360
agc                                                                 363

<210> SEQ ID NO 136
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Gln Val Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Thr Ala Thr Tyr Tyr Cys Gln Gln Trp Ile Phe Asn Pro Pro Thr
                85                  90                  95

Phe Gly Ser Gly Thr Lys Leu Glu Ile Arg
            100                 105

<210> SEQ ID NO 137
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
caaatagtcc tttcacagtc cccagctatt ctttcagcct ctcccggtga aaaggttaca    60
atgacctgcc gggcaagctc cagtgtctca tatatgcact ggtaccaaca aaaacctggc   120
agtagtcctc aggtgtggat ctacgctaca agcaatctcg cttccggggt tcccgtgagg   180
tttagcggaa gcgggtctgg aactagttat tccttgacaa ttagtcgggt tgaagccgag   240
gacaccgcca cttactattg ccaacagtgg atattcaatc cacccacctt cggttcaggt   300
accaagctcg aaatccgt                                                    318

<210> SEQ ID NO 138
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Ala Tyr Leu Gln Gln Ser Gly Ala Glu Leu Val Arg Pro Gly Ala
1               5                   10                  15

Ser Val Lys Met Ser Cys Lys Thr Ser Gly Tyr Thr Phe Ser Ser Tyr
            20                  25                  30

Asn Met His Trp Val Lys Gln Thr Pro Arg Gln Ala Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Thr Arg Ser Asn Tyr Tyr Gly Ser Ser Gly Trp Tyr Phe Asp Val Trp
            100                 105                 110

Gly Thr Gly Thr Thr Val Thr Val Ser Ser
        115                 120

<210> SEQ ID NO 139
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139
caagcctatc ttcaacaatc tggggctgag cttgtccggc caggagcctc cgtcaaaatg    60
agctgcaaaa cctcaggtta tactttagt agctataaca tgcattgggt aaaacaaacc    120
ccccgacaag cattggagtg gatagggcc atataccccg gcaatggaga cacaagttac    180
aaccagaagt ttaaaggcaa agctacactc acagttgaca aatcctcaag tactgcttat    240
atgcaactct cctctctcac ttccgaagac agtgccgtat attttgcac tcggtccaat    300 tactatggat ctagtggctg gtactttgac gtttggggca ctgggacaac tgttacagtg    360
tccagc                                                               366

<210> SEQ ID NO 140
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gln Ile Val Leu Ser Gln Ser Pro Ala Ile Leu Ser Ala Ser Pro Gly
1               5                   10                  15

Glu Lys Val Thr Met Thr Cys Arg Ala Ser Leu Ser Val Ser Ser Met
            20                  25                  30

His Trp Tyr Gln Gln Lys Pro Gly Ser Ser Pro Lys Pro Trp Ile Tyr
         35                  40                  45

Ala Thr Ser Asn Leu Ala Ser Gly Val Pro Ala Arg Phe Ser Gly Ser
         50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ile Phe Asn Pro Pro Thr
                 85                  90                  95

Phe Gly Gly Gly Thr Lys Leu Glu Ile Lys
             100                 105

<210> SEQ ID NO 141
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141
cagattgtcc tgagccaatc cccagcaatt ctgagtgcta gccctggaga gaaggtaaca      60
atgacttgtc gggcatccct tagcgtctca tccatgcatt ggtatcaaca aaagccaggt     120
tcatctccaa aaccctggat ttacgctaca tctaacctgg catctggggt gcctgccaga     180
tttagtggat ctggttccgg cacatcatat tcccttacaa tcagccgagt ggaagccgag     240
gatgctgcaa cctattactg tcaacaatgg atatttaacc ctcccacctt tgggggtggg     300
actaaactcg aaatcaag                                                   318

<210> SEQ ID NO 142
<211> LENGTH: 746
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Glu Ile Val Leu Thr Gln Ser Pro Ala Thr Leu Ser Ala Ser Pro Gly
1               5                  10                  15

Glu Arg Val Thr Leu Ser Cys Ser Ala Ser Ser Ser Val Ser Tyr Met
             20                  25                  30

Asn Trp Tyr Gln Gln Lys Pro Gly Gln Ala Pro Arg Arg Trp Ile Tyr
         35                  40                  45

Asp Ser Ser Lys Leu Ala Ser Gly Val Pro Ala Arg Phe Ser Gly Ser
         50                  55                  60

Gly Ser Gly Arg Asp Tyr Thr Leu Thr Ile Ser Ser Leu Glu Pro Glu
65                  70                  75                  80

Asp Phe Ala Val Tyr Tyr Cys Gln Gln Trp Ser Arg Asn Pro Pro Thr
                 85                  90                  95

Phe Gly Gly Gly Thr Lys Val Glu Ile Lys Gly Gly Ser Glu Gly Lys
             100                 105                 110

Ser Ser Gly Ser Gly Ser Glu Ser Lys Ser Thr Gly Gly Ser Gln Val
         115                 120                 125

Gln Leu Val Gln Ser Gly Ala Glu Val Lys Lys Pro Gly Ser Ser Val
     130                 135                 140

Lys Val Ser Cys Lys Ala Ser Gly Tyr Thr Phe Thr Arg Ser Thr Met
145                 150                 155                 160

-continued

His Trp Val Lys Gln Ala Pro Gly Gln Gly Leu Glu Trp Ile Gly Tyr
                    165                 170                 175

Ile Asn Pro Ser Ser Ala Tyr Thr Asn Tyr Asn Gln Lys Phe Gln Gly
                180                 185                 190

Arg Val Thr Leu Thr Ala Asp Lys Ser Thr Ser Thr Ala Tyr Met Glu
            195                 200                 205

Leu Ser Ser Leu Arg Ser Glu Asp Thr Ala Val Tyr Tyr Cys Ala Ser
        210                 215                 220

Pro Gln Val His Tyr Asp Tyr Ala Gly Phe Pro Tyr Trp Gly Gln Gly
225                 230                 235                 240

Thr Leu Val Thr Val Ser Ser Glu Pro Lys Ser Ser Asp Lys Thr His
                245                 250                 255

Thr Cys Pro Pro Cys Pro Ala Pro Glu Ala Ala Gly Gly Pro Ser Val
                260                 265                 270

Phe Leu Phe Pro Pro Lys Pro Lys Asp Thr Leu Met Ile Ser Arg Thr
            275                 280                 285

Pro Glu Val Thr Cys Val Val Val Ser Val Ser His Glu Asp Pro Glu
        290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
                340                 345                 350

Cys Lys Val Ser Asn Lys Ala Leu Pro Ala Pro Ile Glu Lys Thr Ile
            355                 360                 365

Ser Lys Ala Lys Gly Gln Pro Arg Glu Pro Gln Val Tyr Thr Leu Pro
        370                 375                 380

Pro Ser Arg Glu Glu Met Thr Lys Asn Gln Val Ser Leu Trp Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
                420                 425                 430

Asp Gly Ser Phe Phe Leu Tyr Ser Lys Leu Thr Val Asp Lys Ser Arg
            435                 440                 445

Trp Gln Gln Gly Asn Val Phe Ser Cys Ser Val Met His Glu Ala Leu
        450                 455                 460

His Asn His Tyr Thr Gln Lys Ser Leu Ser Leu Ser Pro Gly Lys Gly
465                 470                 475                 480

Gly Ser Glu Gly Lys Ser Ser Gly Ser Gly Ser Glu Ser Lys Ser Thr
                485                 490                 495

Gly Gly Ser Ala Ile Gln Leu Thr Gln Ser Pro Ser Ser Leu Ser Ala
                500                 505                 510

Ser Val Gly Asp Arg Val Thr Ile Thr Cys Arg Ala Ser Ser Ser Val
            515                 520                 525

Ser Tyr Ile His Trp Phe Gln Gln Lys Pro Gly Lys Ala Pro Lys Pro
        530                 535                 540

Leu Ile Tyr Ala Thr Ser Asn Leu Ala Ser Gly Val Pro Ser Arg Phe
545                 550                 555                 560

Ser Gly Ser Gly Ser Gly Thr Asp Phe Thr Leu Thr Ile Ser Ser Leu
                565                 570                 575

Gln Pro Glu Asp Phe Ala Thr Tyr Tyr Cys Gln Gln Trp Thr Ser Asn
            580                 585                 590

Pro Pro Thr Phe Gly Gln Gly Thr Lys Leu Glu Ile Lys Gly Gly Ser
        595                 600                 605

Glu Gly Lys Ser Ser Gly Ser Gly Ser Glu Ser Lys Ser Thr Gly Gly
    610                 615                 620

Ser Gln Val Gln Leu Val Gln Ser Gly Ala Glu Val Lys Lys Pro Gly
625                 630                 635                 640

Ser Ser Val Lys Val Ser Cys Lys Ala Ser Gly Tyr Thr Phe Thr Ser
                645                 650                 655

Tyr Asn Met His Trp Val Arg Gln Ala Pro Gly Gln Gly Leu Glu Trp
            660                 665                 670

Met Gly Ala Ile Tyr Pro Gly Asn Gly Asp Thr Ser Tyr Ala Gln Lys
        675                 680                 685

Phe Gln Gly Arg Val Thr Ile Thr Ala Asp Lys Ser Thr Ser Thr Ala
690                 695                 700

Tyr Met Glu Leu Ser Ser Leu Arg Ser Glu Asp Thr Ala Val Tyr Tyr
705                 710                 715                 720

Cys Ala Arg Ser Thr Tyr Tyr Gly Gly Asp Trp Tyr Phe Asn Val Trp
                725                 730                 735

Gly Gln Gly Thr Leu Val Thr Val Ser Ser
            740                 745

<210> SEQ ID NO 143
<211> LENGTH: 2238
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143
gagatcgtgc tgacccagtc tcctgccaca ctgagtgctt ctccaggcga gagagtgacc      60
ctgtcctgct ccgcttcctc ctccgtgtcc tacatgaact ggtatcagca gaagcccggc     120
caggctcctc ggagatggat ctacgactct tccaagctgg cctctggtgt gccagccaga     180
ttttctggct ctggctccgg cagagactat accctgacca tctccagcct ggaacctgag     240
gacttcgccg tgtactactg ccagcagtgg tctaggaacc tcctaccctt ggcggaggc      300 accaaggtgg aaatcaaggg cggatctgag ggaaagtcca gcggctccgg cagcgaaagc     360
aagtccaccg gcggaagcca ggttcaactg gttcagtctg gcgccgaagt gaagaaacct     420
ggctcctccg tcaaggtgtc ctgcaaggct tccggctaca cctttaccag atccaccatg     480
cactgggtca gcaggcccc tggacaaggc ttggagtgga tcggctacat caaccccagc     540
tccgcctaca ccaactacaa ccagaaattc cagggcagag tgaccctgac cgccgacaag     600
tctacctcca ccgcctacat ggaactgtcc agcctgagat ctgaggacac cgccgtgtac     660
tactgcgcct ctcctcaggt ccactacgac tacgccggct tccttattg gggccagggc     720 acactggtca ccgtttcttc tgagcccaaa tctagcgaca aaactcacac atgcccaccg     780
tgcccagcac ctgaagccgc cggggggaccg tcagtcttcc tcttccccc aaaacccaag     840 gacaccctca tgatctcccg gacccctgag gtcacatgcg tggtggtgag cgtgagccac     900
gaagaccctg aggtcaagtt caactggtac gtggacggcg tggaggtgca taatgccaag     960
acaaagccgc gggaggagca gtacaacagc acgtaccgtg tggtcagcgt cctcaccgtc    1020
ctgcaccagg actggctgaa tggcaaggag tacaagtgca aggtgtcgaa caaagccctc    1080

```
ccagccccca tcgagaaaac catctccaaa gccaaagggc agccccgaga accacaggtg    1140
tacaccctgc ccccatcccg ggaggagatg accaagaacc aggtcagcct gtggtgcctg    1200
gtcaaaggct tctatcccag cgacatcgcc gtggagtggg agagcaatgg gcagccggag    1260
aacaactaca agaccacgcc tcccgtgctg gactccgacg gctccttctt cctctacagc    1320
aagctcaccg tggacaagag cagatggcag caggggaacg tcttctcatg ctccgtgatg    1380
catgaggctc tgcacaacca ctacacgcag aagtctctct ccctgtctcc gggaaaagga    1440
gggagcgagg gaaagtccag cggaagcggc tctgagtcca atccaccgg agggagcgcc    1500 attcagctga cccagtctcc atcctctctg tccgcctctg tgggcgacag agtgacaatt    1560
acctgccggg cctcctcctc cgtgtcctac atccattggt tccagcagaa gcccggcaag    1620
gcccctaagc tctgatctca cgccacctcc aatctggcct ctggcgtgcc ctccagattt    1680
tccggatctg gctctggaac cgactttacc ctgacaatct ccagcctgca gcctgaggac    1740
ttcgccacct actactgtca gcagtggacc agcaatcctc ctacctttgg ccagggcacc    1800
aagctggaaa tcaagggcgg ctccgagggc aagagcagcg gcagcggcag cgagagcaag    1860
agcaccggcg gcagccaggt tcagctggtt cagtctggtg ccgaagtgaa gaaacctggc    1920
tcctccgtga agtgtcctg caaggcttcc ggctacactt ttaccagcta caacatgcac    1980
tgggtccgac aggcccctgg acaaggattg aatggatgg cgctatcta ccccggcaac    2040 ggcgatacct cttacgccca gaaattccag ggcagagtga ccatcaccgc cgacaagtct    2100
acctccaccg cctacatgga actgtccagc ctgagatctg aggacaccgc cgtgtactac    2160
tgcgcccggt ctacctatta tggcggcgac tggtacttca cgtgtgggg ccagggaacc    2220 ctggtcacag tctcttct                                                   2238
```

<210> SEQ ID NO 144  
<211> LENGTH: 746  
<212> TYPE: PRT  
<213> ORGANISM: Artificial Sequence  
<220> FEATURE:  
<223> OTHER INFORMATION: Description of Artificial Sequence: Synthetic  
      polypeptide

<400> SEQUENCE: 144

```
Glu Ile Val Leu Thr Gln Ser Pro Ala Thr Leu Ser Ala Ser Pro Gly
1               5                   10                  15

Glu Arg Val Thr Leu Ser Cys Ser Ala Ser Ser Ser Val Ser Tyr Met
            20                  25                  30

Asn Trp Tyr Gln Gln Lys Pro Gly Gln Ala Pro Arg Trp Ile Tyr
        35                  40                  45

Asp Ser Ser Lys Leu Ala Ser Gly Val Pro Ala Arg Phe Ser Gly Ser
    50                  55                  60

Gly Ser Gly Arg Asp Tyr Thr Leu Thr Ile Ser Ser Leu Glu Pro Glu
65                  70                  75                  80

Asp Phe Ala Val Tyr Tyr Cys Gln Gln Trp Ser Arg Asn Pro Pro Thr
                85                  90                  95

Phe Gly Gly Gly Thr Lys Val Glu Ile Lys Gly Gly Ser Glu Gly Lys
            100                 105                 110

Ser Ser Gly Ser Gly Ser Glu Ser Lys Ser Thr Gly Gly Ser Gln Val
        115                 120                 125

Gln Leu Val Gln Ser Gly Ala Glu Val Lys Lys Pro Gly Ser Ser Val
    130                 135                 140
```

```
Lys Val Ser Cys Lys Ala Ser Gly Tyr Thr Phe Thr Arg Ser Thr Met
145                 150                 155                 160

His Trp Val Arg Gln Ala Pro Gly Gln Gly Leu Glu Trp Met Gly Tyr
            165                 170                 175

Ile Asn Pro Ser Ser Ala Tyr Thr Asn Tyr Ala Gln Lys Phe Gln Gly
            180                 185                 190

Arg Val Thr Leu Thr Ala Asp Lys Ser Thr Ser Thr Ala Tyr Met Glu
            195                 200                 205

Leu Ser Ser Leu Arg Ser Glu Asp Thr Ala Val Tyr Tyr Cys Ala Ser
210                 215                 220

Pro Gln Val His Tyr Asp Tyr Gly Gly Phe Pro Tyr Trp Gly Gln Gly
225             230                 235                 240

Thr Leu Val Thr Val Ser Ser Glu Pro Lys Ser Ser Asp Lys Thr His
            245                 250                 255

Thr Cys Pro Pro Cys Pro Ala Pro Glu Ala Ala Gly Gly Pro Ser Val
            260                 265                 270

Phe Leu Phe Pro Pro Lys Pro Lys Asp Thr Leu Met Ile Ser Arg Thr
            275                 280                 285

Pro Glu Val Thr Cys Val Val Val Ser Val Ser His Glu Asp Pro Glu
290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
            325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
            355                 360                 365

Ser Lys Ala Lys Gly Gln Pro Arg Glu Pro Gln Val Tyr Thr Leu Pro
370                 375                 380

Pro Ser Arg Glu Glu Met Thr Lys Asn Gln Val Ser Leu Trp Cys Leu
385                 390                 395                 400

Val Lys Gly Phe Tyr Pro Ser Asp Ile Ala Val Glu Trp Glu Ser Asn
            405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
            435                 440                 445

Trp Gln Gln Gly Asn Val Phe Ser Cys Ser Val Met His Glu Ala Leu
450                 455                 460

His Asn His Tyr Thr Gln Lys Ser Leu Ser Leu Ser Pro Gly Lys Gly
465                 470                 475                 480

Gly Ser Glu Gly Lys Ser Ser Gly Ser Gly Ser Glu Ser Lys Ser Thr
            485                 490                 495

Gly Gly Ser Ala Ile Gln Leu Thr Gln Ser Pro Ser Ser Leu Ser Ala
            500                 505                 510

Ser Val Gly Asp Arg Val Thr Ile Thr Cys Arg Ala Ser Ser Ser Val
            515                 520                 525

Ser Tyr Ile His Trp Phe Gln Gln Lys Pro Gly Lys Ala Pro Lys Pro
            530                 535                 540

Leu Ile Tyr Ala Thr Ser Asn Leu Ala Ser Gly Val Pro Ser Arg Phe
545                 550                 555                 560

Ser Gly Ser Gly Ser Gly Thr Asp Phe Thr Leu Thr Ile Ser Ser Leu
```

-continued

```
                   565                 570                 575
Gln Pro Glu Asp Phe Ala Thr Tyr Tyr Cys Gln Gln Trp Thr Ser Asn
                580                 585                 590

Pro Pro Thr Phe Gly Gln Gly Thr Lys Leu Glu Ile Lys Gly Gly Ser
            595                 600                 605

Glu Gly Lys Ser Ser Gly Ser Gly Ser Glu Ser Lys Ser Thr Gly Gly
        610                 615                 620

Ser Gln Val Gln Leu Val Gln Ser Gly Ala Glu Val Lys Lys Pro Gly
625                 630                 635                 640

Ser Ser Val Lys Val Ser Cys Lys Ala Ser Gly Tyr Thr Phe Thr Ser
                645                 650                 655

Tyr Asn Met His Trp Val Arg Gln Ala Pro Gly Gln Gly Leu Glu Trp
            660                 665                 670

Met Gly Ala Ile Tyr Pro Gly Asn Gly Asp Thr Ser Tyr Ala Gln Lys
        675                 680                 685

Phe Gln Gly Arg Val Thr Ile Thr Ala Asp Lys Ser Thr Ser Thr Ala
    690                 695                 700

Tyr Met Glu Leu Ser Ser Leu Arg Ser Glu Asp Thr Ala Val Tyr Tyr
705                 710                 715                 720

Cys Ala Arg Ser Thr Tyr Tyr Gly Gly Asp Trp Tyr Phe Asn Val Trp
                725                 730                 735

Gly Gln Gly Thr Leu Val Thr Val Ser Ser
            740                 745

<210> SEQ ID NO 145
<211> LENGTH: 2238
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
gagatcgtgc tgacccagtc tcctgccaca ctgagtgctt ctccaggcga gagagtgacc      60
ctgtcctgct ccgcttcctc ctccgtgtcc tacatgaact ggtatcagca gaagcccggc     120
caggctcctc ggagatggat ctacgactct tccaagctgg cctctggtgt gccagccaga     180
ttttctggct ctggctccgg cagagactat accctgacca tctccagcct ggaacctgag     240
gacttcgccg tgtactactg ccagcagtgg tctaggaacc ctcctacctt tggcggaggc     300
accaaggtgg aaatcaaggg cggatctgag ggaaagtcca gcggctccgg cagcgaaagc     360
aagtccaccg gcggaagcca ggttcaactg gttcagtctg gcgccgaagt gaagaaacct     420
ggctcctccg tgaaagtgtc ctgcaaggct tccggctaca cttttaccag atccaccatg     480
cactgggtcc gacaggctcc aggacaaggc ttggagtgga tgggctacat caaccccagc     540
tccgcctaca ccaactacgc ccagaaattc cagggcagag tgaccctgac cgccgacaag     600
tctacctcca ccgcctacat ggaactgtcc agcctgagat ctgaggacac cgccgtgtac     660
tactgcgctt ctcctcaggt gcactacgac tacgcggct ttccttattg gggccagggc     720
acactggtca ccgtttcttc tgagcccaaa tctagcgaca aaactcacac atgcccaccg     780
tgcccagcac ctgaagccgc ggggggaccg tcagtcttcc tcttcccccc aaaacccaag     840
gacaccctca tgatctcccg gacccctgag gtcacatgcg tggtggtgag cgtgagccac     900
gaagaccctg aggtcaagtt caactggtac gtggacggcg tggaggtgca taatgccaag     960
acaaagccgc gggaggagca gtacaacagc acgtaccgtg tggtcagcgt cctcaccgtc    1020
```

-continued

```
ctgcaccagg actggctgaa tggcaaggag tacaagtgca aggtgtcgaa caaagccctc    1080
ccagccccca tcgagaaaac catctccaaa gccaaagggc agccccgaga ccacaggtg    1140 tacaccctgc ccccatcccg ggaggagatg accaagaacc aggtcagcct gtggtgcctg    1200
gtcaaaggct tctatcccag cgacatcgcc gtggagtggg agagcaatgg gcagccggag    1260
aacaactaca agaccacgcc tcccgtgctg gactccgacg gctccttctt cctctacagc    1320
aagctcaccg tggacaagag cagatggcag caggggaacg tcttctcatg ctccgtgatg    1380
catgaggctc tgcacaacca ctacacgcag aagtctctct ccctgtctcc gggaaaagga    1440
gggagcgagg gaaagtccag cggaagcggc tctgagtcca aatccaccgg agggagcgcc    1500
attcagctga cccagtctcc atcctctctg tccgcctctg tgggcgacag agtgacaatt    1560
acctgccggg cctcctcctc cgtgtcctac atccattggt tccagcagaa gcccggcaag    1620
gcccctaagc tctgatctca cgccacctcc aatctggcct ctggcgtgcc ctccagattt    1680
tccggatctg gctctggaac cgactttacc ctgacaatct ccagcctgca gcctgaggac    1740
ttcgccacct actactgtca gcagtggacc agcaatcctc tacctttgg ccagggcacc     1800 aagctggaaa tcaagggcgg ctccgagggc aagagcagcg gcagcggcag cgagagcaag    1860
agcaccggcg gcagccaggt tcagctggtt cagtctggtg ccgaagtgaa gaaacctggc    1920
tcctccgtga agtgtcctg caaggcttcc ggctacactt ttaccagcta caacatgcac     1980
tgggtccgac aggcccctgg acaaggattg gaatggatgg gcgctatcta ccccggcaac    2040
ggcgatacct cttacgccca gaaattccag ggcagagtga ccatcaccgc cgacaagtct    2100
acctccaccg cctacatgga actgtccagc ctgagatctg aggacaccgc cgtgtactac    2160
tgcgcccggt ctacctatta tggcggcgac tggtacttca acgtgtgggg ccagggaacc    2220
ctggtcacag tctcttct                                                  2238
```

<210> SEQ ID NO 146
<211> LENGTH: 735
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Gly Gly Ser Glu Gly
            100                 105                 110

Lys Ser Ser Gly Ser Gly Ser Glu Ser Lys Ser Thr Gly Gly Ser Glu
        115                 120                 125

Val Gln Leu Leu Glu Ser Gly Gly Gly Leu Val Gln Pro Gly Gly Ser
```

-continued

```
            130                 135                 140
Leu Arg Leu Ser Cys Ala Ala Ser Gly Phe Thr Phe Ser Ser Tyr Ala
145                 150                 155                 160

Met Ser Trp Val Arg Gln Ala Pro Gly Lys Gly Leu Glu Trp Val Ser
                165                 170                 175

Ala Ile Ser Gly Ser Gly Gly Ser Thr Tyr Tyr Ala Asp Ser Val Lys
                180                 185                 190

Gly Arg Phe Thr Ile Ser Arg Asp Asn Ser Lys Asn Thr Leu Tyr Leu
                195                 200                 205

Gln Met Asn Ser Leu Arg Ala Glu Asp Thr Ala Val Tyr Tyr Cys Ala
        210                 215                 220

Lys Tyr Asp Gly Ile Tyr Gly Glu Leu Asp Phe Trp Gly Gln Gly Thr
225                 230                 235                 240

Leu Val Thr Val Ser Ser Glu Pro Lys Ser Ser Asp Lys Thr His Thr
                245                 250                 255

Cys Pro Pro Cys Pro Ala Pro Glu Ala Ala Gly Gly Pro Ser Val Phe
                260                 265                 270

Leu Phe Pro Pro Lys Pro Lys Asp Thr Leu Met Ile Ser Arg Thr Pro
            275                 280                 285

Glu Val Thr Cys Val Val Val Ser Val Ser His Glu Asp Pro Glu Val
        290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
                340                 345                 350

Lys Val Ser Asn Lys Ala Leu Pro Ala Pro Ile Glu Lys Thr Ile Ser
                355                 360                 365

Lys Ala Lys Gly Gln Pro Arg Glu Pro Gln Val Tyr Thr Leu Pro Pro
        370                 375                 380

Ser Arg Glu Glu Met Thr Lys Asn Gln Val Ser Leu Trp Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Val Leu Asp Ser Asp
                420                 425                 430

Gly Ser Phe Phe Leu Tyr Ser Lys Leu Thr Val Asp Lys Ser Arg Trp
                435                 440                 445

Gln Gln Gly Asn Val Phe Ser Cys Ser Val Met His Glu Ala Leu His
        450                 455                 460

Asn His Tyr Thr Gln Lys Ser Leu Ser Leu Ser Pro Gly Lys Gly Gly
465                 470                 475                 480

Gly Gly Ser Gly Gly Gly Gly Ser Ala Ile Gln Leu Thr Gln Ser Pro
                485                 490                 495

Ser Ser Leu Ser Ala Ser Val Gly Asp Arg Val Thr Ile Thr Cys Arg
                500                 505                 510

Ala Ser Ser Ser Val Ser Tyr Ile His Trp Phe Gln Gln Lys Pro Gly
                515                 520                 525

Lys Ala Pro Lys Pro Leu Ile Tyr Ala Thr Ser Asn Leu Ala Ser Gly
        530                 535                 540

Val Pro Ser Arg Phe Ser Gly Ser Gly Ser Gly Thr Asp Phe Thr Leu
545                 550                 555                 560
```

Thr Ile Ser Ser Leu Gln Pro Glu Asp Phe Ala Thr Tyr Tyr Cys Gln
            565                 570                 575

Gln Trp Thr Ser Asn Pro Pro Thr Phe Gly Gln Gly Thr Lys Leu Glu
        580                 585                 590

Ile Lys Gly Gly Ser Glu Gly Lys Ser Ser Gly Ser Gly Ser Glu Ser
            595                 600                 605

Lys Ser Thr Gly Gly Ser Gln Val Gln Leu Val Gln Ser Gly Ala Glu
        610                 615                 620

Val Lys Lys Pro Gly Ser Ser Val Lys Val Ser Cys Lys Ala Ser Gly
625                 630                 635                 640

Tyr Thr Phe Thr Ser Tyr Asn Met His Trp Val Arg Gln Ala Pro Gly
            645                 650                 655

Gln Gly Leu Glu Trp Met Gly Ala Ile Tyr Pro Gly Asn Gly Asp Thr
        660                 665                 670

Ser Tyr Ala Gln Lys Phe Gln Gly Arg Val Thr Ile Thr Ala Asp Lys
    675                 680                 685

Ser Thr Ser Thr Ala Tyr Met Glu Leu Ser Ser Leu Arg Ser Glu Asp
        690                 695                 700

Thr Ala Val Tyr Tyr Cys Ala Arg Ser Thr Tyr Tyr Gly Gly Asp Trp
705                 710                 715                 720

Tyr Phe Asn Val Trp Gly Gln Gly Thr Leu Val Thr Val Ser Ser
            725                 730                 735

<210> SEQ ID NO 147
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 147
gatattcaga tgactcagag cccctcttca ctgagtgcct cagtagggga tcgtgtgact      60
atcacctgtc gtgcttccca aagcatctcc tcatatttga actggtacca gcagaagcca     120
ggcaaggcac ccaaactgct gatttacgcc gccagttctc tccagagtgg cgttcccagc     180
cgtttctcag gttctggatc tggtaccgat ttcacattga ccatatcatc cctccagcct     240
gaggacttcg ccacctacta ttgccaacag tcatattcta ctccacttac attcggccag     300
ggcaccaagg tggaaattaa gggcggctcc gagggcaaga gcagcggcag cggcagcgag     360
agcaagagca ccggcggcag cgaggtgcag ttgctggagt ccggggggtgg actcgtacaa     420 cctggaggtt ctctgcggtt gtcctgtgct gccagcggat tcacattttc ctcttatgcc     480
atgtcctggg tacgtcaagc acccggcaaa ggacttgagt gggtctccgc tatcagtggt     540 tcaggggat caacctacta tgctgatagt gttaaggggc gttttaccat ctcaagagac     600
aactccaaga cacccctgta cctgcagatg aactcactcc gcgccgagga tacagcagtt     660
tactactgtg ctaagtatga cggcatttac ggcgaactgg acttttgggg acaggggacc     720
ttggtcacag tctccagcga gcccaaatct agcgacaaaa ctcacacatg tccaccgtgc     780
ccagcacctg aagcagcagg ggaccgtca gtcttcctct ccccccaaa acccaaggac     840 accctcatga tctcccggac ccctgaggtc acatgcgtgg tggtgagcgt gagccacgaa     900
gaccctgagg tcaagttcaa ctggtacgtg gacggcgtgg aggtgcataa tgccaagaca     960
aagccgcggg aggagcagta caacagcacg taccgtgtgg tcagcgtcct caccgtcctg    1020

```
caccaggact ggctgaatgg caaggagtac aagtgcaagg tctccaacaa agccctccca    1080
gcccccatcg agaaaaccat ctccaaagcc aaagggcagc cccgagaacc acaggtgtac    1140
accctgcccc catcccggga ggagatgacc aagaaccagg tcagcctgtg gtgcctggtc    1200
aaaggcttct atcccagcga catcgccgtg gagtgggaga gcaatgggca gccggagaac    1260
aactacaaga ccacgcctcc cgtgctggac tccgacggct ccttcttcct ctacagcaag    1320
ctcaccgtgg acaagtctag atggcagcag gggaacgtct tctcatgctc cgtgatgcat    1380
gaggctctgc acaaccacta cacgcagaag agcctctccc tgtctccggg taaaggaggc    1440
ggagggagtg gcgggggagg ctctgcaatc caactaactc aaagtccaag tagtctgtct    1500
gcttccgtgg gcgacagagt gacaatcacc tgtagagcct ccagcagcgt ctcctacatc    1560
cactggttcc agcaaaaacc tggcaaggcc cctaagcctc tgatctacgc cacctccaac    1620
ctggcctctg gcgtgccctc tcggttctcc ggctctggct ccggaaccga cttcaccctg    1680
accatctcca gcctgcagcc tgaggatttt gctacctact actgccagca gtggacctct    1740
aaccctccaa cattcggcca gggcaccaag ctggaaatca agggcggctc cgagggcaag    1800
agcagcggca gcggcagcga gagcaagagc accggcggca gccaagtgca attagtgcaa    1860
agtggtgcaa aagtcaagaa gcctggaagc tccgtgaaag tgtcctgcaa ggcctctggc    1920 tacacctta cctcctacaa catgcactgg gtgcggcagg ctcctggcca gggcctggag    1980
tggatgggcg ctatctaccc cggcaacggc gatacctctt acgcccagaa gttccagggc    2040
agagtgacca tcaccgccga caagtccaca tctacagcct acatggaact gtcctccctg    2100
cggtccgagg acaccgctgt gtactattgt gccagatcta cctactacgg cggcgactgg    2160
tacttcaacg tgtggggcca aggaaccctg gtgaccgtgt ctagc                    2205
```

<210> SEQ ID NO 148
<211> LENGTH: 732
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

```
Asp Ile Gln Met Thr Gln Ser Pro Ser Ser Leu Ser Ala Ser Val Gly
1               5                   10                  15

Asp Arg Val Thr Ile Thr Cys Arg Ala Arg Gln Ser Ile Gly Thr Ala
            20                  25                  30

Ile His Trp Tyr Gln Gln Lys Pro Gly Lys Ala Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Ser Trp Pro Tyr
                85                  90                  95

Thr Phe Gly Gln Gly Thr Lys Leu Glu Ile Lys Gly Gly Ser Glu Gly
            100                 105                 110

Lys Ser Ser Gly Ser Gly Ser Glu Ser Lys Ser Thr Gly Gly Ser Glu
        115                 120                 125

Val Gln Leu Val Glu Ser Gly Gly Gly Leu Val Lys Pro Gly Gly Ser
    130                 135                 140

Leu Arg Leu Ser Cys Ala Ala Ser Gly Phe Thr Phe Ser Arg Tyr Asn
```

```
             145                 150                 155                 160
        Met Asn Trp Val Arg Gln Ala Pro Gly Lys Gly Leu Glu Trp Val Ser
                        165                 170                 175

Ser Ile Ser Thr Ser Ser Asn Tyr Ile Tyr Tyr Ala Asp Ser Val Lys
                        180                 185                 190

Gly Arg Phe Thr Phe Ser Arg Asp Asn Ala Lys Asn Ser Leu Asp Leu
                        195                 200                 205

Gln Met Ser Gly Leu Arg Ala Glu Asp Thr Ala Ile Tyr Tyr Cys Thr
                        210                 215                 220

Arg Gly Trp Gly Pro Phe Asp Tyr Trp Gly Gln Gly Thr Leu Val Thr
        225                 230                 235                 240

Val Ser Ser Glu Pro Lys Ser Ser Asp Lys Thr His Thr Cys Pro Pro
                        245                 250                 255

Cys Pro Ala Pro Glu Ala Ala Gly Gly Pro Ser Val Phe Leu Phe Pro
                        260                 265                 270

Pro Lys Pro Lys Asp Thr Leu Met Ile Ser Arg Thr Pro Glu Val Thr
                        275                 280                 285

Cys Val Val Val Ser Val Ser His Glu Asp Pro Glu Val Lys Phe Asn
                        290                 295                 300

Trp Tyr Val Asp Gly Val Glu Val His Asn Ala Lys Thr Lys Pro Arg
        305                 310                 315                 320

Glu Glu Gln Tyr Asn Ser Thr Tyr Arg Val Val Ser Val Leu Thr Val
                        325                 330                 335

Leu His Gln Asp Trp Leu Asn Gly Lys Glu Tyr Lys Cys Lys Val Ser
                        340                 345                 350

Asn Lys Ala Leu Pro Ala Pro Ile Glu Lys Thr Ile Ser Lys Ala Lys
                        355                 360                 365

Gly Gln Pro Arg Glu Pro Gln Val Tyr Thr Leu Pro Pro Ser Arg Glu
                        370                 375                 380

Glu Met Thr Lys Asn Gln Val Ser Leu Trp Cys Leu Val Lys Gly Phe
        385                 390                 395                 400

Tyr Pro Ser Asp Ile Ala Val Glu Trp Glu Ser Asn Gly Gln Pro Glu
                        405                 410                 415

Asn Asn Tyr Lys Thr Thr Pro Pro Val Leu Asp Ser Asp Gly Ser Phe
                        420                 425                 430

Phe Leu Tyr Ser Lys Leu Thr Val Asp Lys Ser Arg Trp Gln Gln Gly
                        435                 440                 445

Asn Val Phe Ser Cys Ser Val Met His Glu Ala Leu His Asn His Tyr
                        450                 455                 460

Thr Gln Lys Ser Leu Ser Leu Ser Pro Gly Lys Gly Gly Gly Gly Ser
        465                 470                 475                 480

Gly Gly Gly Gly Ser Ala Ile Gln Leu Thr Gln Ser Pro Ser Ser Leu
                        485                 490                 495

Ser Ala Ser Val Gly Asp Arg Val Thr Ile Thr Cys Arg Ala Ser Ser
                        500                 505                 510

Ser Val Ser Tyr Ile His Trp Phe Gln Gln Lys Pro Gly Lys Ala Pro
                        515                 520                 525

Lys Pro Leu Ile Tyr Ala Thr Ser Asn Leu Ala Ser Gly Val Pro Ser
                        530                 535                 540

Arg Phe Ser Gly Ser Gly Ser Gly Thr Asp Phe Thr Leu Thr Ile Ser
        545                 550                 555                 560

Ser Leu Gln Pro Glu Asp Phe Ala Thr Tyr Tyr Cys Gln Gln Trp Thr
                        565                 570                 575
```

```
Ser Asn Pro Pro Thr Phe Gly Gln Gly Thr Lys Leu Glu Ile Lys Gly
            580                 585                 590

Gly Ser Glu Gly Lys Ser Ser Gly Ser Gly Ser Glu Ser Lys Ser Thr
            595                 600                 605

Gly Gly Ser Gln Val Gln Leu Val Gln Ser Gly Ala Glu Val Lys Lys
            610                 615                 620

Pro Gly Ser Ser Val Lys Val Ser Cys Lys Ala Ser Gly Tyr Thr Phe
625                 630                 635                 640

Thr Ser Tyr Asn Met His Trp Val Arg Gln Ala Pro Gly Gln Gly Leu
            645                 650                 655

Glu Trp Met Gly Ala Ile Tyr Pro Gly Asn Gly Asp Thr Ser Tyr Ala
            660                 665                 670

Gln Lys Phe Gln Gly Arg Val Thr Ile Thr Ala Asp Lys Ser Thr Ser
            675                 680                 685

Thr Ala Tyr Met Glu Leu Ser Ser Leu Arg Ser Glu Asp Thr Ala Val
            690                 695                 700

Tyr Tyr Cys Ala Arg Ser Thr Tyr Tyr Gly Gly Asp Trp Tyr Phe Asn
705                 710                 715                 720

Val Trp Gly Gln Gly Thr Leu Val Thr Val Ser Ser
            725                 730
```

<210> SEQ ID NO 149
<211> LENGTH: 2196
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149

```
gacatacaaa tgacacaatc accctcttct ctttctgcaa gcgttggcga ccgtgtcact    60
atcacttgtc gagcccgcca gtccataggt actgccattc actggtatca acagaagcct   120
ggcaaggctc ccaaactcct gattaagtat gccagcgaga gcatttccgg cgtaccttca   180
agattttccg gctccggtag tgggacagat ttcactctca ctatatctag cctccaacca   240
gaagatttcg ccacttacta ctgtcaacaa tcaggttcat ggccttacac tttcggccag   300
gggacaaaat tggagatcaa gggcggctcc gagggcaaga gcagcggcag cggcagcgag   360
agcaagagca ccggcggcag cgaggtgcaa ctggtggagt ctgggggagg cctggtcaag   420
cctgggggt ccctgagact ctcctgtgca gcctctggat tcaccttcag tagatataac   480
atgaactggg tccgccaggc tccagggaag gggctggagt gggtctcatc cattagtact   540
agtagtaatt acatatacta cgcagactca gtgaagggcc gattcacctt ctccagagac   600
aacgccaaga actcactgga tctgcaaatg agcggcctga gccgaggac acggctatt    660
tattactgta cgagaggctg ggggccttt gactactggg gccagggaac cctggtcacc   720
gtctcctcag agcccaaatc tagcgacaaa actcacacat gtccaccgtg cccagcacct   780
gaagcagcag ggggaccgtc agtcttcctc ttccccccaa acccaaggga caccctcatg   840
atctcccgga cccctgaggt cacatgcgtg gtggtgagcg tgagccacga agaccctgag   900
gtcaagttca actggtacgt ggacggcgtg gaggtgcata atgccaagac aaagccgcgg   960
gaggagcagt acaacagcac gtaccgtgtg tcagcgtcc tcaccgtcct gcaccaggac  1020
tggctgaatg gcaaggagta caagtgcaag gtctccaaca agccctccc agccccatc   1080
gagaaaacca tctccaaagc caaagggcag ccccgagaac acaggtgta caccctgccc  1140
```

```
ccatcccggg aggagatgac caagaaccag gtcagcctgt ggtgcctggt caaaggcttc    1200
tatcccagcg acatcgccgt ggagtgggag agcaatgggc agccggagaa caactacaag    1260
accacgcctc ccgtgctgga ctccgacggc tccttcttcc tctacagcaa gctcaccgtg    1320
gacaagtcta gatggcagca ggggaacgtc ttctcatgct ccgtgatgca tgaggctctg    1380
cacaaccact acacgcagaa gagcctctcc ctgtctccgg gtaaaggagg cggagggagt    1440 ggcggggag gctctgcaat ccaactaact caaagtccaa gtagtctgtc tgcttccgtg    1500
ggcgacagag tgacaatcac ctgtagagcc tccagcagcg tctcctacat ccactggttc    1560
cagcaaaaac ctggcaaggc ccctaagcct ctgatctacg ccacctccaa cctggcctct    1620
ggcgtgccct ctcggttctc cggctctggc tccggaaccg acttcaccct gaccatctcc    1680
agcctgcagc ctgaggattt tgctacctac tactgccagc agtggacctc taaccctcca    1740
acattcggcc agggcaccaa gctggaaatc aagggcggct ccgagggcaa gagcagcggc    1800
agcggcagcg agagcaagag caccggcggc agccaagtgc aattagtgca aagtggtgca    1860
gaagtcaaga agcctggaag ctccgtgaaa gtgtcctgca aggcctctgg ctacaccttt    1920
acctcctaca acatgcactg ggtgcggcag gctcctggcc agggcctgga gtggatgggc    1980
gctatctacc ccggcaacgg cgataccttct tacgcccaga gttccagggg cagagtgacc    2040
atcaccgccg acaagtccac atctacagcc tacatggaac tgtcctccct gcggtccgag    2100
gacaccgctg tgtactattg tgccagatct acctactacg gcggcgactg gtacttcaac    2160
gtgtggggcc aaggaaccct ggtgaccgtg tctagc                              2196
```

<210> SEQ ID NO 150
<211> LENGTH: 736
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 150

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Arg Ser
            20                  25                  30

Thr Met His Trp Val Arg Gln Ala Pro Gly Gln Gly Leu Glu Trp Met
        35                  40                  45

Gly Tyr Ile Asn Pro Ser Ser Ala Tyr Thr Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Pro Gln Val His Tyr Asp Tyr Gly Gly Phe Pro Tyr Trp Gly
            100                 105                 110

Gln Gly Thr Leu Val Thr Val Ser Ser Gly Gly Ser Glu Gly Lys Ser
        115                 120                 125

Ser Gly Ser Gly Ser Glu Ser Lys Ser Thr Gly Gly Ser Glu Ile Val
    130                 135                 140

Leu Thr Gln Ser Pro Ala Thr Leu Ser Ala Ser Pro Gly Glu Arg Val
145                 150                 155                 160

Thr Leu Ser Cys Ser Ala Ser Ser Ser Val Ser Tyr Met Asn Trp Tyr
```

```
                165                 170                 175
Gln Gln Lys Pro Gly Gln Ala Pro Arg Arg Trp Ile Tyr Asp Ser Ser
            180                 185                 190

Lys Leu Ala Ser Gly Val Pro Ala Arg Phe Ser Gly Ser Gly Ser Gly
            195                 200                 205

Arg Asp Tyr Thr Leu Thr Ile Ser Ser Leu Glu Pro Glu Asp Phe Ala
            210                 215                 220

Val Tyr Tyr Cys Gln Gln Trp Ser Arg Asn Pro Pro Thr Phe Gly Gly
225                 230                 235                 240

Gly Thr Lys Val Glu Ile Lys Glu Pro Lys Ser Ser Asp Lys Thr His
                245                 250                 255

Thr Cys Pro Pro Cys Pro Ala Pro Glu Ala Ala Gly Gly Pro Ser Val
            260                 265                 270

Phe Leu Phe Pro Pro Lys Pro Lys Asp Thr Leu Met Ile Ser Arg Thr
            275                 280                 285

Pro Glu Val Thr Cys Val Val Val Ser Val Ser His Glu Asp Pro Glu
            290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
            355                 360                 365

Ser Lys Ala Lys Gly Gln Pro Arg Glu Pro Gln Val Tyr Thr Leu Pro
            370                 375                 380

Pro Ser Arg Glu Glu Met Thr Lys Asn Gln Val Ser Leu Trp Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
            435                 440                 445

Trp Gln Gln Gly Asn Val Phe Ser Cys Ser Val Met His Glu Ala Leu
            450                 455                 460

His Asn His Tyr Thr Gln Lys Ser Leu Ser Leu Ser Pro Gly Lys Gly
465                 470                 475                 480

Gly Gly Gly Ser Gly Gly Gly Ser Ala Ile Gln Leu Thr Gln Ser
                485                 490                 495

Pro Ser Ser Leu Ser Ala Ser Val Gly Asp Arg Val Thr Ile Thr Cys
            500                 505                 510

Arg Ala Ser Ser Val Ser Tyr Ile His Trp Phe Gln Gln Lys Pro
            515                 520                 525

Gly Lys Ala Pro Lys Pro Leu Ile Tyr Ala Thr Ser Asn Leu Ala Ser
            530                 535                 540

Gly Val Pro Ser Arg Phe Ser Gly Ser Gly Ser Gly Thr Asp Phe Thr
545                 550                 555                 560

Leu Thr Ile Ser Ser Leu Gln Pro Glu Asp Phe Ala Thr Tyr Tyr Cys
                565                 570                 575

Gln Gln Trp Thr Ser Asn Pro Pro Thr Phe Gly Gln Gly Thr Lys Leu
            580                 585                 590
```

Glu Ile Lys Gly Gly Ser Glu Gly Lys Ser Gly Ser Gly Ser Glu
             595                 600                 605

Ser Lys Ser Thr Gly Gly Ser Gln Val Gln Leu Val Gln Ser Gly Ala
         610                 615                 620

Glu Val Lys Lys Pro Gly Ser Ser Val Lys Val Ser Cys Lys Ala Ser
625                 630                 635                 640

Gly Tyr Thr Phe Thr Ser Tyr Asn Met His Trp Val Arg Gln Ala Pro
                645                 650                 655

Gly Gln Gly Leu Glu Trp Met Gly Ala Ile Tyr Pro Gly Asn Gly Asp
            660                 665                 670

Thr Ser Tyr Ala Gln Lys Phe Gln Gly Arg Val Thr Ile Thr Ala Asp
        675                 680                 685

Lys Ser Thr Ser Thr Ala Tyr Met Glu Leu Ser Ser Leu Arg Ser Glu
    690                 695                 700

Asp Thr Ala Val Tyr Tyr Cys Ala Arg Ser Thr Tyr Tyr Gly Gly Asp
705                 710                 715                 720

Trp Tyr Phe Asn Val Trp Gly Gln Gly Thr Leu Val Thr Val Ser Ser
                725                 730                 735

<210> SEQ ID NO 151
<211> LENGTH: 2208
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151
caggtgcagc tggtgcagag cggcgccgag gtgaagaagc ctggcagcag cgtgaaggtg     60
agctgtaagg ccagcggcta cactttcact aggagcacta tgcactgggt gaggcaggcc    120
cctggccagg gcctggagtg gatgggctac atcaatccta gcagcgccta cactaattac    180
gcccagaagt tccagggcag ggtgactctg actgccgata gagcactag cactgcctac    240 atggagctga gcagcctgag gagcgaggat actgccgtgt actactgtgc cagccctcag    300
gtgcactacg attacggcgg cttcccttac tggggccagg gcactctggt gactgtgagc    360
agcggcggct ccgagggcaa gagcagcggc agcggcagcg agagcaagag caccggcggc    420
agcgagatcg tgctgactca gagccctgcc actctgagcg ccagccctgg cgagagggtg    480
actctgagct gtagcgccag cagcagcgtg agctacatga attggtacca gcagaagcct    540
ggccaggccc ctaggaggtg gatctacgat agcagcaagc tggccagcgg cgtgcctgcc    600
aggttcagcg gcagcggcag cggcagggat tacactctga ctatcagcag cctggagcct    660
gaggatttcg ccgtgtacta ctgtcagcag tggagcagga tcctcctac tttcggcggc    720 ggcactaagg tggagatcaa ggagcccaaa tctagcgaca aaactcacac atgtccaccg    780
tgcccagcac ctgaagcagc aggggaccg tcagtcttcc tcttccccc aaaacccaag    840 gacaccctca tgatctcccg gacccctgag gtcacatgcg tggtggtgag cgtgagccac    900
gaagaccctg aggtcaagtt caactggtac gtggacggcg tggaggtgca taatgccaag    960
acaaagccgc gggaggagca gtacaacagc acgtaccgtg tggtcagcgt cctcaccgtc   1020
ctgcaccagg actggctgaa tggcaaggag tacaagtgca aggtctccaa caaagccctc   1080
ccagccccca tcgagaaaac catctccaaa gccaagggc agcccgaga accacaggtg   1140 tacaccctgc ccccatcccg ggaggagatg accaagaacc aggtcagcct gtggtgcctg   1200

```
gtcaaaggct tctatcccag cgacatcgcc gtggagtggg agagcaatgg gcagccggag  1260
aacaactaca agaccacgcc tcccgtgctg gactccgacg gctccttctt cctctacagc  1320
aagctcaccg tggacaagtc tagatggcag caggggaacg tcttctcatg ctccgtgatg  1380
catgaggctc tgcacaacca ctacacgcag aagagcctct ccctgtctcc gggtaaagga  1440
ggcggaggga gtggcggggg aggctctgca atccaactaa ctcaaagtcc aagtagtctg  1500
tctgcttccg tgggcgacag agtgacaatc acctgtagag cctccagcag cgtctcctac  1560
atccactggt tccagcaaaa acctggcaag gcccctaagc tctgatctca cgccacctcc  1620
aacctggcct ctggcgtgcc ctctcggttc tccggctctg gctccggaac cgacttcacc  1680
ctgaccatct ccagcctgca gcctgaggat tttgctacct actactgcca gcagtggacc  1740
tctaaccctc caacattcgg ccagggcacc aagctggaaa tcaagggcgg ctccgagggc  1800
aagagcagcg gcagcggcag cgagagcaag agcaccggcg gcagccaagt gcaattagtg  1860
caaagtggtg cagaagtcaa gaagcctgga agctccgtga agtgtcctg caaggcctct  1920 ggctacacct ttacctccta caacatgcac tgggtgcggc aggctcctgg ccagggcctg  1980
gagtggatgg gcgctatcta ccccggcaac ggcgatacct cttacgccca gaagttccag  2040
ggcagagtga ccatcaccgc cgacaagtcc acatctacag cctacatgga actgtcctcc  2100
ctgcggtccg aggacaccgc tgtgtactat tgtgccagat ctacctacta cggcggcgac  2160
tggtacttca cgtgtggggg ccaaggaacc ctggtgaccg tgtctagc  2208
```

<210> SEQ ID NO 152
<211> LENGTH: 732
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

```
Asp Ile Gln Met Thr Gln Ser Pro Ser Ser Leu Ser Ala Ser Val Gly
1               5                   10                  15

Asp Arg Val Thr Ile Thr Cys Arg Ala Arg Gln Ser Ile Gly Thr Ala
            20                  25                  30

Ile His Trp Tyr Gln Gln Lys Pro Gly Lys Ala Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Ser Trp Pro Tyr
                85                  90                  95

Thr Phe Gly Gln Gly Thr Lys Leu Glu Ile Lys Gly Gly Ser Glu Gly
            100                 105                 110

Lys Ser Ser Gly Ser Gly Ser Glu Ser Lys Ser Thr Gly Gly Ser Glu
        115                 120                 125

Val Gln Leu Val Glu Ser Gly Gly Gly Leu Val Lys Pro Gly Gly Ser
    130                 135                 140

Leu Arg Leu Ser Cys Ala Ala Ser Gly Phe Thr Phe Ser Arg Tyr Asn
145                 150                 155                 160

Met Asn Trp Val Arg Gln Ala Pro Gly Lys Gly Leu Glu Trp Val Ser
                165                 170                 175

Ser Ile Ser Thr Ser Ser Ser Asn Tyr Ile Tyr Tyr Ala Asp Ser Val Lys
```

```
            180                 185                 190
Gly Arg Phe Thr Phe Ser Arg Asp Asn Ala Lys Asn Ser Leu Asp Leu
            195                 200                 205

Gln Met Ser Gly Leu Arg Ala Glu Asp Thr Ala Ile Tyr Tyr Cys Thr
            210                 215                 220

Arg Gly Trp Gly Pro Phe Asp Tyr Trp Gly Gln Gly Thr Leu Val Thr
225                 230                 235                 240

Val Ser Ser Glu Pro Lys Ser Ser Asp Lys Thr His Thr Cys Pro Pro
            245                 250                 255

Cys Pro Ala Pro Glu Ala Ala Gly Gly Pro Ser Val Phe Leu Phe Pro
            260                 265                 270

Pro Lys Pro Lys Asp Thr Leu Met Ile Ser Arg Thr Pro Glu Val Thr
            275                 280                 285

Cys Val Val Val Ser Val Ser His Glu Asp Pro Glu Val Lys Phe Asn
            290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Glu
            370                 375                 380

Glu Met Thr Lys Asn Gln Val Ser Leu Trp Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
                420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
            450                 455                 460

Thr Gln Lys Ser Leu Ser Leu Ser Pro Gly Lys Gly Gly Gly Gly Ser
465                 470                 475                 480

Gly Gly Gly Gly Ser Gln Ile Val Leu Ser Gln Ser Pro Ala Ile Leu
                485                 490                 495

Ser Ala Ser Pro Gly Glu Lys Val Thr Met Thr Cys Arg Ala Ser Ser
                500                 505                 510

Ser Val Ser Tyr Met His Trp Tyr Gln Gln Lys Pro Gly Ser Ser Pro
            515                 520                 525

Gln Val Trp Ile Tyr Ala Thr Ser Asn Leu Ala Ser Gly Val Pro Val
            530                 535                 540

Arg Phe Ser Gly Ser Gly Ser Gly Thr Ser Tyr Ser Leu Thr Ile Ser
545                 550                 555                 560

Arg Val Glu Ala Glu Asp Thr Ala Thr Tyr Tyr Cys Gln Gln Trp Ile
                565                 570                 575

Phe Asn Pro Pro Thr Phe Gly Ser Gly Thr Lys Leu Glu Ile Arg Gly
                580                 585                 590

Gly Ser Glu Gly Lys Ser Ser Gly Ser Gly Ser Glu Ser Lys Ser Thr
            595                 600                 605
```

Gly Gly Ser Gln Ala Tyr Leu Gln Gln Ser Gly Ala Glu Leu Val Arg
    610                 615                 620

Pro Gly Ala Ser Val Lys Met Ser Cys Lys Ala Ser Gly Tyr Thr Phe
625                 630                 635                 640

Thr Ser Tyr Asn Met His Trp Val Lys Gln Thr Pro Arg Gln Gly Leu
                645                 650                 655

Glu Trp Ile Gly Ala Ile Tyr Pro Gly Asn Gly Asp Thr Ser Tyr Asn
            660                 665                 670

Gln Lys Phe Lys Gly Lys Ala Thr Leu Thr Val Asp Lys Ser Ser Ser
        675                 680                 685

Thr Ala Tyr Met Gln Leu Ser Ser Leu Thr Ser Glu Asp Ser Ala Val
    690                 695                 700

Tyr Phe Cys Ala Arg Val Tyr Tyr Gly Ser Asn Tyr Trp Tyr Phe Asp
705                 710                 715                 720

Val Trp Gly Thr Gly Thr Thr Val Thr Val Ser Ser
                725                 730

<210> SEQ ID NO 153
<211> LENGTH: 2196
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 153
gacatacaaa tgacacaatc accctcttct ctttctgcaa gcgttggcga ccgtgtcact    60
atcacttgtc gagcccgcca gtccataggt actgccattc actggtatca acagaagcct   120
ggcaaggctc ccaaactcct gattaagtat gccagcgaga gcatttccgg cgtaccttca   180
agattttccg gctccggtag tgggacagat tcactctca ctatatctag cctccaacca   240
gaagatttcg ccacttacta ctgtcaacaa tcaggttcat ggcctacac tttcggccag   300 gggacaaaat tggagatcaa gggcggctcc gagggcaaga gcagcggcag cggcagcgag   360
agcaagagca ccggcggcag cgaggtgcaa ctggtggagt ctgggggagg cctggtcaag   420
cctggggggt ccctgagact ctcctgtgca gcctctggat tcacctcag tagatataac   480 atgaactggg tccgccaggc tccagggaag gggctggagt gggtctcatc cattagtact   540
agtagtaatt acatatacta cgcagactca gtgaagggcc gattcacctt ctccagagac   600
aacgccaaga actcactgga tctgcaaatg agcggcctga gccgagga cacggctatt    660 tattactgta cgagaggctg ggggcctttt gactactggg gccagggaac cctggtcacc   720
gtctcctcag agcccaaatc tagcgacaaa actcacacat gtccaccgtg cccagcacct   780
gaagcagcag ggggaccgtc agtcttcctc ttccccccaa acccaagga caccctcatg   840 atctcccgga cccctgaggt cacatgcgtg gtggtgagcg tgagccacga agaccctgag   900
gtcaagttca actggtacgt ggacggcgtg gaggtgcata tgccaagac aaagccgcgg    960 gaggagcagt acaacagcac gtaccgtgtg gtcagcgtcc tcaccgtcct gcaccaggac  1020
tggctgaatg gcaaggagta caagtgcaag gtctccaaca agccctccc agcccccatc  1080 gagaaaacca tctccaaagc caagggcag ccccgagaac acaggtgta cccctgccc    1140 ccatcccggg aggagatgac caagaaccag gtcagcctgt ggtgcctggt caaaggcttc  1200
tatcccagcg acatcgccgt ggagtgggag agcaatgggc agccggagaa caactacaag  1260
accacgcctc ccgtgctgga ctccgacggc tccttcttcc tctacagcaa gctcaccgtg  1320

-continued

```
gacaagtcta gatggcagca ggggaacgtc ttctcatgct ccgtgatgca tgaggctctg    1380
cacaaccact acacgcagaa gagcctctcc ctgtctccgg gtaaaggagg cggagggagt    1440
ggcgggggag gctctcaaat agtcctttca cagtccccag ctattctttc agcctctccc    1500
ggtgaaaagg ttacaatgac ctgccgggca agctccagtg tctcatatat gcactggtac    1560
caacaaaaac ctggcagtag tcctcaggtg tggatctacg ctacaagcaa tctcgcttcc    1620
ggggttcccg tgaggtttag cggaagcggg tctggaacta gttattcctt gacaattagt    1680
cgggttgaag ccgaggacac cgccacttac tattgccaac agtggatatt caatccaccc    1740
accttcggtt caggtaccaa gctcgaaatc cgtggcggct ccgagggcaa gagcagcggc    1800
agcggcagcg agagcaagag caccggcggc agccaagcat atctgcaaca gagcggagct    1860
gagctggttc ggcctggcgc ctctgtaaaa atgagttgca aggccagtgg ttatacattc    1920
acatcatata atatgcactg ggtaaagcaa actccccgac aggggcttga atggattggc    1980
gcaatctatc ccggcaatgg ggatacatcc tacaatcaga aattcaaggg caaggcaaca    2040
ctgaccgttg acaaatcctc atcaacagcc tacatgcagc tcagttccct cactagcgaa    2100
gattctgctg tgtatttctg tgcaagggtg tattatggtt ctaattactg gtatttcgat    2160
gtttggggaa ccggaactac cgtaactgtt tctagc                              2196
```

<210> SEQ ID NO 154  
<211> LENGTH: 733  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 154

```
Asp Ile Gln Met Thr Gln Ser Pro Ser Ser Leu Ser Ala Ser Val Gly
1               5                   10                  15

Asp Arg Val Thr Ile Thr Cys Arg Ala Arg Gln Ser Ile Gly Thr Ala
            20                  25                  30

Ile His Trp Tyr Gln Gln Lys Pro Gly Lys Ala Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Ser Trp Pro Tyr
                85                  90                  95

Thr Phe Gly Gln Gly Thr Lys Leu Glu Ile Lys Gly Gly Ser Glu Gly
            100                 105                 110

Lys Ser Ser Gly Ser Gly Ser Glu Ser Lys Ser Thr Gly Gly Ser Glu
        115                 120                 125

Val Gln Leu Val Glu Ser Gly Gly Leu Val Lys Pro Gly Gly Ser
    130                 135                 140

Leu Arg Leu Ser Cys Ala Ala Ser Gly Phe Thr Phe Ser Arg Tyr Asn
145                 150                 155                 160

Met Asn Trp Val Arg Gln Ala Pro Gly Lys Gly Leu Glu Trp Val Ser
                165                 170                 175

Ser Ile Ser Thr Ser Ser Asn Tyr Ile Tyr Tyr Ala Asp Ser Val Lys
            180                 185                 190

Gly Arg Phe Thr Phe Ser Arg Asp Asn Ala Lys Asn Ser Leu Asp Leu
```

```
            195                 200                 205
Gln Met Ser Gly Leu Arg Ala Glu Asp Thr Ala Ile Tyr Tyr Cys Thr
210                 215                 220

Arg Gly Trp Gly Pro Phe Asp Tyr Trp Gly Gln Gly Thr Leu Val Thr
225                 230                 235                 240

Val Ser Ser Glu Pro Lys Ser Ser Asp Lys Thr His Thr Cys Pro Pro
                245                 250                 255

Cys Pro Ala Pro Glu Ala Ala Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Ser Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Glu
    370                 375                 380

Glu Met Thr Lys Asn Gln Val Ser Leu Trp Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys Gly Gly Gly Gly Ser
465                 470                 475                 480

Gly Gly Gly Gly Ser Gln Ile Val Leu Ser Gln Ser Pro Ala Ile Leu
                485                 490                 495

Ser Ala Ser Pro Gly Glu Lys Val Thr Met Thr Cys Arg Ala Ser Leu
            500                 505                 510

Ser Val Ser Ser Met His Trp Tyr Gln Gln Lys Pro Gly Ser Ser Pro
        515                 520                 525

Lys Pro Trp Ile Tyr Ala Thr Ser Asn Leu Ala Ser Gly Val Pro Ala
    530                 535                 540

Arg Phe Ser Gly Ser Gly Ser Gly Thr Ser Tyr Ser Leu Thr Ile Ser
545                 550                 555                 560

Arg Val Glu Ala Glu Asp Ala Ala Thr Tyr Tyr Cys Gln Gln Trp Ile
                565                 570                 575

Phe Asn Pro Pro Thr Phe Gly Gly Gly Thr Lys Leu Glu Ile Lys Gly
            580                 585                 590

Gly Ser Glu Gly Lys Ser Ser Gly Ser Gly Ser Glu Ser Lys Ser Thr
        595                 600                 605

Gly Gly Ser Gln Ala Tyr Leu Gln Gln Ser Gly Ala Glu Leu Val Arg
    610                 615                 620
```

```
Pro Gly Ala Ser Val Lys Met Ser Cys Lys Thr Ser Gly Tyr Thr Phe
625                 630                 635                 640

Ser Ser Tyr Asn Met His Trp Val Lys Gln Thr Pro Arg Gln Ala Leu
            645                 650                 655

Glu Trp Ile Gly Ala Ile Tyr Pro Gly Asn Gly Asp Thr Ser Tyr Asn
        660                 665                 670

Gln Lys Phe Lys Gly Lys Ala Thr Leu Thr Val Asp Lys Ser Ser Ser
    675                 680                 685

Thr Ala Tyr Met Gln Leu Ser Ser Leu Thr Ser Glu Asp Ser Ala Val
        690                 695                 700

Tyr Phe Cys Thr Arg Ser Asn Tyr Tyr Gly Ser Ser Gly Trp Tyr Phe
705                 710                 715                 720

Asp Val Trp Gly Thr Gly Thr Thr Val Thr Val Ser Ser
                725                 730
```

<210> SEQ ID NO 155
<211> LENGTH: 2199
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 155

```
gacatacaaa tgacacaatc accctcttct ctttctgcaa gcgttggcga ccgtgtcact    60
atcacttgtc gagcccgcca gtccataggt actgccattc actggtatca acagaagcct   120
ggcaaggctc ccaaactcct gattaagtat gccagcgaga gcatttccgg cgtaccttca   180
agattttccg gctccggtag tgggacagat ttcactctca ctatatctag cctccaacca   240
gaagatttcg ccacttacta ctgtcaacaa tcaggttcat ggccttacac tttcggccag   300
gggacaaaat tggagatcaa gggcggctcc gagggcaaga gcagcggcag cggcagcgag   360
agcaagagca ccggcggcag cgaggtgcaa ctggtggagt ctgggggagg cctggtcaag   420
cctgggggt ccctgagact ctcctgtgca gcctctggat tcaccttcag tagatataac   480
atgaactggg tccgccaggc tccagggaag gggctggagt gggtctcatc cattagtact   540
agtagtaatt acatatacta cgcagactca gtgaagggcc gattcacctt ctccagagac   600
aacgccaaga actcactgga tctgcaaatg agcggcctga gagccgagga cacggctatt   660
tattactgta cgagaggctg ggggcctttt gactactggg gccagggaac cctggtcacc   720
gtctcctcag agcccaaatc tagcgacaaa actcacacat gtccaccgtg cccagcacct   780
gaagcagcag ggggaccgtc agtcttcctc ttcccccaa acccaaggac accctcatg     840
atctcccgga cccctgaggt cacatgcgtg gtggtgagcg tgagccacga agaccctgag   900
gtcaagttca actggtacgt ggacggcgtg gaggtgcata atgccaagac aaagccgcgg   960
gaggagcagt acaacagcac gtaccgtgtg gtcagcgtcc tcaccgtcct gcaccaggac  1020
tggctgaatg gcaaggagta caagtgcaag gtctccaaca aagccctccc agcccccatc  1080
gagaaaacca tctccaaagc caaagggcag ccccgagaac cacaggtgta caccctgccc  1140
ccatcccggg aggagatgac caagaaccag gtcagcctgt ggtgcctggt caaaggcttc  1200
tatcccagcg acatcgccgt ggagtgggag agcaatgggc agccggagaa caactacaag  1260
accacgcctc ccgtgctgga ctccgacggc tccttcttcc tctacagcaa gctcaccgtg  1320
gacaagtcta gatggcagca ggggaacgtc ttctcatgct ccgtgatgca tgaggctctg  1380
```

-continued

```
cacaaccact acacgcagaa gagcctctcc ctgtctccgg gtaaaggagg cggagggagt   1440
ggcgggggag gctctcagat tgtcctgagc caatccccag caattctgag tgctagccct   1500
ggagagaagg taacaatgac ttgtcgggca tcccttagcg tctcatccat gcattggtat   1560
caacaaaagc caggttcatc tccaaaaccc tggatttacg ctacatctaa cctggcatct   1620
ggggtgcctg ccagatttag tggatctggt tccggcacat catattccct tacaatcagc   1680
cgagtggaag ccgaggatgc tgcaacctat tactgtcaac aatggatatt taaccctccc   1740
acctttgggg gtgggactaa actcgaaatc aagggcggct ccgagggcaa gagcagcggc   1800
agcggcagcg agagcaagag caccggcggc agccaagcct atcttcaaca atctggggct   1860
gagcttgtcc ggccaggagc ctccgtcaaa atgagctgca aaacctcagg ttatactttt   1920
agtagctata acatgcattg ggtaaaacaa acccccgac aagcattgga gtggataggg   1980
gccatatacc ccggcaatgg agacacaagt tacaaccaga gtttaaagg caaagctaca   2040 ctcacagttg acaaatcctc aagtactgct tatatgcaac tctcctctct cacttccgaa   2100
gacagtgccg tatattttg cactcggtcc aattactatg gatctagtgg ctggtacttt   2160
gacgtttggg gcactgggac aactgttaca gtgtccagc                          2199
```

<210> SEQ ID NO 156
<211> LENGTH: 736
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 156

```
Glu Ile Val Leu Thr Gln Ser Pro Ala Thr Leu Ser Ala Ser Pro Gly
1               5                   10                  15

Glu Arg Val Thr Leu Ser Cys Ser Ala Ser Ser Ser Val Ser Tyr Met
            20                  25                  30

Asn Trp Tyr Gln Gln Lys Pro Gly Gln Ala Pro Arg Arg Trp Ile Tyr
        35                  40                  45

Asp Ser Ser Lys Leu Ala Ser Gly Val Pro Ala Arg Phe Ser Gly Ser
    50                  55                  60

Gly Ser Gly Arg Asp Tyr Thr Leu Thr Ile Ser Ser Leu Glu Pro Glu
65                  70                  75                  80

Asp Phe Ala Val Tyr Tyr Cys Gln Gln Trp Ser Arg Asn Pro Pro Thr
                85                  90                  95

Phe Gly Gly Gly Thr Lys Val Glu Ile Lys Gly Gly Ser Glu Gly Lys
            100                 105                 110

Ser Ser Gly Ser Gly Ser Glu Ser Lys Ser Thr Gly Gly Ser Gln Val
        115                 120                 125

Gln Leu Val Gln Ser Gly Ala Glu Val Lys Lys Pro Gly Ser Ser Val
    130                 135                 140

Lys Val Ser Cys Lys Ala Ser Gly Tyr Thr Phe Thr Arg Ser Thr Met
145                 150                 155                 160

His Trp Val Lys Gln Ala Pro Gly Gln Gly Leu Glu Trp Ile Gly Tyr
                165                 170                 175

Ile Asn Pro Ser Ser Ala Tyr Thr Asn Tyr Asn Gln Lys Phe Gln Gly
            180                 185                 190

Arg Val Thr Leu Thr Ala Asp Lys Ser Thr Ser Thr Ala Tyr Met Glu
        195                 200                 205

Leu Ser Ser Leu Arg Ser Glu Asp Thr Ala Val Tyr Tyr Cys Ala Ser
```

-continued

```
                210                 215                 220

Pro Gln Val His Tyr Asp Tyr Ala Gly Phe Pro Tyr Trp Gly Gln Gly
225                 230                 235                 240

Thr Leu Val Thr Val Ser Ser Glu Pro Lys Ser Ser Asp Lys Thr His
                245                 250                 255

Thr Cys Pro Pro Cys Pro Ala Pro Glu Ala Ala Gly Gly Pro Ser Val
                260                 265                 270

Phe Leu Phe Pro Pro Lys Pro Lys Asp Thr Leu Met Ile Ser Arg Thr
                275                 280                 285

Pro Glu Val Thr Cys Val Val Val Ser Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
                340                 345                 350

Cys Lys Val Ser Asn Lys Ala Leu Pro Ala Pro Ile Glu Lys Thr Ile
                355                 360                 365

Ser Lys Ala Lys Gly Gln Pro Arg Glu Pro Gln Val Tyr Thr Leu Pro
370                 375                 380

Pro Ser Arg Glu Glu Met Thr Lys Asn Gln Val Ser Leu Trp Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
                420                 425                 430

Asp Gly Ser Phe Phe Leu Tyr Ser Lys Leu Thr Val Asp Lys Ser Arg
                435                 440                 445

Trp Gln Gln Gly Asn Val Phe Ser Cys Ser Val Met His Glu Ala Leu
                450                 455                 460

His Asn His Tyr Thr Gln Lys Ser Leu Ser Leu Ser Pro Gly Lys Gly
465                 470                 475                 480

Gly Gly Gly Ser Gly Gly Gly Ser Gln Ile Val Leu Ser Gln Ser
                485                 490                 495

Pro Ala Ile Leu Ser Ala Ser Pro Gly Glu Lys Val Thr Met Thr Cys
                500                 505                 510

Arg Ala Ser Ser Ser Val Ser Tyr Met His Trp Tyr Gln Gln Lys Pro
                515                 520                 525

Gly Ser Ser Pro Gln Val Trp Ile Tyr Ala Thr Ser Asn Leu Ala Ser
                530                 535                 540

Gly Val Pro Val Arg Phe Ser Gly Ser Gly Ser Gly Thr Ser Tyr Ser
545                 550                 555                 560

Leu Thr Ile Ser Arg Val Glu Ala Glu Asp Thr Ala Thr Tyr Tyr Cys
                565                 570                 575

Gln Gln Trp Ile Phe Asn Pro Pro Thr Phe Gly Ser Gly Thr Lys Leu
                580                 585                 590

Glu Ile Arg Gly Gly Ser Glu Gly Lys Ser Ser Gly Ser Gly Ser Glu
                595                 600                 605

Ser Lys Ser Thr Gly Gly Ser Gln Ala Tyr Leu Gln Gln Ser Gly Ala
                610                 615                 620

Glu Leu Val Arg Pro Gly Ala Ser Val Lys Met Ser Cys Lys Ala Ser
625                 630                 635                 640
```

```
Gly Tyr Thr Phe Thr Ser Tyr Asn Met His Trp Val Lys Gln Thr Pro
                645                 650                 655

Arg Gln Gly Leu Glu Trp Ile Gly Ala Ile Tyr Pro Gly Asn Gly Asp
            660                 665                 670

Thr Ser Tyr Asn Gln Lys Phe Lys Gly Lys Ala Thr Leu Thr Val Asp
        675                 680                 685

Lys Ser Ser Ser Thr Ala Tyr Met Gln Leu Ser Ser Leu Thr Ser Glu
690                 695                 700

Asp Ser Ala Val Tyr Phe Cys Ala Arg Val Tyr Tyr Gly Ser Asn Tyr
705                 710                 715                 720

Trp Tyr Phe Asp Val Trp Gly Thr Gly Thr Thr Val Thr Val Ser Ser
                725                 730                 735

<210> SEQ ID NO 157
<211> LENGTH: 2208
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157
gagatcgtgc tgactcagag ccctgccact ctgagcgcca gccctggcga gagggtgact      60
ctgagctgta gcgccagcag cagcgtgagc tacatgaatt ggtaccagca gaagcctggc     120
caggccccta ggaggtggat ctacgatagc agcaagctgg ccagcggcgt gcctgccagg     180
ttcagcggca gcggcagcgg cagggattac actctgacta tcagcagcct ggagcctgag     240
gatttcgccg tgtactactg tcagcagtgg agcaggaatc ctcctacttt cggcggcggc     300
actaaggtgg agatcaaggg cggctccgag ggcaagagca gcggcagcgg cagcgagagc     360
aagagcaccg gcggcagcca ggtgcagctg gtgcagagcg gcgccgaggt gaagaagcct     420
ggcagcagcg tgaaggtgag ctgtaaggcc agcggctaca cttttcactag gagcactatg     480
cactgggtga agcaggcccc tggccagggc ctggagtgga tcggctacat caatcctagc     540
agcgcctaca ctaattacaa tcagaagttc cagggcaggg tgactctgac tgccgataag     600
agcactagca ctgcctacat ggagctgagc agcctgagga gcgaggatac tgccgtgtac     660
tactgtgcca gccctcaggt gcactacgat tacgccggct tcccttactg gggccagggc     720
actctggtga ctgtgagcag cgagcccaaa tctagcgaca aaactcacac atgtccaccg     780
tgcccagcac ctgaagcagc aggggggaccg tcagtcttcc tcttcccccc aaaacccaag     840
gacaccctca tgatctcccg gacccctgag gtcacatgcg tggtggtgag cgtgagccac     900
gaagaccctg aggtcaagtt caactggtac gtggacggcg tggaggtgca taatgccaag     960
acaaagccgc gggaggagca gtacaacagc acgtaccgtg tggtcagcgt cctcaccgtc    1020
ctgcaccagg actggctgaa tggcaaggag tacaagtgca aggtctccaa caaagccctc    1080
ccagccccca tcgagaaaac catctccaaa gccaagggc agccccgaga accacaggtg    1140
tacaccctgc ccccatcccg ggaggagatg accaagaacc aggtcagcct gtggtgcctg    1200
gtcaaaggct tctatcccag cgacatcgcc gtggagtggg agagcaatgg gcagccggag    1260
aacaactaca agaccacgcc tcccgtgctg gactccgacg gctccttctt cctctacagc    1320
aagctcaccg tggacaagtc tagatggcag caggggaacg tcttctcatg ctccgtgatg    1380
catgaggctc tgcacaacca ctacacgcag aagagcctct ccctgtctcc gggtaaagga    1440
ggcggaggga gtggcggggg aggctctcaa atagtccttt cacagtcccc agctattctt    1500
```

-continued

```
tcagcctctc ccggtgaaaa ggttacaatg acctgccggg caagctccag tgtctcatat   1560
atgcactggt accaacaaaa acctggcagt agtcctcagg tgtggatcta cgctacaagc   1620
aatctcgctt ccggggttcc cgtgaggttt agcggaagcg ggtctggaac tagttattcc   1680
ttgacaatta gtcgggttga agccgaggac accgccactt actattgcca acagtggata   1740
ttcaatccac ccaccttcgg ttcaggtacc aagctcgaaa tccgtggcgg ctccgagggc   1800
aagagcagcg gcagcggcag cgagagcaag agcaccggcg gcagccaagc atatctgcaa   1860
cagagcggag ctgagctggt tcggcctggc gcctctgtaa aaatgagttg caaggccagt   1920
ggttatacat tcacatcata taatatgcac tgggtaaagc aaactccccg acaggggctt   1980
gaatggattg gcgcaatcta tcccggcaat ggggatacat cctacaatca gaaattcaag   2040
ggcaaggcaa cactgaccgt tgacaaatcc tcatcaacag cctacatgca gctcagttcc   2100
ctcactagcg aagattctgc tgtgtatttc tgtgcaaggg tgtattatgg ttctaattac   2160
tggtatttcg atgtttgggg aaccggaact accgtaactg tttctagc             2208
```

<210> SEQ ID NO 158
<211> LENGTH: 737
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 158

```
Glu Ile Val Leu Thr Gln Ser Pro Ala Thr Leu Ser Ala Ser Pro Gly
1               5                   10                  15

Glu Arg Val Thr Leu Ser Cys Ser Ala Ser Ser Ser Val Ser Tyr Met
            20                  25                  30

Asn Trp Tyr Gln Gln Lys Pro Gly Gln Ala Pro Arg Arg Trp Ile Tyr
        35                  40                  45

Asp Ser Ser Lys Leu Ala Ser Gly Val Pro Ala Arg Phe Ser Gly Ser
    50                  55                  60

Gly Ser Gly Arg Asp Tyr Thr Leu Thr Ile Ser Ser Leu Glu Pro Glu
65                  70                  75                  80

Asp Phe Ala Val Tyr Tyr Cys Gln Gln Trp Ser Arg Asn Pro Pro Thr
                85                  90                  95

Phe Gly Gly Gly Thr Lys Val Glu Ile Lys Gly Ser Glu Gly Lys
            100                 105                 110

Ser Ser Gly Ser Gly Ser Glu Ser Lys Ser Thr Gly Gly Ser Gln Val
        115                 120                 125

Gln Leu Val Gln Ser Gly Ala Glu Val Lys Lys Pro Gly Ser Ser Val
    130                 135                 140

Lys Val Ser Cys Lys Ala Ser Gly Tyr Thr Phe Thr Arg Ser Thr Met
145                 150                 155                 160

His Trp Val Lys Gln Ala Pro Gly Gln Gly Leu Glu Trp Ile Gly Tyr
                165                 170                 175

Ile Asn Pro Ser Ser Ala Tyr Thr Asn Tyr Asn Gln Lys Phe Gln Gly
            180                 185                 190

Arg Val Thr Leu Thr Ala Asp Lys Ser Thr Ser Thr Ala Tyr Met Glu
        195                 200                 205

Leu Ser Ser Leu Arg Ser Glu Asp Thr Ala Val Tyr Tyr Cys Ala Ser
    210                 215                 220

Pro Gln Val His Tyr Asp Tyr Ala Gly Phe Pro Tyr Trp Gly Gln Gly
```

-continued

```
                225                 230                 235                 240
        Thr Leu Val Thr Val Ser Ser Glu Pro Lys Ser Ser Asp Lys Thr His
                            245                 250                 255
        Thr Cys Pro Pro Cys Pro Ala Pro Glu Ala Ala Gly Gly Pro Ser Val
                            260                 265                 270
        Phe Leu Phe Pro Pro Lys Pro Lys Asp Thr Leu Met Ile Ser Arg Thr
                            275                 280                 285
        Pro Glu Val Thr Cys Val Val Val Ser Val Ser His Glu Asp Pro Glu
                            290                 295                 300
        Val Lys Phe Asn Trp Tyr Val Asp Gly Val Glu Val His Asn Ala Lys
        305                 310                 315                 320
        Thr Lys Pro Arg Glu Glu Gln Tyr Asn Ser Thr Tyr Arg Val Val Ser
                            325                 330                 335
        Val Leu Thr Val Leu His Gln Asp Trp Leu Asn Gly Lys Glu Tyr Lys
                            340                 345                 350
        Cys Lys Val Ser Asn Lys Ala Leu Pro Ala Pro Ile Glu Lys Thr Ile
                            355                 360                 365
        Ser Lys Ala Lys Gly Gln Pro Arg Glu Pro Gln Val Tyr Thr Leu Pro
                370                 375                 380
        Pro Ser Arg Glu Glu Met Thr Lys Asn Gln Val Ser Leu Trp Cys Leu
        385                 390                 395                 400
        Val Lys Gly Phe Tyr Pro Ser Asp Ile Ala Val Glu Trp Glu Ser Asn
                            405                 410                 415
        Gly Gln Pro Glu Asn Asn Tyr Lys Thr Thr Pro Pro Val Leu Asp Ser
                            420                 425                 430
        Asp Gly Ser Phe Phe Leu Tyr Ser Lys Leu Thr Val Asp Lys Ser Arg
                            435                 440                 445
        Trp Gln Gln Gly Asn Val Phe Ser Cys Ser Val Met His Glu Ala Leu
                    450                 455                 460
        His Asn His Tyr Thr Gln Lys Ser Leu Ser Leu Ser Pro Gly Lys Gly
        465                 470                 475                 480
        Gly Gly Gly Ser Gly Gly Gly Ser Gln Ile Val Leu Ser Gln Ser
                            485                 490                 495
        Pro Ala Ile Leu Ser Ala Ser Pro Gly Glu Lys Val Thr Met Thr Cys
                        500                 505                 510
        Arg Ala Ser Leu Ser Val Ser Ser Met His Trp Tyr Gln Gln Lys Pro
                        515                 520                 525
        Gly Ser Ser Pro Lys Pro Trp Ile Tyr Ala Thr Ser Asn Leu Ala Ser
                        530                 535                 540
        Gly Val Pro Ala Arg Phe Ser Gly Ser Gly Ser Gly Thr Ser Tyr Ser
        545                 550                 555                 560
        Leu Thr Ile Ser Arg Val Glu Ala Glu Asp Ala Ala Thr Tyr Tyr Cys
                            565                 570                 575
        Gln Gln Trp Ile Phe Asn Pro Pro Thr Phe Gly Gly Gly Thr Lys Leu
                            580                 585                 590
        Glu Ile Lys Gly Gly Ser Glu Gly Lys Ser Ser Gly Ser Gly Ser Glu
                            595                 600                 605
        Ser Lys Ser Thr Gly Gly Ser Gln Ala Tyr Leu Gln Gln Ser Gly Ala
                            610                 615                 620
        Glu Leu Val Arg Pro Gly Ala Ser Val Lys Met Ser Cys Lys Thr Ser
        625                 630                 635                 640
        Gly Tyr Thr Phe Ser Ser Tyr Asn Met His Trp Val Lys Gln Thr Pro
                            645                 650                 655
```

Arg Gln Ala Leu Glu Trp Ile Gly Ala Ile Tyr Pro Gly Asn Gly Asp
                660                 665                 670

Thr Ser Tyr Asn Gln Lys Phe Lys Gly Lys Ala Thr Leu Thr Val Asp
            675                 680                 685

Lys Ser Ser Ser Thr Ala Tyr Met Gln Leu Ser Ser Leu Thr Ser Glu
        690                 695                 700

Asp Ser Ala Val Tyr Phe Cys Thr Arg Ser Asn Tyr Tyr Gly Ser Ser
705                 710                 715                 720

Gly Trp Tyr Phe Asp Val Trp Gly Thr Gly Thr Val Thr Val Ser
                725                 730                 735

Ser

<210> SEQ ID NO 159
<211> LENGTH: 2211
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 159
gagatcgtgc tgactcagag ccctgccact ctgagcgcca gccctggcga gagggtgact      60
ctgagctgta gcgccagcag cagcgtgagc tacatgaatt ggtaccagca gaagcctggc     120
caggccccta ggaggtggat ctacgatagc agcaagctgg ccagcggcgt gcctgccagg     180
ttcagcggca gcggcagcgg cagggattac actctgacta tcagcagcct ggagcctgag     240
gatttcgccg tgtactactg tcagcagtgg agcaggaatc ctcctacttt cggcggcggc     300
actaaggtgg agatcaaggg cggctccgag ggcaagagca gcggcagcgg cagcgagagc     360
aagagcaccg gcggcagcca ggtgcagctg gtgcagagcg gcgccgaggt gaagaagcct     420
ggcagcagcg tgaaggtgag ctgtaaggcc agcggctaca cttttcactag gagcactatg     480 cactgggtga gcaggccccc tggccagggc ctggagtgga tcggctacat caatcctagc     540
agcgcctaca ctaattacaa tcagaagttc agggcaggg tgactctgac tgccgataag     600
agcactagca ctgcctacat ggagctgagc agcctgagga gcgaggatac tgccgtgtac     660
tactgtgcca gccctcaggt gcactacgat tacgccggct cccttactg gggccagggc     720 actctggtga ctgtgagcag cgagcccaaa tctagcgaca aaactcacac atgtccaccg     780
tgcccagcac ctgaagcagc aggggaccg tcagtcttcc tcttcccccc aaaacccaag     840
gacaccctca tgatctcccg gacccctgag gtcacatgcg tggtggtgag cgtgagccac     900
gaagaccctg aggtcaagtt caactggtac gtggacggcg tggaggtgca taatgccaag     960
acaaagccgc gggaggagca gtacaacagc acgtaccgtg tggtcagcgt cctcaccgtc    1020
ctgcaccagg actggctgaa tggcaaggag tacaagtgca aggtctccaa caaagccctc    1080
ccagccccca tcgagaaaac catctccaaa gccaaaggc agccccgaga accacaggtg    1140
tacaccctgc ccccatcccg ggaggagatg accaagaacc aggtcagcct gtggtgcctg    1200
gtcaaaggct tctatcccag cgacatcgcc gtggagtggg agagcaatgg gcagccggag    1260
aacaactaca agaccacgcc tcccgtgctg gactccgacg gctccttctt cctctacagc    1320
aagctcaccg tggacaagtc tagatggcag caggggaacg tcttctcatg ctccgtgatg    1380
catgaggctc tgcacaacca ctacacgcag aagagcctct ccctgtctcc gggtaaagga    1440
ggcggaggga gtggcggggg aggctctcag attgtcctga ccaatccccc agcaattctg    1500

```
agtgctagcc ctggagagaa ggtaacaatg acttgtcggg catcccttag cgtctcatcc    1560
atgcattggt atcaacaaaa gccaggttca tctccaaaac cctggattta cgctacatct    1620
aacctggcat ctggggtgcc tgccagattt agtggatctg gttccggcac atcatattcc    1680
cttacaatca gccgagtgga agccgaggat gctgcaacct attactgtca acaatggata    1740
tttaaccctc ccacctttgg gggtgggact aaactcgaaa tcaagggcgg ctccgagggc    1800
aagagcagcg gcagcggcag cgagagcaag agcaccggcg gcagccaagc ctatcttcaa    1860
caatctgggg ctgagcttgt ccggccagga gcctccgtca aaatgagctg caaaacctca    1920
ggttatactt ttagtagcta taacatgcat tgggtaaaac aaaccccccg acaagcattg    1980
gagtggatag gggccatata ccccggcaat ggagacacaa gttacaacca gaagtttaaa    2040
ggcaaagcta cactcacagt tgacaaatcc tcaagtactg cttatatgca actctcctct    2100
ctcacttccg aagacagtgc cgtatatttt tgcactcggt ccaattacta tggatctagt    2160
ggctggtact ttgacgtttg gggcactggg acaactgtta cagtgtccag c             2211
```

```
<210> SEQ ID NO 160
<211> LENGTH: 736
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Arg Ser
            20                  25                  30

Thr Met His Trp Val Arg Gln Ala Pro Gly Gln Gly Leu Glu Trp Met
        35                  40                  45

Gly Tyr Ile Asn Pro Ser Ser Ala Tyr Thr Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Pro Gln Val His Tyr Asp Tyr Gly Gly Phe Pro Tyr Trp Gly
            100                 105                 110

Gln Gly Thr Leu Val Thr Val Ser Ser Gly Gly Ser Glu Gly Lys Ser
        115                 120                 125

Ser Gly Ser Gly Ser Glu Ser Lys Ser Thr Gly Gly Ser Glu Ile Val
    130                 135                 140

Leu Thr Gln Ser Pro Ala Thr Leu Ser Ala Ser Pro Gly Glu Arg Val
145                 150                 155                 160

Thr Leu Ser Cys Ser Ala Ser Ser Val Ser Tyr Met Asn Trp Tyr
                165                 170                 175

Gln Gln Lys Pro Gly Gln Ala Pro Arg Arg Trp Ile Tyr Asp Ser Ser
            180                 185                 190

Lys Leu Ala Ser Gly Val Pro Ala Arg Phe Ser Gly Ser Gly Ser Gly
        195                 200                 205

Arg Asp Tyr Thr Leu Thr Ile Ser Ser Leu Glu Pro Glu Asp Phe Ala
    210                 215                 220

Val Tyr Tyr Cys Gln Gln Trp Ser Arg Asn Pro Pro Thr Phe Gly Gly
225                 230                 235                 240
```

```
Gly Thr Lys Val Glu Ile Lys Glu Pro Lys Ser Ser Asp Lys Thr His
            245                 250                 255

Thr Cys Pro Pro Cys Pro Ala Pro Glu Ala Ala Gly Gly Pro Ser Val
            260                 265                 270

Phe Leu Phe Pro Pro Lys Pro Lys Asp Thr Leu Met Ile Ser Arg Thr
            275                 280                 285

Pro Glu Val Thr Cys Val Val Val Ser Val Ser His Glu Asp Pro Glu
        290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
            325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
            355                 360                 365

Ser Lys Ala Lys Gly Gln Pro Arg Glu Pro Gln Val Tyr Thr Leu Pro
            370                 375                 380

Pro Ser Arg Glu Glu Met Thr Lys Asn Gln Val Ser Leu Trp Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
            435                 440                 445

Trp Gln Gln Gly Asn Val Phe Ser Cys Ser Val Met His Glu Ala Leu
450                 455                 460

His Asn His Tyr Thr Gln Lys Ser Leu Ser Leu Ser Pro Gly Lys Gly
465                 470                 475                 480

Gly Gly Gly Ser Gly Gly Gly Ser Gln Ile Val Leu Ser Gln Ser
            485                 490                 495

Pro Ala Ile Leu Ser Ala Ser Pro Gly Glu Lys Val Thr Met Thr Cys
                500                 505                 510

Arg Ala Ser Ser Ser Val Ser Tyr Met His Trp Tyr Gln Gln Lys Pro
            515                 520                 525

Gly Ser Ser Pro Gln Val Trp Ile Tyr Ala Thr Ser Asn Leu Ala Ser
            530                 535                 540

Gly Val Pro Val Arg Phe Ser Gly Ser Gly Ser Gly Thr Ser Tyr Ser
545                 550                 555                 560

Leu Thr Ile Ser Arg Val Glu Ala Glu Asp Thr Ala Thr Tyr Tyr Cys
                565                 570                 575

Gln Gln Trp Ile Phe Asn Pro Pro Thr Phe Gly Ser Gly Thr Lys Leu
            580                 585                 590

Glu Ile Arg Gly Gly Ser Glu Gly Lys Ser Ser Gly Ser Gly Ser Glu
            595                 600                 605

Ser Lys Ser Thr Gly Gly Ser Gln Ala Tyr Leu Gln Gln Ser Gly Ala
            610                 615                 620

Glu Leu Val Arg Pro Gly Ala Ser Val Lys Met Ser Cys Lys Ala Ser
625                 630                 635                 640

Gly Tyr Thr Phe Thr Ser Tyr Asn Met His Trp Val Lys Gln Thr Pro
            645                 650                 655
```

```
Arg Gln Gly Leu Glu Trp Ile Gly Ala Ile Tyr Pro Gly Asn Gly Asp
                660                 665                 670

Thr Ser Tyr Asn Gln Lys Phe Lys Gly Lys Ala Thr Leu Thr Val Asp
            675                 680                 685

Lys Ser Ser Ser Thr Ala Tyr Met Gln Leu Ser Ser Leu Thr Ser Glu
690                 695                 700

Asp Ser Ala Val Tyr Phe Cys Ala Arg Val Tyr Tyr Gly Ser Asn Tyr
705                 710                 715                 720

Trp Tyr Phe Asp Val Trp Gly Thr Gly Thr Thr Val Thr Val Ser Ser
                725                 730                 735

<210> SEQ ID NO 161
<211> LENGTH: 2208
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161
caggtgcagc tggtgcagag cggcgccgag gtgaagaagc ctggcagcag cgtgaaggtg     60
agctgtaagg ccagcggcta cactttcact aggagcacta tgcactgggt gaggcaggcc    120
cctggccagg gcctggagtg gatgggctac atcaatccta gcagcgccta cactaattac    180
gcccagaagt tccagggcag ggtgactctg actgccgata agagcactag cactgcctac    240
atggagctga gcagcctgag gagcgaggat actgccgtgt actactgtgc cagccctcag    300
gtgcactacg attacggcgg cttcccttac tggggccagg gcactctggt gactgtgagc    360
agcggcggct ccgagggcaa gagcagcggc agcggcagcg agagcaagag caccggcggc    420
agcgagatcg tgctgactca gagccctgcc actctgagcg ccagccctgg cgagagggtg    480
actctgagct gtagcgccag cagcagcgtg agctacatga attggtacca gcagaagcct    540
ggccaggccc ctaggaggtg gatctacgat agcagcaagc tggccagcgg cgtgcctgcc    600
aggttcagcg gcagcggcag cggcagggat tacactctga ctatcagcag cctggagcct    660
gaggatttcg ccgtgtacta ctgtcagcag tggagcagga tcctcctac tttcggcggc    720 ggcactaagg tggagatcaa ggagcccaaa tctagcgaca aaactcacac atgtccaccg    780
tgcccagcac ctgaagcagc aggggaccg tcagtcttcc tcttccccc aaaacccaag    840 gacaccctca tgatctcccg gacccctgag gtcacatgcg tggtggtgag cgtgagccac    900
gaagaccctg aggtcaagtt caactggtac gtggacggcg tggaggtgca taatgccaag    960
acaaagccgc gggaggagca gtacaacagc acgtaccgtg tggtcagcgt cctcaccgtc   1020
ctgcaccagg actggctgaa tgcaaggag tacaagtgca aggtctccaa caaagccctc   1080
ccagccccca tcgagaaaac catctccaaa gccaagggc agccccgaga accacaggtg   1140
tacaccctgc ccccatcccg ggaggagatg accaagaacc aggtcagcct gtggtgcctg   1200
gtcaaaggct tctatcccag cgacatcgcc gtggagtggg agagcaatgg gcagccggag   1260
aacaactaca agaccacgcc tcccgtgctg gactccgacg gctccttctt cctctacagc   1320
aagctcaccg tggacaagtc tagatggcag caggggaacg tcttctcatg ctccgtgatg   1380
catgaggctc tgcacaacca ctacacgcag aagagcctct ccctgtctcc gggtaaagga   1440
ggcggaggga gtggcggggg aggctctcaa atagtccttt cacagtcccc agctattctt   1500
tcagcctctc ccggtgaaaa ggttacaatg acctgccggg caagctccag tgtctctat   1560 atgcactggt accaacaaaa acctggcagt agtcctcagg tgtggatcta cgctacaagc   1620
```

```
aatctcgctt ccggggttcc cgtgaggttt agcggaagcg ggtctggaac tagttattcc    1680
ttgacaatta gtcgggttga agccgaggac accgccactt actattgcca acagtggata    1740
ttcaatccac ccaccttcgg ttcaggtacc aagctcgaaa tccgtggcgg ctccgagggc    1800
aagagcagcg gcagcggcag cgagagcaag agcaccggcg gcagccaagc atatctgcaa    1860
cagagcggag ctgagctggt tcggcctggc gcctctgtaa aaatgagttg caaggccagt    1920
ggttatacat tcacatcata taatatgcac tgggtaaagc aaactccccg acaggggctt    1980
gaatggattg gcgcaatcta tcccggcaat ggggatacat cctacaatca gaaattcaag    2040
ggcaaggcaa cactgaccgt tgacaaatcc tcatcaacag cctacatgca gctcagttcc    2100
ctcactagcg aagattctgc tgtgtatttc tgtgcaaggg tgtattatgg ttctaattac    2160
tggtatttcg atgtttgggg aaccggaact accgtaactg tttctagc               2208
```

<210> SEQ ID NO 162
<211> LENGTH: 737
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Arg Ser
            20                  25                  30

Thr Met His Trp Val Arg Gln Ala Pro Gly Gln Gly Leu Glu Trp Met
        35                  40                  45

Gly Tyr Ile Asn Pro Ser Ser Ala Tyr Thr Asn Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Pro Gln Val His Tyr Asp Tyr Gly Gly Phe Pro Tyr Trp Gly
            100                 105                 110

Gln Gly Thr Leu Val Thr Val Ser Ser Gly Ser Glu Gly Lys Ser
        115                 120                 125

Ser Gly Ser Gly Ser Glu Ser Lys Ser Thr Gly Gly Ser Glu Ile Val
    130                 135                 140

Leu Thr Gln Ser Pro Ala Thr Leu Ser Ala Ser Pro Gly Glu Arg Val
145                 150                 155                 160

Thr Leu Ser Cys Ser Ala Ser Ser Val Ser Tyr Met Asn Trp Tyr
                165                 170                 175

Gln Gln Lys Pro Gly Gln Ala Pro Arg Arg Trp Ile Tyr Asp Ser Ser
            180                 185                 190

Lys Leu Ala Ser Gly Val Pro Ala Arg Phe Ser Gly Ser Gly Ser Gly
        195                 200                 205

Arg Asp Tyr Thr Leu Thr Ile Ser Ser Leu Glu Pro Glu Asp Phe Ala
    210                 215                 220

Val Tyr Tyr Cys Gln Gln Trp Ser Arg Asn Pro Pro Thr Phe Gly Gly
225                 230                 235                 240

Gly Thr Lys Val Glu Ile Lys Glu Pro Lys Ser Ser Asp Lys Thr His
                245                 250                 255

-continued

```
Thr Cys Pro Pro Cys Pro Ala Pro Glu Ala Ala Gly Gly Pro Ser Val
            260                 265                 270

Phe Leu Phe Pro Pro Lys Pro Lys Asp Thr Leu Met Ile Ser Arg Thr
            275                 280                 285

Pro Glu Val Thr Cys Val Val Val Ser Val Ser His Glu Asp Pro Glu
            290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
            355                 360                 365

Ser Lys Ala Lys Gly Gln Pro Arg Glu Pro Gln Val Tyr Thr Leu Pro
    370                 375                 380

Pro Ser Arg Glu Glu Met Thr Lys Asn Gln Val Ser Leu Trp Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys Gly
465                 470                 475                 480

Gly Gly Gly Ser Gly Gly Gly Ser Gln Ile Val Leu Ser Gln Ser
                485                 490                 495

Pro Ala Ile Leu Ser Ala Ser Pro Gly Glu Lys Val Thr Met Thr Cys
            500                 505                 510

Arg Ala Ser Leu Ser Val Ser Ser Met His Trp Tyr Gln Gln Lys Pro
            515                 520                 525

Gly Ser Ser Pro Lys Pro Trp Ile Tyr Ala Thr Ser Asn Leu Ala Ser
    530                 535                 540

Gly Val Pro Ala Arg Phe Ser Gly Ser Gly Ser Gly Thr Ser Tyr Ser
545                 550                 555                 560

Leu Thr Ile Ser Arg Val Glu Ala Glu Asp Ala Ala Thr Tyr Tyr Cys
                565                 570                 575

Gln Gln Trp Ile Phe Asn Pro Pro Thr Phe Gly Gly Gly Thr Lys Leu
            580                 585                 590

Glu Ile Lys Gly Gly Ser Glu Gly Lys Ser Ser Gly Ser Gly Ser Glu
        595                 600                 605

Ser Lys Ser Thr Gly Gly Ser Gln Ala Tyr Leu Gln Gln Ser Gly Ala
    610                 615                 620

Glu Leu Val Arg Pro Gly Ala Ser Val Lys Met Ser Cys Lys Thr Ser
625                 630                 635                 640

Gly Tyr Thr Phe Ser Ser Tyr Asn Met His Trp Val Lys Gln Thr Pro
                645                 650                 655

Arg Gln Ala Leu Glu Trp Ile Gly Ala Ile Tyr Pro Gly Asn Gly Asp
            660                 665                 670
```

```
Thr Ser Tyr Asn Gln Lys Phe Lys Gly Lys Ala Thr Leu Thr Val Asp
        675                 680                 685

Lys Ser Ser Ser Thr Ala Tyr Met Gln Leu Ser Ser Leu Thr Ser Glu
        690                 695                 700

Asp Ser Ala Val Tyr Phe Cys Thr Arg Ser Asn Tyr Tyr Gly Ser Ser
705                 710                 715                 720

Gly Trp Tyr Phe Asp Val Trp Gly Thr Gly Thr Val Thr Val Ser
                    725                 730                 735

Ser

<210> SEQ ID NO 163
<211> LENGTH: 2211
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 163
caggtgcagc tggtgcagag cggcgccgag gtgaagaagc tggcagcag cgtgaaggtg       60 agctgtaagg ccagcggcta cactttcact aggagcacta tgcactgggt gaggcaggcc      120
cctggccagg gcctggagtg gatgggctac atcaatccta gcagcgccta cactaattac      180
gcccagaagt tccagggcag ggtgactctg actgccgata agagcactag cactgcctac      240
atggagctga gcagcctgag gagcgaggat actgccgtgt actactgtgc cagccctcag      300
gtgcactacg attacggcgg cttcccttac tggggccagg gcactctggt gactgtgagc      360
agcggcggct ccgagggcaa gagcagcggc agcggcagcg agagcaagag caccggcggc      420
agcgagatcg tgctgactca gagccctgcc actctgagcg ccagccctgg cgagagggtg      480
actctgagct gtagcgccag cagcagcgtg agctacatga attggtacca gcagaagcct      540
ggccaggccc taggagagtg gatctacgat agcagcaagc tggccagcgg cgtgcctgcc      600
aggttcagcg gcagcggcag cggcagggat tacactctga ctatcagcag cctggagcct      660
gaggatttcg ccgtgtacta ctgtcagcag tggagcagga tcctcctac tttcggcggc       720 ggcactaagg tggagatcaa ggagcccaaa tctagcgaca aaactcacac atgtccaccg      780
tgcccagcac ctgaagcagc agggggaccg tcagtcttcc tcttcccccc aaaacccaag      840
gacaccctca tgatctcccg gacccctgag gtcacatgcg tggtggtgag cgtgagccac      900
gaagaccctg aggtcaagtt caactggtac gtggacggcg tggaggtgca taatgccaag      960
acaaagccgc gggaggagca gtacaacagc acgtaccgtg tggtcagcgt cctcaccgtc     1020
ctgcaccagg actggctgaa tggcaaggag tacaagtgca aggtctccaa caaagccctc     1080
ccagccccca tcgagaaaac catctccaaa gccaagggc agccccgaga accacaggtg     1140
tacaccctgc cccatcccg ggaggagatg accaagaacc aggtcagcct gtggtgcctg     1200
gtcaaaggct tctatcccag cgacatcgcc gtggagtggg agagcaatgg gcagccggag     1260
aacaactaca agaccacgcc tcccgtgctg gactccgacg gctccttctt cctctacagc     1320
aagctcaccg tggacaagtc tagatggcag caggggaacg tcttctcatg ctccgtgatg     1380
catgaggctc tgcacaacca ctacacgcag aagagcctct ccctgtctcc gggtaaagga     1440
ggcggaggga gtggcggggg aggctctcag attgtcctga ccaatcccc agcaattctg     1500 agtgctagcc ctgagagaa ggtaacaatg acttgtcggg catcccttag cgtctcatcc     1560
atgcattggt atcaacaaaa gccaggttca tctccaaaac cctggattta cgctacatct     1620
```

```
aacctggcat ctggggtgcc tgccagattt agtggatctg gttccggcac atcatattcc    1680
cttacaatca gccgagtgga agccgaggat gctgcaacct attactgtca acaatggata    1740
tttaaccctc ccacctttgg gggtgggact aaactcgaaa tcaagggcgg ctccgagggc    1800
aagagcagcg gcagcggcag cgagagcaag agcaccggcg gcagccaagc ctatcttcaa    1860
caatctgggg ctgagcttgt ccggccagga gcctccgtca aaatgagctg caaaacctca    1920
ggttatactt ttagtagcta taacatgcat tgggtaaaac aaaccccccg acaagcattg    1980
gagtggatag gggccatata ccccggcaat ggagacacaa gttacaacca gaagtttaaa    2040
ggcaaagcta cactcacagt tgacaaatcc tcaagtactg cttatatgca actctcctct    2100
ctcacttccg aagacagtgc cgtatatttt tgcactcggt ccaattacta tggatctagt    2160
ggctggtact ttgacgtttg gggcactggg acaactgtta cagtgtccag c             2211
```

```
<210> SEQ ID NO 164
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Glu Ile Val Leu Thr Gln Ser Pro Ala Thr Leu Ser Ala Ser Pro Gly
1               5                   10                  15

Glu Arg Val Thr Leu Ser Cys Ser Ala Ser Ser Val Ser Tyr Met
            20                  25                  30

Asn Trp Tyr Gln Gln Lys Pro Gly Gln Ala Pro Arg Arg Trp Ile Tyr
        35                  40                  45

Asp Ser Ser Lys Leu Ala Ser Gly Val Pro Ala Arg Phe Ser Gly Ser
    50                  55                  60

Gly Ser Gly Arg Asp Tyr Thr Leu Thr Ile Ser Ser Leu Glu Pro Glu
65                  70                  75                  80

Asp Phe Ala Val Tyr Tyr Cys Gln Gln Trp Ser Arg Asn Pro Pro Thr
                85                  90                  95

Phe Gly Gly Gly Thr Lys Val Glu Ile Lys Gly Gly Ser Glu Gly Lys
            100                 105                 110

Ser Ser Gly Ser Gly Ser Glu Ser Lys Ser Thr Gly Gly Ser Gln Val
        115                 120                 125

Gln Leu Val Gln Ser Gly Ala Glu Val Lys Lys Pro Gly Ser Ser Val
    130                 135                 140

Lys Val Ser Cys Lys Ala Ser Gly Tyr Thr Phe Thr Arg Ser Thr Met
145                 150                 155                 160

His Trp Val Lys Gln Ala Pro Gly Gln Gly Leu Glu Trp Ile Gly Tyr
                165                 170                 175

Ile Asn Pro Ser Ser Ala Tyr Thr Asn Tyr Asn Gln Lys Phe Gln Gly
            180                 185                 190

Arg Val Thr Leu Thr Ala Asp Lys Ser Thr Ser Thr Ala Tyr Met Glu
        195                 200                 205

Leu Ser Ser Leu Arg Ser Glu Asp Thr Ala Val Tyr Tyr Cys Ala Ser
    210                 215                 220

Pro Gln Val His Tyr Asp Tyr Ala Gly Phe Pro Tyr Trp Gly Gln Gly
225                 230                 235                 240

Thr Leu Val Thr Val Ser Ser Glu Pro Lys Ser Ser Asp Lys Thr His
                245                 250                 255
```

```
Thr Cys Pro Pro Cys Pro Ala Pro Glu Ala Ala Gly Gly Pro Ser Val
                260                 265                 270
Phe Leu Phe Pro Pro Lys Pro Lys Asp Thr Leu Met Ile Ser Arg Thr
            275                 280                 285
Pro Glu Val Thr Cys Val Val Val Ser Val Ser His Glu Asp Pro Glu
        290                 295                 300
Val Lys Phe Asn Trp Tyr Val Asp Gly Val Glu Val His Asn Ala Lys
305                 310                 315                 320
Thr Lys Pro Arg Glu Glu Gln Tyr Asn Ser Thr Tyr Arg Val Val Ser
                325                 330                 335
Val Leu Thr Val Leu His Gln Asp Trp Leu Asn Gly Lys Glu Tyr Lys
            340                 345                 350
Cys Lys Val Ser Asn Lys Ala Leu Pro Ala Pro Ile Glu Lys Thr Ile
        355                 360                 365
Ser Lys Ala Lys Gly Gln Pro Arg Glu Pro Gln Val Tyr Thr Leu Pro
    370                 375                 380
Pro Ser Arg Glu Glu Met Thr Lys Asn Gln Val Ser Leu Trp Cys Leu
385                 390                 395                 400
Val Lys Gly Phe Tyr Pro Ser Asp Ile Ala Val Glu Trp Glu Ser Asn
                405                 410                 415
Gly Gln Pro Glu Asn Asn Tyr Lys Thr Thr Pro Pro Val Leu Asp Ser
            420                 425                 430
Asp Gly Ser Phe Phe Leu Tyr Ser Lys Leu Thr Val Asp Lys Ser Arg
        435                 440                 445
Trp Gln Gln Gly Asn Val Phe Ser Cys Ser Val Met His Glu Ala Leu
    450                 455                 460
His Asn His Tyr Thr Gln Lys Ser Leu Ser Leu Ser Pro Gly Lys
465                 470                 475

<210> SEQ ID NO 165
<211> LENGTH: 1437
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 165
gagatcgtgc tgacccagtc tcctgccaca ctgagtgctt ctccaggcga gagagtgacc      60
ctgtcctgct ccgcttcctc ctccgtgtcc tacatgaact ggtatcagca gaagcccggc     120
caggctcctc ggagatggat ctacgactct ccaagctggg cctctggtgt gccagcagga     180
ttttctggct ctggctccgg cagagactat accctgacca tctccagcct ggaacctgag     240
gacttcgccg tgtactactg ccagcagtgg tctaggaacc ctcctacctt ggcggaggc      300 accaaggtgg aaatcaaggg cggatctgag ggaaagtcca gcggctccgg cagcgaaagc     360
aagtccaccg cggaagcca ggttcaactg gttcagtctg gcgccgaagt gaagaaacct      420
ggctcctccg tcaaggtgtc ctgcaaggct tccggctaca cctttaccag atccaccatg     480
cactgggtca agcaggcccc tggacaaggc ttggagtgga tcggctacat caaccccagc     540
tccgcctaca ccaactacaa ccagaaattc cagggcagat gaccctgac cgccgacaag     600 tctacctcca ccgcctacat ggaactgtcc agcctgagat ctgaggacac cgccgtgtac     660
tactgcgcct ctcctcaggt ccactacgac tacgccggct tccttattg gggccagggc     720 acactggtca ccgtttcttc tgagcccaaa tctagcgaca aaactcacac atgcccaccg     780
```

-continued

```
tgcccagcac ctgaagccgc cggggggaccg tcagtcttcc tcttcccccc aaaacccaag    840
gacaccctca tgatctcccg gacccctgag gtcacatgcg tggtggtgag cgtgagccac    900
gaagaccctg aggtcaagtt caactggtac gtggacggcg tggaggtgca taatgccaag    960
acaaagccgc gggaggagca gtacaacagc acgtaccgtg tggtcagcgt cctcaccgtc   1020
ctgcaccagg actggctgaa tggcaaggag tacaagtgca aggtgtcgaa caaagccctc   1080
ccagccccca tcgagaaaac catctccaaa gccaaagggc agccccgaga accacaggtg   1140
tacaccctgc ccccatcccg ggaggagatg accaagaacc aggtcagcct gtggtgcctg   1200
gtcaaaggct tctatcccag cgacatcgcc gtggagtggg agagcaatgg gcagccggag   1260
aacaactaca agaccacgcc tcccgtgctg gactccgacg gctccttctt cctctacagc   1320
aagctcaccg tggacaagag cagatggcag caggggaacg tcttctcatg ctccgtgatg   1380
catgaggctc tgcacaacca ctacacgcag aagtctctct ccctgtctcc gggaaaa     1437
```

<210> SEQ ID NO 166
<211> LENGTH: 747
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

```
Glu Ile Val Leu Thr Gln Ser Pro Ala Thr Leu Ser Ala Ser Pro Gly
1               5                   10                  15

Glu Arg Val Thr Leu Ser Cys Ser Ala Ser Ser Val Ser Tyr Met
            20                  25                  30

Asn Trp Tyr Gln Gln Lys Pro Gly Gln Ala Pro Arg Arg Trp Ile Tyr
        35                  40                  45

Asp Ser Ser Lys Leu Ala Ser Gly Val Pro Ala Arg Phe Ser Gly Ser
    50                  55                  60

Gly Ser Gly Arg Asp Tyr Thr Leu Thr Ile Ser Ser Leu Glu Pro Glu
65                  70                  75                  80

Asp Phe Ala Val Tyr Tyr Cys Gln Gln Trp Ser Arg Asn Pro Pro Thr
                85                  90                  95

Phe Gly Gly Gly Thr Lys Val Glu Ile Lys Gly Gly Ser Glu Gly Lys
            100                 105                 110

Ser Ser Gly Ser Gly Ser Glu Ser Lys Ser Thr Gly Gly Ser Gln Val
        115                 120                 125

Gln Leu Val Gln Ser Gly Ala Glu Val Lys Lys Pro Gly Ser Ser Val
    130                 135                 140

Lys Val Ser Cys Lys Ala Ser Gly Tyr Thr Phe Thr Arg Ser Thr Met
145                 150                 155                 160

His Trp Val Lys Gln Ala Pro Gly Gln Gly Leu Glu Trp Ile Gly Tyr
                165                 170                 175

Ile Asn Pro Ser Ser Ala Tyr Thr Asn Tyr Asn Gln Lys Phe Gln Gly
            180                 185                 190

Arg Val Thr Leu Thr Ala Asp Lys Ser Thr Ser Thr Ala Tyr Met Glu
        195                 200                 205

Leu Ser Ser Leu Arg Ser Glu Asp Thr Ala Val Tyr Tyr Cys Ala Ser
    210                 215                 220

Pro Gln Val His Tyr Asp Tyr Ala Gly Phe Pro Tyr Trp Gly Gln Gly
225                 230                 235                 240

Thr Leu Val Thr Val Ser Ser Glu Pro Lys Ser Ser Asp Lys Thr His
```

```
                245                 250                 255
Thr Cys Pro Pro Cys Pro Ala Pro Glu Ala Ala Gly Gly Pro Ser Val
                260                 265                 270

Phe Leu Phe Pro Pro Lys Pro Lys Asp Thr Leu Met Ile Ser Arg Thr
                275                 280                 285

Pro Glu Val Thr Cys Val Val Val Ser Val Ser His Glu Asp Pro Glu
                290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
                340                 345                 350

Cys Lys Val Ser Asn Lys Ala Leu Pro Ala Pro Ile Glu Lys Thr Ile
                355                 360                 365

Ser Lys Ala Lys Gly Gln Pro Arg Glu Pro Gln Val Tyr Thr Leu Pro
                370                 375                 380

Pro Ser Arg Glu Glu Met Thr Lys Asn Gln Val Ser Leu Ser Cys Ala
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
                420                 425                 430

Asp Gly Ser Phe Phe Leu Val Ser Lys Leu Thr Val Asp Lys Ser Arg
                435                 440                 445

Trp Gln Gln Gly Asn Val Phe Ser Cys Ser Val Met His Glu Ala Leu
                450                 455                 460

His Asn Arg Phe Thr Gln Lys Ser Leu Ser Leu Ser Pro Gly Lys Gly
465                 470                 475                 480

Gly Gly Gly Ser Gly Gly Gly Ser Gly Gly Gly Ser Gly Gly
                485                 490                 495

Gly Gly Ser Gln Ile Val Leu Ser Gln Ser Pro Ala Ile Leu Ser Ala
                500                 505                 510

Ser Pro Gly Glu Lys Val Thr Met Thr Cys Arg Ala Ser Leu Ser Val
                515                 520                 525

Ser Ser Met His Trp Tyr Gln Gln Lys Pro Gly Ser Ser Pro Lys Pro
                530                 535                 540

Trp Ile Tyr Ala Thr Ser Asn Leu Ala Ser Gly Val Pro Ala Arg Phe
545                 550                 555                 560

Ser Gly Ser Gly Ser Gly Thr Ser Tyr Ser Leu Thr Ile Ser Arg Val
                565                 570                 575

Glu Ala Glu Asp Ala Ala Thr Tyr Tyr Cys Gln Gln Trp Ile Phe Asn
                580                 585                 590

Pro Pro Thr Phe Gly Gly Gly Thr Lys Leu Glu Ile Lys Gly Gly Ser
                595                 600                 605

Glu Gly Lys Ser Ser Gly Ser Gly Ser Glu Ser Lys Ser Thr Gly Gly
                610                 615                 620

Ser Gln Ala Tyr Leu Gln Ser Gly Ala Glu Leu Val Arg Pro Gly
625                 630                 635                 640

Ala Ser Val Lys Met Ser Cys Lys Thr Ser Gly Tyr Thr Phe Ser Ser
                645                 650                 655

Tyr Asn Met His Trp Val Lys Gln Thr Pro Arg Gln Ala Leu Glu Trp
                660                 665                 670
```

Ile Gly Ala Ile Tyr Pro Gly Asn Gly Asp Thr Ser Tyr Asn Gln Lys
        675                 680                 685

Phe Lys Gly Lys Ala Thr Leu Thr Val Asp Lys Ser Ser Thr Ala
690                 695                 700

Tyr Met Gln Leu Ser Ser Leu Thr Ser Glu Asp Ser Ala Val Tyr Phe
705                 710                 715                 720

Cys Thr Arg Ser Asn Tyr Tyr Gly Ser Ser Gly Trp Tyr Phe Asp Val
                725                 730                 735

Trp Gly Thr Gly Thr Thr Val Thr Val Ser Ser
            740                 745

<210> SEQ ID NO 167
<211> LENGTH: 2241
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167
gagatcgtgc tgacccagtc tcctgccaca ctgagtgctt ctccaggcga gagagtgacc      60
ctgtcctgct ccgcttcctc ctccgtgtcc tacatgaact ggtatcagca gaagcccggc     120
caggctcctc ggagatggat ctacgactct tccaagctgg cctctggtgt gccagcagat     180
ttttctggct ctggctccgg cagagactat accctgacca tctccagcct ggaacctgag     240
gacttcgccg tgtactactg ccagcagtgg tctaggaacc tcctaccctt ggcggaggc      300 accaaggtgg aaatcaaggg cggatctgag ggaaagtcca gcggctccgg cagcgaaagc     360
aagtccaccg gcggaagcca ggttcaactg gttcagtctg gcgccgaagt gaagaaacct     420
ggctcctccg tcaaggtgtc ctgcaaggct tccggctaca cctttaccag atccaccatg     480
cactgggtca gcaggcccc tggacaaggc ttggagtgga tcggctacat caaccccagc     540
tccgcctaca ccaactacaa ccagaaattc cagggcagag tgaccctgac cgccgacaag     600
tctacctcca ccgcctacat ggaactgtcc agcctgagat ctgaggacac cgccgtgtac     660
tactgcgcct ctcctcaggt ccactacgac tacgccggct tccttattg gggccagggc     720 acactggtca ccgtttcttc tgagcccaaa tctagcgaca aaactcacac atgcccaccg     780
tgcccagcac ctgaagccgc ggggggaccg tcagtcttcc tcttcccccc aaaacccaag     840
gacaccctca tgatctcccg gacccctgag gtcacatgcg tggtggtgag cgtgagccac     900
gaagaccctg aggtcaagtt caactggtac gtggacggcg tggaggtgca taatgccaag     960
acaaagccgc gggaggagca gtacaacagc acgtaccgtg tggtcagcgt cctcaccgtc    1020
ctgcaccagg actggctgaa tggcaaggag tacaagtgca aggtgtcgaa caaagccctc    1080
ccagccccca tcgagaaaac catctccaaa gccaagggc agccccgaga accacaggtg    1140
tacaccctgc cccatcccg ggaggagatg accaagaacc aggtcagcct gtcctgcgcc    1200
gtcaaaggct tctatcccag cgacatcgcc gtggagtggg agagcaatgg gcagccggag    1260
aacaactaca agaccacgcc tcccgtgctg gactccgacg gctccttctt cctcgtgagc    1320
aagctcaccg tggacaagag cagatggcag caggggaacg tcttctcatg ctccgtgatg    1380
catgaggctc tgcacaaccg gttcacgcag aagtctctct ccctgtctcc gggaaaagga    1440 ggcgaggat ctggcggagg tggaagtggc ggaggcggtt ctggtggtgg tggatctcag    1500
atcgtgctgt ctcagtctcc agctatcctg tctgctagcc ctggcgagaa agtgaccatg    1560

```
acctgtagag ccagcctgtc cgtgtcctcc atgcactggt atcagcagaa gcctggcagc    1620 tccoctaagc cttggatcta cgccacctcc aatctggcct ctggcgtgcc agctagattc    1680
tccggatctg gctccggcac ctcctacagc ctgacaatct ccagagtgga agccgaggat    1740
gccgccacct actactgtca gcagtggatc ttcaaccctc ctaccttcgg cggaggcacc    1800
aagctggaaa tcaagggagg gagcgaggga aagtccagcg gaagcggctc tgagtccaaa    1860
tccaccggag ggagccaggc ttacttgcag cagtctggtg ccgaactcgt tagacctgga    1920
gcctccgtga agatgtcctg caagacctcc ggctacacct ctccagctca acatgcac     1980 tgggtcaagc agacccctcg gcaggctctg aatggatcg cgctatcta tcctggcaac     2040 ggcgacacct cctacaacca gaagttcaag ggcaaagcta ccctgaccgt ggacaagtcc    2100
tcctccaccg cttacatgca gctgtccagc ctgacctctg aggactccgc cgtgtacttc    2160
tgcacccggt ctaactacta cggctcctcc ggctggtact cgatgtgtg gggaaccgga    2220 accaccgtga cagtctcttc t                                             2241
```

<210> SEQ ID NO 168
<211> LENGTH: 743
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

```
Asp Ile Gln Met Thr Gln Ser Pro Ser Leu Ser Ala Ser Val Gly
1               5                   10                  15

Asp Arg Val Thr Ile Thr Cys Arg Ala Arg Gln Ser Ile Gly Thr Ala
            20                  25                  30

Ile His Trp Tyr Gln Gln Lys Pro Gly Lys Ala Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gly Ser Trp Pro Tyr
                85                  90                  95

Thr Phe Gly Gln Gly Thr Lys Leu Glu Ile Lys Gly Gly Ser Glu Gly
            100                 105                 110

Lys Ser Ser Gly Ser Gly Ser Glu Ser Lys Ser Thr Gly Gly Ser Glu
        115                 120                 125

Val Gln Leu Val Glu Ser Gly Gly Gly Leu Val Lys Pro Gly Gly Ser
    130                 135                 140

Leu Arg Leu Ser Cys Ala Ala Ser Gly Phe Thr Phe Ser Arg Tyr Asn
145                 150                 155                 160

Met Asn Trp Val Arg Gln Ala Pro Gly Lys Gly Leu Glu Trp Val Ser
                165                 170                 175

Ser Ile Ser Thr Ser Ser Asn Tyr Ile Tyr Tyr Ala Asp Ser Val Lys
            180                 185                 190

Gly Arg Phe Thr Phe Ser Arg Asp Asn Ala Lys Asn Ser Leu Asp Leu
        195                 200                 205

Gln Met Ser Gly Leu Arg Ala Glu Asp Thr Ala Ile Tyr Tyr Cys Thr
    210                 215                 220

Arg Gly Trp Gly Pro Phe Asp Tyr Trp Gly Gln Gly Thr Leu Val Thr
225                 230                 235                 240
```

```
Val Ser Ser Glu Pro Lys Ser Asp Lys Thr His Thr Cys Pro Pro
                245             250             255
Cys Pro Ala Pro Glu Ala Ala Gly Gly Pro Ser Val Phe Leu Phe Pro
            260             265             270
Pro Lys Pro Lys Asp Thr Leu Met Ile Ser Arg Thr Pro Glu Val Thr
        275             280             285
Cys Val Val Val Ser Val Ser His Glu Asp Pro Glu Val Lys Phe Asn
    290             295             300
Trp Tyr Val Asp Gly Val Glu Val His Asn Ala Lys Thr Lys Pro Arg
305             310             315             320
Glu Glu Gln Tyr Asn Ser Thr Tyr Arg Val Val Ser Val Leu Thr Val
                325             330             335
Leu His Gln Asp Trp Leu Asn Gly Lys Glu Tyr Lys Cys Lys Val Ser
            340             345             350
Asn Lys Ala Leu Pro Ala Pro Ile Glu Lys Thr Ile Ser Lys Ala Lys
        355             360             365
Gly Gln Pro Arg Glu Pro Gln Val Tyr Thr Leu Pro Pro Ser Arg Glu
    370             375             380
Glu Met Thr Lys Asn Gln Val Ser Leu Trp Cys Leu Val Lys Gly Phe
385             390             395             400
Tyr Pro Ser Asp Ile Ala Val Glu Trp Glu Ser Asn Gly Gln Pro Glu
                405             410             415
Asn Asn Tyr Lys Thr Thr Pro Pro Val Leu Asp Ser Asp Gly Ser Phe
            420             425             430
Phe Leu Tyr Ser Lys Leu Thr Val Asp Lys Ser Arg Trp Gln Gln Gly
        435             440             445
Asn Val Phe Ser Cys Ser Val Met His Glu Ala Leu His Asn His Tyr
    450             455             460
Thr Gln Lys Ser Leu Ser Leu Ser Pro Gly Lys Gly Gly Gly Gly Ser
465             470             475             480
Gly Gly Gly Gly Ser Gly Gly Gly Ser Gly Gly Gly Gly Ser Glu
                485             490             495
Ile Val Leu Thr Gln Ser Pro Ala Thr Leu Ser Leu Ser Pro Gly Glu
            500             505             510
Arg Ala Thr Leu Ser Cys Arg Ala Ser Leu Ser Val Ser Ser Met His
        515             520             525
Trp Tyr Gln Gln Lys Pro Gly Gln Ala Pro Arg Leu Leu Ile Tyr Ala
    530             535             540
Thr Ser Asn Leu Ala Ser Gly Ile Pro Ala Arg Phe Ser Gly Ser Gly
545             550             555             560
Ser Gly Thr Asp Phe Thr Leu Thr Ile Ser Ser Leu Glu Pro Glu Asp
                565             570             575
Phe Ala Val Tyr Tyr Cys Gln Gln Trp Ile Phe Asn Pro Pro Thr Phe
            580             585             590
Gly Gly Gly Thr Lys Val Glu Ile Lys Gly Gly Ser Gly Gly Lys Ser
        595             600             605
Ser Gly Ser Gly Ser Glu Ser Lys Ser Thr Gly Gly Ser Gln Val Gln
    610             615             620
Leu Val Gln Ser Gly Ala Glu Val Lys Lys Pro Gly Ser Ser Val Lys
625             630             635             640
Val Ser Cys Lys Ala Ser Gly Tyr Thr Phe Ser Ser Tyr Asn Met His
                645             650             655
```

```
Trp Val Arg Gln Ala Pro Gly Gln Gly Leu Glu Trp Met Gly Ala Ile
            660                 665                 670

Tyr Pro Gly Ala Gly Asp Thr Ser Tyr Ala Gln Lys Phe Gln Gly Arg
        675                 680                 685

Val Thr Ile Thr Ala Asp Glu Ser Thr Ser Thr Ala Tyr Met Glu Leu
        690                 695                 700

Ser Ser Leu Arg Ser Glu Asp Thr Ala Val Tyr Tyr Cys Ala Arg Ser
705                 710                 715                 720

Asn Tyr Tyr Gly Ser Gly Trp Tyr Phe Asp Val Trp Gly Lys Gly
                725                 730                 735

Thr Thr Val Thr Val Ser Ser
            740

<210> SEQ ID NO 169
<211> LENGTH: 2229
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 169
gacatccaga tgacccagtc tccatcctct ctgtccgcct ctgtgggcga cagagtgacc      60
attacctgcc gggccagaca gtctatcggc accgctatcc actggtatca gcagaagcct     120
ggcaaggccc ctaagctgct gattaagtac gcctccgagt ccatctccgg cgtgccctcc     180
agattttctg gctctggatc tggcaccgac tttaccctga caatctccag cctgcagcct     240
gaggacttcg ccacctacta ctgtcagcag tccggctctt ggccttacac ctttggtcag     300
ggcaccaagc tggaaatcaa gggcggatct gagggaaagt ccagcggctc cggcagcgaa     360
agcaagtcca ccggcggaag cgaggtgcag ctggttgaat ctggcggagg actggttaag     420
cctggcggct ctctgagact gtcttgtgct gcttctggct tcaccttcag ccggtacaac     480
atgaactggg tccgacaggc tcctggcaaa ggcctggaat gggtgtcctc catctccacc     540
tccagcaact acatctacta cgccgactcc gtgaagggca gattcacctt ctccagagac     600
aacgccaaga actccctgga cctgcagatg tctggcctga gctgagga caccgctatc     660 tactactgca ccagaggctg ggacccttc gattattggg ccagggaac cctggtcacc     720 gtgtcatctg agcccaaatc tagcgacaaa actcacacat gcccaccgtg cccagcacct     780
gaagccgccg ggggaccgtc agtcttcctc ttccccccaa aacccaagga caccctcatg     840
atctcccgga cccctgaggt cacatgcgtg gtggtgagcg tgagccacga agaccctgag     900
gtcaagttca actggtacgt ggacggcgtg gaggtgcata atgccaagac aaagccgcgg     960
gaggagcagt acaacagcac gtaccgtgtg gtcagcgtcc tcaccgtcct gcaccaggac    1020
tggctgaatg gcaaggagta caagtgcaag gtgtcgaaca agccctccc agcccccatc    1080 gagaaaacca tctccaaagc caaagggcag ccccgagaac cacaggtgta caccctgccc    1140
ccatcccggg aggagatgac caagaaccag gtcagcctgt ggtgcctggt caaaggcttc    1200
tatcccagcg acatcgccgt ggagtgggag agcaatgggc agccggagaa caactacaag    1260
accacgcctc ccgtgctgga ctccgacggc tccttcttcc tctacagcaa gctcaccgtg    1320
gacaagagca ggtggcagca ggggaacgtc ttctcatgct ccgtgatgca tgaggctctg    1380
cacaaccact acacgcagaa gtctctctcc ctgtctccgg gaaaggagg cggaggatct    1440 ggcggaggtg gaagtggcgg aggcggttct ggtggtggtg gatctgagat cgtgctgacc    1500
```

-continued

```
cagtctccag ccacactgtc actgtctcca ggcgagagag ctaccctgtc ctgtagagcc    1560
tctctgtccg tgtcctccat gcactggtat cagcagaagc ctggacaggc ccctcggctg    1620
ctgatctacg ctacctctaa tctggccagc ggtatccccg ccagatttc tggttctggc     1680 tctggcaccg acttaccct gaccatctcc agcctggaac ctgaggactt cgccgtgtac     1740
tactgccagc agtggatctt caaccctcct acctttggcg gaggcaccaa ggtggaaatc    1800
aaggagggga gcgagggaaa gtccagcgga agcggctctg agtccaaatc caccggaggg    1860
agccaggttc aactggttca gtctggcgcc gaagtgaaga aacctggctc ctccgtgaag    1920
gtgtcctgca aggcttccgg ctacaccttc tccagctaca acatgcactg ggtccgacag    1980 gccctggac aaggattgga atggatgggc gctatctacc ctggcgctgg cgatacctct     2040
tacgcccaga aattccaggg cagagtgacc atcaccgccg acgagtctac ctccaccgcc    2100
tacatggaac tgtccagcct gagatctgag gacaccgccg tgtactactg cgcccggtct    2160
aattactacg gctccagcgg ctggtacttc gacgtgtggg gaaagggcac caccgtgaca    2220
gtctcttct                                                            2229
```

<210> SEQ ID NO 170
<211> LENGTH: 747
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

```
Glu Ile Val Leu Thr Gln Ser Pro Ala Thr Leu Ser Ala Ser Pro Gly
1               5                   10                  15

Glu Arg Val Thr Leu Ser Cys Ser Ala Ser Ser Ser Val Ser Tyr Met
            20                  25                  30

Asn Trp Tyr Gln Gln Lys Pro Gly Gln Ala Pro Arg Arg Trp Ile Tyr
        35                  40                  45

Asp Ser Ser Lys Leu Ala Ser Gly Val Pro Ala Arg Phe Ser Gly Ser
    50                  55                  60

Gly Ser Gly Arg Asp Tyr Thr Leu Thr Ile Ser Ser Leu Glu Pro Glu
65                  70                  75                  80

Asp Phe Ala Val Tyr Tyr Cys Gln Gln Trp Ser Arg Asn Pro Pro Thr
                85                  90                  95

Phe Gly Gly Gly Thr Lys Val Glu Ile Lys Gly Gly Ser Glu Gly Lys
            100                 105                 110

Ser Ser Gly Ser Gly Ser Glu Ser Lys Ser Thr Gly Gly Ser Gln Val
        115                 120                 125

Gln Leu Val Gln Ser Gly Ala Glu Val Lys Lys Pro Gly Ser Ser Val
    130                 135                 140

Lys Val Ser Cys Lys Ala Ser Gly Tyr Thr Phe Thr Arg Ser Thr Met
145                 150                 155                 160

His Trp Val Lys Gln Ala Pro Gly Gln Gly Leu Glu Trp Ile Gly Tyr
                165                 170                 175

Ile Asn Pro Ser Ser Ala Tyr Thr Asn Tyr Asn Gln Lys Phe Gln Gly
            180                 185                 190

Arg Val Thr Leu Thr Ala Asp Lys Ser Thr Thr Ala Tyr Met Glu
        195                 200                 205

Leu Ser Ser Leu Arg Ser Glu Asp Thr Ala Val Tyr Tyr Cys Ala Ser
    210                 215                 220
```

```
Pro Gln Val His Tyr Asp Tyr Ala Gly Phe Pro Tyr Trp Gly Gln Gly
225                 230                 235                 240

Thr Leu Val Thr Val Ser Ser Glu Pro Lys Ser Ser Asp Lys Thr His
            245                 250                 255

Thr Cys Pro Pro Cys Pro Ala Pro Glu Ala Ala Gly Gly Pro Ser Val
        260                 265                 270

Phe Leu Phe Pro Pro Lys Pro Lys Asp Thr Leu Met Ile Ser Arg Thr
        275                 280             285

Pro Glu Val Thr Cys Val Val Val Ser Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
                340                 345                 350

Cys Lys Val Ser Asn Lys Ala Leu Pro Ala Pro Ile Glu Lys Thr Ile
                355                 360                 365

Ser Lys Ala Lys Gly Gln Pro Arg Glu Pro Gln Val Tyr Thr Leu Pro
370                 375                 380

Pro Ser Arg Glu Glu Met Thr Lys Asn Gln Val Ser Leu Trp Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
                420                 425                 430

Asp Gly Ser Phe Phe Leu Tyr Ser Lys Leu Thr Val Asp Lys Ser Arg
                435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys Gly
465                 470                 475                 480

Gly Gly Gly Ser Gly Gly Gly Ser Gly Gly Gly Ser Gly Gly
                485                 490                 495

Gly Gly Ser Glu Ile Val Leu Thr Gln Ser Pro Ala Thr Leu Ser Leu
            500                 505                 510

Ser Pro Gly Glu Arg Ala Thr Leu Ser Cys Arg Ala Ser Leu Ser Val
        515                 520                 525

Ser Ser Met His Trp Tyr Gln Gln Lys Pro Gly Gln Ala Pro Arg Leu
530                 535                 540

Leu Ile Tyr Ala Thr Ser Asn Leu Ala Ser Gly Ile Pro Ala Arg Phe
545                 550                 555                 560

Ser Gly Ser Gly Ser Gly Thr Asp Phe Thr Leu Thr Ile Ser Ser Leu
                565                 570                 575

Glu Pro Glu Asp Phe Ala Val Tyr Tyr Cys Gln Gln Trp Ile Phe Asn
                580                 585                 590

Pro Pro Thr Phe Gly Gly Gly Thr Lys Val Glu Ile Lys Gly Gly Ser
                595                 600                 605

Glu Gly Lys Ser Ser Gly Ser Gly Ser Glu Ser Lys Ser Thr Gly Gly
                610                 615                 620

Ser Gln Val Gln Leu Val Gln Ser Gly Ala Glu Val Lys Lys Pro Gly
625                 630                 635                 640

Ser Ser Val Lys Val Ser Cys Lys Ala Ser Gly Tyr Thr Phe Ser Ser
```

```
                        645                 650                 655
Tyr Asn Met His Trp Val Arg Gln Ala Pro Gly Gln Gly Leu Glu Trp
            660                 665                 670

Met Gly Ala Ile Tyr Pro Gly Ala Gly Asp Thr Ser Tyr Ala Gln Lys
        675                 680                 685

Phe Gln Gly Arg Val Thr Ile Thr Ala Asp Glu Ser Thr Ser Thr Ala
    690                 695                 700

Tyr Met Glu Leu Ser Ser Leu Arg Ser Glu Asp Thr Ala Val Tyr Tyr
705                 710                 715                 720

Cys Ala Arg Ser Asn Tyr Tyr Gly Ser Ser Gly Trp Tyr Phe Asp Val
                725                 730                 735

Trp Gly Lys Gly Thr Thr Val Thr Val Ser Ser
            740                 745

<210> SEQ ID NO 171
<211> LENGTH: 2241
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 171
gagatcgtgc tgacccagtc tcctgccaca ctgagtgctt ctccaggcga gagagtgacc        60
ctgtcctgct ccgcttcctc ctccgtgtcc tacatgaact ggtatcagca gaagcccggc       120
caggctcctc ggagatggat ctacgactct tccaagctgg cctctggtgt gccagccaga       180
ttttctggct ctggctccgg cagagactat accctgacca tctccagcct ggaacctgag       240
gacttcgccg tgtactactg ccagcagtgg tctaggaacc tcctaccctt ggcggaggc        300 accaaggtgg aaatcaaggg cggatctgag ggaaagtcca gcggctccgg cagcgaaagc       360
aagtccaccg gcggaagcca ggttcaactg gttcagtctg gcgccgaagt gaagaaacct       420
ggctcctccg tcaaggtgtc ctgcaaggct tccggctaca cctttaccag atccaccatg       480
cactgggtca gcaggccccc tggacaaggc ttggagtgga tcggctacat caaccccagc       540
tccgcctaca ccaactacaa ccagaaattc cagggcagtg tgaccctgac cgccgacaag       600
tctacctcca ccgcctacat ggaactgtcc agcctgagat ctgaggacac cgccgtgtac       660
tactgcgcct ctcctcaggt ccactacgac tacgccggct ttccttattg gggccagggc       720
acactggtca ccgtttcttc tgagcccaaa tctagcgaca aaactcacac atgcccaccg       780
tgcccagcac ctgaagccgc ggggggaccg tcagtcttcc tcttcccccc aaaacccaag       840
gacaccctca tgatctcccg gacccctgag gtcacatgcg tggtggtgag cgtgagccac       900
gaagaccctg aggtcaagtt caactggtac gtggacggcg tggaggtgca taatgccaag       960
acaaagccgc gggaggagca gtacaacagc acgtaccgtg tggtcagcgt cctcaccgtc      1020
ctgcaccagg actggctgaa tggcaaggag tacaagtgca aggtgtcgaa caaagccctc      1080
ccagccccca tcgagaaaac catctccaaa gccaagggc agccccgaga accacaggtg       1140
tacaccctgc ccccatcccg ggaggagatg accaagaacc aggtcagcct gtggtgcctg      1200
gtcaaaggct tctatcccag cgacatcgcc gtggagtggg agagcaatgg gcagccggag      1260
aacaactaca agaccacgcc tcccgtgctg gactccgacg gctccttctt cctctacagc      1320
aagctcaccg tggacaagag cagatggcag caggggaacg tcttctcatg ctccgtgatg      1380
catgaggctc tgcacaacca ctacacgcag aagtctctct ccctgtctcc gggaaaagga      1440
```

-continued

```
ggcggaggat ctggcggagg tggaagtggc ggaggcggtt ctggtggtgg tggatctgag    1500
atcgtgctga cccagtctcc agccacactg tcactgtctc aggcgagag agctaccctg    1560 tcctgtagag cctctctgtc cgtgtcctcc atgcactggt atcagcagaa gcctggacag    1620
gcccctcggc tgctgatcta cgctacctct aatctggcca gcggtatccc cgccagattt    1680
tctggttctg gctctggcac cgactttacc ctgaccatct ccagcctgga acctgaggac    1740
ttcgccgtgt actactgcca gcagtggatc ttcaaccctc ctacctttgg cggaggcacc    1800
aaggtggaaa tcaagggagg gagcgaggga aagtccagcg gaagcggctc tgagtccaaa    1860
tccaccggag ggagccaggt tcaactggtt cagtctggcg ccgaagtgaa gaaacctggc    1920
tcctccgtga aggtgtcctg caaggcttcc ggctacacct tctccagcta caacatgcac    1980
tgggtccgac aggcccctgg acaaggattg aatggatgg cgctatctta ccctggcgct    2040
ggcgatacct cttacgccca gaaattccag ggcagagtga ccatcaccgc cgacgagtct    2100
acctccaccg cctacatgga actgtccagc ctgagatctg aggacaccgc cgtgtactac    2160
tgcgcccggt ctaattacta cggctccagc ggctggtact cgacgtgtg gggaagggc    2220 accaccgtga cagtctcttc t                                              2241
```

<210> SEQ ID NO 172
<211> LENGTH: 451
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 172

```
Gln Val Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Ser Phe
            20                  25                  30

Tyr Trp Ser Trp Ile Arg Gln Pro Ala Asp Glu Gly Leu Glu Trp Ile
        35                  40                  45

Gly Arg Ile Ser Pro Ser Gly Lys Thr Asn Tyr Ile Pro Ser Leu Lys
    50                  55                  60

Ser Arg Ile Ile Met Ser Leu Asp Ala Ser Lys Asn Gln Phe Ser Leu
65                  70                  75                  80

Arg Leu Asn Ser Val Thr Ala Ala Asp Thr Ala Met Tyr Tyr Cys Ala
                85                  90                  95

Arg Gly Glu Tyr Ser Gly Thr Tyr Ser Tyr Ser Phe Asp Val Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
```

```
                210                 215                 220
Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ser Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Ser Cys Ala Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn Arg Phe Thr Gln Lys Ser Leu Ser Leu Ser
        435                 440                 445

Pro Gly Lys
    450

<210> SEQ ID NO 173
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 173
caggttcagc tgcaagagtc tggtcctggc ctggtcaagc cttccgagac actgtctctg      60
acctgctctg tgtccggcgc ctccatctct tccttctact ggtcctggat ccggcagcct    120
gctgacgaag gactggaatg gatcggccgg atcagccctt ctgcaagac  caactacatc    180 cccagcctga gtcccggat  catcatgtcc ctggacgcct ccaagaacca gttctccctg    240
cggctgaact ctgtgaccgc tgccgatacc gccatgtact actgtgccag aggcgagtac    300
tccggcacct actcctacag ctttgacgtg tggggacaag gcaccatggt cacagttct    360 tctgcctcca ccaagggccc atcggtcttc cccctggcac cctcctccaa gagcacctct    420
gggggcacag cggccctggg ctgcctggtc aaggactact ccccgaacc  ggtgacggtg    480 tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaagttgag    660
```

```
cccaaatctt gtgacaaaac tcacacatgc ccaccgtgcc cagcacctga agccgccggg      720
ggaccgtcag tcttcctctt ccccccaaaa cccaaggaca ccctcatgat ctcccggacc      780
cctgaggtca catgcgtggt ggtgagcgtg agccacgaag accctgaggt caagttcaac      840
tggtacgtgg acggcgtgga ggtgcataat gccaagacaa agccgcggga ggagcagtac      900
aacagcacgt accgtgtggt cagcgtcctc accgtcctgc accaggactg gctgaatggc      960
aaggagtaca agtgcaaggt ctcgaacaaa gccctcccag cccccatcga aaaaccatc      1020 tccaaagcca aagggcagcc ccgagaacca caggtgtaca ccctgccccc atcccgggag     1080
gagatgacca agaaccaggt cagcctgtcc tgcgccgtca aaggcttcta tcccagcgac     1140
atcgccgtgg agtgggagag caatgggcag ccggagaaca actacaagac cacgcctccc     1200
gtgctggact ccgacggctc cttcttcctc gtgagcaagc tcaccgtgga caagagcaga     1260
tggcagcagg ggaacgtctt ctcatgctcc gtgatgcatg aggctctgca caaccggttc     1320
acgcagaagt ctctctccct gtctccggga aaa                                  1353
```

<210> SEQ ID NO 174
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

```
Asp Ile Val Met Thr Gln Ser Pro Leu Ser Leu Ser Val Thr Pro Gly
1               5                   10                  15

Glu Pro Ala Ser Ile Ser Cys Arg Ser Ser Glu Ser Leu Leu Asp Ser
            20                  25                  30

Glu Asp Gly Asn Thr Tyr Leu Asp Trp Phe Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Asp Thr Asp Phe Thr Leu His
65                  70                  75                  80

Ile Ser Ser Leu Glu Ala Glu Asp Val Gly Leu Tyr Tyr Cys Met Gln
                85                  90                  95

Arg Met Glu Phe Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 175
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 175

```
gacatcgtga tgacccagtc tccactgagc ctgtctgtga cacctggcga gcctgcctcc      60
atctcctgta gatcttctga gtccctgctg gacagcgagg acggcaatac ctacctggac     120
tggttcctgc agaagcccgg acagtctcct cagctgctga tctacaccct gtcctacaga     180
gcctctggcg tgcccgatag attctccggc tctggctctg gcaccgactt taccctgcac     240
atctccagcc tggaagccga ggatgtgggc ctgtactact gtatgcagcg gatggaattt     300
cccctgacct tcggccaggg caccaaggtg gaaatcaagc gcaccgtggc cgcccctagc     360
gtgtttatct cccctccctc ggatgagcag cttaagtcag gcaccgcatc cgtggtctgc     420
ctgctcaaca acttctaccc gagggaagcc aaagtgcagt ggaaagtgga caacgcgctc     480
cagtcgggaa actcccagga gtccgtgacc gaacaggact ccaaggacag cacttattcc     540
ctgtcctcca ctctgacgct gtcaaaggcc gactacgaga agcacaaggt ctacgcctgc     600
gaagtgaccc atcaggggct ttcctcgccc gtgactaaga gcttcaatcg gggcgaatgc     660
```

<210> SEQ ID NO 176
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 176

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Thr
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Thr Arg Val Asp Ile Ala Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Ser Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Ser
        355                 360                 365
Cys Ala Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Val Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn Arg Phe Thr Gln Lys Ser Leu Ser Leu Ser Pro Gly
        435                 440                 445
Lys

<210> SEQ ID NO 177
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 177
caggttcagc tgcagcagtc tggccctgga ctggtcaagc cctctcagac cctgtctctg    60
acctgtgcca tctccggcga ctccgtgtcc tctaattctg ccacctggaa ctggatccgg   120
cagtccccta gtagaggcct ggaatggctg ggcagaacct actaccggtc caagtggtac   180
aacgactaca ccgtgtccgt gaagtcccgg atcaccatca tccccgacac ctccaagaac   240
cagttctccc tgcagctcaa cagcgtgacc ctgaggata ccgccgtgta ctactgcacc   300
agagtggata tcgccttcga ctactggggc cagggcacac tggttaccgt tcttctgcc   360 tccaccaagg gcccatcggt cttccccctg gcaccctcct ccaagagcac ctctggggc   420 acagcggccc tgggctgcct ggtcaaggac tacttccccg aaccggtgac ggtgtcgtgg   480
aactcaggcg ccctgaccag cggcgtgcac accttcccgg ctgtcctaca gtcctcagga   540
```

```
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaagccgc ggggggaccg    720
tcagtcttcc tcttcccccc aaaacccaag gacaccctca tgatctcccg gacccctgag    780
gtcacatgcg tggtggtgag cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtgtcgaa caaagccctc ccagccccca tcgagaaaac catctccaaa   1020
gccaaagggc agccccgaga accacaggtg tacaccctgc ccccatcccg ggaggagatg   1080
accaagaacc aggtcagcct gtcctgcgcc gtcaaaggct tctatcccag cgacatcgcc   1140
gtggagtggg agagcaatgg gcagccggag aacaactaca agaccacgcc tcccgtgctg   1200
gactccgacg gctccttctt cctcgtgagc aagctcaccg tggacaagag cagatggcag   1260
caggggaacg tcttctcatg ctccgtgatg catgaggctc tgcacaaccg gttcacgcag   1320
aagtctctct ccctgtctcc gggaaaa                                       1347
```

<210> SEQ ID NO 178
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gln Thr Val Val Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn His
            20                  25                  30

Gly Val Asn Trp Tyr Gln Gln Leu Pro Gly Lys Ala Pro Lys Leu Leu
        35                  40                  45

Ile Tyr Asn Asp Asp Leu Leu Pro Ser Gly Val Ser Asp Arg Phe Ser
    50                  55                  60

Gly Ser Thr Ser Gly Thr Ser Gly Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 179
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 179

```
cagacagtgg tcacccagcc tccatctgtg tctgaggccc ctagacagag agtgaccatc      60
tcctgctccg gctcctcctc caacatcggc aatcatggcg tgaactggta tcagcagctg     120
cccggcaagg ctcccaaact gctgatctac aacgacgacc tgctgccttc tggcgtgtcc     180
gacagattct ccggctctac ctctggcacc tctggatccc tggctatctc tggcctgcag     240
tctgaggacg aggccgacta ctattgtgcc gcctgggacg attctctgaa cggcgttgtg     300
tttggcggag gcaccaagct gacagtgttg ggacagccta aggcagcccc ctccgtgacc     360
ctgttcccgc catcatccga agaactgcag gccaacaagg ccacgctcgt gtgcctgatt     420
tccgacttct acccgggggc cgtgactgtg gcctggaagg cagactcaag ccctgtgaag     480
gctggcgtcg agactaccac cccgtcgaag caatccaaca acaaatacgc ggcgtccagc     540
tacctgagcc tgaccctga gcagtggaaa tcccaccggt cctactctgtg ccaagtcacc     600
cacgagggat ccactgtgga aaagaccgtg gcgccgactg agtgttcc                  648
```

<210> SEQ ID NO 180
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Ile Ser Asn Tyr
            20                  25                  30

Tyr Trp Ser Trp Ile Arg Gln Pro Pro Gly Lys Gly Leu Glu Trp Ile
        35                  40                  45

Gly Arg Ile Ser Pro Ser Gly Arg Thr Asn Tyr Asn Pro Ser Leu Lys
    50                  55                  60

Ser Arg Val Thr Met Ser Leu Asp Ala Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Glu Tyr Ser Gly Thr Tyr Ser Tyr Ser Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

-continued

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ser Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Ser Cys Ala Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn Arg Phe Thr Gln Lys Ser Leu Ser Leu Ser
        435                 440                 445

Pro Gly Lys
    450

<210> SEQ ID NO 181
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 181
caggttcagc tgcaagagtc tggccctggc ctggtcaagc cctctcagac cctgtctctg      60
acctgtaccg tgtccggcgt gtccatctcc aactactact ggtcctggat ccggcagcct     120
cctggcaaag gactggaatg gatcggccgc atctctcctt ctggtcgcac caactacaac     180
cccagcctga aaagcagagt gaccatgtct ctggacgcct ccaagaacca gttctccctg     240
aagctgtcct ccgtgaccgc tgctgatacc gccgtgtact actgtgccag aggcgagtac     300
tccggcacct actcctacag cttcgacatc tggggccagg gcaccatggt cacagtctct     360
tctgcctcca ccaagggccc atcggtcttc cccctggcac cctcctccaa gagcacctct     420

```
ggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga gccgccggg     720 ggaccgtcag tcttcctctt ccccccaaaa cccaaggaca ccctcatgat ctcccggacc    780
cctgaggtca catgcgtggt ggtgagcgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt gtcgaacaaa gccctcccag cccccatcga gaaaaccatc   1020
tccaaagcca agggcagcc  ccgagaacca caggtgtaca ccctgccccc atcccgggag   1080
gagatgacca agaaccaggt cagcctgtcc tgcgccgtca aaggcttcta tcccagcgac   1140
atcgccgtgg agtgggagag caatgggcag ccggagaaca actacaagac cacgcctccc   1200
gtgctggact ccgacggctc cttcttcctc gtgagcaagc tcaccgtgga caagagcaga   1260
tggcagcagg ggaacgtctt ctcatgctcc gtgatgcatg aggctctgca caaccggttc   1320
acgcagaagt ctctctccct gtctccggga aaa                                1353

<210> SEQ ID NO 182
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Asp Ile Gln Met Thr Gln Ser Pro Ser Leu Ser Ala Ser Val Gly
1               5                   10                  15

Asp Arg Val Thr Ile Thr Cys Arg Ser Ser Gln Ser Leu Phe Asp Ser
            20                  25                  30

Asp Asp Gly Asn Thr Tyr Leu Asp Trp Phe Gln Gln Lys Pro Gly Gln
        35                  40                  45

Ser Pro Lys Leu Leu Ile Gln Thr Leu Ser Tyr Arg Ala Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Met Gln
                85                  90                  95

Arg Met Glu Phe Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190
```

```
Glu Lys His Lys Val Tyr Ala Cys Glu Val Thr His Gln Gly Leu Ser
            195                 200                 205
Ser Pro Val Thr Lys Ser Phe Asn Arg Gly Glu Cys
        210                 215                 220
```

<210> SEQ ID NO 183
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 183

```
gacatccaga tgacccagtc tccatcctct ctgtccgcct ctgtgggcga cagagtgacc      60
atcacctgtc ggtcctctca gtccctgttc gactctgacg acggcaacac ctacctggac     120
tggttccagc agaagcccgg ccagtctcct aagctgctga tccagacact gtcctacaga     180
gcctctggcg tgccctccag attttccggc tctggctctg caccgactt tacccctgaca     240
atctccagcc tgcagcctga ggacttcgcc acctactact gtatgcagcg gatggaattt     300
cccctgacct cggcggagg caccaaggtg gaaatcaagc gcaccgtggc cgccctagc      360
gtgtttatct ccctccctc ggatgagcag cttaagtcag gcaccgcatc cgtggtctgc     420
ctgctcaaca acttctaccc gagggaagcc aaagtgcagt ggaaagtgga caacgcgctc     480
cagtcgggaa actcccagga gtccgtgacc gaacaggact ccaaggacag cacttattcc     540
ctgtcctcca ctctgacgct gtcaaaggca gactacgaga agcacaaggt ctacgcctgc     600
gaagtgaccc atcagggct tcctcgcc gtgactaaga gcttcaatcg gggcgaatgc      660
```

<210> SEQ ID NO 184
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

```
Gln Ile Thr Leu Lys Glu Ser Gly Pro Thr Leu Val Lys Pro Thr Gln
1               5                   10                  15
Thr Leu Thr Leu Thr Cys Thr Phe Ser Gly Phe Ser Leu Ser Thr Ser
            20                  25                  30
Gly Met Gly Val Ser Trp Ile Arg Gln Pro Pro Gly Lys Ala Leu Glu
        35                  40                  45
Trp Leu Ala His Ile Tyr Trp Asp Asp Lys Arg Tyr Asn Pro Ser
    50                  55                  60
Leu Lys Ser Arg Leu Thr Ile Thr Lys Asp Thr Ser Lys Asn Gln Val
65                  70                  75                  80
Val Leu Thr Met Thr Asn Met Asp Pro Val Asp Thr Ala Thr Tyr Tyr
                85                  90                  95
Cys Ala Arg Leu Tyr Gly Phe Thr Tyr Gly Phe Ala Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Ala Ala Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Ser Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Ser Cys Ala Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Val Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn Arg Phe Thr Gln Lys Ser Leu Ser Leu Ser Pro
        435                 440                 445
Gly Lys
    450

<210> SEQ ID NO 185
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185
cagatcactc tgaaagagtc cggcccaaca ctggtcaagc ctacccagac actcacactg     60
acctgtacct tcagcggatt ttctctgtcc acctctggca tgggcgtgtc ttggatcaga    120
cagcctcctg gcaaggccct ggaatggctg gctcacatct actgggacga tgacaagcgg    180
tacaacccca gcctgaagtc ccggctgacc atcaccaagg acacctccaa gaaccaagtg    240
gtgctgacca tgaccaacat ggaccctgtg ataccgcta cctactactg cgccagactg    300
```

```
tacggcttca cctatggctt cgcctactgg ggccagggca ccctggtgac cgtgtcctct    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaagc cgccggggga    720
ccgtcagtct tcctcttccc cccaaaaccc aaggacaccc tcatgatctc ccggacccct    780
gaggtcacat gcgtggtggt gagcgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtgtc gaacaaagcc ctcccagccc ccatcgagaa aaccatctcc   1020
aaagccaaag ggcagccccg agaaccacag gtgtacaccc tgcccccatc ccgggaggag   1080
atgaccaaga accaggtcag cctgtcctgc gccgtcaaag gcttctatcc cagcgacatc   1140
gccgtggagt gggagagcaa tgggcagccg gagaacaact acaagaccac gcctcccgtg   1200
ctggactccg acggctcctt cttcctcgtg agcaagctca ccgtggacaa gagcagatgg   1260
cagcagggga acgtcttctc atgctccgtg atgcatgagg ctctgcacaa ccggttcacg   1320
cagaagtctc tctccctgtc tccgggaaaa                                    1350

<210> SEQ ID NO 186
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Asp Tyr Asn
            20                  25                  30

Gly Ile Ser Tyr Met His Trp Tyr Gln Gln Lys Pro Gly Gln Pro Pro
        35                  40                  45

Lys Leu Leu Ile Tyr Ala Ala Ser Asn Pro Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ile Ile
                85                  90                  95

Glu Asp Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175
```

```
Tyr Ser Leu Ser Ser Thr Leu Thr Leu Ser Lys Ala Asp Tyr Glu Lys
        180                 185                 190

His Lys Val Tyr Ala Cys Glu Val Thr His Gln Gly Leu Ser Ser Pro
    195                 200                 205

Val Thr Lys Ser Phe Asn Arg Gly Glu Cys
    210                 215
```

<210> SEQ ID NO 187
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 187

```
gatattgtga tgacccagtc ccccgattct ctcgctgtct ctctgggcga acgggctaca    60
atcaactgta gggcttcaca gtctgtcgac tacaacggca tctcttacat gcattggtac   120
cagcagaaac ctggacagcc accaaaactc ctcatctacg ccgcttccaa tcctgaatct   180
ggcgtgcccg accgattttc cggatccggc tctggcaccg actttacact cactattagt   240
agcctccagg ccgaggatgt ggccgtgtac tactgtcagc agatcatcga ggatccttgg   300
acatttggac agggaaccaa agtggagatc aaacgtacgg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc   600
acccatcagg gcctgagctc gcccgtcaca aagagcttca cagggggaga gtgt         654
```

<210> SEQ ID NO 188
<211> LENGTH: 660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 188

```
gacatccaga tgacccagag ccctagcagc ctgagcgcca gcgtgggcga cagagtgacc    60
attacctgca gaagcagcca gagcctgttc gacagcgacg acggcaatac ctacctggac   120
tggttccagc agaagcctgg ccagagccct aagctgctga tccagaccct gagctacaga   180
gccagcggcg tgcctagcag attctccggc agcggctccg gcaccgactt cacccctgacc  240
atcagcagcc tgcagcctga ggacttcgcc acctactact gcatgcagag aatggagttc   300
cctctgacct cggcggcgg caccaaggtg gagatcaagc gtacggtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga acacaaagt ctacgcctgc   600
gaagtcaccc ccatcagggcct gagctcgccc gtcacaaaga gcttcaacag gggagagtgt 660
```

<210> SEQ ID NO 189
<211> LENGTH: 479

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Glu Ile Val Leu Thr Gln Ser Pro Ala Thr Leu Ser Ala Ser Pro Gly
1               5                   10                  15

Glu Arg Val Thr Leu Ser Cys Ser Ala Ser Ser Val Ser Tyr Met
            20                  25                  30

Asn Trp Tyr Gln Gln Lys Pro Gly Gln Ala Pro Arg Arg Trp Ile Tyr
            35                  40                  45

Asp Ser Ser Lys Leu Ala Ser Gly Val Pro Ala Arg Phe Ser Gly Ser
        50                  55                  60

Gly Ser Gly Arg Asp Tyr Thr Leu Thr Ile Ser Ser Leu Glu Pro Glu
65                  70                  75                  80

Asp Phe Ala Val Tyr Tyr Cys Gln Gln Trp Ser Arg Asn Pro Pro Thr
                85                  90                  95

Phe Gly Gly Gly Thr Lys Val Glu Ile Lys Gly Gly Ser Glu Gly Lys
            100                 105                 110

Ser Ser Gly Ser Gly Ser Glu Ser Lys Ser Thr Gly Ser Gln Val
        115                 120                 125

Gln Leu Val Gln Ser Gly Ala Glu Val Lys Lys Pro Gly Ser Ser Val
130                 135                 140

Lys Val Ser Cys Lys Ala Ser Gly Tyr Thr Phe Thr Arg Ser Thr Met
145                 150                 155                 160

His Trp Val Arg Gln Ala Pro Gly Gln Gly Leu Glu Trp Met Gly Tyr
                165                 170                 175

Ile Asn Pro Ser Ser Ala Tyr Thr Asn Tyr Ala Gln Lys Phe Gln Gly
            180                 185                 190

Arg Val Thr Leu Thr Ala Asp Lys Ser Thr Ser Thr Ala Tyr Met Glu
            195                 200                 205

Leu Ser Ser Leu Arg Ser Glu Asp Thr Ala Val Tyr Tyr Cys Ala Ser
210                 215                 220

Pro Gln Val His Tyr Asp Tyr Gly Gly Phe Pro Tyr Trp Gly Gln Gly
225                 230                 235                 240

Thr Leu Val Thr Val Ser Ser Glu Pro Lys Ser Ser Asp Lys Thr His
                245                 250                 255

Thr Cys Pro Pro Cys Pro Ala Pro Glu Ala Ala Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Ser Val Ser His Glu Asp Pro Glu
290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
370                 375                 380
```

Pro Ser Arg Glu Glu Met Thr Lys Asn Gln Val Ser Leu Trp Cys Leu
385                 390                 395                 400

Val Lys Gly Phe Tyr Pro Ser Asp Ile Ala Val Glu Trp Glu Ser Asn
            405                 410                 415

Gly Gln Pro Glu Asn Asn Tyr Lys Thr Thr Pro Pro Val Leu Asp Ser
        420                 425                 430

Asp Gly Ser Phe Phe Leu Tyr Ser Lys Leu Thr Val Asp Lys Ser Arg
    435                 440                 445

Trp Gln Gln Gly Asn Val Phe Ser Cys Ser Val Met His Glu Ala Leu
450                 455                 460

His Asn His Tyr Thr Gln Lys Ser Leu Ser Leu Ser Pro Gly Lys
465                 470                 475

<210> SEQ ID NO 190
<211> LENGTH: 1437
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 190
gagatcgtgc tgacccagtc tcctgccaca ctgagtgctt ctccaggcga gagagtgacc        60
ctgtcctgct ccgcttcctc ctccgtgtcc tacatgaact ggtatcagca gaagcccggc       120
caggctcctc ggagatggat ctacgactct tccaagctgg cctctggtgt gccagccaga       180
ttttctggct ctggctccgg cagagactat accctgacca ctccagcct ggaacctgag       240
gacttcgccg tgtactactg ccagcagtgg tctaggaacc ctcctacctt ggcggaggc       300
accaaggtgg aaatcaaggg cggatctgag ggaaagtcca cgggctccgg cagcgaaagc       360
aagtccaccg gcggaagcca ggttcaactg gttcagtctg gcgccgaagt gaagaaacct       420
ggctcctccg tgaaagtgtc ctgcaaggct tccggctaca cttttaccag atccaccatg       480
cactgggtcc gacaggctcc aggacaaggc ttggagtgga tgggctacat caaccccagc       540
tccgcctaca ccaactacgc ccagaaattc cagggcagag tgaccctgac cgccgacaag       600
tctacctcca ccgcctacat ggaactgtcc agcctgagat ctgaggacac cgccgtgtac       660
tactgcgctt tcctcaggt gcactacgac tacggcggct ttccttattg gggccagggc       720
acactggtca ccgtttcttc tgagcccaaa tctagcgaca aaactcacac atgcccaccg       780
tgcccagcac ctgaagccgc gggggaccg tcagtcttcc tcttcccccc aaaacccaag       840
gacaccctca tgatctcccg gacccctgag gtcacatgcg tggtggtgag cgtgagccac       900
gaagaccctg aggtcaagtt caactggtac gtggacggcg tggaggtgca taatgccaag       960
acaaagccgc gggaggagca gtacaacagc acgtaccgtg tggtcagcgt cctcaccgtc      1020
ctgcaccagg actggctgaa tggcaaggag tacaagtgca aggtctcgaa caaagccctc      1080
ccagccccca tcgagaaaac catctccaaa gccaagggc agccccgaga accacaggtg      1140
tacaccctgc cccatcccg ggaggagatg accaagaacc aggtcagcct gtggtgcctg      1200
gtcaaaggct tctatcccag cgacatcgcc gtggagtggg agagcaatgg gcagccggag      1260
aacaactaca agaccacgcc tcccgtgctg gactccgacg gctccttctt cctctacagc      1320
aagctcaccg tggacaagag cagatggcag caggggaacg tcttctcatg ctccgtgatg      1380
catgaggctc tgcacaacca ctacacgcag aagtctctct ccctgtctcc gggaaaa        1437

```
<210> SEQ ID NO 191
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Ile Ser Asn Tyr
            20                  25                  30

Tyr Trp Ser Trp Ile Arg Gln Pro Pro Gly Lys Gly Leu Glu Trp Ile
        35                  40                  45

Gly Arg Ile Ser Pro Ser Gly Arg Thr Asn Tyr Asn Pro Ser Leu Lys
    50                  55                  60

Ser Arg Val Thr Met Ser Leu Asp Ala Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Glu Tyr Ser Gly Thr Tyr Ser Tyr Ser Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ser Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365
```

| | | | | | | | | | | | |
|---|---|---|---|---|---|---|---|---|---|---|---|
| Leu | Trp | Cys | Leu | Val | Lys | Gly | Phe | Tyr | Pro | Ser | Asp | Ile | Ala | Val | Glu |
| 370 | | | | 375 | | | | | 380 | | |

Leu Trp Cys Leu Val Lys Gly Phe Tyr Pro Ser Asp Ile Ala Val Glu
370                 375                     380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 192
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192
caggttcagc tgcaagagtc tggccctggc ctggtcaagc cctctcagac cctgtctctg      60
acctgtaccg tgtccggcgt gtccatctcc aactactact ggtcctggat ccggcagcct     120
cctggcaaag gactggaatg gatcggccgc atctctcctt ctggtcgcac caactacaac     180
cccagcctga aaagcagagt gaccatgtct ctggacgcct ccaagaacca gttctccctg     240
aagctgtcct ccgtgaccgc tgctgatacc gccgtgtact actgtgccag aggcgagtac     300
tccggcacct actcctacag cttcgacatc tggggccagg gcaccatggt cacagtctct     360
tctgcctcca ccaagggccc atcggtcttc cccctggcac cctcctccaa gagcacctct     420
gggggcacag cggccctggg ctgcctggtc aaggactact cccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gaaagttgag     660
cccaaatctt gtgacaaaac tcacacatgc ccaccgtgcc cagcacctga gccgccggg      720 ggaccgtcag tcttcctctt ccccccaaaa cccaaggaca cctcatgat ctcccggacc      780 cctgaggtca catgcgtggt ggtgagcgtg agccacgaag accctgaggt caagttcaac     840
tggtacgtgg acggcgtgga ggtgcataat gccaagacaa agccgcggga ggagcagtac     900
aacagcacgt accgtgtggt cagcgtcctc accgtcctgc accaggactg gctgaatggc     960
aaggagtaca agtgcaaggt ctcgaacaaa gccctcccag cccccatcga gaaaaccatc    1020
tccaaagcca agggcagccc cgagaaccac aggtgtaca ccctgcccc atcccgggag     1080 gagatgacca agaaccaggt cagcctgtgg tgcctggtca aaggcttcta tcccagcgac    1140
atcgccgtgg agtgggagag caatgggcag ccggagaaca actacaagac cacgcctccc    1200
gtgctggact ccgacggctc cttcttcctc tacagcaagc tcaccgtgga caagagcaga    1260
tggcagcagg ggaacgtctt ctcatgctcc gtgatgcatg aggctctgca caaccactac    1320
acgcagaagt ctctctccct gtctccggga aaa                                 1353

<210> SEQ ID NO 193
<211> LENGTH: 12
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 193

Gly Asp Ser Val Phe Asn Asn Asn Ala Ala Trp Ser
1               5                   10

<210> SEQ ID NO 194
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Arg Thr Tyr Tyr Arg Ser Lys Trp Leu Tyr Asp
1               5                   10

<210> SEQ ID NO 195
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Tyr Ser Ser Ser Phe Asp Tyr
1               5

<210> SEQ ID NO 196
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Gln Val Gln Leu Gln Gln Ser Gly Pro Arg Leu Val Arg Pro Ser Gln
1               5                   10                  15

Thr Leu Ser Leu Thr Cys Ala Ile Ser Gly Asp Ser Val Phe Asn Asn
            20                  25                  30

Asn Ala Ala Trp Ser Trp Ile Arg Gln Ser Pro Ser Arg Gly Leu Glu
        35                  40                  45

Trp Leu Gly Arg Thr Tyr Tyr Arg Ser Lys Trp Leu Tyr Asp Tyr Ala
    50                  55                  60

Val Ser Val Lys Ser Arg Ile Thr Val Asn Pro Asp Thr Ser Arg Asn
65                  70                  75                  80

Gln Phe Thr Leu Gln Leu Asn Ser Val Thr Pro Glu Asp Thr Ala Leu
                85                  90                  95

Tyr Tyr Cys Ala Arg Gly Tyr Ser Ser Ser Phe Asp Tyr Trp Gly Gln
            100                 105                 110

Gly Thr Leu Val Thr Val Ser Ser
        115                 120

<210> SEQ ID NO 197
<211> LENGTH: 450
<212> TYPE: PRT
<213> ORGANISM: Artificial Sequence
<220> FEATURE:
```

-continued

<223> OTHER INFORMATION: Description of Artificial Sequence: Synthetic polypeptide

<400> SEQUENCE: 197

| Gln | Val | Gln | Leu | Gln | Gln | Ser | Gly | Pro | Arg | Leu | Val | Arg | Pro | Ser | Gln |
|---|---|---|---|---|---|---|---|---|---|---|---|---|---|---|---|
| 1 | | | | 5 | | | | | 10 | | | | | 15 | |

Thr Leu Ser Leu Thr Cys Ala Ile Ser Gly Asp Ser Val Phe Asn Asn
               20                  25                  30

Asn Ala Ala Trp Ser Trp Ile Arg Gln Ser Pro Ser Arg Gly Leu Glu
        35                 40                 45

Trp Leu Gly Arg Thr Tyr Tyr Arg Ser Lys Trp Leu Tyr Asp Tyr Ala
    50                  55                 60

Val Ser Val Lys Ser Arg Ile Thr Val Asn Pro Asp Thr Ser Arg Asn
65                     70                75                80

Gln Phe Thr Leu Gln Leu Asn Ser Val Thr Pro Glu Asp Thr Ala Leu
               85                  90                95

Tyr Tyr Cys Ala Arg Gly Tyr Ser Ser Phe Asp Tyr Trp Gly Gln
         100              105            110

Gly Thr Leu Val Thr Val Ser Ser Ala Ser Thr Lys Gly Pro Ser Val
       115              120            125

Phe Pro Leu Ala Pro Ser Ser Lys Ser Thr Ser Gly Gly Thr Ala Ala
   130                135                140

Leu Gly Cys Leu Val Lys Asp Tyr Phe Pro Glu Pro Val Thr Val Ser
145                   150              155              160

Trp Asn Ser Gly Ala Leu Thr Ser Gly Val His Thr Phe Pro Ala Val
             165              170            175

Leu Gln Ser Ser Gly Leu Tyr Ser Leu Ser Ser Val Val Thr Val Pro
         180              185            190

Ser Ser Ser Leu Gly Thr Gln Thr Tyr Ile Cys Asn Val Asn His Lys
             195             200            205

Pro Ser Asn Thr Lys Val Asp Lys Lys Val Glu Pro Lys Ser Cys Asp
   210                215                220

Lys Thr His Thr Cys Pro Pro Cys Pro Ala Pro Glu Ala Ala Gly Gly
225                   230              235              240

Pro Ser Val Phe Leu Phe Pro Pro Lys Pro Lys Asp Thr Leu Met Ile
             245              250            255

Ser Arg Thr Pro Glu Val Thr Cys Val Val Val Ser Val Ser His Glu
         260              265            270

Asp Pro Glu Val Lys Phe Asn Trp Tyr Val Asp Gly Val Glu Val His
       275              280            285

Asn Ala Lys Thr Lys Pro Arg Glu Glu Gln Tyr Asn Ser Thr Tyr Arg
   290                295                300

Val Val Ser Val Leu Thr Val Leu His Gln Asp Trp Leu Asn Gly Lys
305                   310              315              320

Glu Tyr Lys Cys Lys Val Ser Asn Lys Ala Leu Pro Ala Pro Ile Glu
             325              330            335

Lys Thr Ile Ser Lys Ala Lys Gly Gln Pro Arg Glu Pro Gln Val Tyr
         340              345            350

Thr Leu Pro Pro Ser Arg Glu Glu Met Thr Lys Asn Gln Val Ser Leu
             355              360            365

Ser Cys Ala Val Lys Gly Phe Tyr Pro Ser Asp Ile Ala Val Glu Trp
   370                375                380

Glu Ser Asn Gly Gln Pro Glu Asn Asn Tyr Lys Thr Thr Pro Pro Val
385                   390              395              400

```
Leu Asp Ser Asp Gly Ser Phe Phe Leu Val Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn Arg Phe Thr Gln Lys Ser Leu Ser Leu Ser Pro
    435                 440                 445

Gly Lys
    450

<210> SEQ ID NO 198
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Thr Gly Thr Ser Ser Asn Ile Gly Thr Tyr Lys Phe Val Ser
1               5                   10

<210> SEQ ID NO 199
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Glu Val Ser Lys Arg Pro Ser
1               5

<210> SEQ ID NO 200
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Val Ser Tyr Ala Gly Ser Gly Thr Leu Leu
1               5                   10

<210> SEQ ID NO 201
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asn Ile Gly Thr Tyr
            20                  25                  30

Lys Phe Val Ser Trp Tyr Gln Gln His Pro Asp Lys Ala Pro Lys Val
        35                  40                  45

Leu Leu Tyr Glu Val Ser Lys Arg Pro Ser Gly Val Ser Ser Arg Phe
    50                  55                  60

Ser Gly Ser Lys Ser Gly Asn Thr Ala Ser Leu Thr Ile Ser Gly Leu
```

```
                65                  70                  75                  80
Gln Ala Glu Asp Gln Ala Asp Tyr His Cys Val Ser Tyr Ala Gly Ser
                85                  90                  95
Gly Thr Leu Leu Phe Gly Gly Gly Thr Lys Leu Thr Val Leu
               100                 105                 110
```

```
<210> SEQ ID NO 202
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202
```

```
Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asn Ile Gly Thr Tyr
                20                  25                  30
Lys Phe Val Ser Trp Tyr Gln Gln His Pro Asp Lys Ala Pro Lys Val
                35                  40                  45
Leu Leu Tyr Glu Val Ser Lys Arg Pro Ser Gly Val Ser Ser Arg Phe
            50                  55                  60
Ser Gly Ser Lys Ser Gly Asn Thr Ala Ser Leu Thr Ile Ser Gly Leu
65                  70                  75                  80
Gln Ala Glu Asp Gln Ala Asp Tyr His Cys Val Ser Tyr Ala Gly Ser
                85                  90                  95
Gly Thr Leu Leu Phe Gly Gly Gly Thr Lys Leu Thr Val Leu Gly Gln
                100                 105                 110
Pro Lys Ala Ala Pro Ser Val Thr Leu Phe Pro Pro Ser Ser Glu Glu
            115                 120                 125
Leu Gln Ala Asn Lys Ala Thr Leu Val Cys Leu Ile Ser Asp Phe Tyr
130                 135                 140
Pro Gly Ala Val Thr Val Ala Trp Lys Ala Asp Ser Ser Pro Val Lys
145                 150                 155                 160
Ala Gly Val Glu Thr Thr Thr Pro Ser Lys Gln Ser Asn Asn Lys Tyr
                165                 170                 175
Ala Ala Ser Ser Tyr Leu Ser Leu Thr Pro Glu Gln Trp Lys Ser His
                180                 185                 190
Arg Ser Tyr Ser Cys Gln Val Thr His Glu Gly Ser Thr Val Glu Lys
            195                 200                 205
Thr Val Ala Pro Thr Glu Cys Ser
        210                 215
```

```
<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Thr Tyr Ala Met Asn
1               5
```

```
<210> SEQ ID NO 204
<211> LENGTH: 19
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 204

Arg Ile Arg Ser Lys Tyr Asn Asn Tyr Ala Thr Tyr Tyr Ala Ala Ser
1               5                   10                  15

Val Lys Gly

<210> SEQ ID NO 205
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

His Gly Asn Phe Gly Asn Ser Tyr Val Ser Trp Phe Ala Tyr
1               5                   10

<210> SEQ ID NO 206
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 207
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val

```
                35                  40                  45
Ala Arg Ile Arg Ser Lys Tyr Asn Asn Tyr Ala Thr Tyr Tyr Ala Ala
 50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Ala Arg His Gly Asn Phe Gly Asn Ser Tyr Val Ser Trp Phe
                100                 105                 110

Ala Tyr Trp Gly Gln Gly Thr Leu Val Thr Val Ser Ser Ala Ser Thr
            115                 120                 125

Lys Gly Pro Ser Val Phe Pro Leu Ala Pro Cys Ser Arg Ser Thr Ser
        130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Leu Leu Tyr Ser Lys Leu Thr
                405                 410                 415

Val Asp Lys Ser Arg Trp Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys
        450
```

<210> SEQ ID NO 208
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Arg Ser Ser Thr Gly Ala Val Thr Thr Ser Asn Tyr Ala Asn
1               5                   10

<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Thr Asn Lys Arg Ala Pro
1               5

<210> SEQ ID NO 210
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ala Leu Trp Tyr Ser Asn Leu Trp Val
1               5

<210> SEQ ID NO 211
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 212
<211> LENGTH: 215
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 212

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 213
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 213

```
gatattgtga tgactcagtc tccactctcc ctgtccgtca cccctggaga gccggcctcc      60
atctcctgca ggtctagtga gagcctcttg gatagtgaag atggaaacac ctatttggac     120
tggttcctgc agaagccagg gcagtctcct cagctcctga tctatacgct ttcctatcgg     180
gcctctggag tcccagacag gttcagtggc agtgggtcgg acactgattt cacactgcac     240
atcagcagtc tggaggctga ggatgttgga ctttattact gcatgcaacg tatggagttt     300
ccgctcactt tcggccaagg gaccaaggtg gaaatcaaa                            339
```

<210> SEQ ID NO 214
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 214

```
gacatccaga tgacccagag ccctagcagc ctgagcgcca gcgtgggcga cagagtgacc    60
attacctgca gaagcagcca gagcctgttc gacagcgacg acggcaatac ctacctggac   120
tggttccagc agaagcctgg ccagagccct aagctgctga tccagaccct gagctacaga   180
gccagcggcg tgcctagcag attctccggc agcggctccg gcaccgactt caccctgacc   240
atcagcagcc tgcagcctga ggacttcgcc acctactact gcatgcagag aatggagttc   300
cctctgacct tcggcggcgg caccaaggtg gagatcaag                          339
```

<210> SEQ ID NO 215
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gly Gly Ser Glu Gly Lys Ser Ser Gly Ser Gly Ser Glu Ser Lys Ser
1               5                   10                  15

Thr Gly Gly Ser
            20

<210> SEQ ID NO 216
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Gly Gly Gly Ser Gly Gly Gly Ser
1               5

<210> SEQ ID NO 217
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Gly Gly Gly Ser Gly Gly Gly Ser Gly Gly Gly Ser
1               5                   10

<210> SEQ ID NO 218
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gly Gly Gly Ser Gly Gly Gly Ser Gly Gly Gly Ser Gly Gly Gly Ser
1               5                   10                  15

<210> SEQ ID NO 219
<211> LENGTH: 20
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 219

Gly Gly Gly Ser Gly Gly Gly Ser Gly Gly Gly Ser Gly Gly Gly Ser
1               5                   10                  15

Gly Gly Gly Ser
            20

<210> SEQ ID NO 220
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gly Gly Gly Gly Ser Gly Gly Gly Gly Ser Gly Gly Gly Gly Ser
1               5                   10                  15

<210> SEQ ID NO 221
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gly Gly Gly Gly Ser Gly Gly Gly Gly Ser Gly Gly Gly Gly Ser Gly
1               5                   10                  15

Gly Gly Gly Ser
            20

<210> SEQ ID NO 222
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 223
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gly Ser Thr Ser Gly Ser Gly Lys Pro Gly Ser Gly Glu Gly Ser Thr
1               5                   10                  15

Lys Gly

<210> SEQ ID NO 224
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ile Arg Pro Arg Ala Ile Gly Gly Ser Lys Pro Arg Val Ala
1               5                   10

<210> SEQ ID NO 225
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gly Lys Gly Gly Ser Gly Lys Gly Gly Ser Gly Lys Gly Gly Ser
1               5                   10                  15

<210> SEQ ID NO 226
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Gly Lys Gly Ser Gly Gly Lys Gly Ser Gly Gly Lys Gly Ser
1               5                   10                  15

<210> SEQ ID NO 227
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gly Gly Gly Lys Ser Gly Gly Gly Lys Ser Gly Gly Gly Lys Ser
1               5                   10                  15

<210> SEQ ID NO 228
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gly Lys Gly Lys Ser Gly Lys Gly Lys Ser Gly Lys Gly Lys Ser
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229
```

```
Gly Gly Gly Lys Ser Gly Gly Lys Gly Ser Lys Gly Gly Ser
1               5                   10                  15
```

<210> SEQ ID NO 230
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

```
Gly Lys Pro Gly Ser Gly Lys Pro Gly Ser Gly Lys Pro Gly Ser
1               5                   10                  15
```

<210> SEQ ID NO 231
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

```
Gly Lys Pro Gly Ser Gly Lys Pro Gly Ser Gly Lys Pro Gly Ser Gly
1               5                   10                  15

Lys Pro Gly Ser
            20
```

<210> SEQ ID NO 232
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

```
Gly Lys Gly Lys Ser Gly Lys Gly Lys Ser Gly Lys Gly Lys Ser Gly
1               5                   10                  15

Lys Gly Lys Ser
            20
```

<210> SEQ ID NO 233
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

```
Ser Thr Ala Gly Asp Thr His Leu Gly Gly Glu Asp Phe Asp
1               5                   10
```

<210> SEQ ID NO 234
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

```
Gly Glu Gly Gly Ser Gly Glu Gly Gly Ser Gly Glu Gly Gly Ser
1               5                   10                  15
```

<210> SEQ ID NO 235
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Gly Gly Glu Gly Ser Gly Gly Glu Gly Ser Gly Gly Glu Gly Ser
1               5                   10                  15

<210> SEQ ID NO 236
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Gly Glu Gly Glu Ser Gly Glu Gly Glu Ser Gly Glu Gly Glu Ser
1               5                   10                  15

<210> SEQ ID NO 237
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gly Gly Gly Glu Ser Gly Gly Glu Gly Ser Gly Glu Gly Gly Ser
1               5                   10                  15

<210> SEQ ID NO 238
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gly Glu Gly Glu Ser Gly Glu Gly Glu Ser Gly Glu Gly Glu Ser Gly
1               5                   10                  15

Glu Gly Glu Ser
            20

<210> SEQ ID NO 239
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gly Ser Thr Ser Gly Ser Gly Lys Pro Gly Ser Gly Glu Gly Ser Thr
1               5                   10                  15

Lys Gly

<210> SEQ ID NO 240
<211> LENGTH: 19
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 240

Pro Arg Gly Ala Ser Lys Ser Gly Ser Ala Ser Gln Thr Gly Ser Ala
1               5                   10                  15

Pro Gly Ser

<210> SEQ ID NO 241
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gly Thr Ala Ala Ala Gly Ala Gly Ala Ala Gly Gly Ala Ala Ala Gly
1               5                   10                  15

Ala Ala Gly

<210> SEQ ID NO 242
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Thr Ser Gly Ser Ser Gly Ser Gly Ser Gly Gly Ser Gly Ser Gly
1               5                   10                  15

Gly Gly Gly

<210> SEQ ID NO 243
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Gly Lys Pro Gly Ser Gly Lys Pro Gly Ser Gly Lys Pro Gly Ser Gly
1               5                   10                  15

Lys Pro Gly Ser
            20

<210> SEQ ID NO 244
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Gly Ser Gly Ser
1

<210> SEQ ID NO 245
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 245

Ala Pro Ala Pro Ala Pro Ala Pro Ala Pro
1               5                   10

<210> SEQ ID NO 246
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ala Pro Ala Pro Ala Pro Ala Pro Ala Pro Ala Pro Ala Pro Ala Pro
1               5                   10                  15

Ala Pro Ala Pro
            20

<210> SEQ ID NO 247
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Ala Glu Ala Ala Ala Lys Glu Ala Ala Ala Lys Glu Ala Ala Ala Ala
1               5                   10                  15

Lys Glu Ala Ala Ala Ala Lys Glu Ala Ala Ala Lys Ala Ala Ala Ala
            20                  25                  30

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gly Gly Gly Gly Ser Gly Gly Gly Gly Ser
1               5                   10

<210> SEQ ID NO 249
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
            50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 250
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
 65                 70                  75                  80
```

-continued

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ser Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 251
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

```
Glu Ala Ala Gly Gly Pro Ser Val Phe Leu Phe Pro Pro Lys Pro Lys
                115                 120                 125
Asp Thr Leu Met Ile Ser Arg Thr Pro Glu Val Thr Cys Val Val Val
130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Arg Leu Thr Val Asp Lys Ser Arg Trp Gln Glu Gly Asn Val Phe Ser
290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 252
<211> LENGTH: 229
<212> TYPE: PRT
<213> ORGANISM: Homo sapiens

<400> SEQUENCE: 252

Met Ala Arg Leu Ala Leu Ser Pro Val Pro Ser His Trp Met Val Ala
1               5                   10                  15
Leu Leu Leu Leu Leu Ser Ala Glu Pro Val Pro Ala Ala Arg Ser Glu
                20                  25                  30
Asp Arg Tyr Arg Asn Pro Lys Gly Ser Ala Cys Ser Arg Ile Trp Gln
            35                  40                  45
Ser Pro Arg Phe Ile Ala Arg Lys Arg Gly Phe Thr Val Lys Met His
        50                  55                  60
Cys Tyr Met Asn Ser Ala Ser Gly Asn Val Ser Trp Leu Trp Lys Gln
65                  70                  75                  80
Glu Met Asp Glu Asn Pro Gln Gln Leu Lys Leu Glu Lys Gly Arg Met
                85                  90                  95
Glu Glu Ser Gln Asn Glu Ser Leu Ala Thr Leu Thr Ile Gln Gly Ile
                100                 105                 110
Arg Phe Glu Asp Asn Gly Ile Tyr Phe Cys Gln Gln Lys Cys Asn Asn
            115                 120                 125
Thr Ser Glu Val Tyr Gln Gly Cys Gly Thr Glu Leu Arg Val Met Gly
        130                 135                 140
Phe Ser Thr Leu Ala Gln Leu Lys Gln Arg Asn Thr Leu Lys Asp Gly
```

```
                145                 150                 155                 160
Ile Ile Met Ile Gln Thr Leu Leu Ile Leu Phe Ile Ile Val Pro
                    165                 170                 175

Ile Phe Leu Leu Leu Asp Lys Asp Ser Lys Ala Gly Met Glu Glu
                180                 185                 190

Asp His Thr Tyr Glu Gly Leu Asp Ile Asp Gln Thr Ala Thr Tyr Glu
                    195                 200                 205

Asp Ile Val Thr Leu Arg Thr Gly Glu Val Lys Trp Ser Val Gly Glu
            210                 215                 220

His Pro Gly Gln Glu
225

<210> SEQ ID NO 253
<211> LENGTH: 13
<212> TYPE: PRT
<213> ORGANISM: Homo sapiens

<400> SEQUENCE: 253

Ser Glu Asp Arg Tyr Arg Asn Pro Lys Gly Ser Ala Cys
1               5                   10

<210> SEQ ID NO 254
<211> LENGTH: 5
<212> TYPE: PRT
<213> ORGANISM: Homo sapiens

<400> SEQUENCE: 254

Glu Met Glu Asn Pro
1               5

<210> SEQ ID NO 255
<211> LENGTH: 5
<212> TYPE: PRT
<213> ORGANISM: Homo sapiens

<400> SEQUENCE: 255

Gly Phe Ser Thr Leu
1               5

<210> SEQ ID NO 256
<211> LENGTH: 14
<212> TYPE: PRT
<213> ORGANISM: Homo sapiens

<400> SEQUENCE: 256

Gln Asp Gly Asn Glu Glu Met Gly Gly Ile Thr Gln Thr Pro
1               5                   10

<210> SEQ ID NO 257
<211> LENGTH: 5
<212> TYPE: PRT
<213> ORGANISM: Homo sapiens

<400> SEQUENCE: 257

Gly Ser Glu Ile Leu
1               5

<210> SEQ ID NO 258
<211> LENGTH: 6
<212> TYPE: PRT
<213> ORGANISM: Homo sapiens

<400> SEQUENCE: 258
```

```
Pro Arg Gly Ser Lys Pro
1               5

<210> SEQ ID NO 259
<211> LENGTH: 1418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Glu Ile Val Leu Thr Gln Ser Pro Ala Thr Leu Ser Ala Ser Pro Gly
1               5                   10                  15

Glu Arg Val Thr Leu Ser Cys Ser Ala Ser Ser Val Ser Tyr Met
            20                  25                  30

Asn Trp Tyr Gln Gln Lys Pro Gly Gln Ala Pro Arg Trp Ile Tyr
            35                  40                  45

Asp Ser Ser Lys Leu Ala Ser Gly Val Pro Ala Arg Phe Ser Gly
50                  55                  60

Gly Ser Gly Arg Asp Tyr Thr Leu Thr Ile Ser Ser Leu Glu Pro Glu
65                  70                  75                  80

Asp Phe Ala Val Tyr Tyr Cys Gln Gln Trp Ser Arg Asn Pro Pro Thr
                85                  90                  95

Phe Gly Gly Gly Thr Lys Val Glu Ile Lys Gly Ser Glu Gly Lys
                100                 105                 110

Ser Ser Gly Ser Gly Ser Glu Ser Lys Ser Thr Gly Gly Ser Gln Val
            115                 120                 125

Gln Leu Val Gln Ser Gly Ala Glu Val Lys Lys Pro Gly Ser Ser Val
            130                 135                 140

Lys Val Ser Cys Lys Ala Ser Gly Tyr Thr Phe Thr Arg Ser Thr Met
145                 150                 155                 160

His Trp Val Lys Gln Ala Pro Gly Gln Gly Leu Glu Trp Ile Gly Tyr
                165                 170                 175

Ile Asn Pro Ser Ser Ala Tyr Thr Asn Tyr Asn Gln Lys Phe Gln Gly
                180                 185                 190

Arg Val Thr Leu Thr Ala Asp Lys Ser Thr Ser Thr Ala Tyr Met Glu
            195                 200                 205

Leu Ser Ser Leu Arg Ser Glu Asp Thr Ala Val Tyr Tyr Cys Ala Ser
            210                 215                 220

Pro Gln Val His Tyr Asp Tyr Ala Gly Phe Pro Tyr Trp Gly Gln Gly
225                 230                 235                 240

Thr Leu Val Thr Val Ser Ser Glu Pro Lys Ser Ser Asp Lys Thr His
                245                 250                 255

Thr Cys Pro Pro Cys Pro Ala Pro Glu Ala Ala Gly Gly Pro Ser Val
                260                 265                 270

Phe Leu Phe Pro Pro Lys Pro Lys Asp Thr Leu Met Ile Ser Arg Thr
            275                 280                 285

Pro Glu Val Thr Cys Val Val Val Ser Val Ser His Glu Asp Pro Glu
            290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
```

```
                340                 345                 350
Cys Lys Val Ser Asn Lys Ala Leu Pro Ala Pro Ile Glu Lys Thr Ile
            355                 360                 365

Ser Lys Ala Lys Gly Gln Pro Arg Glu Pro Gln Val Tyr Thr Leu Pro
        370                 375                 380

Pro Ser Arg Glu Glu Met Thr Lys Asn Gln Val Ser Leu Trp Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
            450                 455                 460

His Asn His Tyr Thr Gln Lys Ser Leu Ser Leu Ser Pro Gly Lys Gly
465                 470                 475                 480

Gly Gly Gly Ser Gly Gly Gly Gly Ser Gly Gly Gly Gly Ser Gly Gly
                485                 490                 495

Gly Gly Ser Glu Ile Val Leu Thr Gln Ser Pro Ala Thr Leu Ser Leu
            500                 505                 510

Ser Pro Gly Glu Arg Ala Thr Leu Ser Cys Arg Ala Ser Leu Ser Val
        515                 520                 525

Ser Ser Met His Trp Tyr Gln Gln Lys Pro Gly Gln Ala Pro Arg Leu
    530                 535                 540

Leu Ile Tyr Ala Thr Ser Asn Leu Ala Ser Gly Ile Pro Ala Arg Phe
545                 550                 555                 560

Ser Gly Ser Gly Ser Gly Thr Asp Phe Thr Leu Thr Ile Ser Ser Leu
                565                 570                 575

Glu Pro Glu Asp Phe Ala Val Tyr Tyr Cys Gln Gln Trp Ile Phe Asn
            580                 585                 590

Pro Pro Thr Phe Gly Gly Gly Thr Lys Val Glu Ile Lys Gly Gly Ser
        595                 600                 605

Glu Gly Lys Ser Ser Gly Ser Gly Ser Glu Ser Lys Ser Thr Gly Gly
    610                 615                 620

Ser Gln Val Gln Leu Val Gln Ser Gly Ala Glu Val Lys Lys Pro Gly
625                 630                 635                 640

Ser Ser Val Lys Val Ser Cys Lys Ala Ser Gly Tyr Thr Phe Ser Ser
                645                 650                 655

Tyr Asn Met His Trp Val Arg Gln Ala Pro Gly Gln Gly Leu Glu Trp
            660                 665                 670

Met Gly Ala Ile Tyr Pro Gly Ala Gly Asp Thr Ser Tyr Ala Gln Lys
        675                 680                 685

Phe Gln Gly Arg Val Thr Ile Thr Ala Asp Glu Ser Thr Ser Thr Ala
    690                 695                 700

Tyr Met Glu Leu Ser Ser Leu Arg Ser Glu Asp Thr Ala Val Tyr Tyr
705                 710                 715                 720

Cys Ala Arg Ser Asn Tyr Tyr Gly Ser Gly Trp Tyr Phe Asp Val
                725                 730                 735

Trp Gly Lys Gly Thr Thr Val Thr Val Ser Ser Gln Val Gln Leu Gln
        740                 745                 750

Glu Ser Gly Pro Gly Leu Val Lys Pro Ser Glu Thr Leu Ser Leu Thr
    755                 760                 765
```

Cys Ser Val Ser Gly Ala Ser Ile Ser Ser Phe Tyr Trp Ser Trp Ile
        770                 775                 780

Arg Gln Pro Ala Asp Glu Gly Leu Glu Trp Ile Gly Arg Ile Ser Pro
785                 790                 795                 800

Ser Gly Lys Thr Asn Tyr Ile Pro Ser Leu Lys Ser Arg Ile Ile Met
            805                 810                 815

Ser Leu Asp Ala Ser Lys Asn Gln Phe Ser Leu Arg Leu Asn Ser Val
        820                 825                 830

Thr Ala Ala Asp Thr Ala Met Tyr Tyr Cys Ala Arg Gly Glu Tyr Ser
        835                 840                 845

Gly Thr Tyr Ser Tyr Ser Phe Asp Val Trp Gly Gln Gly Thr Met Val
    850                 855                 860

Thr Val Ser Ser Ala Ser Thr Lys Gly Pro Ser Val Phe Pro Leu Ala
865                 870                 875                 880

Pro Ser Ser Lys Ser Thr Ser Gly Gly Thr Ala Ala Leu Gly Cys Leu
            885                 890                 895

Val Lys Asp Tyr Phe Pro Glu Pro Val Thr Val Ser Trp Asn Ser Gly
            900                 905                 910

Ala Leu Thr Ser Gly Val His Thr Phe Pro Ala Val Leu Gln Ser Ser
        915                 920                 925

Gly Leu Tyr Ser Leu Ser Ser Val Val Thr Val Pro Ser Ser Ser Leu
    930                 935                 940

Gly Thr Gln Thr Tyr Ile Cys Asn Val Asn His Lys Pro Ser Asn Thr
945                 950                 955                 960

Lys Val Asp Lys Lys Val Glu Pro Lys Ser Cys Asp Lys Thr His Thr
            965                 970                 975

Cys Pro Pro Cys Pro Ala Pro Glu Ala Ala Gly Gly Pro Ser Val Phe
        980                 985                 990

Leu Phe Pro Pro Lys Pro Lys Asp Thr Leu Met Ile Ser Arg Thr Pro
    995                 1000                1005

Glu Val Thr Cys Val Val Val Ser Val Ser His Glu Asp Pro Glu
    1010                1015                1020

Val Lys Phe Asn Trp Tyr Val Asp Gly Val Glu Val His Asn Ala
    1025                1030                1035

Lys Thr Lys Pro Arg Glu Glu Gln Tyr Asn Ser Thr Tyr Arg Val
    1040                1045                1050

Val Ser Val Leu Thr Val Leu His Gln Asp Trp Leu Asn Gly Lys
    1055                1060                1065

Glu Tyr Lys Cys Lys Val Ser Asn Lys Ala Leu Pro Ala Pro Ile
    1070                1075                1080

Glu Lys Thr Ile Ser Lys Ala Lys Gly Gln Pro Arg Glu Pro Gln
    1085                1090                1095

Val Tyr Thr Leu Pro Pro Ser Arg Glu Glu Met Thr Lys Asn Gln
    1100                1105                1110

Val Ser Leu Ser Cys Ala Val Lys Gly Phe Tyr Pro Ser Asp Ile
    1115                1120                1125

Ala Val Glu Trp Glu Ser Asn Gly Gln Pro Glu Asn Asn Tyr Lys
    1130                1135                1140

Thr Thr Pro Pro Val Leu Asp Ser Asp Gly Ser Phe Phe Leu Val
    1145                1150                1155

Ser Lys Leu Thr Val Asp Lys Ser Arg Trp Gln Gln Gly Asn Val
    1160                1165                1170

-continued

```
Phe Ser Cys Ser Val Met His Glu Ala Leu His Asn Arg Phe Thr
    1175                1180                1185

Gln Lys Ser Leu Ser Leu Ser Pro Gly Lys Asp Ile Val Met Thr
    1190                1195                1200

Gln Ser Pro Leu Ser Leu Ser Val Thr Pro Gly Glu Pro Ala Ser
    1205                1210                1215

Ile Ser Cys Arg Ser Ser Glu Ser Leu Leu Asp Ser Glu Asp Gly
    1220                1225                1230

Asn Thr Tyr Leu Asp Trp Phe Leu Gln Lys Pro Gly Gln Ser Pro
    1235                1240                1245

Gln Leu Leu Ile Tyr Thr Leu Ser Tyr Arg Ala Ser Gly Val Pro
    1250                1255                1260

Asp Arg Phe Ser Gly Ser Gly Ser Asp Thr Asp Phe Thr Leu His
    1265                1270                1275

Ile Ser Ser Leu Glu Ala Glu Asp Val Gly Leu Tyr Tyr Cys Met
    1280                1285                1290

Gln Arg Met Glu Phe Pro Leu Thr Phe Gly Gln Gly Thr Lys Val
    1295                1300                1305

Glu Ile Lys Arg Thr Val Ala Ala Pro Ser Val Phe Ile Phe Pro
    1310                1315                1320

Pro Ser Asp Glu Gln Leu Lys Ser Gly Thr Ala Ser Val Val Cys
    1325                1330                1335

Leu Leu Asn Asn Phe Tyr Pro Arg Glu Ala Lys Val Gln Trp Lys
    1340                1345                1350

Val Asp Asn Ala Leu Gln Ser Gly Asn Ser Gln Glu Ser Val Thr
    1355                1360                1365

Glu Gln Asp Ser Lys Asp Ser Thr Tyr Ser Leu Ser Ser Thr Leu
    1370                1375                1380

Thr Leu Ser Lys Ala Asp Tyr Glu Lys His Lys Val Tyr Ala Cys
    1385                1390                1395

Glu Val Thr His Gln Gly Leu Ser Ser Pro Val Thr Lys Ser Phe
    1400                1405                1410

Asn Arg Gly Glu Cys
    1415
```

<210> SEQ ID NO 260
<211> LENGTH: 748
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

```
Glu Ile Val Leu Thr Gln Ser Pro Ala Thr Leu Ser Ala Ser Pro Gly
1               5                   10                  15

Glu Arg Val Thr Leu Ser Cys Ser Ala Ser Ser Val Ser Tyr Met
            20                  25                  30

Asn Trp Tyr Gln Gln Lys Pro Gly Gln Ala Pro Arg Arg Trp Ile Tyr
            35                  40                  45

Asp Ser Ser Lys Leu Ala Ser Gly Val Pro Ala Arg Phe Ser Gly Ser
    50                  55                  60

Gly Ser Gly Arg Asp Tyr Thr Leu Thr Ile Ser Ser Leu Glu Pro Glu
65                  70                  75                  80

Asp Phe Ala Val Tyr Tyr Cys Gln Gln Trp Ser Arg Asn Pro Pro Thr
                85                  90                  95
```

-continued

```
Phe Gly Gly Gly Thr Lys Val Glu Ile Lys Gly Gly Ser Glu Gly Lys
                100                 105                 110

Ser Ser Gly Ser Gly Ser Glu Ser Lys Ser Thr Gly Ser Gly Ser Gln Val
            115                 120                 125

Gln Leu Val Gln Ser Gly Ala Glu Val Lys Lys Pro Gly Ser Ser Val
        130                 135                 140

Lys Val Ser Cys Lys Ala Ser Gly Tyr Thr Phe Thr Arg Ser Thr Met
145                 150                 155                 160

His Trp Val Lys Gln Ala Pro Gly Gln Gly Leu Glu Trp Ile Gly Tyr
                165                 170                 175

Ile Asn Pro Ser Ser Ala Tyr Thr Asn Tyr Asn Gln Lys Phe Gln Gly
            180                 185                 190

Arg Val Thr Leu Thr Ala Asp Lys Ser Thr Ser Thr Ala Tyr Met Glu
        195                 200                 205

Leu Ser Ser Leu Arg Ser Glu Asp Thr Ala Val Tyr Tyr Cys Ala Ser
210                 215                 220

Pro Gln Val His Tyr Asp Tyr Ala Gly Phe Pro Tyr Trp Gly Gln Gly
225                 230                 235                 240

Thr Leu Val Thr Val Ser Ser Glu Pro Lys Ser Ser Asp Lys Thr His
                245                 250                 255

Thr Cys Pro Pro Cys Pro Ala Pro Glu Ala Ala Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Ser Val Ser His Glu Asp Pro Glu
        290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
370                 375                 380

Pro Ser Arg Glu Glu Met Thr Lys Asn Gln Val Ser Leu Trp Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
        450                 455                 460

His Asn His Tyr Thr Gln Lys Ser Leu Ser Leu Ser Pro Gly Lys Gly
465                 470                 475                 480

Gly Gly Gly Ser Gly Gly Gly Gly Ser Gly Gly Gly Gly Ser Gly Gly
                485                 490                 495

Gly Gly Ser Glu Ile Val Leu Thr Gln Ser Pro Ala Thr Leu Ser Leu
            500                 505                 510
```

Ser Pro Gly Glu Arg Ala Thr Leu Ser Cys Arg Ala Ser Leu Ser Val
                515                 520                 525

Ser Ser Met His Trp Tyr Gln Gln Lys Pro Gly Gln Ala Pro Arg Leu
            530                 535                 540

Leu Ile Tyr Ala Thr Ser Asn Leu Ala Ser Gly Ile Pro Ala Arg Phe
545                 550                 555                 560

Ser Gly Ser Gly Ser Gly Thr Asp Phe Thr Leu Thr Ile Ser Ser Leu
                565                 570                 575

Glu Pro Glu Asp Phe Ala Val Tyr Tyr Cys Gln Gln Trp Ile Phe Asn
            580                 585                 590

Pro Pro Thr Phe Gly Gly Gly Thr Lys Val Glu Ile Lys Gly Gly Ser
            595                 600                 605

Glu Gly Lys Ser Ser Gly Ser Gly Ser Glu Ser Lys Ser Thr Gly Gly
            610                 615                 620

Ser Gln Val Gln Leu Val Gln Ser Gly Ala Glu Val Lys Lys Pro Gly
625                 630                 635                 640

Ser Ser Val Lys Val Ser Cys Lys Ala Ser Gly Tyr Thr Phe Ser Ser
                645                 650                 655

Tyr Asn Met His Trp Val Arg Gln Ala Pro Gly Gln Gly Leu Glu Trp
            660                 665                 670

Met Gly Ala Ile Tyr Pro Gly Ala Gly Asp Thr Ser Tyr Ala Gln Lys
            675                 680                 685

Phe Gln Gly Arg Val Thr Ile Thr Ala Asp Glu Ser Thr Ser Thr Ala
            690                 695                 700

Tyr Met Glu Leu Ser Ser Leu Arg Ser Glu Asp Thr Ala Val Tyr Tyr
705                 710                 715                 720

Cys Ala Arg Ser Asn Tyr Tyr Gly Ser Ser Gly Trp Tyr Phe Asp Val
                725                 730                 735

Trp Gly Lys Gly Thr Thr Val Thr Val Ser Ser His
            740                 745

<210> SEQ ID NO 261
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Gln Val Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Ser Phe
            20                  25                  30

Tyr Trp Ser Trp Ile Arg Gln Pro Ala Asp Glu Gly Leu Glu Trp Ile
        35                  40                  45

Gly Arg Ile Ser Pro Ser Gly Lys Thr Asn Tyr Ile Pro Ser Leu Lys
    50                  55                  60

Ser Arg Ile Ile Met Ser Leu Asp Ala Ser Lys Asn Gln Phe Ser Leu
65                  70                  75                  80

Arg Leu Asn Ser Val Thr Ala Ala Asp Thr Ala Met Tyr Tyr Cys Ala
                85                  90                  95

Arg Gly Glu Tyr Ser Gly Thr Tyr Ser Tyr Ser Phe Asp Val Trp Gly
            100                 105                 110

Gln Gly Thr Met Val Thr Val Ser Ser Ala Ser Thr Lys Gly Pro Ser
        115                 120                 125

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ser Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Ser Cys Ala Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn Arg Phe Thr Gln Lys Ser Leu Ser Leu Ser
        435                 440                 445

Pro Gly Lys
    450

<210> SEQ ID NO 262
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Asp Ile Val Met Thr Gln Ser Pro Leu Ser Leu Ser Val Thr Pro Gly
1               5                   10                  15

Glu Pro Ala Ser Ile Ser Cys Arg Ser Ser Glu Ser Leu Leu Asp Ser
```

```
            20                  25                  30
Glu Asp Gly Asn Thr Tyr Leu Asp Trp Phe Leu Gln Lys Pro Gly Gln
            35                  40                  45

Ser Pro Gln Leu Leu Ile Tyr Thr Leu Ser Tyr Arg Ala Ser Gly Val
        50                  55                  60

Pro Asp Arg Phe Ser Gly Ser Gly Ser Asp Thr Asp Phe Thr Leu His
65                  70                  75                  80

Ile Ser Ser Leu Glu Ala Glu Asp Val Gly Leu Tyr Tyr Cys Met Gln
                85                  90                  95

Arg Met Glu Phe Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 263
<211> LENGTH: 1419
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Glu Ile Val Leu Thr Gln Ser Pro Ala Thr Leu Ser Ala Ser Pro Gly
1               5                   10                  15

Glu Arg Val Thr Leu Ser Cys Ser Ala Ser Ser Ser Val Ser Tyr Met
            20                  25                  30

Asn Trp Tyr Gln Gln Lys Pro Gly Gln Ala Pro Arg Arg Trp Ile Tyr
        35                  40                  45

Asp Ser Ser Lys Leu Ala Ser Gly Val Pro Ala Arg Phe Ser Gly Ser
    50                  55                  60

Gly Ser Gly Arg Asp Tyr Thr Leu Thr Ile Ser Ser Leu Glu Pro Glu
65                  70                  75                  80

Asp Phe Ala Val Tyr Tyr Cys Gln Gln Trp Ser Arg Asn Pro Pro Thr
                85                  90                  95

Phe Gly Gly Gly Thr Lys Val Glu Ile Lys Gly Gly Ser Glu Gly Lys
            100                 105                 110

Ser Ser Gly Ser Gly Ser Glu Ser Lys Ser Thr Gly Gly Ser Gln Val
        115                 120                 125

Gln Leu Val Gln Ser Gly Ala Glu Val Lys Lys Pro Gly Ser Ser Val
    130                 135                 140

Lys Val Ser Cys Lys Ala Ser Gly Tyr Thr Phe Thr Arg Ser Thr Met
145                 150                 155                 160
```

His Trp Val Lys Gln Ala Pro Gly Gln Gly Leu Glu Trp Ile Gly Tyr
             165                 170                 175

Ile Asn Pro Ser Ser Ala Tyr Thr Asn Tyr Asn Gln Lys Phe Gln Gly
         180                 185                 190

Arg Val Thr Leu Thr Ala Asp Lys Ser Thr Ser Thr Ala Tyr Met Glu
             195                 200                 205

Leu Ser Ser Leu Arg Ser Glu Asp Thr Ala Val Tyr Tyr Cys Ala Ser
         210                 215                 220

Pro Gln Val His Tyr Asp Tyr Ala Gly Phe Pro Tyr Trp Gly Gln Gly
225                 230                 235                 240

Thr Leu Val Thr Val Ser Ser Glu Pro Lys Ser Ser Asp Lys Thr His
             245                 250                 255

Thr Cys Pro Pro Cys Pro Ala Pro Glu Ala Ala Gly Gly Pro Ser Val
             260                 265                 270

Phe Leu Phe Pro Pro Lys Pro Lys Asp Thr Leu Met Ile Ser Arg Thr
         275                 280                 285

Pro Glu Val Thr Cys Val Val Ser Val Ser His Glu Asp Pro Glu
         290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
             325                 330                 335

Val Leu Thr Val Leu His Gln Asp Trp Leu Asn Gly Lys Glu Tyr Lys
             340                 345                 350

Cys Lys Val Ser Asn Lys Ala Leu Pro Ala Pro Ile Glu Lys Thr Ile
             355                 360                 365

Ser Lys Ala Lys Gly Gln Pro Arg Glu Pro Gln Val Tyr Thr Leu Pro
         370                 375                 380

Pro Ser Arg Glu Glu Met Thr Lys Asn Gln Val Ser Leu Trp Cys Leu
385                 390                 395                 400

Val Lys Gly Phe Tyr Pro Ser Asp Ile Ala Val Glu Trp Glu Ser Asn
             405                 410                 415

Gly Gln Pro Glu Asn Asn Tyr Lys Thr Thr Pro Pro Val Leu Asp Ser
         420                 425                 430

Asp Gly Ser Phe Phe Leu Tyr Ser Lys Leu Thr Val Asp Lys Ser Arg
             435                 440                 445

Trp Gln Gln Gly Asn Val Phe Ser Cys Ser Val Met His Glu Ala Leu
450                 455                 460

His Asn His Tyr Thr Gln Lys Ser Leu Ser Leu Ser Pro Gly Lys Gly
465                 470                 475                 480

Gly Gly Gly Ser Gly Gly Gly Ser Gly Gly Gly Ser Gly Gly
             485                 490                 495

Gly Gly Ser Glu Ile Val Leu Thr Gln Ser Pro Ala Thr Leu Ser Leu
         500                 505                 510

Ser Pro Gly Glu Arg Ala Thr Leu Ser Cys Arg Ala Ser Leu Ser Val
             515                 520                 525

Ser Ser Met His Trp Tyr Gln Gln Lys Pro Gly Gln Ala Pro Arg Leu
         530                 535                 540

Leu Ile Tyr Ala Thr Ser Asn Leu Ala Ser Gly Ile Pro Ala Arg Phe
545                 550                 555                 560

Ser Gly Ser Gly Ser Gly Thr Asp Phe Thr Leu Thr Ile Ser Ser Leu
             565                 570                 575

Glu Pro Glu Asp Phe Ala Val Tyr Tyr Cys Gln Gln Trp Ile Phe Asn

```
               580             585             590
Pro Pro Thr Phe Gly Gly Thr Lys Val Glu Ile Lys Gly Gly Ser
            595             600             605

Glu Gly Lys Ser Ser Gly Ser Gly Ser Glu Ser Lys Ser Thr Gly Gly
            610             615             620

Ser Gln Val Gln Leu Val Gln Ser Gly Ala Glu Val Lys Lys Pro Gly
625             630             635             640

Ser Ser Val Lys Val Ser Cys Lys Ala Ser Gly Tyr Thr Phe Ser Ser
                645             650             655

Tyr Asn Met His Trp Val Arg Gln Ala Pro Gly Gln Gly Leu Glu Trp
            660             665             670

Met Gly Ala Ile Tyr Pro Gly Ala Gly Asp Thr Ser Tyr Ala Gln Lys
            675             680             685

Phe Gln Gly Arg Val Thr Ile Thr Ala Asp Glu Ser Thr Ser Thr Ala
            690             695             700

Tyr Met Glu Leu Ser Ser Leu Arg Ser Glu Asp Thr Ala Val Tyr Tyr
705             710             715             720

Cys Ala Arg Ser Asn Tyr Tyr Gly Ser Ser Gly Trp Tyr Phe Asp Val
                725             730             735

Trp Gly Lys Gly Thr Thr Val Thr Val Ser Ser His Gln Val Gln Leu
            740             745             750

Gln Glu Ser Gly Pro Gly Leu Val Lys Pro Ser Glu Thr Leu Ser Leu
            755             760             765

Thr Cys Ser Val Ser Gly Ala Ser Ile Ser Ser Phe Tyr Trp Ser Trp
            770             775             780

Ile Arg Gln Pro Ala Asp Glu Gly Leu Glu Trp Ile Gly Arg Ile Ser
785             790             795             800

Pro Ser Gly Lys Thr Asn Tyr Ile Pro Ser Leu Lys Ser Arg Ile Ile
                805             810             815

Met Ser Leu Asp Ala Ser Lys Asn Gln Phe Ser Leu Arg Leu Asn Ser
            820             825             830

Val Thr Ala Ala Asp Thr Ala Met Tyr Tyr Cys Ala Arg Gly Glu Tyr
            835             840             845

Ser Gly Thr Tyr Ser Tyr Ser Phe Asp Val Trp Gly Gln Gly Thr Met
            850             855             860

Val Thr Val Ser Ser Ala Ser Thr Lys Gly Pro Ser Val Phe Pro Leu
865             870             875             880

Ala Pro Ser Ser Lys Ser Thr Ser Gly Gly Thr Ala Ala Leu Gly Cys
                885             890             895

Leu Val Lys Asp Tyr Phe Pro Glu Pro Val Thr Val Ser Trp Asn Ser
            900             905             910

Gly Ala Leu Thr Ser Gly Val His Thr Phe Pro Ala Val Leu Gln Ser
            915             920             925

Ser Gly Leu Tyr Ser Leu Ser Ser Val Val Thr Val Pro Ser Ser Ser
            930             935             940

Leu Gly Thr Gln Thr Tyr Ile Cys Asn Val Asn His Lys Pro Ser Asn
945             950             955             960

Thr Lys Val Asp Lys Lys Val Glu Pro Lys Ser Cys Asp Lys Thr His
                965             970             975

Thr Cys Pro Pro Cys Pro Ala Pro Glu Ala Ala Gly Gly Pro Ser Val
            980             985             990

Phe Leu Phe Pro Pro Lys Pro Lys Asp Thr Leu Met Ile Ser Arg Thr
            995             1000            1005
```

```
Pro Glu Val Thr Cys Val Val Ser Val Ser His Glu Asp Pro
    1010            1015            1020

Glu Val Lys Phe Asn Trp Tyr Val Asp Gly Val Glu Val His Asn
    1025            1030            1035

Ala Lys Thr Lys Pro Arg Glu Glu Gln Tyr Asn Ser Thr Tyr Arg
    1040            1045            1050

Val Val Ser Val Leu Thr Val Leu His Gln Asp Trp Leu Asn Gly
    1055            1060            1065

Lys Glu Tyr Lys Cys Lys Val Ser Asn Lys Ala Leu Pro Ala Pro
    1070            1075            1080

Ile Glu Lys Thr Ile Ser Lys Ala Lys Gly Gln Pro Arg Glu Pro
    1085            1090            1095

Gln Val Tyr Thr Leu Pro Pro Ser Arg Glu Glu Met Thr Lys Asn
    1100            1105            1110

Gln Val Ser Leu Ser Cys Ala Val Lys Gly Phe Tyr Pro Ser Asp
    1115            1120            1125

Ile Ala Val Glu Trp Glu Ser Asn Gly Gln Pro Glu Asn Asn Tyr
    1130            1135            1140

Lys Thr Thr Pro Pro Val Leu Asp Ser Asp Gly Ser Phe Phe Leu
    1145            1150            1155

Val Ser Lys Leu Thr Val Asp Lys Ser Arg Trp Gln Gln Gly Asn
    1160            1165            1170

Val Phe Ser Cys Ser Val Met His Glu Ala Leu His Asn Arg Phe
    1175            1180            1185

Thr Gln Lys Ser Leu Ser Leu Ser Pro Gly Lys Asp Ile Val Met
    1190            1195            1200

Thr Gln Ser Pro Leu Ser Leu Ser Val Thr Pro Gly Glu Pro Ala
    1205            1210            1215

Ser Ile Ser Cys Arg Ser Ser Glu Ser Leu Leu Asp Ser Glu Asp
    1220            1225            1230

Gly Asn Thr Tyr Leu Asp Trp Phe Leu Gln Lys Pro Gly Gln Ser
    1235            1240            1245

Pro Gln Leu Leu Ile Tyr Thr Leu Ser Tyr Arg Ala Ser Gly Val
    1250            1255            1260

Pro Asp Arg Phe Ser Gly Ser Gly Ser Asp Thr Asp Phe Thr Leu
    1265            1270            1275

His Ile Ser Ser Leu Glu Ala Glu Asp Val Gly Leu Tyr Tyr Cys
    1280            1285            1290

Met Gln Arg Met Glu Phe Pro Leu Thr Phe Gly Gln Gly Thr Lys
    1295            1300            1305

Val Glu Ile Lys Arg Thr Val Ala Ala Pro Ser Val Phe Ile Phe
    1310            1315            1320

Pro Pro Ser Asp Glu Gln Leu Lys Ser Gly Thr Ala Ser Val Val
    1325            1330            1335

Cys Leu Leu Asn Asn Phe Tyr Pro Arg Glu Ala Lys Val Gln Trp
    1340            1345            1350

Lys Val Asp Asn Ala Leu Gln Ser Gly Asn Ser Gln Glu Ser Val
    1355            1360            1365

Thr Glu Gln Asp Ser Lys Asp Ser Thr Tyr Ser Leu Ser Ser Thr
    1370            1375            1380

Leu Thr Leu Ser Lys Ala Asp Tyr Glu Lys His Lys Val Tyr Ala
    1385            1390            1395
```

```
Cys Glu Val Thr His Gln Gly Leu Ser Ser Pro Val Thr Lys Ser
    1400                1405                1410

Phe Asn Arg Gly Glu Cys
    1415

<210> SEQ ID NO 264
<211> LENGTH: 9
<212> TYPE: PRT
<213> ORGANISM: Homo sapiens

<400> SEQUENCE: 264

Ile Pro Ala Gly Ile Tyr Ala Pro Ile
1               5

<210> SEQ ID NO 265
<211> LENGTH: 44
<212> TYPE: PRT
<213> ORGANISM: Homo sapiens

<400> SEQUENCE: 265

His Phe Leu Lys Met Glu Ser Leu Asn Phe Ile Arg Ala His Thr Pro
1               5                   10                  15

Tyr Ile Asn Ile Tyr Asn Cys Gly Pro Ala Asn Pro Ser Glu Lys Asn
            20                  25                  30

Ser Pro Ser Thr Gln Tyr Cys Tyr Ser Ile Gln Ser
            35                  40
```